(12) United States Patent
Hadian et al.

(10) Patent No.: US 12,240,854 B2
(45) Date of Patent: *Mar. 4, 2025

(54) TRAF 6 INHIBITORS

(71) Applicant: Helmholtz Zentrum München - Deutsches Forschungszentrum für Gesundheit und Umwelt (GmbH), Neuherberg (DE)

(72) Inventors: Kamyar Hadian, Munich (DE); Jara Kerstin Brenke, Munich (DE); Oliver Plettenburg, Ehlershausen (DE); Gerrit Juerjens, Seelze (DE); Paul Wienecke, Hannover (DE)

(73) Assignee: HELMHOLTZ ZENTRUM MUENCHEN—DEUTSCHES FORSCHUNGSZENTRUM FUERGESUNDHEIT UND UMWELT (GMBH) (DE)

( * ) Notice: Subject to any disclaimer, the term of this patent is extended or adjusted under 35 U.S.C. 154(b) by 1080 days.

This patent is subject to a terminal disclaimer.

(21) Appl. No.: 17/040,074

(22) PCT Filed: Mar. 22, 2019

(86) PCT No.: PCT/EP2019/057248
§ 371 (c)(1),
(2) Date: Sep. 22, 2020

(87) PCT Pub. No.: WO2019/180207
PCT Pub. Date: Sep. 26, 2019

(65) Prior Publication Data
US 2021/0017183 A1   Jan. 21, 2021

(30) Foreign Application Priority Data
Mar. 22, 2018  (EP) .................... 18163317

(51) Int. Cl.
C07D 487/04 (2006.01)
A61P 17/06 (2006.01)
(Continued)

(52) U.S. Cl.
CPC ............ *C07D 487/04* (2013.01); *A61P 17/06* (2018.01); *A61P 19/02* (2018.01); *A61P 35/00* (2018.01);
(Continued)

(58) Field of Classification Search
CPC .. A61P 3/10; A61P 35/00; A61P 25/16; A61P 37/00; A61P 19/02; A61P 17/06;
(Continued)

(56) References Cited

FOREIGN PATENT DOCUMENTS

| WO | 2008115259 A2 | 9/2008 |
| WO | 2011160016 A2 | 12/2011 |
| WO | 2018050286 A1 | 3/2018 |

OTHER PUBLICATIONS

STIC search registry compounds (Compound 1, 2, 4, 6, 7, 10, 11, 13, 16 and 28 of 30), 2012 (Year: 2012).*

(Continued)

*Primary Examiner* — Sarah Pihonak
*Assistant Examiner* — Padmaja S Rao
(74) *Attorney, Agent, or Firm* — Dilworth IP, LLC

(57) ABSTRACT

The invention relates to compounds which are suitable for the treatment of cancer, an immune disease, Parkinson's disease, Cardiac Hypertrophy or Type-2 diabetes and to pharmaceutical compositions containing such compounds. The invention further relates to a kit of parts comprising such compounds.

16 Claims, 28 Drawing Sheets

Specification includes a Sequence Listing.

(51) Int. Cl.
  *A61P 19/02*  (2006.01)
  *A61P 35/00*  (2006.01)
  *A61P 37/06*  (2006.01)
  *C07D 471/04*  (2006.01)
  *C12Q 1/48*  (2006.01)

(52) U.S. Cl.
  CPC ............ A61P 37/06 (2018.01); C07D 471/04 (2013.01); C12Q 1/48 (2013.01); *G01N 2500/02* (2013.01); *G01N 2500/20* (2013.01)

(58) Field of Classification Search
  CPC .......... A61P 37/06; A61P 9/00; C07D 471/04; C07D 487/04
  See application file for complete search history.

(56) References Cited

OTHER PUBLICATIONS

Database Registry (Online) Chemical Abstracts Service, Columbus, OH, Feb. 29, 2012, XP002791304, Database accession No. 1358702-32-5, abstract.
Database Registry (Online) Chemical Abstracts Service, Columbus, OH, Feb. 29, 2012, XP002791305, Database accession No. 1358555-82-4, abstract.
Database Registry (Online) Chemical Abstracts Service, Columbus, OH, Feb. 29, 2012, XP002791306, Database accession No. 1358555-26-6, abstract.
Database Registry (Online) Chemical Abstracts Service, Columbus, OH, Feb. 29, 2012, XP002791307, Database accession No. 1358439-26-5, abstract.
Database Registry (Online) Chemical Abstracts Service, Columbus, OH, Feb. 29, 2012, XP002791308, Database accession No. 1358098-89-1, abstract.
Database Registry (Online) Chemical Abstracts Service, Columbus, OH, Feb. 29, 2012, XP002791309, Database accession No. 1358051-97-4, abstract.
Database Registry (Online) Chemical Abstracts Service, Columbus, OH, Apr. 6, 2010, XP002791310, Database accession No. 1217096-48-4, abstract.
Database Registry (Online) Chemical Abstracts Service, Columbus, OH, Oct. 25, 2009, XP002791311, Database accession No. 1189856-01-6, abstract.
Database Registry (Online) Chemical Abstracts Service, Columbus, OH, Oct. 23, 2009, XP002791312, Database accession No. 1189657-45-1, abstract.
Database Registry (Online) Chemical Abstracts Service, Columbus, OH, Oct. 22, 2009, XP002791313, Database accession No. 1189419-84-8, abstract.
Database Registry (Online) Chemical Abstracts Service, Columbus, OH, Sep. 16, 2009, XP002791314, Database accession No. 1184966-26-4, abstract.
Database Registry (Online) Chemical Abstracts Service, Columbus, OH, Aug. 20, 2008, XP002791315, Database accession No. 1015884-96-4, abstract.
International Search Report issued in International Patent Application No. PCT/EP2019/057248 dated Jul. 31, 2019.

\* cited by examiner

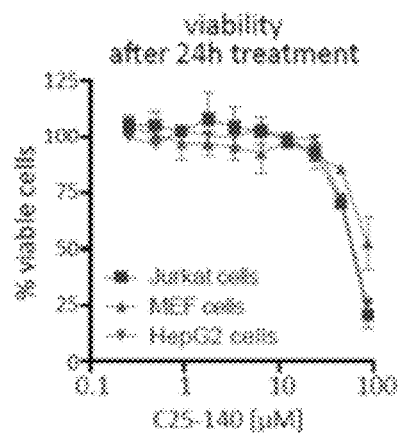
Fig. 3A
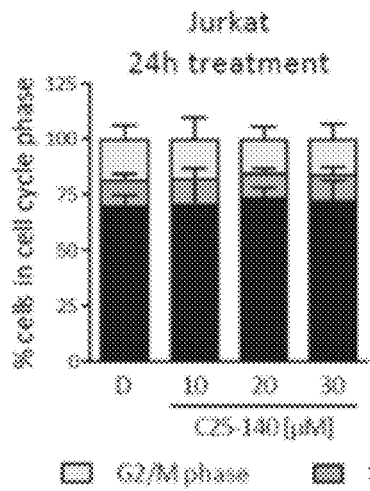
Fig. 3B
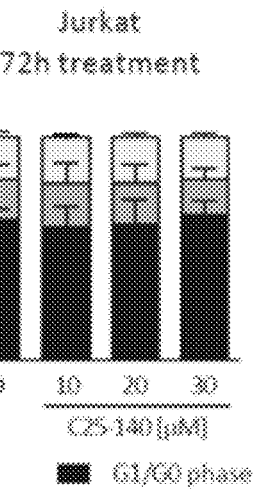
Fig. 3C
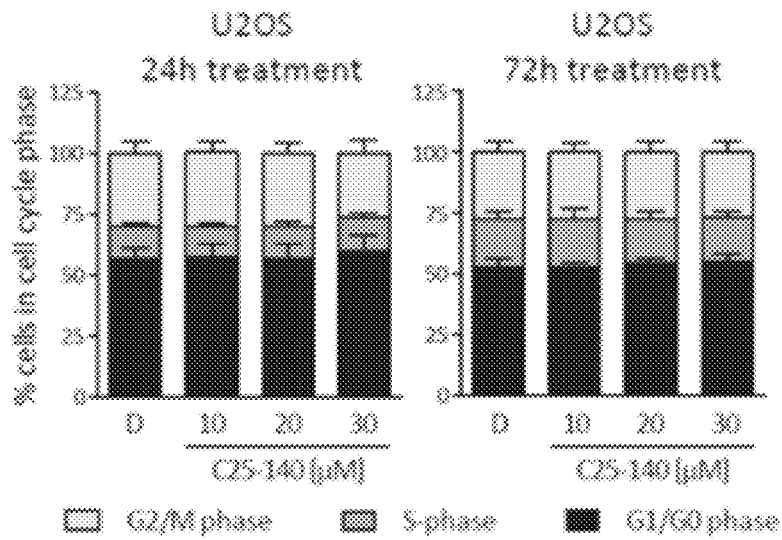
Fig. 3DFig. 3E

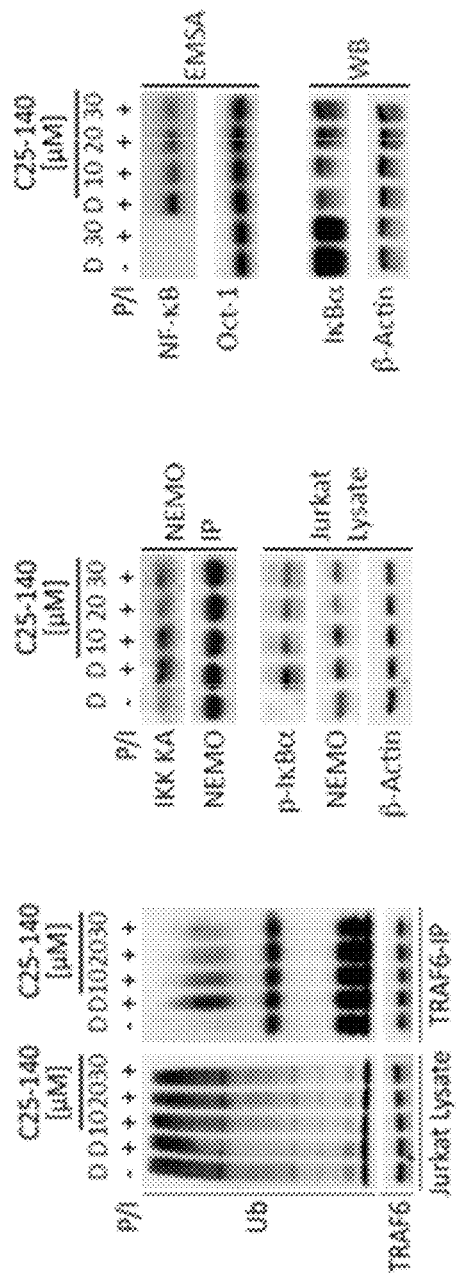
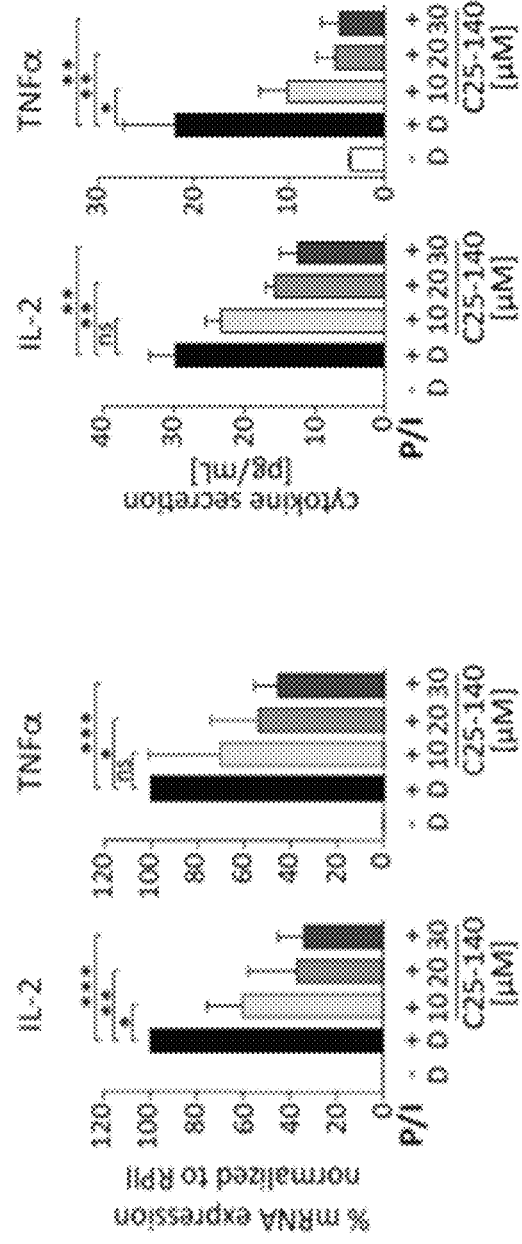
Fig. 6A  Fig. 6B  Fig. 6C
Fig. 6D  Fig. 6E

| ADME test | Result |
|---|---|
| Plasma stability (1µM) | t₁/₂ > 240min |
| Plasma protein binding assay (1µM) | 96.8 % |
| Microsomal stability (1µM) | Ke = 0.0054/min<br>t₁/₂ = 121.01min<br>CLint = 0.74mL/min/mg |
| LogD, pH 7.4 (0.1mM in PBS; 1mM in Octanol) | 2.83 |
| Caco-2 assay (10µM) | Papp = 48.92 × 10⁻⁶ cm/s |
| CYP450 inhibition (20µM) | CYP1A2: 25.73 %<br>CYP2C9: 94.20 %<br>CYP2C19: 82.53 %<br>CYP2D6: 67.34 %<br>CYP3A4: 45.76 % |
| hERG patch clamp inhibition | 10µM: 51 %<br>3µM: 36 %<br>1µM: 28.1 % |

Fig. 9A

| | IV<br>[10mg/kg] | PO<br>[10mg/kg] | IP<br>[10mg/kg] |
|---|---|---|---|
| Tmax | Tmax = 5min | Tmax = 15min | Tmax = 15min |
| Cmax | Cmax = 9.7µg/mL | Cmax = 3.4µg/mL | Cmax = 4.2µg/mL |
| AUC0-∞ | AUC = 286µg*min/mL | AUC = 138µg*min/mL | AUC = 104µg*min/mL |
| Mean Residence Time | MRTinf = 32min | MRTinf = 114min | MRTinf = 53min |
| Elimination half-life | t₁/₂ = 80.6min | t₁/₂ = 127.1min | t₁/₂ = 184min |
| Elimination rate constant | Kel = 0.0086/min | Kel = 0.0054/min | Kel = 0.0038/min |
| Volume of Distribution | Vd = 4.1L/kg | Vd = 13.3L/kg | Vd = 25.6L/kg |
| Clearance | CL = 35.53mL/min/kg | CL = 72.38mL/min/kg | CL = 96.2mL/min/kg |

Fig. 9B

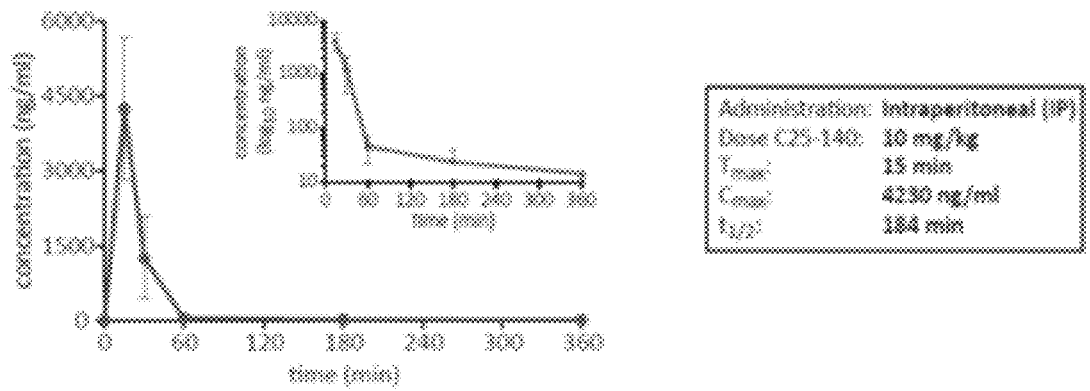

Fig. 9C

| | Assay | Ligand or Substrate | Species | Tissue | Response (graph) | Response |
|---|---|---|---|---|---|---|
| Transporter | Transporter, Adenosine | [3H]Nitrobenzylthioinosine | Guinea pig | cerebral cortex | | 25 |
| | Transporter, Glutamine (GlnT) | D-[2,3]H]Asp | Human | recombinant | | 28 |
| | Transporter, GABA | [3H]GABA | Rat | cerebral cortex | | -3 |
| | Transporter, Norepinephrine (NET) | [125I]RTI-55 | Human | recombinant | | 34 |
| | Transporter, Serotonin (5-Hydroxytryptamine) | [125I]RTI-55 | Human | recombinant | | 14 |
| | GABAA, Flunitrazepam, Central | [3H]Flunitrazepam | Rat | brain (minus cerebellum) | | 5 |
| | GABAA, Ro 15-1788, Hippocampus | [3H]Ro 15-1788 | Rat | hippocampus | | 5 |
| | GABAA, Chloride Channel, TBOB | [3H]TBOB | Rat | cerebral cortex | | 13 |
| | Glutamate, AMPA | [3H]AMPA | Rat | cerebral cortex | | 34 |
| | Glutamate, Kainate | [3H]Kainic acid | Rat | brain (minus cerebellum) | | 17 |
| | Glutamate, NMDA, Agonism | [3H]CGP-39653 | Rat | cerebral cortex | | -1 |
| Ion Channels | Glutamate, NMDA, Glycine | [3H]MDL 105,519 | Rat | cerebral cortex | | 9 |
| | Glutamate, NMDA, Phencyclidine | [3H]TCP | Rat | cerebral cortex | | 13 |
| | Glutamate, NMDA, Polyamine | [3H]Ifenprodil | Rat | spinal cord | | 6 |
| | Glycine, Strychnine-Sensitive | [3H]Strychnine | Rat | spinal cord | | 0 |
| | Nicotinic Acetylcholine | [125I]Epibatidine | Human | IMR-32 cells | | -1 |
| | Nicotinic Acetylcholine Alpha1, Bungarotoxin | [125I]Alpha Bungarotoxin | Human | recombinant | | 9 |
| | Serotonin (5-Hydroxytryptamine) 5-HT3 | [3H]GR-65630 | Rat | brain | | -3 |
| | Calcium Channel L-Type, Benzothiazepine | [3H]Diltiazem | Rat | cerebral cortex | | -1 |
| | Calcium Channel L-Type, Dihydropyridine | [3H]Nitrendipine | Rat | brain | | 24 |
| | Calcium Channel N-Type, Phenylalkylamine | [3H]{-}-Gamma-Homoepoxyepipristine (D-888) | Rat | tropical brain | | 5 |
| | Potassium Channel [KATP] | [125I]lsu-Conotoxin GVIA | Hamster | pancreatic HIT-T15 B-cells | | 8 |
| | Potassium Channel hERG | [3H]Glyburide | Human | recombinant | | 20 |
| | Sodium Channel, Site 2 | [3H]Astemizole | Rat | brain | | -30 |
| Nuclear receptors | Androgen (Testosterone) | [3H]Batrachotoxinin | Human | recombinant | | 4 |
| | Estrogen ERalpha | [3H]Mesulergine | Human | LNCaP clone FGC cells | | -1 |
| | Glucocorticoid | [3H]Estradiol | Human | recombinant | | 0 |
| | Progesterone PR-B | [3H]Dexamethasone | Human | recombinant | | 7 |
| Kinases | Protein Tyrosine Kinase, Insulin Receptor | [3H]Progesterone | Human | Y-1/b cells | | 13 |
| | Protein Tyrosine Kinase, LCK | Poly(Glu:Tyr) | Human | recombinant | | -3 |
| | Protein Ser/Thr Kinase, PKC, Non-Selective | Poly(Glu:Tyr) | Human | recombinant | | 5 |
| | Cyclooxygenase COX-1 | Histone | Rat | brain | | 0 |
| | Cyclooxygenase COX-2 | Arachidonic acid | Human | platelets | | 23 |
| | ATPase, Na+/K+, Heart, Pig | Arachidonic acid | Human | recombinant | | 35 |
| | Monoamine Oxidase MAO-A | ATP | Pig | heart | | 6 |
| Non-Kinase Enzymes | Monoamine Oxidase MAO-B | Kynuramine | Human | recombinant | | 3 |
| | Phosphodiesterase PDE3 | Kynuramine | Human | recombinant | | 5 |
| | Phosphodiesterase PDE4 | [3H]cAMP + cAMP | Human | platelets | | 2 |
| | Peptidase, CTSG (Cathepsin G) | [3H]cAMP + cAMP | Human | U937 cells | | 8 |
| | Peptidase, Angiotensin Converting Enzyme | Suc-Ala-Ala-Pro-Phe-AMC | Human | neutrophils | | -3 |
| | Cholinesterase, Acetyl, ACES | N-[3-(2-furyl) acryloyl]-Phe-Gly-Gly (FAPGG) | Rabbit | lung | | 4 |
| | | Acetylthiocholine | Human | recombinant | | 20 |

Fig. 10B

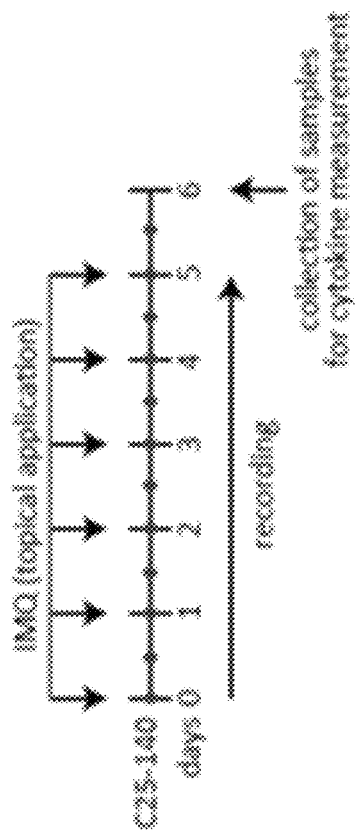
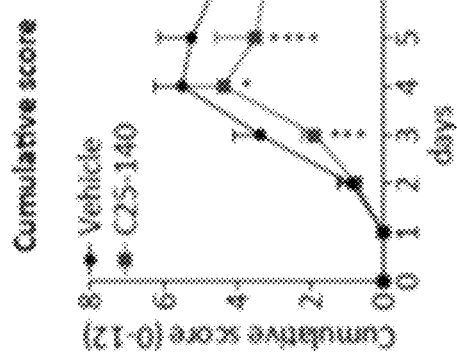
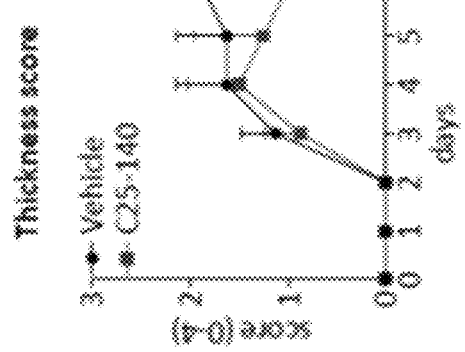
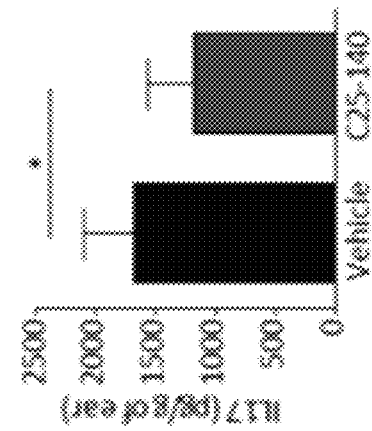
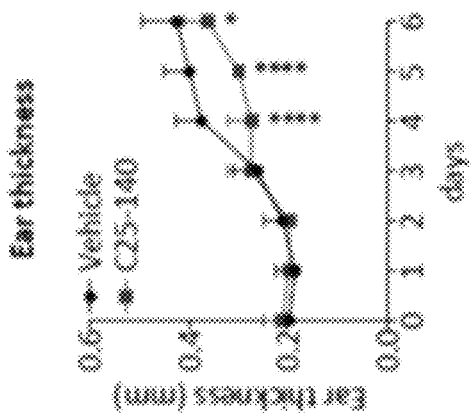
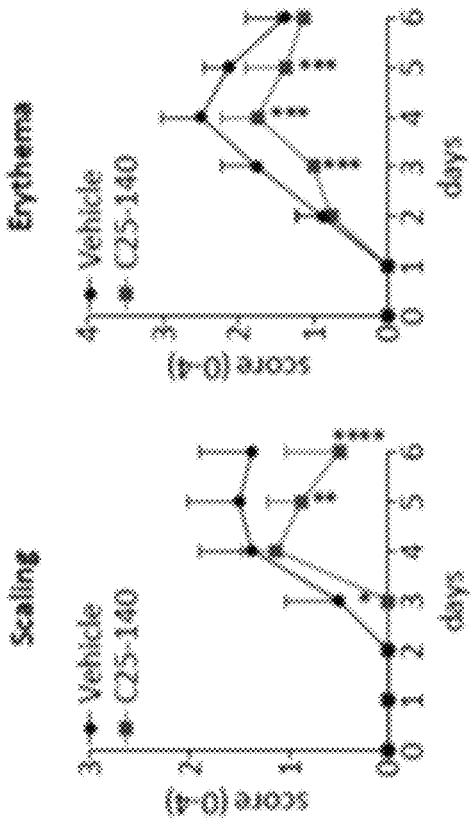
Fig. 12A
Fig. 12B
Fig. 12C
Fig. 12D
Fig. 12E
Fig. 12F
Fig. 12G

| Tissue Origin | Cell Line | Absolute IC50 (µM) C25-140 |
|---|---|---|
| bladder | HT-1376 | 49,96 |
| | RT112/84 | 80 |
| | RT4 | 80 |
| blood | Jurkat clone E6-1 | 51,76 |
| | Molt-4 | 43,06 |
| | HL-60 | 37,47 |
| | Kasumi-1 | 40,83 |
| | ML-2 | 47,57 |
| | THP-1 | 61,66 |
| | HBL-1 | 43,64 |
| | HuT 78 | 53,27 |
| | Raji | 33,42 |
| | Ramos | 60,6 |
| | SU-DHL-4 | 31,88 |
| | SU-DHL-5 | 28 |
| | SU-DHL-6 | 66,11 |
| | U-2932 | 66,15 |
| | U-937 | 44,62 |
| | WSU-DLCL2 | 54,02 |
| | NCI-H929 | 50,08 |
| | OPM2 | 49,81 |
| | RPMI 8226 | 49,07 |
| | OCI-LY7 | 39,1 |
| | SU-DHL-8 | 22,89 |
| bone | HOS | 80 |
| | Saos-2 | 80 |
| | SJSA-1 | 80 |
| | U-2 OS | 80 |
| brain and nerve | U251 | 80 |
| | U-87 MG | 80 |
| breast | MCF7 | 80 |
| | MDA-MB-231 | 80 |
| | MDA-MB-436 | 80 |
| | MDA-MB-468 | 77,23 |
| | BT474 | 80 |
| | HCC1954 | 80 |
| | T47D | 80 |
| cervix | HeLa | 80 |

Fig. 16A

| Tissue Origin | Cell Line | Absolute IC50 (µM) C25-140 |
|---|---|---|
| colorectum | COLO 205 | 80 |
| | HCT 116 | 61,07 |
| | HCT-15 | 70,87 |
| | HT-29 | 66,48 |
| | RKO | 65,2 |
| | SW480 | 80 |
| esophagus | KYSE-150 | 64,48 |
| | KYSE-270 | 80 |
| | KYSE-410 | 72,26 |
| kidney | 786-O | 80 |
| | SK-NEP-1 | 65,68 |
| liver | Hep G2/C3A | 80 |
| | HUH-7 | 80 |
| | SK-HEP-1 | 55,49 |
| lung | A549 | 70 |
| | HCC827 | 80 |
| | NCI-H1299 | 68,83 |
| | NCI-H1395 | 80 |
| | NCI-H1975 | 80 |
| | NCI-H292 | 80 |
| | NCI-H460 | 80 |
| | NCI-H520 | 80 |
| | PC-9 | 67,49 |
| | SK-MES-1 | 60,84 |
| | NCI-H209 | 80 |
| | NCI-H526 | 80 |
| muscle | A-673 | 80 |
| pancreas | BxPC-3 | 80 |
| | MIA PaCa-2 | 51,09 |
| | PANC-1 | 80 |
| pharynx | FaDu | 64,09 |
| prostate | LNCaP clone FGC | 59,58 |
| | PC-3 | 80 |
| skin | A-431 | 80 |
| | SK-MEL-28 | 80 |
| soft tissue | HT-1080 | 80 |
| stomach/gastric | SNU-5 | 80 |
| thyroid | SW579 | 80 |
| | TT | 80 |
| uterus | Ishikawa | 80 |
| bone marrow (N) | HS-5 | 80 |
| breast (N) | MCF 10A | 80 |

| compound ID | IC$_{50}$ Alphascreen |
|---|---|
| C140 | +++ |
| HZM06-1 | ++ |
| HZM06-2 | ++ |
| HZM06-3 | ++ |
| HZM06-4 | ++++ |
| HZM06-6 | +++ |
| HZM06-7 | ++ |
| HZM06-8 | +++ |
| HZM06-9 | +++ |
| HZM06-10 | +++ |
| HZM06-11 | + |
| HZM06-18 | + |
| HZM06-21 | + |
| HZM06-22 | + |
| HZM06-23 | ++ |
| HZM06-24 | +++ |
| HZM06-25 | ++ |
| HZM06-26 | +++ |
| HZM06-27 | +++ |
| HZM06-28 | +++ |
| HZM06-29 | +++ |
| HZM-11-5 | ++ |
| HZM-11-9 | ++ |
| HZM-11-11 | ++ |
| OR-001 | + |
| OR-004 | ++ |
| OR-005 | ++++ |
| OR-006 | + |
| OR-007 | ++ |
| OR-008 | + |
| OR-010 | ++ |
| OR-012 | ++ |
| OR-013 | + |
| OR-014 | ++ |
| OR-021 | +++ |
| OR-023 | ++ |
| OR-024 | +++ |
| OR-026 | ++ |
| OR-027 | + |
| OR-028 | ++ |
| OR-031 | + |
| OR-033 | ++ |

+: ≥30% Inhibition @ 100 μM
++ IC 50 ≤ 30μM
+++: IC 50 ≤ 10μM
++++: IC 50 ≤ 3μM

AlphaScreen®
TRAF6 activity ubiquitination assay

SEQUENCE LISTING

```
<160> NUMBER OF SEQ ID NOS: 34

<210> SEQ ID NO 1
<211> LENGTH: 33
<212> TYPE: DNA
<213> ORGANISM: Artificial
<220> FEATURE:
<223> OTHER INFORMATION: EMSA oligonucleotide

<400> SEQUENCE: 1
gatccagggc tggggattcc ccatctccac agg                              33
```

```
<210> SEQ ID NO 2
<211> LENGTH: 33
<212> TYPE: DNA
<213> ORGANISM: Artificial
<220> FEATURE:
<223> OTHER INFORMATION: EMSA Oligonucleotide

<400> SEQUENCE: 2
gatccctgtg gagatgggga atccccagcc ctg                               33

<210> SEQ ID NO 3
<211> LENGTH: 26
<212> TYPE: DNA
<213> ORGANISM: Artificial
<220> FEATURE:
<223> OTHER INFORMATION: ESMA oligonucleotide

<400> SEQUENCE: 3
gatctgtcga atgcaaatca ctagaa                                       26

<210> SEQ ID NO 4
<211> LENGTH: 26
<212> TYPE: DNA
<213> ORGANISM: Artificial
<220> FEATURE:
<223> OTHER INFORMATION: EMSA oligonucleotide

<400> SEQUENCE: 4
gatcttctag tgatttgcat tcgaca                                       26

<210> SEQ ID NO 5
<211> LENGTH: 20
<212> TYPE: DNA
<213> ORGANISM: Artificial
<220> FEATURE:
<223> OTHER INFORMATION: Mouse A20 for

<400> SEQUENCE: 5
gctcaactgg tgtcgtgaag                                              20

<210> SEQ ID NO 6
<211> LENGTH: 20
<212> TYPE: DNA
<213> ORGANISM: Artificial
<220> FEATURE:
<223> OTHER INFORMATION: Mouse A20 rev

<400> SEQUENCE: 6
atgaggcagt ttccatcacc                                              20

<210> SEQ ID NO 7
<211> LENGTH: 20
<212> TYPE: DNA
<213> ORGANISM: Artificial
<220> FEATURE:
<223> OTHER INFORMATION: Mouse beta-Actin for

<400> SEQUENCE: 7
cctctatgcc aacacagtgc                                              20

<210> SEQ ID NO 8
<211> LENGTH: 20
<212> TYPE: DNA
<213> ORGANISM: Artificial
<220> FEATURE:
<223> OTHER INFORMATION: Mouse beta-Actin rev
```

```
<400> SEQUENCE: 8
gtactcctgc ttgctgatcc                                                    20

<210> SEQ ID NO 9
<211> LENGTH: 20
<212> TYPE: DNA
<213> ORGANISM: Artificial
<220> FEATURE:
<223> OTHER INFORMATION: Mouse ICAM-1 for

<400> SEQUENCE: 9
cgctcagaag aaccaccttc                                                    20

<210> SEQ ID NO 10
<211> LENGTH: 21
<212> TYPE: DNA
<213> ORGANISM: Artificial
<220> FEATURE:
<223> OTHER INFORMATION: Mouse ICAM-1 rev

<400> SEQUENCE: 10
ggagacgcag aggaccttaa c                                                  21

<210> SEQ ID NO 11
<211> LENGTH: 20
<212> TYPE: DNA
<213> ORGANISM: Artificial
<220> FEATURE:
<223> OTHER INFORMATION: Mouse IL-1beta for

<400> SEQUENCE: 11
tcagcacctc acaagcagag                                                    20

<210> SEQ ID NO 12
<211> LENGTH: 22
<212> TYPE: DNA
<213> ORGANISM: Artificial
<220> FEATURE:
<223> OTHER INFORMATION: Mouse IL-1beta rev

<400> SEQUENCE: 12
gcccatactt taggaagaca cg                                                 22

<210> SEQ ID NO 13
<211> LENGTH: 21
<212> TYPE: DNA
<213> ORGANISM: Artificial
<220> FEATURE:
<223> OTHER INFORMATION: Mouse IL-2 for

<400> SEQUENCE: 13
gagtgccaat tcgatgatga g                                                  21

<210> SEQ ID NO 14
<211> LENGTH: 20
<212> TYPE: DNA
<213> ORGANISM: Artificial
<220> FEATURE:
<223> OTHER INFORMATION: Mouse IL-2 rev

<400> SEQUENCE: 14
agggcttgtt gagatgatgc                                                    20

<210> SEQ ID NO 15
<211> LENGTH: 20
```

```
<212> TYPE: DNA
<213> ORGANISM: Artificial
<220> FEATURE:
<223> OTHER INFORMATION: Mouse VCAM for

<400> SEQUENCE: 15
cccctcattc cttaccaccc                                               20

<210> SEQ ID NO 16
<211> LENGTH: 21
<212> TYPE: DNA
<213> ORGANISM: Artificial
<220> FEATURE:
<223> OTHER INFORMATION: Mouse VCAM rev

<400> SEQUENCE: 16
agttggggat tcggttgttc t                                             21

<210> SEQ ID NO 17
<211> LENGTH: 24
<212> TYPE: DNA
<213> ORGANISM: Artificial
<220> FEATURE:
<223> OTHER INFORMATION: Human IL-2 for

<400> SEQUENCE: 17
cacagctaca actggagcat ttac                                          24

<210> SEQ ID NO 18
<211> LENGTH: 21
<212> TYPE: DNA
<213> ORGANISM: Artificial
<220> FEATURE:
<223> OTHER INFORMATION: Human IL-2 rev

<400> SEQUENCE: 18
tgctgattaa gtccctgggt c                                             21

<210> SEQ ID NO 19
<211> LENGTH: 21
<212> TYPE: DNA
<213> ORGANISM: Artificial
<220> FEATURE:
<223> OTHER INFORMATION: Human TNFalpha for

<400> SEQUENCE: 19
cccagggacc tctctctaat c                                             21

<210> SEQ ID NO 20
<211> LENGTH: 20
<212> TYPE: DNA
<213> ORGANISM: Artificial
<220> FEATURE:
<223> OTHER INFORMATION: Human TNFalpha rev

<400> SEQUENCE: 20
gctacaggct tgtcactcgg                                               20

<210> SEQ ID NO 21
<211> LENGTH: 18
<212> TYPE: DNA
<213> ORGANISM: Artificial
<220> FEATURE:
<223> OTHER INFORMATION: Human RNA Polymerase II for

<400> SEQUENCE: 21
```
gcaccacgtc caatgaca                                                    18

<210> SEQ ID NO 22
<211> LENGTH: 18
<212> TYPE: DNA
<213> ORGANISM: Artificial
<220> FEATURE:
<223> OTHER INFORMATION: Human RNA Polymerase II rev

<400> SEQUENCE: 22
gtgcggctgc ttccataa                                                    18

<210> SEQ ID NO 23
<211> LENGTH: 118
<212> TYPE: PRT
<213> ORGANISM: Artificial
<220> FEATURE:
<223> OTHER INFORMATION: TRAF6-His-protein

<400> SEQUENCE: 23

Met Glu Glu Ile Gln Gly Tyr Asp Val Glu Phe Asp Pro Pro Leu Glu
1               5                   10                  15

Ser Lys Tyr Glu Cys Pro Ile Cys Leu Met Ala Leu Arg Glu Ala Val
            20                  25                  30

Gln Thr Pro Cys Gly His Arg Phe Cys Lys Ala Cys Ile Ile Lys Ser
        35                  40                  45

Ile Arg Asp Ala Gly His Lys Cys Pro Val Asp Asn Glu Ile Leu Leu
    50                  55                  60

Glu Asn Gln Leu Phe Pro Asp Asn Phe Ala Lys Arg Glu Ile Leu Ser
65                  70                  75                  80

Leu Met Val Lys Cys Pro Asn Glu Gly Cys Leu His Lys Met Glu Leu
                85                  90                  95

Arg His Leu Glu Asp His Gln Ala His Cys Glu Phe Ala Leu Gly Ala
            100                 105                 110

His His His His His His
        115

<210> SEQ ID NO 24
<211> LENGTH: 118
<212> TYPE: PRT
<213> ORGANISM: Artificial
<220> FEATURE:
<223> OTHER INFORMATION: C70A mutant according to Figure 22

<400> SEQUENCE: 24

Met Glu Glu Ile Gln Gly Tyr Asp Val Glu Phe Asp Pro Pro Leu Glu
1               5                   10                  15

Ser Lys Tyr Glu Ala Pro Ile Cys Leu Met Ala Leu Arg Glu Ala Val
            20                  25                  30

Gln Thr Pro Cys Gly His Arg Phe Cys Lys Ala Cys Ile Ile Lys Ser
        35                  40                  45

Ile Arg Asp Ala Gly His Lys Cys Pro Val Asp Asn Glu Ile Leu Leu
    50                  55                  60

Glu Asn Gln Leu Phe Pro Asp Asn Phe Ala Lys Arg Glu Ile Leu Ser
65                  70                  75                  80

Leu Met Val Lys Cys Pro Asn Glu Gly Cys Leu His Lys Met Glu Leu
                85                  90                  95

Arg His Leu Glu Asp His Gln Ala His Cys Glu Phe Ala Leu Gly Ala
            100                 105                 110

```
His His His His His His
            115

<210> SEQ ID NO 25
<211> LENGTH: 150
<212> TYPE: PRT
<213> ORGANISM: Homo sapiens

<400> SEQUENCE: 25

Gly Leu Pro Arg Arg Ile Ile Lys Glu Thr Gln Arg Leu Leu Ala Glu
1               5                   10                  15

Pro Val Pro Gly Ile Lys Ala Glu Pro Asp Glu Ser Asn Ala Arg Tyr
            20                  25                  30

Phe His Val Val Ile Ala Gly Pro Gln Asp Ser Pro Phe Glu Gly Gly
        35                  40                  45

Thr Phe Lys Leu Glu Leu Phe Leu Pro Glu Glu Tyr Pro Met Ala Ala
    50                  55                  60

Pro Lys Val Arg Phe Met Thr Lys Ile Tyr His Pro Asn Val Asp Lys
65                  70                  75                  80

Leu Gly Arg Ile Cys Leu Asp Ile Leu Lys Asp Lys Trp Ser Pro Ala
                85                  90                  95

Leu Gln Ile Arg Thr Val Leu Leu Ser Ile Gln Ala Leu Leu Ser Ala
            100                 105                 110

Pro Asn Pro Asp Asp Pro Leu Ala Asn Asp Val Ala Glu Gln Trp Lys
        115                 120                 125

Thr Asn Glu Ala Gln Ala Ile Glu Thr Ala Arg Ala Trp Thr Arg Leu
    130                 135                 140

Tyr Ala Met Asn Asn Ile
145                 150

<210> SEQ ID NO 26
<211> LENGTH: 183
<212> TYPE: PRT
<213> ORGANISM: Homo sapiens

<400> SEQUENCE: 26

Met Ala Ser Met Thr Gly Gly Gln Gln Met Gly Arg Gly Ser Pro Gly
1               5                   10                  15

Glu Val Gln Ala Ser Tyr Leu Lys Ser Gln Ser Lys Leu Ser Asp Glu
            20                  25                  30

Gly Arg Leu Glu Pro Arg Lys Phe His Cys Lys Gly Val Lys Val Pro
        35                  40                  45

Arg Asn Phe Arg Leu Leu Glu Glu Leu Glu Glu Gly Gln Lys Gly Val
    50                  55                  60

Gly Asp Gly Thr Val Ser Trp Gly Leu Glu Asp Asp Glu Asp Met Thr
65                  70                  75                  80

Leu Thr Arg Trp Thr Gly Met Ile Ile Gly Pro Pro Arg Thr Ile Tyr
                85                  90                  95

Glu Asn Arg Ile Tyr Ser Leu Lys Ile Glu Cys Gly Pro Lys Tyr Pro
            100                 105                 110

Glu Ala Pro Pro Phe Val Arg Phe Val Thr Lys Ile Asn Met Asn Gly
        115                 120                 125

Val Asn Ser Ser Asn Gly Val Val Asp Pro Arg Ala Ile Ser Val Leu
    130                 135                 140

Ala Lys Trp Gln Asn Ser Tyr Ser Ile Lys Val Val Leu Gln Glu Leu
145                 150                 155                 160
```

```
Arg Arg Leu Met Met Ser Lys Glu Asn Met Lys Leu Pro Gln Pro Pro
                165                 170                 175

Glu Gly Gln Cys Tyr Ser Asn
                180

<210> SEQ ID NO 27
<211> LENGTH: 305
<212> TYPE: PRT
<213> ORGANISM: Homo sapiens

<400> SEQUENCE: 27

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
        210                 215                 220

Gly Ser Pro Glu Phe Met Gln Ile Phe Val Lys Thr Leu Thr Gly Lys
225                 230                 235                 240

Thr Ile Thr Leu Glu Val Glu Pro Ser Asp Thr Ile Glu Asn Val Lys
                245                 250                 255

Ala Lys Ile Gln Asp Lys Glu Gly Ile Pro Pro Asp Gln Gln Arg Leu
                260                 265                 270

Ile Phe Ala Gly Lys Gln Leu Glu Asp Gly Arg Thr Leu Ser Asp Tyr
            275                 280                 285

Asn Ile Gln Lys Glu Ser Thr Leu His Leu Val Leu Arg Leu Arg Gly
        290                 295                 300

Gly
305

<210> SEQ ID NO 28
<211> LENGTH: 124
<212> TYPE: PRT
<213> ORGANISM: Homo sapiens
```

<400> SEQUENCE: 28

```
Met Glu Glu Ile Gln Gly Tyr Asp Val Glu Phe Asp Pro Pro Leu Glu
1               5                   10                  15

Ser Lys Tyr Glu Cys Pro Ile Cys Leu Met Ala Leu Arg Glu Ala Val
            20                  25                  30

Gln Thr Pro Cys Gly His Arg Phe Cys Lys Ala Cys Ile Ile Lys Ser
        35                  40                  45

Ile Arg Asp Ala Gly His Lys Cys Pro Val Asp Asn Glu Ile Leu Leu
    50                  55                  60

Glu Asn Gln Leu Phe Pro Asp Asn Phe Ala Lys Arg Glu Ile Leu Ser
65                  70                  75                  80

Leu Met Val Lys Cys Pro Asn Glu Gly Cys Leu His Lys Met Glu Leu
                85                  90                  95

Arg His Leu Glu Asp His Gln Ala His Cys Glu Phe Ala Leu Asp His
            100                 105                 110

Gly Leu Ser Ala Trp Ser His Pro Gln Phe Glu Lys
        115                 120
```

<210> SEQ ID NO 29
<211> LENGTH: 124
<212> TYPE: PRT
<213> ORGANISM: Artificial
<220> FEATURE:
<223> OTHER INFORMATION: Ubc13 binding mutant (TRAF6 D57K, sequence D57K mutant)

<400> SEQUENCE: 29

```
Met Glu Glu Ile Gln Gly Tyr Lys Val Glu Phe Asp Pro Pro Leu Glu
1               5                   10                  15

Ser Lys Tyr Glu Cys Pro Ile Cys Leu Met Ala Leu Arg Glu Ala Val
            20                  25                  30

Gln Thr Pro Cys Gly His Arg Phe Cys Lys Ala Cys Ile Ile Lys Ser
        35                  40                  45

Ile Arg Asp Ala Gly His Lys Cys Pro Val Asp Asn Glu Ile Leu Leu
    50                  55                  60

Glu Asn Gln Leu Phe Pro Asp Asn Phe Ala Lys Arg Glu Ile Leu Ser
65                  70                  75                  80

Leu Met Val Lys Cys Pro Asn Glu Gly Cys Leu His Lys Met Glu Leu
                85                  90                  95

Arg His Leu Glu Asp His Gln Ala His Cys Glu Phe Ala Leu Asp His
            100                 105                 110

Gly Leu Ser Ala Trp Ser His Pro Gln Phe Glu Lys
        115                 120
```

<210> SEQ ID NO 30
<211> LENGTH: 112
<212> TYPE: PRT
<213> ORGANISM: Homo sapiens

<400> SEQUENCE: 30

```
Gly Ser Met Glu Glu Ile Gln Gly Tyr Asp Val Glu Phe Asp Pro Pro
1               5                   10                  15

Leu Glu Ser Lys Tyr Glu Cys Pro Ile Cys Leu Met Ala Leu Arg Glu
            20                  25                  30

Ala Val Gln Thr Pro Cys Gly His Arg Phe Cys Lys Ala Cys Ile Ile
        35                  40                  45
```

```
Lys Ser Ile Arg Asp Ala Gly His Lys Cys Pro Val Asp Asn Glu Ile
    50                  55                  60

Leu Leu Glu Asn Gln Leu Phe Pro Asp Asn Phe Ala Lys Arg Glu Ile
65                  70                  75                  80

Leu Ser Leu Met Val Lys Cys Pro Asn Glu Gly Cys Leu His Lys Met
                85                  90                  95

Glu Leu Arg His Leu Glu Asp His Gln Ala His Cys Glu Phe Ala Leu
                100                 105                 110

<210> SEQ ID NO 31
<211> LENGTH: 174
<212> TYPE: PRT
<213> ORGANISM: Artificial
<220> FEATURE:
<223> OTHER INFORMATION: human Ubc13 + His Tag

<400> SEQUENCE: 31

Gly Ser Pro Glu Phe Ala Gly Leu Pro Arg Arg Ile Ile Lys Glu Thr
1               5                   10                  15

Gln Arg Leu Leu Ala Glu Pro Val Pro Gly Ile Lys Ala Glu Pro Asp
                20                  25                  30

Glu Ser Asn Ala Arg Tyr Phe His Val Val Ile Ala Gly Pro Gln Asp
                35                  40                  45

Ser Pro Phe Glu Gly Gly Thr Phe Lys Leu Glu Leu Phe Leu Pro Glu
    50                  55                  60

Glu Tyr Pro Met Ala Ala Pro Lys Val Arg Phe Met Thr Lys Ile Tyr
65                  70                  75                  80

His Pro Asn Val Asp Lys Leu Gly Arg Ile Cys Leu Asp Ile Leu Lys
                85                  90                  95

Asp Lys Trp Ser Pro Ala Leu Gln Ile Arg Thr Val Leu Leu Ser Ile
                100                 105                 110

Gln Ala Leu Leu Ser Ala Pro Asn Pro Asp Asp Pro Leu Ala Asn Asp
                115                 120                 125

Val Ala Glu Gln Trp Lys Thr Asn Glu Ala Gln Ala Ile Glu Thr Ala
                130                 135                 140

Arg Ala Trp Thr Arg Leu Tyr Ala Met Asn Asn Ile Gly Ala Asp Tyr
145                 150                 155                 160

Lys Asp Asp Asp Asp Lys Gly Ala His His His His His
                165                 170

<210> SEQ ID NO 32
<211> LENGTH: 496
<212> TYPE: PRT
<213> ORGANISM: Artificial
<220> FEATURE:
<223> OTHER INFORMATION: GST-OTUB1

<400> SEQUENCE: 32

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
                35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Ala Ala Glu Glu Pro Gln Gln Lys Gln Glu Pro Leu Gly
225                 230                 235                 240

Ser Asp Ser Glu Gly Val Asn Cys Leu Ala Tyr Asp Glu Ala Ile Met
                245                 250                 255

Ala Gln Gln Asp Arg Ile Gln Gln Glu Ile Ala Val Gln Asn Pro Leu
            260                 265                 270

Val Ser Glu Arg Leu Glu Leu Ser Val Leu Tyr Lys Glu Tyr Ala Glu
        275                 280                 285

Asp Asp Asn Ile Tyr Gln Gln Lys Ile Lys Asp Leu His Lys Lys Tyr
    290                 295                 300

Ser Tyr Ile Arg Lys Thr Arg Pro Asp Gly Asn Cys Phe Tyr Arg Ala
305                 310                 315                 320

Phe Gly Phe Ser His Leu Glu Ala Leu Leu Asp Asp Ser Lys Glu Leu
                325                 330                 335

Gln Arg Phe Lys Ala Val Ser Ala Lys Ser Lys Glu Asp Leu Val Ser
            340                 345                 350

Gln Gly Phe Thr Glu Phe Thr Ile Glu Asp Phe His Asn Thr Phe Met
        355                 360                 365

Asp Leu Ile Glu Gln Val Glu Lys Gln Thr Ser Val Ala Asp Leu Leu
    370                 375                 380

Ala Ser Phe Asn Asp Gln Ser Thr Ser Asp Tyr Leu Val Val Tyr Leu
385                 390                 395                 400

Arg Leu Leu Thr Ser Gly Tyr Leu Gln Arg Glu Ser Lys Phe Phe Glu
                405                 410                 415

His Phe Ile Glu Gly Gly Arg Thr Val Lys Glu Phe Cys Gln Gln Glu
            420                 425                 430

Val Glu Pro Met Cys Lys Glu Ser Asp His Ile His Ile Ala Leu
        435                 440                 445

Ala Gln Ala Leu Ser Val Ser Ile Gln Val Glu Tyr Met Asp Arg Gly
450                 455                 460

Glu Gly Gly Thr Thr Asn Pro His Ile Phe Pro Glu Gly Ser Glu Pro
465                 470                 475                 480

Lys Val Tyr Leu Leu Tyr Arg Pro Gly His Tyr Asp Ile Leu Tyr Lys
                485                 490                 495
```

```
<210> SEQ ID NO 33
<211> LENGTH: 380
<212> TYPE: PRT
<213> ORGANISM: Artificial
<220> FEATURE:
<223> OTHER INFORMATION: GST-Ubc13

<400> SEQUENCE: 33

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Ala Gly Leu Pro Arg Arg Ile Ile Lys Glu Thr
225                 230                 235                 240

Gln Arg Leu Leu Ala Glu Pro Val Pro Gly Ile Lys Ala Glu Pro Asp
                245                 250                 255

Glu Ser Asn Ala Arg Tyr Phe His Val Val Ile Ala Gly Pro Gln Asp
            260                 265                 270

Ser Pro Phe Glu Gly Gly Thr Phe Lys Leu Glu Leu Phe Leu Pro Glu
        275                 280                 285

Glu Tyr Pro Met Ala Ala Pro Lys Val Arg Phe Met Thr Lys Ile Tyr
    290                 295                 300

His Pro Asn Val Asp Lys Leu Gly Arg Ile Cys Leu Asp Ile Leu Lys
305                 310                 315                 320

Asp Lys Trp Ser Pro Ala Leu Gln Ile Arg Thr Val Leu Leu Ser Ile
                325                 330                 335
```

```
Gln Ala Leu Leu Ser Ala Pro Asn Pro Asp Asp Pro Leu Ala Asn Asp
            340                 345                 350

Val Ala Glu Gln Trp Lys Thr Asn Glu Ala Gln Ala Ile Glu Thr Ala
            355                 360                 365

Arg Ala Trp Thr Arg Leu Tyr Ala Met Asn Asn Ile
            370                 375                 380

<210> SEQ ID NO 34
<211> LENGTH: 181
<212> TYPE: PRT
<213> ORGANISM: Artificial
<220> FEATURE:
<223> OTHER INFORMATION: His-tagged Uev1a

<400> SEQUENCE: 34

Ser Pro Gly Glu Val Gln Ala Ser Tyr Leu Lys Ser Gln Ser Lys Leu
1               5                   10                  15

Ser Asp Glu Gly Arg Leu Glu Pro Arg Lys Phe His Cys Lys Gly Val
            20                  25                  30

Lys Val Pro Arg Asn Phe Arg Leu Leu Glu Glu Leu Glu Glu Gly Gln
            35                  40                  45

Lys Gly Val Gly Asp Gly Thr Val Ser Trp Gly Leu Glu Asp Asp Glu
        50                  55                  60

Asp Met Thr Leu Thr Arg Trp Thr Gly Met Ile Ile Gly Pro Pro Arg
65                  70                  75                  80

Thr Ile Tyr Glu Asn Arg Ile Tyr Ser Leu Lys Ile Glu Cys Gly Pro
                85                  90                  95

Lys Tyr Pro Glu Ala Pro Pro Phe Val Arg Phe Val Thr Lys Ile Asn
            100                 105                 110

Met Asn Gly Val Asn Ser Ser Asn Gly Val Val Asp Pro Arg Ala Ile
            115                 120                 125

Ser Val Leu Ala Lys Trp Gln Asn Ser Tyr Ser Ile Lys Val Val Leu
        130                 135                 140

Gln Glu Leu Arg Arg Leu Met Met Ser Lys Glu Asn Met Lys Leu Pro
145                 150                 155                 160

Gln Pro Pro Glu Gly Gln Cys Tyr Ser Asn Ala Ala Leu Glu His
                165                 170                 175

His His His His
        180
```

TRAF 6 INHIBITORS

SEQUENCE LISTING

The instant application contains a Sequence Listing which has been submitted electronically in ASCII format and is hereby incorporated by reference in its entirety. Said ASCII copy, created on Mar. 22, 2018, is named 298-011_ST25.txt and is 26,380 bytes in size.

BACKGROUND

The TRAF protein family comprises seven members, i.e. TRAF1, TRAF2, TRAF3, TRAF4, TRAF5, TRAF6 and TRAF7, which largely display homologies in their domain structures (Xie, P., *TRAF molecules in cell signaling and in human diseases*. J Mol Signal, 2013. 8(1): p. 7 and Zotti, T., P. Vito, and R. Stilo, *The seventh ring: exploring TRAF7 functions*. J Cell Physiol, 2012. 227(3): p. 1280-4). Studies of the past years have unraveled a large number of signaling receptor families that embrace TRAF proteins for signal progression. These pathways include Toll-like receptors (TLRs), IL-1 receptor family, T-cell receptor, IL-17 receptors, TNF receptors and others. TRAF-dependent signaling pathways mainly facilitate activation of (i) the transcription factor NF-κB and (ii) mitogen-activated protein kinases (MAPKs), thereby contributing to the control of various cellular processes such as survival, proliferation, differentiation, activation, cytokine production and autophagy (Xie, P., *TRAF molecules in cell signaling and in human diseases*. J Mol Signal, 2013. 8(1): p. 7). Hence, distinct alterations in TRAF family members have been shown to contribute to the pathogenesis of individual human diseases including autoimmunity, immunodeficiency and cancer (Hildebrand, J. M., Z. Yi, C. M. Buchta, et al., *Roles of tumor necrosis factor receptor associated factor 3 (TRAF3) and TRAF5 in immune cell functions*. Immunol Rev, 2011. 244(1): p. 55-74; Namjou, B., C. B. Choi, I. T. Harley, et al., *Evaluation of TRAF6 in a large multiancestral lupus cohort*. Arthritis Rheum, 2012. 64(6): p. 1960-9 and Netea, M. G., C. Wijmenga, and L. A. O'Neill, *Genetic variation in Toll-like receptors and disease susceptibility*. Nat Immunol, 2012. 13(6): p. 535-42).

The TRAF6 protein functions both as an adaptor protein as well as an E3 ubiquitin ligase to activate the transcription factor NF-κB. In particular, TRAF6 exhibits a RING domain and four Zincfinger domains at its N-terminus, whereas the C-terminal TRAF domain contains a Coiled-Coil and a conserved MATH domain (Yin, Q., S. C. Lin, B. Lamothe, et al., *E2 interaction and dimerization in the crystal structure of TRAF6*. Nat Struct Mol Biol, 2009. 16(6): p. 658-66). TRAF6 directly interacts with the heterodimeric E2 enzyme Ubc13/Uev1a with its N-terminus (RING and Zincfinger1) to attach K63-linked ubiquitin chains to its substrate proteins. This process is critical for progression of signal transduction in several cellular signaling processes like T-cell receptor mediated NF-κB activation (Oeckinghaus, A., E. Wegener, V. Welteke, et al., *Malt1 ubiquitination triggers NF-kappaB signaling upon T-cell activation*. EMBO J, 2007. 26(22): p. 4634-45) or innate immune response including IL-1β and Toll-like receptor signaling (Bhoj, V. G. and Z. J. Chen, *Ubiquitylation in innate and adaptive immunity*. Nature, 2009. 458(7237): p. 430-7). Moreover, TRAF6 is involved in IL-17 receptor signaling as well as in DNA damage response (Xie, P., *TRAF molecules in cell signaling and in human diseases*. J Mol Signal, 2013. 8(1): p. 7 and Walsh, M. C., J. Lee, and Y. Choi, *Tumor necrosis factor receptor-associated factor 6 (TRAF6) regulation of development, function, and homeostasis of the immune system*. Immunol Rev, 2015. 266(1): p. 72-92). Overexpression of TRAF6 as well as enhanced TRAF6 activity have been shown to promote chronic immune stimulation and cytokine secretion, thereby causing a broad variety of disorders including autoimmune diseases, inflammation and cancer. Taken together, targeting TRAF6 activity by disrupting the TRAF6-Ubc13 binding displays a very attractive novel strategy to counteract disease formation.

Previous studies have mainly focused on inhibiting the protein-protein interaction (PPI) between the E3 ligase and its substrate in order to diminish ubiquitination; with p53-Mdm2 being the most prominent example (Vassilev, L. T., B. T. Vu, B. Graves, et al., *In vivo activation of the p53 pathway by small-molecule antagonists of MDM2*. Science, 2004. 303(5659): p. 844-8). International patent application WO 2011/160016 A2 relates to an isolated protein fragment that includes a binding pocket or active site on an E3 ligase that modulates the E2-E3 interface, and to an agent that interacts with such a binding pocket. WO 2011/160016 A2, however, only mentions two agents denoted as CRIN-1 and CRIN-2 for such purpose.

Thus, there is a great need for new, first-in-class inhibitor scaffolds which can inhibit TRAF6, in particular TRAF6 E3 ligase activity by disrupting its interaction to the E2 enzyme Ubc13.

The inventors of the present invention have conducted intensive studies and found surprisingly, that the compounds according to Formula I, Formula II, Formula III, Formula IV, and Formula XX, which are described in more detail below, satisfy this need. Without wishing to be bound by theory, the inventors believe that the compounds according to the present invention target the protein-protein interaction of TRAF6 (E3 ligase)-Ubc13 (E2 enzyme) and thereby interrupt this biological pathway (E2-E3 inhibitors). In particular, it is believed that the compounds counteract the catalytic activity of TRAF6 and thereby leading to reduced NF-κB activation.

The compounds according to the present invention are effective in reducing NF-κB activation in cell lines (see FIG. 4 and FIG. 6) as well as in primary T cells obtained from BALBc mice (see FIG. 8). Further, it was found by the inventors that the compounds according to the present invention ameliorate Rheumatoid Arthritis disease outcome in a CIA mouse model (see FIG. 13), ameliorate Psoriasis disease outcome in an IMQ-induced psoriasis mouse model (see FIG. 12), selectively kill ABC-DLBCL with chronic MYD88 signaling (see FIG. 14), reduce gain of weight in a T2D mouse model and additionally reduce IL-1β expression (see FIG. 11), reduce proliferation of U2OS cells to the same degree as 2Gy irradiation and application of the compounds together with irradiation leads to synergistic effects (see FIG. 15), and the compounds affect immune receptor signaling in primary human peripheral blood mononuclear cells (see FIG. 7). On a molecular basis, without wishing to be bound by theory, it is believed that the compounds of the present application disrupt TRAF6-Ubc13 binding (see Discussion).

Of further interest are assays which allow efficient screening for E3 ligase inhibitors.

Schneider et al., Biochimica et Biophysica Acta (BBA)—Molecular Cell Research 2012, Volume 1823, Issue 11, pages 2038-2045 report an Assay related to E3 ligase, based on an AlphaLisa based approach utilizing Tandem-repeated-Ubiquitin-Binding-Entities (TUBEs). This technology is based on antibody-dependent recognition of the E3 ligase and a GST-tagged TUBE detection of ubiquitin.

The inventors of the present invention found an effective AlphaScreen microtiter-plate-based, screenable ubiquitination assay, which is, compared with conventional ubiquitination assays based on Western Blot analyses, suitable for higher throughput, has improved sensitivity and quantitative output of data sets. Furthermore, the homogeneous assay format requires no washing steps that would complicate the execution of iterative testing of compounds during the lead optimization phase. Another advantage is, that different RING E3 ligases, like TRAF6, cIAP1 and RNF8 can be used. This allows counter-screening of active compounds against other RING E3 ligases to assess their specificity towards TRAF6 over other E3 RING ligases.

SUMMARY

Accordingly, the present invention provides in a first aspect a compound for use in the treatment of cancer, an immune disease, Parkinson's disease, Cardiac Hypertrophy or Type-2 diabetes, said compound having a structure according to Formula I

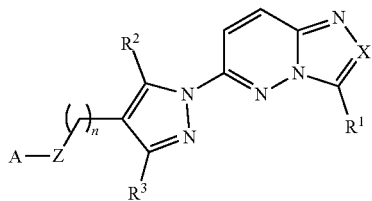

(I)

wherein

X is selected from the group consisting of N and CH;

$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl;

$R^2$ and $R^3$ are independently selected from the group consisting of hydrogen, $(C_1-C_6)$alkyl, $(C_1-C_6)$haloalkyl and $(C_3-C_8)$cycloalkyl;

n is an integer between 0 and 3;

Z is selected from the group consisting of C=O, C=S and $CH_2$;

A is selected from the group consisting of —N($R^4$)($R^5$) and

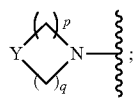

$R^4$ is hydrogen or $(C_1-C_6)$alkyl;

$R^5$ is selected from the group consisting of $(C_6-C_{10})$aryl $(C_1-C_6)$alkyl, $(C_3-C_{10})$heteroaryl$(C_1-C_6)$alkyl, $(C_3-C_{10})$heteroaryl$(C_1-C_6)$heteroalkyl and $(C_6-C_{10})$aryl $(C_1-C_6)$heteroalkyl, which are optionally substituted by one or more identical or different substituents selected from the group consisting of halogen, $(C_1-C_4)$alkyl, $(C_1-C_4)$haloalkyl and —$OR^6$;

$R^6$ is $(C_1-C_4)$alkyl or $(C_1-C_4)$haloalkyl;

Y is selected from the group consisting of N—B, CH—B and O;

B is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl, $(C_1-C_6)$alkyl and N($R^7$) ($R^8$), which are optionally substituted by one or more identical or different substituents selected from the group consisting of halogen, $(C_1-C_4)$alkyl, $(C_1-C_4)$haloalkyl and —$OR^6$;

$R^7$ is hydrogen or $(C_1-C_6)$alkyl;

$R^8$ is selected from the group consisting of $(C_6-C_{10})$aryl, $(C_3-C_{10})$heteroaryl, $(C_6-C_{10})$aryl$(C_1-C_6)$alkyl, $C_3-C_{10})$ heteroaryl$(C_1-C_6)$alkyl and $(C_1-C_6)$alkyl;

p is an integer between 1 and 2;

q is an integer between 1 and 3;

or a pharmaceutically acceptable salt, solvate or hydrate thereof.

In a second aspect, the present invention provides a pharmaceutical composition for use in the treatment of cancer, an immune disease, Parkinson's disease, Cardiac Hypertrophy or Type-2 diabetes, wherein said composition comprises a compound having a structure according to Formula I

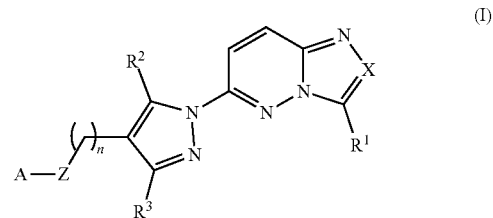

(I)

wherein

X is selected from the group consisting of N and CH;

$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl;

$R^2$ and $R^3$ are independently selected from the group consisting of hydrogen, $(C_1-C_6)$alkyl, $(C_1-C_6)$haloalkyl and $(C_3-C_8)$cycloalkyl;

n is an integer between 0 and 3;

Z is selected from the group consisting of C=O, C=S and $CH_2$;

A is selected from the group consisting of —N($R^4$)($R^5$) and

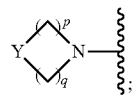

$R^4$ is hydrogen or $(C_1-C_6)$alkyl;

$R^5$ is selected from the group consisting of $(C_6-C_{10})$aryl $(C_1-C_6)$alkyl, $(C_3-C_{10})$heteroaryl$(C_1-C_6)$alkyl, $(C_3-C_{10})$heteroaryl$(C_1-C_6)$heteroalkyl and $(C_6-C_{10})$aryl $(C_1-C_6)$heteroalkyl, which are optionally substituted by one or more identical or different substituents selected from the group consisting of halogen, $(C_1-C_4)$alkyl, $(C_1-C_4)$haloalkyl and —$OR^6$;

$R^6$ is $(C_1-C_4)$alkyl or $(C_1-C_4)$haloalkyl;

Y is selected from the group consisting of N—B, CH—B and O;

B is selected from the group consisting of $(C_6-C_{10})$aryl, $(C_3-C_{10})$heteroaryl, $(C_6-C_{10})$aryl$(C_1-C_6)$alkyl, $(C_3$-

$C_{10}$)heteroaryl($C_1$-$C_6$)alkyl, ($C_1$-$C_6$)alkyl and $N(R^7)$ ($R^8$), which are optionally substituted by one or more identical or different substituents selected from the group consisting of halogen, ($C_1$-$C_4$)alkyl, ($C_1$-$C_4$)haloalkyl and —$OR^6$;

$R^7$ is hydrogen or ($C_1$-$C_6$)alkyl;

$R^8$ is selected from the group consisting of ($C_6$-$C_{10}$)aryl, ($C_3$-$C_{10}$)heteroaryl, ($C_6$-$C_{10}$)aryl($C_1$-$C_6$)alkyl, $C_3$-$C_{10}$) heteroaryl($C_1$-$C_6$)alkyl and ($C_1$-$C_6$)alkyl;

p is an integer between 1 and 2;

q is an integer between 1 and 3;

or a pharmaceutically acceptable salt, solvate or hydrate thereof.

In a third aspect, the present invention provides a compound for use in medicine, said compound having a structure according to Formula I

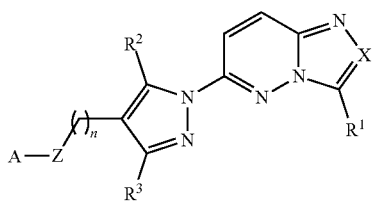

(I)

wherein

X is selected from the group consisting of N and CH;

$R^1$ is selected from the group consisting of hydrogen, ($C_1$-$C_6$)alkyl, ($C_1$-$C_6$)haloalkyl, ($C_3$-$C_8$)cycloalkyl, ($C_6$-$C_{10}$)aryl, ($C_6$-$C_{10}$)aryl($C_1$-$C_6$)alkyl, ($C_3$-$C_{10}$)heteroaryl and ($C_3$-$C_{10}$)heteroaryl($C_1$-$C_6$)alkyl;

$R^2$ and $R^3$ are independently selected from the group consisting of hydrogen, ($C_1$-$C_6$)alkyl, ($C_1$-$C_6$)haloalkyl and ($C_3$-$C_8$)cycloalkyl;

n is an integer between 0 and 3;

Z is selected from the group consisting of C=O, C=S and $CH_2$;

A is selected from the group consisting of —$N(R^4)(R^5)$ and

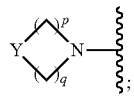

$R^4$ is hydrogen or ($C_1$-$C_6$)alkyl;

$R^5$ is selected from the group consisting of ($C_6$-$C_{10}$)aryl ($C_1$-$C_6$)alkyl, ($C_3$-$C_{10}$)heteroaryl($C_1$-$C_6$)alkyl, ($C_3$-$C_{10}$)heteroaryl($C_1$-$C_6$)heteroalkyl and ($C_6$-$C_{10}$)aryl ($C_1$-$C_6$)heteroalkyl, which are optionally substituted by one or more identical or different substituents selected from the group consisting of halogen, ($C_1$-$C_4$)alkyl, ($C_1$-$C_4$)haloalkyl and —$OR^6$;

$R^6$ is ($C_1$-$C_4$)alkyl or ($C_1$-$C_4$)haloalkyl;

Y is selected from the group consisting of N—B, CH—B and O;

B is selected from the group consisting of ($C_6$-$C_{10}$)aryl, ($C_3$-$C_{10}$)heteroaryl, ($C_6$-$C_{10}$)aryl($C_1$-$C_6$)alkyl, ($C_3$-$C_{10}$)heteroaryl($C_1$-$C_6$)alkyl, ($C_1$-$C_6$)alkyl and $N(R^7)$ ($R^8$), which are optionally substituted by one or more identical or different substituents selected from the group consisting of halogen, ($C_1$-$C_4$)alkyl, ($C_1$-$C_4$)haloalkyl and —$OR^6$;

$R^7$ is hydrogen or ($C_1$-$C_6$)alkyl;

$R^8$ is selected from the group consisting of ($C_6$-$C_{10}$)aryl, ($C_3$-$C_{10}$)heteroaryl, ($C_6$-$C_{10}$)aryl($C_1$-$C_6$)alkyl, $C_3$-$C_{10}$) heteroaryl($C_1$-$C_6$)alkyl and ($C_1$-$C_6$)alkyl;

p is an integer between 1 and 2;

q is an integer between 1 and 3;

or a pharmaceutically acceptable salt, solvate or hydrate thereof.

In some embodiments said compound having a structure according to Formula I is a compound having a structure according to Formula (II)

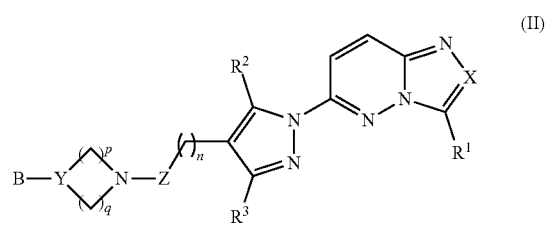

(II)

wherein

X is selected from the group consisting of N and CH;

$R^1$ is selected from the group consisting of hydrogen, ($C_1$-$C_6$)alkyl, ($C_1$-$C_6$)haloalkyl, ($C_3$-$C_8$)cycloalkyl, ($C_6$-$C_{10}$)aryl, ($C_6$-$C_{10}$)aryl($C_1$-$C_6$)alkyl, ($C_3$-$C_{10}$)heteroaryl and ($C_3$-$C_{10}$)heteroaryl($C_1$-$C_6$)alkyl, preferably hydrogen, ($C_1$-$C_6$)alkyl, ($C_3$-$C_8$)cycloalkyl, ($C_6$-$C_{10}$) aryl and ($C_6$-$C_{10}$)aryl($C_1$-$C_6$)alkyl;

$R^2$ and $R^3$ are independently selected from the group consisting of hydrogen, ($C_1$-$C_6$)alkyl, ($C_1$-$C_6$)haloalkyl and ($C_3$-$C_8$)cycloalkyl, preferably ($C_1$-$C_6$)alkyl and ($C_1$-$C_6$)haloalkyl;

n is an integer between 0 and 3, preferably 1-3, more preferably 1-2, even more preferably 2;

Z is selected from the group consisting of C=O, C=S and $CH_2$, preferably C=O;

Y is N or CH;

B is selected from the group consisting of ($C_6$-$C_{10}$)aryl, ($C_3$-$C_{10}$)heteroaryl, ($C_6$-$C_{10}$)aryl($C_1$-$C_6$)alkyl, ($C_3$-$C_{10}$)heteroaryl($C_1$-$C_6$)alkyl, ($C_1$-$C_6$)alkyl and $N(R^7)$ ($R^8$), which are optionally substituted by one or more identical or different substituents selected from the group consisting of halogen, ($C_1$-$C_4$)alkyl, ($C_1$-$C_4$) haloalkyl and —$OR^6$, preferably halogen and —$OR^6$;

$R^7$ is hydrogen or ($C_1$-$C_6$)alkyl, preferably hydrogen;

$R^8$ is selected from the group consisting of ($C_6$-$C_{10}$)aryl, ($C_3$-$C_{10}$)heteroaryl, ($C_6$-$C_{10}$)aryl($C_1$-$C_6$)alkyl, ($C_3$-$C_{10}$)heteroaryl($C_1$-$C_6$)alkyl and ($C_1$-$C_6$)alkyl, preferably ($C_6$-$C_{10}$)aryl($C_1$-$C_6$)alkyl, ($C_3$-$C_{10}$)heteroaryl($C_1$-$C_6$)alkyl, more preferably ($C_6$-$C_{10}$)aryl($C_1$-$C_6$)alkyl;

p is an integer between 1 and 2;

q is an integer between 1 and 3;

or a pharmaceutically acceptable salt, solvate or hydrate thereof.

In some embodiments said compound having a structure according to Formula (I) or Formula (II) is characterized in that X is N.

In some embodiments said compound having a structure according to Formula (I) or Formula (II) is characterized in that Z is C=O.

In some embodiments said compound having a structure according to Formula (I) or Formula (II) is characterized in that, $R^1$ is selected from the group consisting of hydrogen, $(C_1-C_4)$alkyl, $(C_3-C_6)$cycloalkyl, $(C_6-C_{10})$aryl and $(C_6-C_{10})$aryl$(C_1-C_6)$alkyl;

$R^2$ and $R^3$ are independently selected from the group consisting of $(C_1-C_4)$alkyl and $(C_1-C_4)$haloalkyl;

n is an integer between 1 and 3, preferably 1-2, more preferably 2; and $R^5$ is selected from the group consisting of $(C_6-C_{10})$aryl$(C_1-C_6)$alkyl, $(C_3-C_{10})$heteroaryl$(C_1-C_6)$alkyl and $(C_3-C_{10})$heteroaryl$(C_1-C_6)$heteroalkyl, which are optionally substituted by one or more identical or different substituents selected from the group consisting of halogen, $(C_1-C_4)$alkyl, $(C_1-C_4)$haloalkyl and —$OR^6$, preferably halogen.

In some embodiments said compound having a structure according to Formula (I) is a compound having a structure according to Formula (III)

(III)

wherein n is an integer between 1 and 3, preferably 1-2, more preferably 2;

Y is N or CH;

B is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl and $(C_1-C_6)$alkyl, which are optionally substituted by one or more identical or different substituents selected from the group consisting of halogen, $(C_1-C_4)$alkyl, $(C_1-C_4)$haloalkyl and —$OR^6$, preferably halogen and —$OR^6$;

q is an integer between 1-3, preferably 1-2, more preferably 2;

or a pharmaceutically acceptable salt, solvate or hydrate thereof.

In some embodiments said compound having a structure according to Formula (I) is a compound having a structure according to Formula (IV)

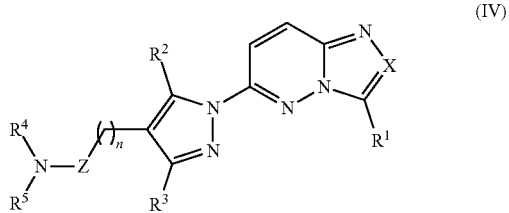

(IV)

wherein

X is selected from the group consisting of N and CH;

$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl, preferably hydrogen and $(C_1-C_6)$alkyl, more preferably $(C_1-C_6)$alkyl;

$R^2$ and $R^3$ are independently selected from the group consisting of hydrogen, $(C_1-C_6)$alkyl, $(C_1-C_6)$haloalkyl and $(C_3-C_8)$cycloalkyl, preferably $(C_1-C_6)$alkyl and $(C_1-C_6)$haloalkyl, more preferably $(C_1-C_6)$alkyl;

n is an integer between 0 and 3, preferably 1-3, more preferably 1-2, even more preferably 2;

Z is selected from the group consisting of C=O, C=S and $CH_2$, preferably C=O;

$R^4$ is hydrogen or $(C_1-C_6)$alkyl, preferably hydrogen;

$R^5$ is selected from the group consisting of $(C_1-C_{10})$aryl$(C_1-C_6)$alkyl, $(C_3-C_{10})$heteroaryl$(C_1-C_6)$alkyl, $(C_3-C_{10})$heteroaryl$(C_1-C_6)$heteroalkyl and $(C_6-C_{10})$aryl$(C_1-C_6)$heteroalkyl, which are optionally substituted by one or more identical or different substituents selected from the group consisting of halogen, $(C_1-C_4)$alkyl, $(C_1-C_4)$haloalkyl and —$OR^6$, preferably halogen; $R^6$ is $(C_1-C_4)$alkyl or $(C_1-C_4)$haloalkyl;

or a pharmaceutically acceptable salt, solvate or hydrate thereof.

In some embodiments said cancer is selected from the group consisting of lymphoma such as diffuse large B-cell lymphoma (DLBCL) and MALT lymphoma, multiple myeloma (MM), lung cancer, lung adenocarcinoma, colon cancer, prostate cancer, breast cancer, osteosarcoma, pancreatic cancer and esophageal squamous cell carcinoma (ESCC).

In some embodiments said immune disease is an autoimmune disease, preferably an autoimmune disease selected from the group consisting of psoriasis, rheumatoid arthritis, celiac disease, inflammatory bowel disease such as Crohn's disease and ulcerative colitis, multiple sclerosis and diabetes mellitus type 1.

In a fourth aspect, the present invention provides a compound having a structure according to Formula I,

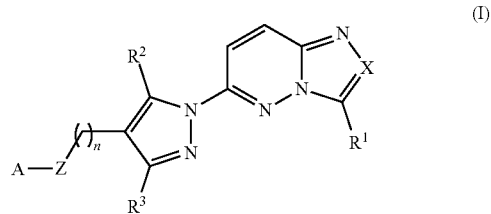

(I)

wherein

X is selected from the group consisting of N and CH;

$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl;

$R^2$ and $R^3$ are independently selected from the group consisting of hydrogen, $(C_1-C_6)$alkyl, $(C_1-C_6)$haloalkyl and $(C_3-C_8)$cycloalkyl;

n is an integer between 0 and 3;

Z is selected from the group consisting of C=O, C=S and $CH_2$;

A is selected from the group consisting of

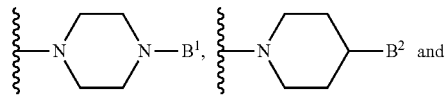 and

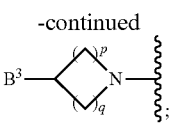

B¹ is $(C_6-C_{10})$aryl$(C_1-C_6)$alkyl or $(C_3-C_{10})$heteroaryl$(C_1-C_6)$alkyl, which are optionally substituted by one or more identical or different substituents selected from the group consisting of halogen, $(C_1-C_4)$alkyl, $(C_1-C_4)$haloalkyl and —OR⁶;

B² is $(C_6-C_{10})$aryl$(C_1-C_6)$alkyl substituted by one or more identical or different substituents selected from the group consisting of halogen, $(C_1-C_4)$alkyl, $(C_1-C_4)$haloalkyl and —OR⁶, or B² is $C_3-C_{10}$)heteroaryl$(C_1-C_6)$alkyl, which is optionally substituted by one or more identical or different substituents selected from the group consisting of halogen, $(C_1-C_4)$alkyl, $(C_1-C_4)$haloalkyl and —OR⁶;

B³ is selected from the group consisting of hydrogen, $(C_6-C_{10})$aryl$(C_1-C_6)$alkyl, $(C_3-C_{10})$heteroaryl$(C_1-C_6)$alkyl, $(C_1-C_6)$alkyl and N(R⁷)(R⁸), which are optionally substituted by one or more identical or different substituents selected from the group consisting of halogen, $(C_1-C_4)$alkyl, $(C_1-C_4)$haloalkyl and —OR⁶;

R⁶ is $(C_1-C_4)$alkyl or $(C_1-C_4)$haloalkyl;

R⁷ is hydrogen or $(C_1-C_6)$alkyl;

R⁸ is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl and $(C_1-C_6)$alkyl;

p is 1 and
q is an integer between 1 and 2, or
p is 2 and
q is 3;
or a pharmaceutically acceptable salt, solvate or hydrate thereof.

In some embodiments said compound is selected from the group consisting of 1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperazin-1-yl)propan-1-one, (R,S)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperazin-1-yl)propan-1-one, 1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, (R)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, (S)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one, 1-(4-benzylpiperidin-1-yl)-3-(3,5-dimethyl-1-(3-phenyl-[1,2,4]triazolo[4,3-b]pyridazin-6-yl)-1H-pyrazol-4-yl)propan-1-one, 3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one, 1-(4-benzylpiperidin-1-yl)-3-(3,5-dimethyl-1-(3-methylimidazo[1,2-b]pyridazin-6-yl)-1H-pyrazol-4-yl)propan-1-one, 1-(4-benzylpiperidin-1-yl)-2-(3,5-dimethyl-1-(3-methyl-[1,2,4]triazolo[4,3-b]pyridazin-6-yl)-1H-pyrazol-4-yl)ethan-1-one, 1-(4-benzylpiperidin-1-yl)-3-(3,5-dimethyl-1-(3-methyl-[1,2,4]triazolo[4,3-b]pyridazin-6-yl)-1H-pyrazol-4-yl)propane-1-thione, 6-(4-(3-(4-benzylpiperidin-1-yl)propyl)-3,5-dimethyl-1H-pyrazol-1-yl)-3-methyl-[1,2,4]triazolo[4,3-b]pyridazine, 1-(azepan-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-morpholinopropan-1-one, N-(3-chlorobenzyl)-3-(3,5-dimethyl-1-(3-methyl-[1,2,4]triazolo[4,3-b]pyridazin-6-yl)-1H-pyrazol-4-yl)-N-methylpropanamide, 3-(3,5-dimethyl-1-(3-methyl-[1,2,4]triazolo[4,3-b]pyridazin-6-yl)-1H-pyrazol-4-yl)-1-(4-(furan-2-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-phenylpropan-2-yl)piperazin-1-yl)propan-1-one, 1-(4-(3,4-dimethoxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(naphthalen-2-ylmethyl)piperazin-1-yl)propan-1-one, 1-(4-(3-chlorobenzyl)piperidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzylazetidin-1-yl)-3-(3,5-dimethyl-1-(3-methyl-[1,2,4]triazolo[4,3-b]pyridazin-6-yl)-1H-pyrazol-4-yl)propan-1-one, 1-(3-(benzylamino)azetidin-1-yl)-3-(3,5-dimethyl-1-(3-methyl-[1,2,4]triazolo[4,3-b]pyridazin-6-yl)-1H-pyrazol-4-yl)propan-1-one, N-benzyl-3,5-dimethyl-1-(3-methyl-[1,2,4]triazolo[4,3-b]pyridazin-6-yl)-1H-pyrazole-4-carboxamide, (3-benzylpyrrolidin-1-yl)(3,5-dimethyl-1-(3-methyl-[1,2,4]triazolo[4,3-b]pyridazin-6-yl)-1H-pyrazol-4-yl)methanone, 1-(3-benzylpyrrolidin-1-yl)-3-(5-isopropyl-3-methyl-1-(3-methyl-[1,2,4]triazolo[4,3-b]pyridazin-6-yl)-1H-pyrazol-4-yl)propan-1-one, and 1-(3-benzylpyrrolidin-1-yl)-3-(3-methyl-1-(3-methyl-[1,2,4]triazolo[4,3-b]pyridazin-6-yl)-5-(trifluoromethyl)-1H-pyrazol-4-yl)propan-1-one.

In some embodiments said compound is selected from the group consisting of 3-(3,5-dimethyl-1-(3-methyl-[1,2,4]triazolo[4,3-b]pyridazin-6-yl)-1H-pyrazol-4-yl)-1-(4-phenylpiperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperazin-1-yl)propan-1-one, 1-(4-benzylpiperidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorophenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(3-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-phenylpiperazin-1-yl)propan-1-one, 1-(4-(3-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(1-([1,2,4]triazolo[4,3-b]pyridazin-6-yl)-3,5-dimethyl-1H-pyrazol-4-yl)-1-(4-(pyridin-2-yl)piperazin-1-yl)propan-1-one, 3-(3,5-dimethyl-1-(3-methyl-[1,2,4]triazolo[4,3-b]pyridazin-6-yl)-1H-pyrazol-4-yl)-N-((5-methylfuran-2-yl)methyl)propanamide, 3-(3,5-dimethyl-1-(3-methyl-[1,2,4]triazolo[4,3-b]pyridazin-6-yl)-1H-pyrazol-4-yl)-1-(4-(2-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-N-(3-phenylpropyl)propanamide, 3-(1-([1,2,4]triazolo[4,3-b]pyridazin-6-yl)-3,5-dimethyl-1H-pyrazol-4-yl)-1-(4-benzylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(2,5-dimethylphenyl)piperazin-1-yl)propan-1-one, N-(4-chlorobenzyl)-3-(3,5-dimethyl-1-(3-methyl-[1,2,4]triazolo[4,3-b]pyridazin-6-yl)-1H-pyrazol-4-yl)propanamide, 3-(3,5-dimethyl-1-(3-methyl-[1,2,4]triazolo[4,3-b]pyridazin-6-yl)-1H-pyrazol-4-yl)-N-(thiophen-2-ylmethyl)propanamide, N-(2-(1H-indol-3-yl)ethyl)-3-(3,5-dimethyl-1-(3-methyl-[1,2,4]triazolo[4,3-b]pyridazin-6-yl)-1H-pyrazol-4-yl)propanamide, N-benzyl-3-(3,5-dimethyl-1-(3-methyl-[1,2,4]triazolo[4,3-b]pyridazin-6-yl)-1H-pyrazol-4-yl)propanamide, 3-(1-([1,2,4]triazolo[4,3-b]pyridazin-6-yl)-3,5-dimethyl-1H-pyrazol-4-yl)-N-(3-phenylpropyl)propanamide, 3-(3,5-dimethyl-1-(3-methyl-[1,2,4]triazolo[4,3-b]pyridazin-6-yl)-1H-pyrazol-4-yl)-1-(4-ethylpiperazin-1-yl)propan-1-one, 3-(1-([1,2,4]triazolo[4,3-b]pyridazin-6-yl)-3,5-dimethyl-1H-pyrazol-4-yl)-1-(4-methylpiperidin-1-yl)propan-1-one, 3-(1-([1,2,4]triazolo[4,3-b]pyridazin-6-yl)-3,5-dimethyl-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-N-(2-fluorobenzyl)propanamide, 3-(3,5-dimethyl-1-(3-methyl-[1,2,4]triazolo[4,3-b]pyridazin-6-yl)-1H-pyrazol-4-yl)-N-(2-((furan-2-ylmethyl)thio)ethyl)propanamide, 1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperazin-1-yl)propan-1-one, 1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperazin-1-yl)propan-1-one, (R)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, (S)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one, 1-(4-benzylpiperidin-1-yl)-3-(3,5-dimethyl-1-(3-phenyl-[1,2,4]triazolo[4,3-b]pyridazin-6-yl)-1H-pyrazol-4-yl)propan-1-one, 3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one, 1-(4-benzylpiperidin-1-yl)-3-(3,5-dimethyl-1-(3-methylimidazo[1,2-b]pyridazin-6-yl)-1H-pyrazol-4-yl)propan-1-one,
1-(4-benzylpiperidin-1-yl)-2-(3,5-dimethyl-1-(3-methyl-[1,2,4]triazolo[4,3-b]pyridazin-6-yl)-1H-pyrazol-4-yl)ethan-1-one,
1-(4-benzylpiperidin-1-yl)-3-(3,5-dimethyl-1-(3-methyl-[1,2,4]triazolo[4,3-b]pyridazin-6-yl)-1H-pyrazol-4-yl)propane-1-thione,
6-(4-(3-(4-benzylpiperidin-1-yl)propyl)-3,5-dimethyl-1H-pyrazol-1-yl)-3-methyl-[1,2,4]triazolo[4,3-b]pyridazine,
1-(azepan-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-morpholinopropan-1-one,
N-(3-chlorobenzyl)-3-(3,5-dimethyl-1-(3-methyl-[1,2,4]triazolo[4,3-b]pyridazin-6-yl)-1H-pyrazol-4-yl)-N-methylpropanamide,
3-(3,5-dimethyl-1-(3-methyl-[1,2,4]triazolo[4,3-b]pyridazin-6-yl)-1H-pyrazol-4-yl)-1-(4-(furan-2-ylmethyl)piperazin-1-yl)propan-1-one,
3-(3,5-dimethyl-1-(3-methyl-[1,2,4]triazolo[4,3-b]pyridazin-6-yl)-1H-pyrazol-4-yl)-1-(4-(2-phenylpropan-2-yl)piperazin-1-yl)propan-1-one,
1-(4-(3,4-dimethoxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(4-(naphthalen-2-ylmethyl)piperazin-1-yl)propan-1-one,
1-(4-(3-chlorobenzyl)piperidin-1-yl)-3-(3,5-dimethyl-1-(3-methyl-[1,2,4]triazolo[4,3-b]pyridazin-6-yl)-1H-pyrazol-4-yl)propan-1-one,
1-(3-benzylazetidin-1-yl)-3-(3,5-dimethyl-1-(3-methyl-[1,2,4]triazolo[4,3-b]pyridazin-6-yl)-1H-pyrazol-4-yl)propan-1-one,
1-(3-(benzylamino)azetidin-1-yl)-3-(3,5-dimethyl-1-(3-methyl-[1,2,4]triazolo[4,3-b]pyridazin-6-yl)-1H-pyrazol-4-yl)propan-1-one,
N-benzyl-3,5-dimethyl-1-(3-methyl-[1,2,4]triazolo[4,3-b]pyridazin-6-yl)-1H-pyrazole-4-carboxamide,
(3-benzylpyrrolidin-1-yl)(3,5-dimethyl-1-(3-methyl-[1,2,4]triazolo[4,3-b]pyridazin-6-yl)-1H-pyrazol-4-yl)methanone,
1-(3-benzylpyrrolidin-1-yl)-3-(5-isopropyl-3-methyl-1-(3-methyl-[1,2,4]triazolo[4,3-b]pyridazin-6-yl)-1H-pyrazol-4-yl)propan-1-one,
1-(3-benzylpyrrolidin-1-yl)-3-(3-methyl-1-(3-methyl-[1,2,4]triazolo[4,3-b]pyridazin-6-yl)-5-(trifluoromethyl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(4-(3-methoxyphenyl)piperazin-1-yl)propan-1-one,
1-benzyl-4-(3-(3,5-dimethyl-1-(3-methyl-[1,2,4]triazolo[4,3-b]pyridazin-6-yl)-1H-pyrazol-4-yl)propanoyl)piperazin-2-one,
1-(4-benzylpiperidin-1-yl)-3-(3,5-diethyl-1-(3-isopropyl-[1,2,4]triazolo[4,3-b]pyridazin-6-yl)-1H-pyrazol-4-yl)propan-1-one,
1-(3-benzylpyrrolidin-1-yl)-3-(1-(3-isopropyl-[1,2,4]triazolo[4,3-b]pyridazin-6-yl)-3,5-dimethyl-1H-pyrazol-4-yl)propan-1-one,
1-(3-benzylpyrrolidin-1-yl)-3-(1-(3-ethyl-[1,2,4]triazolo[4,3-b]pyridazin-6-yl)-3,5-dimethyl-1H-pyrazol-4-yl)propan-1-one,
1-(2,2-dimethylpyrrolidin-1-yl)-3-(1-(3-isopropyl-[1,2,4]triazolo[4,3-b]pyridazin-6-yl)-3,5-dimethyl-1H-pyrazol-4-yl)propan-1-one,
1-(3,3-dimethylpyrrolidin-1-yl)-3-(1-(3-isopropyl-[1,2,4]triazolo[4,3-b]pyridazin-6-yl)-3,5-dimethyl-1H-pyrazol-4-yl)propan-1-one,
1-(3-benzylpyrrolidin-1-yl)-3-(3,5-diethyl-1-(3-isopropyl-[1,2,4]triazolo[4,3-b]pyridazin-6-yl)-1H-pyrazol-4-yl)propan-1-one,
3-(3,5-diethyl-1-(3-isopropyl-[1,2,4]triazolo[4,3-b]pyridazin-6-yl)-1H-pyrazol-4-yl)-1-(3,3-dimethylpyrrolidin-1-yl)propan-1-one,
1-((1S)-2-azabicyclo[2.2.1]heptan-2-yl)-3-(1-(3-isopropyl-[1,2,4]triazolo[4,3-b]pyridazin-6-yl)-3,5-dimethyl-1H-pyrazol-4-yl)propan-1-one,
(1S,5R)-3-(3-(1-(3-ethyl-[1,2,4]triazolo[4,3-b]pyridazin-6-yl)-3,5-dimethyl-1H-pyrazol-4-yl)propanoyl)-2,3,4,5-tetrahydro-1,5-methanopyrido[1,2-d][1,4]diazepin-7(1H)-one,
1-((1S)-2-azabicyclo[2.2.1]heptan-2-yl)-3-(1-(3-ethyl-[1,2,4]triazolo[4,3-b]pyridazin-6-yl)-3,5-dimethyl-1H-pyrazol-4-yl)propan-1-one,
3-(3,5-dimethyl-1-(3-(trifluoromethyl)-[1,2,4]triazolo[4,3-b]pyridazin-6-yl)-1H-pyrazol-4-yl)-1-(pyrrolidin-1-yl)propan-1-one,
1-(4-benzylpiperidin-1-yl)-3-(1-(3-isopropyl-[1,2,4]triazolo[4,3-b]pyridazin-6-yl)-3,5-dimethyl-1H-pyrazol-4-yl)propan-1-one,
1-(4-benzylpiperidin-1-yl)-3-(1-(3-ethyl-[1,2,4]triazolo[4,3-b]pyridazin-6-yl)-3,5-dimethyl-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(3,3-dimethylpyrrolidin-1-yl)propan-1-one,
3-(1-(3-ethyl-[1,2,4]triazolo[4,3-b]pyridazin-6-yl)-3,5-dimethyl-1H-pyrazol-4-yl)-1-(pyrrolidin-1-yl)propan-1-one,
3-(1-(3-isopropyl-[1,2,4]triazolo[4,3-b]pyridazin-6-yl)-3,5-dimethyl-1H-pyrazol-4-yl)-1-(pyrrolidin-1-yl)propan-1-one,
3-(3,5-diethyl-1-(3-isopropyl-[1,2,4]triazolo[4,3-b]pyridazin-6-yl)-1H-pyrazol-4-yl)-1-(3,3-dimethylpyrrolidin-1-yl)propan-1-one,
1-(3-benzylpyrrolidin-1-yl)-3-(3,5-diethyl-1-(3-methyl-[1,2,4]triazolo[4,3-b]pyridazin-6-yl)-1H-pyrazol-4-yl)propan-1-one,
1-(4-benzyl-1,4-diazepan-1-yl)-3-(3,5-dimethyl-1-(3-methyl-[1,2,4]triazolo[4,3-b]pyridazin-6-yl)-1H-pyrazol-4-yl)propan-1-one,
1-(4-benzylpiperidin-1-yl)-3-(3-isopropyl-5-methyl-1-(3-methyl-[1,2,4]triazolo[4,3-b]pyridazin-6-yl)-1H-pyrazol-4-yl)propan-1-one,
3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one,
1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one,
1-(4-benzylpiperidin-1-yl)-2-(3,5-dimethyl-1-(3-methyl-[1,2,4]triazolo[4,3-b]pyridazin-6-yl)-1H-pyrazol-4-yl)propan-1-one,
1-(4-benzylpiperazin-1-yl)-2-(3,5-dimethyl-1-(3-methyl-[1,2,4]triazolo[4,3-b]pyridazin-6-yl)-1H-pyrazol-4-yl)propan-1-one,
1-(4-benzylpiperazin-1-yl)-3-(3,5-dimethyl-1-(3-methylimidazo[1,2-b]pyridazin-6-yl)-1H-pyrazol-4-yl)propan-1-one, 1-(3-benzylpiperazin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 1-(3-benzylpiperidin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpiperidin-1-yl)-3-(3,5-dimethyl-1-(3-methylimidazo[1,2-b]pyridazin-6-yl)-1H-pyrazol-4-yl)propan-1-one, 1-(3-benzylpyrrolidin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpyrrolidin-1-yl)-3-(3,5-dimethyl-1-(3-methylimidazo[1,2-b]pyridazin-6-yl)-1H-pyrazol-4-yl)propan-1-one, 2-(3,5-dimethyl-1-(3-methyl-[1,2,4]triazolo[4,3-b]pyridazin-6-yl)-1H-pyrazol-4-yl)-1-(4-phenethylpiperidin-1-yl)propan-1-one, 3-(3,5-dimethyl-1-(3-methylimidazo[1,2-b]pyridazin-6-yl)-1H-pyrazol-4-yl)-1-(4-phenethylpiperidin-1-yl)propan-1-one.

In another aspect, the present invention relates to a pharmaceutical composition comprising said compound having a structure according to Formula (I) or said compound selected from the group above and at least one pharmaceutically acceptable carrier.

In another aspect, the present invention relates to a kit comprising said compound having a structure according to Formula (I) said compound selected from the group above or said pharmaceutical composition and at least one pharmaceutically acceptable carrier.

Moreover, the invention is directed to a compound having a structure according to formula (XX)

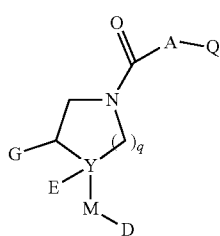

(XX)

wherein in formula (XX),

Q is selected from group A) consisting of

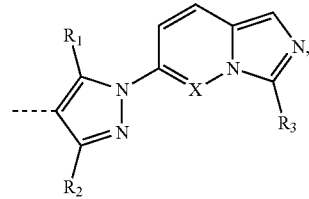

(XXa)

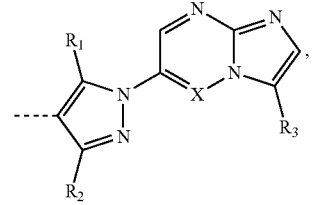

(XXb)

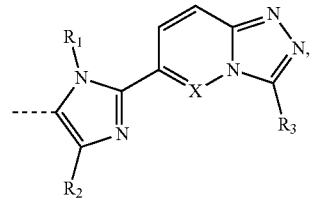

(XXc)

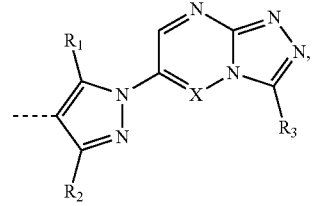

(XXd)

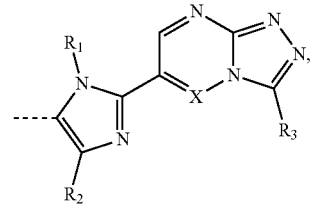

(XXe)

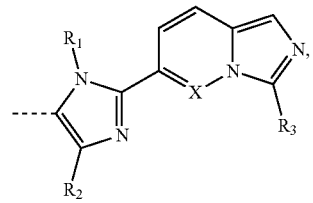

(XXf)

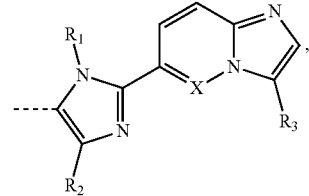

(XXg)

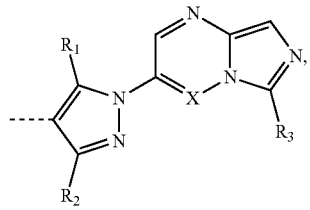

(XXh)

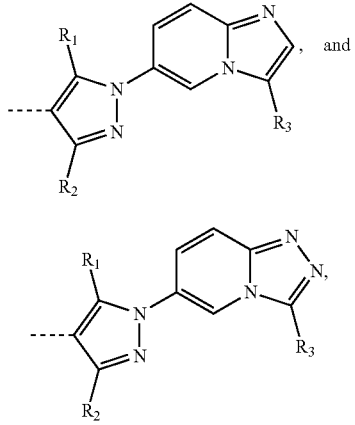

(XXi)

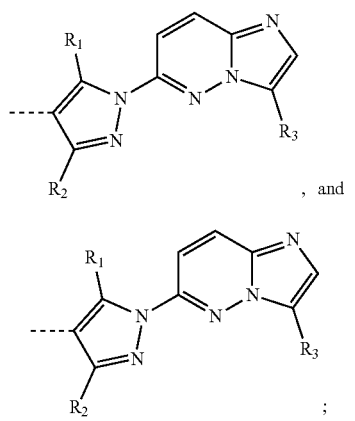

(XXj)

X is selected from the group consisting of CH, and N;
$R_1$ and $R_2$ are independently selected from the group consisting of hydrogen, $(C_1-C_6)$haloalkyl and —$(C_3-C_8)$cycloalkyl, $(C_1-C_6)$alkyl, preferably $(C_1-C_6)$alkyl, more preferably methyl $R_3$ is selected from the group consisting of hydrogen, —$(C_1-C_6)$alkyl, —$(C_1-C_6)$haloalkyl, $(C_3-C_8)$cycloalkyl, —$(C_6-C_{10})$aryl, —$(C_6-C_{10})$aryl$(C_1-C_6)$alkyl, —$(C_3-C_{10})$heteroaryl, —$(C_3-C_{10})$heteroaryl$(C_1-C_6)$alkyl, —CONH$(C_6-C_{10})$Aryl, —CONH$_2$, and —CON$((C_1-C_6)$alkyl)$(C_6-C_{10})$Aryl, preferably —$(C_1-C_6)$alkyl;

or Q is selected from group B) consisting of (XXk)

(XXl)

$R_1$ and $R_2$ are independently selected from the group consisting of hydrogen, $(C_1-C_6)$haloalkyl, —$(C_3-C_8)$cycloalkyl, and $(C_1-C_6)$alkyl, preferably $(C_1-C_6)$alkyl, more preferably methyl $R_3$ is selected from the group consisting of hydrogen, —$(C_1-C_6)$alkyl, —$(C_1-C_6)$haloalkyl, $(C_3-C_8)$cycloalkyl, —$(C_6-C_{10})$aryl, —$(C_6-C_{10})$aryl$(C_1-C_6)$alkyl, —$(C_3-C_{10})$heteroaryl-$(C_3-C_{10})$heteroaryl$(C_1-C_6)$alkyl; —CONH$(C_6-C_{10})$Aryl, —CONH$_2$, and —CON$((C_1-C_6)$alkyl)$(C_6-C_{10})$Aryl, preferably —$(C_1-C_6)$alkyl;

if Q is selected from group A)
then
A is selected from the group consisting of —(CH$_2$)$_3$—, —(CH$_2$)$_2$—, —CH$_2$—, and cyclopropyl; preferably —(CH$_2$)$_2$—;

G is selected from the group consisting of hydrogen, —$(C_3-C_{10})$heteroaryl, $(C_6-C_{10})$aryl$(C_1-C_6)$alkyl and $(C_6-C_{10})$aryl; which are optionally substituted by one or more identical or different substituents, preferably the one or more identical or different substituents are selected from the group consisting of halogen, —$(C_1-C_4)$alkyl, —$(C_1-C_4)$haloalkyl, —CO$(C_1-C_4)$alkyl, —CN, —NC, —$(C_6-C_{10})$aryl, —$(C_3-C_{10})$heteroaryl, —NH$(C_1-C_4)$alkyl, —N$((C_1-C_4)$alkyl)$_2$, —NO, —SO$_2$$(C_1-C_4)$alkyl, —NHSO$_2$$(C_1-C_4)$alkyl, —CONH$_2$, —CF$_3$, —COOH, —NO$_2$, —NHCO$(C_1-C_4)$alkyl, —CO$_2$$(C_1-C_4)$alkyl, —CONH$(C_1-C_4)$alkyl, —CONH$_2$, —OR$_6$, —SO$_2$NH$_2$, —CH$_2$COOH, —CH$_2$OR$_6$, and —SO$_2$Ph:

D is selected from the group consisting of hydrogen, —$(C_3-C_{10})$heteroaryl for example

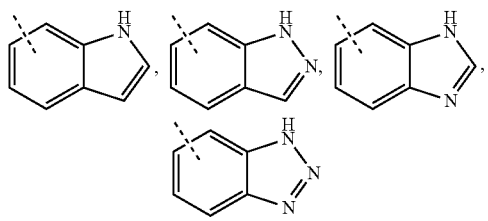

—$(C_3-C_{10})$aryl for example phenyl,

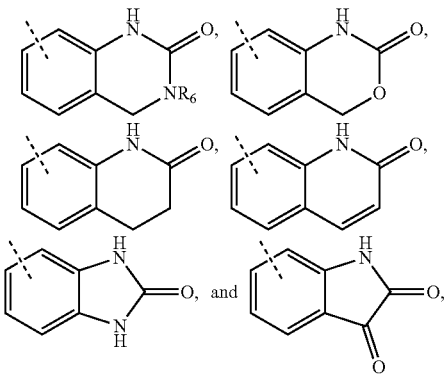

—$(C_6-C_{10})$aryl$(C_1-C_6)$alkyl, —$(C_3-C_{10})$heteroaryl$(C_1-C_6)$alkyl, —$(C_1-C_6)$alkyl,

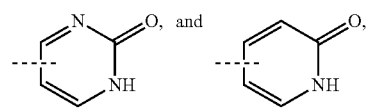

which are optionally substituted by one or more identical or different substituents, preferably the one or more identical or different substituents are selected from the group consisting of halogen, —$(C_1-C_4)$alkyl, —$(C_1-C_4)$haloalkyl, —CO$(C_1-C_4)$alkyl, —CN, —NC, —$(C_6-C_{10})$aryl, —$(C_3-C_{10})$heteroaryl, —NH$(C_1-C_4)$alkyl, —N$((C_1-C_4)$alkyl)$_2$, —NO, —SO$_2$$(C_1-C_4)$alkyl, —NHSO$_2$$(C_1-C_4)$alkyl, —CONH$_2$, —CF$_3$, —COOH, —NO$_2$, —NHCO$(C_1-C_4)$alkyl, —CO$_2$$(C_1-C_4)$alkyl, —CONH$(C_1-C_4)$alkyl, —CONH$_2$, —OR$_6$, —SO$_2$NH$_2$, —CH$_2$COOH, —CH$_2$OR$^6$; —COCH$_2$SO$_2$Ph, —NHCONHR$_6$, —CONHOR$_6$, —CONHCN, NHCOOR$_6$,

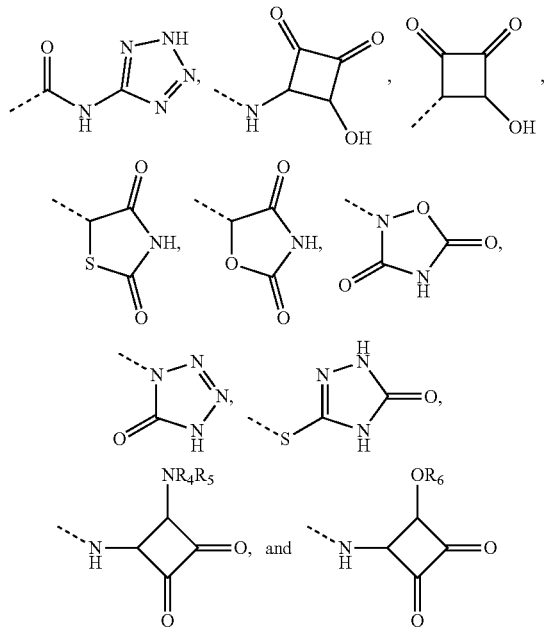

preferably the at least one —(C$_3$-C$_{10}$)heteroaryl substituent is selected from the group consisting of

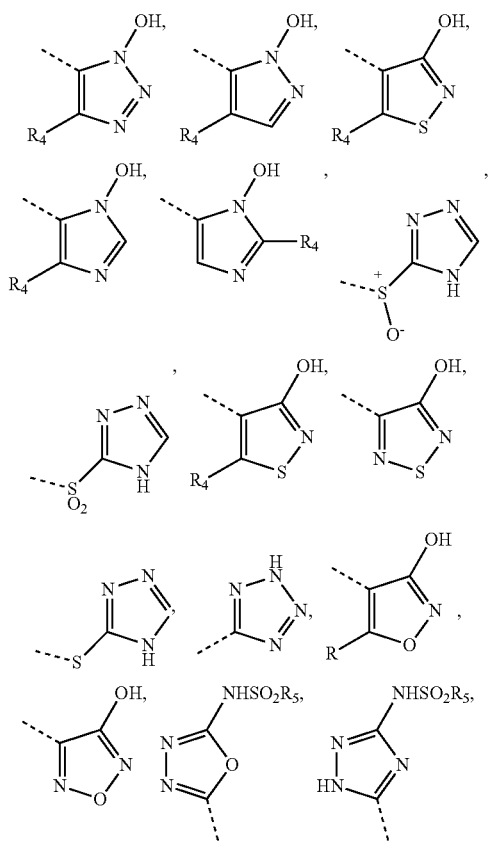

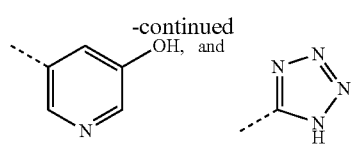

R$_6$ is selected from the group consisting of hydrogen, —(C$_1$-C$_4$)alkyl, and —(C$_1$-C$_4$)haloalkyl;

E is selected from the group consisting of hydrogen, —(C$_1$-C$_6$)alkyl and not present;

Y is selected from the group consisting of C, and N;

M is selected from the group consisting of hydrogen, —CR$_4$R$_5$—, NH, O and not present;

R$_4$ and R$_5$ are independently selected from the group consisting of hydrogen, —(C$_1$-C$_4$)alkyl q is 1 or 2;

if Q is selected from group B) then

A is selected from the group consisting of —(CH$_2$)$_2$— and cyclopropyl; G is selected from the group consisting of hydrogen, —(C$_1$-C$_6$)alkyl-, —(C$_3$-C$_{10}$)heteroaryl, (C$_6$-C$_{10}$)aryl(C$_1$-C$_6$)alkyl and (C$_6$-C$_{10}$)aryl; which are optionally substituted by one or more identical or different substituents, preferably the one or more identical or different substituents are selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —NH((C$_1$-C$_4$)alkyl)-, —N((C$_1$-C$_4$)alkyl)$_2$, —NO, —SO$_2$(C$_1$-C$_4$)alkyl, —NHSO$_2$(C$_1$-C$_4$)alkyl, —CONH$_2$, —CF$_3$, —COOH, —NO$_2$, —NHCO(C$_1$-C$_4$)alkyl, —CO$_2$(C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; and —SO$_2$Ph;

D is selected from the group consisting of hydrogen, phenyl, napthyl, —(C$_3$-C$_{10}$)heteroaryl for example

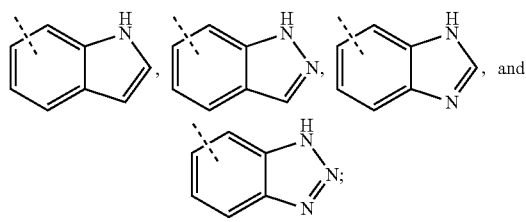

benzyl, —(C$_3$-C$_{10}$)heteroaryl(C$_1$-C$_6$)alkyl, —(C$_1$-C$_6$)alkyl,

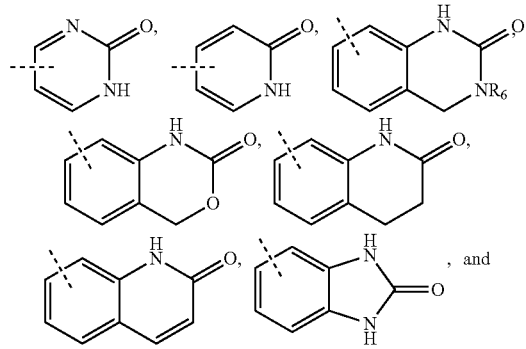

-continued

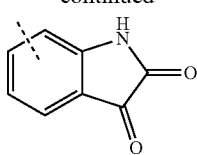

which are optionally substituted by one or more identical or different substituents, the one or more identical or different substituents are selected from the group consisting of halogen, —($C_1$-$C_4$)alkyl, —($C_1$-$C_4$)haloalkyl, —CO($C_1$-$C_4$)alkyl, —CN, —NC, —($C_6$-$C_{10}$)aryl, —($C_3$-$C_{10}$)heteroaryl, —NH($C_1$-$C_4$)alkyl, —N(($C_1$-$C_4$)alkyl)$_2$, —NO, —SO$_2$($C_1$-$C_4$)alkyl, —NHSO($C_1$-$C_4$)alkyl, —NHSO$_2$($C_1$-$C_4$)alkyl, —CONH$_2$, —CF$_3$, —COOH, —NO$_2$, —NHCO($C_1$-$C_4$)alkyl, —CO$_2$($C_1$-$C_4$)alkyl, —CONH($C_1$-$C_4$)alkyl, —CONH$_2$, —OR$_6$, —SO$_2$NH$_2$, —CH$_2$COOH, —CH$_2$OR$_6$; —COCH$_2$SO$_2$Ph, —NHCONHR$_6$, —CONHOR$_6$, —SO$_2$Ph, —CONHCN, NHCOOR$_6$,

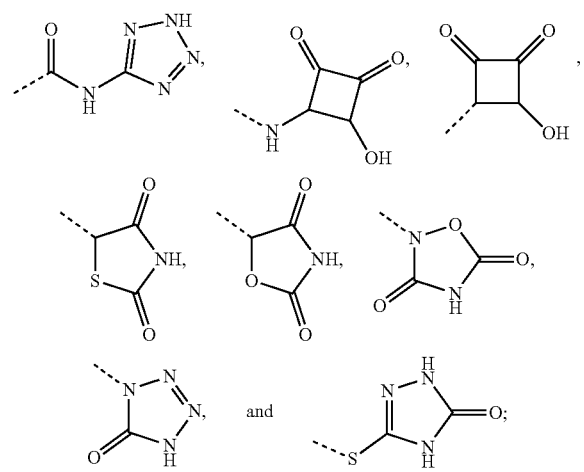

preferably the —($C_3$-$C_{10}$)heteroaryl substituent is selected from the group consisting of

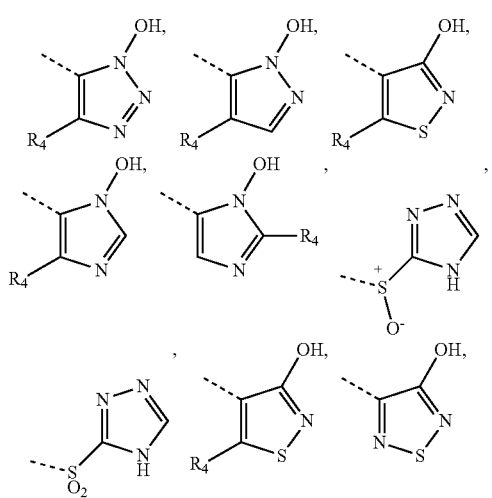

-continued

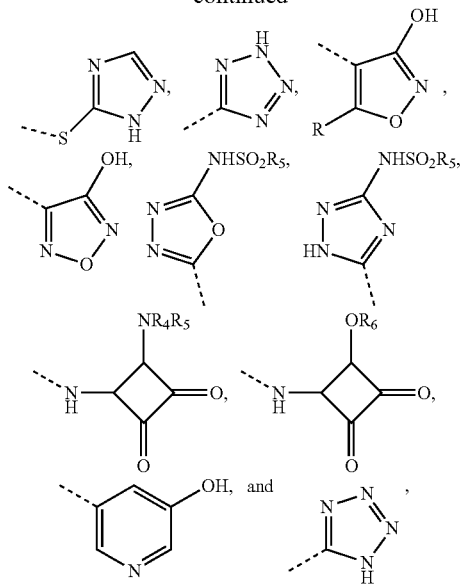

$R_6$ is selected from the group consisting of hydrogen, —($C_1$-$C_4$)alkyl, and —($C_1$-$C_4$)haloalky E is selected from the group consisting of hydrogen, —($C_1$-$C_6$)alkyl and not present;

Y is selected from the group consisting of C, and N;

M is selected from the group consisting of hydrogen, —CR$_4$R$_5$—, NH, O and not present;

$R_4$ and $R_5$ are independently selected from the group consisting of hydrogen, —($C_1$-$C_4$)alkyl, q is 1 or 2;

wherein D is not unsubstituted phenyl if $R_1$ and $R_2$ are both methyl, $R_3$ is methyl or unsubstituted phenyl; Q is formula (XXk), G is hydrogen, q is 2, E is H, M is —CH$_2$—, A is —CH$_2$CH$_2$— and Y is C;

wherein D is not unsubstituted phenyl if $R_1$ and $R_2$ are both methyl, or ethyl $R_3$ is methyl, ethyl, isopropyl, cyclopropyl, or unsubstituted benzyl; Q is formula (XXI), G is hydrogen, q is 2, E is H, M is —CH$_2$—, A is —CH$_2$CH$_2$— and Y is C;

wherein D is not unsubstituted phenyl if $R_1$ and $R_2$ are both methyl, or ethyl $R_3$ is methyl, ethyl, isopropyl, cyclopropyl, or unsubstituted benzyl; Q is formula (XXI), G is hydrogen, q is 2, E is not present, M is —C(CH$_3$)$_2$—, A is —CH$_2$CH$_2$— and Y is N wherein D is not unsubstituted 2-pyridyl, phenyl only substituted in meta position with —OMe, phenyl only substituted in para position with F if G is hydrogen, q is 2, E is H or not present if Y is N, M is —CH$_2$, or not present, A is —CH$_2$CH$_2$— and Y is C or N, $R_1$ and $R_2$ are both methyl, $R_3$ is methyl and Q is formula (XXI);

wherein D is not unsubstituted 2-naphtyl, phenyl substituted only in meta position with Cl, 2-furyl or phenyl substituted only in meta and para position with —OMe if $R_1$ and $R_2$ are both methyl, $R_3$ is methyl; Q is formula (XXI), G is hydrogen, q is 2, E is not present, M is —CH$_2$—, A is —CH$_2$CH$_2$— and Y is N;

wherein D is not unsubstituted Bn if Q is formula (XXk), M is —CH$_2$, A is —CH$_2$CH$_2$—, E is H present, Y is C, G is hydrogen, and q is 2, $R_1$ and $R_2$ are both methyl and $R_3$ is methyl;

wherein D is not hydrogen if M is —CH$_2$—, A is —CH$_2$CH$_2$—, q is 1, Y is C, E is methyl, $R_1$ and $R_2$ are both methyl or both ethyl, $R_3$ is methyl or isopropyl and Q is formula (XXI);

wherein M is not hydrogen, if E is hydrogen, G is hydrogen, A is —CH$_2$CH$_2$—, q is 1 and Y is C, R$_1$ and R$_2$ are both methyl, R$_3$ is —CF$_3$, ethyl or isopropyl, and Q is formula (XXI);

wherein D is not unsubstituted phenyl if E is hydrogen, M is —CH$_2$, A is —CH$_2$CH$_2$—, q is 1, Y is C; R$_1$ and R$_2$ are both methyl or ethyl, R$_3$ is methyl, ethyl or isopropyl, and Q is formula (XXI) and G is hydrogen;

wherein G is not unsubstituted benzyl if E is hydrogen, M is hydrogen, A is —CH$_2$CH$_2$—, q is 1, Y is C; R$_1$ and R$_2$ are both methyl or ethyl, R$_3$ is methyl, ethyl or isopropyl, and Q is formula (XXI);

wherein D is not unsubstituted phenyl if E is hydrogen, M is —CH$_2$, A is —CH$_2$CH$_2$—, q is 1, Y is C; R$_1$ and R$_2$ are both methyl, R$_3$ is methyl, Q is formula (XXk) and G is hydrogen;

wherein G is not unsubstituted benzyl if E is hydrogen, M is hydrogen, A is —CH$_2$CH$_2$—, q is 1, Y is C, R$_1$ and R$_2$ are both methyl or both ethyl, R$_3$ is methyl, and Q is formula (XXk);

wherein D is not unsubstituted phenyl if E is hydrogen, M is not present, q is 2, Y is C, A is —CH$_2$CH$_2$—, G is hydrogen, R$_1$ and R$_2$ are both methyl, R$_3$ is methyl and Q is formula (XXI);

or a pharmaceutically acceptable salt, solvate or hydrate thereof.

Furthermore, the invention is directed to a compound selected from the group consisting of 3-(3,5-dimethyl-1-(3-methyl-[1,2,4]triazolo[4,3-b]pyridazin-6-yl)-1H-pyrazol-4-yl)-1-(4-phenethylpiperidin-1-yl)propan-1-one, 1-(3-benzylpiperidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-a]pyridin-6-yl)-1H-pyrazol-4-yl)-1-(4-phenethylpiperidin-1-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoic acid, 1-(3-benzylpiperidin-1-yl)-3-(3,5-dimethyl-1-(3-methyl-[1,2,4]triazolo[4,3-a]pyridin-6-yl)-1H-pyrazol-4-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-methylbenzamide, 1-(3-benzylpyrrolidin-1-yl)-3-(3,5-dimethyl-1-(3-methyl-[1,2,4]triazolo[4,3-a]pyridin-6-yl)-1H-pyrazol-4-yl)propan-1-one, 1-(3-benzylpiperazin-1-yl)-3-(3,5-dimethyl-1-(3-methyl-[1,2,4]triazolo[4,3-b]pyridazin-6-yl)-1H-pyrazol-4-yl)propan-1-one hydrochloride, methyl 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoate, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 1-(4-benzylpiperazin-1-yl)-3-(3,5-dimethyl-1-(3-methyl-[1,2,4]triazolo[4,3-a]pyridin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoic acid, methyl 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoate, 1-(4-(2-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2,6-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-acetylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(naphthalen-1-ylmethyl)piperazin-1-yl)propan-1-one, 1-(4-(3,4-difluorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-(3,5-dimethyl-1-(3-methyl-[1,2,4]triazolo[4,3-b]pyridazin-6-yl)-1H-pyrazol-4-yl)-1-(4-(4-methylbenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-5-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-iodobenzyl)piperazin-1-yl)propan-1-one, N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)acetamide, 1-(4-([1,1'-biphenyl]-4-ylmethyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-(dimethylamino)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-nitrobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(methylsulfonyl)benzyl)piperazin-1-yl)propan-1-one, N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)methanesulfonamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 1-(4-((1H-indazol-6-yl)methyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-methylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-hydroxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(trifluoromethyl)benzyl)piperazin-1-yl)propan-1-one, 1-(4-(3,4-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-methylbenzoic acid, 3-(3,5-dimethyl-1-(3-methyl-[1,2,4]triazolo[4,3-b]pyridazin-6-yl)-1H-pyrazol-4-yl)-1-(4-(3-methyl-4-nitrobenzyl)piperazin-1-yl)propan-1-one, 1-(4-(3-chloro-4-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzoic acid, 3-(3,5-dimethyl-1-(3-methyl-[1,2,4]triazolo[4,3-b]pyridazin-6-yl)-1H-pyrazol-4-yl)-1-(4-(3-iodobenzyl)piperazin-1-yl)propan-1-one, 1-(4-(3-acetylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-(3,5-dimethyl-1-(3-methyl-[1,2,4]triazolo[4,3-b]pyridazin-6-yl)-1H-pyrazol-4-yl)-1-(4-(3-methylbenzyl)piperazin-1-yl)propan-1-one, 2-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 1-(4-([1,1'-biphenyl]-3-ylmethyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methyl-5-nitrobenzyl)piperazin-1-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzenesulfonamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-fluorobenzoic acid, 1-(4-(2,4-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3,5-difluoro-4-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-hydroxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-6-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-nitrobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-7-ylmethyl)piperazin-1-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-methylbenzamid, 3-(3,5-dimethyl-1-(3-methyl-[1,2,4]triazolo[4,3-b]pyridazin-6-yl)-1H-pyrazol-4-yl)-1-(4-(quinolin-8-ylmethyl)piperazin-1-yl)propan-1-one, 1-(4-(3-(2H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-(methylsulfonyl)benzyl)piperazin-1-yl)propan-1-one, N-(3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)methanesulfonamide, 3-(3,5-dimethyl-1-(3-methyl-[1,2,4]triazolo[4,3-b]pyridazin-6-yl)-1H-pyrazol-4-yl)-1-(4-(3-fluorobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluoro-3-(trifluoromethyl)benzyl)piperazin-1-yl)propan-1-one, 1-(4-(2,5-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-bromobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3-bromobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2,4-difluoro-3-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-methylbenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-methyl-4-nitrobenzyl)piperazin-1-yl)propan-1-one, 1-(4-(4-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-(2H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(isoquinolin-8-ylmethyl)piperazin-1-yl)propan-1-one, 1-(4-((1H-indol-6-yl)methyl)piperazin-1-yl)-3-(3,5-dimethyl-1-(3-methyl-[1,2,4]triazolo[4,3-b]pyridazin-6-yl)-1H-pyrazol-4-yl)propan-1-one, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2H-chromen-2-one, 3-(3,5-dimethyl-1-(3-methyl-[1,2,4]triazolo[4,3-b]pyridazin-6-yl)-1H-pyrazol-4-yl)-1-(4-(4-(phenylsulfonyl)benzyl)piperazin-1-yl)propan-1-one, 1-(4-benzyl-4-methylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzyl-4-ethylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzyl-4-propylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-ethylpyrrolidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-propylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-N-(1-phenylpiperidin-4-yl)propanamide, 3-(3,5-dimethyl-1-(3-methyl-[1,2,4]triazolo[4,3-b]pyridazin-6-yl)-1H-pyrazol-4-yl)-1-(4-(phenylamino)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-phenoxypiperidin-1-yl)propan-1-one, 1-(4-benzylpiperidin-1-yl)-3-(3,5-dimethyl-1-(7-methylimidazo[1,5-b]pyridazin-2-yl)-1H-pyrazol-4-yl)propan-1-one, 2-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)acetic acid, 3-(3,5-dimethyl-1-(3-methyl-[1,2,4]triazolo[4,3-b]pyridazin-6-yl)-1H-pyrazol-4-yl)-1-(4-(4-(hydroxymethyl)benzyl)piperazin-1-yl)propan-1-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)pyridin-2(1H)-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)pyridin-2(1H)-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-1,3-dihydro-2H-benzo[d]imidazol-2-one, 3-(3,5-dimethyl-1-(3-methyl-[1,2,4]triazolo[4,3-b]pyridazin-6-yl)-1H-pyrazol-4-yl)-1-(3-(1-phenylpropyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(4-hydroxyphenyl)propyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(3-hydroxyphenyl)propyl)pyrrolidin-1-yl)propan-1-one, 1-(3-(4-(1H-tetrazol-5-yl)benzyl)pyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(3-(2-methyl-4-(1H-tetrazol-5-yl)benzyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(2-(3-hydroxyphenyl)propan-2-yl)pyrrolidin-1-yl)propan-1-one, 1-(4-(3-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-5-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluorobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 1-(4-(2-chloro-4-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one, 1-(4-(2-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-ethylbenzyl)piperazin-1-yl)propan-1-one, N-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)sulfonyl)acetamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-(methylsulfonyl)benzamide, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3,4-dihydroisoquinolin-1(2H)-one, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)isoquinolin-1(2H)-one, 3-(3,5-dimethyl-1-(3-methyl-[1,2,4]triazolo[4,3-b]pyridazin-6-yl)-1H-pyrazol-4-yl)-1-(4-(4-(3-hydroxy-5-methylisoxazol-4-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(4-hydroxy-1,2,5-oxadiazol-3-yl)benzyl)piperazin-1-yl)propan-1-one, 3-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)-4-hydroxycyclobutane-1,2-dione, 3-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)amino)-4-hydroxycyclobutane-1,2-dione, 5-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)thiazolidine-2,4-dione, 3-(3,5-Dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 1-(4-(2-Chloro-5-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-5-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-4-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-4-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-3-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-3-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 3-(3,5-Dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one 3-(3,5-Dimethyl-1-(3-methyl-[1,2,4]triazolo[4,3-b]pyridazin-6-yl)-1H-pyrazol-4-yl)-1-(4-(2-methyl-3-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(2-methyl-3-(1H-tetrazol-5-yl)benzyl)piperazin-1-yl)propan-1-one, 3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-5-fluorobenzonitrile, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzonitrile, 4-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 2-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-methylbenzonitrile, 3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-2-methylbenzonitrile, 2-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 3-chloro-4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-chloro-4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-3-fluorobenzonitrile, 4-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, or a pharmaceutically acceptable salt, solvate or hydrate thereof In another aspect, the present invention relates to a pharmaceutical composition comprising said compound having a structure according to Formula (XX) or said compound selected from the group above and at least one pharmaceutically acceptable carrier.

In another aspect, the present invention relates to a kit comprising said compound having a structure according to Formula (XX) said compound selected from the group above or said pharmaceutical composition and at least one pharmaceutically acceptable carrier.

Further, the present invention relates to an assay for the determination of the inhibition activity of an inhibitor I1, wherein a protein P1 comprising at least one linker L1, catalyzes the polymerization of a protein monomer PM1 comprising at least one linker L2, comprising the steps:
  a) polymerization of the protein monomer PM1 catalyzed by the protein P1 in the presence of inhibitor I1, wherein protein monomer PM1 is transferred from a protein P2 to protein P1;
  b) binding of a further molecule M1 to the linker L1 of P1 and further molecule M2 to the linker L2 of the polymerized monomer PM1;
  c) interaction of the molecule M1 bound to linker L1 and molecule M2 bound to linker L2 with each other, resulting in the generation of a detectable signal;
  d) detection of the generated signal;
and wherein binding of the inhibitor I1 to protein P1 inhibits the catalytic activity of protein P1.

Moreover, the present invention relates to a kit for an assay for the determination of the inhibition activity of an E3 Ligase inhibitor, comprising:

A kit for an assay for the determination of the inhibition activity of an E3 Ligase inhibitor, comprising:
  a) an E3 Ligase inhibitor, more preferably a RING E3 ligase inhibitor, most preferably a cIAP1, RNF8 or, TRAF6 inhibitor, in particular preferred an inhibitor selected from a compound according to formula (I), (II), (III), (IV) and/or (XX);
  b) a E3 Ligase, preferably a RING E3 ligase, more preferably TRAF6, cIAP1, or RNF8, comprising a linker L1, wherein the linker L1 is preferably selected from the group consisting of a histidine-tag, GST-tag, Biotin-tag, StrepII-tag, more preferably a histidine-tag;
  c) ubiquitin; comprising a linker, wherein the linker L2 is preferably selected from the group consisting of a histidine-tag, GST-tag, Biotin-tag, StrepII-tag, more preferably a GST-tag;
  d) a further molecule M1 capable of binding to the linker L1, wherein preferably the molecule M1 is selected from the group consisting of nickel-chelate acceptor beads, Glutathione acceptor beads, Strep-Tactin acceptor beads, Streptavidin acceptor beads, preferably nickel-chelate acceptor beads or selected from the group consisting of Glutathione-donor beads, nickel-chelate donor beads, Strep-Tactin donor beads, Streptavidin donor beads, preferably Glutathione-Donor beads nickel-chelate acceptor beads, wherein M1 is selected from acceptor beads if M2 is selected from donor beads or M1 is selected from donor beads if M2 is selected from acceptor beads;
  e) a further molecule M2 capable of binding to the linker L2, wherein preferably the molecule M2 is selected from the group consisting of nickel-chelate acceptor beads, Glutathione acceptor beads, Strep-Tactin acceptor beads, Streptavidin acceptor beads, preferably nickel-chelate acceptor beads or selected from the group consisting of Glutathione-donor beads, nickel-chelate donor beads, Strep-Tactin donor beads, Streptavidin donor beads, preferably Glutathione-Donor beads, wherein M2 is selected from acceptor beads if M1 is selected from donor beads or M2 is selected from donor beads if M1 is selected from acceptor beads;

f) optionally a further protein P3, wherein preferably the further protein is a ubiquitin activating enzyme UBE1:

g) optionally adenosine triphosphate (ATP);

h) optionally a microplate detector for AlphaScreen®/AlphaLISA® detection.

Other features and advantages of the instant invention will be apparent from the following detailed description, figures and claims.

BRIEF DESCRIPTION OF THE DRAWINGS

FIG. 3: Effects of C25-140 on cell viability and the cell cycle. (A) C25-140 does not considerably affect metabolic activity and cell viability up to 50 μM concentration after 24 hours incubation as observed in three different cell lines (MEF, HepG2 and Jurkat cells). Only at the highest dose of 100 μM toxicity is noticeable. (B-C) The cell cycle progression in Jurkat T-cells and (D-E) U2OS cells is not impaired after 24 hours and 72 hours of C25-140 treatment. C25-140 is equal to compound 3 of the description.

FIG. 6: C25-140 impairs T-cell receptor signaling in Jurkat T-cells. (A) TRAF6 auto-ubiquitination induced upon T-cell receptor (TCR) stimulation by PMA/Ionomycin (P/I) is dose-dependently reduced by C25-140 treatment. (B) IKK kinase activity is diminished after C25-140 treatment, which in turn leads to (C) lower IκBα degradation and attenuated NF-κB activation. (D-E) mRNA levels and cytokine secretion of the TCR target genes IL-2 and TNFα are dose-dependently decreased. IKK KA means IKK kinase activity. C25-140 is equal to compound 3 of the description.

FIG. 9: ADME and pharmacokinetic studies of C25-140. (A) Absorption, distribution, metabolism and excretion (ADME) parameters of C25-140 revealed a stable and adequate small molecule for further drug development. (B-C) Pharmacokinetic studies of intravenously (IV), perorally (PO) and intraperitoneally (IP) administered C25-140 demonstrate moderate in vivo half life, a rapid initial distribution phase and a good bioavailability. C25-140 is equal to compound 3 of the description.

FIG. 12: C25-140 ameliorates symptoms of an IMQ-induced psoriasis. (A) Design of the psoriasis mouse study. IMQ was applied once daily and C25-140 was applied topically twice daily to the shaved back and the right ear. Parameters were scored every day and samples for IL-17 cytokine measurement were collected at day 6. (B) C25-140 reduces the cumulative score that consists of (C) the thickness score of the back, (D) the scaling score and (E) the erythema score of the back. (F) The ear thickness is significantly reduced upon C25-140 treatment. (G) The abundance of the cytokine IL-17 is decreased in the presence of C25-140. C25-140 is equal to compound 3 of the description.

FIG. 13: C25-140 eases symptoms of Collagen-Induced-Arthritis. (A) Design of the Collagen-Induced-Arthritis mouse study. Rheumatoid arthritis (RA) was induced by injection of collagen. At day 21, mice received a collagen booster injection inducing the development of arthritic symptoms. 7 days later, C25-140 was administered for 14 days twice daily. Mice were scored for the arthritic index (AI) daily and euthanized on day 42. Limbs were collected for histopathology analysis. (B) During this study, the body weight was measured on a regular basis and do not show any signs of weight loss. (C) The AI of C25-140 treated mice is dose-dependently reduced compared to control mice. (D-E) The overall histological score of the limbs including inflammation, pannus formation, cartilage damage, and bone resorption could be attenuated by C25-140 treatment. (F) Histopathology slides from the ankle and the hindpaw of each individual group support the results of the scored parameters. C25-140 is equal to compound 3 of the description.

Figure 14:
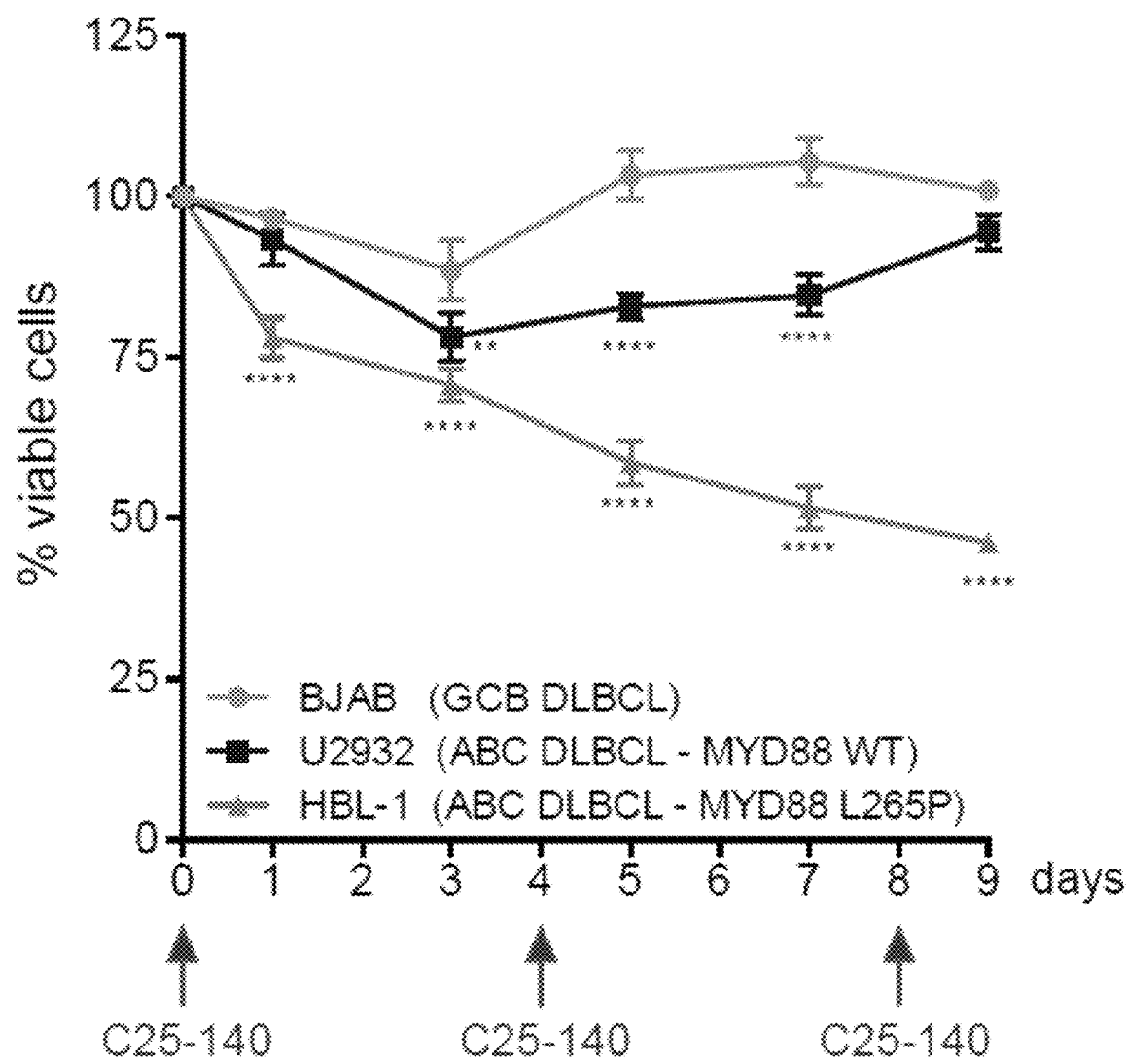

FIG. 14: C25-140 decreases survival rate of MYD88-dependent ABC-DLBCL cells. Viability of MYD88-dependent ABC-DLBCL (HBL1) is diminished by C25-140 treatment at 30 µM of C25-140, whereas MYD88 wildtype ABC DLBCL (U2932) and germinal center B cell (GCB) DLBCLs (BJAB) are not affected by C25-140 treatment. The compound was added at day 0, 4 and 8. C25-140 is equal to compound 3 of the description.

Figure 15:
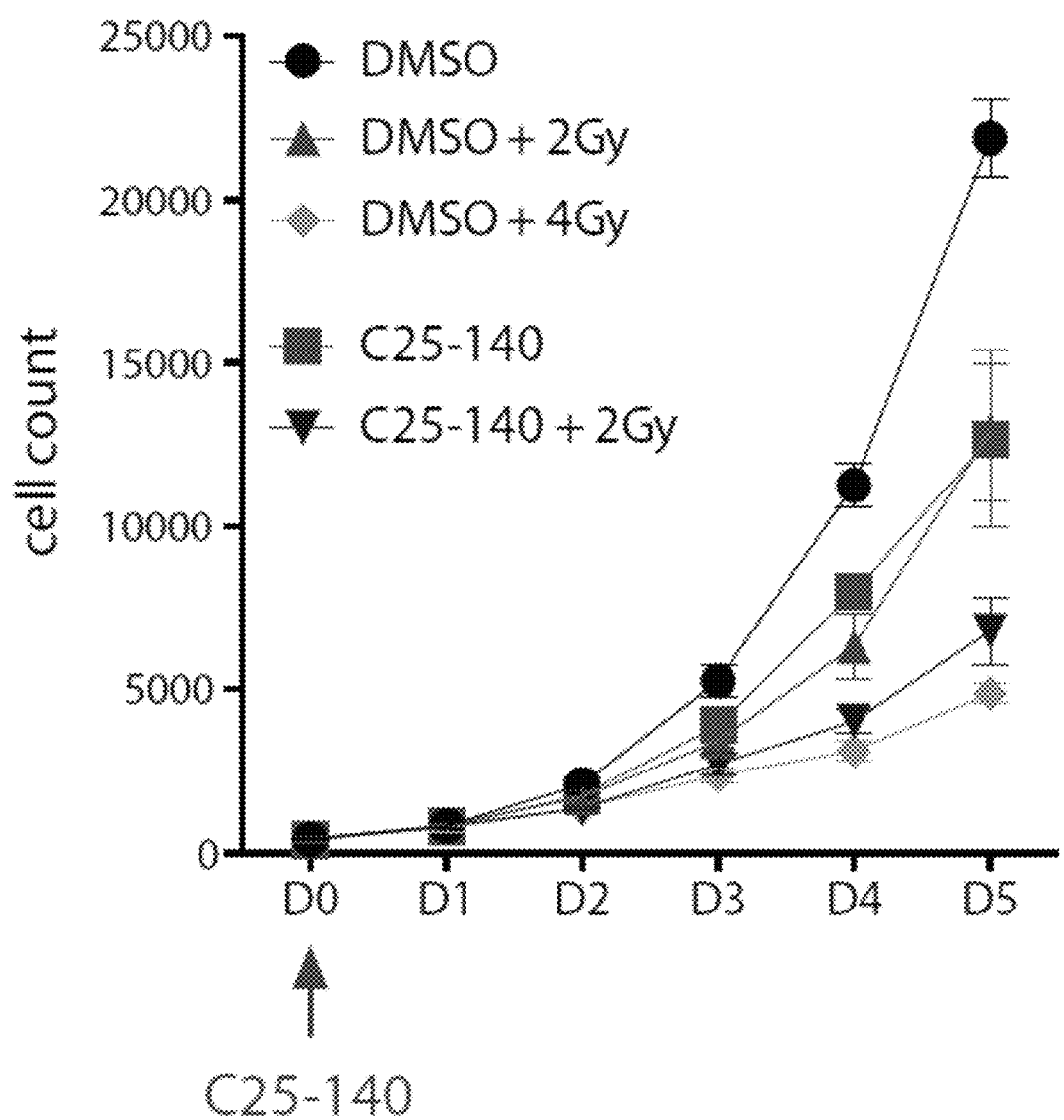

FIG. 15: Combinatorial therapy of irradiation and C25-140 treatment exhibits synergistic effect on osteosarcoma cell growth. Osteosarcoma cell growth is reduced by either C25-140 treatment at 30 µM or 2Gy irradiation. This combination (30 µM C25-140+2Gy) decreases cell growth to the same extent as the higher dose of irradiation (4Gy). C25-140 is equal to compound 3 of the description.

FIG. 16: Analysis of the effect of C25-140 on a panel of oncological cell lines. 78 oncological cell lines from different origin were tested whether they would loose viability upon C25-140 treatment. Two control cell lines were used (HS-5 and MCF 10A). Various cancer cell lines died upon C25-140 treatment, but not the control cell lines. Major effects were visible in cancer cells of blood origin, although also other cancer cell lines of other origins were affected. C25-140 is equal to compound 3 of the description.

Figure 17A:
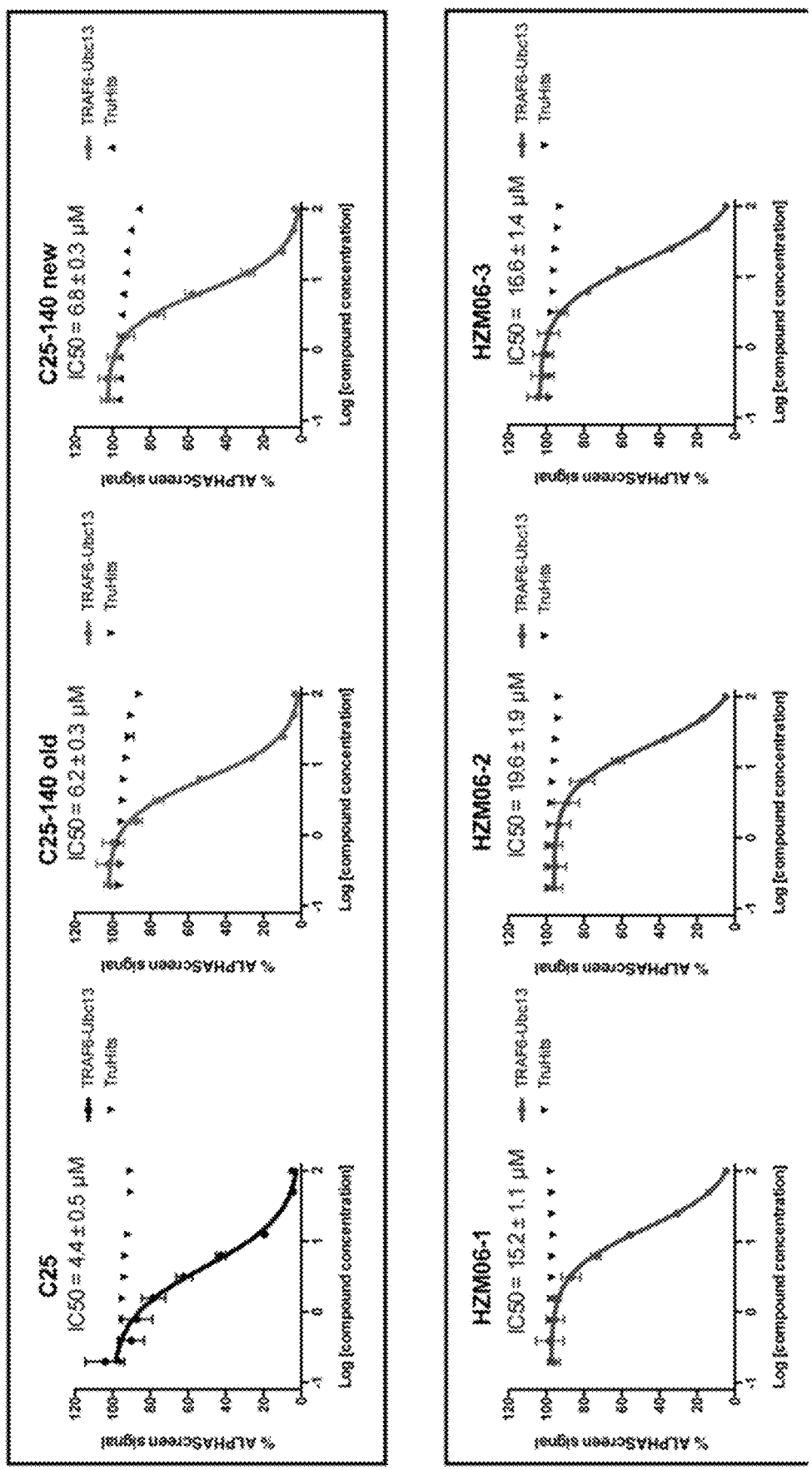
Figure 17B:
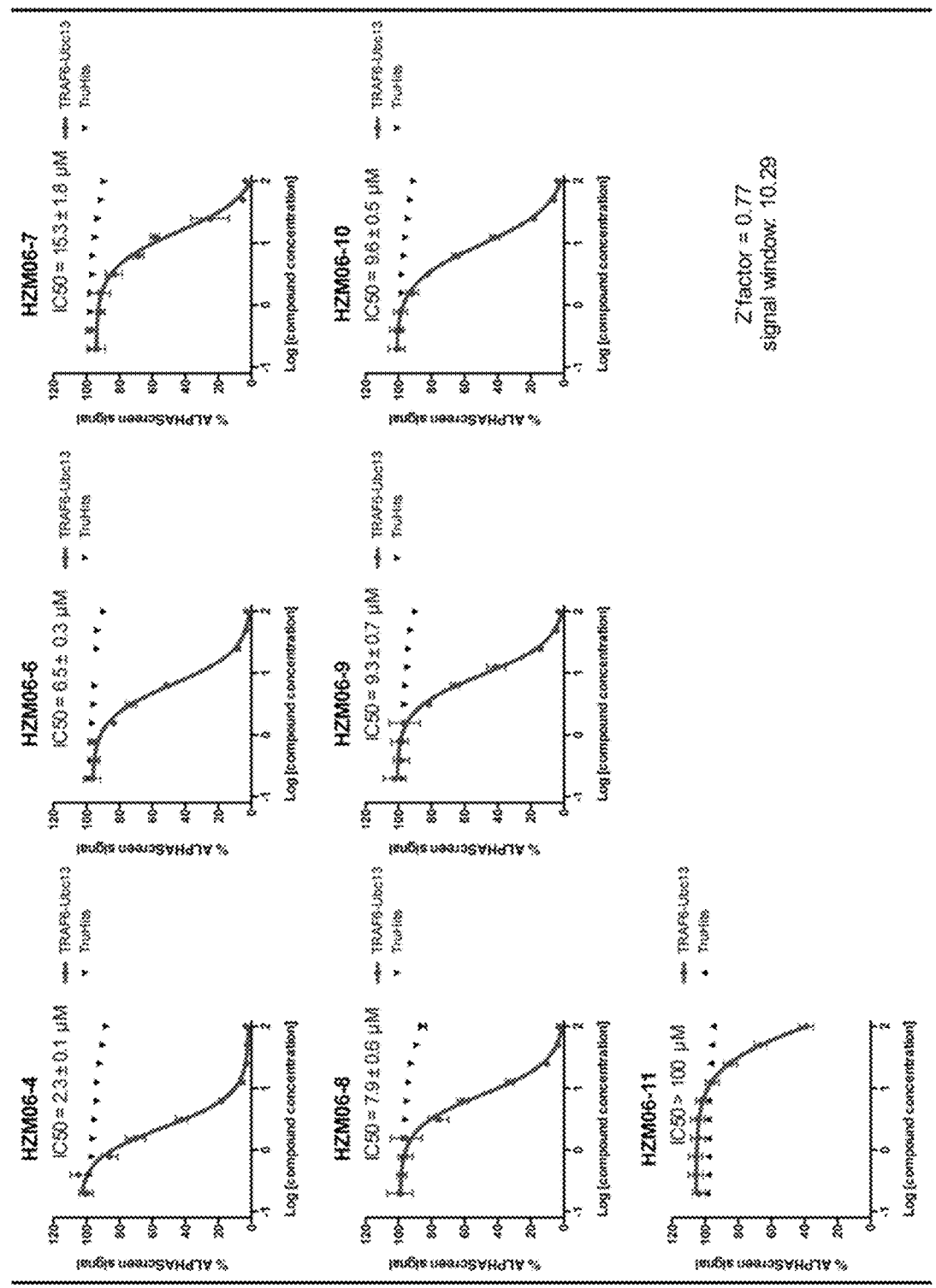

FIG. 17: Analysis of 9 structural analogs of C25-140 in ALPHAScreen assays. 9 commercially non-available structural analogs of C25-140 were tested in serial dilution experiments using the ALPHAScreen assay. All of the tested compounds show inhibitory activity with HZM06-04 exhibiting the most prominent effect. Importantly, none of the tested small molecules unspecifically interfered with the ALPHAScreen technology in TruHits experiments. C25 is equal to compound 1, C25-140 is equal to compound 3, HZM06-1 is equal to compound 28, HZM06-2 is equal to compound 29, HZM06-3 is equal to compound 30, HZM06-4 is equal to compound 31, HZM06-6 is equal to compound 32, HZM06-7 is equal to compound 33, HZM06-8 is equal to compound 34, HZM06-9 is equal to compound 35 and HZM06-10 is equal to compound 36 of the description. Z'factor is 0.77 and signal window is 10.29.

Figure 18A:
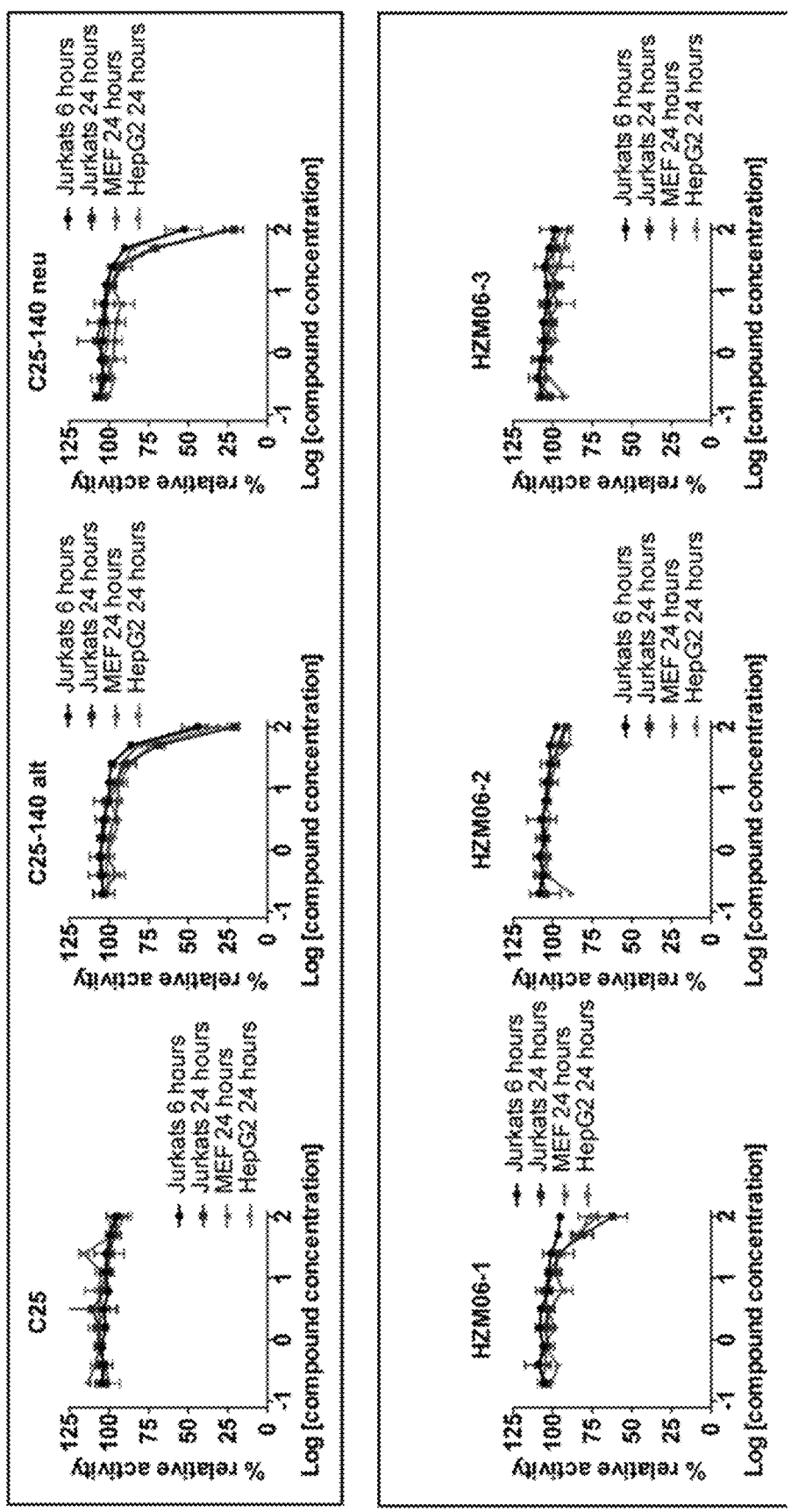
Figure 18B:
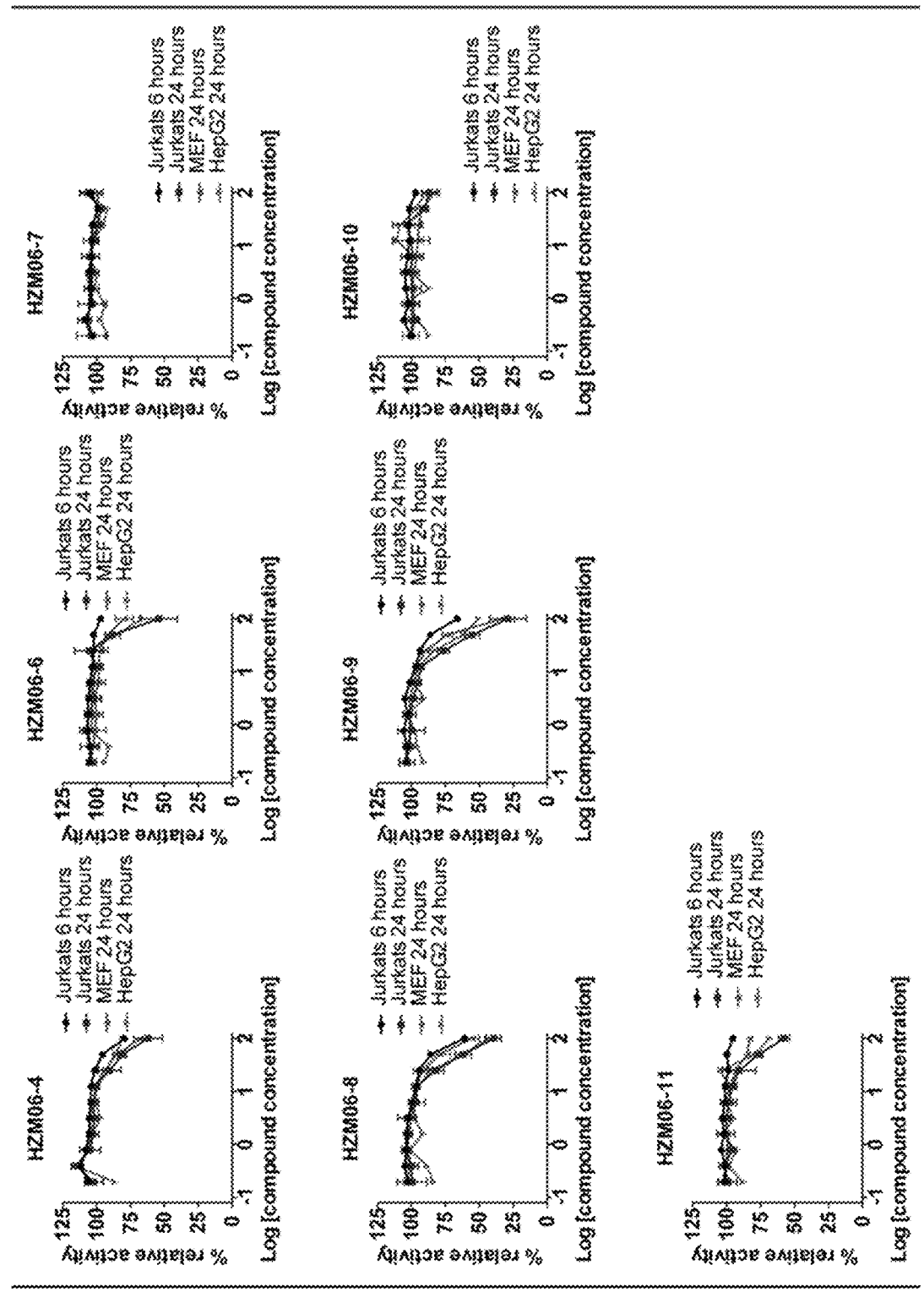

FIG. 18: Cytotoxicity measurement of 9 structural analogs of C25-140 in various cell lines. Jurkat, HepG2 and MEF cells were tested for their viability upon treatment with the 9 analogs for 6 or 24 hours. All small molecules exhibit less cytotoxicity compared to C25-140. C25 is equal to compound 1, C25-140 is equal to compound 3, HZM06-1 is equal to compound 28, HZM06-2 is equal to compound 29, HZM06-3 is equal to compound 30, HZM06-4 is equal to compound 31, HZM06-6 is equal to compound 32, HZM06-7 is equal to compound 33, HZM06-8 is equal to compound 34, HZM06-9 is equal to compound 35 and HZM06-10 is equal to compound 36 of the description.

Figure 19:
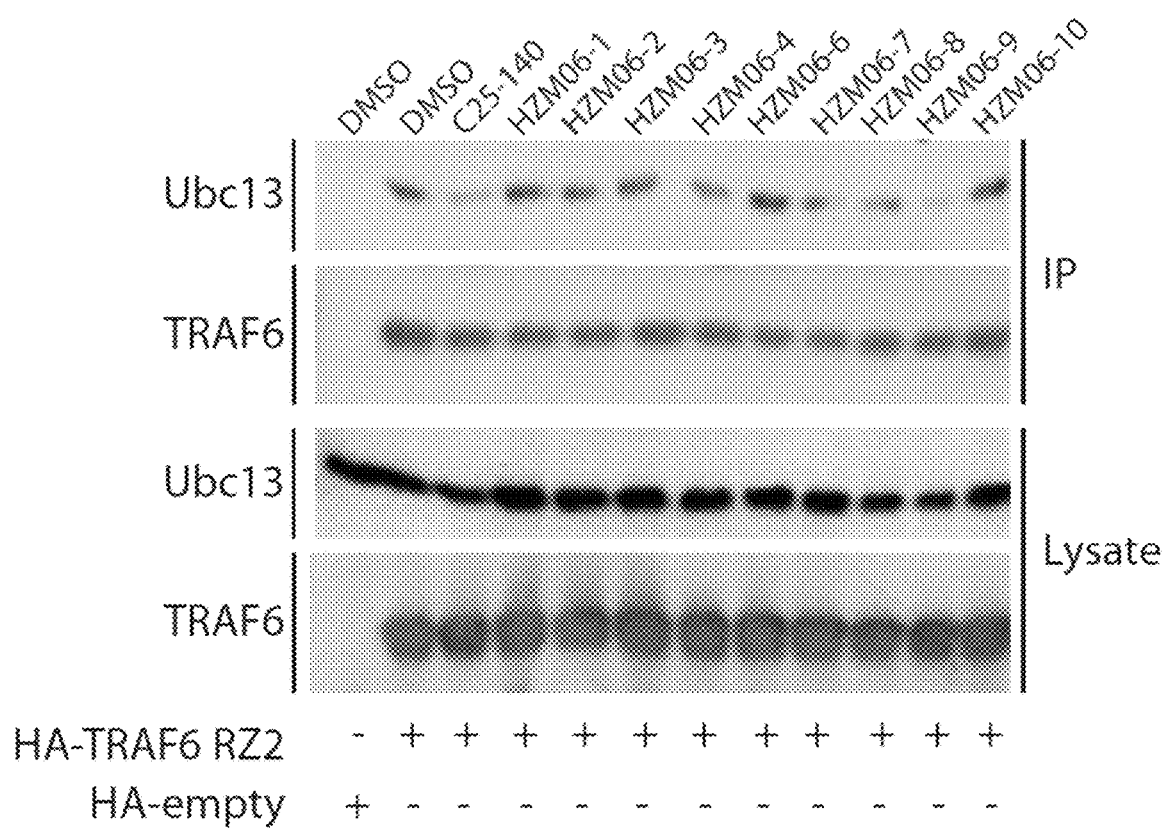

FIG. 19: Co-Immunoprecipitation studies of 9 structural analogs of C25-140 reveal inhibitory potential of individual analogs in cells. In co-Immunoprecipitation studies, individual compounds including C25-140, HZM06-04, HZM06-07, HZM06-08 and HZM06-09 demonstrated inhibition of TRAF6-Ubc13 binding in HEK293T cells. C25 is equal to compound 1, C25-140 is equal to compound 3, HZM06-1 is equal to compound 28, HZM06-2 is equal to compound 29, HZM06-3 is equal to compound 30, HZM06-4 is equal to compound 31, HZM06-6 is equal to compound 32, HZM06-7 is equal to compound 33, HZM06-8 is equal to compound 34, HZM06-9 is equal to compound 35 and HZM06-10 is equal to compound 36 of the description.

FIG. 20: Analog compounds. All compounds were tested in the ALPHAScreen assay. Level of inhibition is indicated.

Figure 21:
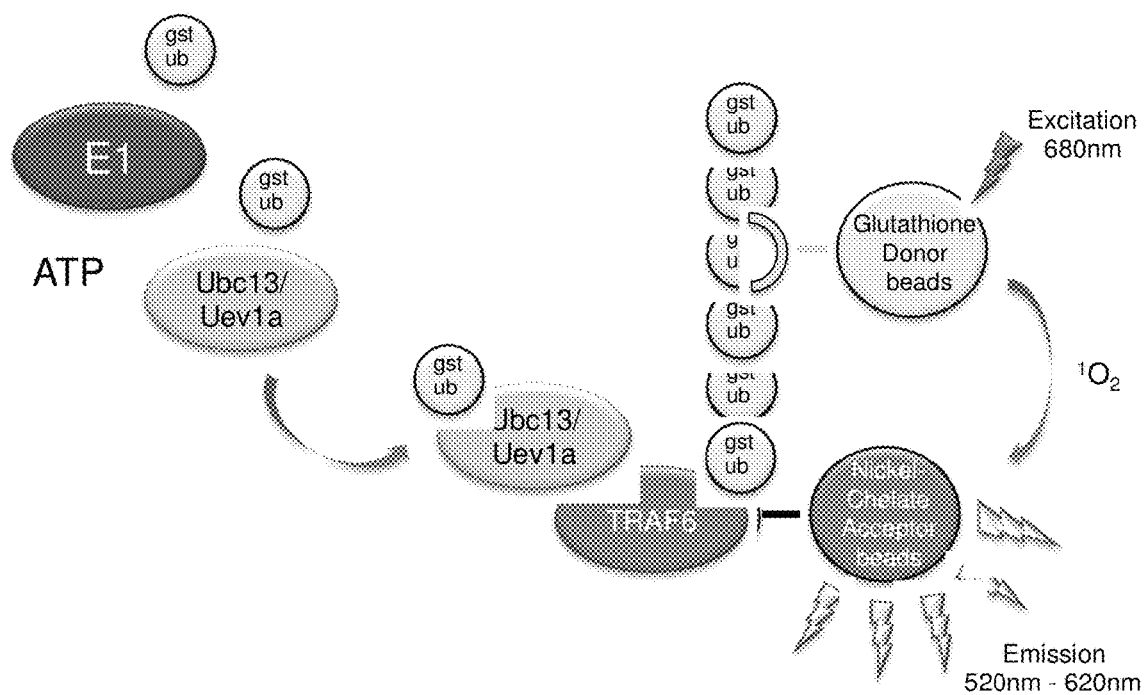
Figure 22:
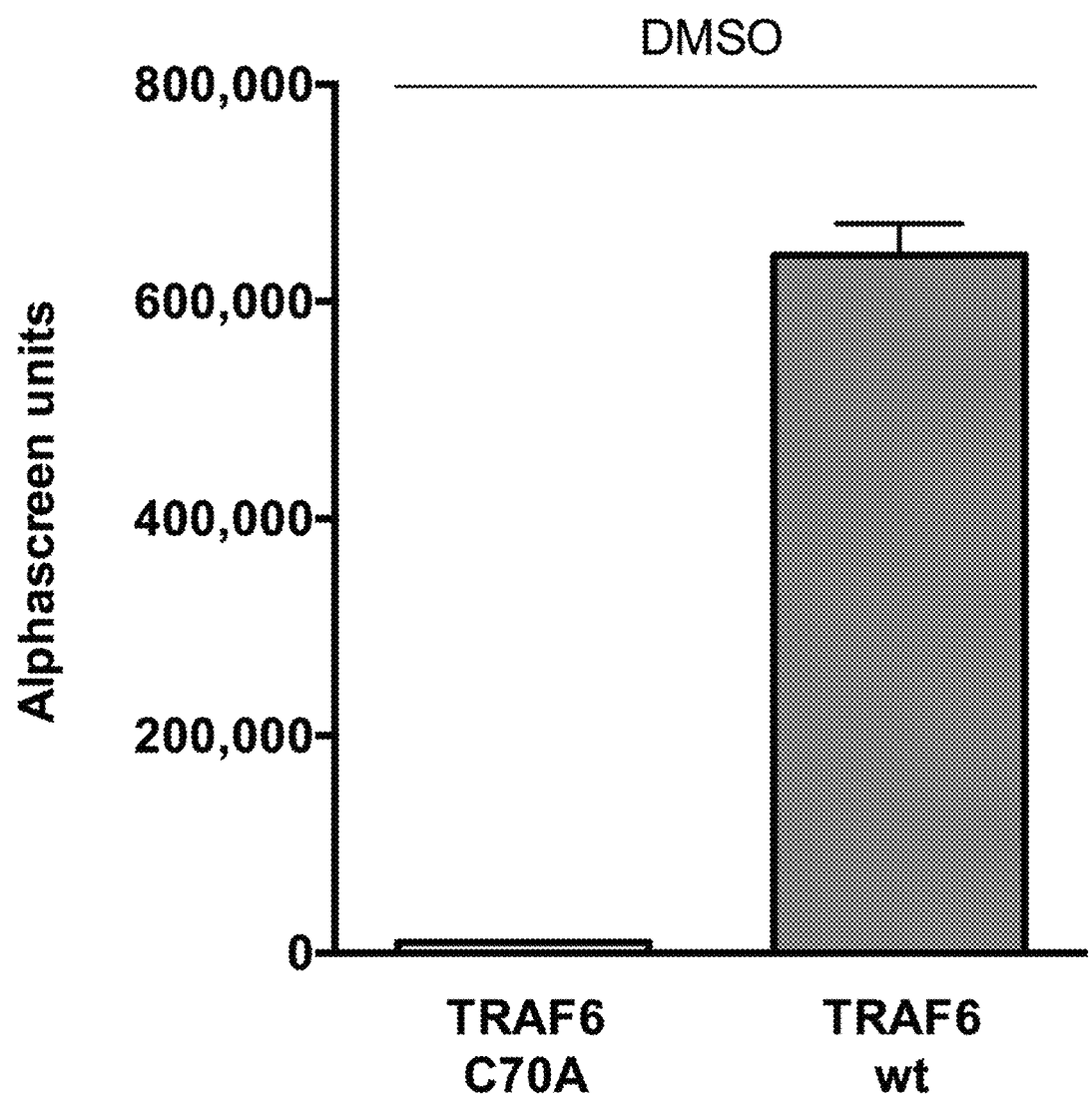

FIG. 21: FIG. 21 depicts one embodiment of the inventive assay. The ability of TRAF6 to generate poly-ubiquitin chains relies on its interaction with Ubc13. Covalent conjugation of single ubiquitin molecules to a poly-ubiquitin chain is measured. To this end, GST-tagged ubiquitin molecules are added to untagged E1, E2 (Ubc13/Uev1a) and E3 (TRAF6) proteins. The addition of ATP initiates the ubiquitination reaction and the generation of poly-ubiquitin chains as well as the auto-ubiquitination of TRAF6 in iterative cycles. First, E1 protein is activated by binding ubiquitin in an ATP-dependent manner. Next, the ubiquitin from ubiquitin-bound E1 is transferred to the E2 conjugating enzyme Ubc13. The ubiquitin-charged Ubc13 protein subsequently interacts with the TRAF6 RING E3 ligase to conjugate ubiquitin molecules. Here, GST-ubiquitin molecules are conjugated to TRAF6 in order to form a poly-ubiquitin chain. The proximity of GST-Ubiquitin to his-tagged TRAF6 will allow the transfer of the singlet oxygen from GST-bound Glutathione-Donor beads to His-bound Nickel-Chelate-Acceptor beads resulting in light generation that can be measured in a plate reader. As a negative control, the TRAF6 wildtype protein is replaced by the TRAF6 mutant C70A, which is no longer able to bind Ubc13 and thereby looses its ability to form poly-ubiquitin chains. Notably, the TRAF6 C70A mutant defines the maximum inhibition (=minimum signal) that compounds can achieve as E1 and E2 enzymes together are also slightly able to conjugate ubiquitin molecules. However, the addition of the TRAF6 wildtype protein to the ubiquitination assay mixture initiates a 60-fold induction of poly-ubiquitin-chain generation (FIG. 22). Altogether, test compounds binding to TRAF6 will impede its interaction to Ubc13 and will therefore interfere with ubiquitin-conjugation, resulting in reduced poly-ubiquitin-chains species and AlphaScreen® signals.

FIG. 22: See FIG. 21.

DETAILED DESCRIPTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments described throughout the specification should not be construed to limit the present invention to only the explicitly described embodiments. This description should be understood to support and encompass embodiments which combine the explicitly described embodiments with any number of the disclosed and/or preferred elements. Furthermore, any permutations and combinations of all elements described herein should be considered disclosed by the description of the present application unless the context indicates otherwise. For example, if in one embodiment $R^1$ of the compounds of the invention is heteroaryl (such as pyrazolyl) and in another embodiment of the compounds of the invention B is a substituted or unsubstituted phenyl ring, then in a preferred embodiment, $R^1$ of the compounds of the invention is heteroaryl (such as pyrazolyl) and B is a substituted or unsubstituted phenyl ring.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Compounds

In order that the present invention may be more readily understood, certain terms are first defined. Additional definitions are set forth throughout the description.

As used herein and throughout the entire description, the term "alkyl" refers to a monoradical of a saturated straight or branched hydrocarbon. Preferably, the alkyl group comprises from 1 to 6 carbon atoms, i.e., 1, 2, 3, 4, 5 or 6 carbon atoms, preferably 1 to 4 carbon atoms. In another embodiment, the alkyl group employed contains 1-5 carbon atoms ($C_{1-5}$-alkyl). In another embodiment, the alkyl group employed contains 1-4 carbon atoms ($C_{1-4}$ alkyl). In another embodiment, the alkyl group employed contains 1-3 carbon atoms ($C_{1-3}$ alkyl). In another embodiment, the alkyl group employed contains 1-2 carbon atoms ($C_{1-2}$ alkyl). In another embodiment, the alkyl group employed is methyl. Examples of alkyl radicals include, but are not limited to, methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl and the like, which may bear one or more substituents. Alkyl group substituents include, but are not limited to, any of the substituents described herein, that result in the formation of a stable moiety. A substituted alkyl group can be substituted in any positions, provided that the resulting compound is sufficiently stable and is suitable as a pharmaceutical active compound. The prerequisite that a specific group and a compound of any one of formulas I, II, III, IV and XX is sufficiently stable and suitable as a pharmaceutical active compound, applies in general with respect to all groups in the compounds of any one of formulas I, II, III, IV and XX. If an alkyl group can be monosubstituted or polysubstituted by fluorine, it can be unsubstituted, i.e. not carry fluorine atoms, or substituted, for example by 1, 2, 3, 4, 5, 6, 7, 8, 9, 10 or 11 fluorine atoms, preferably by 1, 2, 3, 4 or 5 fluorine atoms, which can be present in any positions. For example, in a fluoro-substituted alkyl group one or more methyl groups can carry three fluorine atoms each and be present as trifluoromethyl groups, and/or one or more methylene groups ($CH_2$) can carry two fluorine atoms each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethanesulfanyl-(CF$_3$—S—), trifluoromethanesulfinyl-(CF$_3$—S(O)—) and trifluoromethanesulfonyl-(CF$_3$—S(O)$_2$—). In some embodiments the alkyl group may be substituted by one or more identical or different substituents chosen from halogen, hydroxyl, cyano, (C$_1$-C$_6$)alkyl-O— and (C$_1$-C$_6$)alkyl-S(O)$_m$—. Examples of (C$_1$-C$_6$)alkyl-O— are methoxy, ethoxy, n-propoxy, isopropoxy, n-butoxy, isobutoxy, tert-butoxy and n-pentoxy. Examples of alkyl-S(O)$_m$— are methanesulfanyl-(CH$_3$—S—, methylsulfanyl), methanesulfinyl-(CH$_3$—S(O)—), methanesulfonyl-(CH$_3$—S(O)$_2$—), ethanesulfanyl-(CH$_3$—CH$_2$—S—, ethylsulfanyl-), ethanesulfinyl-(CH$_3$—CH$_2$—S(O)—), ethanesulfonyl-(CH$_3$—CH$_2$—S(O)$_2$—), 1-methylethanesulfanyl-((CH$_3$)$_2$CH—S—, 1-methylethylsulfanyl-), 1-methylethanesulfinyl-((CH$_3$)$_2$CH—S(O)—) and 1-methylethanesulfonyl-((CH$_3$)$_2$CH— S(O)$_2$—). In one embodiment of the invention the number m is chosen from 0 and 2, wherein all numbers m are independent of each other and can be identical or different. For example, if the alkyl group is substituted by a CF$_3$—S— group, the CF$_3$—S— group is bonded to this alkyl group via the sulfur as it is symbolized by the terminal line (hyphen) next to the sulfur atom representing a free bond. In some embodiments the alkyl chain is a linear. In some embodiments the alkyl chain is branched. In some embodiments the alkyl chain is substituted. In some embodiment the alkyl chain is unsubstituted. In some embodiments the alkyl chain is linear and substituted or unsubstituted. In some embodiments the alkyl chain is branched and substituted or unsubstituted.

As used herein and throughout the entire description, the term "alkylene" refers to a diradical of a saturated straight or branched hydrocarbon. Preferably, the alkylene comprises from 1 to 6 carbon atoms, i.e., 1, 2, 3, 4, 5 or 6 carbon atoms, more preferably 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like. Alkylene groups may be cyclic or acyclic, branched or unbranched, substituted or unsubstituted. Alkylene group substituents include, but are not limited to, any of the substituents described herein, that result in the formation of a stable moiety.

As used herein and throughout the entire description, the term "haloalkyl" refers to an alkyl group substituted by one halogen substituent up to per halo-substitution. The halogen substituent is preferably fluorine. The haloalkyl is preferably a perfluoroalkyl. In some embodiments, the haloalkyl group employed in the invention contains 1-6 carbon atoms (C$_{1-6}$ haloalkyl). In another embodiment, the haloalkyl group employed contains 1-5 carbon atoms (C$_{1-5}$ haloalkyl). In another embodiment, the haloalkyl group employed contains 1-4 carbon atoms (C$_{1-4}$ haloalkyl). In another embodiment, the haloalkyl group employed contains 1-3 carbon atoms (C$_{1-3}$ haloalkyl). In another embodiment, the haloalkyl group employed contains 1-2 carbon atoms (C$_{1-2}$ haloalkyl). In another embodiment, the haloalkyl group employed contains 1-carbon atom (C$_1$ haloalkyl). In another embodiment, the haloalkyl group employed is trifluoromethyl. Exemplary fluoro-substituted C$_1$-C$_2$ alkyl includes —CFH$_2$, —CF$_2$H, —CF$_3$, CH$_2$CH$_2$F, —CH$_2$CHF$_2$, —CHFCH$_3$, —CHFCH$_3$, —CF$_2$CHF$_2$. Perfluoro-substituted C$_1$-C$_2$ haloalkyl, for example include —CF$_3$, and —CF$_2$CF$_3$.

As used herein and throughout the entire description, the term "heteroalkyl," as used herein, refers to an alkyl moiety, as defined herein, which contain one or more heteroatoms (e.g., oxygen, sulfur, nitrogen, phosphorus, or silicon atoms) in between carbon atoms. The heteroalkyl may be substituted or unsubstituted. In certain embodiments, the heteroalkyl group contains 1-6 carbon atoms and 1-3 heteroatoms (C$_{1-6}$ heteroalkyl). In certain embodiments, the heteroalkyl group contains 1-5 carbon atoms and 1-3 heteroatoms (C$_{1-5}$ heteroalkyl). In certain embodiments, the heteroalkyl group contains 1-4 carbon atoms and 1-2 heteroatoms (C$_{1-4}$ heteroalkyl). In certain embodiments, the heteroalkyl group contains 1-3 carbon atoms and 1 heteroatom (C$_{1-3}$ heteroalkyl). In certain embodiments, the heteroalkyl group contains 1-2 carbon atoms and 1 heteroatom (C$_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. In certain embodiments the heteroalkyl group is a substituted heteroalkyl group containing 1-6 carbon atoms and 1-3 heteroatoms (C$_{1-6}$ heteroalkyl). In certain embodiments the heteroalkyl group is an unsubstituted heteroalkyl group containing 1-6 carbon atoms and 1-3 heteroatoms (C$_{1-6}$ heteroalkyl). In some embodiments the heteroalkyl is an alkyl moiety wherein on methylene group is replaced by S. In some embodiments the heteroalkyl is an alkyl moiety wherein on methylene group is replaced by O. In some embodiments the heteroalkyl is an alkyl moiety wherein on methylene group is replaced by NR$^A$, wherein R$^A$ is selected from the group consisting of hydrogen, substituted or unsubstituted (C$_1$-C$_6$)alkyl, substituted or unsubstituted (C$_3$-C$_8$)cycloalkyl, substituted or unsubstituted (C$_6$-C$_{14}$)aryl and substituted or unsubstituted (C$_3$-C$_{14}$) heteroaryl. In some embodiments heteroalkyl is —CH$_2$SCH$_3$. In some embodiments heteroalkyl is —CH$_2$OCH$_3$.

As used herein and throughout the entire description, the term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. In certain embodiments, the alkenyl group employed in the invention contains 2-20 carbon atoms ($C_{2-20}$ alkenyl). In some embodiments, the alkenyl group employed in the invention contains 2-15 carbon atoms ($C_{2-15}$ alkenyl). In another embodiment, the alkenyl group employed contains 2-10 carbon atoms ($C_{2-10}$ alkenyl). In still other embodiments, the alkenyl group contains 2-8 carbon atoms ($C_{2-8}$ alkenyl). In yet other embodiments, the alkenyl group contains 2-6 carbons ($C_{2-6}$ alkenyl). In yet other embodiments, the alkenyl group contains 2-5 carbons ($C_{2-5}$ alkenyl). In yet other embodiments, the alkenyl group contains 2-4 carbons ($C_{2-4}$ alkenyl). In yet other embodiments, the alkenyl group contains 2-3 carbons ($C_{2-3}$ alkenyl). In yet other embodiments, the alkenyl group contains 2 carbons ($C_2$ alkenyl). The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. Alkenyl group substituents include, but are not limited to, any of the substituents described herein, that result in the formation of a stable moiety. A substituted alkenyl group can be substituted in any positions, provided that the resulting compound is sufficiently stable and is suitable as a pharmaceutical active compound. The prerequisite that a specific group and a compound of any one of formulas I, II, III, IV, and XX is sufficiently stable and suitable as a pharmaceutical active compound, applies in general with respect to all groups in the compounds of any one of formulas I, II, III, IV, and XX. In some embodiments the alkenyl group may be substituted by one or more identical or different substituents chosen from halogen, hydroxyl, cyano, ($C_1$-$C_6$)alkyl-O— and ($C_1$-$C_6$)alkyl-S(O)$_m$—. In one embodiment of the invention the number m is chosen from 0 and 2, wherein all numbers m are independent of each other and can be identical or different. In some embodiments the alkenyl chain is a linear. In some embodiments the alkenyl chain is branched. In some embodiments the alkenyl chain is substituted. In some embodiment the alkenyl chain is unsubstituted. In some embodiments the alkenyl chain is linear and substituted or unsubstituted. In some embodiments the alkenyl chain is branched and substituted or unsubstituted. Alkenyl group substituents include, but are not limited to, any of the substituents described herein, that result in the formation of a stable moiety.

As used herein and throughout the entire description, the term "cycloalkyl" or "cycloaliphatic" or "carbocyclic" or "carbocycle" represents cyclic non-aromatic versions of "alkyl" and "alkenyl" with preferably 3 to 8 carbon atoms i.e., 3, 4, 5, 6, 7 or 8 carbon atoms, more preferably 3 to 7 carbon atoms. In another embodiment, the cycloalkyl group employed in the invention contains 3-7 carbon atoms ($C_{3-7}$ cycloalkyl). In another embodiment, the cycloalkyl group employed in the invention contains 3-6 carbon atoms ($C_{3-6}$ cycloalkyl). In another embodiment, the cycloalkyl group employed in the invention contains 3-5 carbon atoms ($C_{3-5}$ cycloalkyl). In another embodiment, the cycloalkyl group employed in the invention contains 3-4 carbon atoms ($C_{3-4}$ cycloalkyl). In another embodiment, the cycloalkyl group employed in the invention contains 3 carbon atoms ($C_3$ cycloalkyl). Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl and cyclooctenyl. The double bond in a cycloalkenyl group can be present in any position with respect to the carbon atom in position 1 via which the group is bonded to the reminder of the molecule, i.e. for example to the nitrogen atom in the compounds having a structure according to formula I, and cycloalkenyl can thus be cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, for example. In preferred embodiments of the present invention, a cycloalkyl group, such as ($C_3$-$C_7$)-cycloalkyl, in the definition of any group is chosen from a subgroup of any two or more of the said specific cycloalkyl groups, for example from cyclopropyl and cyclobutyl, or from cyclopropyl, cyclobutyl and cyclopentyl, or from cyclopropyl, cyclopentyl and cyclohexyl, or from cyclopentyl and cyclohexyl, or from cyclopentyl, cyclohexyl and cycloheptyl. Similarly, in preferred embodiments a cycloalkenyl group is chosen from a subgroup of any two or more of the said specific cycloalkenyl groups, for example from cyclopentenyl and cyclohexenyl, or from cyclohexenyl and cycloheptenyl, or from cyclopent-1-enyl, cyclopent-2-enyl, cyclohex-1-enyl, cyclohex-2-enyl, cyclohept-1-enyl and cyclohept-2-enyl, or from cyclopent-2-enyl, cyclopent-3-enyl, cyclohex-2-enyl, cyclohex-3-enyl, cyclohept-2-enyl, cyclohept-3-enyl and cyclohept-4-enyl, or from cyclopent-2-enyl and cyclohex-2-enyl, or from cyclopent-2-enyl, cyclohex-2-enyl and cyclohept-2-enyl. Cycloalkyl groups and cycloalkenyl groups generally are optionally substituted by one or more ($C_1$-$C_4$)-alkyl substituents. I.e., they are unsubstituted, i.e. do not carry alkyl substituents, or substituted, for example by 1, 2, 3 or 4 identical or different ($C_1$-$C_4$)-alkyl substituents, for example by methyl groups and/or ethyl groups and/or isopropyl groups and/or tert-butyl groups, in particular by methyl groups, which substituents can be present in any positions. Examples of alkyl-substituted cycloalkyl groups are 1-methyl-cyclopropyl, 2,2-dimethyl-cyclopropyl, 1-methyl-cyclopentyl, 2,3-dimethyl-cyclopentyl, 1-methyl-cyclohexyl, 4-methyl-cyclohexyl, 4-isopropyl-cyclohexyl, 4-tert-butyl-cyclohexyl and 3,3,5,5-tetramethyl-cyclohexyl. Examples of alkyl-substituted cycloalkenyl groups are 1-methyl-cyclopent-2-enyl, 2-methyl-cyclopent-2-enyl, 3-methyl-cyclopent-2-enyl, 3,4-dimethyl-cyclopent-3-enyl, 1-methyl-cyclohex-2-enyl, 2-methyl-cyclohex-2-enyl, 3-methyl-cyclohex-2-enyl, 4-methyl-cyclohex-2-enyl, 2-methyl-cyclohex-3-enyl, 3-methyl-cyclohex-3-enyl, 4-methyl-cyclohex-3-enyl, 2,3-dimethyl-cyclohex-2-enyl, 4,4-dimethyl-cyclohex-2-enyl, 3,4-dimethyl-cyclohex-3-enyl. Cycloalkyl groups and cycloalkenyl groups generally also are optionally substituted by one or more fluorine atoms. I.e., they are unsubstituted, i.e. do not carry fluorine atoms, or substituted, for example by 1, 2, 3, 4, 5, 6, 7, 8, 9, 10 or 11 fluorine atoms, preferably by 1, 2, 3, 4, 5 or 6 fluorine atoms. Cycloalkyl groups and cycloalkenyl groups can also be substituted simultaneously by fluorine and alkyl. The fluorine atoms can be present in any positions and can also be present in an alkyl substituent. Examples of fluoro-substituted cycloalkyl groups are 1-fluoro-cyclopropyl, 2,2-difluoro-cyclopropyl, 3,3-difluoro-cyclobutyl, 1-fluoro-cyclohexyl, 4,4-difluoro-cyclohexyl and 3,3,4,4,5,5-hexafluoro-cyclohexyl. Examples of fluoro-substituted cycloalkenyl groups are 1-fluoro-cyclopent-2-enyl, 1-fluoro-cyclohex-2-enyl, 4-fluoro-cyclohex-2-enyl, 4,4-difluoro-cyclohex-2-enyl. In one embodiment of the invention, cycloalkyl groups are not optionally substituted by substituents chosen from fluorine and ($C_1$-$C_4$)-alkyl. If a cycloalkyl group or cycloalkenyl group can be substituted by further substituents like hydroxy, it can be substituted by one or more such further substituents like hydroxy only and not by substituents chosen from fluorine and ($C_1$-$C_4$)-alkyl, or by one or more such further substituents and simultaneously by one or more substituents chosen from fluorine and ($C_1$-$C_4$)-alkyl. The number of such further substituents like hydroxy which can be present on a cycloalkyl or cycloalkenyl group, preferably is 1, 2 or 3, more preferably 1 or 2, for example 1. The total number of all substituents in a cycloalkyl group or cycloalkenyl group preferably is 1, 2, 3, 4, 5, 6, 7 or 8, more preferably 1, 2, 3, 4 or 5, for example 1, 2 or 3. Such further substituents like hydroxy can be present in any positions, provided that the resulting compound is sufficiently stable and is suitable as a subgroup in a pharmaceutical active compound. Preferably, a hydroxy substituent is not present in position 1 of a cycloalkenyl group or cycloalkyl group and in a cycloalkenyl group a hydroxy substituent is not present on a carbon atom which is part of the double bond. Examples of hydroxy-substituted cycloalkyl groups are 3-hydroxy-cyclobutyl, 2-hydroxy-cyclopentyl, 3-hydroxy-cyclopentyl, 3,4-dihydroxy-cyclopentyl, 2-hydroxy-cyclohexyl, 3-hydroxy-cyclohexyl, 4-hydroxy-cyclohexyl, 2,3-dihydroxy-cyclohexyl, 2,4-dihydroxy-cyclohexyl, 3,4-dihydroxy-cyclohexyl, 3,5-dihydroxy-cyclohexyl, 3,4,5-trihydroxy-cyclohexyl, 2-hydroxy-cycloheptyl, 3-hydroxy-cycloheptyl, 4-hydroxy-cycloheptyl. Examples of hydroxy-substituted cycloalkenyl groups are 5-hydroxy-cyclopent-2-enyl, 4-hydroxy-cyclohex-2-enyl, 5-hydroxy-cyclohex-2-enyl, 6-hydroxy-cyclohex-2-enyl, 6-hydroxy-cyclohex-3-enyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl. Cycloalkyl group substituents include, but are not limited to, any of the substituents described herein, that result in the formation of a stable moiety.

As used herein and throughout the entire description, the term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

As used herein and throughout the entire description, the term "aryl" or "aromatic ring" refers to an aromatic mono- or polycyclic ring system having 6-10 ring atoms, of which all the ring atoms are carbon, and which may be substituted or unsubstituted. In certain embodiments of the present invention, "aryl" refers to a mono or bicyclic $C_6$-$C_{10}$ aromatic ring system having one or two aromatic rings which include, but are not limited to, phenyl, biphenyl, naphthyl, and the like, which may bear one or more substituents. Preferably, the aryl group contains 6 to 10 carbon atoms, which can be arranged in one ring (e.g., phenyl) or two or more condensed rings (e.g., naphthyl). Exemplary aryl groups include cyclopropenylium, cyclopentadienyl, phenyl, indenyl, naphthyl and azulenyl. Preferably, "aryl" refers to a monocyclic ring containing 6 carbon atoms or an aromatic bicyclic ring system containing 10 carbon atoms. Preferred examples are substituted or unsubstituted phenyl and naphthyl. Even more preferred is substituted or unsubstituted phenyl. In certain embodiments, the aryl group employed in the invention contains 7-10 carbon atoms ($C_{7-10}$ aryl). In another embodiment, the aryl group employed in the invention contains 6-8 carbon atoms ($C_{6-8}$ aryl). In another embodiment, the aryl group employed in the invention contains 6 carbon atoms ($C_6$ aryl). In another embodiment, the aryl group employed in the invention contains 10 carbon atoms ($C_{10}$ aryl).

In substituted aryl groups, the substituents can be present in any positions. In monosubstituted phenyl groups, the substituent can be present in the 2-position, the 3-position or the 4-position. In disubstituted phenyl groups, the substituents can be present in 2, 3-position, 2,4-position, 2,5-position, 2,6-position, 3,4-position or 3,5-position. In trisubstituted phenyl groups, the substituents can be present in 2, 3,4-position, 2,3,5-position, 2,3,6-position, 2,4,5-position, 2,4,6-position or 3,4,5-position. If a phenyl group carries four substituents, of which one, two, three or four substituents can be fluorine atoms, for example, the unsubstituted ring carbon atom can be present in the 2-position, the 3-position or the 4-position. If a polysubstituted phenyl group or heteroaryl group carries different substituents, each substituent can be present in any suitable position, and the present invention comprises all positional isomers. The number of substituents in a substituted phenyl group can be 1, 2, 3, 4 or 5. Preferably, a substituted phenyl group, and likewise a substituted heteroaryl group, carries 1, 2 or 3, in particular 1 or 2, identical or different substituents. In a preferred embodiment the substituted phenyl group carries 1 substituent in 2, 3 or 4-position. In preferred embodiments of the invention, the substituents in substituted phenyl and heteroaryl groups are chosen from any subgroup of the substituents listed in the respective definition, for example by substituents chosen from halogen, substituted or unsubstituted ($C_1$-$C_6$)-alkyl, ($C_1$-$C_4$)-haloalkyl, —$NO_2$, cyano, halogen, substituted or unsubstituted ($C_1$-$C_6$)alkyl-O—, substituted or unsubstituted ($C_6$-$C_{14}$)aryl($C_1$-$C_6$)alkyl-O—, —C(O)$NH_2$, —C(O)NH(($C_1$-$C_6$)-alkyl), —C(O)N(($C_1$-$C_6$)-alkyl)$_2$, —NH(($C_1$-$C_6$)alkyl-O($C_1$-$C_6$)alkyl)), —NH(($C_1$-$C_6$)alkyl-OH), azido, —NH(C(=O)($C_1$-$C_6$)alkyl) and —N(($C_1$-$C_6$)alkyl)(C(=O)($C_1$-$C_6$)alkyl).

As used herein and throughout the entire description, the term "arylene" refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety.

As used herein and throughout the entire description, the term "heteroaryl" or "heteroaromatic ring" means an aryl group as defined above in which one or more carbon atoms in the aryl group are replaced by heteroatoms of O, S, or N. Preferably, the heteroaryl group contains 3 to 10 carbon atoms. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of 0 atoms is 1, the maximum number of S atoms is 1, and the maximum total number of O and S atoms is 2. In certain embodiments, the heteroaryl group employed in the invention is a five membered aromatic monocyclic ring wherein 1, 2, or 3 carbon atoms are replaced by the same or different heteroatoms of O, N, or S. In certain embodiments, the heteroaryl group employed in the invention is a five membered aromatic monocyclic ring wherein 1, 2, or 3 carbon atoms are replaced by the same or different heteroatoms of 0. In certain embodiments, the heteroaryl group employed in the invention is a five membered aromatic monocyclic ring wherein 1, 2, or 3 carbon atoms are replaced by the same or different heteroatoms of O and N. In certain embodiments, the heteroaryl group employed in the invention is a five membered aromatic monocyclic ring wherein 1, 2, or 3 carbon atoms are replaced by the same or different heteroatoms of O and S. In certain embodiments, the heteroaryl group employed in the invention is a five membered aromatic monocyclic ring wherein 1, 2, or 3 carbon atoms are replaced by the same or different heteroatoms of N and S. In certain embodiments, the heteroaryl group employed in the invention is a six membered aromatic monocyclic ring wherein 1, 2, or 3 carbon atoms are replaced by the same or different heteroatoms of O, S or N. In certain embodiments, the heteroaryl group employed in the invention is a six membered aromatic monocyclic ring wherein 1, 2, or 3 carbon atoms are replaced by N. In certain embodiments, the heteroaryl group employed in the invention is an aromatic bicyclic system wherein 1, 2, 3, 4, or 5 carbon atoms are replaced with the same or different heteroatoms of O, N, or S. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, azaindolyl (4-, 5-6- and 7-), diazaindolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, pyrrolopyrrolyl, and the like, which may bear one or more substituents. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl. Exemplary bicyclic heteroaryl groups 7-azaindolyl, 6-azaindolyl, 5-azaindolyl, 4-azaindolyl, benzofuranyl and indolyl. Heteroaryl substituents include, but are not limited to, any of the substituents described herein, that result in the formation of a stable moiety.

In substituted heteroaryl groups, the substituents can be present in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position, in a 1H-pyrazol-4-yl group in the 3-position and/or in the 5-position and/or in the 1-position, in a 1H-pyrazol-1-yl group in the 3-position and/or in the 5-position and/or in the 4-position, in a 1H-indol-1-yl group in the 2-position and/or in the 3-position and/or in the 4-position and/or in the 5-position and/or in the 6-position and/or in the 7-position, in a 1H-indol-3-yl group in the 1-position and/or in the 2-position and/or in the 4-position and/or in the 5-position and/or in the 6-position and/or in the 7-position. The substituted heteroaryl groups can be monosubstituted or polysubstituted, i.e. the carry more than one substituent. In preferred embodiments a 1H-indol-1-yl group is substituted in 2-position and 3-position and/or in 6-position and 7-position. In other preferred embodiments a 1H-indol-3-yl group is substituted in 1-position and 7-position and/or in 6-position and 7-position. Preferably, a substituted heteroaryl group is substituted by one, two or three, in particular one or two, for example one, identical or different substituents. If a ring nitrogen atom is present which can carry a hydrogen atom or a substituent, the substituent on this nitrogen atom can be a methyl group, an ethyl group, a propyl group or a tert-butyl group, for example, which groups can also be monosubstituted or polysubstituted by fluorine. Generally, suitable ring nitrogen atoms in an aromatic ring of a heteroaryl group, for example the nitrogen atom in a pyridinyl group can also carry an oxido substituent —O⁻ and compounds of formula I, formula II, formula III, formula IV, and XX thus be present in the form of an N-oxide.

As used herein and throughout the entire description, the term "heteroarylene" refers to a biradical derived from a heteroaryl group, as defined herein, by removal of two hydrogen atoms. Heteroarylene groups may be substituted or unsubstituted.

As used herein and throughout the entire description, the terms "arylalkyl" and "heteroarylalkyl" are meant to include those radicals in which an aryl group and heteroaryl group, respectively, is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Preferably the Arylalkyl is a substituted or unsubstituted $(C_6-C_{10})$aryl$(C_1-C_6)$alkyl. Preferably the Heteroarylalkyl is a substituted or unsubstituted $(C_3-C_{10})$heteroaryl$(C_1-C_6)$alkyl. In some embodiments the alkyl chain is a linear. In some embodiments the alkyl chain is branched. In some embodiments the alkyl chain is substituted. In some embodiments the alkyl chain is unsubstituted. In some embodiments the alkyl chain is linear and substituted or unsubstituted. In some embodiments the alkyl chain is branched and substituted or unsubstituted.

As used herein and throughout the entire description, the terms "arylheteroalkyl" and "heteroarylheteroalkyl" are meant to include those radicals in which an aryl group and heteroaryl group, respectively, is attached to an heteroalkyl group. In some embodiments the heteroalkyl chain is a linear. In some embodiments the heteroalkyl chain is branched. In some embodiments the heteroalkyl chain is substituted. In some embodiments the heteroalkyl chain is unsubstituted. In some embodiments the heteroalkyl chain is linear and substituted or unsubstituted. In some embodiments the heteroalkyl chain is branched and substituted or unsubstituted.

As used herein and throughout the entire description, the term "halogen" or "halo" means fluoro, chloro, bromo, or iodo.

As used herein and throughout the entire description, the term "cyano" mean —CN.

As used herein and throughout the entire description, the term "azido" means $N_3$.

As used herein and throughout the entire description, the term "optionally substituted" or "substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group different from hydrogen such as $(C_1-C_6)$alkyl, $(C_1-C_6)$heteroalkyl, $(C_1-C_6)$haloalkyl; $(C_2-C_6)$alkenyl, $(C_3-C_8)$cycloalkyl, $(C_6-C_{10})$aryl, $(C_6-C_{10})$aryl$(C_1-C_6)$alkyl, $(C_3-C_{10})$heteroaryl, $(C_3-C_{10})$heteroaryl$(C_1-C_6)$alkyl, halogen, —CN, —NO$_2$, —OR$^{16}$, —N(R$^{162}$)(R$^{163}$), —N(R$^{161}$)(OR$^{161}$), —S(O)$_{0-2}$R$^{161}$,
—S(O)$_{1-2}$OR$^{161}$, —OS(O)$_{1-2}$R$^{161}$, —OS(O)$_{1-2}$OR$^{161}$, —S(O)$_{1-2}$N(R$^{162}$)(R$^{163}$), —OS(O)$_{1-2}$N(R$^{162}$)(R$^{163}$), —N(R$^{161}$)S(O)$_{1-2}$R$^{161}$, —NR$^{161}$S(O)$_{1-2}$OR$^{161}$, —NR$^{161}$S(O)$_{1-2}$N(R$^{162}$)(R$^{163}$), —C(=W)R$^{161}$, —C(=W)WR$^{161}$, —WC(=W)R$^{161}$, and —WC(=W)WR$^{161}$; wherein R$^{161}$, R$^{162}$, and R$^{163}$ are independently selected from the group consisting of —H, alkyl, alkenyl, alkynyl, cycloalkyl, aryl and heteroaryl, preferably wherein R$^{161}$, R$^{162}$, and R$^{163}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl; R$^{164}$ is independently selected from the group consisting of —H, alkyl, alkenyl, alkynyl, cycloalkyl, aryl, heteroaryl, and —OR$^{161}$; W is independently selected from O, S, and N(R$^{164}$).

As used herein and throughout the entire description, the term "optional" or "optionally" as used herein means that the subsequently described event, circumstance or condition may or may not occur, and that the description includes instances where said event, circumstance, or condition occurs and instances in which it does not occur.

As used herein and throughout the entire description, the term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

As used herein and throughout the entire description, the term "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Physiologically acceptable salts of the compounds of the present invention are in particular salts with a nontoxic salt component and preferably are pharmaceutically utilizable salts. They can contain inorganic or organic salt components. Such salts can be formed, for example, from compounds of the present invention which contain an acidic group, for example a carboxylic acid group (HO—CO—) or a sulfonic acid group (HO—S(O)$_2$—) and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the present invention with bases for the preparation of the salts are in general carried out according to customary procedures in a solvent or diluent. On account of the physiological and chemical stability, advantageous salts of acidic groups are in many cases sodium, potassium, magnesium or calcium salts or ammonium salts which can also carry one or more organic groups on the nitrogen atom. Compounds of the present invention which contain a basic, i.e. protonatable, group, for example an amino group or another basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the present invention by reaction with an acid in a solvent or diluent according to customary procedures. As usual, in particular in the case of acid addition salts of a compound containing two or more basic groups, in an obtained salt the ratio of the salt components can deviate upward or downward from the stoichiometric ratio, such as the molar ratio 1:1 or 1:2 in the case of the acid addition salt of a compound of the present invention containing one or two basic groups with a monovalent acid, and vary depending on the applied conditions. The present invention comprises also salts containing the components in a non-stoichiometric ratio, and an indication that an acid addition salt of a compound of the present invention contains an acid in equimolar amount, for example, also allows for a lower or higher amount of acid in the obtained salt, for example about 0.8 or about 1.1 mol of acid per mol of compound of the present invention. If the compounds of the present invention simultaneously contain an acidic and a basic group in the molecule, the invention also includes internal salts (betaines, zwitterions) in addition to the salt forms mentioned. The present invention also comprises all salts of the compounds of the present invention which, because of low physiological tolerability, are not directly suitable for use as a pharmaceutical, but are suitable as intermediates for chemical reactions or for the preparation of physiologically acceptable salts, for example by means of anion exchange or cation exchange. A subject of the present invention also are solvates of the compounds of the present invention and their salts, such as hydrates and adducts with alcohols like $(C_1-C_4)$-alkanols, in particular physiologically acceptable solvates, as well as active metabolites of compounds of the present As used herein and throughout the entire description, the term "pharmaceutically acceptable" may in particular mean approved by a regulatory agency or other generally recognized pharmacopoeia for use in animals, and more particularly in humans.

The present invention comprises all stereoisomeric forms of the compounds of the formula I, for example, all possible enantiomers and diastereomers including cis/trans isomers. The invention likewise comprises mixtures of two or more stereoisomeric forms, for example mixtures of enantiomers and/or diastereomers including cis/trans isomers, in all ratios.

Asymmetric centers contained in the compounds of the formula I for example in unsubstituted or substituted alkyl groups or in the stereogenic carbon CH—B, in case that p and q are not equal, depicted in formula I, can all independently of one another have the S configuration or the R configuration. The invention relates to enantiomers, both the levorotatory and the dextrorotatory antipode, in enantiomerically pure form and substantially enantiomerically pure form and in the form of racemates and in the form of mixtures of the two enantiomers in all ratios. The invention likewise relates to diastereomers in the form of pure and substantially pure diastereomers and in the form of mixtures of two or more diastereomers in all ratios. The invention also comprises all cis/trans isomers of the compounds of the formula I, for example, in pure form and substantially pure form and in the form of mixtures of the cis isomer and the trans isomer in all ratios. Cis/trans isomerism can occur in substituted cycloalkane rings for example. The preparation of individual stereoisomers, if desired, can be carried out by resolution of a mixture according to customary methods, for example by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the present invention.

In one aspect, the present invention provides compounds having a structure according to formula I, in any of their stereoisomeric forms or a mixture of stereoisomeric forms in any ratio, and the physiologically acceptable salts thereof, and the physiologically acceptable solvates or hydrates of any of them,

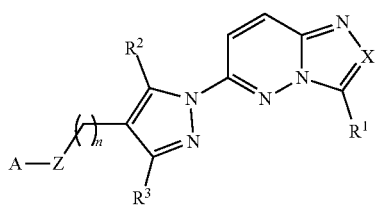

(I)

wherein

X is selected from the group consisting of N and CH;

$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl;

$R^2$ and $R^3$ are independently selected from the group consisting of hydrogen, $(C_1-C_6)$alkyl, $(C_1-C_6)$haloalkyl and $(C_3-C_8)$cycloalkyl;

n is an integer between 0 and 3;

Z is selected from the group consisting of C=O, C=S and $CH_2$;

A is selected from the group consisting of $-N(R^4)(R^5)$ and

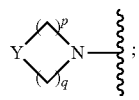

$R^4$ is hydrogen or $(C_1-C_6)$alkyl;

$R^5$ is selected from the group consisting of $(C_6-C_{10})$aryl $(C_1-C_6)$alkyl, $(C_3-C_{10})$heteroaryl$(C_1-C_6)$alkyl, $(C_3-C_{10})$heteroaryl$(C_1-C_6)$heteroalkyl and $(C_6-C_{10})$aryl $(C_1-C_6)$heteroalkyl, which are optionally substituted by one or more identical or different substituents selected from the group consisting of halogen, $(C_1-C_4)$alkyl, $(C_1-C_4)$haloalkyl and $-OR^6$;

$R^6$ is $(C_1-C_4)$alkyl or $(C_1-C_4)$haloalkyl;

Y is selected from the group consisting of N—B, CH—B and O;

B is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl, $(C_1-C_6)$alkyl and $N(R^7)$ $(R^8)$, which are optionally substituted by one or more identical or different substituents selected from the group consisting of halogen, $(C_1-C_4)$alkyl, $(C_1-C_4)$ haloalkyl and $-OR^6$;

$R^7$ is hydrogen or $(C_1-C_6)$alkyl;

$R^8$ is selected from the group consisting of $(C_6-C_{10})$aryl, $(C_3-C_{10})$heteroaryl, $(C_6-C_{10})$aryl$(C_1-C_6)$alkyl, $C_3-C_{10})$ heteroaryl$(C_1-C_6)$alkyl and $(C_1-C_6)$alkyl;

p is an integer between 1 and 2; and q is an integer between 1 and 3;

In some embodiments X is N. In some embodiments X is CH.

In some embodiments $R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl, in other embodiments from hydrogen, $(C_1-C_4)$alkyl, $(C_1-C_4)$ haloalkyl, $(C_3-C_6)$cycloalkyl, $(C_6-C_{10})$aryl, $(C_6-C_{10})$aryl $(C_1-C_4)$alkyl, $(C_3-C_{10})$heteroaryl and $(C_3-C_{10})$heteroaryl $(C_1-C_4)$alkyl, in other embodiments from hydrogen, $(C_1-C_6)$ alkyl, $(C_1-C_6)$haloalkyl, $(C_3-C_8)$cycloalkyl, $(C_6-C_{10})$aryl and $(C_6-C_{10})$aryl$(C_1-C_6)$alkyl, in other embodiments from hydrogen, $(C_1-C_6)$alkyl, $(C_3-C_8)$cycloalkyl, $(C_6-C_{10})$aryl and $(C_6-C_{10})$aryl$(C_1-C_6)$alkyl, in other embodiments from hydrogen, $(C_1-C_4)$alkyl, $(C_3-C_6)$cycloalkyl, $(C_6-C_{10})$aryl and $(C_6-C_{10})$aryl$(C_1-C_4)$alkyl, in other embodiments from hydrogen, $(C_1-C_4)$alkyl, $(C_3-C_6)$cycloalkyl and $(C_6)$aryl, $(C_6)$aryl$(C_1-C_4)$alkyl, in other embodiments from hydrogen, $(C_1-C_6)$alkyl and $(C_1-C_6)$haloalkyl, in other embodiments from hydrogen, $(C_1-C_4)$alkyl and $(C_1-C_4)$haloalkyl, in other embodiments from hydrogen, $(C_2-C_6)$alkyl and $(C_2-C_6)$ haloalkyl, in other embodiments from hydrogen, $(C_3-C_6)$ alkyl and $(C_3-C_6)$haloalkyl, in other embodiments from hydrogen and $(C_1-C_6)$alkyl, in other embodiments from hydrogen and $(C_1-C_4)$alkyl, in other embodiments from hydrogen and $(C_3-C_4)$alkyl, in other embodiments $R^1$ is $(C_1-C_6)$alkyl, preferably $(C_1-C_4)$alkyl, more preferably $(C_1-C_2)$alkyl, even more preferably methyl. In some embodiments $R^1$ is $(C_6-C_{10})$aryl, preferably wherein aryl is selected from the group of substituted or unsubstituted naphthyl and substituted or unsubstituted phenyl, more preferably wherein aryl is substituted or unsubstituted phenyl. In some embodiments $R^1$ is $(C_1-C_6)$haloalkyl, preferably $-CF_3$, in other embodiments $(C_3-C_8)$cycloalkyl, preferably substituted or unsubstituted cyclopropyl, in other embodiments $(C_6-C_{10})$aryl$(C_1-C_6)$alkyl, preferably $(C_6)$aryl$(C_1-C_6)$alkyl, more preferably substituted or unsubstituted benzyl. The alkyl, cycloalkyl, aryl, arylalkyl, heteroaryl and heteroarylalkyl may be substituted by one or more identical or different substituents selected from the group consisting of substituted or unsubstituted $(C_1-C_6)$alkyl, substituted or unsubstituted $(C_1-C_6)$haloalkyl, $-OR^{26}$, halogen and cyano, preferably halogen, $(C_1-C_4)$alkyl, $(C_1-C_4)$haloalkyl and —OR$^{26}$, wherein R$^{26}$ is selected from the group consisting of hydrogen, substituted or unsubstituted (C$_1$-C$_6$) alkyl and substituted or unsubstituted (C$_2$-C$_6$)alkenyl, preferably from hydrogen and substituted or unsubstituted (C$_1$-C$_6$)alkyl. Preferably the number of substituents in a substituted group R$^1$ is one, two, three or four, more preferably one, two or three, for example one or two. The substituents in a substituted group R$^1$ can be present on carbon atoms in any positions as indicated above with respect to substituted alkyl, cycloalkyl, aryl, arylalkyl, heteroaryl and heteroarylalky groups in general.

In some embodiments R$^2$ and R$^3$ are independently selected from the group consisting of hydrogen, (C$_1$-C$_6$)alkyl, (C$_1$-C$_6$)haloalkyl and (C$_3$-C$_8$)cycloalkyl, in other embodiments from hydrogen, (C$_1$-C$_6$)alkyl and (C$_1$-C$_6$)haloalkyl, in other embodiments from C$_1$-C$_6$)alkyl, (C$_1$-C$_6$)haloalkyl and (C$_3$-C$_8$)cycloalkyl, in other embodiments from C$_1$-C$_6$)alkyl and (C$_1$-C$_6$)haloalkyl, in other embodiments R$^2$ and R$^3$ are hydrogen, in other embodiments R$^2$ and R$^3$ are (C$_1$-C$_6$)alkyl, preferably (C$_1$-C$_4$)alkyl, more preferably (C$_1$-C$_2$)alkyl, even more preferably methyl, in other embodiments R$^2$ and R$^3$ are (C$_1$-C$_6$)haloalkyl, preferably (C$_1$-C$_4$)haloalkyl, more preferably (C$_1$-C$_2$)haloalkyl, even more preferably —CF$_3$, in other embodiments one of R$^2$ and R$^3$ is hydrogen and the other (C$_1$-C$_6$)alkyl, preferably methyl in other embodiments one of R$^2$ and R$^3$ is hydrogen and the other (C$_1$-C$_6$)haloalkyl, preferably —CF$_3$, in other embodiments one of R$^2$ and R$^3$ is hydrogen and the other (C$_3$-C$_8$)cycloalkyl, preferably cyclopropyl, in other embodiments one of R$^2$ and R$^3$ is (C$_1$-C$_6$)alkyl, preferably (C$_1$-C$_4$) alkyl, more preferably (C$_1$-C$_2$)alkyl, even more preferably methyl and the other (C$_1$-C$_6$)haloalkyl, preferably (C$_1$-C$_4$) haloalkyl, more preferably (C$_1$-C$_2$)haloalkyl, even more preferably —CF$_3$, in other embodiments one of R$^2$ and R$^3$ is (C$_1$-C$_6$)alkyl, preferably (C$_1$-C$_4$)alkyl, more preferably (C$_1$-C$_2$)alkyl, even more preferably methyl and the other (C$_3$-C$_8$)cycloalkyl, preferably (C$_3$-C$_6$)cycloalkyl, more preferably cycloalkyl, in other embodiments one of R$^2$ and R$^3$ is methyl and the other one iso-propyl or ethyl, in other embodiments one of R$^2$ and R$^3$ is selected from the group consisting of methyl, ethyl, propyl and iso-propyl and the other one is (C$_1$-C$_6$)haloalkyl, preferably selected from —CF$_3$, —CH$_2$CF$_3$, —CF$_2$CF$_3$, more preferably —CF$_3$. The alkyl and cycloalkyl may be substituted by one or more identical or different substituents selected from the group consisting of substituted or unsubstituted (C$_1$-C$_6$)alkyl, substituted or unsubstituted (C$_1$-C$_6$)haloalkyl, —OR$^{26}$, halogen and cyano, preferably halogen, (C$_1$-C$_4$)alkyl, (C$_1$-C$_4$)haloalkyl and —OR$^{26}$, wherein R$^{26}$ is selected from the group consisting of hydrogen, substituted or unsubstituted (C$_1$-C$_6$) alkyl and substituted or unsubstituted (C$_2$-C$_6$)alkenyl, preferably from hydrogen and substituted or unsubstituted (C$_1$-C$_6$)alkyl. Preferably the number of substituents in a substituted group R$^2$ and/or R$^3$ is one, two, three or four, more preferably one, two or three, for example one or two. The substituents in a substituted group R$^2$ and/or R$^3$ can be present on carbon atoms in any positions as indicated above with respect to substituted alkyl and cycloalkyl groups in general.

In some embodiments n is an integer between 0 and 3, in other embodiments n is 0, 1, 2, or 3, in other embodiments n is an integer between 1 and 3, in other embodiments n is an integer between 1 and 2, in other embodiments n is 1, in other embodiments n is 2, in other embodiments n is 3, in other embodiments n is 0.

In some embodiments Z is selected from the group consisting of C=O, C=S and CH$_2$, in other embodiments from C=O and C=S, in other embodiments from C=O and CH$_2$, in other embodiments from C=S and CH$_2$, in other embodiments Z is C=O, in other embodiments Z is C=S, in other embodiments Z is CH$_2$.

In some embodiments A is selected from the group consisting of —N(R$^4$)(R$^5$),

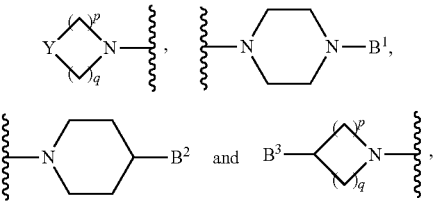

in other embodiments from —N(R$^4$)(R$^5$) and

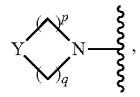

in other embodiments from

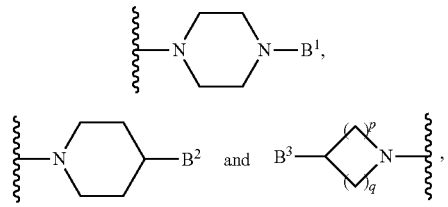

in other embodiments A is —N(R$^4$)(R$^5$), in other embodiments A is

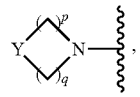

in other embodiments A is

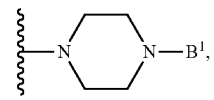

in other embodiments A is

in other embodiments A is

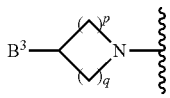

In some embodiments $R^4$ is hydrogen or $(C_1\text{-}C_6)$alkyl, in other embodiments hydrogen or $(C_1\text{-}C_4)$alkyl, in other embodiments hydrogen or $(C_3\text{-}C_4)$alkyl, in other embodiments hydrogen or $(C_1\text{-}C_2)$alkyl, in other embodiments $R^4$ is hydrogen, in other embodiments $R^4$ is $(C_1\text{-}C_6)$alkyl, preferably $(C_1\text{-}C_4)$alkyl, more preferably $(C_1\text{-}C_2)$alkyl, even more preferably methyl. The alkyl may be substituted by one or more identical or different substituents selected from the group consisting of halogen and cyano, preferably halogen. Preferably the number of substituents in a substituted group $R^4$ is one, two, three or four, more preferably one, two or three, for example one or two. The substituents in a substituted group $R^4$ can be present on carbon atoms in any positions as indicated above with respect to substituted alkyl group in general.

In some embodiments $R^5$ is selected from the group consisting of $(C_6\text{-}C_{10})$aryl$(C_1\text{-}C_6)$alkyl, $(C_3\text{-}C_{10})$heteroaryl$(C_1\text{-}C_6)$alkyl, $(C_3\text{-}C_{10})$heteroaryl$(C_1\text{-}C_6)$heteroalkyl and $(C_6\text{-}C_{10})$aryl$(C_1\text{-}C_6)$heteroalkyl, in other embodiments from $(C_6)$aryl$(C_1\text{-}C_6)$alkyl, $(C_3\text{-}C_{10})$heteroaryl$(C_1\text{-}C_6)$alkyl, $(C_3\text{-}C_{10})$heteroaryl$(C_1\text{-}C_6)$heteroalkyl and $(C_6)$aryl$(C_1\text{-}C_6)$heteroalkyl, in other embodiments from $(C_6\text{-}C_{10})$aryl$(C_1\text{-}C_6)$alkyl, $(C_3\text{-}C_{10})$heteroaryl$(C_1\text{-}C_6)$alkyl and $(C_3\text{-}C_{10})$heteroaryl$(C_1\text{-}C_6)$heteroalkyl, in other embodiments from $(C_6\text{-}C_{10})$aryl$(C_1\text{-}C_6)$alkyl and $(C_3\text{-}C_{10})$heteroaryl$(C_1\text{-}C_6)$alkyl, preferably $(C_6)$aryl$(C_1\text{-}C_6)$alkyl and $(C_3\text{-}C_{10})$heteroaryl$(C_1\text{-}C_6)$alkyl. In some embodiments $R^5$ is $(C_6\text{-}C_{10})$aryl$(C_1\text{-}C_6)$alkyl, preferably wherein aryl is selected from the group of substituted or unsubstituted naphthyl and substituted or unsubstituted phenyl, more preferably wherein aryl is substituted or unsubstituted phenyl, in other embodiments $R^5$ is $(C_6)$aryl$(C_1\text{-}C_6)$alkyl, in other embodiments $R^5$ is substituted or unsubstituted benzyl, in other embodiments $R^5$ is selected from the group consisting of benzyl, 2-fluorobenzyl, 3-fluorobenzyl, 4-fluorobenzyl, 2-chlorobenzyl, 3-chlorobenzyl, 4-chlorobenzyl, 3-Phenylpropyl and phenethyl, preferably benzyl, 3-chlorobenzyl, 4-chlorobenzyl and 3-Phenylpropyl. In some embodiments $R^5$ is $(C_3\text{-}C_{10})$heteroaryl$(C_1\text{-}C_6)$alkyl, in other embodiments selected from the group consisting of 5-methylfuran-2-ylmethyl, thiophen-2-ylmethyl, and 2-(1H-indol-3-yl)ethyl, preferably, 5-methylfuran-2-ylmethyl and 2-(1H-indol-3-yl)ethyl. In some embodiments $R^5$ is $(C_3\text{-}C_{10})$heteroaryl$(C_1\text{-}C_6)$heteroalkyl, in other embodiments selected from the group consisting of furan-2-yl-methylthiomethyl, thiophen-2-yl-methylthiomethyl, furan-2-yl-methoxymethyl, thiophen-2-yl-methoxymethyl, preferably furan-2-yl-methylthiomethyl. In some embodiments $R^5$ is $(C_6\text{-}C_{10})$aryl$(C_1\text{-}C_6)$heteroalkyl, preferably $(C_6)$aryl$(C_1\text{-}C_6)$ heteroalkyl, preferably wherein aryl is selected from the group of substituted or unsubstituted naphthyl and substituted or unsubstituted phenyl, more preferably wherein aryl is substituted or unsubstituted phenyl. The arylalkyl, heteroarylalkyl, heteroarylheteroalkyl and arylheteroalkyl may be substituted by one or more identical or different substituents selected from the group consisting of of halogen, $(C_1\text{-}C_4)$alkyl, $(C_1\text{-}C_4)$haloalkyl and —$OR^6$, preferably halogen, more preferably chlorine or fluorine, even more preferably chlorine, even more preferably chlorine, preferably methyl. Preferably the number of substituents in a substituted group $R^5$ is one, two, three or four, more preferably one, two or three, for example one or two. The substituents in a substituted group $R^5$ can be present on carbon atoms in any positions as indicated above with respect to substituted alkyl group in general.

In some embodiments $R^6$ is $(C_1\text{-}C_4)$alkyl or $(C_1\text{-}C_4)$haloalkyl, in other embodiments $(C_1\text{-}C_2)$alkyl or $(C_1\text{-}C_2)$haloalkyl, in other embodiments $(C_1\text{-}C_4)$alkyl, preferably methyl, in other embodiments $(C_1\text{-}C_4)$haloalkyl, preferably —$CF_3$. The alkyl may be substituted by one or more identical or different substituents selected from the group consisting of halogen and cyano, preferably halogen. Preferably the number of substituents in a substituted group $R^6$ is one, two, three or four, more preferably one, two or three, for example one or two. The substituents in a substituted group $R^6$ can be present on carbon atoms in any positions as indicated above with respect to substituted alkyl group in general.

In some embodiments $Y^1$ is selected from the group consisting of N—B, CH—B and O, preferably of N—B and CH—B. In some embodiments $Y^1$ is of N—B, in other embodiments $Y^1$ is CH—B, in other embodiments $Y^1$ is O.

In some embodiments B is selected from the group consisting of $(C_6\text{-}C_{10})$aryl, $(C_3\text{-}C_{10})$heteroaryl, $(C_6\text{-}C_{10})$aryl$(C_1\text{-}C_6)$alkyl, $(C_3\text{-}C_{10})$heteroaryl$(C_1\text{-}C_6)$alkyl, $(C_1\text{-}C_6)$alkyl and $N(R^7)(R^8)$, in other embodiments from $(C_6\text{-}C_{10})$aryl, $(C_3\text{-}C_{10})$heteroaryl, $(C_6\text{-}C_{10})$aryl$(C_1\text{-}C_6)$alkyl and $(C_3\text{-}C_{10})$heteroaryl$(C_1\text{-}C_6)$alkyl, in other embodiments from $(C_6\text{-}C_{10})$aryl, $(C_3\text{-}C_{10})$heteroaryl and $(C_6\text{-}C_{10})$aryl$(C_1\text{-}C_6)$alkyl, in other embodiments from $(C_6)$aryl, $(C_3\text{-}C_{10})$heteroaryl and $(C_6)$aryl$(C_1\text{-}C_6)$alkyl. In some embodiments B is $(C_6\text{-}C_{10})$ aryl, preferably wherein aryl is selected from the group of substituted or unsubstituted naphthyl and substituted or unsubstituted phenyl, more preferably wherein aryl is substituted or unsubstituted phenyl. In some embodiments B is selected from the group consisting of phenyl, 3-methoxyphenyl, 4-fluorophenyl, 4-methoxyphenyl, 2-fluorophenyl, 2, 5-dimethylphenyl, preferably phenyl, 4-fluorophenyl and 3-methoxyphenyl, more preferably phenyl and 3-methoxyphenyl. In some embodiments B is $(C_3\text{-}C_{10})$heteroaryl, in other embodiments B is $(C_3\text{-}C_{10})$heteroaryl containing 1-3 nitrogen atoms, preferably 1-2 nitrogen atoms, more preferably 1 nitrogen atom, in other embodiments B is selected from the group consisting of pyridine-2-yl, pyridine-3-yl, pyridine-4-yl, preferably pyridine-2-yl. In some embodiments B is $(C_6\text{-}C_{10})$aryl$(C_1\text{-}C_6)$alkyl, in other embodiments $(C_6)$aryl$(C_1\text{-}C_6)$alkyl, in other embodiments substituted or unsubstituted benzyl, in other embodiments selected from the group consisting of benzyl, 2-chlorobenzyl, 2-fluorobenzyl, 3-chlorobenzyl, 3-fluorobenzyl, 4-chlorobenzyl, 4-fluorobenzyl, 2-methoxybenzyl, 3-methoxybenzyl, 4-methoxybenzyl, 2,3-dimethoxybenzyl, 3,4-dimethoxybenzyl, 2,4-dimethoxybenzyl and 3,5-dimethoxybenzyl, preferably benzyl and 3-chlorobenzyl, more preferably benzyl. In some embodiments B is $(C_3\text{-}C_{10})$heteroaryl$(C_1\text{-}C_6)$alkyl, preferably wherein the heteroaryl part is an oxygen containing heteroaryl such as furanyl or a sulfur containing heteroaryl such as thiophene or a nitrogen containing heteroaryl such as indole or diazaindole. In other embodiments the $(C_3\text{-}C_{10})$heteroaryl$(C_1\text{-}C_6)$alkyl is selected from pyridine-2-ylmethyl, pyridine-3-ylmethyl, pyridine-4-ylmethyl, of 5-methylfuran-2-ylmethyl, furan-2-ylmethyl, furan-3-ylmethyl, thiophen-2-ylmethyl and thiophen-3-ylmethyl, preferably pyridine-2-ylmethyl and furan-2-ylmethyl, more preferably pyridine-2-ylmethyl. In some embodiments B is $(C_1\text{-}C_6)$ alkyl, preferably $(C_1\text{-}C_4)$alkyl, in other embodiments selected from the group consisting of methyl, ethyl, propyl, iso-propyl, butyl, sec-butyl and tert-butyl, preferably methyl or ethyl. In some embodiments B is $N(R^7)(R^8)$, preferably wherein $R^7$ is hydrogen and $R^8$ as defined below, preferably wherein $R^7$ is $(C_1-C_6)$alkyl, preferably methyl and $R^8$ as defined below. The aryl, heteroaryl, arylalkyl, heteroarylalkyl, alkyl and $N(R^7)(R^8)$ group may be substituted by one or more identical or different substituents selected from the group consisting of halogen, $(C_1-C_4)$alkyl, $(C_1-C_4)$haloalkyl and —$OR^6$, preferably halogen and —$OR^6$. Preferably the number of substituents in a substituted group B is one, two, three or four, more preferably one, two or three, for example one or two. The substituents in a substituted group B can be present on carbon atoms in any positions as indicated above with respect to substituted aryl, heteroaryl, arylalkyl, heteroarylalkyl, alkyl and $N(R^7)(R^8)$ group in general.

$B^1$ is $(C_6-C_{10})$aryl$(C_1-C_6)$alkyl or $(C_3-C_{10})$heteroaryl$(C_1-C_6)$alkyl. In some embodiments $B^1$ is $(C_6-C_{10})$aryl$(C_1-C_6)$alkyl, in other embodiments $(C_6)$aryl$(C_1-C_6)$alkyl, in other embodiments $(C_{10})$aryl$(C_1-C_6)$alkyl, in other embodiments substituted or unsubstituted benzyl, in other embodiments substituted or unsubstituted naphthalen-2-ylmethyl, in other embodiments selected from the group consisting of naphthalen-2-ylmethyl, benzyl, 2-chlorobenzyl, 2-fluorobenzyl, 3-chlorobenzyl, 3-fluorobenzyl, 4-chlorobenzyl, 4-fluorobenzyl, 2-methoxybenzyl, 3-methoxybenzyl, 4-methoxybenzyl, 2,3-dimethoxybenzyl, 3,4-dimethoxybenzyl, 2,4-dimethoxybenzyl, naphthalen-2-ylmethyl and 3,5-dimethoxybenzyl, preferably benzyl, 4-fluorobenzyl, 2,4-dimethoxybenzyl and 3-methoxybenzyl, more preferably benzyl. In some embodiments $B^1$ is $(C_3-C_{10})$heteroaryl$(C_1-C_6)$alkyl, preferably wherein the heteroaryl part is an oxygen containing heteroaryl such as furanyl or a sulfur containing heteroaryl such as thiophen or a nitrogen containing heteroaryl such as pyridine, indole or diazaindole. In other embodiments the $(C_3-C_{10})$heteroaryl$(C_1-C_6)$alkyl is selected from pyridine-2-ylmethyl, pyridine-3-ylmethyl, pyridine-4-ylmethyl, of 5-methylfuran-2-ylmethyl, furan-2-ylmethyl, furan-3-ylmethyl, thiophen-2-ylmethyl and thiophen-3-ylmethyl, preferably pyridine-2-ylmethyl and furan-2-ylmethyl, more preferably pyridine-2-ylmethyl. The arylalkyl and heteroarylalkyl group may be substituted by one or more identical or different substituents selected from the group consisting of halogen, $(C_1-C_4)$alkyl, $(C_1-C_4)$haloalkyl and —$OR^6$, preferably halogen and —$OR^6$. Preferably the number of substituents in a substituted group $B^1$ is one, two, three or four, more preferably one, two or three, for example one or two. The substituents in a substituted group $B^1$ can be present on carbon atoms in any positions as indicated above with respect to substituted arylalkyl and heteroarylalkyl group in general.

In some embodiments $B^2$ is $(C_6-C_{10})$aryl$(C_1-C_6)$alkyl substituted by one or more identical or different substituents selected from the group consisting of halogen, $(C_1-C_4)$alkyl, $(C_1-C_4)$haloalkyl and —$OR^6$, preferably halogen and —$OR^6$. In some embodiments $B^2$ is $(C_6)$aryl$(C_1-C_6)$alkyl, in other embodiments $(C_{10})$aryl$(C_1-C_6)$alkyl, in other embodiments substituted or unsubstituted benzyl, in other embodiments substituted or unsubstituted naphthalen-2-ylmethyl, in other embodiments selected from the group consisting of 2-chlorobenzyl, 2-fluorobenzyl, 3-chlorobenzyl, 3-fluorobenzyl, 4-chlorobenzyl, 4-fluorobenzyl, 2-methoxybenzyl, 3-methoxybenzyl, 4-methoxybenzyl, 2,3-dimethoxybenzyl, 3,4-dimethoxybenzyl, 2,4-dimethoxybenzyl and 3,5-dimethoxybenzyl, preferably 4-fluorobenzyl and 3-methoxybenzyl. In some embodiments $B^2$ is $C_3-C_{10}$heteroaryl$(C_1-C_6)$alkyl, preferably wherein the heteroaryl part is an oxygen containing heteroaryl such as furanyl or a sulfur containing heteroaryl such as thiophen or a nitrogen containing heteroaryl such as pyridine, indole or diazaindole. In other embodiments the $(C_3-C_{10})$heteroaryl$(C_1-C_6)$alkyl is selected from pyridine-2-ylmethyl, pyridine-3-ylmethyl, pyridine-4-ylmethyl, of 5-methylfuran-2-ylmethyl, furan-2-ylmethyl, furan-3-ylmethyl, thiophen-2-ylmethyl and thiophen-3-ylmethyl, preferably pyridine-2-ylmethyl and furan-2-ylmethyl, more preferably pyridine-2-ylmethyl. The heteroarylalkyl group may be substituted by one or more identical or different substituents selected from the group consisting of halogen, $(C_1-C_4)$alkyl, $(C_1-C_4)$haloalkyl and —$OR^6$, preferably halogen and —$OR^6$. Preferably the number of substituents in a substituted group $B^2$ is one, two, three or four, more preferably one, two or three, for example one or two. The substituents in a substituted group $B^2$ can be present on carbon atoms in any positions as indicated above with respect to substituted arylalkyl and heteroarylalkyl group in general.

$B^3$ is selected from the group consisting of $(C_1-C_{10})$aryl$(C_1-C_6)$alkyl, $(C_3—C)$heteroaryl$(C_1-C_6)$alkyl, $(C_1-C_6)$alkyl and $N(R^7)(R^8)$. In some embodiments $B^3$ is selected from the group consisting of $(C_6-C_{10})$aryl$(C_1-C_6)$alkyl and $(C_3-C_{10})$heteroaryl$(C_1-C_6)$alkyl, in other embodiments $B^3$ is $(C_6-C_{10})$aryl$(C_1-C_6)$alkyl. In some embodiments $B^3$ is $(C_6-C_{10})$aryl$(C_1-C_6)$alkyl, in other embodiments $(C_6)$aryl$(C_1-C_6)$alkyl, in other embodiments substituted or unsubstituted benzyl, in other embodiments substituted or unsubstituted benzyl, in other embodiments substituted or unsubstituted naphthalen-2-ylmethyl, in other embodiments selected from the group consisting of benzyl, naphthalen-2-ylmethyl, 2-chlorobenzyl, 2-fluorobenzyl, 3-chlorobenzyl, 3-fluorobenzyl, 4-chlorobenzyl, 4-fluorobenzyl, 2-methoxybenzyl, 3-methoxybenzyl, 4-methoxybenzyl, 2,3-dimethoxybenzyl, 3,4-dimethoxybenzyl, 2,4-dimethoxybenzyl and 3,5-dimethoxybenzyl, preferably benzyl and 3-chlorobenzyl, more preferably benzyl. In some embodiments $B^3$ is $(C_3-C_{10})$heteroaryl$(C_1-C_6)$alkyl, preferably wherein the heteroaryl part is an oxygen containing heteroaryl such as furanyl or a sulfur containing heteroaryl such as thiophen or a nitrogen containing heteroaryl such as pyridine, indole or diazaindole. In other embodiments the $(C_3-C_{10})$heteroaryl$(C_1-C_6)$alkyl is selected from pyridine-2-ylmethyl, pyridine-3-ylmethyl, pyridine-4-ylmethyl, of 5-methylfuran-2-ylmethyl, furan-2-ylmethyl, furan-3-ylmethyl, thiophen-2-ylmethyl and thiophen-3-ylmethyl, preferably pyridine-2-ylmethyl and furan-2-ylmethyl, more preferably pyridine-2-ylmethyl. In some embodiments $B^3$ is $(C_1-C_6)$alkyl, preferably $(C_1-C_4)$alkyl, in other embodiments selected from the group consisting of methyl, ethyl, propyl, isopropyl, butyl, sec-butyl and tert-butyl, preferably methyl or ethyl. In some embodiments $B^3$ is $N(R^7)(R^8)$, preferably wherein $R^7$ is hydrogen and $R^8$ as defined below, preferably wherein $R^7$ is $(C_1-C_6)$alkyl, preferably methyl and $R^8$ as defined below. The arylalkyl, heteroarylalkyl, alkyl and $N(R^7)(R^8)$ group may be substituted by one or more identical or different substituents selected from the group consisting of halogen, $(C_1-C_4)$alkyl, $(C_1-C_4)$haloalkyl and —$OR^6$, preferably halogen and —$OR^6$. Preferably the number of substituents in a substituted group $B^3$ is one, two, three or four, more preferably one, two or three, for example one or two. The substituents in a substituted group $B^3$ can be present on carbon atoms in any positions as indicated above with respect to substituted arylalkyl, heteroarylalkyl, alkyl and $N(R^7)(R^8)$ group in general.

In some embodiments $R^7$ is hydrogen or $(C_1-C_6)$alkyl, in other embodiments hydrogen or $(C_1-C_4)$alkyl, in other embodiments hydrogen or $(C_3-C_4)$alkyl, in other embodiments hydrogen or $(C_1-C_2)$alkyl, in other embodiments $R^7$ is hydrogen, in other embodiments $R^7$ is $(C_1-C_6)$alkyl, preferably $(C_1-C_4)$alkyl, more preferably $(C_1-C_2)$alkyl, even more preferably methyl. The alkyl may be substituted by one or more identical or different substituents selected from the group consisting of halogen and cyano, preferably halogen. Preferably the number of substituents in a substituted group $R^7$ is one, two, three or four, more preferably one, two or three, for example one or two. The substituents in a substituted group $R^7$ can be present on carbon atoms in any positions as indicated above with respect to substituted alkyl group in general.

In some embodiments $R^8$ is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl and $(C_1-C_6)$alkyl, in other embodiments from $(C_6-C_{10})$aryl, $(C_3-C_{10})$heteroaryl, $(C_6-C_{10})$aryl$(C_1-C_6)$alkyl and $C_3-C_{10}$heteroaryl$(C_1-C_6)$alkyl, in other embodiments from $(C_6-C_{10})$aryl and $(C_3-C_{10})$heteroaryl, in other embodiments from $(C_6-C_{10})$aryl$(C_1-C_6)$alkyl and $C_3-C_{10}$heteroaryl$(C_1-C_6)$alkyl, in other embodiments from $(C_6)$aryl, $(C_3-C_{10})$heteroaryl, $(C_6)$aryl$(C_1-C_6)$alkyl, $C_3-C_{10}$heteroaryl$(C_1-C_6)$alkyl and $(C_1-C_6)$alkyl. In some embodiments $R^8$ is $(C_6-C_{10})$aryl, preferably wherein aryl is selected from the group of substituted or unsubstituted naphthyl and substituted or unsubstituted phenyl, more preferably wherein aryl is substituted or unsubstituted phenyl. In some embodiments $R^8$ is $(C_3-C_{10})$heteroaryl, in other embodiments $(C_3-C_{10})$heteroaryl contains 1-3 nitrogen atoms, preferably 1-2 nitrogen atoms, more preferably 1 nitrogen atom, such as pyridine-2-yl, pyridine-3-yl, pyridine-4-yl. In some embodiments $R^8$ is $(C_6-C_{10})$aryl$(C_1-C_6)$alkyl, in other embodiments $(C_6)$aryl$(C_1-C_6)$alkyl, in other embodiments substituted or unsubstituted benzyl, in other embodiments selected from the group consisting of benzyl, 2-chlorobenzyl, 2-fluorobenzyl, 3-chlorobenzyl, 3-fluorobenzyl, 4-chlorobenzyl, 4-fluorobenzyl, 2-methoxybenzyl, 3-methoxybenzyl, 4-methoxybenzyl, 2,3-dimethoxybenzyl, 3,4-dimethoxybenzyl, 2,4-dimethoxybenzyl and 3,5-dimethoxybenzyl, preferably benzyl and 3-chlorobenzyl, more preferably benzyl. In some embodiments $R^8$ is $(C_3-C_{10})$heteroaryl$(C_1-C_6)$alkyl, preferably wherein the heteroaryl part is an oxygen containing heteroaryl such as furanyl or a sulfur containing heteroaryl such as thiophene or a nitrogen containing heteroaryl such as indole or diazaindole. In other embodiments the $(C_3-C_{10})$heteroaryl$(C_1-C_6)$alkyl is selected from pyridine-2-ylmethyl, pyridine-3-ylmethyl, pyridine-4-ylmethyl, of 5-methylfuran-2-ylmethyl, furan-2-ylmethyl, furan-3-ylmethyl, thiophen-2-ylmethyl and thiophen-3-ylmethyl, preferably pyridine-2-ylmethyl and furan-2-ylmethyl, more preferably pyridine-2-ylmethyl. In some embodiments $R^8$ is $(C_1-C_6)$alkyl, preferably $(C_1-C_4)$alkyl, in other embodiments selected from the group consisting of methyl, ethyl, propyl, iso-propyl, butyl, sec-butyl and tert-butyl, preferably methyl or ethyl. The aryl, heteroaryl, arylalkyl, heteroarylalkyl and alkyl group may be substituted by one or more identical or different substituents selected from the group consisting of halogen, $(C_1-C_4)$alkyl, $(C_1-C_4)$haloalkyl and —$OR^6$, preferably halogen and —$OR^6$. Preferably the number of substituents in a substituted group B is one, two, three or four, more preferably one, two or three, for example one or two. The substituents in a substituted group B can be present on carbon atoms in any positions as indicated above with respect to substituted aryl, heteroaryl, arylalkyl, heteroarylalkyl and alkyl group in general.

In some embodiments p is an integer between 1 and 2, in other embodiments p is 1, in other embodiments p is 2.

In some embodiments q is an integer between 1 and 3, in other embodiments q is 1, 2, or 3, in other embodiments q is an integer between 1 and 2, in other embodiments q is 1, in other embodiments q is 2, in other embodiments q is 3.

In some embodiments p is 1 and q is 1, in other embodiments p is 1 and q is 2, in other embodiments p is 1 and q is 3, in other embodiments p is 2 and q is 2, in other embodiments p is 2 and q is 3.

In some embodiments the compound having a structure according to Formula (I) is a compound having a structure according to Formula (II)

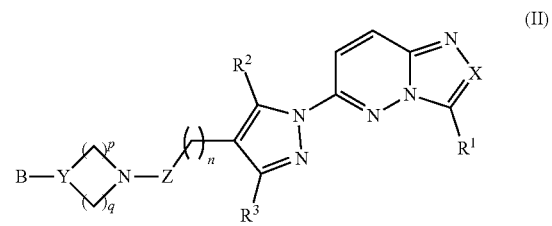

wherein $R^1$, $R^2$, $R^3$, X, Y, Z, B, n, p and q are defined as above and below.

Y is CH or N. In some embodiments Y is CH, in other embodiments Y is N.

In some embodiments the compound having a structure according to Formula (I) is a compound having a structure according to Formula (III)

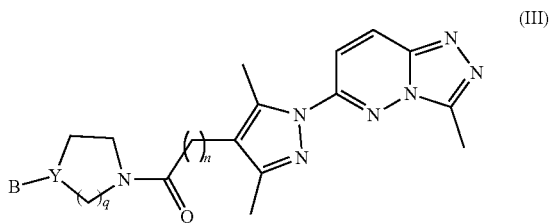

wherein Y, B, n and q are defined as above and below.

In some embodiments the compound having a structure according to Formula (I) is a compound having a structure according to Formula (IV)

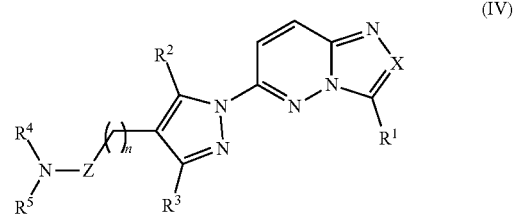

wherein $R^1$, $R^2$, $R^3$, $R^4$, $R^5$, X, Z and n are defined as above and below.

In some embodiments A is

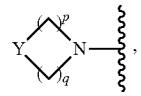

p is 1 and q is 1, in other embodiments A is

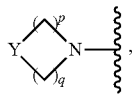

p is 2 and q is 1, in other embodiments A is

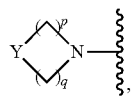

p is 2 and q is 2, in other embodiments A is

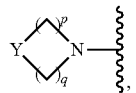

p is 2 and q is 3,

In some embodiments the compound having a structure according to Formula (I) is characterized in that, X is selected from the group consisting of N and CH;

$R^1$ is selected from the group consisting of hydrogen, $(C_1$-$C_6)$alkyl, $(C_1$-$C_6)$haloalkyl, $(C_3$-$C_8)$cycloalkyl, $(C_6$-$C_{10})$aryl, $(C_6$-$C_{10})$aryl$(C_1$-$C_6)$alkyl, $(C_3$-$C_{10})$heteroaryl and $(C_3$-$C_{10})$heteroaryl$(C_1$-$C_6)$alkyl;

$R^2$ and $R^3$ are independently selected from the group consisting of hydrogen, $(C_1$-$C_6)$alkyl, $(C_1$-$C_6)$haloalkyl and $(C_3$-$C_8)$cycloalkyl;

n is an integer between 0 and 3;

Z is selected from the group consisting of C=O, C=S and $CH_2$;

A is selected from the group consisting of

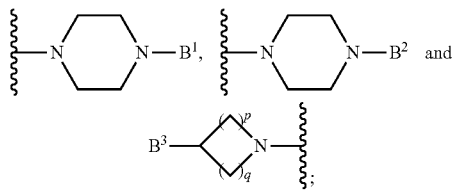

$B^1$ is $(C_6$-$C_{10})$aryl$(C_1$-$C_6)$alkyl or $(C_3$-$C_{10})$heteroaryl$(C_1$-$C_6)$alkyl, which are optionally substituted by one or more identical or different substituents selected from the group consisting of halogen, $(C_1$-$C_4)$alkyl, $(C_1$-$C_4)$haloalkyl and —$OR^6$;

$B^2$ is $(C_6$-$C_{10})$aryl$(C_1$-$C_6)$alkyl substituted by one or more identical or different substituents selected from the group consisting of halogen, $(C_1$-$C_4)$alkyl, $(C_1$-$C_4)$haloalkyl and —$OR^6$, or $B^2$ is $C_3$-$C_{10})$heteroaryl$(C_1$-$C_6)$alkyl, which is optionally substituted by one or more identical or different substituents selected from the group consisting of halogen, $(C_1$-$C_4)$alkyl, $(C_1$-$C_4)$haloalkyl and —$OR^6$;

$B^3$ is selected from the group consisting of hydrogen, $(C_6$-$C_{10})$aryl$(C_1$-$C_6)$alkyl, $(C_3$-$C_{10})$heteroaryl$(C_1$-$C_6)$alkyl, $(C_1$-$C_6)$alkyl and $N(R^7)(R^8)$, which are optionally substituted by one or more identical or different substituents selected from the group consisting of halogen, $(C_1$-$C_4)$alkyl, $(C_1$-$C_4)$haloalkyl and —$OR^6$;

$R^6$ is $(C_1$-$C_4)$alkyl or $(C_1$-$C_4)$haloalkyl;

$R^7$ is hydrogen or $(C_1$-$C_6)$alkyl;

$R^8$ is selected from the group consisting of $(C_6$-$C_{10})$aryl, $(C_3$-$C_{10})$heteroaryl, $(C_6$-$C_{10})$aryl$(C_1$-$C_6)$alkyl, $(C_3$-$C_{10})$heteroaryl$(C_1$-$C_6)$alkyl and $(C_1$-$C_6)$alkyl;

p is 1 and q is an integer between 1 and 2, or p is 2 and q is 3;

or a pharmaceutically acceptable salt, solvate or hydrate thereof.

In some embodiments the compound having a structure according to Formula (I) is a compound having a structure according to Formula (II), wherein X is selected from the group consisting of N and CH, preferably N, preferably CH;

$R^1$ is selected from the group consisting of hydrogen, $(C_1$-$C_6)$alkyl, $(C_1$-$C_6)$haloalkyl, $(C_3$-$C_8)$cycloalkyl, $(C_6$-$C_{10})$aryl, $(C_6$-$C_{10})$aryl$(C_1$-$C_6)$alkyl, $(C_3$-$C_{10})$heteroaryl and $(C_3$-$C_{10})$heteroaryl$(C_1$-$C_6)$alkyl, preferably hydrogen, $(C_1$-$C_6)$alkyl, $(C_3$-$C_8)$cycloalkyl, $(C_6$-$C_{10})$aryl and $(C_6$-$C_{10})$aryl$(C_1$-$C_6)$alkyl;

$R^2$ and $R^3$ are independently selected from the group consisting of hydrogen, $(C_1$-$C_6)$alkyl, $(C_1$-$C_6)$haloalkyl and $(C_3$-$C_8)$cycloalkyl, preferably $(C_1$-$C_6)$alkyl and $(C_1$-$C_6)$haloalkyl;

n is an integer between 0 and 3, preferably 1-3, more preferably 1-2, even more preferably 2;

Z is selected from the group consisting of C=O, C=S and $CH_2$, preferably C=O;

Y is N or CH;

B is selected from the group consisting of $(C_6$-$C_{10})$aryl, $(C_3$-$C_{10})$heteroaryl, $(C_6$-$C_{10})$aryl$(C_1$-$C_6)$alkyl, $(C_3$-$C_{10})$heteroaryl$(C_1$-$C_6)$alkyl, $(C_1$-$C_6)$alkyl and $N(R^7)(R^8)$, which are optionally substituted by one or more identical or different substituents selected from the group consisting of halogen, $(C_1$-$C_4)$alkyl, $(C_1$-$C_4)$haloalkyl and —$OR^6$, preferably halogen and —$OR^6$;

$R^7$ is hydrogen or $(C_1$-$C_6)$alkyl, preferably hydrogen;

$R^8$ is selected from the group consisting of $(C_6$-$C_{10})$aryl, $(C_3$-$C_{10})$heteroaryl, $(C_6$-$C_{10})$aryl$(C_1$-$C_6)$alkyl, $(C_3$-$C_{10})$heteroaryl$(C_1$-$C_6)$alkyl and $(C_1$-$C_6)$alkyl, preferably $(C_6$-$C_{10})$aryl$(C_1$-$C_6)$alkyl, $(C_3$-$C_{10})$heteroaryl$(C_1$-$C_6)$alkyl, more preferably $(C_6$-$C_{10})$aryl$(C_1$-$C_6)$alkyl;

p is an integer between 1 and 2;

q is an integer between 1 and 3;

or a pharmaceutically acceptable salt, solvate or hydrate thereof.

In some embodiments the compound having a structure according to Formula (I) or Formula (II) is characterized in that, $R^1$ is selected from the group consisting of hydrogen, $(C_1$-$C_4)$alkyl, $(C_3$-$C_6)$cycloalkyl, $(C_6$-$C_{10})$aryl and $(C_6$-$C_{10})$aryl$(C_1$-$C_6)$alkyl;

$R^2$ and $R^3$ are independently selected from the group consisting of $(C_1$-$C_4)$alkyl and $(C_1$-$C_4)$haloalkyl;

n is an integer between 1 and 3, preferably 1-2, more preferably 2; and $R^5$ is selected from the group consisting of $(C_1$-$C_{10})$aryl $(C_1$-$C_6)$alkyl, $(C_3$-$C_{10})$heteroaryl$(C_1$-$C_6)$alkyl and $(C_3$-$C_{10})$heteroaryl$(C_1$-$C_6)$heteroalkyl, which are optionally substituted by one or more identical or different substituents selected from the group consisting of halogen, $(C_1-C_4)$alkyl, $(C_1-C_4)$haloalkyl and —$OR^6$, preferably halogen.

In some embodiments the compound having a structure according to Formula (I) is a compound having a structure according to Formula (III)
wherein
n is an integer between 1 and 3, preferably 1-2, more preferably 2;
Y is N or CH;
B is selected from the group consisting of $(C_6-C_{10})$aryl, $(C_3-C_{10})$heteroaryl, $(C_6-C_{10})$aryl$(C_1-C_6)$alkyl, $(C_3-C_{10})$heteroaryl$(C_1-C_6)$alkyl and $(C_1-C_6)$alkyl, which are optionally substituted by one or more identical or different substituents selected from the group consisting of halogen, $(C_1-C_4)$alkyl, $(C_1-C_4)$haloalkyl and —$OR^6$, preferably halogen and —$OR^6$;
q is an integer between 1-3, preferably 1-2, more preferably 2;
or a pharmaceutically acceptable salt, solvate or hydrate thereof.

In some embodiments the compound having a structure according to Formula (I) is a compound having a structure according to Formula (IV),
wherein
X is selected from the group consisting of N and CH;
$R^1$ is selected from the group consisting of hydrogen, $(C_1-C_6)$alkyl, $(C_1-C_6)$haloalkyl, $(C_3-C_8)$cycloalkyl, $(C_6-C_{10})$aryl, $(C_6-C_{10})$aryl$(C_1-C_6)$alkyl, $(C_3-C_{10})$heteroaryl and $(C_3-C_{10})$heteroaryl$(C_1-C_6)$alkyl, preferably hydrogen and $(C_1-C_6)$alkyl, more preferably $(C_1-C_6)$alkyl;
$R^2$ and $R^3$ are independently selected from the group consisting of hydrogen, $(C_1-C_6)$alkyl, $(C_1-C_6)$haloalkyl and $(C_3-C_8)$cycloalkyl, preferably $(C_1-C_6)$alkyl and $(C_1-C_6)$haloalkyl, more preferably $(C_1-C_6)$alkyl;
n is an integer between 0 and 3, preferably 1-3, more preferably 1-2, even more preferably 2;
Z is selected from the group consisting of C=O, C=S and $CH_2$, preferably C=O;
$R^4$ is hydrogen or $(C_1-C_6)$alkyl, preferably hydrogen;
$R^5$ is selected from the group consisting of $(C_1-C_{10})$aryl$(C_1-C_6)$alkyl, $(C_3-C_{10})$heteroaryl$(C_1-C_6)$alkyl, $(C_3-C_{10})$heteroaryl$(C_1-C_6)$heteroalkyl and $(C_6-C_{10})$aryl$(C_1-C_6)$heteroalkyl, which are optionally substituted by one or more identical or different substituents selected from the group consisting of halogen, $(C_1-C_4)$alkyl, $(C_1-C_4)$haloalkyl and —$OR^6$, preferably halogen;
$R^6$ is $(C_1-C_4)$alkyl or $(C_1-C_4)$haloalkyl;
or a pharmaceutically acceptable salt, solvate or hydrate thereof.

In some embodiments compound of Formula (I) is selected from the list consisting of
1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(4-(3-methoxybenzyl)piperazin-1-yl)propan-1-one,
3-(3,5-dimethyl-1-(3-methyl-[1,2,4]triazolo[4,3-b]pyridazin-6-yl)-1H-pyrazol-4-yl)-1-(4-(4-fluorobenzyl)piperazin-1-yl)propan-1-one,
1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one,
3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one,
3-(3,5-dimethyl-1-(3-methyl-[1,2,4]triazolo[4,3-b]pyridazin-6-yl)-1H-pyrazol-4-yl)-1-(4-(3-methoxybenzyl)piperidin-1-yl)propan-1-one,
3-(3,5-dimethyl-1-(3-methyl-[1,2,4]triazolo[4,3-b]pyridazin-6-yl)-1H-pyrazol-4-yl)-1-(4-(4-fluorobenzyl)piperidin-1-yl)propan-1-one,
3-(3,5-dimethyl-1-(3-methyl-[1,2,4]triazolo[4,3-b]pyridazin-6-yl)-1H-pyrazol-4-yl)-1-(4-(pyridin-2-ylmethyl)piperidin-1-yl)propan-1-one,
3-(3,5-dimethyl-1-(3-methyl-[1,2,4]triazolo[4,3-b]pyridazin-6-yl)-1H-pyrazol-4-yl)-1-(4-(pyridin-2-ylmethyl)piperazin-1-yl)propan-1-one,
(R)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one,
(S)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one,
1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one,
1-(4-benzylpiperidin-1-yl)-3-(3,5-dimethyl-1-(3-phenyl-[1,2,4]triazolo[4,3-b]pyridazin-6-yl)-1H-pyrazol-4-yl)propan-1-one,
3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one,
1-(4-benzylpiperidin-1-yl)-3-(3,5-dimethyl-1-(3-methylimidazo[1,2-b]pyridazin-6-yl)-1H-pyrazol-4-yl)propan-1-one,
1-(4-benzylpiperidin-1-yl)-2-(3,5-dimethyl-1-(3-methyl-[1,2,4]triazolo[4,3-b]pyridazin-6-yl)-1H-pyrazol-4-yl)ethan-1-one,
1-(4-benzylpiperidin-1-yl)-3-(3,5-dimethyl-1-(3-methyl-[1,2,4]triazolo[4,3-b]pyridazin-6-yl)-1H-pyrazol-4-yl)propane-1-thione,
6-(4-(3-(4-benzylpiperidin-1-yl)propyl)-3,5-dimethyl-1H-pyrazol-1-yl)-3-methyl-[1,2,4]triazolo[4,3-b]pyridazine,
1-(azepan-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-morpholinopropan-1-one,
N-(3-chlorobenzyl)-3-(3,5-dimethyl-1-(3-methyl-[1,2,4]triazolo[4,3-b]pyridazin-6-yl)-1H-pyrazol-4-yl)-N-methylpropanamide,
3-(3,5-dimethyl-1-(3-methyl-[1,2,4]triazolo[4,3-b]pyridazin-6-yl)-1H-pyrazol-4-yl)-1-(4-(furan-2-ylmethyl)piperazin-1-yl)propan-1-one,
3-(3,5-dimethyl-1-(3-methyl-[1,2,4]triazolo[4,3-b]pyridazin-6-yl)-1H-pyrazol-4-yl)-1-(4-(2-phenylpropan-2-yl)piperazin-1-yl)propan-1-one,
1-(4-(3,4-dimethoxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-b]pyridazin-6-yl)-1H-pyrazol-4-yl)-1-(4-(naphthalen-2-ylmethyl)piperazin-1-yl)propan-1-one, 1-(4-(3-chlorobenzyl)piperidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzylazetidin-1-yl)-3-(3,5-dimethyl-1-(3-methyl-[1,2,4]triazolo[4,3-b]pyridazin-6-yl)-1H-pyrazol-4-yl)propan-1-one, 1-(3-(benzylamino)azetidin-1-yl)-3-(3,5-dimethyl-1-(3-methyl-[1,2,4]triazolo[4,3-b]pyridazin-6-yl)-1H-pyrazol-4-yl)propan-1-one, N-benzyl-3,5-dimethyl-1-(3-methyl-[1,2,4]triazolo[4,3-b]pyridazin-6-yl)-1H-pyrazole-4-carboxamide, (3-benzylpyrrolidin-1-yl)(3,5-dimethyl-1-(3-methyl-[1,2,4]triazolo[4,3-b]pyridazin-6-yl)-1H-pyrazol-4-yl)methanone, 1-(3-benzylpyrrolidin-1-yl)-3-(5-isopropyl-3-methyl-1-(3-methyl-[1,2,4]triazolo[4,3-b]pyridazin-6-yl)-1H-pyrazol-4-yl)propan-1-one, 1-(3-benzylpyrrolidin-1-yl)-3-(3-methyl-1-(3-methyl-[1,2,4]triazolo[4,3-b]pyridazin-6-yl)-5-(trifluoromethyl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-phenylpiperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxyphenyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperazin-1-yl)propan-1-one, 1-(4-benzylpiperidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorophenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(3-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-phenylpiperazin-1-yl)propan-1-one, 1-(4-(3-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(1-([1,2,4]triazolo[4,3-b]pyridazin-6-yl)-3,5-dimethyl-1H-pyrazol-4-yl)-1-(4-(pyridin-2-yl)piperazin-1-yl)propan-1-one, 3-(3,5-dimethyl-1-(3-methyl-[1,2,4]triazolo[4,3-b]pyridazin-6-yl)-1H-pyrazol-4-yl)-N-((5-methylfuran-2-yl)methyl)propanamide, 3-(3,5-dimethyl-1-(3-methyl-[1,2,4]triazolo[4,3-b]pyridazin-6-yl)-1H-pyrazol-4-yl)-1-(4-(2-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-N-(3-phenylpropyl)propanamide, 3-(1-([1,2,4]triazolo[4,3-b]pyridazin-6-yl)-3,5-dimethyl-1H-pyrazol-4-yl)-1-(4-benzylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(2,5-dimethylphenyl)piperazin-1-yl)propan-1-one, N-(4-chlorobenzyl)-3-(3,5-dimethyl-1-(3-methyl-[1,2,4]triazolo[4,3-b]pyridazin-6-yl)-1H-pyrazol-4-yl)propanamide, 3-(3,5-dimethyl-1-(3-methyl-[1,2,4]triazolo[4,3-b]pyridazin-6-yl)-1H-pyrazol-4-yl)-N-(thiophen-2-ylmethyl)propanamide, N-(2-(1H-indol-3-yl)ethyl)-3-(3,5-dimethyl-1-(3-methyl-[1,2,4]triazolo[4,3-b]pyridazin-6-yl)-1H-pyrazol-4-yl)propanamide, N-benzyl-3-(3,5-dimethyl-1-(3-methyl-[1,2,4]triazolo[4,3-b]pyridazin-6-yl)-1H-pyrazol-4-yl)propanamide, 3-(1-([1,2,4]triazolo[4,3-b]pyridazin-6-yl)-3,5-dimethyl-1H-pyrazol-4-yl)-N-(3-phenylpropyl)propanamide, 3-(3,5-dimethyl-1-(3-methyl-[1,2,4]triazolo[4,3-b]pyridazin-6-yl)-1H-pyrazol-4-yl)-1-(4-ethylpiperazin-1-yl)propan-1-one, 3-(1-([1,2,4]triazolo[4,3-b]pyridazin-6-yl)-3,5-dimethyl-1H-pyrazol-4-yl)-1-(4-methylpiperidin-1-yl)propan-1-one, 3-(1-([1,2,4]triazolo[4,3-b]pyridazin-6-yl)-3,5-dimethyl-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-N-(2-fluorobenzyl)propanamide, and 3-(3,5-dimethyl-1-(3-methyl-[1,2,4]triazolo[4,3-b]pyridazin-6-yl)-1H-pyrazol-4-yl)-N-(2-((furan-2-ylmethyl)thio)ethyl)propanamide.

In some embodiments compound of Formula (I) is selected from the list consisting of 1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperazin-1-yl)propan-1-one, 1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperidin-1-yl)propan-1-one, 3-(3,5-dimethyl-1-(3-methyl-[1,2,4]triazolo[4,3-b]
pyridazin-6-yl)-1H-pyrazol-4-yl)-1-(4-(pyridin-2-ylm-
ethyl)piperazin-1-yl)propan-1-one,
(R)-1-(3-benzylpyrrolidin-1-yl)-3-(3,5-dimethyl-1-(3-
methyl-[1,2,4]triazolo[4,3-b]pyridazin-6-yl)-1H-pyrazol-
4-yl)propan-1-one,
(S)-1-(3-benzylpyrrolidin-1-yl)-3-(3,5-dimethyl-1-(3-
methyl-[1,2,4]triazolo[4,3-b]pyridazin-6-yl)-1H-pyrazol-
4-yl)propan-1-one,
1-(4-benzylpiperidin-1-yl)-3-(1-(3-cyclopropyl-[1,2,4]tri-
azolo[4,3-b]pyridazin-6-yl)-3,5-dimethyl-1H-pyrazol-4-
yl)propan-1-one,
1-(4-benzylpiperidin-1-yl)-3-(3,5-dimethyl-1-(3-phenyl-[1,
2,4]triazolo[4,3-b]pyridazin-6-yl)-1H-pyrazol-4-yl)pro-
pan-1-one,
3-(1-(3-benzyl-[1,2,4]triazolo[4,3-b]pyridazin-6-yl)-3,5-di-
methyl-1H-pyrazol-4-yl)-1-(4-benzylpiperidin-1-yl)pro-
pan-1-one,
1-(4-benzylpiperidin-1-yl)-3-(3,5-dimethyl-1-(3-methylimi-
dazo[1,2-b]pyridazin-6-yl)-1H-pyrazol-4-yl)propan-1-
one,
1-(4-benzylpiperidin-1-yl)-2-(3,5-dimethyl-1-(3-methyl-[1,
2,4]triazolo[4,3-b]pyridazin-6-yl)-1H-pyrazol-4-yl)
ethan-1-one,
1-(4-benzylpiperidin-1-yl)-3-(3,5-dimethyl-1-(3-methyl-[1,
2,4]triazolo[4,3-b]pyridazin-6-yl)-1H-pyrazol-4-yl)pro-
pane-1-thione,
6-(4-(3-(4-benzylpiperidin-1-yl)propyl)-3,5-dimethyl-1H-
pyrazol-1-yl)-3-methyl-[1,2,4]triazolo[4,3-b]pyridazine,
1-(azepan-1-yl)-3-(3,5-dimethyl-1-(3-methyl-[1,2,4]tri-
azolo[4,3-b]pyridazin-6-yl)-1H-pyrazol-4-yl)propan-1-
one,
3-(3,5-dimethyl-1-(3-methyl-[1,2,4]triazolo[4,3-b]
pyridazin-6-yl)-1H-pyrazol-4-yl)-1-morpholinopropan-1-
one,
N-(3-chlorobenzyl)-3-(3,5-dimethyl-1-(3-methyl-[1,2,4]tri-
azolo[4,3-b]pyridazin-6-yl)-1H-pyrazol-4-yl)-N-methyl-
propanamide,
3-(3,5-dimethyl-1-(3-methyl-[1,2,4]triazolo[4,3-b]
pyridazin-6-yl)-1H-pyrazol-4-yl)-1-(4-(furan-2-ylm-
ethyl)piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(2-phenylpropan-
2-yl)piperazin-1-yl)propan-1-one,
1-(4-(3,4-dimethoxybenzyl)piperazin-1-yl)-3-(3,5-dim-
ethyl-1-(3-methyl-[1,2,4]triazolo[4,3-b]pyridazin-6-yl)-
1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(naphthalen-2-yl-
methyl)piperazin-1-yl)propan-1-one,
1-(4-(3-chlorobenzyl)piperidin-1-yl)-3-(3,5-dimethyl-1-(3-
methyl-[1,2,4]triazolo[4,3-b]pyridazin-6-yl)-1H-pyrazol-
4-yl)propan-1-one,
1-(3-benzylazetidin-1-yl)-3-(3,5-dimethyl-1-(3-methyl-[1,
2,4]triazolo[4,3-b]pyridazin-6-yl)-1H-pyrazol-4-yl)pro-
pan-1-one,
1-(3-(benzylamino)azetidin-1-yl)-3-(3,5-dimethyl-1-(3-
methyl-[1,2,4]triazolo[4,3-b]pyridazin-6-yl)-1H-pyrazol-
4-yl)propan-1-one,
N-benzyl-3,5-dimethyl-1-(3-methyl-[1,2,4]triazolo[4,3-b]
pyridazin-6-yl)-1H-pyrazole-4-carboxamide,
(3-benzylpyrrolidin-1-yl)(3,5-dimethyl-1-(3-methyl-[1,2,4]
triazolo[4,3-b]pyridazin-6-yl)-1H-pyrazol-4-yl)metha-
none,
1-(3-benzylpyrrolidin-1-yl)-3-(5-isopropyl-3-methyl-1-(3-
methyl-[1,2,4]triazolo[4,3-b]pyridazin-6-yl)-1H-pyrazol-
4-yl)propan-1-one, and
1-(3-benzylpyrrolidin-1-yl)-3-(3-methyl-1-(3-methyl-[1,2,
4]triazolo[4,3-b]pyridazin-6-yl)-5-(trifluoromethyl)-1H-
pyrazol-4-yl)propan-1-one.

In some embodiments compound of Formula (I) is selected from the list consisting of 3-(3,5-dimethyl-1-(3-methyl-[1,2,4]triazolo[4,3-b]
pyridazin-6-yl)-1H-pyrazol-4-yl)-1-(4-phenylpiperazin-
1-yl)propan-1-one,
3-(3,5-dimethyl-1-(3-methyl-[1,2,4]triazolo[4,3-b]
pyridazin-6-yl)-1H-pyrazol-4-yl)-1-(4-(3-methoxyphe-
nyl)piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(pyridin-2-yl)pip-
erazin-1-yl)propan-1-one,
1-(4-benzylpiperidin-1-yl)-3-(3,5-dimethyl-1-(3-methyl-[1,
2,4]triazolo[4,3-b]pyridazin-6-yl)-1H-pyrazol-4-yl)pro-
pan-1-one,
3-(3,5-dimethyl-1-(3-methyl-[1,2,4]triazolo[4,3-b]
pyridazin-6-yl)-1H-pyrazol-4-yl)-1-(4-(4-fluorophenyl)
piperazin-1-yl)propan-1-one,
3-(1-([1,2,4]triazolo[4,3-b]pyridazin-6-yl)-3,5-dimethyl-
1H-pyrazol-4-yl)-1-(4-(4-fluorophenyl)piperazin-1-yl)
propan-1-one,
3-(3,5-dimethyl-1-(3-methyl-[1,2,4]triazolo[4,3-b]
pyridazin-6-yl)-1H-pyrazol-4-yl)-1-(pyrrolidin-1-yl)pro-
pan-1-one,
3-(3,5-dimethyl-1-(3-methyl-[1,2,4]triazolo[4,3-b]
pyridazin-6-yl)-1H-pyrazol-4-yl)-1-(4-(4-methoxyphe-
nyl)piperazin-1-yl)propan-1-one,
3-(1-([1,2,4]triazolo[4,3-b]pyridazin-6-yl)-3,5-dimethyl-
1H-pyrazol-4-yl)-1-(4-(3-methoxyphenyl)piperazin-1-yl)
propan-1-one,
3-(1-([1,2,4]triazolo[4,3-b]pyridazin-6-yl)-3,5-dimethyl-
1H-pyrazol-4-yl)-1-(4-(4-methoxyphenyl)piperazin-1-yl)
propan-1-one,
3-(1-([1,2,4]triazolo[4,3-b]pyridazin-6-yl)-3,5-dimethyl-
1H-pyrazol-4-yl)-1-(4-phenylpiperazin-1-yl)propan-1-
one,
1-(4-(3-chlorobenzyl)piperazin-1-yl)-3-(3,5-dimethyl-1-(3-
methyl-[1,2,4]triazolo[4,3-b]pyridazin-6-yl)-1H-pyrazol-
4-yl)propan-1-one,
3-(1-([1,2,4]triazolo[4,3-b]pyridazin-6-yl)-3,5-dimethyl-
1H-pyrazol-4-yl)-1-(4-(pyridin-2-yl)piperazin-1-yl)pro-
pan-1-one,
3-(3,5-dimethyl-1-(3-methyl-[1,2,4]triazolo[4,3-b]
pyridazin-6-yl)-1H-pyrazol-4-yl)-N-((5-methylfuran-2-
yl)methyl)propanamide,
3-(3,5-dimethyl-1-(3-methyl-[1,2,4]triazolo[4,3-b]
pyridazin-6-yl)-1H-pyrazol-4-yl)-1-(4-(2-fluorophenyl)
piperazin-1-yl)propan-1-one,
3-(3,5-dimethyl-1-(3-methyl-[1,2,4]triazolo[4,3-b]
pyridazin-6-yl)-1H-pyrazol-4-yl)-N-(3-phenylpropyl)
propanamide,
3-(1-([1,2,4]triazolo[4,3-b]pyridazin-6-yl)-3,5-dimethyl-
1H-pyrazol-4-yl)-1-(4-benzylpiperidin-1-yl)propan-1-
one,
3-(3,5-dimethyl-1-(3-methyl-[1,2,4]triazolo[4,3-b]
pyridazin-6-yl)-1H-pyrazol-4-yl)-1-(4-(2,5-dimethylphe-
nyl)piperazin-1-yl)propan-1-one,
N-(4-chlorobenzyl)-3-(3,5-dimethyl-1-(3-methyl-[1,2,4]tri-
azolo[4,3-b]pyridazin-6-yl)-1H-pyrazol-4-yl)propana-
mide,
3-(3,5-dimethyl-1-(3-methyl-[1,2,4]triazolo[4,3-b]
pyridazin-6-yl)-1H-pyrazol-4-yl)-N-(thiophen-2-ylm-
ethyl)propanamide, N-(2-(1H-indol-3-yl)ethyl)-3-(3,5-dimethyl-1-(3-methyl-[1,2,4]triazolo[4,3-b]pyridazin-6-yl)-1H-pyrazol-4-yl)propanamide, N-benzyl-3-(3,5-dimethyl-1-(3-methyl-[1,2,4]triazolo[4,3-b]pyridazin-6-yl)-1H-pyrazol-4-yl)propanamide, 3-(1-([1,2,4]triazolo[4,3-b]pyridazin-6-yl)-3,5-dimethyl-1H-pyrazol-4-yl)-N-(3-phenylpropyl)propanamide, 3-(3,5-dimethyl-1-(3-methyl-[1,2,4]triazolo[4,3-b]pyridazin-6-yl)-1H-pyrazol-4-yl)-1-(4-ethylpiperazin-1-yl)propan-1-one, 3-(1-([1,2,4]triazolo[4,3-b]pyridazin-6-yl)-3,5-dimethyl-1H-pyrazol-4-yl)-1-(4-methylpiperidin-1-yl)propan-1-one, 3-(1-([1,2,4]triazolo[4,3-b]pyridazin-6-yl)-3,5-dimethyl-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-N-(2-fluorobenzyl)propanamide, 3-(3,5-dimethyl-1-(3-methyl-[1,2,4]triazolo[4,3-b]pyridazin-6-yl)-1H-pyrazol-4-yl)-N-(2-((furan-2-ylmethyl)thio)ethyl)propanamide, In some embodiments compound of Formula (I) is selected from the list consisting of:

3-(3,5-dimethyl-1-(3-methyl-[1,2,4]triazolo[4,3-b]pyridazin-6-yl)-1H-pyrazol-4-yl)-1-(4-phenylpiperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperazin-1-yl)propan-1-one, 1-(4-benzylpiperidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorophenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(3-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-(4-methoxyphenyl)piperazin-1-yl)propan-1-one, 3-(1-([1,2,4]triazolo[4,3-b]pyridazin-6-yl)-3,5-dimethyl-1H-pyrazol-4-yl)-1-(4-phenylpiperazin-1-yl)propan-1-one, 1-(4-(3-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(1-([1,2,4]triazolo[4,3-b]pyridazin-6-yl)-3,5-dimethyl-1H-pyrazol-4-yl)-1-(4-(pyridin-2-yl)piperazin-1-yl)propan-1-one, 3-(3,5-dimethyl-1-(3-methyl-[1,2,4]triazolo[4,3-b]pyridazin-6-yl)-1H-pyrazol-4-yl)-N-((5-methylfuran-2-yl)methyl)propanamide, 3-(3,5-dimethyl-1-(3-methyl-[1,2,4]triazolo[4,3-b]pyridazin-6-yl)-1H-pyrazol-4-yl)-1-(4-(2-fluorophenyl)piperazin-1-yl)propan-1-one, 3-(3,5-dimethyl-1-(3-methyl-[1,2,4]triazolo[4,3-b]pyridazin-6-yl)-1H-pyrazol-4-yl)-N-(3-phenylpropyl)propanamide, 3-(1-([1,2,4]triazolo[4,3-b]pyridazin-6-yl)-3,5-dimethyl-1H-pyrazol-4-yl)-1-(4-benzylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(2,5-dimethylphenyl)piperazin-1-yl)propan-1-one, N-(4-chlorobenzyl)-3-(3,5-dimethyl-1-(3-methyl-[1,2,4]triazolo[4,3-b]pyridazin-6-yl)-1H-pyrazol-4-yl)propanamide, 3-(3,5-dimethyl-1-(3-methyl-[1,2,4]triazolo[4,3-b]pyridazin-6-yl)-1H-pyrazol-4-yl)-N-(thiophen-2-ylmethyl)propanamide, N-(2-(1H-indol-3-yl)ethyl)-3-(3,5-dimethyl-1-(3-methyl-[1,2,4]triazolo[4,3-b]pyridazin-6-yl)-1H-pyrazol-4-yl)propanamide, N-benzyl-3-(3,5-dimethyl-1-(3-methyl-[1,2,4]triazolo[4,3-b]pyridazin-6-yl)-1H-pyrazol-4-yl)propanamide, 3-(1-([1,2,4]triazolo[4,3-b]pyridazin-6-yl)-3,5-dimethyl-1H-pyrazol-4-yl)-N-(3-phenylpropyl)propanamide, 3-(3,5-dimethyl-1-(3-methyl-[1,2,4]triazolo[4,3-b]pyridazin-6-yl)-1H-pyrazol-4-yl)-1-(4-ethylpiperazin-1-yl)propan-1-one, 3-(1-([1,2,4]triazolo[4,3-b]pyridazin-6-yl)-3,5-dimethyl-1H-pyrazol-4-yl)-1-(4-methylpiperidin-1-yl)propan-1-one, 3-(1-([1,2,4]triazolo[4,3-b]pyridazin-6-yl)-3,5-dimethyl-1H-pyrazol-4-yl)-1-(pyrrolidin-1-yl)propan-1-one, 3-(3,5-dimethyl-1-(3-methyl-[1,2,4]triazolo[4,3-b]pyridazin-6-yl)-1H-pyrazol-4-yl)-N-(2-fluorobenzyl)propanamide, 3-(3,5-dimethyl-1-(3-methyl-[1,2,4]triazolo[4,3-b]pyridazin-6-yl)-1H-pyrazol-4-yl)-N-(2-((furan-2-ylmethyl)thio)ethyl)propanamide, 1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperazin-1-yl)propan-1-one, 1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxybenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluorobenzyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-(pyridin-2-ylmethyl)piperazin-1-yl)propan-1-one, (R)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, (S)-1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one, 1-(4-benzylpiperidin-1-yl)-3-(3,5-dimethyl-1-(3-phenyl-[1,2,4]triazolo[4,3-b]pyridazin-6-yl)-1H-pyrazol-4-yl)propan-1-one, 3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one, 1-(4-benzylpiperidin-1-yl)-3-(3,5-dimethyl-1-(3-methylimidazo[1,2-b]pyridazin-6-yl)-1H-pyrazol-4-yl)propan-1-one, 1-(4-benzylpiperidin-1-yl)-2-(3,5-dimethyl-1-(3-methyl-[1,2,4]triazolo[4,3-b]pyridazin-6-yl)-1H-pyrazol-4-yl)ethan-1-one, 1-(4-benzylpiperidin-1-yl)-3-(3,5-dimethyl-1-(3-methyl-[1,2,4]triazolo[4,3-b]pyridazin-6-yl)-1H-pyrazol-4-yl)propane-1-thione, 6-(4-(3-(4-benzylpiperidin-1-yl)propyl)-3,5-dimethyl-1H-pyrazol-1-yl)-3-methyl-[1,2,4]triazolo[4,3-b]pyridazine, 1-(azepan-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-morpholinopropan-1-one, N-(3-chlorobenzyl)-3-(3,5-dimethyl-1-(3-methyl-[1,2,4]triazolo[4,3-b]pyridazin-6-yl)-1H-pyrazol-4-yl)-N-methylpropanamide, 3-(3,5-dimethyl-1-(3-methyl-[1,2,4]triazolo[4,3-b]pyridazin-6-yl)-1H-pyrazol-4-yl)-1-(4-(furan-2-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-phenylpropan-2-yl)piperazin-1-yl)propan-1-one, 1-(4-(3,4-dimethoxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(naphthalen-2-ylmethyl)piperazin-1-yl)propan-1-one, 1-(4-(3-chlorobenzyl)piperidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzylazetidin-1-yl)-3-(3,5-dimethyl-1-(3-methyl-[1,2,4]triazolo[4,3-b]pyridazin-6-yl)-1H-pyrazol-4-yl)propan-1-one, 1-(3-(benzylamino)azetidin-1-yl)-3-(3,5-dimethyl-1-(3-methyl-[1,2,4]triazolo[4,3-b]pyridazin-6-yl)-1H-pyrazol-4-yl)propan-1-one, N-benzyl-3,5-dimethyl-1-(3-methyl-[1,2,4]triazolo[4,3-b]pyridazin-6-yl)-1H-pyrazole-4-carboxamide, (3-benzylpyrrolidin-1-yl)(3,5-dimethyl-1-(3-methyl-[1,2,4]triazolo[4,3-b]pyridazin-6-yl)-1H-pyrazol-4-yl)methanone, 1-(3-benzylpyrrolidin-1-yl)-3-(5-isopropyl-3-methyl-1-(3-methyl-[1,2,4]triazolo[4,3-b]pyridazin-6-yl)-1H-pyrazol-4-yl)propan-1-one, 1-(3-benzylpyrrolidin-1-yl)-3-(3-methyl-1-(3-methyl-[1,2,4]triazolo[4,3-b]pyridazin-6-yl)-5-(trifluoromethyl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methoxyphenyl)piperazin-1-yl)propan-1-one, 1-benzyl-4-(3-(3,5-dimethyl-1-(3-methyl-[1,2,4]triazolo[4,3-b]pyridazin-6-yl)-1H-pyrazol-4-yl)propanoyl)piperazin-2-one, 1-(4-benzylpiperidin-1-yl)-3-(3,5-diethyl-1-(3-isopropyl-[1,2,4]triazolo[4,3-b]pyridazin-6-yl)-1H-pyrazol-4-yl)propan-1-one, 1-(3-benzylpyrrolidin-1-yl)-3-(1-(3-isopropyl-[1,2,4]triazolo[4,3-b]pyridazin-6-yl)-3,5-dimethyl-1H-pyrazol-4-yl)propan-1-one, 1-(3-benzylpyrrolidin-1-yl)-3-(1-(3-ethyl-[1,2,4]triazolo[4,3-b]pyridazin-6-yl)-3,5-dimethyl-1H-pyrazol-4-yl)propan-1-one, 1-(2,2-dimethylpyrrolidin-1-yl)-3-(1-(3-isopropyl-[1,2,4]triazolo[4,3-b]pyridazin-6-yl)-3,5-dimethyl-1H-pyrazol-4-yl)propan-1-one, 1-(3,3-dimethylpyrrolidin-1-yl)-3-(1-(3-isopropyl-[1,2,4]triazolo[4,3-b]pyridazin-6-yl)-3,5-dimethyl-1H-pyrazol-4-yl)propan-1-one, 1-(3-benzylpyrrolidin-1-yl)-3-(3,5-diethyl-1-(3-isopropyl-[1,2,4]triazolo[4,3-b]pyridazin-6-yl)-1H-pyrazol-4-yl)propan-1-one, 3-(3,5-diethyl-1-(3-isopropyl-[1,2,4]triazolo[4,3-b]pyridazin-6-yl)-1H-pyrazol-4-yl)-1-(3,3-dimethylpyrrolidin-1-yl)propan-1-one, 1-((1S)-2-azabicyclo[2.2.1]heptan-2-yl)-3-(1-(3-isopropyl-[1,2,4]triazolo[4,3-b]pyridazin-6-yl)-3,5-dimethyl-1H-pyrazol-4-yl)propan-1-one, (1S,5R)-3-(3-(1-(3-ethyl-[1,2,4]triazolo[4,3-b]pyridazin-6-yl)-3,5-dimethyl-1H-pyrazol-4-yl)propanoyl)-2,3,4,5-tetrahydro-1,5-methanopyrido[1,2-d][1,4]diazepin-7(1H)-one, 1-((1S)-2-azabicyclo[2.2.1]heptan-2-yl)-3-(1-(3-ethyl-[1,2,4]triazolo[4,3-b]pyridazin-6-yl)-3,5-dimethyl-1H-pyrazol-4-yl)propan-1-one, 3-(3,5-dimethyl-1-(3-(trifluoromethyl)-[1,2,4]triazolo[4,3-b]pyridazin-6-yl)-1H-pyrazol-4-yl)-1-(pyrrolidin-1-yl)propan-1-one, 1-(4-benzylpiperidin-1-yl)-3-(1-(3-isopropyl-[1,2,4]triazolo[4,3-b]pyridazin-6-yl)-3,5-dimethyl-1H-pyrazol-4-yl)propan-1-one, 1-(4-benzylpiperidin-1-yl)-3-(1-(3-ethyl-[1,2,4]triazolo[4,3-b]pyridazin-6-yl)-3,5-dimethyl-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(3,3-dimethylpyrrolidin-1-yl)propan-1-one, 3-(1-(3-ethyl-[1,2,4]triazolo[4,3-b]pyridazin-6-yl)-3,5-dimethyl-1H-pyrazol-4-yl)-1-(pyrrolidin-1-yl)propan-1-one, 3-(1-(3-isopropyl-[1,2,4]triazolo[4,3-b]pyridazin-6-yl)-3,5-dimethyl-1H-pyrazol-4-yl)-1-(pyrrolidin-1-yl)propan-1-one, 3-(3,5-diethyl-1-(3-isopropyl-[1,2,4]triazolo[4,3-b]pyridazin-6-yl)-1H-pyrazol-4-yl)-1-(3,3-dimethylpyrrolidin-1-yl)propan-1-one, 1-(3-benzylpyrrolidin-1-yl)-3-(3,5-diethyl-1-(3-methyl-[1,2,4]triazolo[4,3-b]pyridazin-6-yl)-1H-pyrazol-4-yl)propan-1-one, 1-(4-benzyl-1,4-diazepan-1-yl)-3-(3,5-dimethyl-1-(3-methyl-[1,2,4]triazolo[4,3-b]pyridazin-6-yl)-1H-pyrazol-4-yl)propan-1-one, 1-(4-benzylpiperidin-1-yl)-3-(3-isopropyl-5-methyl-1-(3-methyl-[1,2,4]triazolo[4,3-b]pyridazin-6-yl)-1H-pyrazol-4-yl)propan-1-one, 3-(1-(3-benzyl-[1,2,4]triazolo[4,3-b]pyridazin-6-yl)-3,5-dimethyl-1H-pyrazol-4-yl)-1-(4-benzylpiperidin-1-yl)propan-1-one, 1-(4-benzylpiperidin-1-yl)-3-(1-(3-cyclopropyl-[1,2,4]triazolo[4,3-b]pyridazin-6-yl)-3,5-dimethyl-1H-pyrazol-4-yl)propan-1-one, 1-(4-benzylpiperidin-1-yl)-2-(3,5-dimethyl-1-(3-methyl-[1,2,4]triazolo[4,3-b]pyridazin-6-yl)-1H-pyrazol-4-yl)propan-1-one, 1-(4-benzylpiperazin-1-yl)-2-(3,5-dimethyl-1-(3-methyl-[1,2,4]triazolo[4,3-b]pyridazin-6-yl)-1H-pyrazol-4-yl)propan-1-one, 1-(4-benzylpiperazin-1-yl)-3-(3,5-dimethyl-1-(3-methylimidazo[1,2-b]pyridazin-6-yl)-1H-pyrazol-4-yl)propan-1-one, 1-(3-benzylpiperazin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpiperazin-1-yl)-3-(3,5-dimethyl-1-(3-methyl-[1,2,4]triazolo[4,3-b]pyridazin-6-yl)-1H-pyrazol-4-yl)propan-1-one, 1-(3-benzylpiperidin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpiperidin-1-yl)-3-(3,5-dimethyl-1-(3-methylimidazo[1,2-b]pyridazin-6-yl)-1H-pyrazol-4-yl)propan-1-one, 1-(3-benzylpyrrolidin-1-yl)-2-(3,5-dimethyl-1-(3-methyl-[1,2,4]triazolo[4,3-b]pyridazin-6-yl)-1H-pyrazol-4-yl)propan-1-one, 1-(3-benzylpyrrolidin-1-yl)-3-(3,5-dimethyl-1-(3-methylimidazo[1,2-b]pyridazin-6-yl)-1H-pyrazol-4-yl)propan-1-one, 2-(3,5-dimethyl-1-(3-methyl-[1,2,4]triazolo[4,3-b]pyridazin-6-yl)-1H-pyrazol-4-yl)-1-(4-phenethylpiperidin-1-yl)propan-1-one, 3-(3,5-dimethyl-1-(3-methylimidazo[1,2-b]pyridazin-6-yl)-1H-pyrazol-4-yl)-1-(4-phenethylpiperidin-1-yl)propan-1-one.

A further embodiment of the present invention is directed to a compound having a structure according to formula (XX) in any of their stereoisomeric forms or a mixture of stereoisomeric forms in any ratio, and the physiologically acceptable salts thereof, and the physiologically acceptable solvates or hydrates of any of them,

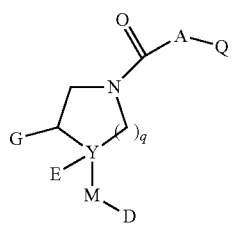

(XX)

wherein in formula (XX),

Q may be selected from group A) consisting of

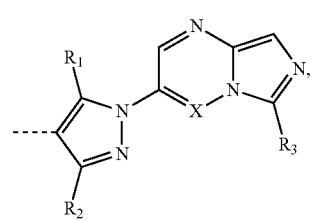

(XXa)

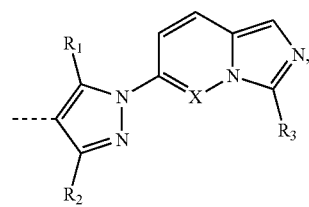

(XXb)

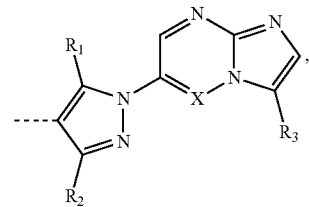

(XXc)

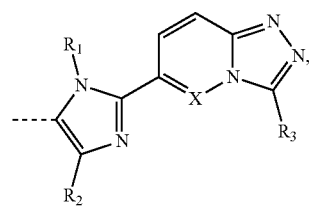

(XXd)

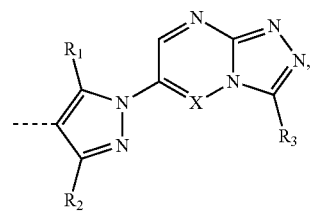

(XXe)

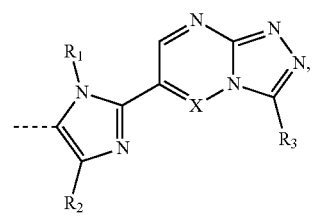

(XXf)

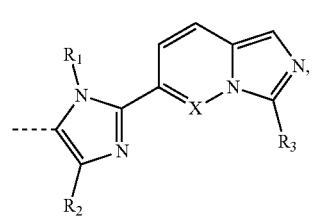

(XXg)

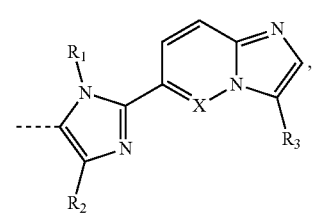
(XXh)

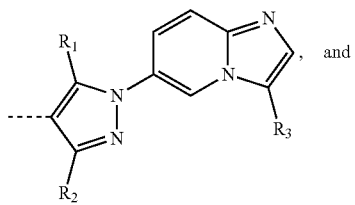
(XXi), and

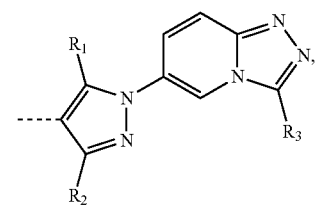
(XXj)

X is selected from the group consisting of CH, and N;
R$_1$ and R$_2$ are independently selected from the group consisting of hydrogen, (C$_1$-C$_6$)haloalkyl and —(C$_3$-C$_8$)cycloalkyl, (C$_1$-C$_6$)alkyl, preferably (C$_1$-C$_6$)alkyl, more preferably methyl
R$_3$ is selected from the group consisting of hydrogen, —(C$_1$-C$_6$)alkyl, —(C$_1$-C$_6$)haloalkyl, (C$_3$-C$_8$)cycloalkyl, —(C$_6$-C$_{10}$)aryl, —(C$_6$-C$_{10}$)aryl(C$_1$-C$_6$)alkyl, —(C$_3$-C$_{10}$)heteroaryl, —(C$_3$-C$_{10}$)heteroaryl(C$_1$-C$_6$)alkyl, —CONH(C$_6$-C$_{10}$)Aryl, —CONH$_2$, and —CON((C$_1$-C$_6$)alkyl)(C$_6$-C$_{10}$)Aryl, preferably —(C$_1$-C$_6$)alkyl.

Alternatively, Q may be selected from group B) consisting of

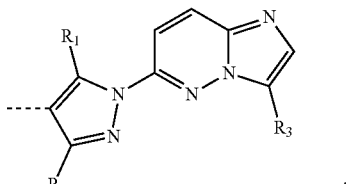
(XXk)

, and

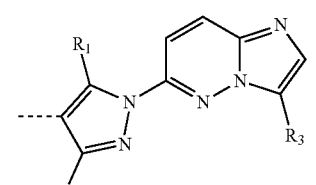
(XXl)
;

R$_1$ and R$_2$ are independently selected from the group consisting of hydrogen, (C$_1$-C$_6$)haloalkyl and —(C$_3$-C$_8$)cycloalkyl, (C$_1$-C$_6$)alkyl, preferably (C$_1$-C$_6$)alkyl, more preferably methyl
R$_3$ is selected from the group consisting of hydrogen, —(C$_1$-C$_6$)alkyl, —(C$_1$-C$_6$)haloalkyl, (C$_3$-C$_8$)cycloalkyl, —(C$_6$-C$_{10}$)aryl, —(C$_6$-C$_{10}$)aryl(C$_1$-C$_6$)alkyl, —(C$_3$-C$_{10}$)heteroaryl, —(C$_3$-C$_{10}$)heteroaryl(C$_1$-C$_6$)alkyl; —CONH(C$_6$-C$_{10}$)Aryl, —CONH$_2$, and —CON((C$_1$-C$_6$)alkyl)(C$_6$-C$_{10}$)Aryl, preferably —(C$_1$-C$_6$)alkyl.

If Q is selected from group A),
then
A is selected from the group consisting of —(CH$_2$)$_3$—, —(CH$_2$)$_2$—, —CH$_2$—, and cyclopropyl; preferably —(CH$_2$)$_2$—.
G is selected from the group consisting of hydrogen, —(C$_1$-C$_6$)alkyl-, —(C$_3$-C$_{10}$)heteroaryl, (C$_6$-C$_{10}$)aryl (C$_1$-C$_6$)alkyl and (C$_6$-C$_{10}$)aryl; which are optionally substituted by one or more identical or different substituents, preferably the one or more identical or different substituents are selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —NH(C$_1$-C$_4$)alkyl-N((C$_1$-C$_4$)alkyl)$_2$, —NO, —SO$_2$(C$_1$-C$_4$)alkyl, —NHSO$_2$(C$_1$-C$_4$)alkyl, —CONH$_2$, —CF$_3$, —COOH, —NO$_2$, —NHCO(C$_1$-C$_4$)alkyl, —CO$_2$(C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; and —SO$_2$Ph.
D is selected from the group consisting of hydrogen, —(C$_3$-C$_{10}$)heteroaryl for example

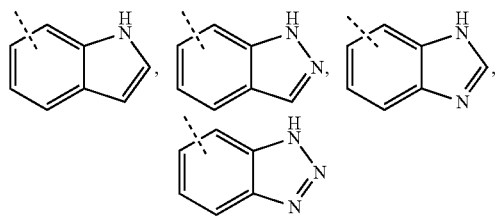

—(C$_6$-C$_{10}$)aryl for example phenyl,

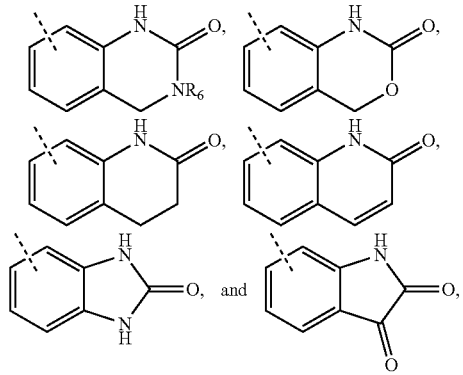

—(C$_1$-C$_{10}$)aryl(C$_1$-C$_6$)alkyl for example benzyl, —(C$_3$-C$_{10}$)heteroaryl(C$_1$-C$_6$)alkyl, —(C$_1$-C$_6$)alkyl,

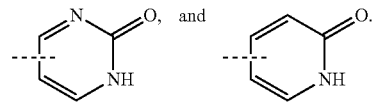

These substituents of which D is selected, may be optionally substituted by one or more identical or different substituents. Preferably the one or more identical or different substituents are selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —NH(C$_1$-C$_4$)alkyl, —N((C$_1$-C$_4$)alkyl)$_2$, —NO, —SO$_2$(C$_1$-C$_4$)alkyl, —NHSO(C$_1$-C$_4$)alkyl, —NHSO$_2$(C$_1$-C$_4$)alkyl, —CONH$_2$, —CF$_3$, —COOH, —NO$_2$, —NHCO(C$_1$-C$_4$)alkyl, —CO$_2$(C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; —COCH$_2$SO$_2$Ph, —NHCONHR$_6$, —CONHOR$_6$, —CONHCN, NHCOOR$_6$,

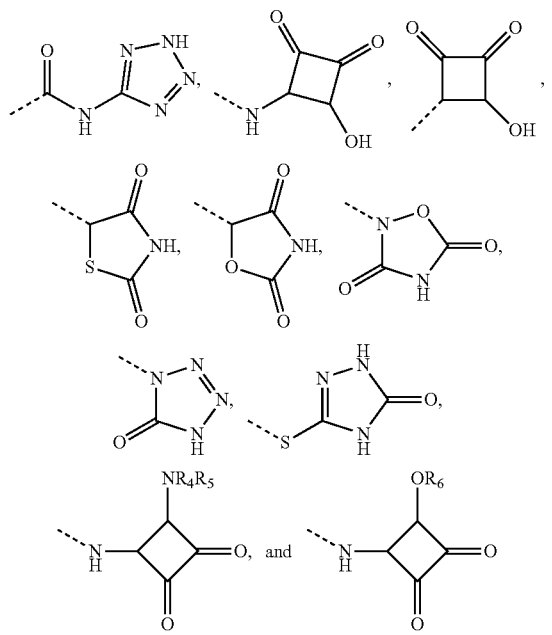

preferably the at least one —(C$_3$-C$_{10}$)heteroaryl substituent is selected from the group consisting of

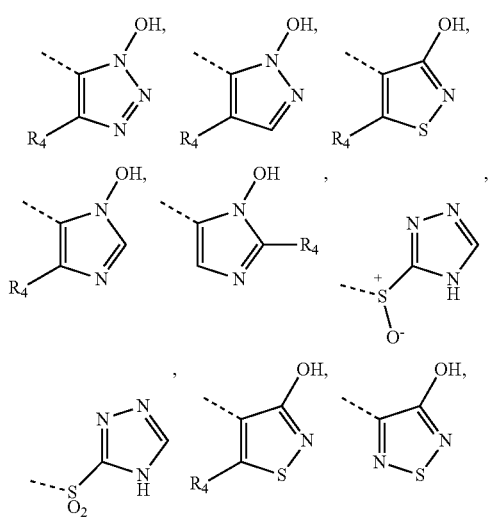

-continued

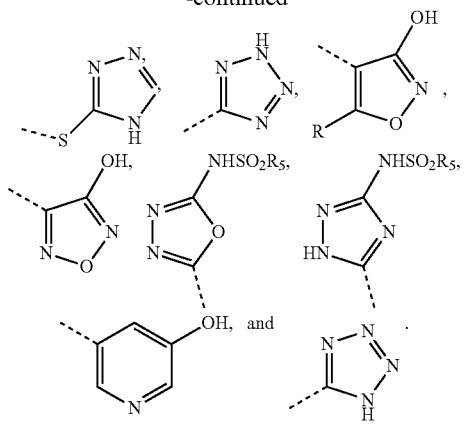

R$_6$ is selected from the group consisting of hydrogen, —(C$_1$-C$_4$)alkyl, and —(C$_1$-C$_4$)haloalkyl;
R$_4$ and R$_5$ are independently selected from the group consisting of hydrogen, —(C$_1$-C$_4$)alkyl;
E is selected from the group consisting of hydrogen, —(C$_1$-C$_6$)alkyl and not present;
Y is selected from the group consisting of C, and N;
M is selected from the group consisting of hydrogen, —CR$_4$R$_5$—, NH, O and not present;
q is 1 or 2;
if Q is selected from group B) then
A is selected from the group consisting of —(CH$_2$)$_2$— and cyclopropyl;
G is selected from the group consisting of hydrogen, —(C$_1$-C$_6$)alkyl-, —(C$_3$-C$_{10}$)heteroaryl, (C$_6$-C$_{10}$)aryl (C$_1$-C$_6$)alkyl and (C$_6$-C$_{10}$)aryl; which are optionally substituted by one or more identical or different substituents, preferably the one or more identical or different substituents are selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —NH(C$_1$-C$_4$)alkyl-N((C$_1$-C$_4$)alkyl)$_2$, —NO, —SO$_2$(C$_1$-C$_4$)alkyl, —NHSO$_2$(C$_1$-C$_4$)alkyl, —CONH$_2$, —CF$_3$, —COOH, —NO$_2$, —NHCO(C$_1$-C$_4$)alkyl, —CO$_2$(C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; and —SO$_2$Ph.
D is selected from the group consisting of hydrogen, phenyl, napthyl, —(C$_3$-C$_{10}$)heteroaryl for example

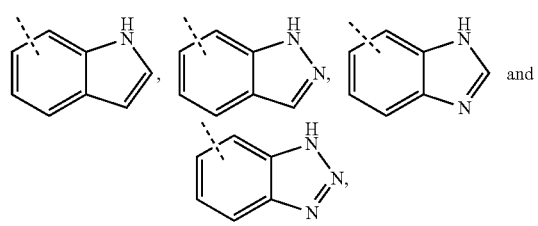

benzyl, —(C$_3$-C$_{10}$)heteroaryl(C$_1$-C$_6$)alkyl, —(C$_1$-C$_6$)alkyl

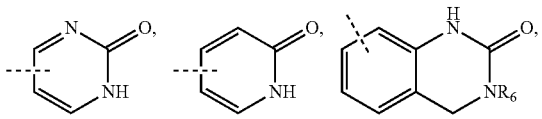

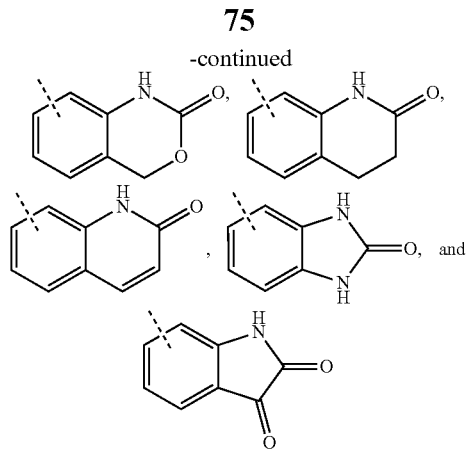

which are optionally substituted by one or more identical or different substituents, the one or more identical or different substituents are selected from the group consisting of halogen, —($C_1$-$C_4$)alkyl, —($C_1$-$C_4$)haloalkyl, —CO($C_1$-$C_4$)alkyl, —CN, —NC, —($C_6$-$C_{10}$)aryl, —($C_3$-$C_{10}$)heteroaryl, —NH($C_1$-$C_4$)alkyl, —NH($C_1$-$C_4$)alkyl, —N(($C_1$-$C_4$)alkyl)$_2$, —NO, —SO$_2$($C_1$-$C_4$)alkyl, —NHSO($C_1$-$C_4$)alkyl, —NHSO$_2$($C_1$-$C_4$)alkyl, —CONH$_2$, —CF$_3$, —COOH, —NO$_2$, —NHCO($C_1$-$C_4$)alkyl, —CO$_2$($C_1$-$C_4$)alkyl, —CONH($C_1$-$C_4$)alkyl, —OR$_6$, —SO$_2$NH$_2$, —CH$_2$COOH, —CH$_2$OR$^6$; —COCH$_2$SO$_2$Ph, —NHCONHR$_6$, —CONHOR$_6$, —SO$_2$Ph, —CONHCN, NHCOOR$_6$,

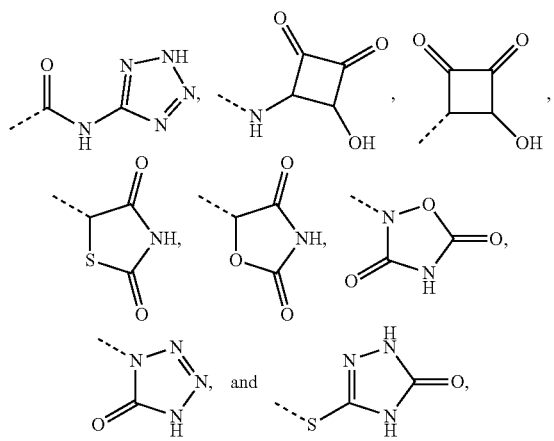

preferably the —($C_3$-$C_{10}$)heteroaryl substituent is selected from the group consisting of

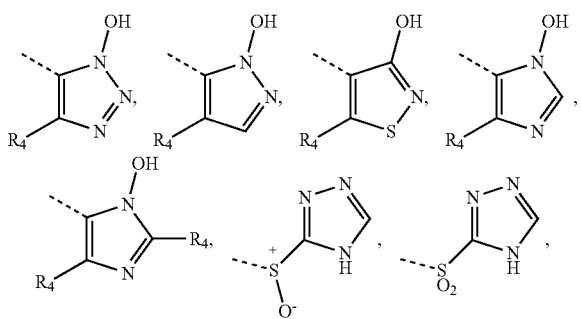

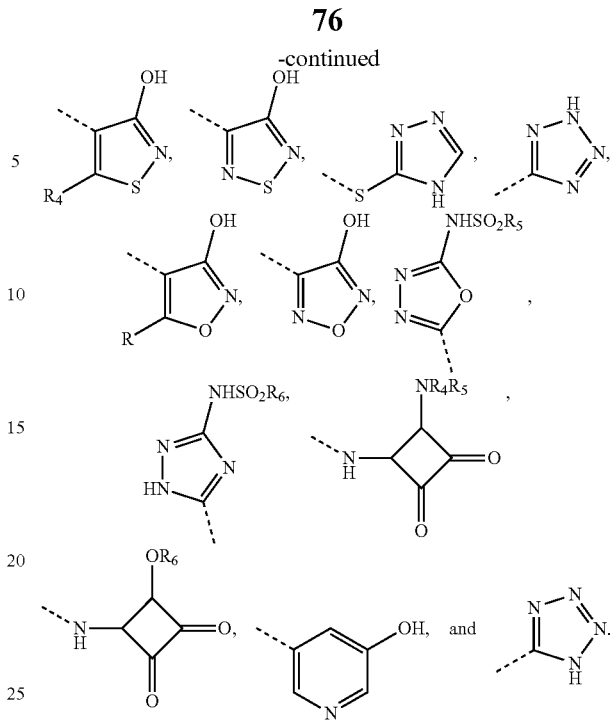

$R_6$ is selected from the group consisting of hydrogen, —$C_3$-cycloalkyl-($C_1$-$C_4$)alkyl, and —($C_1$-$C_4$)haloalky.

E is selected from the group consisting of hydrogen, —($C_1$-$C_6$)alkyl and not present.

Y is selected from the group consisting of C, and N.

M is selected from the group consisting of hydrogen, —CR$_4$R$_5$—, NH, O and not present.

R$_4$ and R$_5$ are independently selected from the group consisting of hydrogen, —($C_1$-$C_4$)alkyl and —$C_3$-cycloalkyl.

q is 1 or 2.

Wherein D is not unsubstituted phenyl if R$_1$ and R$_2$ are both methyl, R$_3$ is methyl or unsubstituted phenyl; Q is formula (XXk), G is hydrogen, q is 2, E is H, M is —CH$_2$—, A is —CH$_2$CH$_2$— and Y is C.

Wherein D is not unsubstituted phenyl if R$_1$ and R$_2$ are both methyl, or ethyl R$_3$ is methyl, ethyl, isopropyl, cyclopropyl, or unsubstituted benzyl; Q is formula (XXI), G is hydrogen, q is 2, E is H, M is —CH$_2$—, A is —CH$_2$CH$_2$— and Y is C.

Wherein D is not unsubstituted phenyl if R$_1$ and R$_2$ are both methyl, or ethyl R$_3$ is methyl, ethyl, isopropyl, cyclopropyl, or unsubstituted benzyl; Q is formula (XXI), G is hydrogen, q is 2, E is not present, M is —C(CH$_3$)$_2$—, A is —CH$_2$CH$_2$— and Y is N.

Wherein D is not unsubstituted 2-pyridyl, phenyl only substituted in meta position with —OMe, phenyl only substituted in para position with F if G is hydrogen, q is 2, E is H or not present if Y is N, M is —CH$_2$, or not present, A is —CH$_2$CH$_2$— and Y is C or N, R$_1$ and R$_2$ are both methyl, R$_3$ is methyl and Q is formula (XXI).

Wherein D is not unsubstituted 2-naphtyl, phenyl substituted only in meta position with Cl, 2-furyl or phenyl substituted only in meta and para position with —OMe if R$_1$ and R$_2$ are both methyl, R$_3$ is methyl; Q is formula (XXI), G is hydrogen, q is 2, E is not present, M is —CH$_2$—, A is —CH$_2$CH$_2$— and Y is N.

Wherein D is not unsubstituted Bn if Q is formula (XXk), M is —CH$_2$, A is —CH$_2$CH$_2$—, E is H present, Y is C, G is hydrogen, and q is 2, R$_1$ and R$_2$ are both methyl and R$_3$ is methyl.

Wherein D is not hydrogen if M is —CH$_2$—, A is —CH$_2$CH$_2$—, q is 1, Y is C, E is methyl, R$_1$ and R$_2$ are both methyl or ethyl, R$_3$ is methyl or isopropyl and Q is formula (XXI).

Wherein M is not hydrogen, if E is hydrogen, G is hydrogen, A is —CH$_2$CH$_2$—, q is 1 and Y is C, R$_1$ and R$_2$ are both methyl, R$_3$ is —CF$_3$, ethyl or isopropyl, and Q is formula (XXI).

Wherein D is not unsubstituted phenyl if E is hydrogen, M is —CH$_2$, A is —CH$_2$CH$_2$—, q is 1 and Y is C; R$_1$ and R$_2$ are both methyl or both ethyl, R$_3$ is methyl, ethyl or isopropyl, and Q is formula (XXI) and G is hydrogen.

Wherein G is not unsubstituted benzyl if E is hydrogen, M is hydrogen, A is —CH$_2$CH$_2$—, q is 1 and Y is C; R$_1$ and R$_2$ are both methyl or both ethyl, R$_3$ is methyl, ethyl or isopropyl, and Q is formula (XXI).

Wherein D is not unsubstituted phenyl if E is hydrogen, M is —CH$_2$, A is —CH$_2$CH$_2$—, q is 1 and Y is C; R$_1$ and R$_2$ are both methyl, R$_3$ is methyl, and Q is formula (XXk) and G is hydrogen.

Wherein G is not unsubstituted benzyl if E is hydrogen, M is hydrogen, A is —CH$_2$CH$_2$—, q is 1 and Y is C; R$_1$ and R$_2$ are both methyl or both ethyl, R$_3$ is methyl, and Q is formula (XXk).

Wherein D is not unsubstituted phenyl if E is hydrogen, M is not present, q is 2, Y is C, A is —CH$_2$CH$_2$—, G is hydrogen, R$_1$ and R$_2$ are both methyl, R$_3$ is methyl and Q is formula (XXI).

A further embodiment, relates to a compound according to formula (XX).

The general limitations for formula (XX) apply as described above, with the following differences:

Q is selected from group A) or B), preferably group B).
If Q is selected from group A), X is N;
If Q is selected from group B),
M is selected from the group hydrogen, —CH$_2$—, NH and O.

Another embodiment of the present invention relates to a further compound according to formula (XX).

The general limitations for formula (XX) apply as described above, with the following differences:

Q is selected from group A) or B), preferably group B);
If Q is selected from group A), X is N.
If Q is selected from group B),
G is not present.
D is selected from the group consisting of —(C$_3$-C$_{10}$)heteroaryl, unsubstituted benzyl, unsubstituted phenyl, phenyl comprising at least one substituent in ortho position;
Phenyl comprising at least one substituent in meta position, wherein the meta substituent is selected from C, Br or I, —CONH$_2$, —CO$_2$(C$_1$-C$_4$)alkyl, —(C$_1$-C$_4$)alkyl, —NO$_2$, —COOH, —(C$_6$-C$_{10}$)aryl, preferably Ph, —CN, —CO(C$_1$-C$_4$)alkyl, —RO$_6$, —(C$_3$-C$_{10}$)heteroaryl, —NHSO$_2$(C$_1$-C$_4$)alkyl, F if the para position is not substituted with F, —CF$_3$, and —SO$_2$(C$_1$-C$_4$)alkyl;
Phenyl comprising at least two different substituents in ortho and para position;
Phenyl comprising at least one substituent in para position, wherein the para substituent is selected from the group consisting of, —OR$_6$, —CH$_2$OR$_6$, CH$_2$COOH—COOH, —NO$_2$, —(C$_6$-C$_{10}$)aryl, preferably Ph, —NHCO(C$_1$-C$_4$)alkyl, —CO(C$_1$-C$_4$)alkyl, —CO$_2$(C$_1$-C$_4$)alkyl, —N((C$_1$-C$_4$)alkyl)$_2$, —SO$_2$(C$_1$-C$_4$)alkyl, —NHSO$_2$(C$_1$-C$_4$)alkyl, —CONH$_2$, —SO$_2$NH$_2$, —(C$_3$-C$_{10}$)heteroaryl, and not present;
R$_6$ is selected from the group consisting of hydrogen, —(C$_1$-C$_4$)alkyl, and —(C$_1$-C$_4$)haloalkyl,
M is selected from the group consisting of hydrogen, —CH$_2$, NH, O.

A further embodiment of the invention relates to a further compound according to formula (XX).

The general limitations for formula (XX) apply as described above, with the following differences:

Q is selected from group A) or B), preferably group B).
If Q is selected from group A), X is N.
If Q is selected from group B):
G is not present.
D is selected from the group consisting of —(C$_3$-C$_{10}$)heteroaryl, wherein the —(C$_3$-C$_{10}$)heteroaryl group is not an unsubstituted quinoline-5-yl group, an unsubstituted quinoline-7-yl group, an unsubstituted indol group, an 2-oxo-2H-chromen-6-yl group, an unsubstituted 1H-indazole-6-yl,
unsubstituted phenyl; phenyl substituted in ortho position with —(C$_1$-C$_4$)alkyl;
phenyl comprising at least one substituent in meta position, wherein the meta substituent is selected from C, Br or I, —(C$_1$-C$_4$)alkyl, —NO$_2$, —COOH, —CN, —CO(C$_1$-C$_4$)alkyl, —RO$_6$, —(C$_3$-C$_{10}$)heteroaryl, —CF$_3$, and —SO$_2$(C$_1$-C$_4$)alkyl,
phenyl comprising at least two different substituents in ortho and para position;
phenyl comprising at least one substituent in para position, wherein the para substituent is selected from the group consisting of —OH, —CH$_2$OR$_6$, —CH$_2$OOH, —O(C$_1$-C$_4$)alkyl, —COOH, —CO$_2$(C$_1$-C$_4$)alkyl, —SO$_2$NH$_2$, —(C$_3$-C$_{10}$)heteroaryl,
and not present,
R$_6$ is selected from the group consisting of hydrogen, —(C$_1$-C$_4$)alkyl, and —(C$_1$-C$_4$)haloalkyl
M is selected from the group consisting of hydrogen, —CH$_2$, and NH,
or a pharmaceutically acceptable salt, solvate or hydrate thereof.

Further, the invention is directed to a compound selected from the group consisting of 3-(3,5-dimethyl-1-(3-methyl-[1,2,4]triazolo[4,3-b]pyridazin-6-yl)-1H-pyrazol-4-yl)-1-(4-phenethylpiperidin-1-yl)propan-1-one,
1-(3-benzylpiperidin-1-yl)-3-(3,5-dimethyl-1-(3-methyl-[1,2,4]triazolo[4,3-b]pyridazin-6-yl)-1H-pyrazol-4-yl)propan-1-one,
3-(3,5-dimethyl-1-(3-methyl-[1,2,4]triazolo[4,3-a]pyridin-6-yl)-1H-pyrazol-4-yl)-1-(4-phenethylpiperidin-1-yl)propan-1-one,
3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoic acid,
1-(3-benzylpiperidin-1-yl)-3-(3,5-dimethyl-1-(3-methyl-[1,2,4]triazolo[4,3-a]pyridin-6-yl)-1H-pyrazol-4-yl)propan-1-one,
3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-methylbenzamide,
1-(3-benzylpyrrolidin-1-yl)-3-(3,5-dimethyl-1-(3-methyl-[1,2,4]triazolo[4,3-a]pyridin-6-yl)-1H-pyrazol-4-yl)propan-1-one,
1-(3-benzylpiperazin-1-yl)-3-(3,5-dimethyl-1-(3-methyl-[1,2,4]triazolo[4,3-b]pyridazin-6-yl)-1H-pyrazol-4-yl)propan-1-one hydrochloride,
methyl 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoate, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 1-(4-benzylpiperazin-1-yl)-3-(3,5-dimethyl-1-(3-methyl-[1,2,4]triazolo[4,3-a]pyridin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoic acid, methyl 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzoate, 1-(4-(2-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-chlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2,6-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-acetylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(naphthalen-1-ylmethyl)piperazin-1-yl)propan-1-one, 1-(4-(3,4-difluorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-(3,5-dimethyl-1-(3-methyl-[1,2,4]triazolo[4,3-b]pyridazin-6-yl)-1H-pyrazol-4-yl)-1-(4-(4-methylbenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-5-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-iodobenzyl)piperazin-1-yl)propan-1-one, N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)acetamide, 1-(4-([1,1'-biphenyl]-4-ylmethyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-(dimethylamino)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-nitrobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(methylsulfonyl)benzyl)piperazin-1-yl)propan-1-one, N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)methanesulfonamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 1-(4-((1H-indazol-6-yl)methyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-methylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(4-hydroxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(trifluoromethyl)benzyl)piperazin-1-yl)propan-1-one, 1-(4-(3,4-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-methylbenzoic acid, 3-(3,5-dimethyl-1-(3-methyl-[1,2,4]triazolo[4,3-b]pyridazin-6-yl)-1H-pyrazol-4-yl)-1-(4-(3-methyl-4-nitrobenzyl)piperazin-1-yl)propan-1-one, 1-(4-(3-chloro-4-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzoic acid, 3-(3,5-dimethyl-1-(3-methyl-[1,2,4]triazolo[4,3-b]pyridazin-6-yl)-1H-pyrazol-4-yl)-1-(4-(3-iodobenzyl)piperazin-1-yl)propan-1-one, 1-(4-(3-acetylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-(3,5-dimethyl-1-(3-methyl-[1,2,4]triazolo[4,3-b]pyridazin-6-yl)-1H-pyrazol-4-yl)-1-(4-(3-methylbenzyl)piperazin-1-yl)propan-1-one, 2-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 1-(4-([1,1'-biphenyl]-3-ylmethyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-methyl-5-nitrobenzyl)piperazin-1-yl)propan-1-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzenesulfonamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-fluorobenzoic acid, 1-(4-(2,4-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3,5-difluoro-4-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-hydroxybenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-6-ylmethyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-nitrobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(quinolin-7-ylmethyl)piperazin-1-yl)propan-1-one, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzamide, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-methylbenzamid, 3-(3,5-dimethyl-1-(3-methyl-[1,2,4]triazolo[4,3-b]pyridazin-6-yl)-1H-pyrazol-4-yl)-1-(4-(quinolin-8-ylmethyl)piperazin-1-yl)propan-1-one, 1-(4-(3-(2H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-(methylsulfonyl)benzyl)piperazin-1-yl)propan-1-one, N-(3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)methanesulfonamide, 3-(3,5-dimethyl-1-(3-methyl-[1,2,4]triazolo[4,3-b]pyridazin-6-yl)-1H-pyrazol-4-yl)-1-(4-(3-fluorobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-fluoro-3-(trifluoromethyl)benzyl)piperazin-1-yl)propan-1-one, 1-(4-(2,5-dichlorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-bromobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3-bromobenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2,4-difluoro-3-hydroxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-methylbenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-methyl-4-nitrobenzyl)piperazin-1-yl)propan-1-one, 1-(4-(4-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(3-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(4-(2H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(isoquinolin-8-ylmethyl)piperazin-1-yl)propan-1-one, 1-(4-((1H-indol-6-yl)methyl)piperazin-1-yl)-3-(3,5-dimethyl-1-(3-methyl-[1,2,4]triazolo[4,3-b]pyridazin-6-yl)-1H-pyrazol-4-yl)propan-1-one, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2H-chromen-2-one, 3-(3,5-dimethyl-1-(3-methyl-[1,2,4]triazolo[4,3-b]pyridazin-6-yl)-1H-pyrazol-4-yl)-1-(4-(4-(phenylsulfonyl)benzyl)piperazin-1-yl)propan-1-one, 1-(4-benzyl-4-methylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzyl-4-ethylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(4-benzyl-4-propylpiperidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-ethylpyrrolidin-1-yl)-3-(3,5-dimethyl-1-(3-methyl-[1,2,4]triazolo[4,3-b]pyridazin-6-yl)-1H-pyrazol-4-yl)propan-1-one, 1-(3-benzyl-3-propylpyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-N-(1-phenylpiperidin-4-yl)propanamide, 3-(3,5-dimethyl-1-(3-methyl-[1,2,4]triazolo[4,3-b]pyridazin-6-yl)-1H-pyrazol-4-yl)-1-(4-(phenylamino)piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-phenoxypiperidin-1-yl)propan-1-one, 1-(4-benzylpiperidin-1-yl)-3-(3,5-dimethyl-1-(7-methylimidazo[1,5-b]pyridazin-2-yl)-1H-pyrazol-4-yl)propan-1-one, 2-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)acetic acid, 3-(3,5-dimethyl-1-(3-methyl-[1,2,4]triazolo[4,3-b]pyridazin-6-yl)-1H-pyrazol-4-yl)-1-(4-(4-(hydroxymethyl)benzyl)piperazin-1-yl)propan-1-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)pyridin-2(1H)-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)pyridin-2(1H)-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-1,3-dihydro-2H-benzo[d]imidazol-2-one, 3-(3,5-dimethyl-1-(3-methyl-[1,2,4]triazolo[4,3-b]pyridazin-6-yl)-1H-pyrazol-4-yl)-1-(3-(1-phenylpropyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(4-hydroxyphenyl)propyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(3-hydroxyphenyl)propyl)pyrrolidin-1-yl)propan-1-one, 1-(3-(4-(1H-tetrazol-5-yl)benzyl)pyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(3-(2-methyl-4-(1H-tetrazol-5-yl)benzyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(2-(3-hydroxyphenyl)propan-2-yl)pyrrolidin-1-yl)propan-1-one, 1-(4-(3-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-(trifluoromethyl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-5-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluorobenzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 1-(4-(2-chloro-4-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one, 1-(4-(2-cyclopropylbenzyl)piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-ethylbenzyl)piperazin-1-yl)propan-1-one, N-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)sulfonyl)acetamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-(methylsulfonyl)benzamide, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3,4-dihydroisoquinolin-1(2H)-one, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)isoquinolin-1(2H)-one, 3-(3,5-dimethyl-1-(3-methyl-[1,2,4]triazolo[4,3-b]pyridazin-6-yl)-1H-pyrazol-4-yl)-1-(4-(4-(3-hydroxy-5-methylisoxazol-4-yl)benzyl)piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(4-hydroxy-1,2,5-oxadiazol-3-yl)benzyl)piperazin-1-yl)propan-1-one, 3-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)-4-hydroxycyclobutane-1,2-dione, 3-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)amino)-4-hydroxycyclobutane-1,2-dione, 5-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)thiazolidine-2,4-dione, 3-(3,5-Dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(2-fluoro-4-(1H-tetrazol-5-yl)benzyl)piperazin-1-yl)propan-1-one, 1-(4-(2-Chloro-5-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-5-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-4-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-4-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-3-(1H-tetrazol-5-yl)benzyl)piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-3-(1H-tetrazol-5-yl)benzyl)piperazin-1-yl)-3-(3,5-dimethyl-1-(3-(trifluoromethyl)-[1,2,4]triazolo[4,3-b]pyridazin-6-yl)-1H-pyrazol-4-yl)propan-1-on, 3-(3,5-Dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(3-fluoro-5-(1H-tetrazol-5-yl)benzyl)piperazin-1-yl)propan-1-one 3-(3,5-Dimethyl-1-(3-methyl-[1,2,4]triazolo[4,3-b]pyridazin-6-yl)-1H-pyrazol-4-yl)-1-(4-(2-methyl-3-(1H-tetrazol-5-yl)benzyl)piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(2-methyl-3-(1H-tetrazol-5-yl)benzyl)piperazin-1-yl)propan-1-one, 3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-5-fluorobenzonitrile, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzonitrile, 4-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 2-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-methylbenzonitrile, 3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-2-methylbenzonitrile, 2-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 3-chloro-4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, 3-chloro-4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile, 4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-3-fluorobenzonitrile, 4-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile, or a pharmaceutically acceptable salt, solvate or hydrate thereof.

A selection of compounds within the scope of, or use within the methods, of the present invention is listed in the following Table 1.
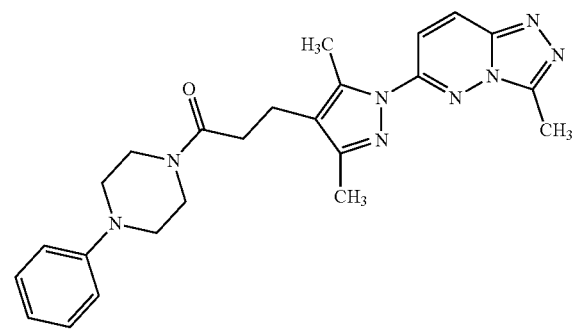
(C25)
1
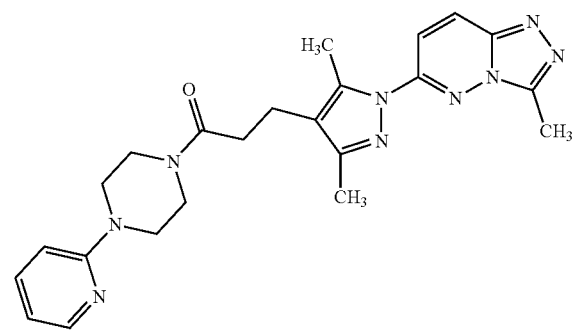 [SMILES: Cc1nn(-c2ccc3nnc(C)n3n2)c(C)c1CCC(=O)N1CCN(c2ccccn2)CC1]
2
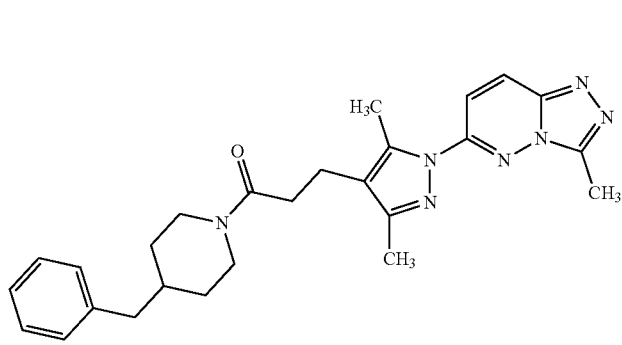
(C25-140)
3
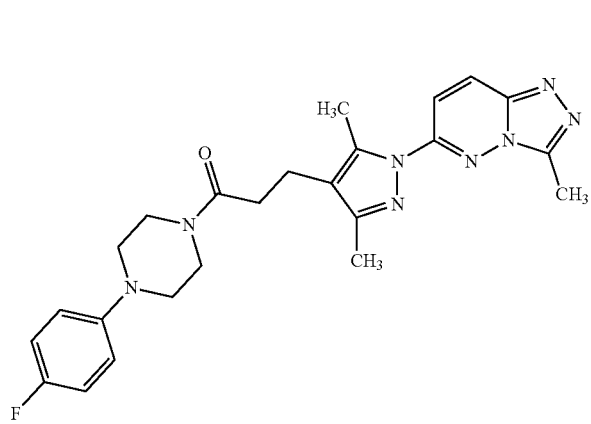 [SMILES: Cc1nn(-c2ccc3nnc(C)n3n2)c(C)c1CCC(=O)N1CCN(c2ccc(F)cc2)CC1]
4

-continued
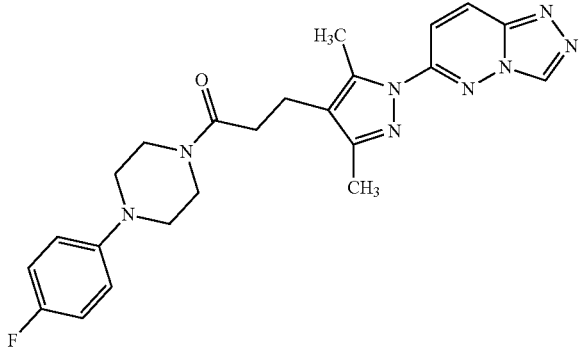 [SMILES: Cc1nn(-c2ccc3nncn3n2)c(C)c1CCC(=O)N1CCN(c2ccc(F)cc2)CC1]
5
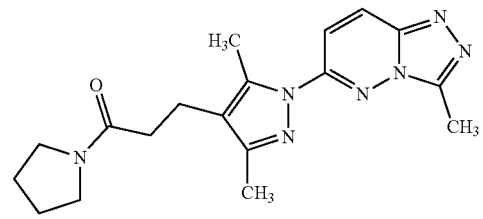 [SMILES: Cc1nn(-c2ccc3nnc(C)n3n2)c(C)c1CCC(=O)N1CCCC1]
6
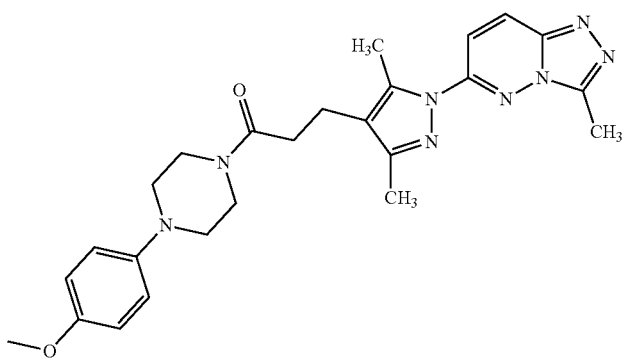 [SMILES: COc1ccc(N2CCN(C(=O)CCc3c(C)nn(-c4ccc5nnc(C)n5n4)c3C)CC2)cc1]
7
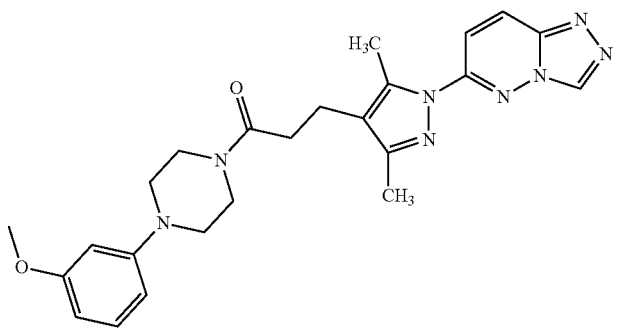 [SMILES: COc1cccc(N2CCN(C(=O)CCc3c(C)nn(-c4ccc5nncn5n4)c3C)CC2)c1]
8
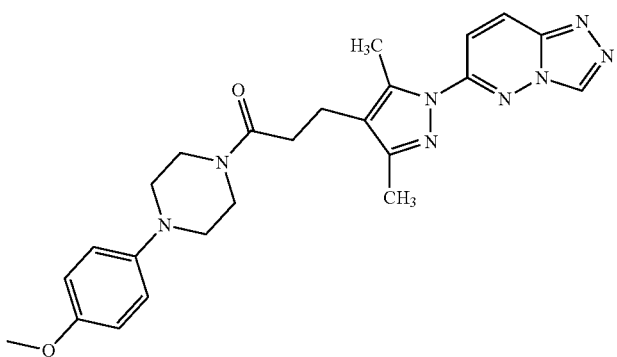 [SMILES: COc1ccc(N2CCN(C(=O)CCc3c(C)nn(-c4ccc5nncn5n4)c3C)CC2)cc1]
9

-continued
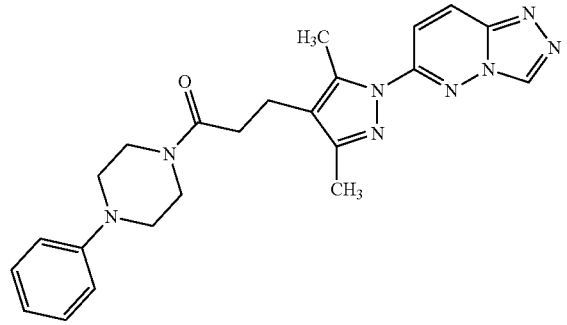 [SMILES: Cc1nn(-c2ccc3nncn3n2)c(C)c1CCC(=O)N1CCN(c2ccccc2)CC1]
10
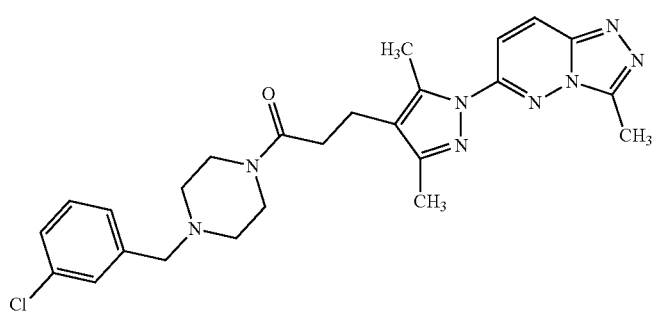 [SMILES: Cc1nn(-c2ccc3nnc(C)n3n2)c(C)c1CCC(=O)N1CCN(Cc2cccc(Cl)c2)CC1]
11
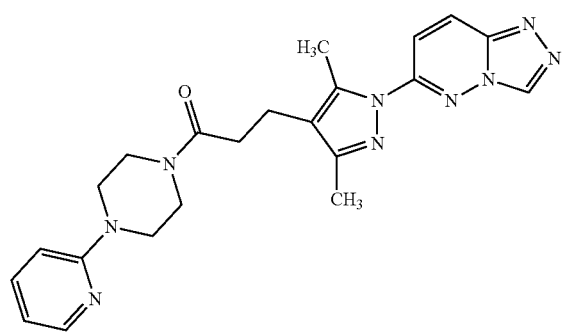 [SMILES: Cc1nn(-c2ccc3nncn3n2)c(C)c1CCC(=O)N1CCN(c2ccccn2)CC1]
12
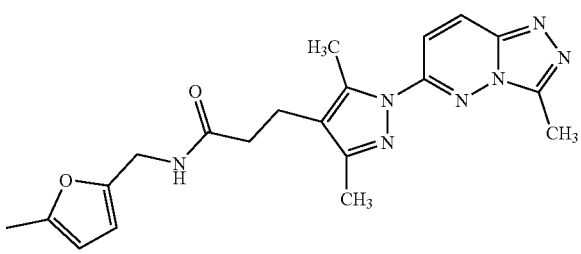 [SMILES: Cc1ccc(CNC(=O)CCc2c(C)nn(-c3ccc4nnc(C)n4n3)c2C)o1]
13
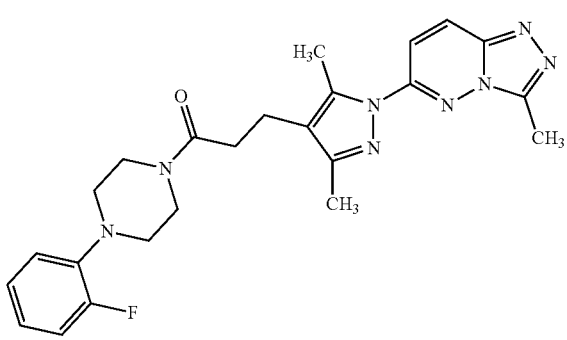 [SMILES: Cc1nn(-c2ccc3nnc(C)n3n2)c(C)c1CCC(=O)N1CCN(c2ccccc2F)CC1]
14

-continued
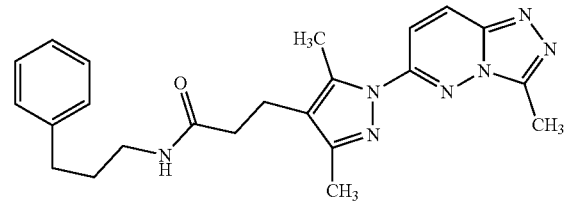 [SMILES: Cc1nn(-c2ccc3nnc(C)n3n2)c(C)c1CCC(=O)NCCCc1ccccc1]
15
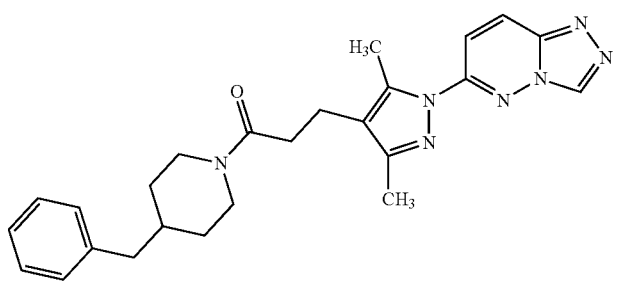 [SMILES: Cc1nn(-c2ccc3nncn3n2)c(C)c1CCC(=O)N1CCC(Cc2ccccc2)CC1]
16
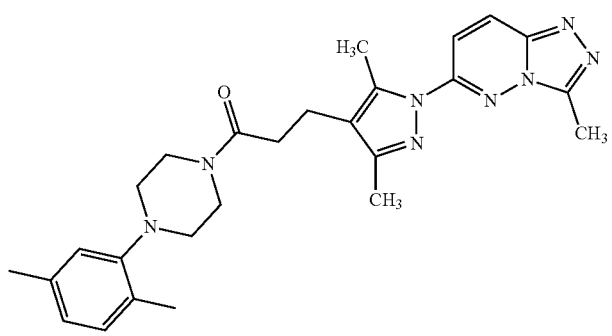 [SMILES: Cc1ccc(C)c(N2CCN(C(=O)CCc3c(C)nn(-c4ccc5nnc(C)n5n4)c3C)CC2)c1]
17
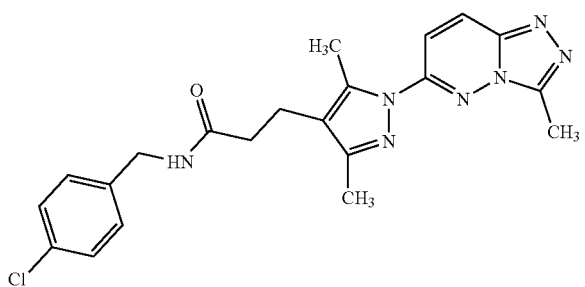 [SMILES: Cc1nn(-c2ccc3nnc(C)n3n2)c(C)c1CCC(=O)NCc1ccc(Cl)cc1]
18
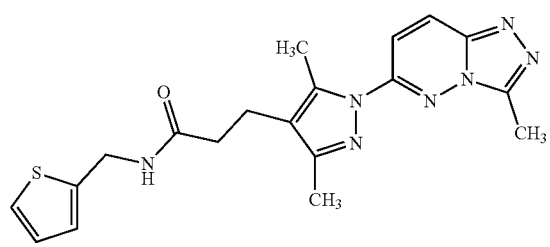 [SMILES: Cc1nn(-c2ccc3nnc(C)n3n2)c(C)c1CCC(=O)NCc1cccs1]
19
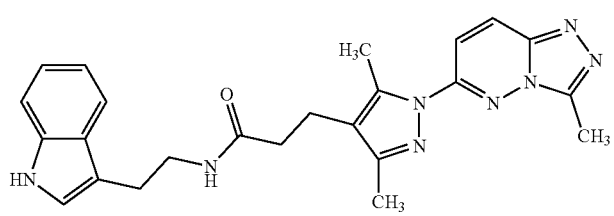 [SMILES: Cc1nn(-c2ccc3nnc(C)n3n2)c(C)c1CCC(=O)NCCc1c[nH]c2ccccc12]
20

-continued
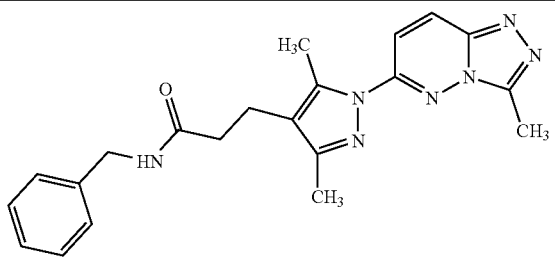
21
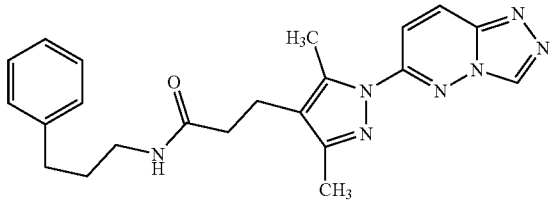 [SMILES: Cc1nn(-c2ccc3nncn3n2)c(C)c1CCC(=O)NCCCc1ccccc1]
22
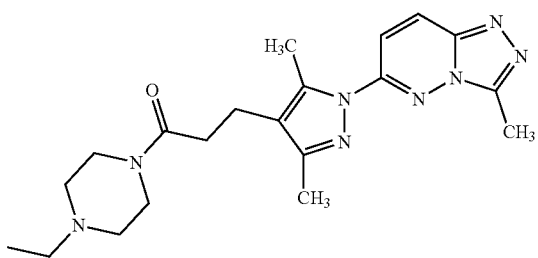 [SMILES: CCN1CCN(C(=O)CCc2c(C)nn(-c3ccc4nnc(C)n4n3)c2C)CC1]
23
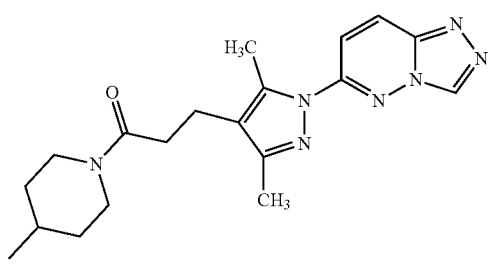 [SMILES: Cc1nn(-c2ccc3nncn3n2)c(C)c1CCC(=O)N1CCC(C)CC1]
24
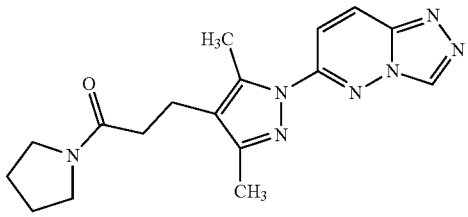 [SMILES: Cc1nn(-c2ccc3nncn3n2)c(C)c1CCC(=O)N1CCCC1]
25
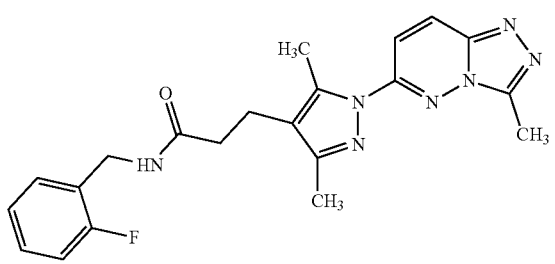 [SMILES: Cc1nn(-c2ccc3nnc(C)n3n2)c(C)c1CCC(=O)NCc1ccccc1F]
26

-continued
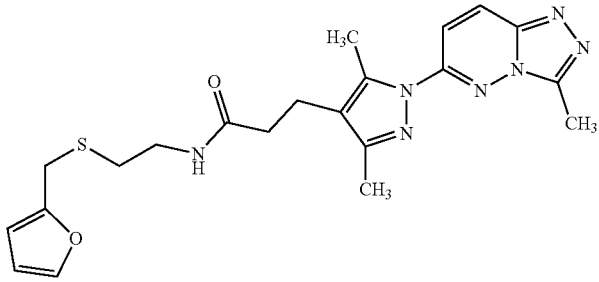 [SMILES: Cc1nn(-c2ccc3nnc(C)n3n2)c(C)c1CCC(=O)NCCSCc1ccco1]
27
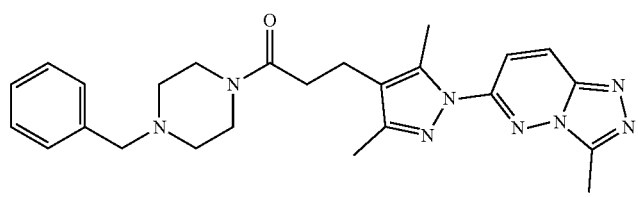
28
(HZM06-1)
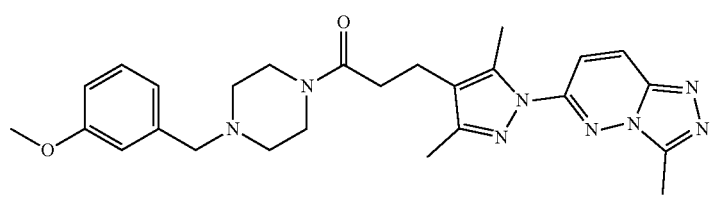
29
(HZM06-2)
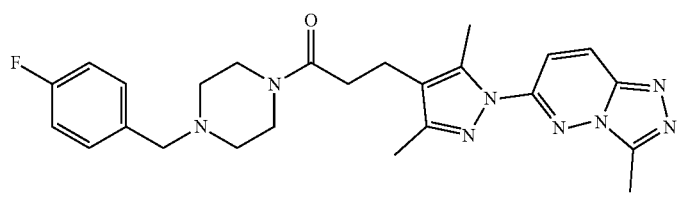
30
(HZM06-3)
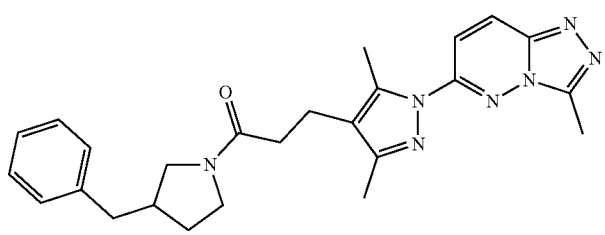
31
(HZM06-4)
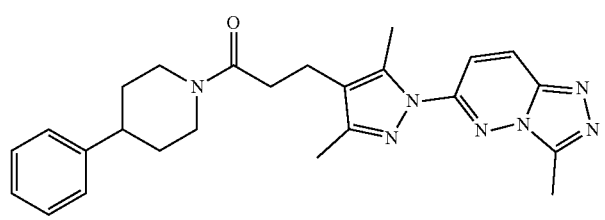
32
(HZM06-6)

-continued
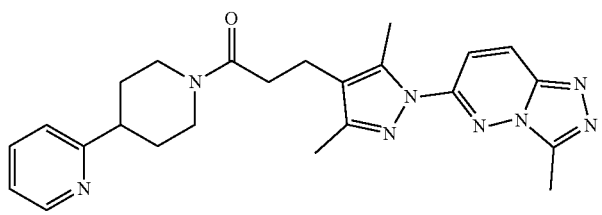
(HZM06-7) 33
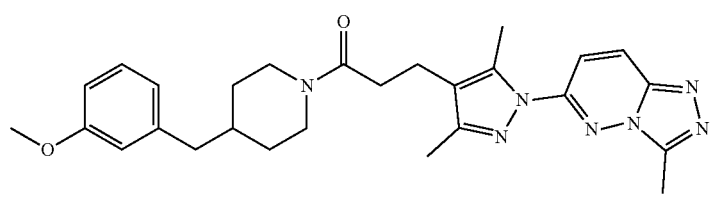
(HZM06-8) 34
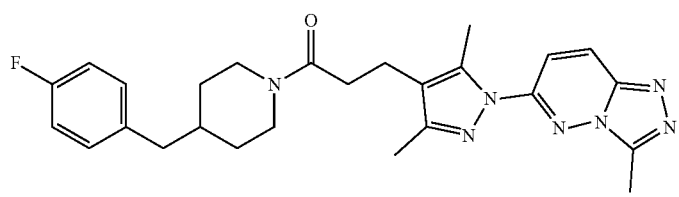
(HZM06-9) 35
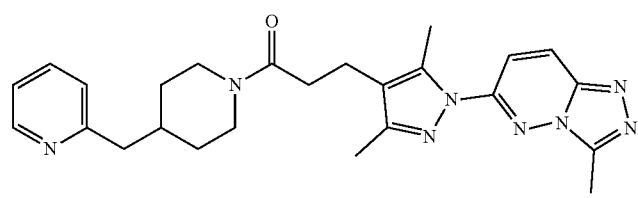
(HZM06-10) 36
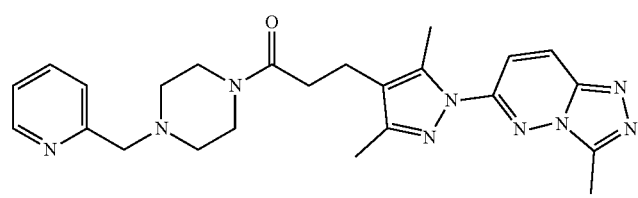
(HZM06-11) 37
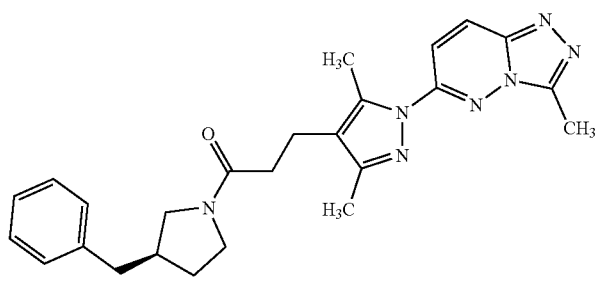 [SMILES: Cc1nn(-c2ccc3nnc(C)n3n2)c(C)c1CCC(=O)N1CC[C@@H](Cc2ccccc2)C1]
38

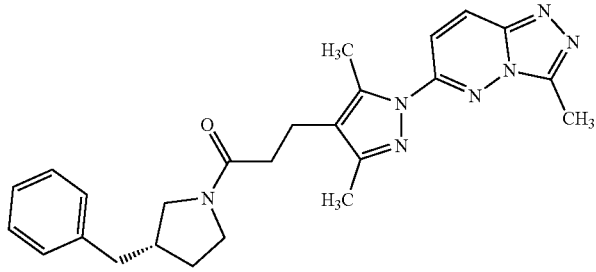 [SMILES: Cc1nn(-c2ccc3nnc(C)n3n2)c(C)c1CCC(=O)N1CC[C@H](Cc2ccccc2)C1]
39
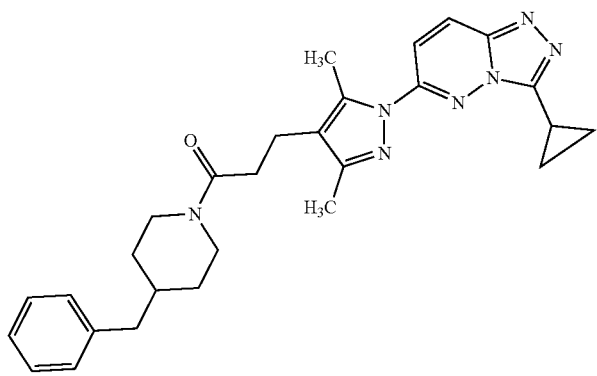 [SMILES: Cc1nn(-c2ccc3nnc(C4CC4)n3n2)c(C)c1CCC(=O)N1CCC(Cc2ccccc2)CC1]
40
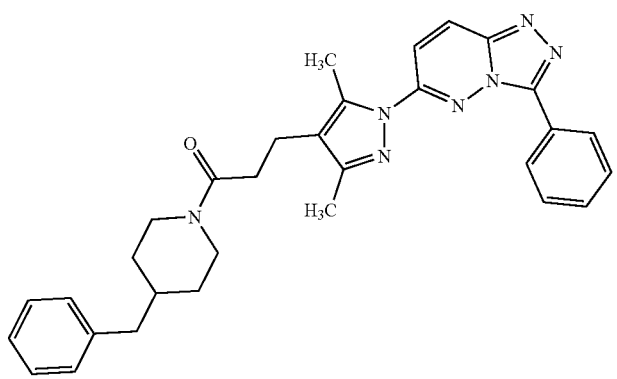
41
(HZM11-11)
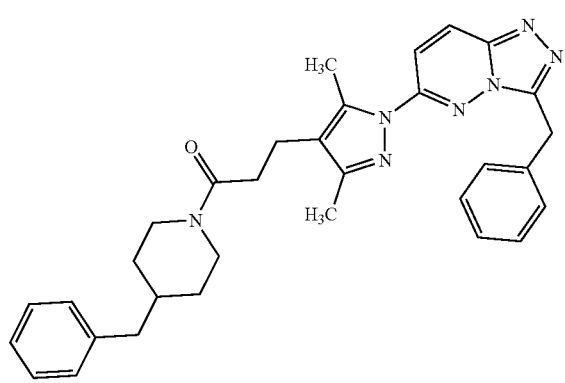 [SMILES: Cc1nn(-c2ccc3nnc(Cc4ccccc4)n3n2)c(C)c1CCC(=O)N1CCC(Cc2ccccc2)CC1]
42

-continued
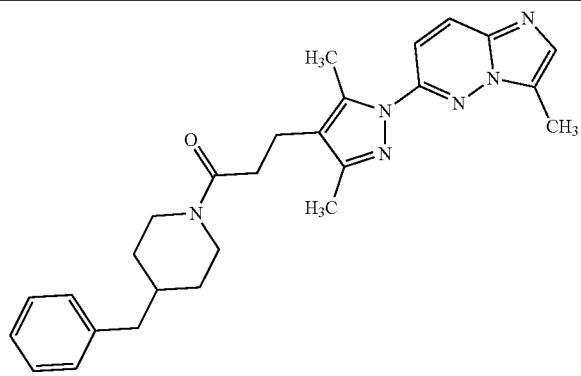
(HZM11-9)
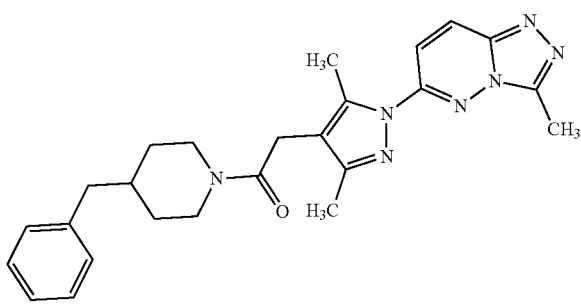
(HZM06-18)
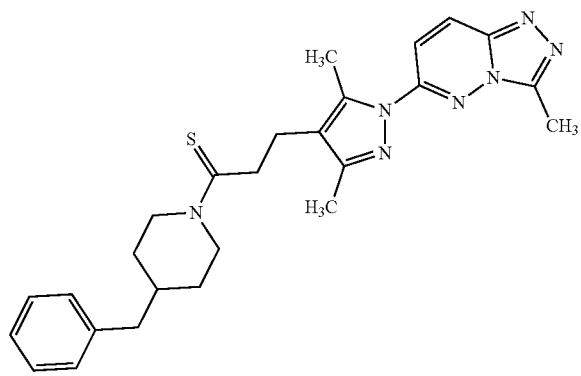 [SMILES: Cc1nn(-c2ccc3nnc(C)n3n2)c(C)c1CCC(=S)N1CCC(Cc2ccccc2)CC1]
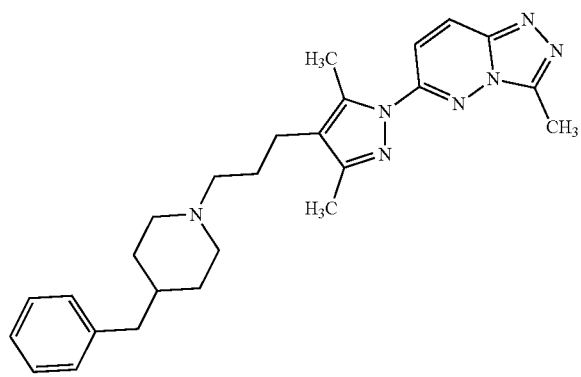 [SMILES: Cc1nn(-c2ccc3nnc(C)n3n2)c(C)c1CCCN1CCC(Cc2ccccc2)CC1]

47
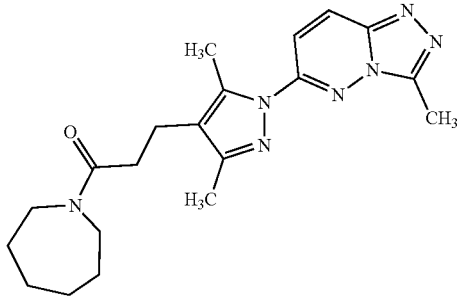
(HZM06-21)
48
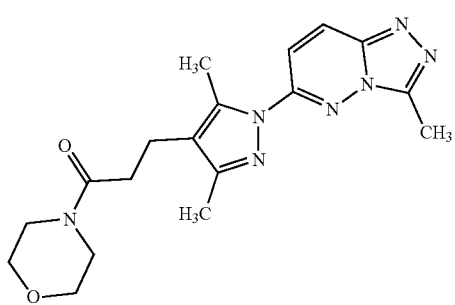
(HZM06-22)
49
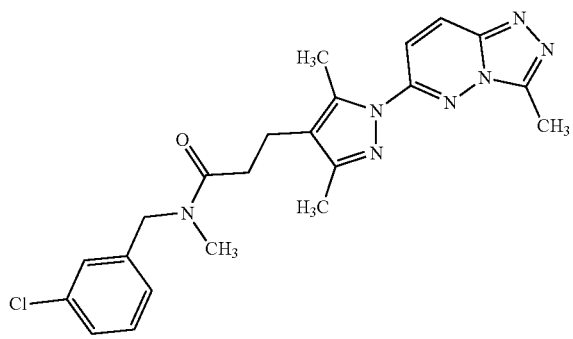
(HZM06-23)
50
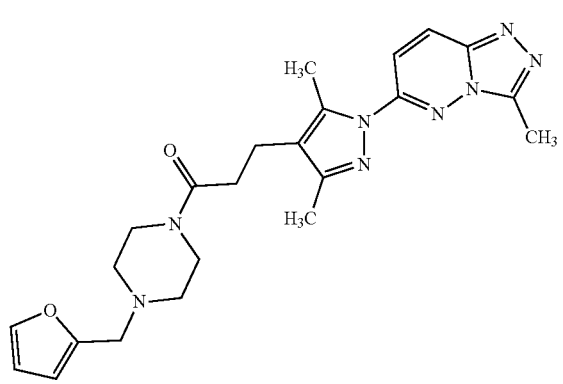
(HZM06-24)

51
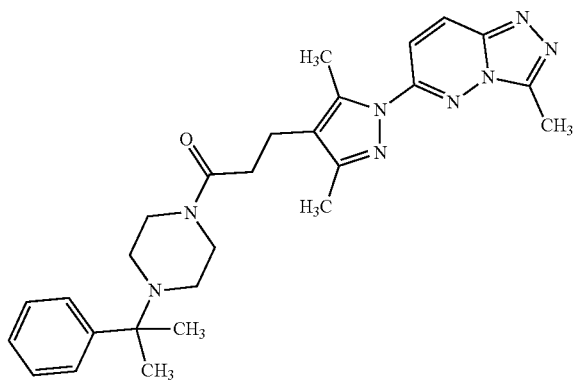
(HZM06-25)
52
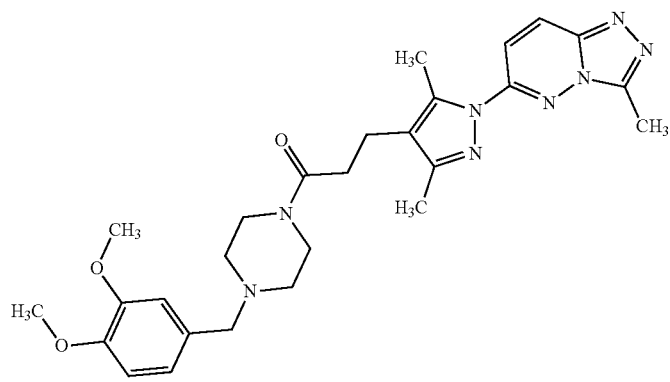
(HZM 06-26)
53
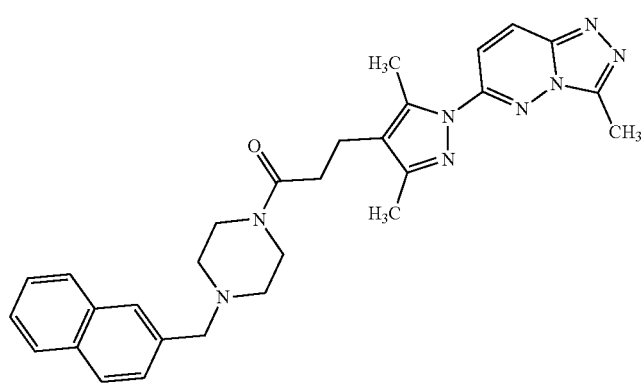
(HZM06-27)

54
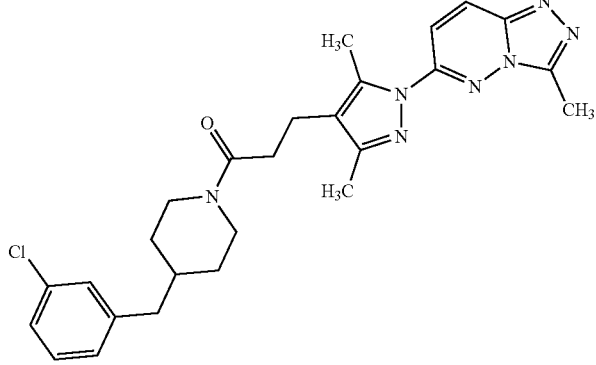
(HZM06-28)
55
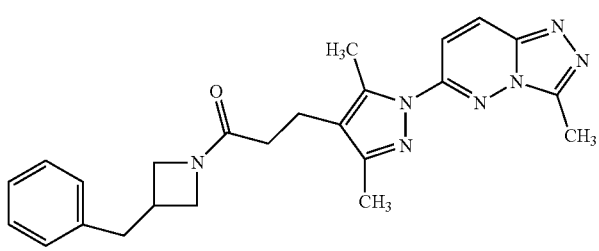
(HZM06-29)
56
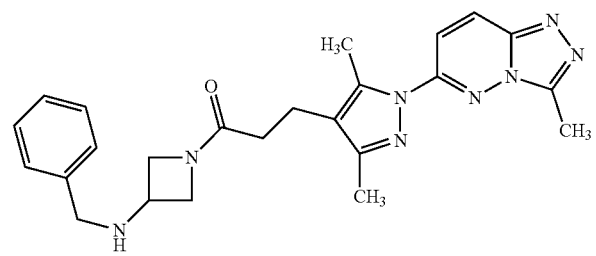 [SMILES: Cc1nn(-c2ccc3nnc(C)n3n2)c(C)c1CCC(=O)N1CC(NCc2ccccc2)C1]
57
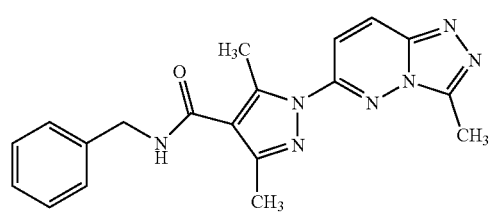 [SMILES: Cc1nn(-c2ccc3nnc(C)n3n2)c(C)c1C(=O)NCc1ccccc1]
58
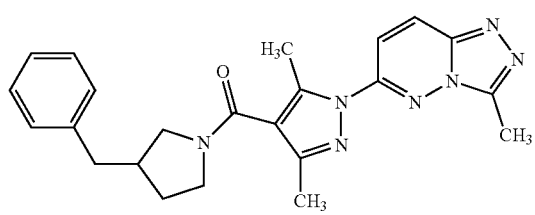 [SMILES: Cc1nn(-c2ccc3nnc(C)n3n2)c(C)c1C(=O)N1CCC(Cc2ccccc2)C1]
59
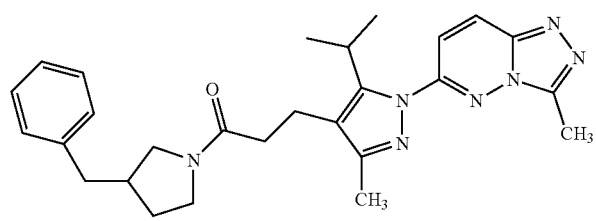 [SMILES: Cc1nn(-c2ccc3nnc(C)n3n2)c(C(C)C)c1CCC(=O)N1CCC(Cc2ccccc2)C1]

-continued
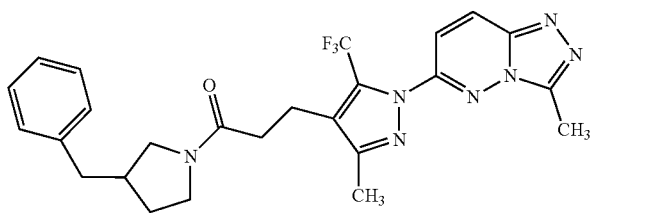 [SMILES: Cc1nn(-c2ccc3nnc(C)n3n2)c(C(F)(F)F)c1CCC(=O)N1CCC(Cc2ccccc2)C1]
60
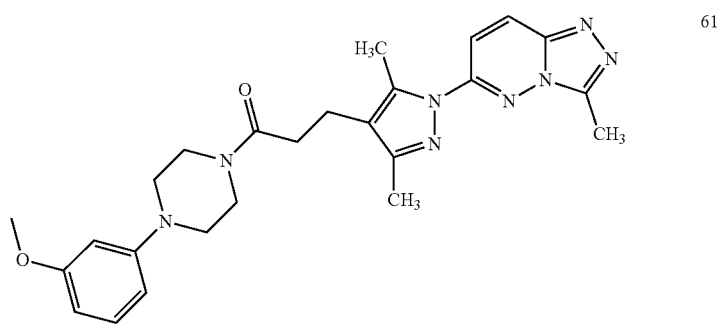
61
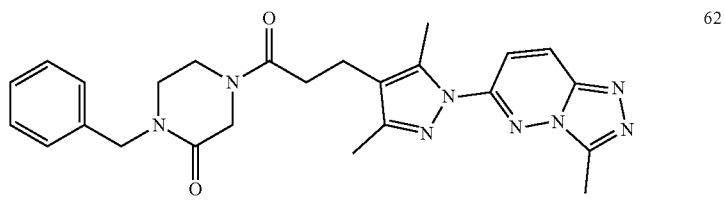
62
(HZM11-5)
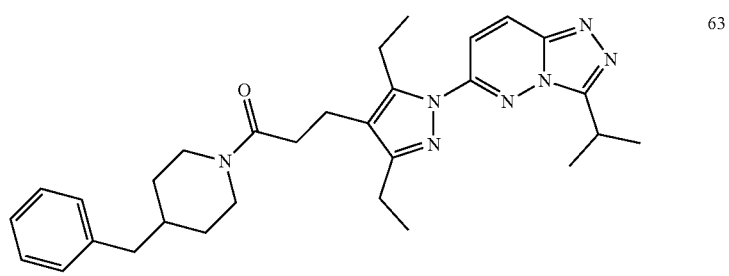
63
(OR-001)
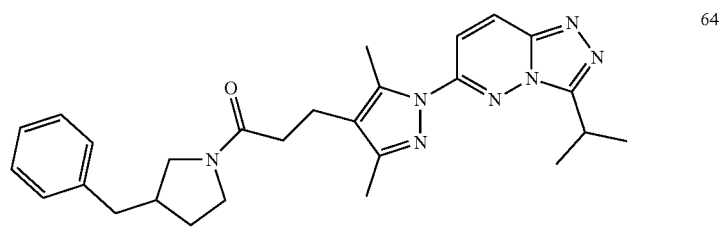
64
(OR-004)
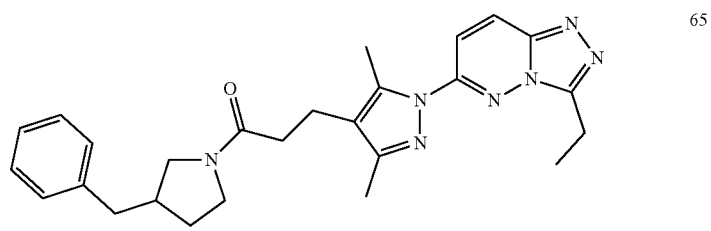
65
(OR-005)

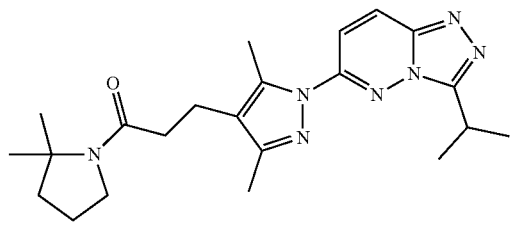
(OR-006) 66
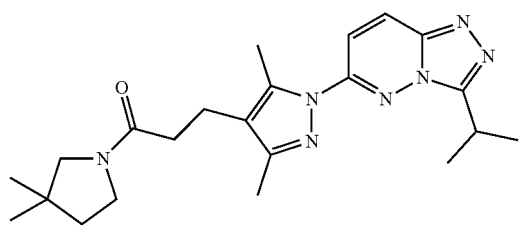
(OR-007) 67
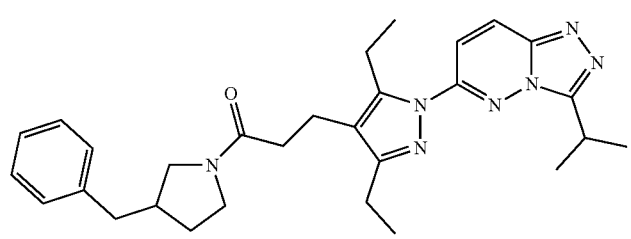
(OR-008) 68
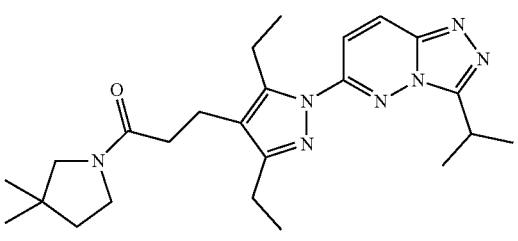
(OR-010) 69
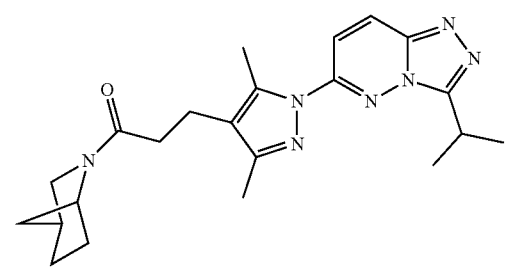
(OR-012) 70

-continued
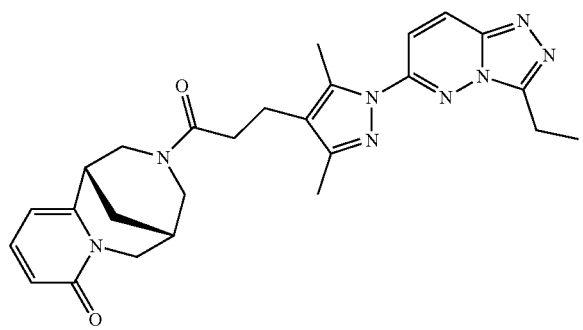
(OR-013)  71
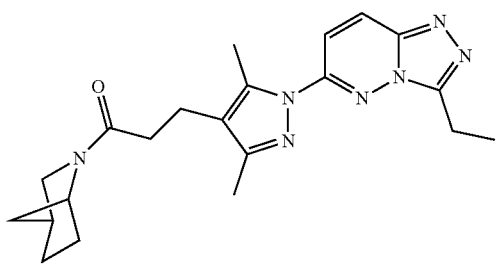
(OR-014)  72
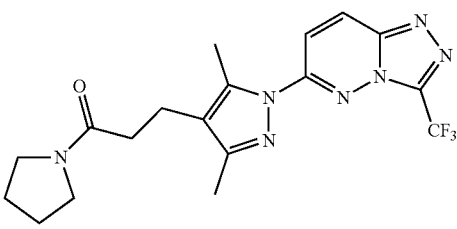
(OR-021)  73
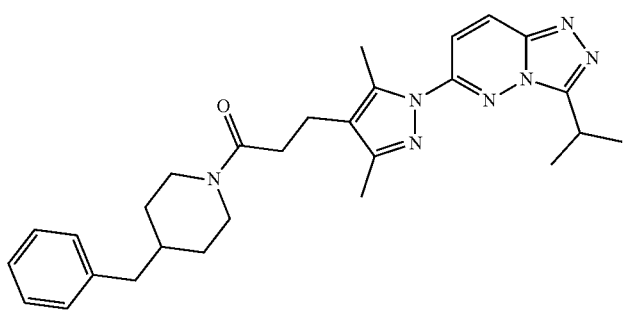
(OR-023)  74
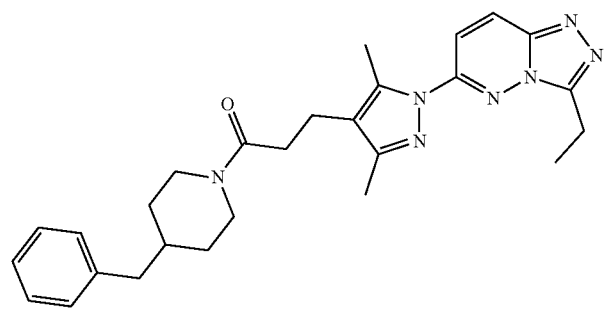
(OR-024)  75

-continued
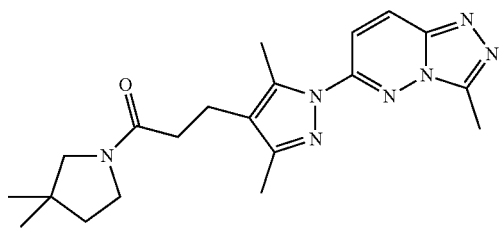
(OR-026)
76
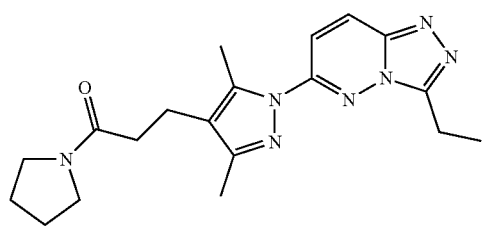
(OR-027)
77
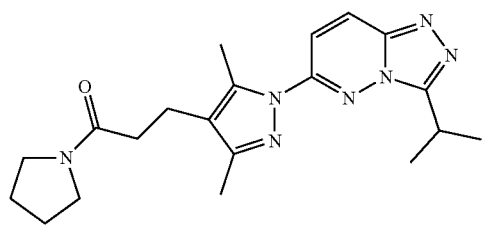
(OR-028)
78
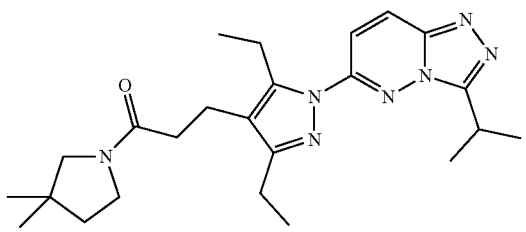
(OR-031)
79
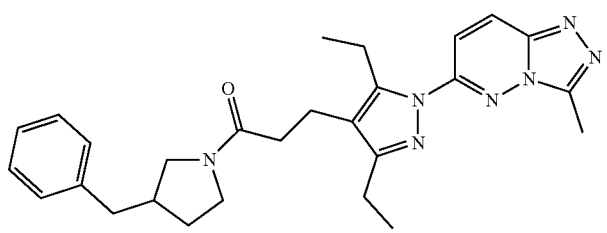
(OR-033)
80

81
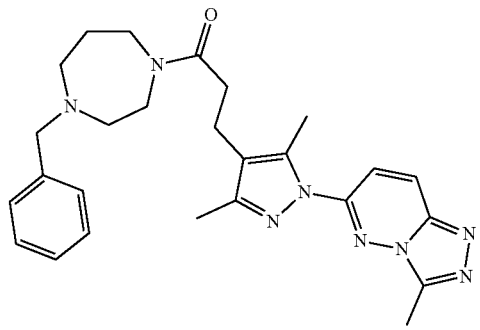 [SMILES: Cc1nn(-c2ccc3nnc(C)n3n2)c(C)c1CCC(=O)N1CCCN(Cc2ccccc2)CC1]
82
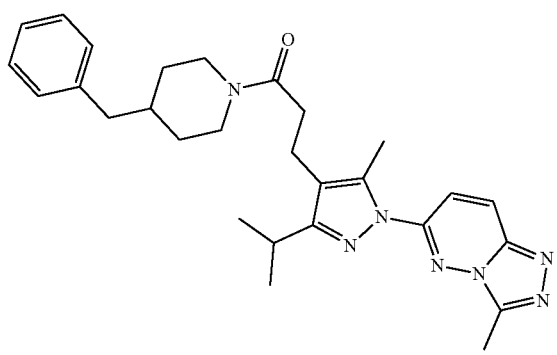 [SMILES: Cc1c(CCC(=O)N2CCC(Cc3ccccc3)CC2)c(C(C)C)nn1-c1ccc2nnc(C)n2n1]
83
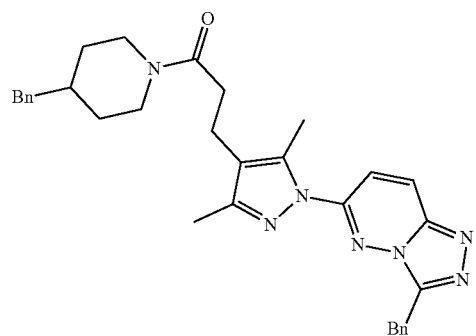 [SMILES: Cc1nn(-c2ccc3nnc(Cc4ccccc4)n3n2)c(C)c1CCC(=O)N1CCC(Cc2ccccc2)CC1]
84
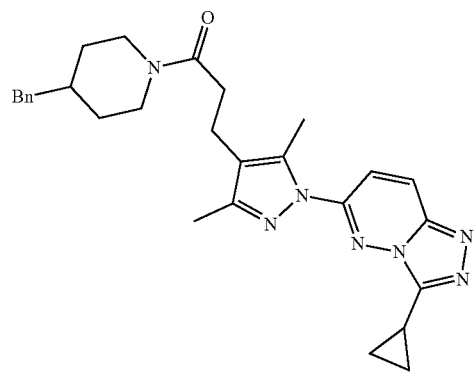 [SMILES: Cc1nn(-c2ccc3nnc(C4CC4)n3n2)c(C)c1CCC(=O)N1CCC(Cc2ccccc2)CC1]

| | |
|---|---|
| 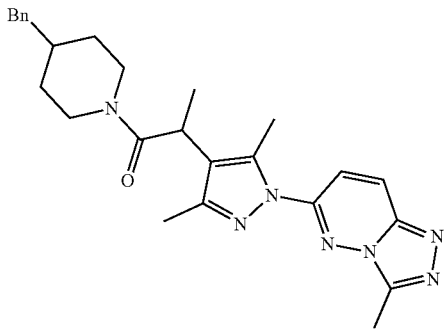 | 85 |
| 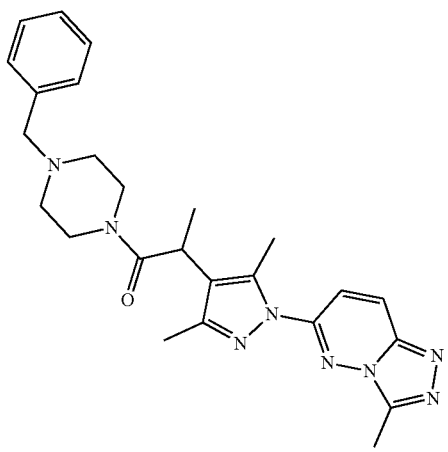 | 86 |
| 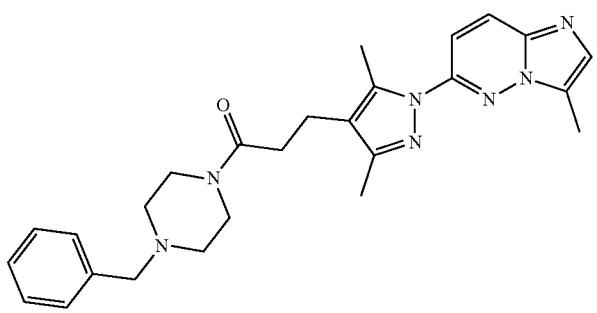 | 87 |
| 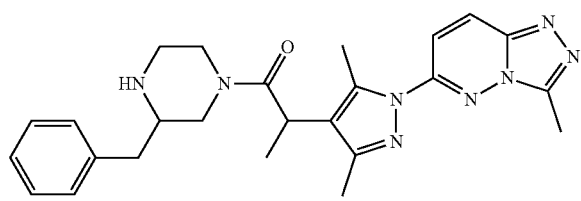 | 88 |
| 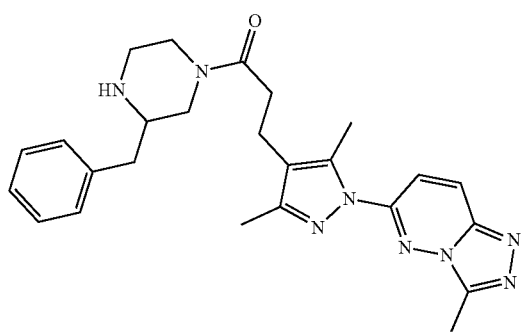 | 89 |

-continued
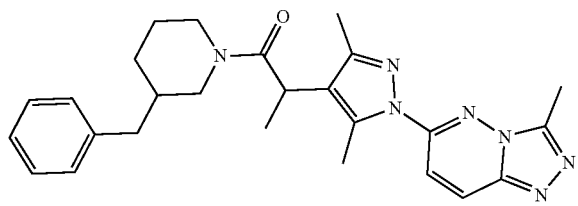 [SMILES: Cc1nn(-c2ccc3nnc(C)n3n2)c(C)c1C(C)C(=O)N1CCCC(Cc2ccccc2)C1]
90
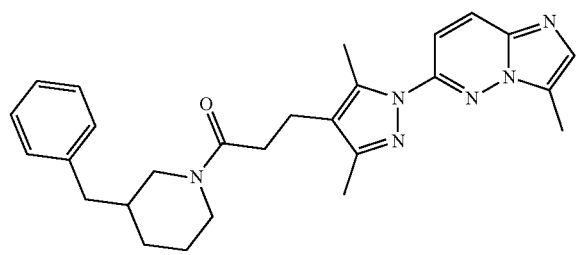 [SMILES: Cc1nn(-c2ccc3ncc(C)n3n2)c(C)c1CCC(=O)N1CCCC(Cc2ccccc2)C1]
91
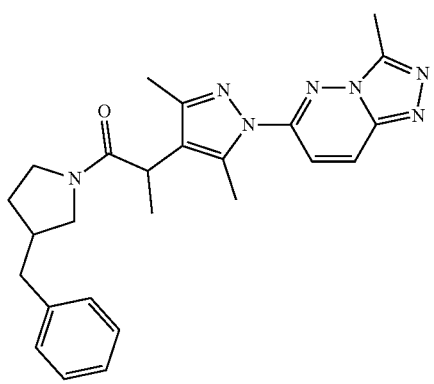 [SMILES: Cc1nn(-c2ccc3nnc(C)n3n2)c(C)c1C(C)C(=O)N1CCC(Cc2ccccc2)C1]
92
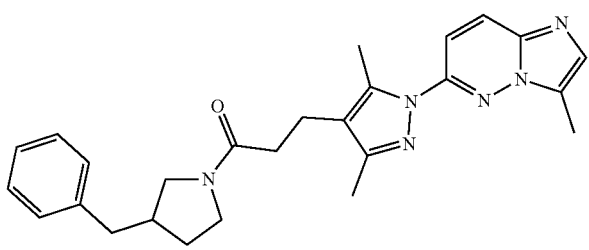 [SMILES: Cc1nn(-c2ccc3ncc(C)n3n2)c(C)c1CCC(=O)N1CCC(Cc2ccccc2)C1]
93
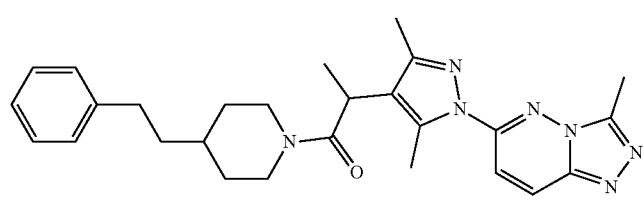 [SMILES: Cc1nn(-c2ccc3nnc(C)n3n2)c(C)c1C(C)C(=O)N1CCC(CCc2ccccc2)CC1]
94

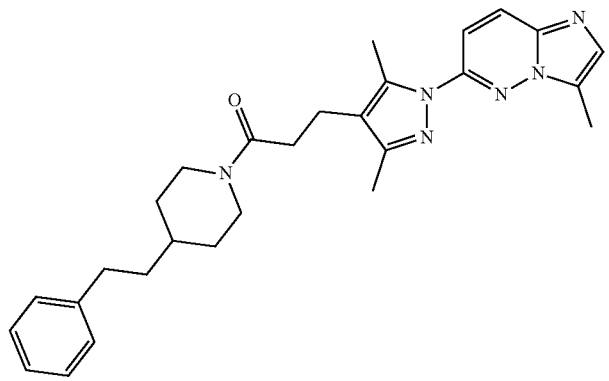 [SMILES: Cc1nn(-c2ccc3ncc(C)n3n2)c(C)c1CCC(=O)N1CCC(CCc2ccccc2)CC1]
95
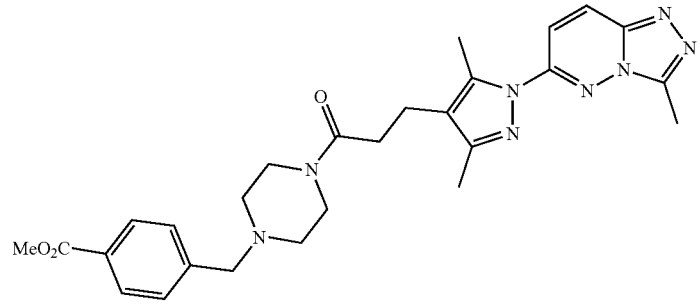 [SMILES: COC(=O)c1ccc(CN2CCN(C(=O)CCc3c(C)nn(-c4ccc5nnc(C)n5n4)c3C)CC2)cc1]
96
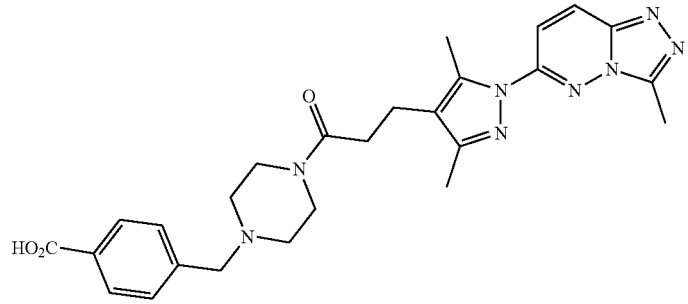 [SMILES: Cc1nn(-c2ccc3nnc(C)n3n2)c(C)c1CCC(=O)N1CCN(Cc2ccc(C(=O)O)cc2)CC1]
97
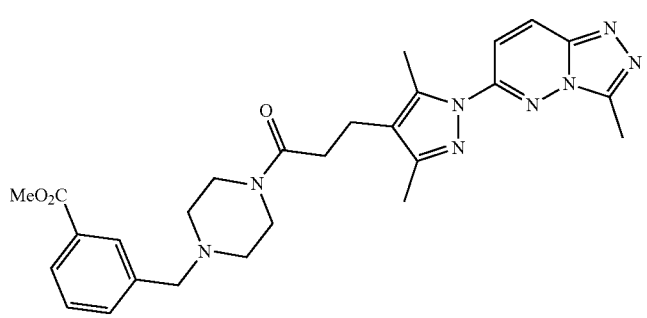 [SMILES: COC(=O)c1cccc(CN2CCN(C(=O)CCc3c(C)nn(-c4ccc5nnc(C)n5n4)c3C)CC2)c1]
98
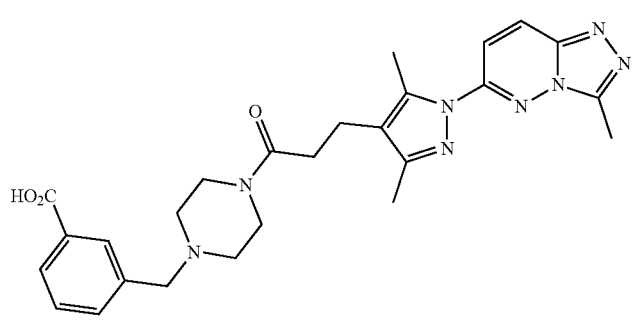 [SMILES: Cc1nn(-c2ccc3nnc(C)n3n2)c(C)c1CCC(=O)N1CCN(Cc2cccc(C(=O)O)c2)CC1]
99

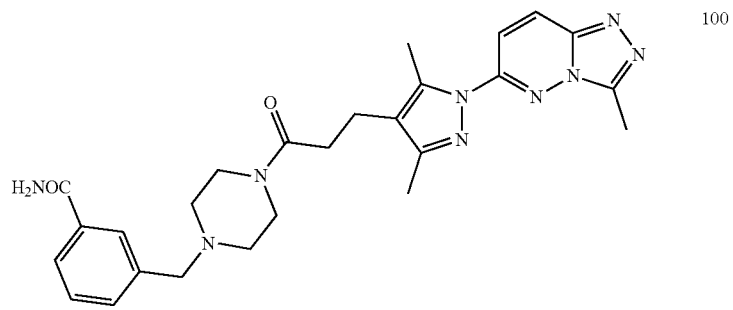
100
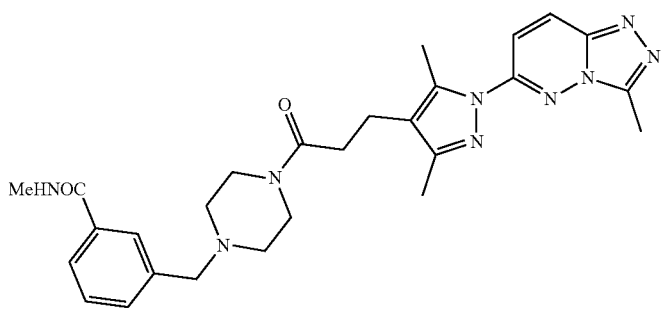
101
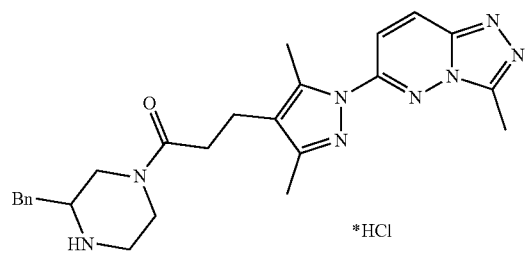 [SMILES: Cc1nn(-c2ccc3nnc(C)n3n2)c(C)c1CCC(=O)N1CCNC(Cc2ccccc2)C1]
102
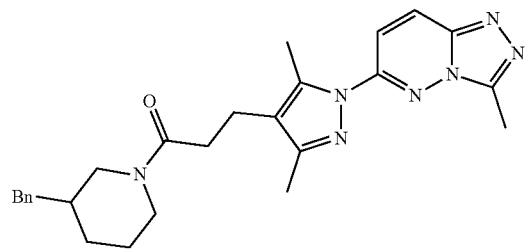 [SMILES: Cc1nn(-c2ccc3nnc(C)n3n2)c(C)c1CCC(=O)N1CCCC(Cc2ccccc2)C1]
103
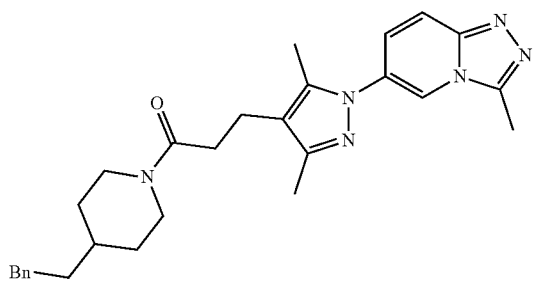 [SMILES: Cc1nn(-c2ccc3nnc(C)n3c2)c(C)c1CCC(=O)N1CCC(CCc2ccccc2)CC1]
104

-continued
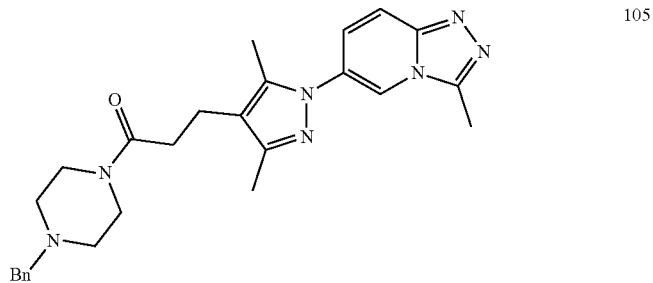
105
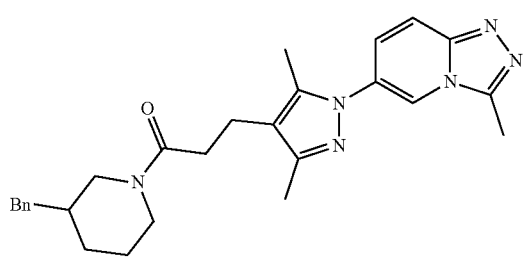 [SMILES: Cc1nn(-c2ccc3nnc(C)n3c2)c(C)c1CCC(=O)N1CCCC(Cc2ccccc2)C1]
106
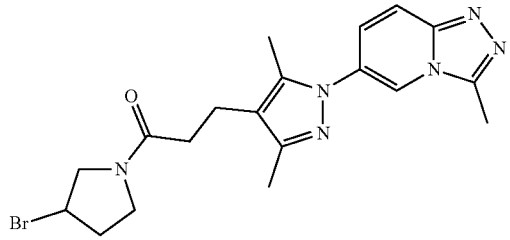 [SMILES: Cc1nn(-c2ccc3nnc(C)n3c2)c(C)c1CCC(=O)N1CCC(Br)C1]
107
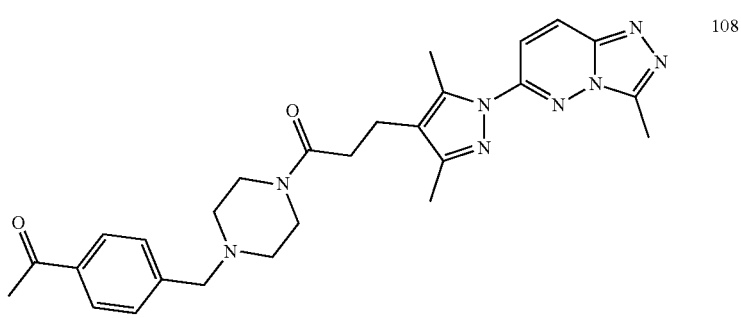
108
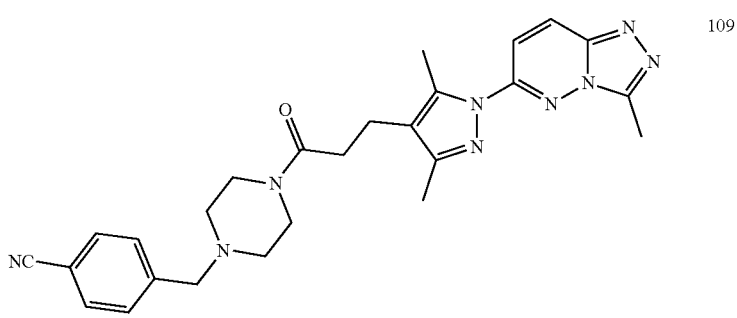
109

-continued
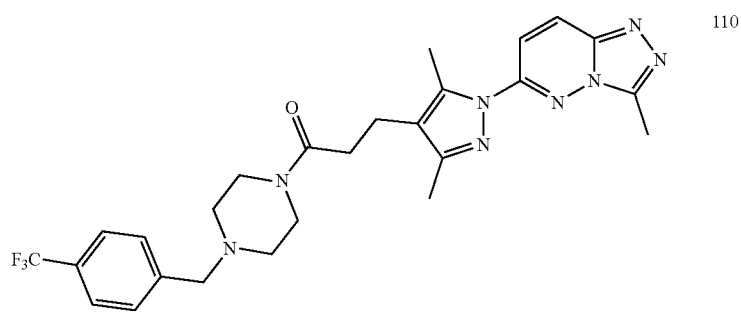
110
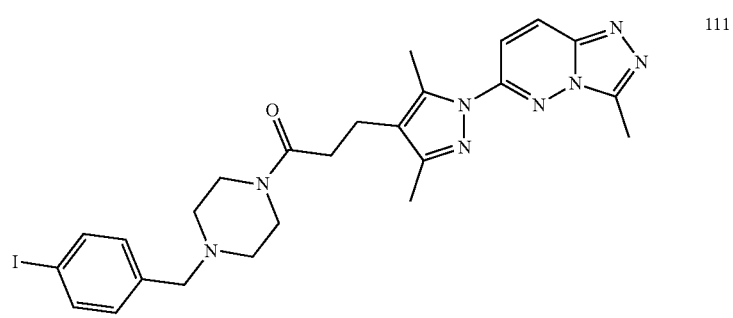
111
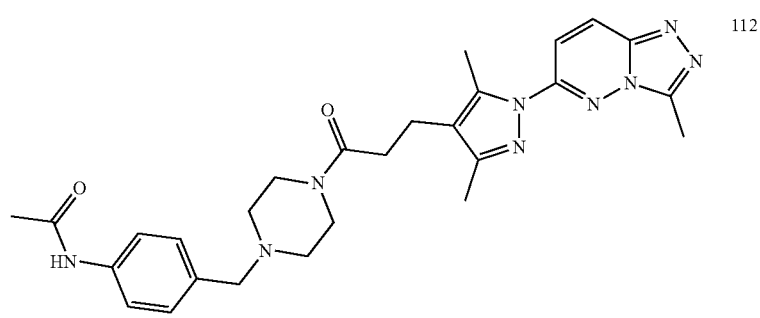
112
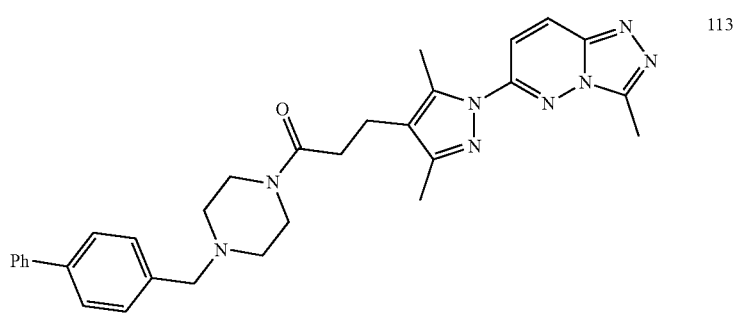
113
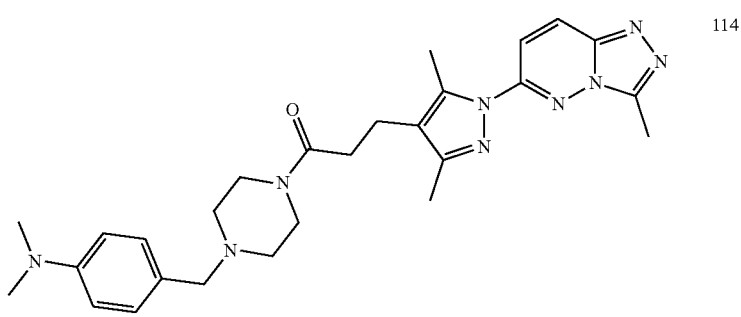
114

115
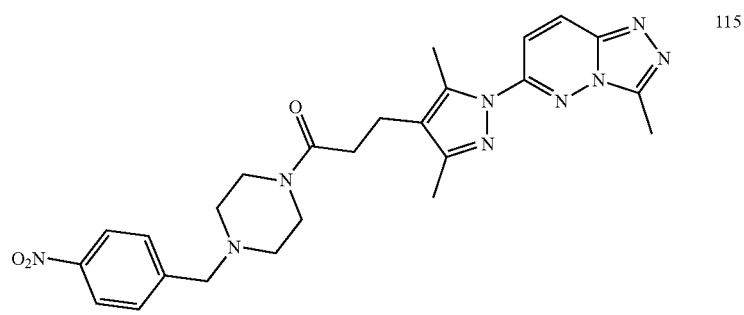
116
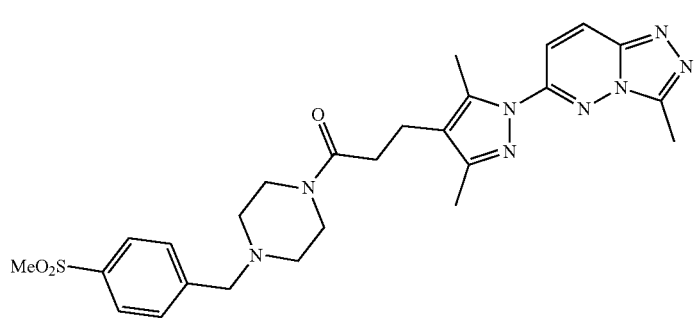
117
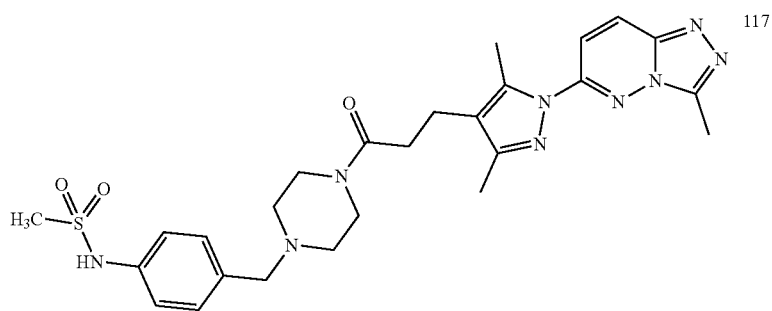
118
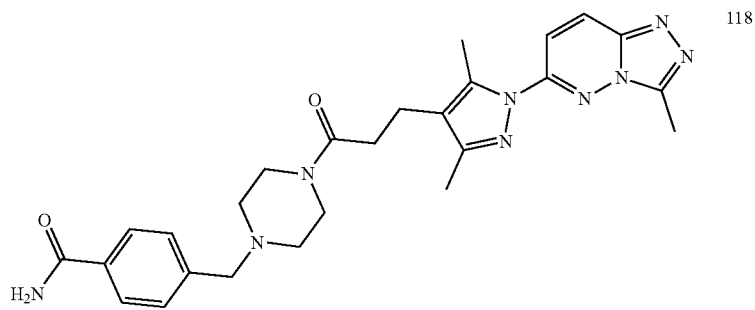
119
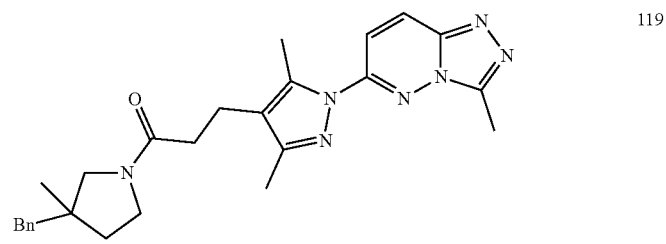

-continued
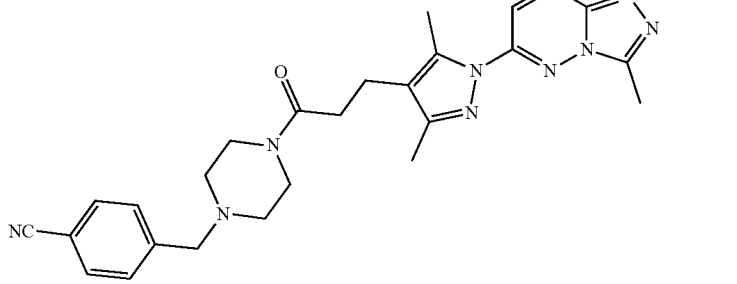
120
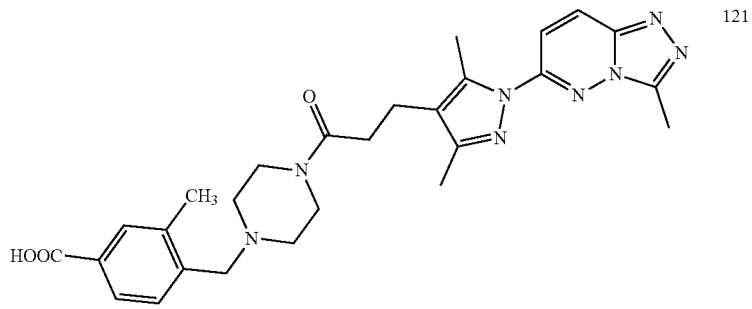
121
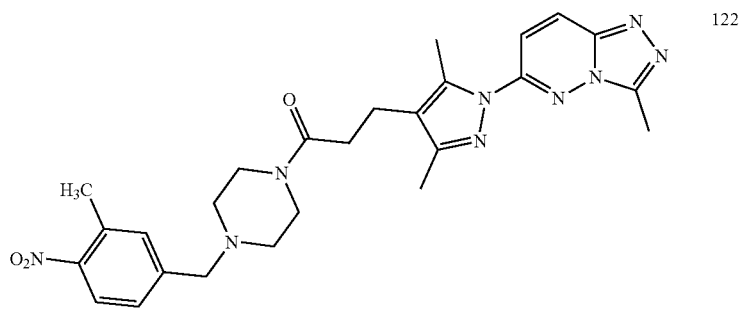
122
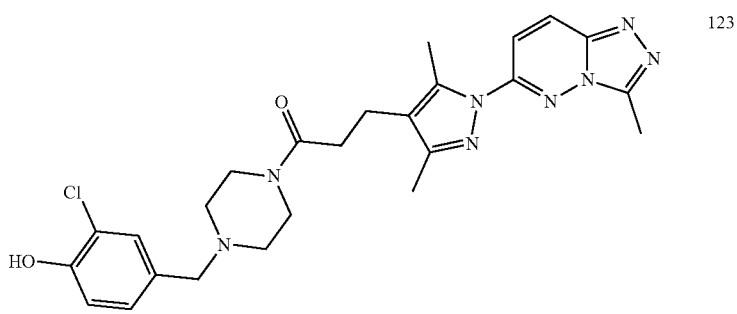
123
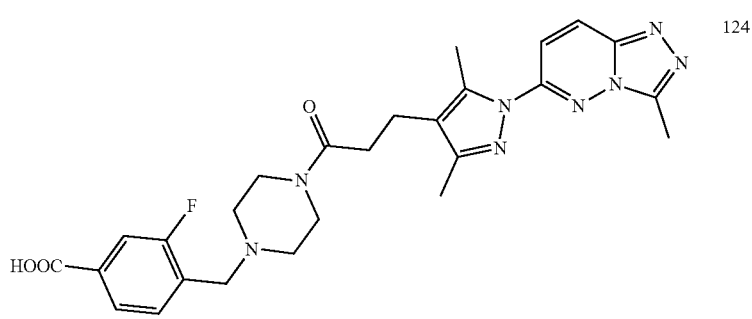
124

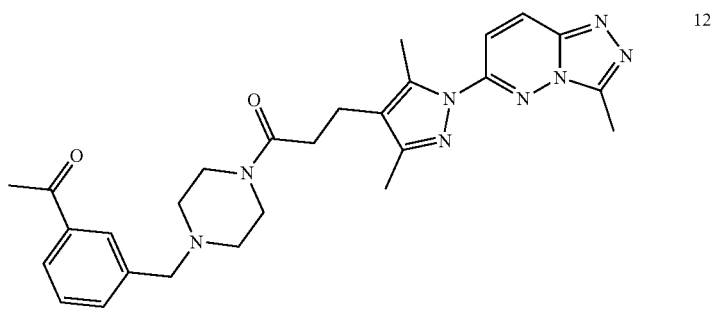
125
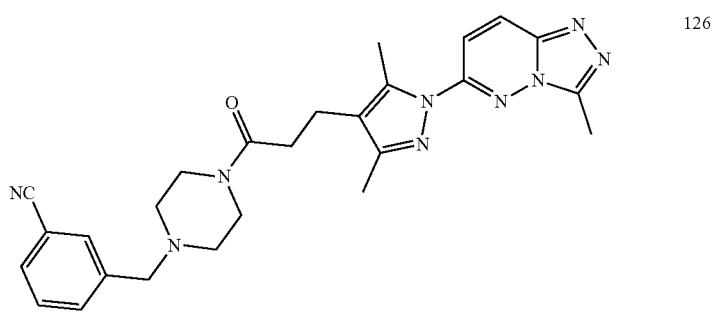
126
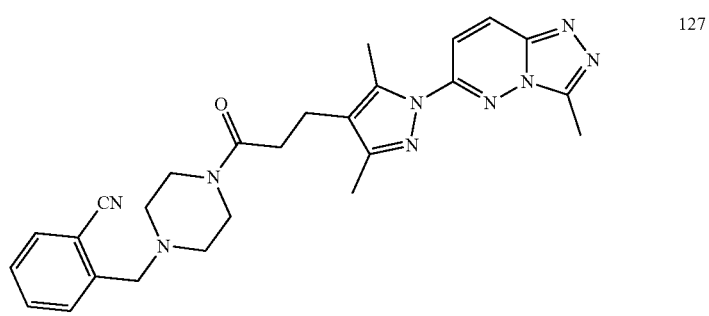
127
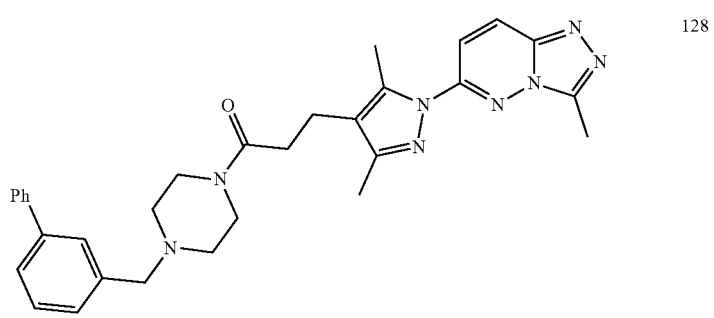
128
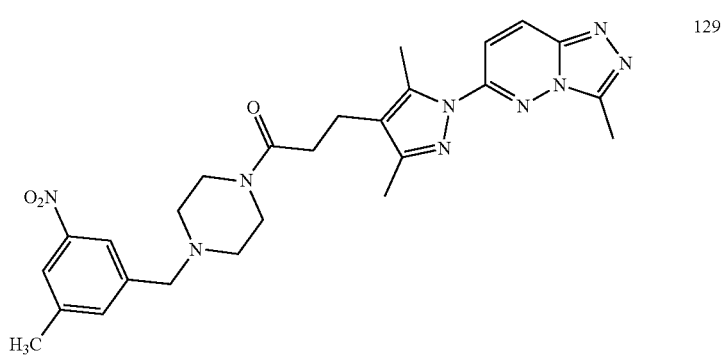
129

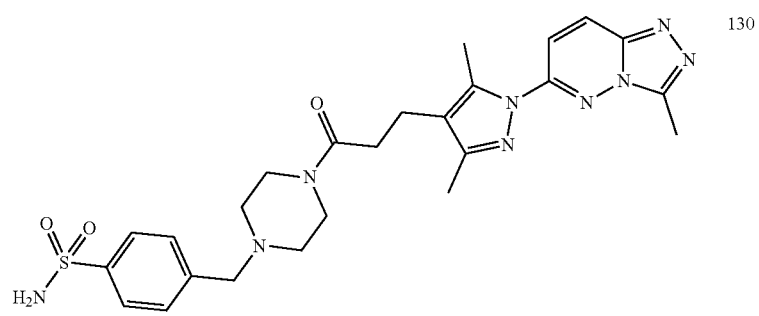
130
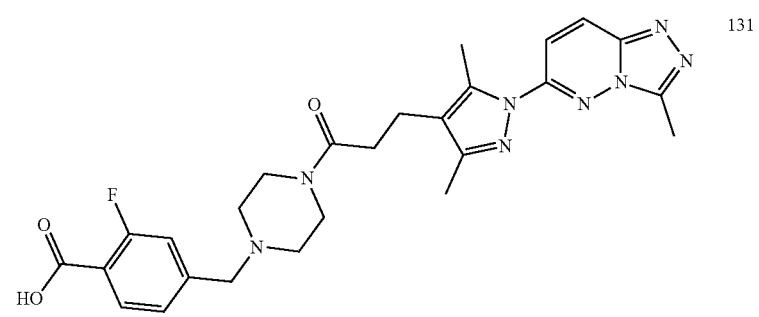
131
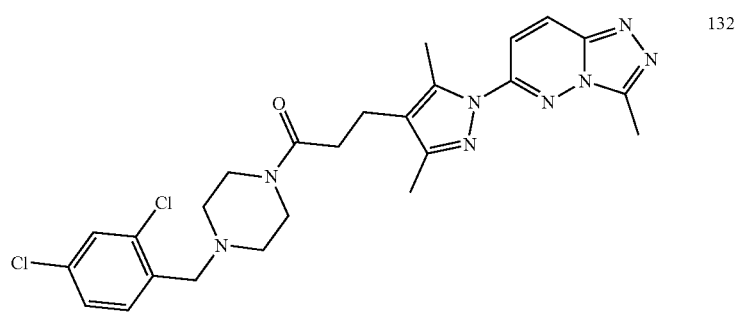
132
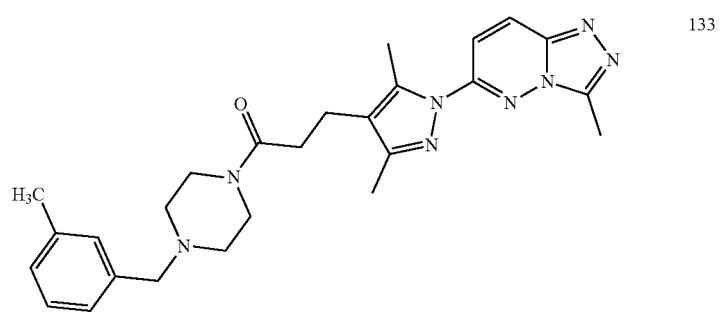
133
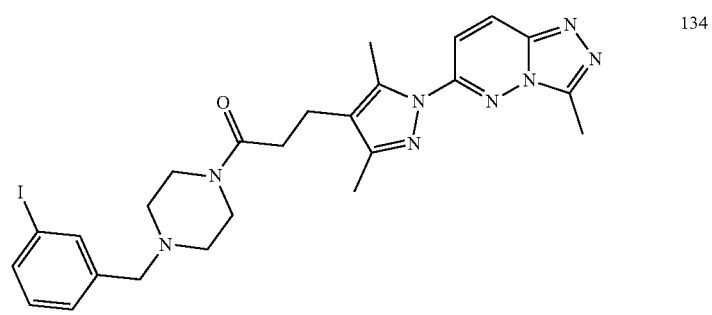
134

-continued
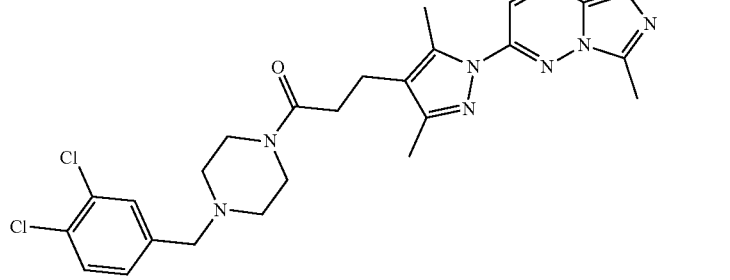
135
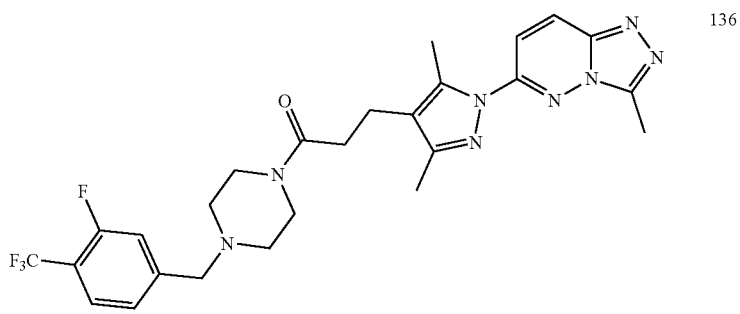
136
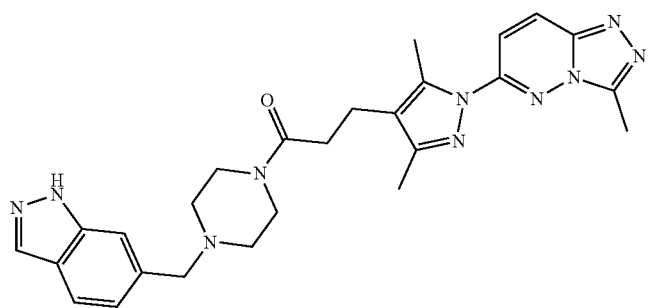 [SMILES: Cc1nn(-c2ccc3nnc(C)n3n2)c(C)c1CCC(=O)N1CCN(Cc2ccc3cn[nH]c3c2)CC1]
137
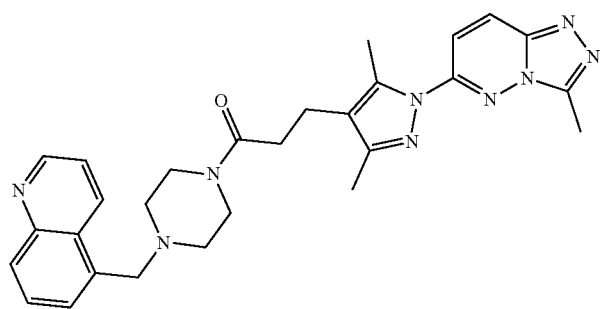
138
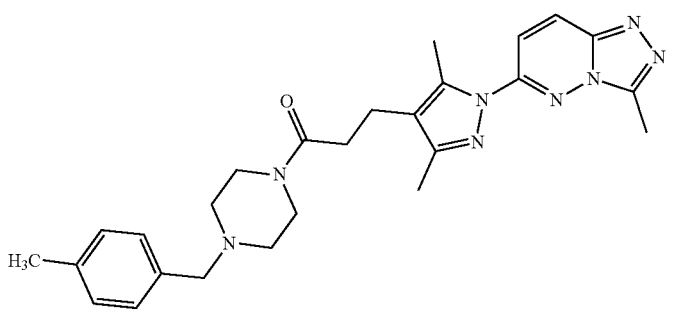 [SMILES: Cc1ccc(CN2CCN(C(=O)CCc3c(C)nn(-c4ccc5nnc(C)n5n4)c3C)CC2)cc1]
139

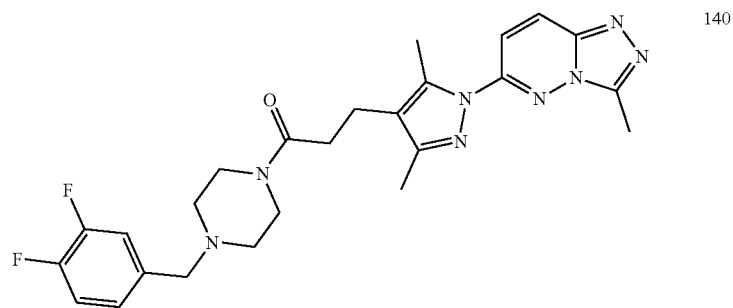
140
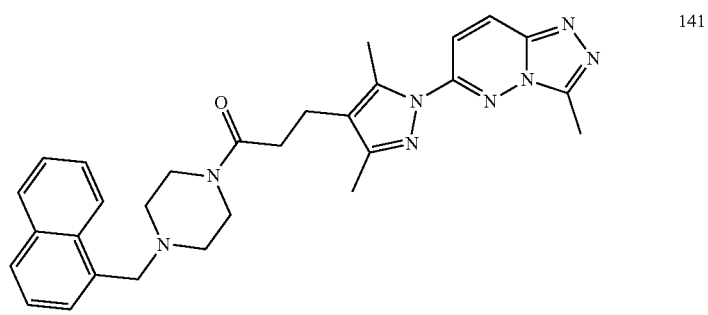
141
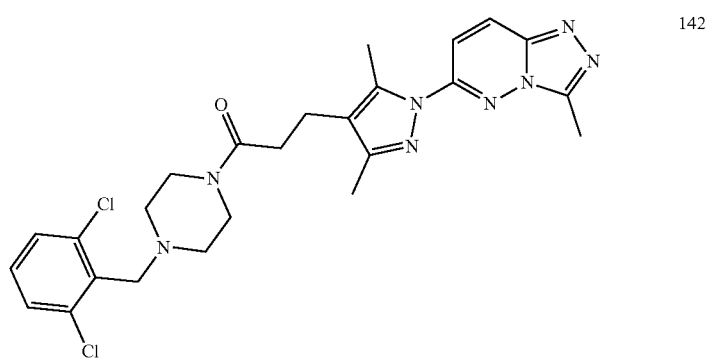
142
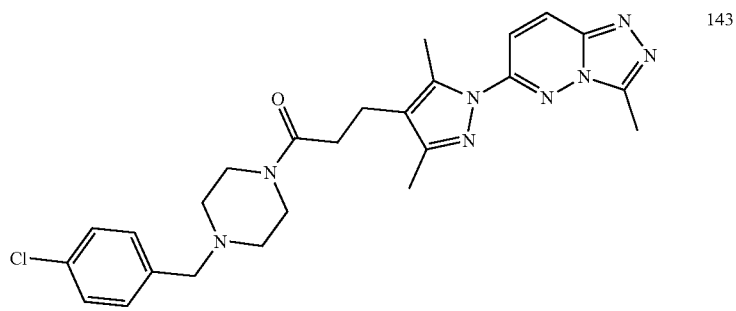
143
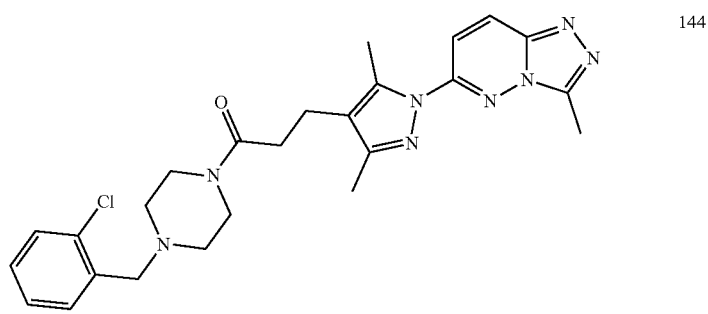
144

-continued
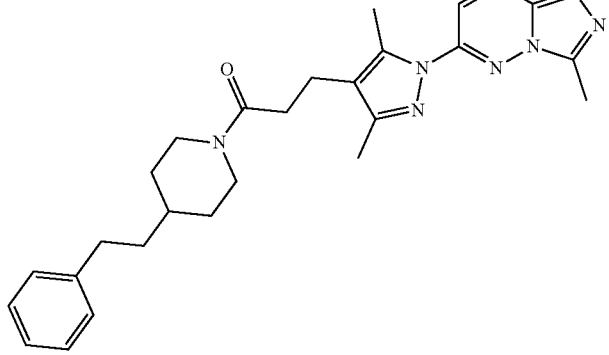
145
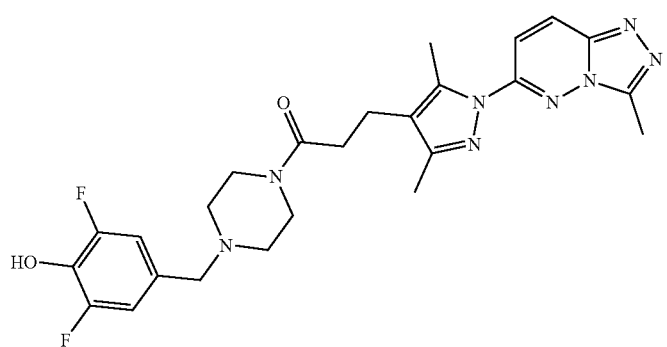 [SMILES: Cc1nn(-c2ccc3nnc(C)n3n2)c(C)c1CCC(=O)N1CCN(Cc2cc(F)c(O)c(F)c2)CC1]
146
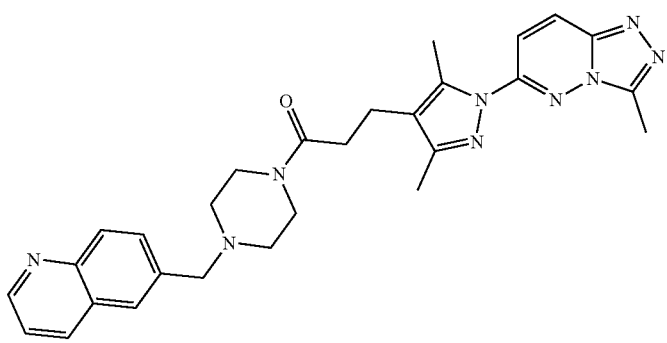 [SMILES: Cc1nn(-c2ccc3nnc(C)n3n2)c(C)c1CCC(=O)N1CCN(Cc2ccc3ncccc3c2)CC1]
147
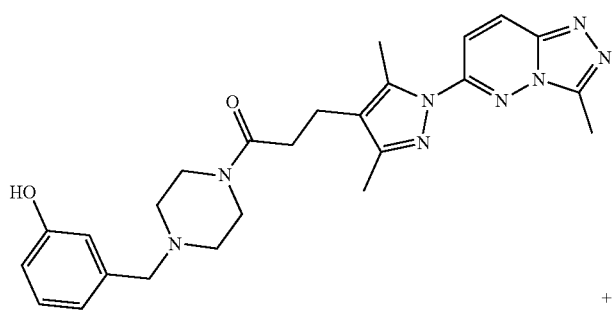
148

-continued
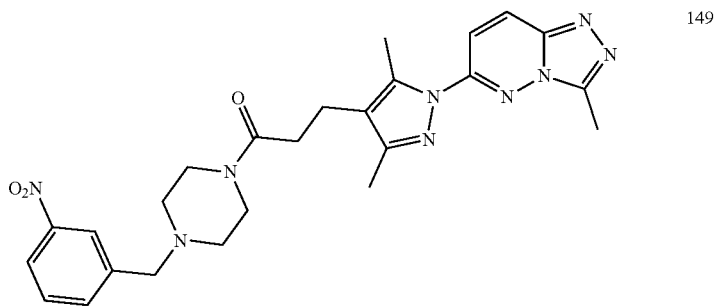
149
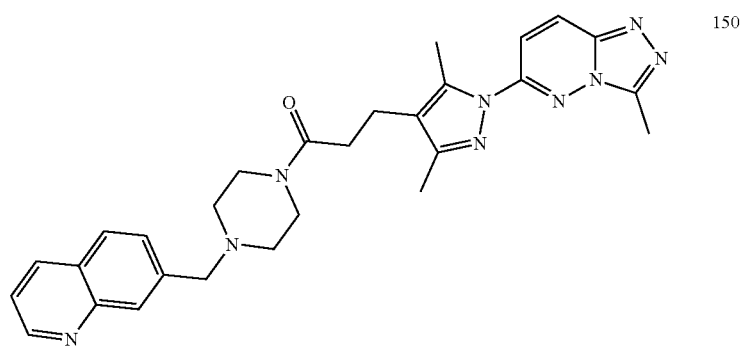
150
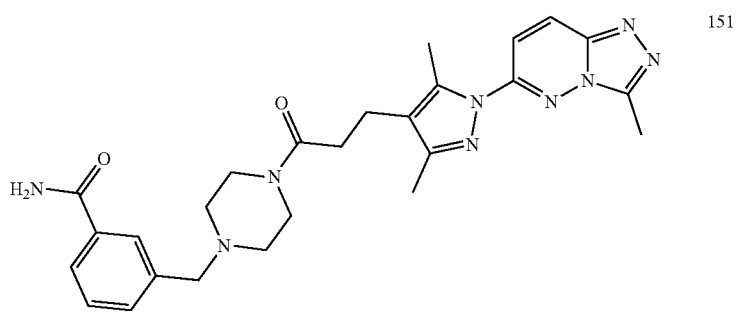
151
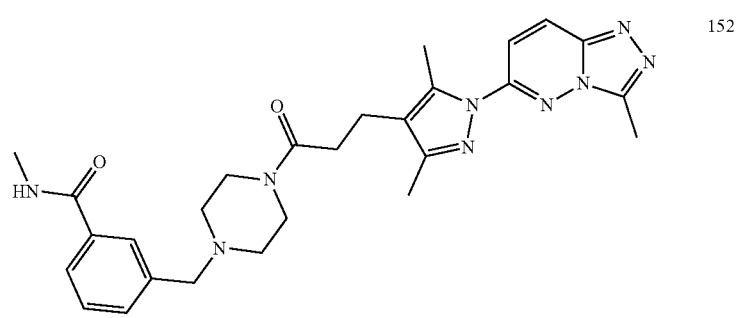
152
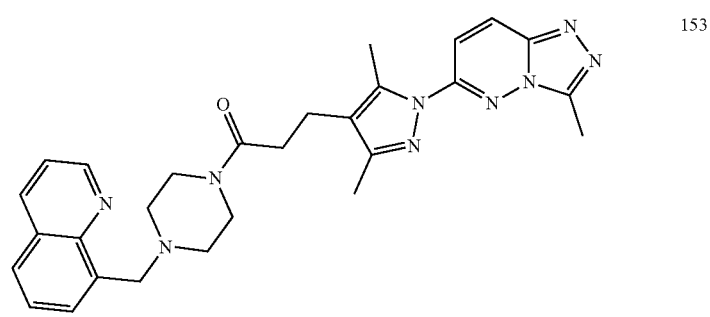
153

-continued
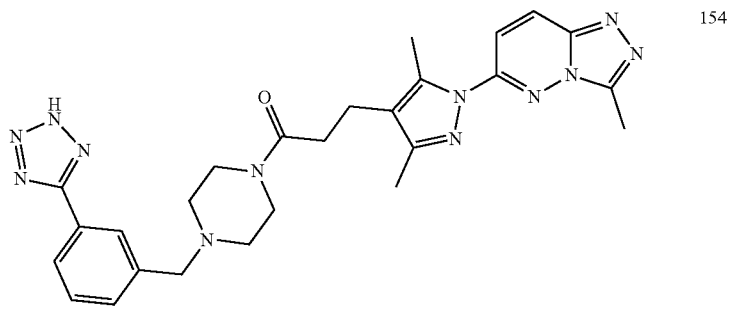
154
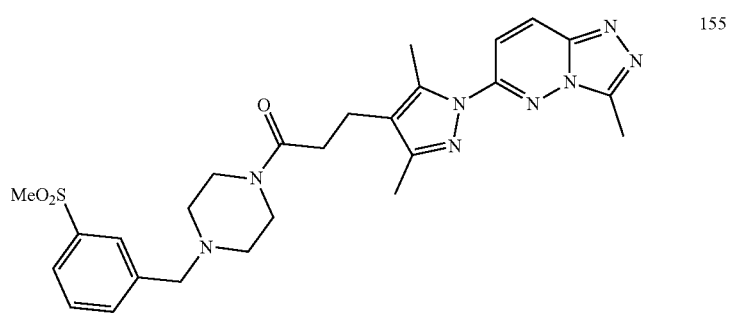
155
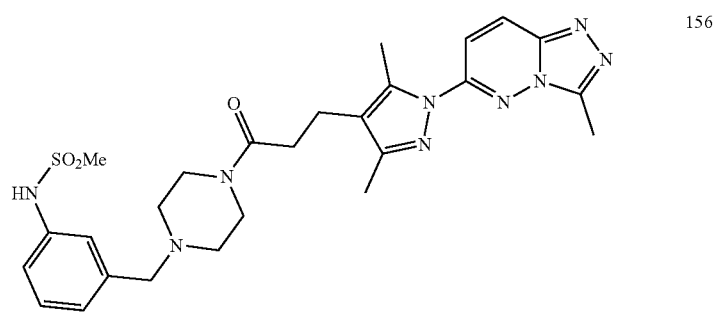
156
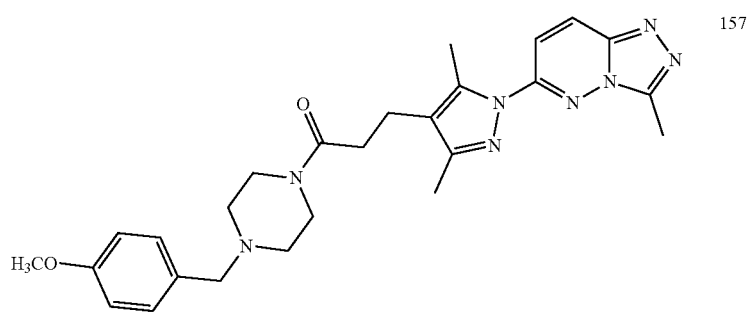
157
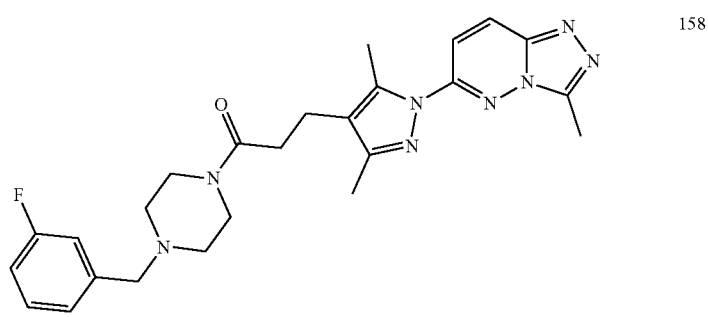
158

-continued
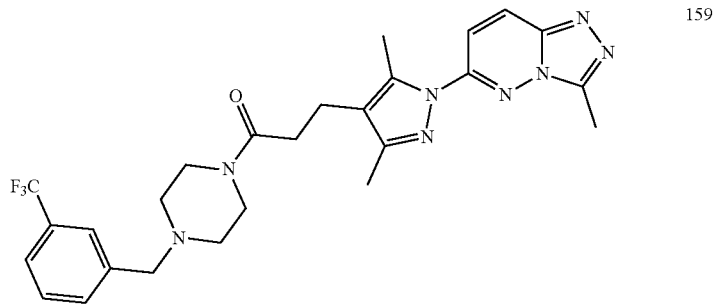
159
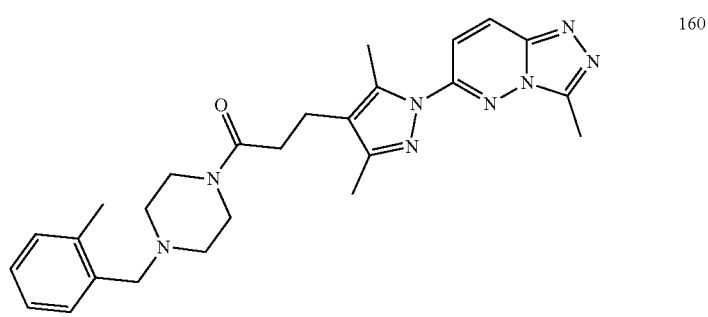
160
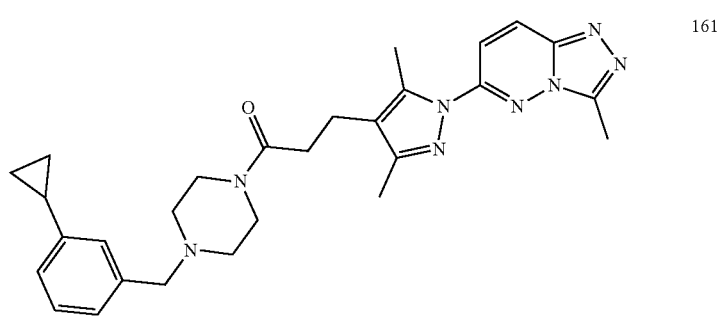
161
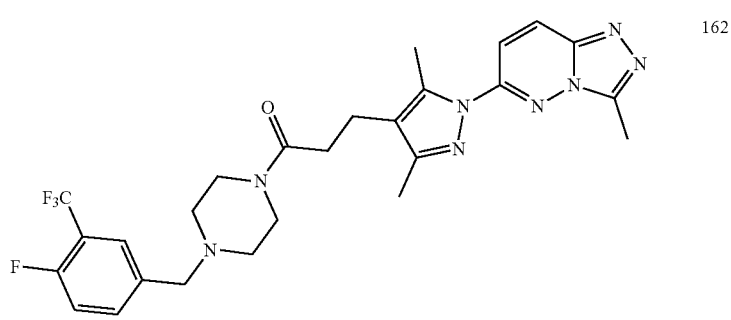
162
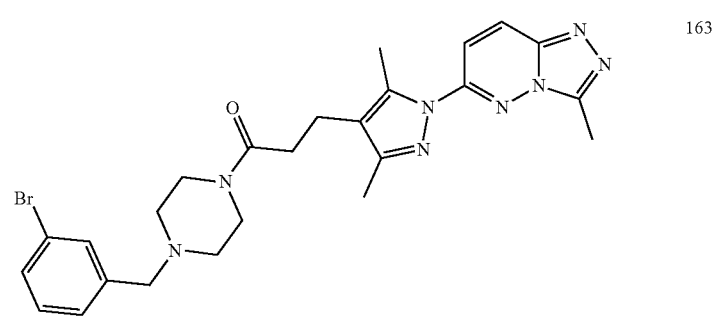
163

164
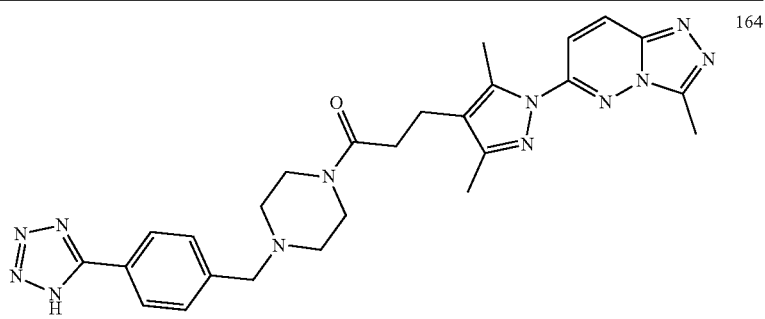
165
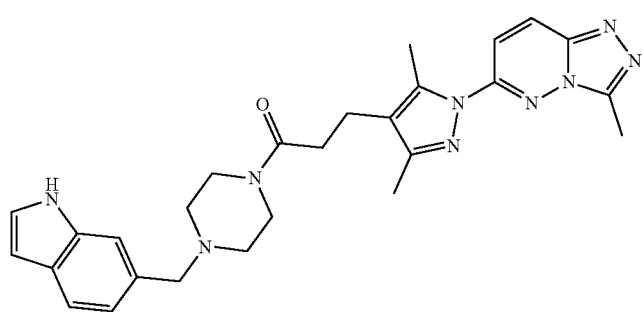 [SMILES: Cc1nn(-c2ccc3nnc(C)n3n2)c(C)c1CCC(=O)N1CCN(Cc2ccc3cc[nH]c3c2)CC1]
166
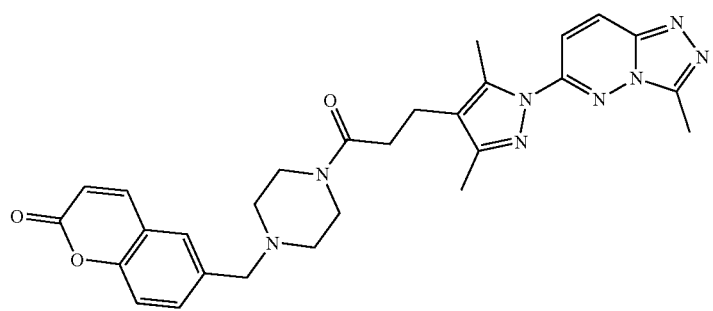 [SMILES: Cc1nn(-c2ccc3nnc(C)n3n2)c(C)c1CCC(=O)N1CCN(Cc2ccc3oc(=O)ccc3c2)CC1]
167
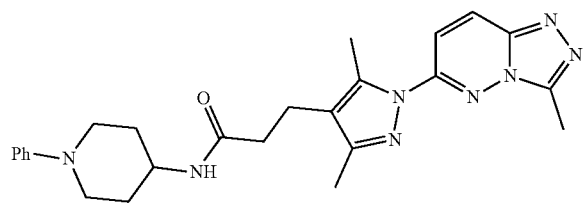 [SMILES: Cc1nn(-c2ccc3nnc(C)n3n2)c(C)c1CCC(=O)NC1CCN(c2ccccc2)CC1]
168
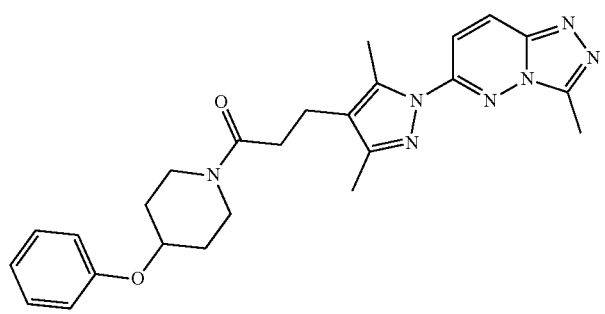 [SMILES: Cc1nn(-c2ccc3nnc(C)n3n2)c(C)c1CCC(=O)N1CCC(Oc2ccccc2)CC1]

-continued
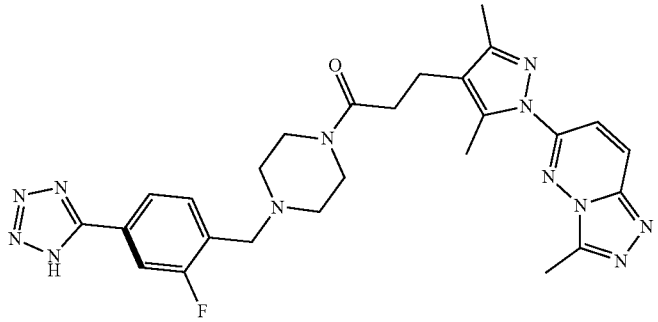
169
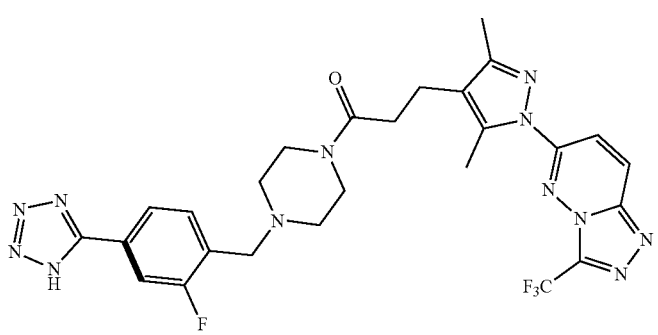
170
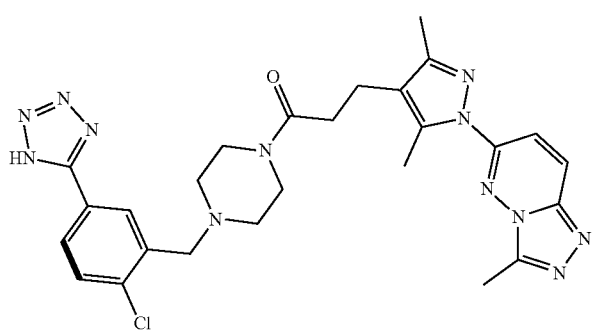
171
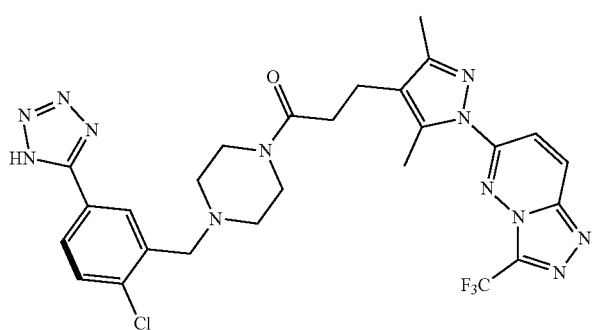
172
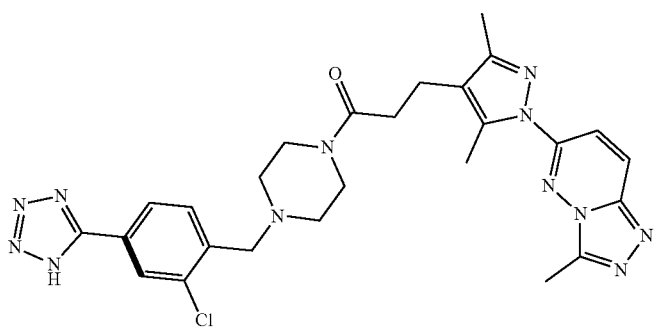
173

174
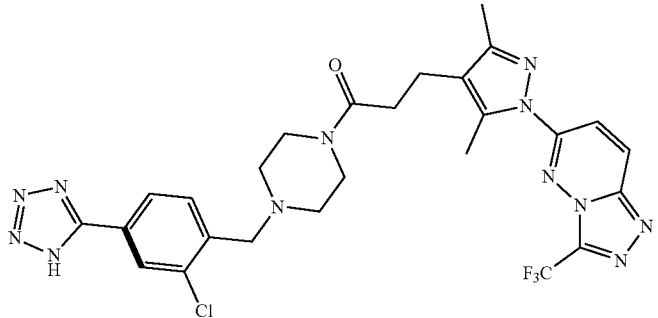
175
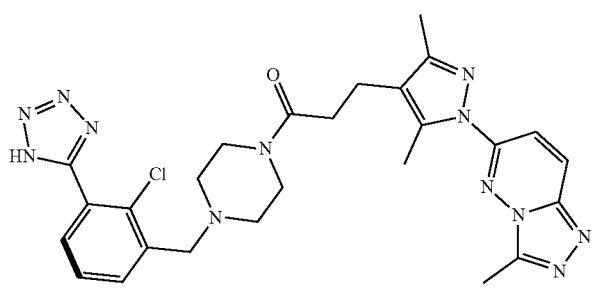
176
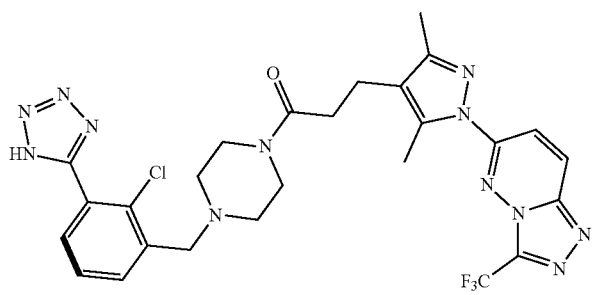
177
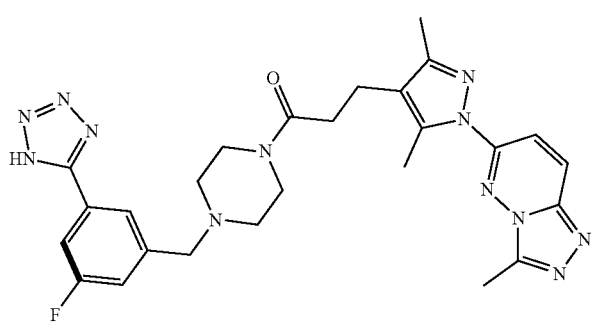
178
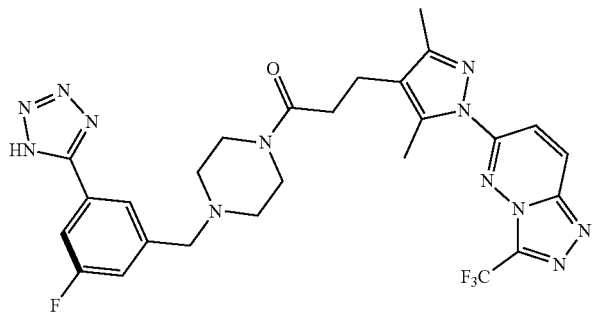

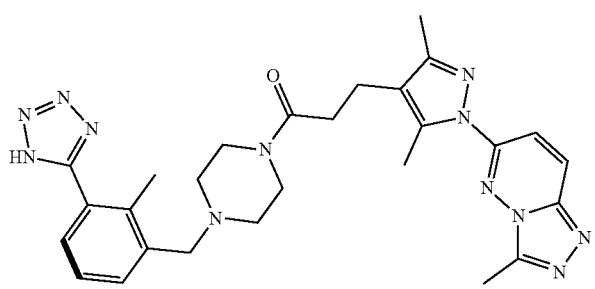
179
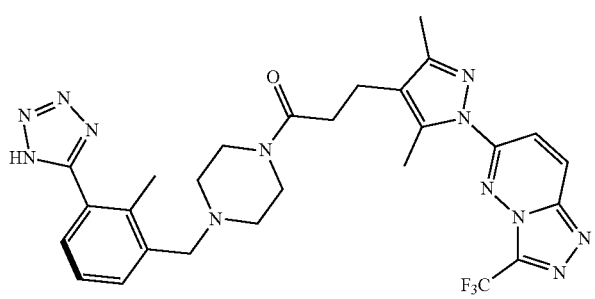
180
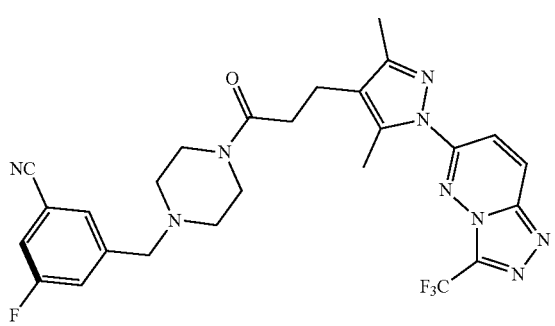
181
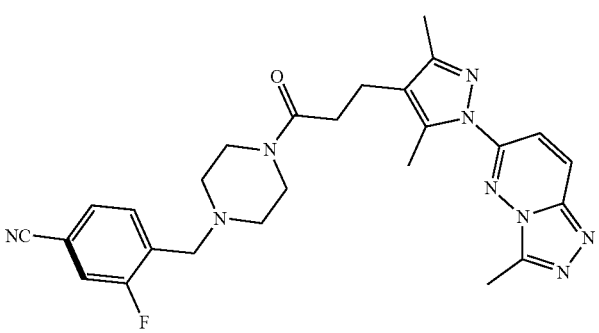
182
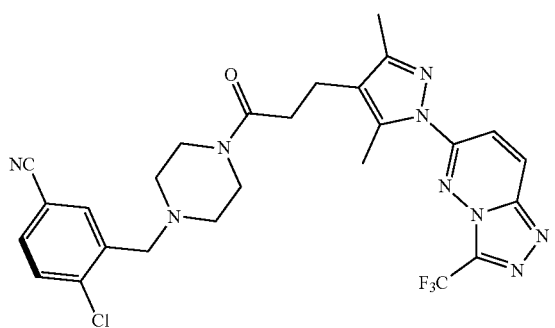
183

184
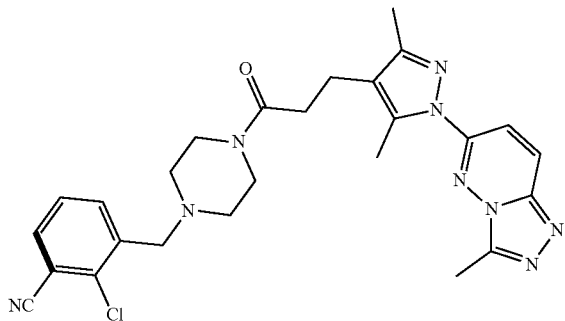
185
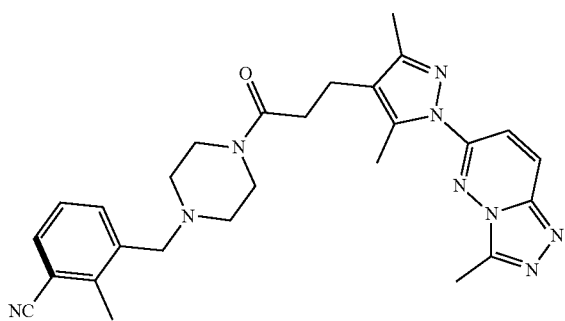
186
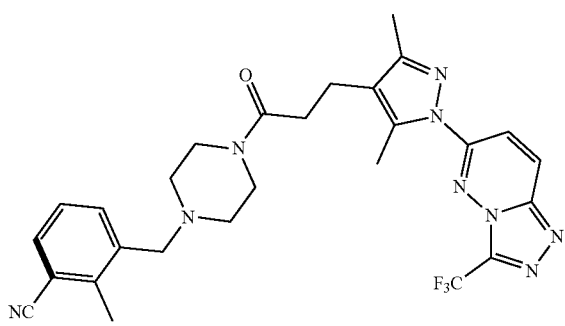
187
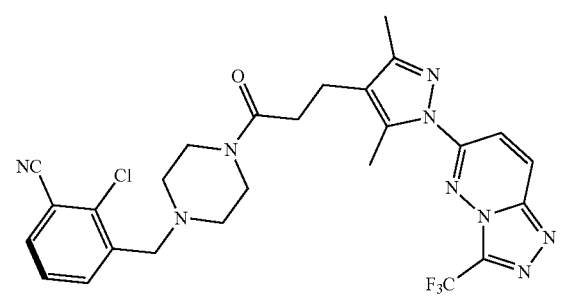
188
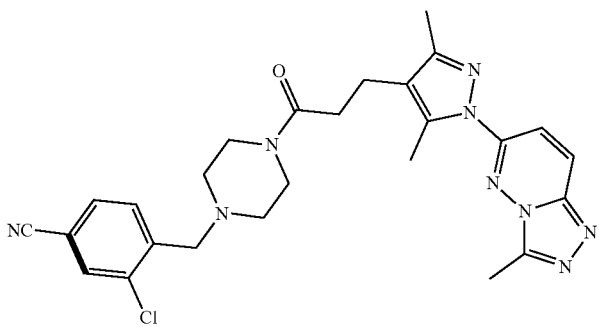

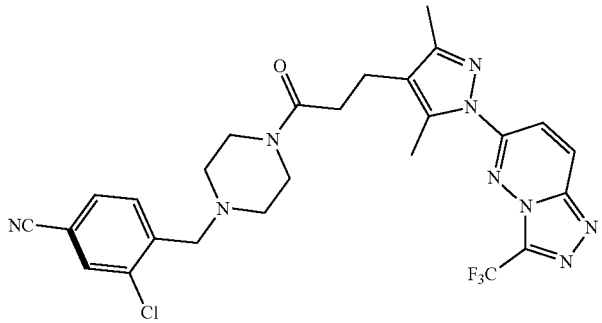

189

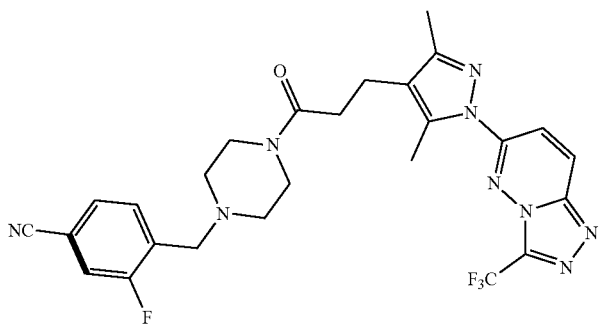

190

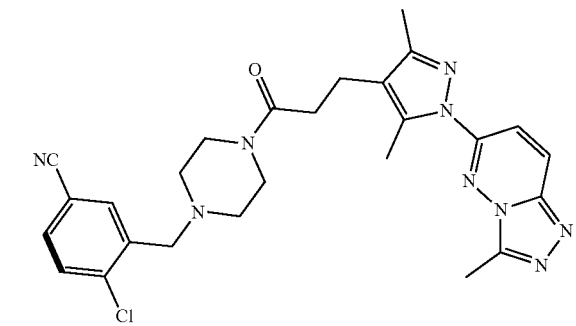

191

In a further aspect, the present invention provides a compound of the invention (in particular those specified above with respect to any of formulas (I), (II), (III), (IV), (XX) as well as the compounds of table 1 for use as medicament.

As it is evident from the examples, the inventors have found that the compounds of the invention inhibit or reduce the TRAF6-Ubc13 interaction, in particular the compounds of the invention inhibit or reduce the enzymatic activity of TRAF6. In some embodiments the compounds of the invention are selective inhibitors of TRAF6. In some embodiments, the compounds of the present invention exhibit pharmacological properties (bioavailability, toxicity, side effects, dosing, patient compliance, compatibility, stability, half-life, etc.), which are in at least one aspect superior to the pharmacological properties of known TRAF6 inhibitors.

In preferred compounds of the invention any one or more structural elements such as groups, substituents and numbers are defined as in any of the preferred definitions of the elements or in any specified embodiment and/or can have one or more of the specific meanings which are mentioned as examples of elements, wherein all combinations of one or more preferred definitions and embodiments and/or specific meanings are a subject of the present invention. Also with respect to all preferred compounds of the formula I, formula II, formula Ill, formula IV and formula XX, all their stereoisomeric forms and mixtures of stereoisomeric forms in all ratios, and their physiologically acceptable salts, and the physiologically acceptable solvates of any of them, are a subject of the present invention. Similarly, also with respect to all specific compounds disclosed herein, such as the example compounds, which represent embodiments of the invention wherein the various groups and numbers in the general definition of the compounds of the formula I, formula II, formula Ill, formula IV and formula XX have the specific meanings present in the respective specific compound, all their stereoisomeric forms and mixtures of stereoisomeric forms in all ratios, and their physiologically acceptable salts, and the physiologically acceptable solvates of any of them, are a subject of the present invention. In particular, a subject of the invention are all specific compounds disclosed herein, independently thereof whether they are disclosed as a free compound and/or as a specific salt, both in the form of the free compound and in the form of all its physiologically acceptable salts, and if a specific salt is disclosed, additionally in the form of this specific salt, and the physiologically acceptable solvates thereof.

The compounds of the present invention can be prepared as described below or prepared by methods analogous thereto, which are readily known and available to one of ordinary skill in the art of organic synthesis. The synthetic access to the compounds according to the invention, i.e. the compounds of Formulas (I), (II), (III), (IV) and (XX) is further illustrated by the example compounds in the description.

In the course of the synthesis of the compounds of the formula I, the heterocycles of the formula V can be treated with hydrazine to the corresponding compounds of the formula VI, followed by a condensation with a compound of the formula VII to yield a compound of formula VIII, which can be saponified to the compound of the formula IX, wherein the groups X, $R^1$, $R^2$ and $R^3$ as well as the number n are defined as in compound of formula I. $LG_1$ is any leaving group suitable for the chemical transformation of compound V to compound VI, such as a halide, tosylate and the like. $R^L$ is any residue suitable for the chemical reaction of compound VI with compound VII to give compound VIII, i.e. stable under the reaction conditions and cleavable under different reaction conditions to allow the preparation of compound IX, such as an alkyl group like methyl or ethyl. Additional functional groups can be present in protected form or in the form of a precursor group which is later converted into the final group. The applied hydrazine for the transformation of compound V to compound VI can be hydrazine or a hydrazine equivalent such as hydrazine hydrate or a hydrazine salt. The reaction of hydrazine or hydrazine equivalent with the compound V is usually carried out at temperatures from about 0° C.-150° C., preferably between 30° C.-100° C. Hydrolytic workup of the reaction mixture or isolation of the product by filtration, which like the workup of all reactions in the preparation of the compounds of formula I can generally be performed under standard conditions, then yields the compound of formula VI.

The condensation reaction of compound VI with compound VII is preferably conducted under acidic conditions such as in acidic acid as solvent to yield a compound of the formula VIII. The reaction is usually carried out at temperatures from about 30° C.-180° C., preferably between 50° C.-150° C.

The compound of the formula VIII is transformed to a compound of the formula IX under acidic or basic conditions, preferably under basic conditions. The saponification can be carried out under acidic conditions by treating the compound of the formula VIII with strong acids such as HBr in a suitable solvent. The saponification can be carried out under basic conditions by treating the compound of the formula VIII with a base such as NaOH, LiOH or KOH in a suitable solvent. The reaction is usually carried out at temperatures from about 0° C.-150° C., preferably between 30° C.-130° C.

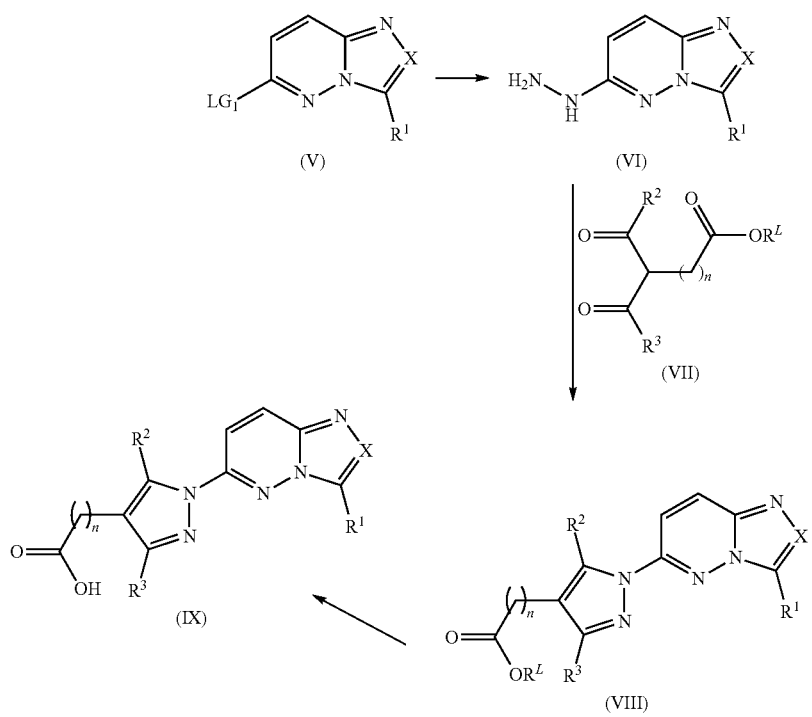

The compounds of the formula IX an then be coupled under standard conditions for the formation of an amide bond with the compounds of the formula X to give a compound of the formula XI. The groups $R^1$, $R^2$, $R^3$, X and Y and the numbers n, p and q are defined as in the compounds of formula I and additional functional groups can be present in protected form or in the form of a precursor group which is later converted into the final group. The compounds of the formula IX are as defined above. For the formation of the amide bond, the carboxylic acid of the formula IX is usually converted into a reactive derivative, which can be isolated or prepared in situ, or activated in situ by a customary amide coupling reagent.

For example, the compound of the formula IX can be converted into a carboxylic acid chloride by treatment with thionyl chloride, oxalyl chloride or (1-chloro-2-methyl-propenyl)-dimethylamine, into a reactive ester, or into a mixed anhydride by treatment with an alkyl chloroformate like ethyl chloroformate or isobutyl chloroformate. Alternatively, the compound of formula IX can be activated with a reagent such as propanephosphonic anhydride, an N,N'-carbonyldiazole like N,N'-carbonyldiimidazole (CDI), a carbodiimide like N,N'-diisopropylcarbodiimide (DIC), N,N'-dicyclohexylcarbodiimide (DCC) or N-ethyl-N'-(3-dimethylaminopropyl)carbodiimide hydrochloride (EDC), a carbodiimide together with an additive like 1-hydroxybenzotriazole (HOBT) or 1-hydroxy-7-azabenzotriazole (HOAT), a uronium-based coupling reagent like O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), or a phosphonium-based coupling reagent like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromothpyrrolidinophosphonium hexafluorophosphate (PyBroP). The activation of the compound of the formula IX and the reaction of the activated compound of the formula IX or a reactive carboxylic acid derivative with the compound of the formula X is generally carried out in an inert solvent, such as an ether like tetrahydrofuran (THF), dioxane or 1,2-dimethoxyethane (DME), or a hydrocarbon like toluene or a chlorinated hydrocarbon like dichloromethane or chloroform, or an amide like dimethylformamide (DMF) or N-methylpyrrolidin-2-one (NMP), for example, or a mixture of solvents, at temperatures from about 0° C. to about 60° C. in the presence of a suitable base such as a tertiary amine like triethylamine, ethyl-diisopropylamine, N-methylmorpholine or pyridine, or a basic alkaline metal compound such as an alkaline metal carbonate like sodium carbonate, potassium carbonate or cesium carbonate, for example. The carboxylic acids of the formula IX, or compounds which instead of the carboxylic acid group depicted in formula IX contain a carboxylic acid derivative group, for example, a carboxylic acid chloride group, can be obtained from the corresponding esters, such as 5-ethyl-4-hydroxy-1-methyl-2-oxo-1,2-dihydroquinoline-3-carboxylic acid by saponification.

In case all the groups of the formula XI have the desired meanings comprised by the definition of the compounds of the formula I, the compound of the formula XI thus obtained is already a final compound of the formula. In case any of the groups of the formula XI are present in protected form or in form of a precursor group, the compound of the formula XI thus obtained can finally be converted into the desired compound of the formula I by removal of the protecting groups and/or conversion of any other groups. As indicated above, in order to avoid an undesired course of a reaction or side reactions, in any one or more steps in the synthesis of the compounds of the formula I functional groups can be present in protected form or in the form of a precursor group. Besides in the final step of the synthesis of a compound of the formula I, protective groups can be removed, and precursor groups be converted, also at other stages of the synthesis. Respective synthetic strategies and details about suitable protective groups and their introduction and removal are well known to a person skilled in the art and are found in P. G. M. Wuts and T. W. Greene, Greene's Protective Groups in Organic Synthesis, 4. ed. (2007), John Wiley & Sons, for example.

In addition, in order to obtain further compounds of the formula I, various other transformations of functional group can be carried out in compounds of the formula I or compounds of the formula XI or other compounds occurring in the synthesis of the compounds of the formula I.

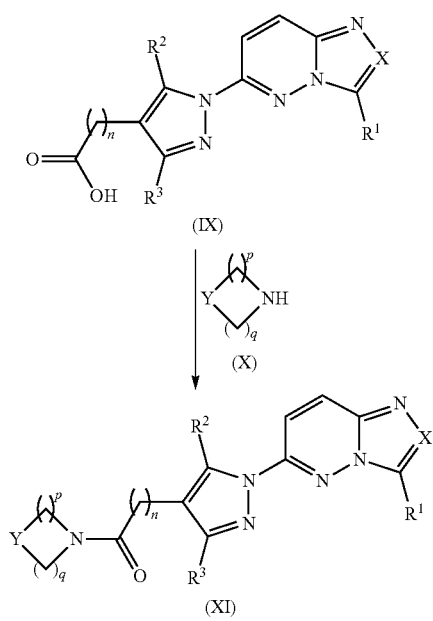

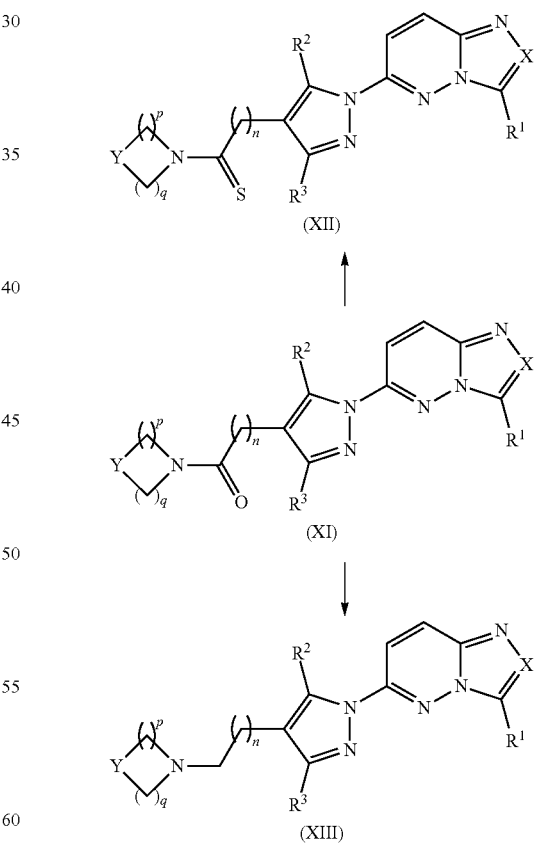

The compounds of the formula XI can also be converted into the compound of the formula XII or XIII. The groups $R^1$, $R^2$, $R^3$, X and Y and the numbers n, p and q are defined as in the compounds of formula I and additional functional groups can be present in protected form or in the form of a precursor group which is later converted into the final group. The compounds of the formula XI are as defined above.

The conversion of the carbonyl group of the compound of the formula XI to the thiocarbonyl group of the compound of the formula XII can be carried out with various reagents known in the art, such as Lawesson's reagent, ammonium phosphorodithionate or by the $PSCl_3/H_2O/Et_3N$ system. The applied solvent and reaction time depends on the utilized reagent or reagent combination.

The reduction of the of the carbonyl group of the compound of the formula XI to the compound of the formula XII can be carried out with various reagents known in the art, such as by metal mediated reduction like platinum-catalyzed reduction, zinc-catalyzed reduction, reduction mediated by complexes like tris(pentafluorophenyl)boron $B(C_6F_5)_3$ or $[Ir(COE)_2Cl]_2$ or reduction by hydride transfer with reagents like lithium aluminum hydrate ($LiAlH_4$).

In case all the groups of the formulas XII and XIII have the desired meanings comprised by the definition of the compounds of the formula I, the compound of the formulas XII and XIII thus obtained are already a final compound of the formula. In case any of the groups of the formulas XII and XIII are present in protected form or in form of a precursor group, the compound of the formulas XII and XIII thus obtained can finally be converted into the desired compound of the formula I by removal of the protecting groups and/or conversion of any other groups.

The starting compounds and building blocks for the synthesis of the compounds of the formula I are commercially available or can be prepared according to procedures described in the literature or analogously to such procedures.

The order in which groups are introduced in the course of the synthesis of a compound of the formula I can also be different from the ones outlined above. For example, thiocarbonyl group of the compound of the formula XII might be introduced by converting the carbonyl group of the compound of the formula VIII into the corresponding thioester. In particular, other routes of synthesis may in fact be applied to certain embodiments of the compounds disclosed herein. The person of ordinary skill is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

Pharmaceutical Compositions

In a further aspect, the present invention provides a pharmaceutical composition comprising a compound as specified above under the heading "Compounds" and one or more pharmaceutically acceptable excipients.

The compounds described in present invention (in particular those specified above such as those of formula (I), (II), (III), (IV) and/or (XX), as well as the compounds of table 1 are preferably administered to a patient in need thereof via a pharmaceutical composition. In one embodiment, the pharmaceutical composition comprises a compound as described above (e.g. having the general formula (I), (II), (III), (IV) and/or (XX), as well as the compounds of table 1 or a hydrate, solvate, salt, complex, racemic mixture, diastereomer, enantiomer, or tautomer thereof or an isotopically enriched form of any of the foregoing) and one or more pharmaceutically acceptable excipients.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds used in to the present invention are generally applied in "pharmaceutically acceptable amounts" and in "pharmaceutically acceptable preparations". Such compositions may contain salts, buffers, preserving agents, carriers and optionally other therapeutic agents.

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound used in the present invention, either alone or in combination with one or more additional active compounds, may be coated in a material to protect the active compound(s) from the action of acids and other natural conditions that may inactivate the active compound.

Examples of suitable aqueous and non-aqueous carriers which may be employed in the pharmaceutical compositions used according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions used according to the present invention is contemplated.

Additional active compounds can be administered together with, before or after the compound used in the present invention (in particular that specified above such as those of (I), (II), (III), (IV), and/or (XX) as well as the compounds of table 1 or incorporated into the compositions). In one embodiment, the pharmaceutical composition described herein comprises a compound as described above (e.g. having the general formula (I), (II), (III), (IV), and/or (XX) as well as the compounds of table 1 or a hydrate, solvate, salt, complex, racemic mixture, diastereomer, enantiomer, or tautomer thereof or an isotopically enriched form of any of the foregoing), at least one additional active compound, and one or more pharmaceutically acceptable excipients.

The "additional active compound" (which is not a compound having formula (I), (II), (III), (IV) and/or (XX), as well as the compounds of table 1 as specified herein) may be selected from any compound which can be used in the treatment of cancer and/or immune diseases. The additional active compound may induce an additive or synergistic therapeutic effect.

The pharmaceutical composition described herein may comprise, in addition to the compound having a structure according to formula (I), (II), (III), (IV) and/or (XX), or the compounds of table 1 as described above, at least one, e.g., 1, 2, 3, 4, 5, 6, 7 or 8, additional active compounds. According to the present teaching, the at least additional active compound, for example the anticancer drug, and/or an agent for the treatment of immune diseases, may be formulated together with the compound having a structure according to formula (I), (II), (III), (IV) and/or (XX), or the compounds of table 1 as described above in a single pharmaceutical composition. Alternatively, the pharmaceutical composition may be structured as kit of parts, wherein the compound having a structure according to formula (I), (II), (III), (IV) and/or (XX), or the compounds of table 1 is provided in a first formulation and the at least one additional active compound, for example the anticancer drug and/or an agent for the treatment of immune diseases, is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the compound having a structure according to formula (I), (II), (III), (IV), and/or (XX) or the compounds of table 1 as described above. Alternatively, the present teaching envisages administering the compound having a structure according to formula (I), (II), (III), (IV) and/or (XX), or the compounds of table 1 as described above, formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years. In some embodiments the kit of parts comprises a compound having a structure according to formula (I), (II), (III), (IV) and/or (XX), or the compounds of table 1 as described above, or a pharmaceutical composition containing a compound having a structure according to formula (I), (II), (III), (IV) and/or (XX), or the compounds of table 1 as described above, and at least one pharmaceutically acceptable carrier.

The compositions may also contain adjuvants such as preservatives, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the active compounds, which may be used in a suitable hydrated form, and/or the pharmaceutical compositions used according to the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999.).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound used in the present invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7:27(1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions used according to the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound used according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound used according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound used according to the present invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Actual dosage levels of the active ingredients in the pharmaceutical compositions used according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds used according to the present invention at levels lower than that required in order to achieve the desired therapeutic effect and gradually increase the dosage until the desired effect is achieved. In general, a suitable daily dose of a composition used according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound used according to the present invention to be administered alone, it is preferable to administer the compound as a pharmaceutical formulation/composition.

For oral administration, the pharmaceutical composition used according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the compound is orally administered in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the compound is parenterally administered (e.g., intravenously, intramuscularly, or subcutaneously), in a concentration of at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The pharmaceutical composition used according to the present invention can be formulated for parenteral administration by injection, for example, by bolus injection or continuous infusion. In one embodiment, the compounds or compositions used according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions used according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition used according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions used according to the present invention which are suitable for vaginal administration also include pessaries, tampons, creams, gels, pastes, foams or spray formulations containing such carriers as are known in the art to be appropriate. Dosage forms for the topical or transdermal administration of compositions used according to the present invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

In one embodiment, the compounds used according to the present invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. The ability of a compound to inhibit TRAF6 can be evaluated by using any of the in vitro or cell-based assays described herein measuring the TRAF6 activity/inhibition. Alternatively, the properties of a compound described in the present invention can be evaluated by examining the ability of the compound in appropriate animal model systems known to the skilled practitioner. A therapeutically effective amount of a compound used according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition used according to the invention can also, if desired, be presented in a pack, or dispenser device which can contain one or more unit dosage forms containing the active compound. The pack can for example comprise metal or plastic foil, such as blister pack. The pack or dispenser device can be accompanied with instruction for administration.

The pharmaceutical composition used according to the invention can be administered as sole active agent or can be administered in combination with other therapeutically and/or cosmetically active agents. In one embodiment, the pharmaceutical composition used according to the invention contains, or is administered with, one or more other therapeutically active agents selected from the group consisting of antiviral agents, antibodies (which are directed against an antigen of an animal pathogenic virus or another microorganism (e.g., a pathogenic bacterium or fungi) or against a cancer antigen), agents stimulating the immune system of the subject (e.g., interferons, such as interferon alpha or interferon beta, imiquimod, and resiquimod), and antimicrobial agents.

Therapeutic and Other Applications

In further aspects, the present application provides a compound as specified above under the heading "Compounds" or a pharmaceutical composition as specified above under the heading "Pharmaceutical compositions" for use in therapy.

Generally, the present invention demonstrates that the compounds having a structure according to formula (I), (II), (III), (IV) and/or (XX), or the compounds of table 1 as described herein under the heading "Compounds" or a pharmaceutical composition as specified above under the heading "Pharmaceutical compositions" are capable of inhibiting or reducing the TRAF6-Ubc13 interaction, in particular capable of inhibiting or reducing the enzymatic activity of TRAF6.

Thus, in one aspect, the present invention is directed to a compound having a structure according to formula (I), (II), (III), (IV) and/or (XX), or a compound of table 1 and hydrates, solvates, salts, complexes, racemic mixtures, diastereomers, enantiomers, and tautomers thereof and isotopically enriched forms of any of the foregoing, for use in the treatment of a TRAF6 associated disease, in particular for use in the treatment of cancer, an immune disease, Parkinson's disease, Cardiac Hypertrophy or Type-2 diabetes, preferably cancer, an immune disease and Type-2 diabetes, more preferably cancer or an immune disease. Optionally, the method comprises the step of administering at least one additional active compound to the individual. The at least one additional active compound can be administered together with, before or after the compound having a structure according to formula (I), (II), (III), (IV) and/or (XX), or the compound of table 1.

As used herein and throughout the entire description, the term "disease associated with TRAF6" means any pathological state or disease which occurs cumulatively by an overexpression of TRAF6 or correlates to an overexpression or activity of TRAF6.

It has been shown TRAF6 activity or overexpression is associated to the following pathologies:

Rheumatoid Arthritis (RA): Disease onset and progression of RA is significantly dependent on various signaling pathways of the innate and adaptive immune response (McInnes, I. B., C. D. Buckley, and J. D. Isaacs, *Cytokines in rheumatoid arthritis—shaping the immunological landscape*. Nat Rev Rheumatol, 2016. 12(1): p. 63-8; McInnes, I. B. and G. Schett, *Cytokines in the pathogenesis of rheumatoid arthritis*. Nat Rev Immunol, 2007. 7(6): p. 429-42; Schett, G., J. M. Dayer, and B. Manger, *Interleukin-1 function and role in rheumatic disease*. Nat Rev Rheumatol, 2016. 12(1): p. 14-24; Choy, E., *Understanding the dynamics: pathways involved in the pathogenesis of rheumatoid arthritis*. Rheumatology (Oxford), 2012. 51 Suppl 5: p. v3-11; McInnes, I. B. and G. Schett, *The pathogenesis of rheumatoid arthritis*. N Engl J Med, 2011. 365(23): p. 2205-19; Brzustewicz, E. and E. Bryl, *The role of cytokines in the pathogenesis of rheumatoid arthritis—Practical and potential application of cytokines as biomarkers and targets of personalized therapy*. Cytokine, 2015. 76(2): p. 527-36 and Joosten, L. A., S. Abdollahi-Roodsaz, C. A. Dinarello, et al., *Toll-like receptors and chronic inflammation in rheumatic diseases: new developments*. Nat Rev Rheumatol, 2016. 12(6): p. 344-57). Intriguingly, all these pathways (IL-1β, TLR, Th1, Th17 and more) employ TRAF6 E3 ligase activity for proper pathway activation, signal progression and cytokine (IL-1β, TNFα, IL-6 and more) secretion. Moreover, TRAF6 has been implicated to play a role in osteoclast differentiation (Lamothe, B., W. K. Webster, A. Gopinathan, et al., *TRAF6 ubiquitin ligase is essential for RANKL signaling and osteoclast differentiation*. Biochem Biophys Res Commun, 2007. 359(4): p. 1044-9). Finally, studies on single nucleotide polymorphisms have linked TRAF6 to RA (Namjou, B., C. B. Choi, I. T. Harley, et al., *Evaluation of TRAF6 in a large multiancestrallupus cohort*. Arthritis Rheum, 2012. 64(6): p. 1960-9). Thus, inhibition of TRAF6-Ubc13 interaction is a novel strategy to counteract inflammation and bone resorption in RA. Our proof-of-concept study in a CIA-induced preclinical RA mouse model clearly verifies this hypothesis that inhibition of TRAF6-Ubc13 interaction by C25-140 (compound 3) indeed ameliorates RA disease outcomes (see FIG. 11). Further, it has been shown that TRAF6 expression is markedly elevated in joints of CIA-induced RA mice and that siTRAF6 treatment of CIA-induced RA mice ameliorates arthritis index as well as inflammation and bone destruction (Wang, H., W. Chen, L. Wang, et al., *Tumor necrosis factor receptor-associated factor 6 promotes migration of rheumatoid arthritis fibroblast-like synoviocytes*. Mol Med Rep, 2015. 11(4): p. 2761-6). Intriguingly, the results from the genetic depletion of TRAF6 perfectly correlate with our TRAF6 activity inhibitor study. Finally, a study observing 44 RA patients and 9 Osteoarthritis patients revealed that TRAF6 expression is only increased in the RA patient pool, again underlining the argument that TRAF6 might be dominantly involved in synovial inflammation and bone resorption through osteoclast differentiation (Zhu, L. J., L. Dai, D. H. Zheng, et al., *Upregulation of tumor necrosis factor receptor-associated factor 6 correlated with synovitis severity in rheumatoid arthritis*. Arthritis Res Ther, 2012. 14(3): p. R133) and thereby be an interesting target for RA treatment.

Figure 10A:
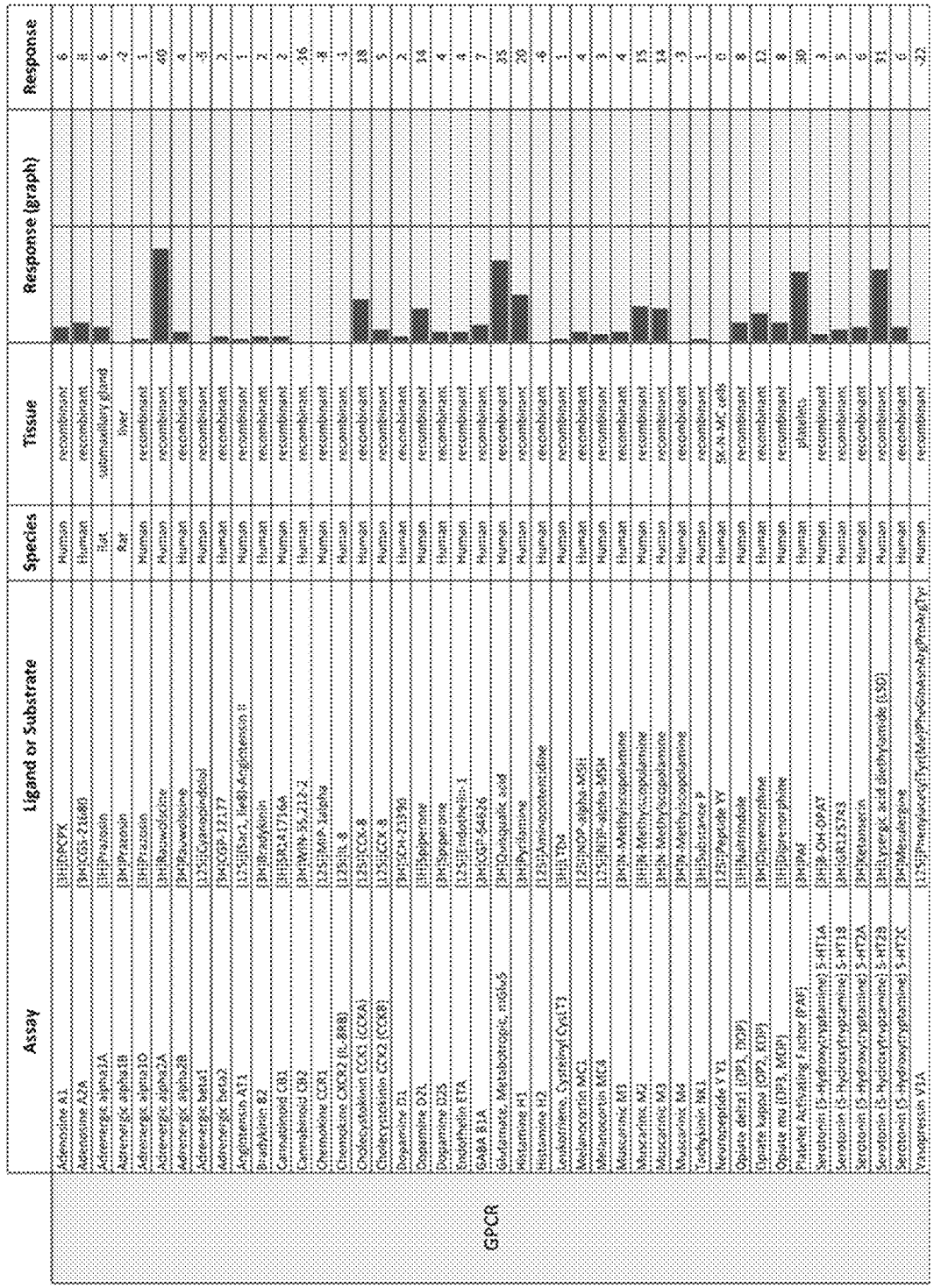
FIG. 10: SafetyScreen87 to evaluate the in vivo safety of compound C25-140. Here, 87 assays were carried out at Eurofins Cerep Panlabs. The 87 primary molecular targets included kinases, non-kinase enzymes, nuclear receptors, GPCRs, transporters and ion channels that were tested at a compound concentration of 10 μM C25-140. C25-140 did not markedly affect any of the 87 molecular targets. The assay, ligand/substrate, species and the tissue are indicated. The percentage response is shown. C25-140 is equal to compound 3 of the description.

Psoriasis: The pathogenesis of psoriasis is largely dependent on IL-17 signaling, which involves TRAF6 as an important component in signal progression to cytokine expression (Baliwag, J., D. H. Barnes, and A. Johnston, *Cytokines in psoriasis*. Cytokine, 2015. 73(2): p. 342-50; Grine, L., L. Dejager, C. Libert, et al., *An inflammatory triangle in psoriasis: TNF, type I IFNs and IL-17*. Cytokine Growth Factor Rev, 2015. 26(1): p. 25-33 and Gu, C., L. Wu, and X. Li, *IL-17 family: cytokines, receptors and signaling*. Cytokine, 2013. 64(2): p. 477-85). Moreover, studies on activation of TLR7 by imiquimod (IMQ) have shown that this drives psoriasis, thereby providing evidence that TLRs and the innate immune response are also involved in disease formation (Gilliet, M., C. Conrad, M. Geiges, et al., *Psoriasis triggered by toll-like receptor 7 agonist imiquimod in the presence of dermal plasmacytoid dendritic cell precursors. Arch Dermatol, 2004. 140(12): p. 1490-5). All TLRs except TLR3 employ TRAF6 as a central regulator for signal transduction. In line with this, the present application provides evidence from an IMQ-induced psoriasis mouse study that inhibition of TRAF6-Ubc13 interaction by C25-140 ameliorates disease outcomes (see FIG. 10).

Inflammatory Bowel Disease (IBD): Inflammation in IBD (Crohn's disease and ulcerative colitis) relies on K63-ubiquitination events facilitated by TRAF6. It has been shown that the E3 ligase activity of TRAF6 is critical for disease development (Watanabe, T., N. Asano, G. Meng, et al., *NOD2 downregulates colonic inflammation by IRF4-mediated inhibition of K63-linked polyubiquitination of RICK and TRAF6*. Mucosal Immunol, 2014. 7(6): p. 1312-25 and Wei, J., C. Wei, M. Wang, et al., *The GTPase-activating protein GIT2 protects against colitis by negatively regulating Toll-like receptor signaling*. Proc Natl Acad Sci USA, 2014. 111(24): p. 8883-8). Moreover, a recent study proved that TLR2 signaling is involved in the emergence of colitis as a peptide inhibitor of TLR2 receptor ameliorated DSS-induced colitis (Shmuel-Galia, L., T. Aychek, A. Fink, et al., *Neutralization of pro-inflammatory monocytes by targeting TLR2 dimerization ameliorates colitis*. EMBO J, 2016. 35(6): p. 685-98). In TLR2 signaling, TRAF6 is a key regulator of signal progression toward NF-κB and cytokine expression. Consequently, an inhibitor of TRAF6 activity should be very suitable for treating IBD. In addition, a clinical study looking at IBD patient samples discovered that TRAF6 levels are elevated in both Crohn's disease and ulcerative colitis (Shen, J., Y. Qiao, Z. Ran, et al., *Different activation of TRAF4 and TRAF6 in inflammatory bowel disease*. Mediators Inflamm, 2013. 2013: p. 647936), again highlighting the potential of targeting TRAF6 for IBD treatment.

Type-1 diabetes (T1D): IL-1 mediated NF-κB activation in synergy with TNFα and IFNγ is the main driver for inflammation and apoptosis in β-cells (Bending, D., P. Zaccone, and A. Cooke, *Inflammation and type one diabetes*. Int Immunol, 2012. 24(6): p. 339-46; Csorba, T. R., A. W. Lyon, and M. D. Hollenberg, *Autoimmunity and the pathogenesis of type 1 diabetes*. Crit Rev Clin Lab Sci, 2010. 47(2): p. 51-71 and Mandrup-Poulsen, T., L. Pickersgill, and M. Y. Donath, *Blockade of interleukin 1 in type 1 diabetes mellitus*. Nat Rev Endocrinol, 2010. 6(3): p. 158-66). Accordingly, inhibition of IL-1 signaling in animal models reduced T1D outcome and improved glycaemia as well as β-cell function (Mandrup-Poulsen, T., L. Pickersgill, and M. Y. Donath, *Blockade of interleukin 1 in type 1 diabetes mellitus*. Nat Rev Endocrinol, 2010. 6(3): p. 158-66). To date, antibody based IL-1 antagonists have been used in clinical trials with effects on disease onset (Baumann, B., H. H. Salem, and B. O. Boehm, *Anti-inflammatory therapy in type 1 diabetes*. Curr Diab Rep, 2012. 12(5): p. 499-509). Also, TLRs have been shown to be involved in inflammation of insulitis (Eizirik, D. L., M. L. Colli, and F. Ortis, *The role of inflammation in insulitis and beta-cell loss in type 1 diabetes*. Nat Rev Endocrinol, 2009. 5(4): p. 219-26). TRAF6 is a central regulator of IL-1 and TLR signaling and thereby could represent a novel strategy to reduce inflammation in the pre-diabetes phase of insulitis to prevent β-cell death.

Multiple Sclerosis (MS): Previous studies have shown that experimental autoimmune encephalitis (EAE), a mouse model for MS, is increased by Th1 and Th17 immune responses (Jager, A., V. Dardalhon, R. A. Sobel, et al., *Th1, Th17, and Th9 effector cells induce experimental autoimmune encephalomyelitis with different pathological phenotypes*. J Immunol, 2009. 183(11): p. 7169-77 and Zepp, J., L. Wu, and X. Li, *IL-17 receptor signaling and T helper 17-mediated autoimmune demyelinating disease*. Trends Immunol, 2011. 32(5): p. 232-9). Here, IL-17 is described to be the main driver for development of MS (Zepp, J., L. Wu, and X. Li, *IL-17 receptor signaling and T helper 17-mediated autoimmune demyelinating disease*. Trends Immunol, 2011. 32(5): p. 232-9 and Petermann, F. and T. Korn, *Cytokines and effector T cell subsets causing autoimmune CNS disease*. FEBS Lett, 2011. 585(23): p. 3747-57). Again, TRAF6 activity plays a central role in Th1 and Th17 signaling and might be an excellent target for MS treatment.

Celiac disease: Ingestion of wheat, barley or rye mediates inflammation of the small intestine in patients with celiac disease. Here, gluten elicits an adaptive Th1 immune response in individuals with specific genetic predispositions. Moreover, it has been demonstrated that α-amylase/trypsin inhibitors (ATIs), pest resistance molecules in wheat, act as activators of the innate immune responses. ATIs bind the TLR4-MD2-CD14 complex and promote activation and secretion of proinflammatory cytokines (Junker, Y., S. Zeissig, S. J. Kim, et al., *Wheat amylase trypsin inhibitors drive intestinal inflammation via activation of toll-like receptor 4*. J Exp Med, 2012. 209(13): p. 2395-408). TRAF6 plays a critical role in Th1 immune response and TLR4 signaling and may serve as a novel target for treatment of celiac disease.

Autoimmune diseases in general: Autoimmune diseases originate through combinatorial elevation of immune and inflammatory signaling processes such as Th1, Th17, TLR, IL-1 and TNF. As TRAF6 is a major regulator in almost all of these signaling pathways towards NF-κB activation, it is very likely that inhibition of TRAF6 activity is a valid strategy to generally target autoimmunity. The cell-based experiments in the present application demonstrate that the TRAF6-Ubc13 inhibitor is counteracting these signaling processes.

Diffuse large B-cell lymphoma (DLBCL): DLBCL are subdivided into two major groups, i.e. activated B-cell (ABC) type and germinal B-cell (GCB) type. Survival of ABC DLBCL relies on a variety of different mutations leading to constitutive active NF-κB signaling. Major mutations are within the B-cell receptor (BCR) and MYD88 signaling (Nagel, D., M. Vincendeau, A. C. Eitelhuber, et al., *Mechanisms and consequences of constitutive NF-kappaB activation in B-cell lymphoid malignancies*. Oncogene, 2014. 33(50): p. 5655-65 and Ngo, V. N., R. M. Young, R. Schmitz, et al., *Oncogenically active MYD88 mutations in human lymphoma*. Nature, 2011. 470(7332): p. 115-9). Current therapeutics mainly concentrates on BCR signaling with compounds targeting e.g. BTK, MALT1, cIAP (Krappmann, D. and M. Vincendeau, *Mechanisms of NF-kappaB deregulation in lymphoid malignancies*. Semin Cancer Biol, 2016 and Wilson, W. H., *Treatment strategies for aggressive lymphomas: what works?* Hematology Am Soc Hematol Educ Program, 2013. 2013: p. 584-90). However, to date IRAK4 inhibitors are the only available tool to reduce MYD88 signaling (Kelly, P. N., D. L. Romero, Y. Yang, et al., *Selective interleukin-1 receptor-associated kinase 4 inhibitors for the treatment of autoimmune disorders and lymphoid malignancy*. J Exp Med, 2015. 212(13): p. 2189-201). The data of the present application in DLBCL with C25-140 (compound 3) verifies that this compound selectively kills ABC-DLBCL with chronic MYD88 signaling (see FIG. 12). In line with this, an Ubc13 inhibitor was also successful in reducing NF-κB signaling and survival of ABC-DLBCL cells (Pulvino, M., Y. Liang, D. Oleksyn, et al., *Inhibition of proliferation and survival of diffuse large*

B-cell lymphoma cells by a small-molecule inhibitor of the ubiquitin-conjugating enzyme Ubc13-Uev1A. Blood, 2012. 120(8): p. 1668-77). However, inhibition of Ubc13 as an E2 enzyme has too broad effects on cellular signaling.

MALT lymphoma: MALT lymphoma contains an API2-MALT1 fusion protein due to chromosomal translocation. Beside others, this fusion protein cooperates with TRAF6 to initiate NF-κB activation leading to cancer development (Krappmann, D. and M. Vincendeau, *Mechanisms of NF-kappaB deregulation in lymphoid malignancies*. Semin Cancer Biol, 2016 and Staudt, L. M., *Oncogenic activation of NF-kappaB*. Cold Spring Harb Perspect Biol, 2010. 2(6): p. a000109). These pathways lead to proliferation, survival and resistance to therapies. Hence, inhibition of TRAF6 activity might be beneficial in MALT lymphoma.

Multiple Myeloma (MM): Main drivers of malignant growth of MM are genomic instability within the tumor and the interaction between myeloma cells and the bone marrow microenvironment. Here, various signaling pathways are activated, including MAPK, JAK-STAT3, (PI3K)-AKT, NF-κB, Wnt, Notch, IGF and pleiotrophin signaling pathways leading to increased cytokine and growth factor secretion, cell proliferation and osteoclast activity. Clinically, MM is characterized by osteolytic lesions, anemia, renal failure, hypercalcaemia, peripheral neuropathies and more. However, the bone disease is the most clinically significant factor for morbidity. TRAF6 is involved in osteoclastogenesis in MM through its critical role in NF-κB activation by RANK signaling. Here, the TRAF6 ligase activity in combination with Ubc13 is essential for signal progression. Thus, an inhibitor of TRAF6 activity has the great potential to inhibit RANK signaling and thereby reduce bone metastasis and osteoclastogenesis in MM. Importantly, decoy peptides disconnecting TRAF6 from the RANK receptor or siRNAs against TRAF6 already showed encouraging results in osteoclastogenesis and growth inhibition, respectively (Liu, H., S. Tamashiro, S. Baritaki, et al., *TRAF6 activation in multiple myeloma: a potential therapeutic target*. Clin Lymphoma Myeloma Leuk, 2012. 12(3): p. 155-63). It is therefore very likely that MM can be treated by inhibiting TRAF6.

Lung cancer: It has been shown that the 11p13 locus is amplified in various lung cancers (NSCLC and SCLC lines). This amplification is associated with a TRAF6 upregulation, thereby defining TRAF6 as an amplified oncogene in lung carcinoma. Amplified TRAF6 promotes Ras-driven activation of the pro-inflammatory transcription factor NF-κB and subsequent tumor-promoting responses (Starczynowski, D. T., W. W. Lockwood, S. Delehouzee, et al., *TRAF6 is an amplified oncogene bridging the RAS and NF-kappaB pathways in human lung cancer*. J Clin Invest, 2011. 121(10): p. 4095-105). It has also been shown that the E3 ligase activity of TRAF6 is essential for EGFR-driven NF-κB activation and lung cancer progression (Pan, D., C. Jiang, Z. Ma, et al., *MALT1 is required for EGFR-induced NF-kappaB activation and contributes to EGFR-driven lung cancer progression*. Oncogene, 2016. 35(7): p. 919-28). Therefore, TRAF6 inhibition can be a good strategy for combination therapy in Ras-driven lung cancers, especially in cancers that are resistant for current first line therapy.

Lung adenocarcinoma: The expression level of TRAF6 is significantly higher in lung adenocarcinoma cells and TRAF6 is involved in the proliferation and invasion of potential lung adenocarcinoma cells (Zhong, L., F. Cao, and Q. You, *Effect of TRAF6 on the biological behavior of human lung adenocarcinoma cell*. Tumour Biol, 2013. 34(1): p. 231-9), thereby implicating that its inhibition might be relevant as a therapeutic approach for this type of cancer.

Colon cancer: TRAF6 has an increased expression in colon cancer tissues when compared to normal paracancerous tissues. The expression level of TRAF6 negatively correlated with the 5-year survival rate leading to a decreased survival of patients with high TRAF6 expression levels (Zhang, T., H. Wang, and L. Han, *Expression and Clinical Significance of Tumor Necrosis Factor Receptor-Associated Factor 6 in Patients With Colon Cancer*. Iran Red Crescent Med J, 2016. 18(1): p. e23931). This indicates that TRAF6 plays an important role in the onset of colon cancer and drugs targeting TRAF6 may have potential to treat this disease. Another study also demonstrated that TRAF6 expression is up-regulated in colon cancers, which correlates to the grade/stage of the tumor. RNAi experiments with siTRAF6 reduced proliferation of colon cancer cells in combination with treatment of the conventional anti-cancer drugs 5-fluorouracil and etoposide (Sun, H., X. Li, L. Fan, et al., *TRAF6 is upregulated in colon cancer and promotes proliferation of colon cancer cells*. Int J Biochem Cell Biol, 2014. 53: p. 195-201). Hence, inhibition of TRAF6 may advance the effects of these drugs in combinatorial treatments.

Prostate cancer: It has been shown that TRAF6 ubiquitinates TGFβ type I receptor (TβRI) and Presenilin 1 (PS1) to facilitate the cleavage of the N-terminal intracellular domain (ICD) of TβRI by TACE and PS1. The ICD subsequently translocates to the nucleus, where it acts as a transcriptional regulator of genes involved in tumor cell invasiveness. Importantly, the E3 ligase activity of TRAF6 is essential for this process (Gudey, S. K., R. Sundar, Y. Mu, et al., *TRAF6 stimulates the tumor-promoting effects of TGFbeta type I receptor through polyubiquitination and activation of presenilin 1*. Sci Signal, 2014. 7(307): p. ra2 and Mu, Y., R. Sundar, N. Thakur, et al., *TRAF6 ubiquitinates TGFbeta type I receptor to promote its cleavage and nuclear translocation in cancer*. Nat Commun, 2011. 2: p. 330). Moreover, TGFβ induces MAPK signaling in a TRAF6-dependent manner to produce Snail1. This process induces invasiveness in aggressive prostate cancers (Thakur, N., S. K. Gudey, A. Marcusson, et al., *TGFbeta-induced invasion of prostate cancer cells is promoted by c-Jun-dependent transcriptional activation of Snail1*. Cell Cycle, 2014. 13(15): p. 2400-14). Therefore, TRAF6 seems to be a good target in human prostate cancers.

Breast Cancer: In a recent study, it was shown that TLR2 signaling is promoting breast cancer development. Accordingly, TLR2 depletion or knockdown of its downstream regulators (MYD88 and IRAK1) decreased breast cancer growth (Scheeren, F. A., A. H. Kuo, L. J. van Weele, et al., *A cell-intrinsic role for TLR2-MYD88 in intestinal and breast epithelia and oncogenesis*. Nat Cell Biol, 2014. 16(12): p. 1238-48). Another study revealed that the TLR9-TRAF6 axis is markedly involved in breast cancer cell invasion. They also showed that samples from breast cancer patients comprise elevated levels of TLR9 (Ilvesaro, J. M., M. A. Merrell, L. Li, et al., *Toll-like receptor 9 mediates CpG oligonucleotide-induced cellular invasion*. Mol Cancer Res, 2008. 6(10): p. 1534-43). Both studies imply that targeting TRAF6 as a main regulator of TLR2 and TLR9 signaling might be beneficial for breast cancer treatment.

Osteosarcoma: The expression level of TRAF6 is significantly higher in osteosarcoma tissues. Moreover, the expression level was even higher if the osteosarcoma was based on a lung metastasis. This study could also demonstrate that TRAF6 positively regulated proliferation and invasion capacity of an osteosarcoma cell line (Meng, Q., M. Zheng, H. Liu, et al., *TRAF6 regulates proliferation, apoptosis, and invasion of osteosarcoma cell*. Mol Cell Biochem, 2012. 371(1-2): p. 177-86). The data in the present application show that C25-140 (compound 3) is reducing proliferation of U2OS cells to the same degree as 2Gy irradiation and that C25-140 together with irradiation has synergistic effects (see FIG. 13). Thus, TRAF6 inhibition represents a strategy to interfere with osteosarcoma in combinatorial drug/radiation therapies.

Pancreatic cancer: In a clinical study, it was shown that TRAF6 levels are up-regulated in tissues of 53 pancreatic cancer patients. Moreover, overexpression of TRAF6 in pancreatic cancer cells induced cell proliferation and migration. In contrast, knock-down of TRAF6 using RNAi decreased tumorigenicity of pancreatic cancer cells. More importantly, siRNAs against TRAF6 reduced tumor growth in vivo (Rong, Y., D. Wang, W. Wu, et al., *TRAF6 is over-expressed in pancreatic cancer and promotes the tumorigenicity of pancreatic cancer cells*. Med Oncol, 2014. 31(11): p. 260.). In conclusion, TRAF6 represents a new target to develop pancreatic cancer therapeutics.

Esophageal squamous cell carcinoma (ESCC): TRAF6 expression is up-regulated in ESCC based on a study analyzing 38 patient samples. Moreover, TRAF6 was increased in ESCC cell lines. In line with this, TRAF6 overexpression promoted ESCC cell growth, while siRNAs against TRAF6 had adverse effects. Finally, siRNA against TRAF6 efficiently reduced tumor growth in vivo (Yao, F., Q. Han, C. Zhong, et al., *TRAF6 promoted the tumorigenicity of esophageal squamous cell carcinoma*. Tumour Biol, 2013. 34(5): p. 3201-7). Consequently, TRAF6 may represent an attractive target for development of ESCC therapeutics.

Parkinson's disease (PD): Chronic inflammation is thought to influence PD development (Block, M. L. and J. S. Hong, *Microglia and inflammation-mediated neurodegeneration: multiple triggers with a common mechanism*. Prog Neurobiol, 2005. 76(2): p. 77-98). A recent study demonstrated that Parkin facilitates proteasomal degradation of TRAF2 and TRAF6 to protect against an inflammatory response and cytokine-induced cell death by TNF and IL-1 pathways. In cases of loss of Parkin or Parkin mutations, this protection is abolished. Accordingly, a large number of human PD tissues show elevated TRAF6 levels (Chung, J. Y., H. R. Park, S. J. Lee, et al., *Elevated TRAF2/6 expression in Parkinson's disease is caused by the loss of Parkin E3 ligase activity*. Lab Invest, 2013. 93(6): p. 663-76). Thus, inhibition of TRAF6 could be a possible therapeutic strategy in Parkin-dependent PD patients.

Cardiac Hypertrophy: A recent study demonstrated that TRAF6 levels are increased in pathological cardiac hypertrophy as a consequence of ROS production. More importantly, the authors demonstrate that the E3 ligase activity of TRAF6 to hyper-activate TAK1 is critical for the cardiac hypertrophy response (Ji, Y. X., P. Zhang, X. J. Zhang, et al., *The ubiquitin E3 ligase TRAF6 exacerbates pathological cardiac hypertrophy via TAK1-dependent signalling*. Nat Commun, 2016. 7: p. 11267). These data suggest that inhibition of TRAF6 activity might be a good opportunity to treat pathological cardiac hypertrophy.

Type-2 diabetes (T2D): Diet-induced obesity is able to facilitate inflammation and insulin resistance through IL-1β (Tack, C. J., R. Stienstra, L. A. Joosten, et al., *Inflammation links excess fat to insulin resistance: the role of the interleukin-1 family*. Immunol Rev, 2012. 249(1): p. 239-52). Moreover, it has been shown that monocytes of obese patients comprise higher levels of TRAF6, thereby linking TRAF6 to metabolic disorders (Hulsmans, M., E. Van Dooren, C. Mathieu, et al., *Decrease of miR-146b-5p in monocytes during obesity is associated with loss of the anti-inflammatory but not insulin signaling action of adiponectin*. PLoS One, 2012. 7(2): p. e32794). Several other studies have additionally demonstrated the significance of TLR4 signaling for development of insulin resistance (Pal, D., S. Dasgupta, R. Kundu, et al., *Fetuin-A acts as an endogenous ligand of TLR4 to promote lipid-induced insulin resistance*. Nat Med, 2012. 18(8): p. 1279-85 and Uchimura, K., M. Hayata, T. Mizumoto, et al., *The serine protease prostasin regulates hepatic insulin sensitivity by modulating TLR4 signalling*. Nat Commun, 2014. 5: p. 3428). Finally, mice deficient in CD40-TRAF6 signaling exhibited reduced gain of weight and reduction of adipose tissue in a high-fat-diet model (Chatzigeorgiou, A., T. Seijkens, B. Zarzycka, et al., *Blocking CD40-TRAF6 signaling is a therapeutic target in obesity-associated insulin resistance*. Proc Natl Acad Sci USA, 2014. 111(7): p. 2686-91). These studies altogether imply TRAF6 being a therapeutic target for obesity-induced insulin resistance. The data of the present application clearly demonstrate that C25-140 (compound 3) reduces gain of weight in a T2D mouse model and additionally reduces IL-1β expression (see FIG. 9).

The terms "disease", "disorder" and "condition", when used in the context of treatment or therapy (including prophylactic therapy), are used herein interchangeably and refer to any pathological state, including cancer, in particular those pathological states (including cancer forms) described herein.

In a further aspect, the present invention provides a pharmaceutical composition for use in the treatment of a disease associated with TRAF6, in particular for the treatment of cancer, an immune disease, Parkinson's disease, Cardiac Hypertrophy or Type-2 diabetes, said composition comprising a compound having a structure according to formula (I), (II), (III) (IV) and/or (XX), or a compound of table 1, and one or more excipients, and optionally at least one additional active compound. The at least one additional active compound can be administered together with, before or after the compound having a structure according to formula (I), (II), (III), (IV) and/or (XX), or the compound of table 1.

In a further aspect, the present invention provides a method for treating and/or preventing a condition, disorder or disease that is associated with TRAF 6 overexpression, said method comprising administering a therapeutically effective amount of a compound as described herein (in particular a therapeutically effective amount of a compound having a structure according to formula (I), (II), (III), (IV and/or (XX)), or a compound of table 1 to an individual in need thereof). Optionally, the method comprises the step of administering at least one additional active compound to the individual. The at least one additional active compound can be administered together with, before or after the compound having a structure according to formula (I), (II), (III), (IV) and/or (XX), or the compound of table 1.

As used herein and throughout the entire description, the term "Subject" or "individual" are used interchangeably and mean animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. The subject is preferably a mammal, more preferably a human.

As used herein and throughout the entire description, the term "amount effective" in the context of a composition or dosage form for administration to a subject refers to an amount of the composition or dosage form sufficient to provide a benefit in the treatment of cancer, an immune disease, Parkinson's disease, Cardiac Hypertrophy or Type-2 diabetes, to delay or minimize symptoms associated with cancer, an immune disease, Parkinson's disease, Cardiac Hypertrophy or Type-2 diabetes, or to cure or ameliorate the cancer, an immune disease, Parkinson's disease, Cardiac Hypertrophy or Type-2 diabetes. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In any of the above therapeutic aspects, the at least one additional active compound may be selected from the additional active compounds described above.

In any of the above therapeutic aspects, wherein the method comprises the steps of administering a compound having a structure according to formula (I), (II), (III), (IV) and/or (XX), or a compound of table 1 as specified above and administering at least one additional active compound, the at least additional active compound, may be formulated together with the compounds of the invention as described above in a single pharmaceutical composition. Alternatively, the pharmaceutical composition may be structured as kit of parts, wherein the compound having a structure according to formula (I), (II), (III), (IV) and/or (XX), or the compound of table 1 is provided in a first formulation and the at least one additional active compound is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the compound having a structure according to formula (I), (II), (III), (IV) and/or (XX), or the compound of table 1. Alternatively, the present teaching envisages administering the compound having a structure according to formula (I), (II), (III), (IV) and/or (XX), or the compound of table 1 formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

In some embodiments the disease associated with TRAF6 is cancer, an immune disease, Parkinson's disease, Cardiac Hypertrophy or Type-2 diabetes, preferably cancer, an immune disease and Type-2 diabetes, more preferably cancer or an immune disease.

Cancer is preferably selected from the group consisting of lymphoma such as diffuse large B-cell lymphoma (DLBCL) and MALT lymphoma, multiple myeloma (MM), lung cancer, lung adenocarcinoma, colon cancer, prostate cancer, breast cancer, osteosarcoma, pancreatic cancer and esophageal squamous cell carcinoma (ESCC), in other embodiments diffuse large B-cell lymphoma (DLBCL) and osteosarcoma.

The immune disease is preferably an autoimmune disease. The autoimmune disease is preferably selected from the group consisting of psoriasis, rheumatoid arthritis, celiac disease, inflammatory bowel disease such as Crohn's disease and ulcerative colitis, multiple sclerosis and diabetes mellitus type 1, in other embodiments psoriasis, rheumatoid arthritis and multiple sclerosis, in other embodiments psoriasis and rheumatoid arthritis.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease.

Generally, the amount of a compound according to the invention as described herein (in particular the amount of a compound having a structure according to formula (I), (II), (III), (IV) and/or (XX), or a compound of table 1) administered daily to an individual may be at most 100 mg/kg (such as at most 50 mg/kg, at most 40 mg/kg, at most 30 mg/kg, at most 20 mg/kg, at most 10 mg/kg, at most 9 mg/kg, at most 8 mg/kg, at most 7 mg/kg, at most 6 mg/kg, at most 5 mg/kg, at most 4 mg/kg, at most 3 mg/kg, at most 2 mg/kg, or at most 1 mg/kg), depending on factors such as the condition of the subject to be treated and the mode of administration. For example, the amount of a compound according to the invention as described herein (in particular the amount of a compound having a structure according to formula (I), (II), (III), (IV) and/or (XX), or a compound of table 1) administered daily to an individual may range from about 0.01 mg/kg to 100 mg/kg (such as from about 0.05 mg/kg to 50 mg/kg, from about 0.1 mg/kg to 40 mg/kg, from about 0.2 mg/kg to 30 mg/kg, from about 0.3 mg/kg to 20 mg/kg, from about 0.4 mg/kg to 10 mg/kg, from about 0.5 mg/kg to 9 mg/kg, from about 0.6 mg/kg to 8 mg/kg, from about 0.7 mg/kg to 7 mg/kg, from about 0.8 mg/kg to 6 mg/kg, from about 0.9 mg/kg to 5 mg/kg, from about 1 mg/kg to 4 mg/kg, or from about 2 mg/kg to 3 mg/kg) depending on factors such as the condition of the subject to be treated and the mode of administration.

In one embodiment, the compound according to the invention as described herein (in particular the compound having a structure according to formula (I), (II), (III), (IV) and/or (XX), or the compound of table 1) is orally administered in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the compound according to the invention as described herein (in particular the compound having a structure according to formula (I), (II), (III), (IV) and/or (XX), or the compound of table 1) is parenterally administered (e.g., intravenously, intramuscularly, or subcutaneously), in a concentration of at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

The embodiments and definitions of terms described in the context of the means such as compounds according to Formula (I), Formula (II), Formula (III), Formula (IV), Formula (XX) and/or Table 1 of the invention are equally applicable to the methods and uses described above, mutatis mutandis.

The present invention also envisions a method of treating in a subject a disease associated with TRAF6 overexpression or activity, comprising administering to said subject an efficient amount of a compound according to Formula (I), Formula (II), Formula (III), Formula (IV), Formula (XX) and/or Table 1 or a pharmaceutically acceptable salt, solvate or hydrate thereof or a pharmaceutical composition comprising said compound. Said method preferably comprises further administering at least one additional pharmaceutically active compound. The above described aspects, embodiments, definitions, etc. are also applicable to said method of treatment, mutatis mutandis.

Moreover, the invention is related to an assay for the determination of the inhibition activity of an inhibitor I1.

The inhibitor I1 inhibits the catalytic activity of a protein P1 . . . .

Preferably the inhibitor I1 is an E3 Ligase inhibitor, more preferably a RING E3 ligase inhibitor, most preferably a TRAF6, cIAP1 or RNF8 inhibitor, in particular preferred an inhibitor selected from a compound according to formula (I), (II), (III), (IV) and/or (XX).

Preferably, the protein P1 is a E3 Ligase, more preferably a RING E3 ligase, most preferably cIAP1, RNF8 or, TRAF6.

In the assay the protein P1 comprises at least one linker L1.

Preferably, the at least one linker L1 is a histidine-tag, glutathione S-transferase-tag (GST-tag), Biotin-tag or a StrepII-tag, more preferably a histidine-tag.

Preferably, the final concentration of the protein P1, based on the initially added amount relative overall volume of the assay solution, is 2 to 4 nmol/µl, more preferably 2.5 to 3 nmol/µl, most preferably 2.6 to 2.8 nmol/µl. The "overall volume of the assay solution" is to be understood as the volume obtained after all reagents and/or solvents are added.

Protein P1 catalyzes the polymerization of a protein monomer PM1.

Preferably, the protein monomer PM1 is ubiquitin.

Preferably, the final concentration of the protein monomer PM1, based on the initially added amount relative to the overall volume of the assay solution is 0.5 to 10 nmol/µl, more preferably 2 to 8 nmol/µl, most preferably 4 to 6 nmol/µl. The initially added amount is stated for protein monomer PM1 since, protein monomer PM1 is consumed in the polymerization reaction during the assay, by catalysis of P1.

The protein monomer PM1 comprises at least one linker L2.

Preferably the linker L2 is a glutathione S-transferase-tag (GST-tag), histidine-tag, Biotin-tag or a StrepII-tag, more preferably a GST-tag.

Preferably, linker L1 is different from linker L2.

The assay comprises at least the steps a), b), c) and d).

In step a), the polymerization of the protein monomer PM1 is catalyzed by the protein P1 in the presence of inhibitor I1, wherein protein monomer PM1 is transferred from a protein P2 to protein P1.

Preferably, step a) and thus the following steps b), c), d) are carried out with the same inhibitor I1, several times, wherein in each run the concentration of the inhibitor I1 is varied. Preferably, the inhibitor is varied in the concentration range 10 fmol/µl to 200 pmol/µl, more preferably 100 fmol/µl to 100 pmol/µl.

The protein P2 may comprise more than one enzyme.

Preferably, the protein P2 comprises the enzymes Ubc13 and UeV1a.

Preferably, the final concentration of the protein P2, based on the initially added amount relative to the overall volume of the assay solution is 5 to 25 nmol/µl, more preferably 10 to 20 nmol/µl, most preferably 11 to 14 nmol/µl.

In step b), a further molecule M1 binds to the linker L1 of P1 and a further molecule M2 binds to the linker 2 of the polymerized monomer PM1.

The molecules M1 and M2 comprise a structural element which binds specifically to a recognition structure in the respective linker. For example, molecule M1 may be Glutathione-donor beads and linker L1 may be a GST-tag. The Glutathione structure in the Glutathione-donor beads bind specifically to the GST-tag linker L1.

Preferably, the molecule M1 and the molecule M2 are each selected from donor beads or acceptor beads, wherein either M1 is selected from donor beads and M2 is selected from acceptor beads or vice versa. Donor beads may be selected from Glutathione-donor beads, nickel-chelate donor beads, Strep-Tactin donor beads and Streptavidin donor beads, more preferably Glutathione-donor beads. Acceptor beads may be selected from the group consisting of nickel-chelate acceptor beads, Glutathione acceptor beads, Strep-Tactin acceptor beads and Streptavidin acceptor beads, more preferably nickel-chelate acceptor beads. Donor beads comprise a molecule which releases or generates a particle, preferably with a low lifespan, which can interact with particular structures in the acceptor beads, triggering the release of a detectable signal from the acceptor beads.

For example, in one embodiment, the donor beads may comprise a photosensitizer which upon irradiation with electromagnetic radiation generates singlet oxygen from ambient oxygen. The singlet oxygen interacts with a thioxene derivative in the acceptor beads generating a chemiluminescence. This energy is transferred to fluorophores within the same acceptor bead resulting in a detectable emission of electromagnetic radiation of a certain wavelength.

Preferably, the final concentration of the molecule M1, based on the initially added amount relative to the overall volume of the assay solution is $2*10^{-5}$ to $20*10^{-5}$ µg/µl, more preferably $5*10^{-5}$ to $15*10^{-5}$ µg/µl, most preferably $8*10^{-5}$ to $12*10^{-5}$ µg/µl.

Preferably, the final concentration of the molecule M2, based on the initially added amount relative to the overall volume of the assay solution is $2*10^{-5}$ to $20*10^{-5}$ µg/µl, more preferably $5*10^{-5}$ to $15*10^{-5}$ µg/µl, most preferably $8*10^{-5}$ to $12*10^{-5}$ µg/µl.

In step c), the molecule M1 bound to linker L1 and molecule M2 bound to linker L2 interact with each other in a manner resulting in the generation of a detectable signal.

The interaction may comprise the direct interaction of molecule M1 and molecule M2 or the transfer of a particle from molecule M1 to molecule M2 or vice versa, which may be for example a single atom, molecule, cation, anion or radical. The transferred particle may be in an excited stage, wherein the excitation may be achieved by applying an external energy source. Preferably, the transferred particle is singlet oxygen. Preferably, the energy for achieving the excitation of the transferred particle is transferred by electromagnetic radiation. Preferably, the external electromagnetic radiation for excitation has a wavelength of 300 nm to 1000 nm, more preferably of 500 to 800 nm, most preferably of 600 to 700 nm. The irradiation of the assay may be achieved for example by a suitable light source, such as a laser. Preferably, the ability of molecule M1 and the molecule M2 to interact with each other is dependent on their distance to each other and/or electromagnetic irradiation with an external radiation source.

If a particle is transferred from molecule M1 to molecule M2 or vice versa, the distance for their interaction may be limited, for example due to the lifespan of the particle transferred. Preferably, the distance between molecule M1 and molecule M2, when molecule M1 and molecule M2 are bound to the respective linker L1 and linker L2 in step c), is not more than 800 nm, more preferably not more than 500 nm, most preferably not more than 300 nm and in particular preferred not more than 200 nm in order to be able to interact with each other. Preferably, the transferred particle is singlet oxygen, generated from ambient oxygen by Glutathione-donor beads during irradiation of with electromagnetic radiation.

The detectable signal generated in step c) may be emitted electromagnetic radiation, preferably emitted electromagnetic radiation. Preferably, the electromagnetic radiation is emitted after transfer of a particle from molecule M1 to molecule M2 or vice versa. Preferably, the emitted electromagnetic radiation has a wavelength of 300 to 800 nm, preferably of 400 to 700 nm, most preferably of 500 to 650 nm.

In step d) the generated signal is detected. If the generated signal is emitted electromagnetic radiation, the signal may be detected for example with a microplate detector for AlphaScreen®/AlphaLISA®. The strength of the detected signal correlates to the degree of inhibition of protein P1 by the inhibitor I1.

In order to determine the extent of the generated signal for the case of maximum possible inhibition, a negative control may be carried out. Therein, the protein P1 is replaced by a mutant of P1 which is not able to bind to protein P2 for the transfer of protein monomer PM1 from protein P2 to protein P1. Thus, while all other necessary components as stated above, for the normal assay are present, the difference in the negative control is only the use of an inactive protein P1, in the negative control. No polymerization of protein monomer PM1 takes place and therefore, in effect the steps a), b) and c) are not carried out.

Optionally, the assay comprises a further step e), which is carried out before step a), wherein protein monomer PM1 is bound to a protein P3, preferably with activation by at least one molecule adenosine triphosphate (ATP), followed by transfer of the protein monomer P1 from protein P3 to protein P2.

Preferably, protein P3 is ubiquitin activating enzyme UBE1.

The steps a) to d) and optionally step e) are preferably carried out at 25 to 45° C., more preferably at 30 to 42° C., most preferably at 35 to 38° C.

The assay may be carried out in a microtiter-plate, optionally as high-throughput assay.

Moreover, the invention is directed to a kit for an assay for the determination of the inhibition activity of an E3 Ligase inhibitor.

The kit comprises:
i) an E3 Ligase inhibitor, preferably a RING E3 ligase inhibitor, more preferably a cIAP1, RNF8 or, TRAF6 inhibitor, most preferably an inhibitor having a structure according to any one of formula (I), (II), (III), (IV) and/or formula (XX),
j) an E3 Ligase, preferably a RING E3 ligase, more preferably TRAF6, cIAP1, or RNF8, comprising a linker L1, wherein the linker L1 is preferably a histidine-tag;
k) ubiquitin; comprising a linker, wherein the linker L2 is preferably a GST-tag;
l) a further molecule M1 capable of binding to the linker L1, wherein preferably the molecule M1 is nickel-chelate acceptor beads;
m) a further molecule M2 capable of binding to the linker L2, wherein preferably the molecule M2 is Gluta-thione-donor beads;
n) optionally a further protein P3, wherein preferably the further protein is a ubiquitin activating enzyme UBE1.
o) optionally adenosine triphosphate (ATP),
p) optionally a microplate detector for AlphaScreen®/AlphaLISA® detection;

Further, the invention shall be explained in more detail by the following Examples.

1) Materials and Methods 1.1) HPLC

The HPLC system was an Agilent 1100 (Agilent, USA) equipped with a quaternary pump, a vacuum degasser, a VWD detector, a column oven, a Rheodyne-7725i manual sampler and an HPLC column (CNW Athena C18-WP, 3 µm, 2.1×50 mm). Sample preparation: 1.0 mg sample was dissolved in 0.8 ml solvent A and 0.4 ml solvent B, and filtered through a 0.45 µm nylon membrane prior to analysis. Mobile phase: Solvent A was acetonitrile and solvent B was 0.1% phosphoric acid in water.

Method 1:

Gradient elution was programmed as follows: A/B=5/95 (v/v, 0 min)→95/5 (v/v, 4 min)→95/5 (v/v, 5.9 min)→5/95 (v/v, 6.0 min). Column temperature: 25° C. Flow rate: 0.40 ml/min. Detection wavelength: 254 nm. Injection volume: 2 µl.

Method 2:

Gradient elution was programmed as follows: A/B=20/80 (v/v, 0 min)→95/5 (v/v, 3 min)→95/5 (v/v, 5.9 min)→5/95 (v/v, 6.0 min). Column temperature: 35° C. Flow rate: 0.45 ml/min. Detection wavelength: 254 nm. Injection volume: 2 µl.

2) Compounds 2.1) Preparation of 1-(3-methyl-[1,2,4]triazolo[4,3-b]pyridazin-6-yl)hydrazine (P571-1)

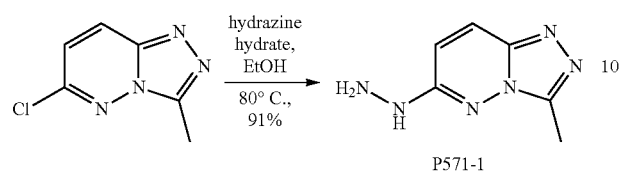

To a solution of 6-chloro-3-methyl-[1,2,4]triazolo[4,3-b]pyridazine (2.80 g, 16.6 mol) in EtOH (30.0 mL) was added hydrazine hydrate (85%, 2.93 mL, 49.8 mmol). The reaction mixture was heated to 80° C. for 4 h. TLC check (EtOAc, UV) showed starting material ($R_f$=0.10) was consumed. The reaction was cooled to 25° C. The precipitate appeared and 2.50 g desired product was obtained after filtration.

Yield: 2.50 g (91%)

$^1$H NMR: (400 MHz, DMSO-$d_6$): δ (ppm)=7.84 (d, 1H), 6.75 (d, 1H), 4.28 (s, 2H), 2.52 (s, 3H)

Ref.: *Polish Journal of Chemistry*, 1996, 70, 10, 683-692

2.2) Preparation of ethyl 3-(3,5-dimethyl-1-(3-methyl-[1,2,4]triazolo[4,3-b]pyridazin-6-yl)-1H-pyrazol-4-yl)propanoate (P571-2)

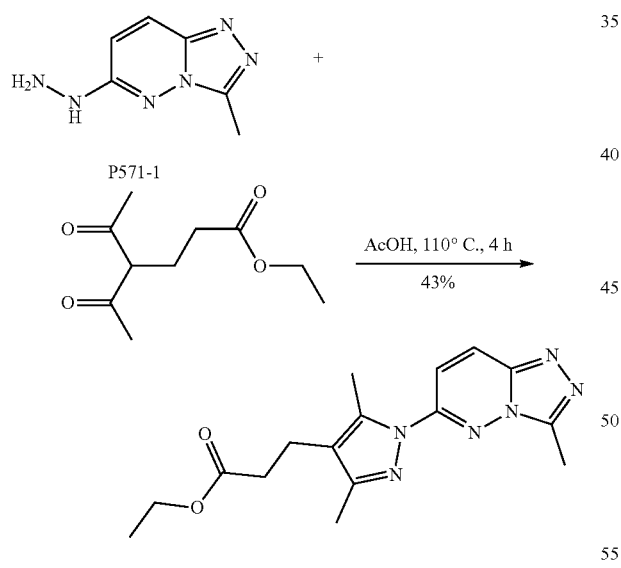

A mixture of P571-1 (1.50 g, 9.14 mmol) and ethyl 4-acetyl-5-oxohexanoate (2.01 g, 10.1 mmol) in AcOH (15.0 mL) was heated to 110° C. for 4 h. TLC check (EtOAc, UV) showed desired product as main spot ($R_f$=0.20) could be observed. The reaction was concentrated to remove AcOH. The residue was diluted with EtOAc and washed with 5% NaHCO$_3$ solution, brine and dried over Na$_2$SO$_4$. The residue was re-crystallized from Et$_2$O to give 1.30 g pure desired product.

Yield: 1.30 g (43%)

$^1$H NMR: (400 MHz, Methanol-$d_4$): δ (ppm)=8.36 (d, 1H), 7.84 (d, 1H), 4.05 (q, 2H), 2.70 (t, 2H), 2.68 (s, 3H), 2.59 (s, 3H), 2.23 (s, 3H), 1.16 (t, 3H)

Ref.: *European Journal of Medicinal Chemistry*, 2013, 69, 701-710

2.3) Preparation of ethyl 3-(3,5-dimethyl-1-(3-methyl-[1,2,4]triazolo[4,3-b]pyridazin-6-yl)-1H-pyrazol-4-yl)propanoic acid (P571-3)

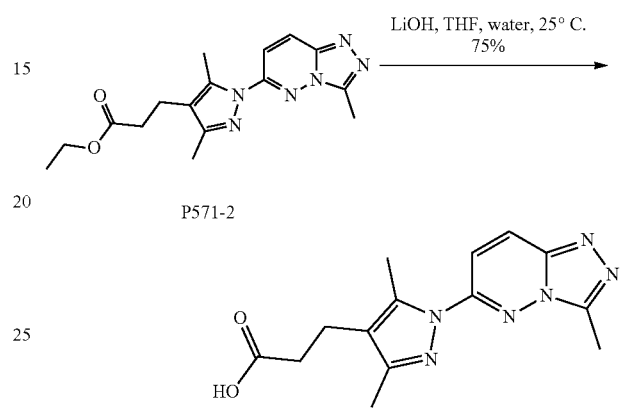

To a solution of P571-2 (1.30 g, 3.96 mmol) in THF (15.0 mL) and water (5.00 mL) was added LiOH·H$_2$O (498 mg, 11.9 mmol). The reaction mixture was stirred at 25° C. for 4 h. TLC check (EtOAc, UV) showed starting material ($R_f$=0.20) was consumed and desired product as main spot ($R_f$=0.05). The reaction mixture was concentrated to remove THF. The residue was adjusted to pH=3 with 6 N HCl to give a precipitate. The solid was collected by filtration, washed with water and dried to give 900 mg pure desired product.

Yield: 900 mg (75%)

$^1$H NMR: (400 MHz, DMSO-$d_6$): δ (ppm)=12.19 (s, 1H), 8.36 (d, 1H), 7.85 (d, 1H), 2.68 (s, 3H), 2.65 (d, 2H), 2.60 (s, 3H), 2.40 (t, 2H), 2.23 (s, 3H)

Ref.: *European Journal of Medicinal Chemistry*, 2013, 69, 701-710

2.4.1) Preparation of 1-(4-benzylpiperazin-1-yl)-3-(3,5-dimethyl-1-(3-methyl-[1,2,4]triazolo[4,3-b]pyridazin-6-yl)-1H-pyrazol-4-yl)propan-1-one (HZM06-1)

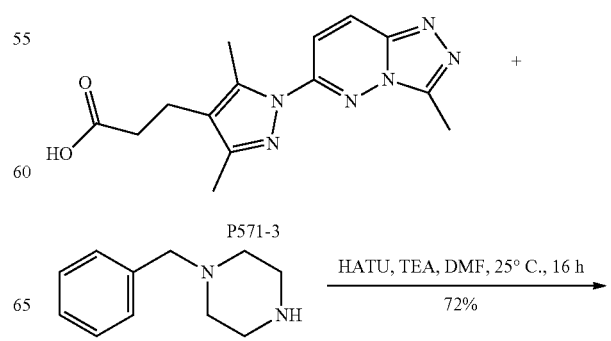

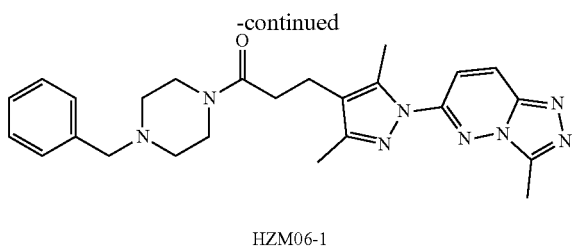

HZM06-1

A mixture of P571-3 (50.0 mg, 0.17 mmol), HATU (69.6 mg, 0.18 mmol), 1-benzylpiperazine (58.7 mg, 0.33 mmol) and TEA (33.7 mg, 0.33 mmol) in DMF (3.00 mL) was stirred at 25° C. for 16 h. TLC check (10% MeOH in EtOAc, UV) showed starting material ($R_f$=0.10) was consumed and desired product as main spot ($R_f$=0.30). The reaction mixture was diluted with water (15.0 mL) and extracted with EtOAc (10.0 mL×5). The combined organic phase was washed with water and brine, dried over $Na_2SO_4$ and purified by Chromatotron (silica gel, 50% MeOH in EtOAc) to give 55.0 mg pure target compound.

Yield: 55.0 mg (72%)
$^1$H NMR: (400 MHz, DMSO-$d_6$): δ (ppm)=8.38 (d, 1H), 7.86 (d, 1H), 7.30-7.25 (m, 1H), 7.23-7.20 (m, 2H), 3.44 (t, 2H), 3.39 (s, 2H), 2.66 (s, 3H), 2.63 (d, 2H), 2.58 (s, 3H), 2.46 (d, 2H), 2.26 (t, 2H), 2.22 (s, 3H), 2.17 (t, 2H)
LC/MS: m/z=459.2, Rt=3.57 min (method 1)

2.4.2 Preparation of 1-(4-Benzylpiperidin-1-yl)-3-(3,5-dimethyl-1-(3-methyl-[1,2,4]-triazolo-[4,3-b]-pyridazin-6-yl)-1H-pyrazol-4-yl)-propan-1-one C25-140

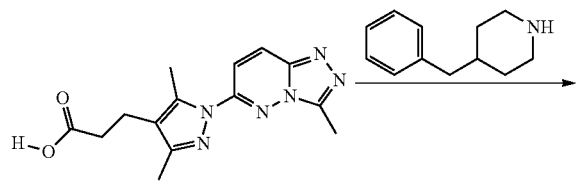

A round-bottomed flask filled with a solution of 3-(3,5-Dimethyl-1-(3-methyl-[1,2,4]-triazolo-[4,3-b]-pyridazin-6-yl)-1H-pyrazol-4-yl)-propanoic acid (50 mg, 0.17 mmol), in dimethylformamide (3 mL), were added 4-benzylpiperidine (0.06 mL, 0.33 mmol), HATU (68.52 mg, 0.18 mmol)) and triethyl amine (0.04 mL, 0.306 mmol). The resulting reaction mixture was stirred at room temperature until complete consumption of the starting material (17 h) was observed. It was then diluted with water (15 mL) and extracted with ethyl acetate (3×10 mL). The combined organic layers were dried over $MgSO_4$, filtered and concentrated in vacuo. The product was purified by flash chromatography eluting with a linear gradient of ethyl acetate/methanol 100:00→50:50 as eluent. The combination of the appropriate fractions yielded 55 mg (70%) of the title product: $^1$H NMR (400 MHz, DMSO-$d_6$): δ 8.4 (d, J=10 Hz, 1H), 7.88 (d, J=10 Hz, 1H), 7.33-7.09 (br m, 3H), 7.10-6.99 (br m, 2H), 4.39 (br d, 1H), 3.76 (br d, 1H), 2.86 (t, 1H), 2.71-2.61 (br m, 6H), 2.59 (s, 3H), 2.47-2.14 (br m, 4H), 2.24 (s, 3H), 1.77-1.63 (br m, 1H), 1.59-1.43 (br m, 2H), 0.99-0.73 (br m, 2H); LC-MS (ESI+) m/z: [M+H]$^+$ Calcd. for $C_{26}H_{32}N_7O$ 458.58 found 458.61, $t_R$=1.16 min.

2.5) Preparation of 1-(4-(3-methoxybenzyl)piperazin-1-yl)-3-(3,5-dimethyl-1-(3-methyl-[1,2,4]triazolo[4,3-b]pyridazin-6-yl)-1H-pyrazol-4-yl)propan-1-one (HZM06-2)

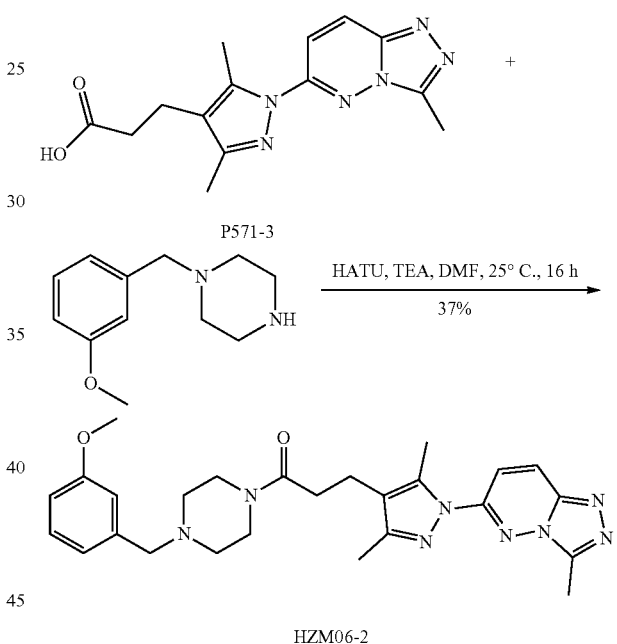

HZM06-2

A mixture of P571-3 (50.0 mg, 0.17 mmol), HATU (69.6 mg, 0.18 mmol), 1-(3-methoxybenzyl)piperazine (68.7 mg, 0.33 mmol) and TEA (33.7 mg, 0.33 mmol) in DMF (3.00 mL) was stirred at 25° C. for 16 h. TLC check (10% MeOH in EtOAc, UV) showed starting material ($R_f$=0.10) was consumed and desired product as main spot ($R_f$=0.30). The reaction mixture was diluted with water (15.0 mL) and extracted with EtOAc (10.0 mL×5). The combined organic phase was washed with water and brine, dried over $Na_2SO_4$ and purified by Chromatotron (silica gel, 50% MeOH in EtOAc) to give 30.0 mg pure target compound.

Yield: 30.0 mg (37%)
$^1$H NMR: (400 MHz, $D_2O$): δ (ppm)=8.38 (d, 1H), 7.86 (d, 1H), 7.22-7.15 (m, 1H), 6.82-6.75 (m, 2H), 3.71 (s, 3H), 3.44 (d, 2H), 3.36 (s, 2H), 2.67 (s, 3H), 2.64 (d, 2H), 2.58 (s, 3H), 2.46 (d, 2H), 2.27 (s, 2H), 2.23 (s, 3H), 2.18 (d, 2H)
LC/MS: m/z=489.1, Rt=3.64 min (method 1)

2.6) Preparation of 1-(4-(4-fluorobenzyl)piperazin-1-yl)-3-(3,5-dimethyl-1-(3-methyl-[1,2,4]triazolo[4,3-b]pyridazin-6-yl)-1H-pyrazol-4-yl)propan-1-one (HZM06-3)

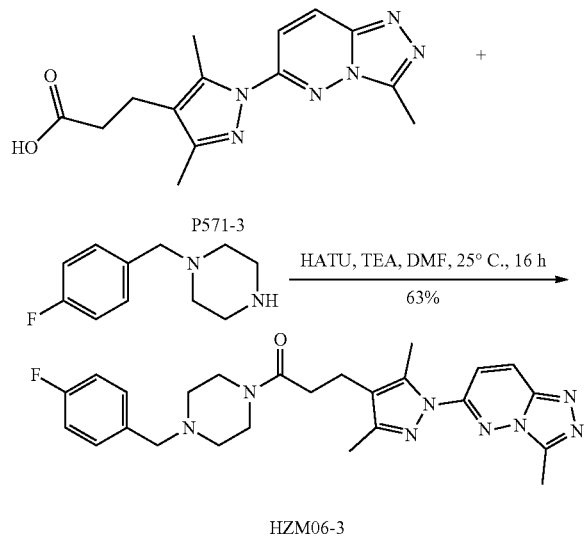

A mixture of P571-3 (50.0 mg, 0.17 mmol), HATU (69.6 mg, 0.18 mmol), 1-(4-fluorobenzyl)piperazine (64.7 mg, 0.33 mmol) and TEA (33.7 mg, 0.33 mmol) in DMF (3.00 mL) was stirred at 25° C. for 16 h. TLC check (10% MeOH in EtOAc, UV) showed starting material ($R_f$=0.10) was consumed and desired product as main spot ($R_f$=0.30). The reaction mixture was diluted with water (15.0 mL) and extracted with EtOAc (10.0 mL×5). The combined organic phase was washed with water and brine, dried over $Na_2SO_4$ and purified by Chromatotron (silica gel, 50% MeOH in EtOAc) to give 50.0 mg target compound.

Yield: 50.0 mg (63%)

$^1$H NMR: (400 MHz, DMSO-$d_6$): δ (ppm)=8.38 (d, 1H), 7.85 (d, 1H), 7.28-7.23 (m, 1H), 7.13-7.08 (m, 2H), 3.45 (d, 2H), 3.38 (s, 2H), 2.67 (s, 3H), 2.63 (d, 2H), 2.58 (s, 3H), 2.46 (d, 2H), 2.26 (t, 2H), 2.22 (s, 3H), 2.18 (d, 2H)

LC/MS: m/z=477.1, Rt=3.64 min (method 1)

2.7) Preparation of 1-(3-benzylpyrrolidin-1-yl)-3-(3,5-dimethyl-1-(3-methyl-[1,2,4]triazolo[4,3-b]pyridazin-6-yl)-1H-pyrazol-4-yl)propan-1-one (HZM06-4)

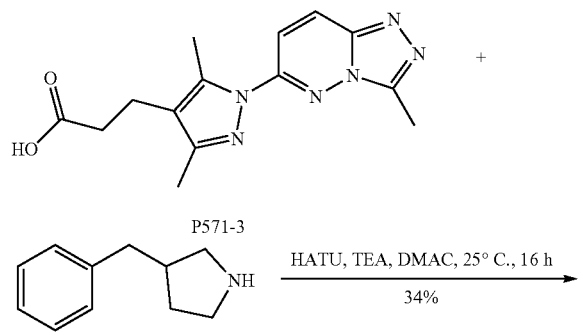

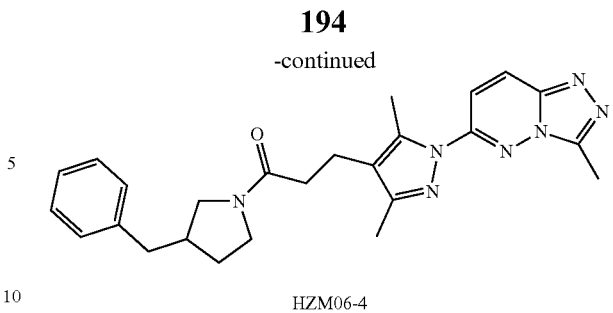

A mixture of P571-3 (200 mg, 0.67 mmol), HATU (253 mg, 0.67 mmol), 3-benzylpyrrolidine (107 mg, 0.67 mmol) and TEA (135 mg, 1.33 mmol) in DMAC (5.00 mL) was stirred at 25° C. for 16 h. HPLC-UV check showed starting material was consumed and desired product as main peak. The reaction mixture was diluted with water (15.0 mL) and extracted with EtOAc (10.0 mL×5). The combined organic phase was washed with water and brine, dried over $Na_2SO_4$ and purified by basic $Al_2O_3$ column (10% MeOH in EtOAc) to give 100 mg pure target compound.

Yield: 100 mg (34%)

$^1$H NMR: (400 MHz, DMSO-$d_6$): δ (ppm)=8.36 (dd, 1H), 7.84 (dd, 1H), 7.29-7.19 (m, 2H), 7.16 (t, 3H), 3.49-3.35 (m, 2H), 3.23-3.13 (m, 1H), 3.04-2.89 (m, 1H), 2.67 (d, 3H), 2.65-2.60 (m, 2H), 2.57 (d, 3H), 2.46-2.32 (m, 2H), 2.22 (d, 3H), 1.95-1.75 (m, 1H), 1.61-1.41 (m, 1H)

LC/MS: m/z=444.3, Rt=3.55 min (method 2)

2.8) Preparation of 3-(3,5-dimethyl-1-(3-methyl-[1,2,4]triazolo[4,3-b]pyridazin-6-yl)-1H-pyrazol-4-yl)-1-(4-phenylpiperidin-1-yl)propan-1-one (HZM06-6)

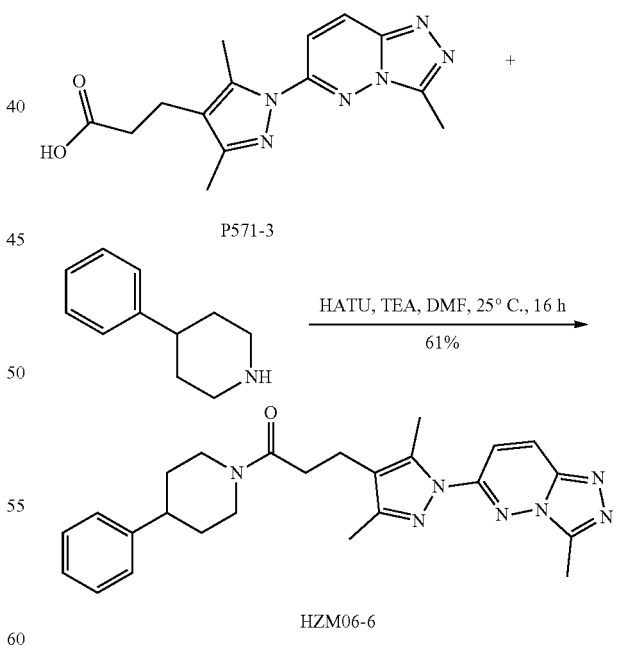

A mixture of P571-3 (50.0 mg, 0.17 mmol), HATU (69.6 mg, 0.18 mmol), 4-phenylpiperidine (64.7 mg, 0.33 mmol) and TEA (33.7 mg, 0.33 mmol) in DMF (3.00 mL) was stirred at 25° C. for 16 h. TLC check (10% MeOH in EtOAc, UV) showed starting material ($R_f$=0.10) was consumed and desired product as main spot ($R_f$=0.30). The reaction mixture was diluted with water (15.0 mL) and extracted with EtOAc (10.0 mL×5). The combined organic phase was washed with water and brine, dried over Na₂SO₄ and purified by Chromatotron (silica gel, 50% MeOH in EtOAc) to give 45.0 mg pure target compound.

Yield: 45.0 mg (61%)

¹H NMR: (400 MHz, DMSO-d₆): δ (ppm)=8.36 (d, 1H), 7.84 (d, 1H), 7.15-7.02 (m, 5H), 4.57 (d, 1H), 3.90 (d, 1H), 3.03 (t, 1H), 2.69-2.64 (m, 2H), 2.62 (s, 3H), 2.60 (s, 3H), 2.47-2.37 (m, 1H), 2.26 (s, 3H), 1.71 (dd, 2H), 1.32-1.13 (m, 2H)

LC/MS: m/z=444.3, Rt=4.59 min (method 1)

2.9) Preparation of 3-(3,5-dimethyl-1-(3-methyl-[1,2,4]triazolo[4,3-b]pyridazin-6-yl)-1H-pyrazol-4-yl)-1-(4-(pyridin-2-yl)piperidin-1-yl)propan-1-one (HZM06-7)

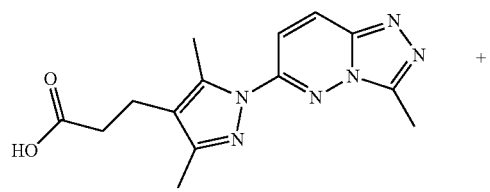

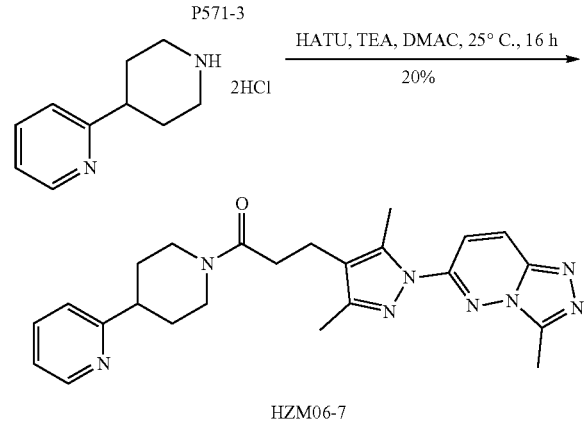

A mixture of P571-3 (128 mg, 0.43 mmol), HATU (178 mg, 0.47 mmol), 2-(piperidin-4-yl)pyridine dihydrochloride (100 mg, 0.43 mmol) and TEA (172 mg, 1.70 mmol) in DMAC (3.00 mL) was stirred at 25° C. for 16 h. HPLC check showed starting material was consumed and desired product as main peak. The reaction mixture was diluted with water (15.0 mL) and extracted with EtOAc (10.0 mL×5). The combined organic phase was washed with water and brine, dried over Na₂SO₄ and purified by Chromatotron (basic Al₂O₃, 50% MeOH in EtOAc) to give 37.0 mg pure target compound.

Yield: 37.0 mg (20%)

¹H NMR: (400 MHz, DMSO-d₆): δ (ppm)=8.34 (d, 1H), 8.32 (d, 1H), 7.82 (d, 1H), 7.56 (td, 1H), 7.14 (d, 1H), 7.09 (ddd, 1H), 4.55 (d, 1H), 3.90 (d, 1H), 3.06 (t, 1H), 2.73-2.65 (m, 2H), 2.63 (s, 3H), 2.59 (s, 3H), 2.25 (s, 3H), 1.80 (dd, 2H), 1.47-1.23 (m, 2H)

LC/MS: m/z=445.2, Rt=3.44 min (method 1)

2.10) Preparation of 1-(4-(3-methoxybenzyl)piperidin-1-yl)-3-(3,5-dimethyl-1-(3-methyl-[1,2,4]triazolo[4,3-b]pyridazin-6-yl)-1H-pyrazol-4-yl)propan-1-one (HZM06-8)

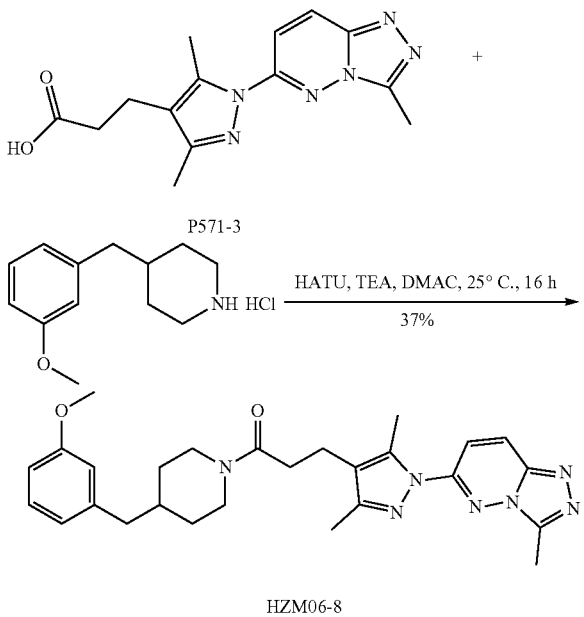

A mixture of P571-3 (50.0 mg, 0.17 mmol), HATU (69.6 mg, 0.18 mmol), 4-(3-methoxybenzyl)piperidine hydrochloride (80.0 mg, 0.33 mmol) and TEA (67.4 mg, 0.67 mmol) in DMF (3.00 mL) was stirred at 25° C. for 16 h. TLC check (10% MeOH in EtOAc, UV) showed starting material (R_f=0.10) was consumed and desired product as main spot (R_f=0.30). The reaction mixture was diluted with water (15.0 mL) and extracted with EtOAc (10.0 mL×5). The combined organic phase was washed with water and brine, dried over Na₂SO₄ and purified by Chromatotron (silica gel, 50% MeOH in EtOAc) followed by re-crystallized from Et₂O to give 30.0 mg pure target compound.

Yield: 30.0 mg (37%)

¹H NMR: (400 MHz, D₂O): δ (ppm)=8.38 (d, 1H), 7.87 (d, 1H), 7.11 (t, 1H), 6.74-6.69 (m, 1H), 6.65-6.57 (m, 2H), 4.38 (d, 1H), 3.76 (d, 1H), 3.69 (s, 3H), 2.85 (t, 1H), 2.67 (s, 3H), 2.59 (s, 3H), 2.47-2.38 (m, 2H), 2.23 (s, 3H), 1.69 (s, 1H), 1.51 (m, 2H), 0.99-0.70 (m, 2H)

LC/MS: m/z=488.2, Rt=4.87 min (method 1)

2.11) Preparation of 1-(4-(4-fluorobenzyl)piperidin-1-yl)-3-(3,5-dimethyl-1-(3-methyl-[1,2,4]triazolo[4,3-b]pyridazin-6-yl)-1H-pyrazol-4-yl)propan-1-one (HZM06-9)

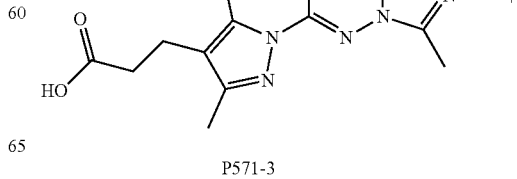

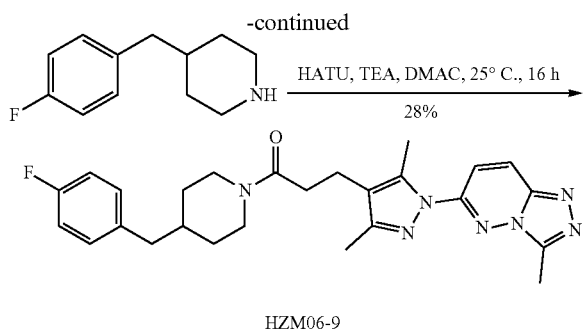

A mixture of P571-3 (100 mg, 0.33 mmol), HATU (133 mg, 0.35 mmol), 4-(4-fluorobenzyl)piperidine (64.0 mg, 0.33 mmol) and TEA (67.4 mg, 0.67 mmol) in DMAC (3.00 mL) was stirred at 25° C. for 16 h. TLC check (10% MeOH in EtOAc, UV) showed starting material ($R_f$=0.10) was consumed and desired product as main spot ($R_f$=0.30). The reaction mixture was diluted with water (15.0 mL) and extracted with EtOAc (10.0 mL×5). The combined organic phase was washed with water and brine, dried over $Na_2SO_4$ and purified by Chromatotron (silica gel, 50% MeOH in EtOAc) to give 45.0 mg pure target compound.

Yield: 45.0 mg (28%)

$^1$H NMR: (400 MHz, DMSO-$d_6$): δ (ppm)=8.36 (d, 1H), 7.84 (d, 1H), 7.14-7.05 (m, 2H), 7.04-6.96 (m, 2H), 4.36 (d, 1H), 3.75 (d, 1H), 2.83 (t, 1H), 2.65 (s, 3H), 2.57 (s, 3H), 2.41-2.36 (m, 2H), 2.21 (s, 3H), 1.72-1.58 (m, 1H), 1.48 (dd, 2H), 0.98-0.72 (m, 2H) LC/MS: m/z=476.1, Rt=4.97 min (method 1)

2.12) Preparation of 3-(3,5-dimethyl-1-(3-methyl-[1,2,4]triazolo[4,3-b]pyridazin-6-yl)-1H-pyrazol-4-yl)-1-(4-((pyridin-2-yl)methyl)piperidin-1-yl)propan-1-one (HZM06-10)

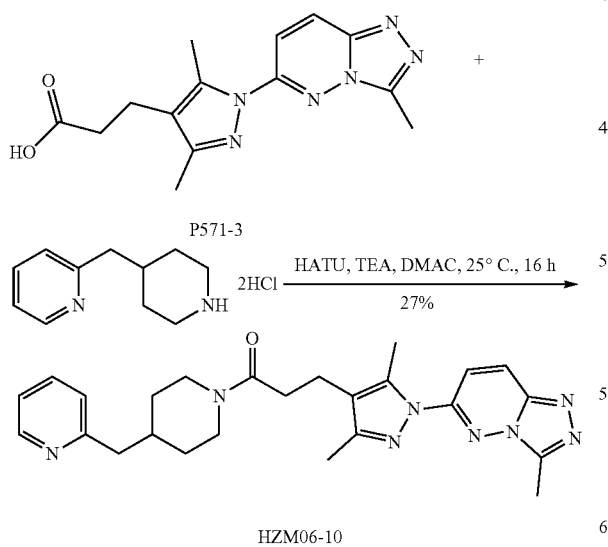

A mixture of P571-3 (120 mg, 0.40 mmol), HATU (160 mg, 0.42 mmol), 2-((piperidin-4-yl)methyl)pyridine dihydrochloride (100 mg, 0.40 mmol) and TEA (162 mg, 1.61 mmol) in DMAC (3.00 mL) was stirred at 25° C. for 16 h. HPLC check showed starting material was consumed and desired product as main peak. The reaction mixture was diluted with water (15.0 mL) and extracted with EtOAc (10.0 mL×5). The combined organic phase was washed with water and brine, dried over $Na_2SO_4$ and purified by Chromatotron (basic $Al_2O_3$, 50% MeOH in EtOAc) to give 50.0 mg pure target compound.

Yield: 50.0 mg (27%)

$^1$H NMR: (400 MHz, Methanol-$d_4$): δ (ppm)=8.41 (dt, 1H), 8.37 (d, 1H), 7.86 (d, 1H), 7.62 (td, 1H), 7.16 (ddd, 1H), 7.09 (d, 1H), 4.37 (d, 1H), 3.76 (d, 1H), 2.86 (q, 1H), 2.67 (s, 3H), 2.65-2.61 (m, 2H), 2.58 (s, 3H), 2.54 (dd, 2H), 2.47-2.35 (m, 2H), 2.23 (s, 3H), 1.50 (dd, 2H), 1.10-0.80 (m, 2H)

LC/MS: m/z=459.2, Rt=3.49 min (method 1)

2.13) Preparation of 3-(3,5-dimethyl-1-(3-methyl-[1,2,4]triazolo[4,3-b]pyridazin-6-yl)-1H-pyrazol-4-yl)-1-(4-((pyridin-2-yl)methyl)piperazin-1-yl)propan-1-one (HZM06-11)

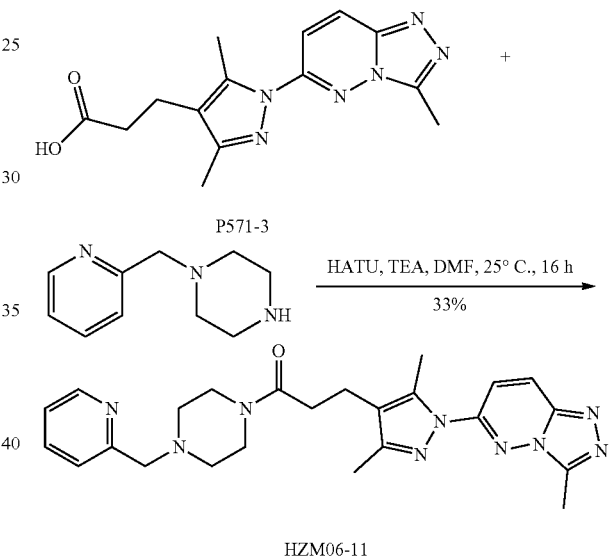

A mixture of P571-3 (50.0 mg, 0.17 mmol), HATU (69.6 mg, 0.18 mmol), 1-((pyridin-2-yl)methyl)piperazine (59.0 mg, 0.33 mmol) and TEA (33.7 mg, 0.33 mmol) in DMF (3.00 mL) was stirred at 25° C. for 16 h. HPLC check showed starting material was consumed and desired product as main peak. The reaction mixture was diluted with water (15.0 mL) and extracted with EtOAc (10.0 mL×5). The combined organic phase was washed with water and brine, dried over $Na_2SO_4$ and purified by Chromatotron (silica gel, MeOH) to give 25.0 mg pure target compound.

Yield: 25.0 mg (33%)

$^1$H NMR: (400 MHz, DMSO-$d_6$): δ (ppm)=8.43 (dt, 1H), 8.37 (d, 1H), 7.85 (d, 1H), 7.73 (td, 1H), 7.41-7.37 (m, 1H), 7.23 (ddd, 1H), 3.52 (s, 2H), 3.46 (t, 2H), 3.39 (d, 2H), 2.67 (s, 3H), 2.64 (d, 2H), 2.58 (s, 3H), 2.47 (d, 2H), 2.33 (t, 2H), 2.26 (t, 2H), 2.23 (s, 3H)

LC/MS: m/z=460.2, Rt=3.48 min (method 1)

The following compounds were obtained according to a synthetic procedure similar to the one described for Example HZM06-11:

| Compound of Table 1 | LC/MS: m/z (M + H+) | LC/MS: R$_t$ (min) | $^1$H NMR: δ (ppm) (400 MHz) |
|---|---|---|---|
| 41 (HZM11-11) | 520.3 | 4.74 (method 1) | CDCl3: 8.42-8.33 (m, 2H), 8.22 (d, J = 10.0 Hz, 1H), 8.09 (d, J = 10.0 Hz, 1H), 7.56 (d, J = 6.9 Hz, 3H), 7.22 (dd, J = 21.1, 7.3 Hz, 3H), 7.07 (d, J = 7.3 Hz, 2H), 4.63 (d, J = 13.3 Hz, 1H), 3.73 (d, J = 13.6 Hz, 1H), 2.83-2.75 (m, 2H), 2.66 (s, 3H), 2.54-2.41 (m, 5H), 2.30 (s, 3H), 1.78-1.59 (m, 3H), 1.07 (ddd, J = 46.8, 12.5, 4.0 Hz, 1H) |
| 43 (HZM11-9) | 457.3 | 3.92 (method 1) | CDCl3: 7.98 (d, J = 9.7 Hz, 1H), 7.80 (d, J = 9.7 Hz, 1H), 7.56 (s, 1H), 7.26-7.10 (m, 3H), 7.06 (d, J = 7.2 Hz, 2H), 4.63 (dq, J = 13.3, 2.2 Hz, 1H), 3.74 (dd, J = 12.7, 3.2 Hz, 1H), 2.98-2.72 (m, 3H), 2.64 (s, 3H), 2.54 (s, 3H), 2.29 (s, 3H), 1.76-1.55 (m, 2H), 1.06 (ddd, J = 63.5, 12.3, 4.2 Hz, 2H) |
| 44 (HZM06-18) | 444.2 | 3.95 (method 1) | CDCl3: 8.37 (d, J = 9.9 Hz, 1H), 7.87 (d, J = 10.0 Hz, 1H), 7.28 (t, J = 7.6 Hz, 2H), 7.18 (dd, J = 7.3, 4.5 Hz, 3H), 4.35 (d, J = 12.9 Hz, 1H), 4.01 (d, J = 13.6 Hz, 1H), 3.60-3.44 (m, 2H), 3.01 (t, J = 12.7 Hz, 1H), 2.68 (s, 3H), 2.54 (s, 3H), 2.53-2.51 (m, 2H), 2.13 (s, 3H), 1.78 (s, 1H), 1.60 (t, J = 13.0 Hz, 2H), 1.22-0.89 (m, 2H) |
| 48 (HZM06-22) | 370.1 | 3.06 (method 1) | CDCl3: 8.36 (d, J = 10.0 Hz, 1H), 7.84 (d, J = 10.0 Hz, 1H), 3.52 (t, J = 4.8 Hz, 2H), 3.47 (t, J = 4.7 Hz, 2H), 3.43 (t, J = 4.8 Hz, 2H), 3.38 (d, J = 4.9 Hz, 2H), 2.68 (s, 3H), 2.64 (d, J = 7.8 Hz, 2H), 2.59 (s, 3H), 2.49-2.45 (m, 2H), 2.24 (s, 3H) |
| 49 (HZM06-23) | 438.1 | 4.11 (method 1) | CDCl3: 8.36 (dd, J = 10.0, 5.5 Hz, 1H), 7.85 (dd, J = 10.0, 7.5 Hz, 1H), 7.38-7.00 (m, 4H), 4.54 (d, J = 28.6 Hz, 2H), 2.91 (s, 3H), 2.85 (d, J = 8.3 Hz, 2H), 2.67 (d, J = 4.6 Hz, 5H), 2.60 (d, J = 3.2 Hz, 3H), 2.26 (s, 2H), 2.14 (s, 1H) |
| 50 (HZM06-24) | 449.1 | 2.79 (method 1) | CDCl3: 8.37 (d, J = 10.0 Hz, 1H), 7.85 (d, J = 10.0 Hz, 1H), 7.54 (dd, J = 1.8, 0.9 Hz, 1H), 6.35 (dd, J = 3.1, 1.9 Hz, 1H), 6.22 (dd, J = 3.2, 0.8 Hz, 1H), 3.44 (s, 2H), 3.42 (d, J = 5.1 Hz, 2H), 3.36 (d, J = 4.9 Hz, 2H), 2.67 (s, 3H), 2.63 (t, J = 7.5 Hz, 2H), 2.57 (s, 3H), 2.47 (t, J = 7.4 Hz, 2H), 2.29 (t, J = 5.2 Hz, 2H), 2.24 (m, 2H), 2.22 (s, 3H) |
| 51 (HZM06-25) | 487.2 | 2.93 (method 1) | CDCl3: 8.36 (dd, J = 10.0, 1.0 Hz, 1H), 7.83 (dd, J = 10.0, 1.0 Hz, 1H), 7.41 (dt, J = 8.3, 1.1 Hz, 2H), 7.25 (t, J = 7.6 Hz, 2H), 7.19-7.12 (m, 1H), 3.43-3.37 (m, 2H), 3.28 (t, J = 4.7 Hz, 2H), 2.64 (d, J = 1.0 Hz, 3H), 2.62 (m, 2H), 2.55 (s, 3H), 2.43 (t, J = 7.4 Hz, 2H), 2.28 (t, J = 5.1 |

-continued

| Compound of Table 1 | LC/MS: m/z (M + H$^+$) | LC/MS: R$_t$ (min) | $^1$H NMR: δ (ppm) (400 MHz) |
|---|---|---|---|
| | | | Hz, 2H), 2.13 (t, J = 4.9 Hz, 2H), 1.17 (s, 6H) |
| 52 (HZM06-26) | 519.2 | 2.88 (method 1) | CDCl3: 8.38 (d, J = 10.0 Hz, 1H), 7.85 (d, J = 9.9 Hz, 1H), 6.91-6.73 (m, 2H), 6.69 (s, 1H), 3.71 (s, 7H), 3.44 (s, 2H), 3.37 (s, 6H), 3.16 (d, J = 5.0 Hz, 1H), 2.88 (d, J = 14.6 Hz, 2H), 2.67 (s, 3H), 2.63 (d, J = 7.4 Hz, 2H), 2.58 (s, 3H), 2.26 (s, 2H), 2.23 (s, 3H), 2.16 (s, 2H), 1.09 (t, J = 7.0 Hz, 1H) |
| 53 (HZM06-27) | 509.2 | 3.05 (method 1) | CDCl3: 8.39 (d, J = 10.0 Hz, 1H), 7.85 (m, 4H), 7.68 (d, J = 1.5 Hz, 1H), 7.52-7.39 (m, 3H), 3.55 (s, 2H), 3.47 (s, 2H), 3.38 (m, 2H), 2.66 (s, 3H), 2.64 (d, J = 7.6 Hz, 2H), 2.58 (s, 3H), 2.48 (d, J = 7.1 Hz, 2H), 2.36-2.29 (m, 2H), 2.24 (m, 2H), 2.22 (s, 3H) |
| 54 (HZM06-28) | 492.1 | 2.97 (method 1) | CDCl3: 8.37 (d, J = 10.0 Hz, 1H), 7.86 (d, J = 10.0 Hz, 1H), 7.32-7.18 (m, 2H), 7.16 (d, J = 1.9 Hz, 1H), 7.03 (dt, J = 7.1, 1.7 Hz, 1H), 4.38 (d, J = 13.0 Hz, 1H), 3.77 (d, J = 13.5 Hz, 1H), 3.41-3.35 (m, 2H), 2.85 (t, J = 12.5 Hz, 1H), 2.67 (s, 3H), 2.66-2.61 (m, 2H), 2.59 (s, 3H), 2.42 (m, 4H), 2.23 (s, 3H), 1.71 (ddd, J = 11.0, 7.5, 3.8 Hz, qH), 1.50 (dd, J = 30.8, 12.8 Hz, 2H) |
| 55 (HZM06-29) | 430.1 | 3.56 (method 1) | CDCl3: 8.36 (dd, J = 10.0, 0.7 Hz, 1H), 7.85 (dd, J = 10.0, 0.7 Hz, 1H), 7.25-7.17 (m, 2H), 7.17-7.07 (m, 3H), 4.05 (t, J = 7.8 Hz, 1H), 3.86 (t, J = 8.1 Hz, 1H), 3.66-3.54 (m, 1H), 3.55-3.46 (m, 1H), 2.83-2.70 (m, 3H), 2.66 (s, 3H), 2.61 (m, 2H), 2.59 (s, 3H), 2.23 (s, 3H), 2.22-2.16 (m, 2H) |
| 62 (HZM11-05) | 473.3 | 3.75 (method 1) | CDCl3: 8.11 (dd, J = 10.0, 3.1 Hz, 1H), 8.05-7.97 (m, 1H), 7.37-7.29 (m, 3H), 7.24 (d, J = 6.2 Hz, 2H), 4.60 (d, J = 7.7 Hz, 2H), 4.24 (d, J = 8.02 Hz, 2H), 3.78 (t, J = 5.5 Hz, 1.3H), 3.56 (s, 0.6 H), 3.26 (q, J = 7.2, 6.4 Hz, 2H), 2.79 (t, J = 4.1 Hz, 5H), 2.65 (d, J = 12.1 Hz, 3H), 2.49 (q, J = 6.6, 5.4 Hz, 2H), 2.28 (d, J = 11.3 Hz, 3H) |
| 63 (OR-001) | 514.37 | 1.32 (method 3) | CDCl$_3$: 8.15 (d, J = 9.12 Hz, 1H), 8.07 (d, J = 9.12 Hz; 1H), 7.33-7.07 (br m, 5H), 4.66 (br d, J = 13 Hz, 1H), 3.77 (br d, J = 13 Hz, 1H), 3.58 (quin, J = 7.6 Hz, 1H), 3.14 (q, J = 7.7 Hz, 2H), 2.98-2.87 (br t, J = 11.9 Hz, 1H), 2.85-2.75 (br m, 1H), 2.67 (q, J = 7.7 Hz, 2H), 2.6-2.45 (br m, 6H), 1.85-1.61 (br m, 3H), 1.55 (d s, 6H), 1.39-1.23 (br m, 5H), 1.22-0.96 (br m, 2H) |

-continued

| Compound of Table 1 | LC/MS: m/z (M + H⁺) | LC/MS: R_t (min) | ¹H NMR: δ (ppm) (400 MHz) |
|---|---|---|---|
| 64 (OR-004) | | | |
| 65 (OR-005) | | | |
| 66 (OR-006) | 410.34 | 1.12 (method 3) | CDCl₃: 8.15 (d, J = 9.8 Hz, 1H), 8.04 (d, J = 9.8 Hz; 1H), 3.61 (qin, J = 7 Hz, 1H), 3.42 (t, J = 6.4 Hz, 2H), 2.79 (t, J = 7.5 Hz, 2H), 2.68 (s, 3H), 2.37 (t, J = 8 Hz, 2H), 2.31 (s, 3H), 1.89-1.74 (br m, 4H), 1.56 (d s, 6H), 1.48 (s, 6H) |
| 71 (OR-013) | 487.39 | 0.87 (method 3) | CDCl₃: 8.10 (d, J = 9.6 Hz, 1H), 8.04-749 (m, 1H), 7.35-7.23 (m, 1H), 6.46 (t, J = 8.5 Hz, 1H), 6.09 (dd, J = 6.4 Hz, 1H), 4.81 (dd, J = 13.2 Hz, 1H), 4.19-4.06 (m, 1H), 4.00-3.80 (m, 2H), 3.44-3.27 (m, 1H), 3.24-3.06 (m, 3H), 2.94-2.80 (m, 1H), 2.74-2.33 (br m, 5H), 2.29-2.12 (m, 4H), 2.11-1.90 (m, 3H), 1.52 (t, J = 7.7 Hz, 3H), 1.41 (t, J = 7.7 Hz, 1H) |
| 72 (OR-014) | 394.3 | 0.95 (method 3) | CDCl3: mixture of conformers ratio ca. 9:11 8.18 (d, J = 9.8 Hz, 1H), 8.09 (dd, J = 9.8; 1.9 Hz, 1H), 4.65 (s, 0.46H), 4.05 (s, 0.56H), 3.37-3.12 (m, 5H), 2.88-2.76 (m, 2H), 2.68 (s, 3H), 2.63-2.34 (m, 2H), 2.32 (s, 3H), 1.75-1.25 (br m, 9H) |
| 73 (OR-021) | 408.3 | 1.06 (method 3) | CDCl₃: 8.29 (d, J = 10 Hz, 1H), 8.22 (d, J = 10 Hz; 1H), 3.43 (br d, J = 51.6 Hz, 4H), 2.84 (t, J = 7.4 Hz, 2H), 2.67 (s, 3H), 2.47 (t, J = 7.4 Hz, 2H), 2.33 (s, 3H), 1.92 (br s, 4H) |
| 74 (OR-023) | 486.3 | 1.23 (method 3) | DMSO: 8.40 (d, J = 10 Hz, 1H), 7.90 (d, J = 10 Hz, 1H), 4.4 (br d, J = 12.6 Hz, 1H), 3.76 (br d, J = 12.6 Hz, 1H), 3.52 (quin, J = 7.1 Hz, 1H), 2.85 (br t, J = 13.3 Hz, 1H), 2.74-2.27 (br m, 9H), 2.24 (s, 3H), 1.76-1.60 (br m, 1H), 1.54 (br d, J = 12.3 Hz, 1H), 1.50-1.34 (m, 8H), 0.99-0.62 (d m, 2H) |
| 75 (OR-024) | 472.3 | 1.19 (method 3) | DMSO: 8.37 (d, J = 10 Hz, 1H), 7.89 (d, J = 10 Hz, 1H), 7.26-7.09 (m, 3H), 7.06-6.96 (m, 2H), 4.39 (br d, J = 14.1 Hz, 1H), 3.77 (br d, J = 14.1 Hz, 1H), 3.09 (q, J = 8.46 Hz, 2H), 2.85 (t, J = 12.7 Hz, 1H), 2.71-2.61 (m, 1H), 2.58 (s, 3H), 2.45-2.30 (m, 4H), 2.23 (s, 3H), 1.75-1.63 (br m, 1H), 1.60-1.42 (br m, 2H), 1.41-1.35 (m, 5H), 0.99-068 (br m, 2H) |
| 76 (OR-026) | 382.3 | 0.98 (method 3) | CDCl3: 8.13 ( d, J = 9.3 Hz, 1H), 8.03 (d, J = 9.3 Hz; 1H), 3.56 (t, J = 7.3 Hz, 1H), 3.41 (t, J = 7 Hz, 1H), 3.24 (s, 1H), 3.06 (s, 1H), 2.88-2.74 (br m, 5H), 2.68 (s, 3H), 2.48-2.37 (br m, 2H), 2.31 (s, 3H), 1,71 (t, J = 7.3 Hz, |

| Compound of Table 1 | LC/MS: m/z (M + H+) | LC/MS: R$_t$ (min) | $^1$H NMR: δ (ppm) (400 MHz) |
|---|---|---|---|
| | | | 1H), 1.65 (t, J = 7.3 Hz, 1H), 1.06 (d s, 6H) |
| 77 (OR-027) | 368.3 | 0.94 (method 3) | CDCl3: 8.13 ( d, J = 10 Hz, 1H), 8.02 (d, J = 10 Hz; 1H), 3.50 (t, J = 7 Hz, 2H), 3.35 (t, J = 7 Hz, 2H), 3.19 (q, J = 7.5 Hz, 2H), 2.83 (t, J = 8 Hz, 2H), 2.68 (s, 3H), 2.45 (t, J = 7.3 Hz, 2H), 2.31 (s, 3H), 1.99-1.80 (br m, 4H), 1.52 (t, J = 7.5 Hz, 3H) |
| 78 (OR-028) | 382.3 | 0.98 (method 3) | CDCl3: 8.15 ( d, J = 10 Hz, 1H), 8.04 (d, J = 10 Hz; 1H), 3.60 (quin, J = 7 Hz, 1H), 3.49 (t, J = 6.7 Hz, 2H), 3.35 (t, J = 7 Hz, 2H), 2.83 (t, J = 7.5 Hz, 2H), 2.68 (s, 3H), 2.46 (t, J = 7.2 Hz, 2H), 2.31 (s, 3H), 1.99-1.80 (br m, 4H), 1.56 (d s, 6H) |
| 79 (OR-031) | 438.3 | 1.17 (method 3) | CDCl3: 8.16 (d, J = 10 Hz, 1H), 8.08 (dd, J = 10; 1.7 Hz; 1H), 3.65-3.52 (br m, 2H), 3.44 (t, J = 7.5 Hz, 1H), 3.26 (s, 1H), 3.15(q, J = 7.2 Hz, 2H), 3.08 (s, 1H), 2.88-2.79 (m, 2H), 2.68 (q, J = 7.7 Hz, 2H), 2.49-2.39 (br m, 2H), 1.74 (t, J = 6.6 Hz, 1H), 1.65 (t, J = 6.6 Hz 1H), 1.56 (d s, 6H) 1.36-1.23 (br m, 6H), 1.08 (d s, 6H) |
| 80 (OR-033) | 472.3 | 1.19 (method 3) | CDCl3: 8.18-8.06 (m, 2H), 7.37-7.10 (m, 5H), 3.77.365 (m, 1H), 3.53-327 (m, 2H), 3.20-3.08 (m, 2H), 3.77-3.97 (m, 1H), 2.87-2.33 (br m, 7H), 2.09-1.97 (br m, 2H), 1.75-156 (br m, 2H), 1.38-1.25 (br m, 9H) |
| 81 | 472.9 | 0.14 (method 4) | CDCl$_3$: (2 rotamers) 8.07 (d, 0.5 H, J = 9.9 Hz), 8.07 (d, 0.5 Hz, J = 9.9 Hz), 7.97 (d, 1H, J = 9.9 Hz), 7.33-7.20 (m, 5H), 3.67 (t, 1H, 5.5 Hz), 3.65 (t, 1H, J = 6.3 Hz), 3.59 (s, 2H), 3.48 (t, 1H, J = 6.3 Hz), 3.44 (t, 1H, J = 5.0 Hz), 2.82 (t, 1H, J = 7.7 Hz), 2.81 (t, 1H, J = 7.8 Hz), 2.77 (s, 3H), 2.69-2.64 (m, 1H), 2.67 (s, 1.5H), 2.66 (s, 1.5H), 2.60 (m, 2H), 2.55 (m, 2H), 2.48 (tt, 2H, J = 10.5, 7.9 H), 2.30 (s, 1.5H), 2.28 (s, 1.5H), 1.84 (tt, 2H, J = 12.1, 6.1 Hz) |
| 82 | 486 | 1.15 (method 4) | CDCl$_3$: 8.09 (d, 1H, J = 9.9 Hz), 7.79 (d, 1H, J = 9.9 Hz), 7.23-7.29 (m, 3H), 7.17-7.21 (m, 1 H), 7.10-7.12 (m, 2H), 4.64 (m, 1H), 3.75-3.85 (m, 2H), 2.95 (dd, 1H, J = 12.8, 2.4 Hz), 2.86-2.91 (m, 2H), 2.77 (s, 3H), 2.46-2.60 (m, 5H), 2.26 (s, 3H), 1.65-1.81 (m, 4H), 7.16 (d, 6H, J = 7.2 Hz), 1.04-1.20 (m, 2H) |
| 83 | 534.6 | 1.28 (method 3) | CDCl$_3$: 8.08 (d, 1H, J = 10.2 Hz), 7.98 (d, 1H, J = 9.9 Hz), 7.16-7.32 (m, 8H), 7.05-7.10 |

| Compound of Table 1 | LC/MS: m/z (M + H+) | LC/MS: R$_t$ (min) | ¹H NMR: δ (ppm) (400 MHz) |
|---|---|---|---|
| | | | (m, 2H), 4.62 (m, 1H), 4.54 (s, 2H), 3.71 (m, 1H), 2.87 (dt, 1H, J = 13.0, 2.4 Hz), 2.71-2.77 (m, 2H), 2.40-2.59 (m, 5H), 2.42 (s, 3H), 2.25 (s, 3H), 1.57-1.80 (m, 3H), 1.12 (dddd, 1H, J = 12.3, 12.3, 12.3, 4.0 Hz), 0.98 (dddd, 1H, J = 12.3, 12.3, 12.3, 3.9 Hz) |
| 84 | 484.4 | 1.21 (method 3) | CDCl₃: 8.05 (d, 1H, J = 10.2 Hz), 7.95 (d, 1H, 9.9 Hz), 7.16-7.28 (m, 3H), 7.06-7.10 (m, 2H), 4.64 (m, 1H), 3.74 (m, 1H), 2.90 (ddd, 1H, J = 13.2, 13.2, 2.7 Hz), 2.76-2.82 (m, 2H), 2.67 (s, 3H), 2.43-2.60 (m, 5H), 2.39 (m, 1H), 2.29 (s, 3H), 1.60-1.80 (m, 4H), 1.37 (ddd, 1H, J = 4.7, 7.1, 4.7 Hz), 1.17-1.23 (m, 2H), 1.14 (dddd, 1H, J = 12.0, 12.0, 12.0, 3.4 Hz), 1.00 (dddd, 1H, J = 12.2, 12.2, 12.2, 4.0 Hz) |
| 85 | 458.4 | 1.19 (method 3) | MeOD (2 rotamers): 8.27 (d, J = 10.0 Hz, 0.6 H), 8.20 (d, J = 10.0 Hz, 0.4 H), 8.06 (d, J = 10.0 Hz, 0.6 H), 8.00 (d, J = 10.0 Hz, 0.4 H), 7.26-6.91 (m, 5 H), 4.59 (d, J = 13.2 Hz, 0.6 H), 4.52 (d, J = 13.1 Hz, 0.4 H), 4.02-3.90 (m, 1 H), 3.73-3.61 (m, 1 H), 2.94 (t, J = 12.0 Hz, 0.6 H), 2.76 (s, 1.8 H), 2.76-2.68 (m, 0.6 H), 2.74 (s, 1.2 H), 2.64 (s, 1.2 H), 2.62 (s, 1.8 H), 2.59-2.53 (m, 1 H), 2.44-2.33 (m, 1.2 H), 2.25 (s, 1.8 H), 2.21 (s, 1.2 H), 1.82-1.71 (m, 1 H), 1.67 (d, J = 13.2 Hz, 1.2 H), 1.59 (d, J = 12.0 Hz, 0.8 H), 1.34 (d, J = 7.04 Hz, 1.2 H), 1.31 (d, J = 6.88 Hz, 1.8 H), 1.28-1.19 (m, 0.8 H), 1.04-0.92 (m, 0.6 H), 0.40-0.26 (m, 0.6 H) |
| 86 | 458.25/459.35 | 0.84 (method 3) | CD₃OD: 8.26 (d, J = 10.0 Hz, 1 H), 8.06 (d, J = 10.0 Hz, 1 H), 7.25-7.20 (m, 4 H), 7.17-7.11 (m, 1 H), 3.98 (q, J = 6.9 Hz, 1 H), 3.87-3.77 (m, 1 H), 3.54-3.48 (m, 1 H), 3.46 (d, J = 1.3 Hz, 2 H), 3.41-3.25 (m, 2 H), 2.76 (s, 3 H), 2.64 (s, 3 H), 2.58-2.50 (m, 1 H), 2.43-2.34 (m, 1 H), 2.33-2.26 (m, 1 H), 2.24 (s, 3 H), 1.95-1.86 (m, 1 H), 1.33 (d, J = 6.9 Hz, 3 H) |
| 87 | 457.26/458.35 | 0.78 (method 3) | CD₃OD: 8.07 (d, J = 9.7 Hz, 1 H), 7.78 (d, J = 9.8 Hz, 1 H), 7.57 (d, J = 0.6 Hz, 1 H), 7.21-7.15 (m, 3 H), 7.15-7.09 (m, 2 H), 3.62-3.56 (m, 2 H), 3.44-3.38 (m, 2 H), 3.36 (s, 2 H), 2.81 (t, J = 7.1 Hz, 2 H), 2.61 (s, 3 H), 2.60-2.56 (m, 2 H), 2.51 (s, 3 H), 2.39-2.34 (m, |

| Compound of Table 1 | LC/MS: m/z (M + H+) | LC/MS: R$_t$ (min) | $^1$H NMR: δ (ppm) (400 MHz) |
|---|---|---|---|
| | | | 2 H), 2.27 (s, 3 H), 2.13-2.07 (m, 2 H) |
| 88 | 458.25/459.35 | 0.86 + 0.88 (method 3) | — |
| 89 | 457.26/458.31 | 0.83 (method 3) | Mixture of conformers (ca. 0.6:0.4) D$_2$O: 8.31 (t, J = 9.6 Hz, 1 H), 8.04 (dd, J = 9.7 Hz, 4.5 Hz, 1 H), 7.82 (b, J = 0.8 Hz, 1 H), 7.30-7.06 (m, 5 H), 4.40 (d, J = 14.7 Hz, 0.6 H), 4.21-4.12 (m, 0.4 H), 3.92-3.84 (m, 0.4 H), 3.80 (d, J = 13.3 Hz, 0.6 H), 3.66-3.55 (m, 0.4 H), 3.48-3.38 (m, 1 H), 3.37-3.27 (m, 0.8 H), 3.29-3.21 (m, 1.2 H), 3.21-3.08 (m, 1 H), 3.00-2.85 (m, 1.8 H), 2.85-2.78 (m, 2 H), 2.78-2.70 (m, 2 H), 2.55 (s, 1.2 H), 2.54 (s, 1.2 H), 2.53 (s, 1.8 H), 2.46 (s, 1.8 H), 2.27 (s, 1.2 H), 2.16 (s, 1.8 H) |
| 90 | 457.26/458.35 | 1.16 + 1.19 (method 3) | — |
| 91 | 456.26/457.35 | 1.10 (method 3) | Mixture of conformers (ca. 0.6:0.4) CD$_3$OD: 8.01 (d, J = 9.7 Hz, 0.6 H), 7.98 (d, J = 9.8 Hz, 0.4 H), 7.72 (d, J = 7.8 Hz, 0.6 H), 7.70 (d, J = 7.7 Hz, 0.4 H), 7.53 (d, J = 1.4 Hz, 1 H), 7.18-6.99 (m, 5 H), 4.42 (d, J = 12.2 Hz, 0.6 H), 4.27 (dd, J = 12.7 Hz, 3.6 Hz, 0.4 H), 3.70 (d, J = 13.2 Hz, 0.4 H), 3.65-3.59 (m, 0.6 H), 3.08-2.98 (m, 0.4 H), 2.80-2.62 (m, 3.4 H), 2.66-2.50 (m, 2.2 H), 2.59 (s, 1.2 H), 2.50 (s, 1.2 H), 2.49 (s, 1.8 H), 2.49 (1.8 H), 2.41 (d, J = 7.3 Hz, 1.2 H), 2.35 (dd, J = 13.6 Hz, 6.7 Hz, 0.8 H), 2.26 (s, 1.2 H), 2.17 (s, 1.8 H), 1.67-1.54 (m, 0.6 H), 1.62-1.55 (m, 0.8 H), 1.43-1.26 (m, 1.6 H), 1.25-1.08 (m, 2 H) |
| 92 | 443.24/444.35 | 1.12 (method 3) | Mixture of diastereomers + conformers CD$_3$OD: 8.31-8.20 (m, 1 H), 8.13-7.97 (m, 1 H), 7.29-6.95 (5 H), 3.90-3.72 (m, 1 H), 3.72-3.27 (m, 2.5 H), 3.23-2.90 (m, 1.5 H), 2.80-2.75 (m, 3 H), 2.71 (s, 0.8 H), 2.70-2.50 (m, 2 H), 2.67 (s, 0.7 H), 2.58 (s, 0.8 H), 2.55 (s, 0.7 H), 2.46-2.30 (m, 1 H), 2.28 (s, 0.7 H), 2.24 (s, 0.6 H), 2.20 (s, 0.9 H), 2.16 (s, 0.8 H), 2.07-1.87 (m, 1 H), 1.72-1.53 (m, 1 H), 1.38-1.29 (m, 3 H) |
| 93 | 442.25/443.35 | 1.04 (method 3) | Mixture of conformers (ca. 0.5:0.5) CD$_3$OD: 8.00 (d, J = 9.7 Hz, 0.5 H), 7.99 (d, J = 9.8 Hz, 0.5 H), |

-continued

| Compound of Table 1 | LC/MS: m/z (M + H+) | LC/MS: R$_t$ (min) | $^1$H NMR: δ (ppm) (400 MHz) |
|---|---|---|---|
| | | | 7.73 (d, J = 9.8 Hz, 0.5 H), 7.72 (d, J = 9.8 Hz, 0.5 H), 7.55 (s, 0.5 H), 7.53 (s, 0.5 H), 7.21-6.99 (m, 5 H), 3.60-3.54 (m, 0.5 H), 3.50 (dd, J = 11.9 Hz, 7.1 Hz, 0.5 H), 3.46-3.39 (m, 0.5 H), 3.37-3.24 (m, 1 H), 3.08 (dd, J = 11.9 Hz, 7.6 Hz, 0.5 H), 2.93 (t, J = 9.3 Hz, 0.5 H), 2.82-2.74 (m, 2 H), 2.64-2.47 (m, 2 H), 2.60 (s, 1.5 H), 2.54 (s, 1.5 H), 2.51 (s, 3 H), 2.50-2.42 (m, 2 H), 2.41-2.30 (m, 1 H), 2.27 (s, 1.5 H), 2.22 (s, 1.5 H), 1.98-1.88 (m, 1 H), 1.65-1.47 (m, 1 H), 1.38-1.19 (m, 0.5 H) |
| 94 | 471.27/472.35 | 1.24 (method 3) | Mixture of rotamers (ca. 0.6: 0.4) CD$_3$OD: 8.26-8.19 (m, 1 H), 8.08-8.00 (m, 1 H), 7.26-6.96 (m, 5 H), 4.62 (d, J = 13.2 Hz, 0.6 H), 4.54 (d, J = 13.2 Hz, 0.4 H), 4.03-3.93 (m, 1 H), 3.74-3.64 (m, 1 H), 2.97 (t, J = 12.1 Hz, 0.6 H), 2.75-2.71 (m, 0.4 H), 2.75 (s, 1.2 H), 2.70-2.60 (m, 0.4 H), 2.69 (s, 1.8 H), 2.68 (s, 1.8 H), 2.66 (s, 1.2 H), 2.64-2.58 (m, 1.4 H), 2.48 (t, J = 7.9 Hz, 1.2 H), 2.29 (s, 1.8 H), 2.23 (s, 1.2 H), 1.79 (d, J = 12.9 Hz, 1 H), 1.73 (d, J = 12.9 Hz, 0.4 H), 1.60-1.38 (m, 3.6 H), 1.36-1.32 (m, 3 H), 1.24-1.12 (m, 0.8 H), 1.05-0.93 (m, 0.6 H), 0.42-0.29 (m, 0.6 H) |
| 95 | 470.28/471.35 | 1.13 (method 3) | CD$_3$OD: 7.97 (d, J = 9.7 Hz, 1 H), 7.73 (d, J = 9.7 Hz, 1 H), 7.52 (d, J = 0.5 Hz, 1 H), 7.15-7.04 (m, 3 H), 6.92-6.87 (m, 2 H), 4.54 (d, J = 13.1 Hz, 1 H), 3.80 (d, J = 13.6 Hz, 1 H), 3.00-2.81 (m, 2 H), 2.81-2.69 (m, 2 H), 2.61 (s, 3 H), 2.56-2.42 (m, 2 H), 2.52 (s, 3 H), 2.46-2.41 (m, 2 H), 2.29 (s, 3 H), 1.73 (d, J = 12.4 Hz, 1 H), 1.63(d, J = 13.0 Hz, 1 H), 1.50-1.39 (m, 1 H), 1.36-1.27 (m, 2 H), 1.05-0.93 (m, 1 H), 0.61-0.47 (m, 1 H) |
| 181 | 555.21/556.3 | 0.98 | CDCl3: 8.26 (d, J = 10.1 Hz, 1H), 8.21 (d, J = 10.1 Hz, 1H), 7.45 (d, J = 8.9 Hz, 1H), 7.31 (d, J = 9.0 Hz, 1H), 7.25 (d, J = 1.4 Hz, 1H), 3.66 (t, J = 4.8 Hz, 2H), 3.51 (s, 2H), 3.47-3.40 (m, 2H), 2.79 (t, 2H), 2.64 (s, 3H), 2.48 (t, 3H), 2.29 (s, 3H) |
| 182 | 501.24/502.3 | 0.84 | CDCl3: 8.08 (d, J = 10.0 Hz, 1H), 7.96 (d, J = 10.0 Hz, 1H), 7.53 (t, J = 7.5 Hz, 1H), 7.42 (dd, J = 7.9, 1.4 Hz, |

| Compound of Table 1 | LC/MS: m/z (M + H⁺) | LC/MS: R$_t$ (min) | ¹H NMR: δ (ppm) (400 MHz) |
|---|---|---|---|
| | | | 1H), 7.31 (dd, J = 9.2, 1.4 Hz, 1H), 3.68-3.61 (m, 2H), 3.57 (s, 2H), 3.44-3.37 (m, 2H), 2.82-2.72 (m, 5H), 2.64 (s, 3H), 2.51-2.34 (m, J = 26.8, 12.4, 6.5 Hz, 6H), 2.27 (s, 3H) |
| 183 | 571.18/572.22 | 0.98 | CDCl3 8.26 (d, J = 10.1 Hz, 1H), 8.21 (d, J = 10.1 Hz, 1H), 7.81 (d, J = 1.3 Hz, 1H), 7.57-7.41 (m, 2H), 3.74-3.64 (m, J = 2.7 Hz, 2H), 3.58 (s, 2H), 3.50-3.39 (m, J = 11.3, 6.9 Hz, 2H), 2.82 (t, J = 24.3, 17.1 Hz, 2H), 2.63 (s, 3H), 2.56-2.36 (m, 6H), 2.29 (s, 3H) |
| 184 | 517.21/518.30 | 0.86 | CDCl3: 8.10 (d, J = 10.0 Hz, 1H), 7.98 (d, J = 10.0 Hz, 1H), 7.71 (d, J = 7.6 Hz, 1H), 7.59 (dd, J = 7.7, 1.6 Hz, 1H), 7.35 (t, J = 7.7 Hz, 1H), 3.64 (d, J = 13.1 Hz, 4H), 3.48-3.39 (m, 2H), 2.84-2.74 (m, 5H), 2.65 (s, 3H), 2.47 (dd, J = 18.4, 11.1 Hz, 6H), 2.28 (s, 3H) |
| 185 | 497.27/498.30 | 0.86 | CDCl3: 8.12 (d, J = 10.0 Hz, 1H), 8.02 (d, 1H), 7.58 (d, J = 7.7 Hz, 1H), 7.47 (d, J = 6.9 Hz, 1H), 7.26 (t, J = 7.7 Hz, 1H), 3.67 (s, 2H), 3.56-3.39 (m, 4H), 2.90-2.77 (m, 5H), 2.70 (s, 3H), 2.60 (s, 3H), 2.52 (t, 2H), 2.42 (d, J = 26.9 Hz, 4H), 2.33 (s, 3H) |
| 186 | 551.24/552.32 | 1.06 | CDCl3: 8.30 (d, J = 10.1 Hz, 1H), 8.25 (d, J = 10.1 Hz, 1H), 7.57 (d, J = 7.7 Hz, 1H), 7.47 (d, J = 7.4 Hz, 1H), 7.26 (t, J = 7.7 Hz, 1H), 3.73-3.62 (m, J = 3.3 Hz, 2H), 3.51 (s, 2H), 3.48-3.39 (m, J = 12.6, 8.0 Hz, 2H), 2.83 (t, 2H), 2.67 (s, 3H), 2.60 (s, 3H), 2.52 (t, 3H), 2.48-2.37 (m, 4H), 2.33 (s, 3H) |
| 187 | 571.18/572.26 | 0.99 | CDCl3: 8.28 (d, J = 10.1 Hz, 1H), 8.24 (d, J = 10.1 Hz, 1H), 7.73 (dd, J = 7.8, 1.6 Hz, 1H), 7.61 (dd, J = 7.7, 1.6 Hz, 1H), 3.70-3.65 (m, 2H), 3.64 (s, 2H), 3.48-3.40 (m, 2H), 2.84-2.77 (m, 2H), 2.64 (s, 3H), 2.51 (t, J = 7.5 Hz, 4H), 2.47-2.42 (m, 2H), 2.30 (s, 3H) |
| 188 | 517.21/518.30 | 0.86 | 8.08 (d, J = 10.0 Hz, 1H), 7.96 (d, J = 10.0 Hz, 1H), 7.65-7.49 (m, 3H), 3.68-3.62 (m, 2H), 3.60 (s, 2H), 3.45-3.37 (m, 2H), 2.83-2.72 (m, 5H), 2.64 (s, 3H), 2.52-2.34 (m, 6H), 2.26 (d, J = 2.9 Hz, 3H) |
| 189 | 571.18/572.18 | 0.99 | CDCl3: 8.23 (q, J = 10.1 Hz, 1H), 7.69-7.58 (m, 1H), 7.53 (dd, J = 8.0, 1.5 Hz, 1H), 3.75-3.38 (m, 3H), 2.77 (t, J = 17.6, 9.6 Hz, 1H), 2.62 (s, 2H), 2.50 (t, J = 18.9, 10.8 Hz, 2H), 2.41 (t, 1H), 2.28 (s, 1H), 2.03 (s, 1H), 1.37 (t, J = 7.1 Hz, 1H), 1.24 (t, J = 7.1 Hz, 1H) |

| Compound of Table 1 | LC/MS: m/z (M + H⁺) | LC/MS: R_t (min) | ¹H NMR: δ (ppm) (400 MHz) |
|---|---|---|---|
| 190 | 555.21/556.28 | 1.07 | CDCl3: 8.27 (d, J = 10.1 Hz, 1H), 8.23 (d, J = 10.1 Hz, 1H), 7.56 (t, J = 7.5 Hz, 1H), 7.45 (dd, J = 7.9, 1.3 Hz, 1H), 7.34 (dd, J = 9.2, 1.4 Hz, 1H), 7.28 (s, 1H), 3.68 (dd, J = 11.9, 7.3 Hz, 3H), 3.60 (s, 2H), 3.48-3.40 (m, 2H), 2.85-2.76 (m, 3H), 2.64 (s, 4H), 2.56-2.44 (m, 5H), 2.44-2.37 (m, 3H), 2.30 (s, 4H) |
| 191 | 517.21/518.30 | 0.86 | CDCl3: 8.11 (d, J = 10.0 Hz, 1H), 8.00 (d, J = 10.0 Hz, 1H), 7.45 (s, 1H), 7.36-7.27 (m, 2H), 3.67 (t, J = 4.7 Hz, 2H), 3.53 (s, 2H), 3.45 (t, 2H), 2.86-2.75 (m, 6H), 2.67 (s, 3H), 2.50 (t, 2H), 2.47-2.35 (m, 5H), 2.30 (s, 4H) |

LC-MS Method 3: Waters Acquity H UPLC CLASS system, with Aquity UPLC BEH C18 column (1.7 μm, 2.1×50 mm), flowrate 0.8 mL/min, using a 3 min gradient method with a mobile phase consisting of water/acetonitrile (0.05% v/v TFA added to each of the two solvents): 95:5 (0 min)→5:95 (1.00 min)→5:95 (2.25 min)→95:5 (2.27 min)→95:5 (3 min).

LC-MS Method 4 (Agilent 1200 Series LC system; Agilent 6130 Quadrupole detector; column: LUNA C18(2) column (3 μm, 10×2 mm):

| | | |
|---|---|---|
| 0.0-0.2 min | 7% | CH₃CN |
| 0.2-1.8 min | 7 → 95% | CH₃CN |
| 1.8-1.9 min | 95% | CH₃CN |
| 1.9-2.0 min | 95 → 7% | CH₃CN |

A suitable nitrile containing starting material (1 eq., 0.06 mmol) was dissolved in DMF (1.6 mL) and sodium azide (1.5 eq.) and CuCl (0.2 eq.) were added. The mixture was stirred at 120° C. for 12 h, then cooled to 0° C. and 4M HCl was added. The mixture was diluted with a mixture of dichloromethane:isopropanol (4:1) and washed with ammonium chloride solution. The organic layer was dried over sodium sulfate, filtered and volatiles were removed in vacuo to yield the corresponding tetrazole derivatives. Using this procedure, the following examples were obtained starting from the corresponding compounds listed in the table above:

| Compound of Table 1 | LC/MS: m/z (M + H⁺) | LC/MS: R_t (min) | ¹H NMR: δ (ppm) (400 MHz) |
|---|---|---|---|
| 169 | 544.26/545.30 | 0.81 | DMSO: 8.39-8.33 (m, 1H), 8.10-7.75 (m, 4H), 3.86-3.68 (m, 2H), 3.08 (d, J = 3.7 Hz, 2H), 2.93-2.79 (m, 5H), 2.73 (s, 3H), 2.70-2.56 (m, J = 23.0, 9.5, 3.6 Hz, 8H), 2.27-2.20 (m, 3H) |
| 170 | 598.23/599.33 | 0.93 | CD3CN: 8.29 (d, J = 10.0 Hz, 1H), 8.16-7.83 (m, 4H), 3.91-3.00 (m, J = 108.8, 106.6, 34.3 Hz, 8H), 2.89 (s, 2H), 2.80 (d, J = 3.2 Hz, 2H), 2.75-2.66 (m, 2H), 2.58 (s, 5H), 2.26 (s, 3H) |
| 171 | 560.23/561.33 | 0.84 | DMSO: 8.60 (s, 0.9H), 8.20 (d, J = 8.1 Hz, 0.8H), 7.92 (s, 1H), 7.80 (d, J = 8.3 Hz, 0.9H), 4.54 (s, 2.1H), 2.75 (d, J = 7.6 Hz, 1H), 2.69-2.58 (m, 6H), 2.57 (s, 43H), 2.21 (s, 3H) |
| 172 | 614.20/615.22 | 0.94 | DMSO: 8.65-8.56 (m, 2.1H), 8.17 (d, J = 9.7 Hz, 1H), 8.10 (s, 0.6H), 7.82 (d, J = 8.4 Hz, 0.6H), 2.75 (d, J = 4.6 Hz, 0.9H), 2.65 (d, J = 13.2 Hz, 2.9H), 2.58 (d, J = |

| Compound of Table 1 | LC/MS: m/z (M + H⁺) | LC/MS: R$_t$ (min) | ¹H NMR: δ (ppm) (400 MHz) |
| --- | --- | --- | --- |
| | | | 4.2 Hz, 1.5H), 2.55 (s, 3H), 2.35-2.28 (m, 1.6H), 2.27-2.22 (m, 2.9H) |
| 173 | 560.23/561.30 | 0.83 | DMSO: 8.42-7.89 (m, 8H), 7.84 (d, J = 9.7 Hz, 1H), 7.73 (dd, J = 15.3, 7.1 Hz, 1H), 3.73 (s, 2H), 3.64-2.97 (m, 8H), 2.66 (m, 5H), 2.58 (s, 3H), 2.29 (s, 2H), 2.23 (s, 3H) |
| 174 | 614.20/615.29 | 0.93 | DMSO: 8.61 (d, J = 10.1 Hz, 1.3H), 8.21 (s, 1.3H), 8.12 (d, J = 10.0 Hz, 2.4H), 8.09-7.99 (m, 2.1H), 2.80 (d, J = 4.8 Hz, 1H), 2.63 (d, J = 6.8 Hz, 2H), 2.60-2.53 (m, 5H), 2.25 (d, J = 6.0 Hz, 3H) |
| 175 | 560.23/561.24 | 0.81 | DMSO: 8.40 (s, 0.4H), 8.32 (d, J = 7.2 Hz, 0.7H), 8.21 (d, J = 8.0 Hz, 0.4H), 8.14 (s, 0.7H), 8.11-7.79 (m, 1.5H), 7.65 (t, J = 7.7 Hz, 0.5H), 4.46 (d, J = 44.4 Hz, 2H), 3.13-3.02 (m, 2H), 2.68 (s, 3H), 2.62 (d, J = 7.0 Hz, 3H), 2.58 (d, J = 4.6 Hz, 3H), 2.29-2.16 (m, 3H) |
| 176 | 614.20/615.26 | 0.99 | CDCl3: 8.61 (d, J = 9.5 Hz, 1.5H), 8.19 (s, 1H), 8.04 (d, J = 7.3 Hz, 1.8H), 7.84 (s, 1H), 7.63 (s, 1H), 2.56 (d, J = 12.7 Hz, 5H), 2.25 (s, 3H) |
| 177 | 544.26/545.30 | 0.83 | DMSO: 8.47 (s, 0.8H), 8.23 (d, J = 9.3 Hz, 1H), 7.84 (d, J = 9.0 Hz, 0.8H), 2.64 (d, J = 17.2 Hz, 5H), 2.58 (d, J = 4.4 Hz, 6.4H), 2.22 (s, 3H) |
| 178 | 598.23/599.29 | 0.95 | CDCl3: 8.60 (d, J = 10.1 Hz, 1.2H), 8.39 (d, J = 9.9 Hz, 0.8H), 8.26-8.17 (m, 1.6H), 8.10 (s, 0.9H), 7.89-7.67 (m, 1.9H), 2.62 (d, J = 6.6 Hz, 4H), 2.59-2.53 (m, 5H), 2.24 (s, 3H) |
| 179 | 540.28/541.33 | 0.80 | DMSO: 8.39 (s, 1.4H), 7.86 (d, J = 7.5 Hz, 2.1H), 7.46 (t, J = 7.7 Hz, 1.1H), 3.81-3.73 (m, 1.8H), 3.30-2.92 (m, 7.9H), 2.89 (s, 0.4H), 2.76 (d, J = 8.0 Hz, 1.6H), 2.66 (d, J = 12.2 Hz, 7.7H), 2.59 (s, 6.9H), 2.54 (s, 3H), 2.24 (s, 3H) |
| 180 | 594.25/595.25 | 0.93 | CD3CN: 8.29 (d, J = 10.0 Hz, 1H), 8.16-7.83 (m, 4H), 3.91-3.00 (m, J = 108.8, 106.6, 34.3 Hz, 8H), 2.89 (s, 2H), 2.80 (d, J = 3.2 Hz, 2H), 2.75-2.66 (m, 2H), 2.58 (s, 5H), 2.26 (s, 3H) |

2.14) Preparation of 1-(4-benzylpiperidin-1-yl)-3-(3, 5-dimethyl-1-(3-methyl-[1,2,4]triazolo[4,3-b]pyridazin-6-yl]-1H-pyrazol-4-yl)propane-1-thione (45)

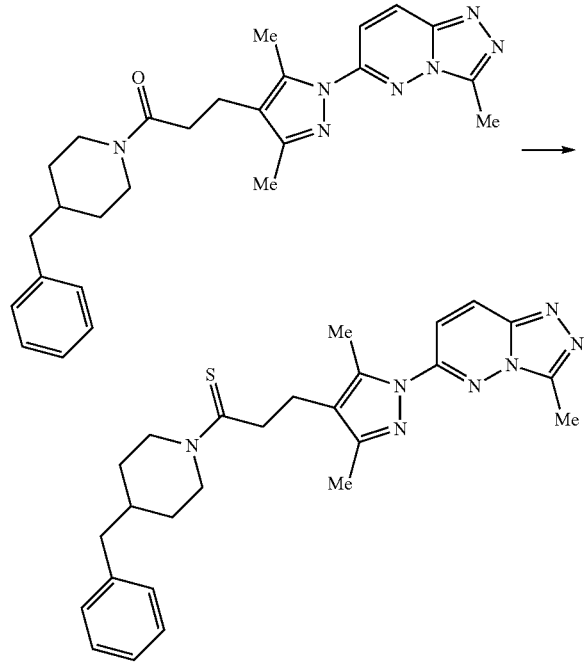

Example C25-140 was dissolved in toluene and Lawesson's reagent (0.6 eq.) added. The reaction mixture was stirred at 110° C. in a sealed tube for 3 h. The crude mixture was concentrated in vacuo and purified via column chromatography over silica (CH$_2$Cl$_2$/IPrOH) to obtain the desired product (96% yield).

$^1$H NMR: (400 MHz, CDCl$_3$): δ (ppm)=8.08 (d, 1H, J=9.9 Hz), 7.98 (d, 1H, J=9.9 Hz), 7.21-7.25 (m, 2H), 7.16-7.21 (m, 1H), 7.03-7.07 (m, 2H), 5.67 (m, 1H), 4.14 (m, 1H), 3.05 (ddd, 1H, J=12.5, 12.5, 2.0 Hz), 2.85-3.00 (m, 5H), 2.76 (s, 3H), 2.66 (s, 3H), 2.57 (dd, 1H, J=13.5, 6.7 Hz), 2.44 (dd, 1H, J=13.3, 7.5 Hz), 2.29 (s, 3H), 1.67-1.91 (m, 3H), 1.35 (dddd, 1H, J=12.5, 12.5, 12.5, 3.3 Hz), 1.03 (dddd, 1H, J=12.3, 12.3, 12.3, 4.0 Hz)

LC/MS: m/z=473.9, R$_t$=1.55 min (method 4)

2.15) Preparation of 6-(4-(3-(4-benzylpiperidin-1-yl)-3,5-dimethyl-1H-pyrazol-1-yl)-3-methyl-[1,2,4]triazolo[4,3-b]pyridazine (46)

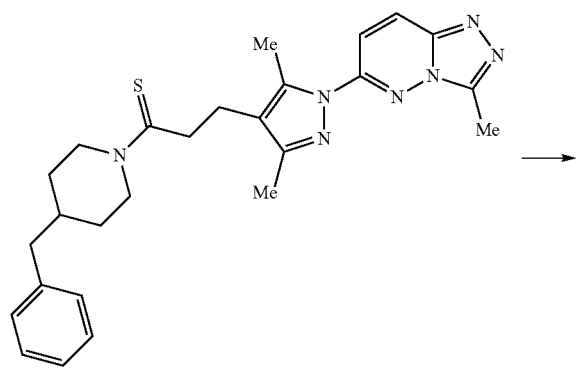

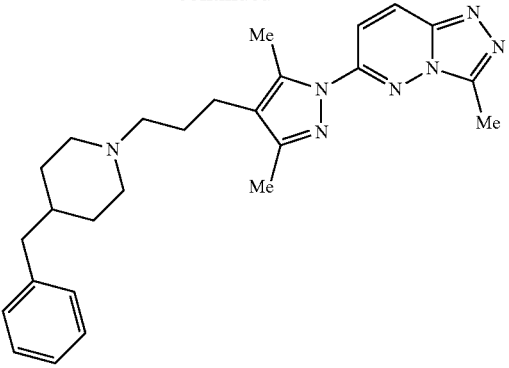

To a solution of thioamide 45 in THF, MeI (50 eq.) was added. The reaction was stirred at room temperature until complete conversion, the solvent was removed in vacuo. The crude mixture was dissolved in ethyl acetate and water (1:1) and NaBH$_3$CN (1.1 eq.) was added. The mixture was stirred until completion of the reaction, quenched by addition of 20% aqueous sodium hydroxide solution and extracted several times with diethyl ether. The combined organic layers were dried over Na$_2$SO$_4$, the solvent removed in vacuo and the crude product was purified via column chromatography over silica (CH$_2$Cl$_2$/MeOH) to obtain the desired product (41%).

$^1$H NMR: (400 MHz, CDCl$_3$): δ (ppm)=8.06 (d, 1H, 10.2 Hz), 7.99 (d, 1H, J=9.9 Hz), 7.24-7.29 (m, 2H), 7.16-7.21 (m, 1H), 7.11-7.15 (m, 2H) 2.97 (d, 1H, J=12.3 Hz), 2.77 (s, 3H), 2.63 (s, 3H), 2.54 (d, 1H, J=6.8 Hz), 2.37-2.47 (m, 5H), 2.26 (s, 3H), 1.95 (t, 2H, J=11.3 Hz), 1.62-1.78 (m, 4H), 1.48-1.61 (m, 1H), 1.34-1.44 (m, 2H)

LC/MS: m/z=444.0, R$_t$=1.16 min (method 4)

2.16) Preparation of Methyl 2-methyl-3-phenylpropanoate

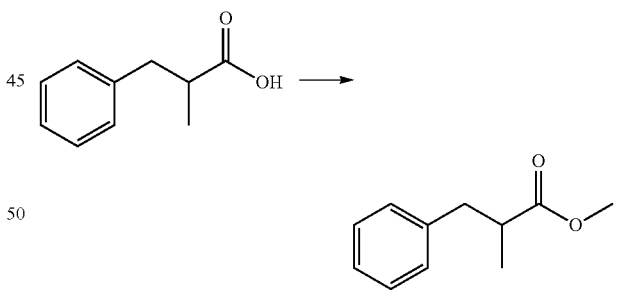

To a solution of 2-methyl-3-phenylpropanoic acid (4.9 g, 29.84 mmol) in MeOH (100 mL) was added thionyl chloride (7.1 g, 59.68 mmol) in MeOH (10 mL) at 0° C. The reaction mixture was stirred 16 h at room temperature. The solvent was evaporated in vacuo, the residue washed with saturated aqueous Na$_2$CO$_3$ solution and extracted with EtOAc (3×). The combined organic layers were washed with saturated aqueous NaCl solution and dried over Na$_2$SO$_4$. Filtration and evaporating the solvent yielded the title compound as a yellow liquid (5.1 g, 95%); $^1$H NMR (400 MHz, CDCl$_3$): δ 7.31-7.25 (m, 2H), 7.23-7.13 (m, 3H), 3.64 (s, 3H), 3.03 (q, J=6.5 Hz, 1H), 2.79-2.61 (m, 2H), 1.15 (d, J=6.8 Hz, 3H); R$_f$=0.51 (PE/EtOAc=9:1).

2.17) Preparation of Methyl 2-benzyl-3-cyano-2-methylpropanoate

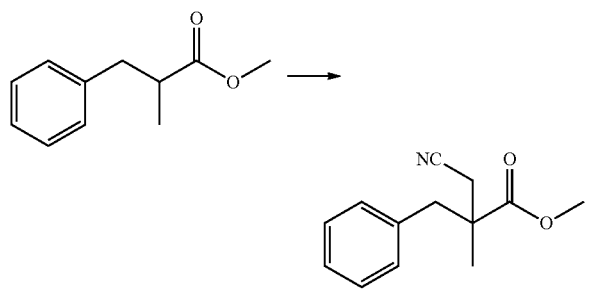

Diisopropylamine (3.0 g, 29.62 mmol) was dissolved in dry THF (7 mL) and nBuLi in hexanes (1.6 M, 18.5 mL, 26.93 mmol) was added at −78° C. dropwise. After stirring for 1 h at the same temperature methyl 2-methyl-3-phenylpropanoate (4.8 g, 26.93 mmol) was added dropwise and the reaction mixture was stirred 1 h at −78° C. Bromoacetonitrile (3.6 g, 29.62 mmol) was added dropwise, the mixture was slowly warmed to room temperature and stirred overnight. 1 M HCl and saturated aqueous NaCl solution were added and the aqueous layer extracted with diethylether (3×). The combined organic layers were washed with saturated aqueous NaHCO₃ solution (2×), H₂O (2×) and saturated aqueous NaCl solution. Drying over Na₂SO₄, filtration and evaporation of the solvent gave the crude product that was purified by flash chromatography eluting with a gradient of PE/EtOAc 100:00-80:20. The title compound was obtained as a colorless liquid (4.1 g, 69%); $^1$H NMR (400 MHz, CDCl₃): δ 7.33-7.23 (m, 3H), 7.14-7.09 (m, 2H), 3.73 (s, 3H), 3.12 (d, J=13.7 Hz, 1H), 2.91 (d, J=13.7 Hz, 1H), 2.57 (d, J=16.8 Hz, 1H), 2.47 (d, J=16.8 Hz, 1H), 1.43 (s, 3H); $R_f$=0.29 (PE/EtOAc=9:1).

2.18) Preparation of 4-Benzyl-4-methylpyrrolidin-2-one

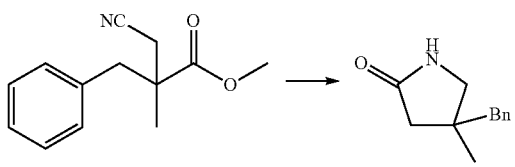 [SMILES: COC(=O)C(C)(CC#N)Cc1ccccc1 ; CC1(Cc2ccccc2)CNC(=O)C1]

Methyl 2-benzyl-3-cyano-2-methylpropanoate (4.1 g, 18.73 mmol) was dissolved in THF (66 mL) and H₂O (33 mL). CoCl₂·6H₂O (2.2 g, 9.37 mmol) and NaBH₄ (3.5 g, 93.66 mmol) were added portionwise. The reaction mixture was stirred 48 h at room temperature and filtered. The solvent was evaporated in vacuo and the residue purified by flash chromatography eluting with a gradient of DCM/MeOH 100:00→90:10. The title compound was obtained as a colorless solid (1.4 g, 41%); LC-MS (ESI+) m/z: [M+H]⁺ Calcd. for C₁₂H₁₅NO 189.12 found 190.24, $t_R$=0.99 min (method a).

2.19) Preparation of 3-Benzyl-3-methylpyrrolidine

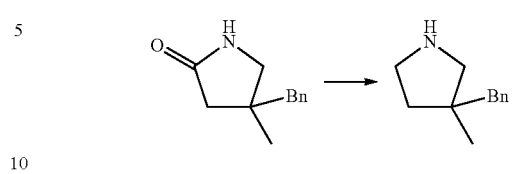

To a suspension of LiAlH₄ (880 mg, 3.70 mmol) in diethylether (15 mL) was added 4-benzyl-4-methylpyrrolidin-2-one (1.4 g, 7.40 mmol) in THF (3 mL) dropwise. The reaction mixture was refluxed for 15 h. Saturated aqueous Na₂SO₄ solution was added dropwise until no more hydrogen gas evolved. Filtration and evaporating of the solvent in vacuo yielded the title compound as a colorless liquid (1.2 g, 93%). LC-MS (ESI+) m/z: [M+H]⁺ Calcd. for C₁₂H₁₇N, 175.28 found 176.24, $t_R$=0.85 min (method a).

2.20) Preparation of 3-(3,5-dimethyl-1-(3-methyl-[1,2,4]triazolo[4,3-b]pyridazin-6-yl)-1H-pyrazol-4-yl)-1-(piperazin-1-yl)propan-1-one

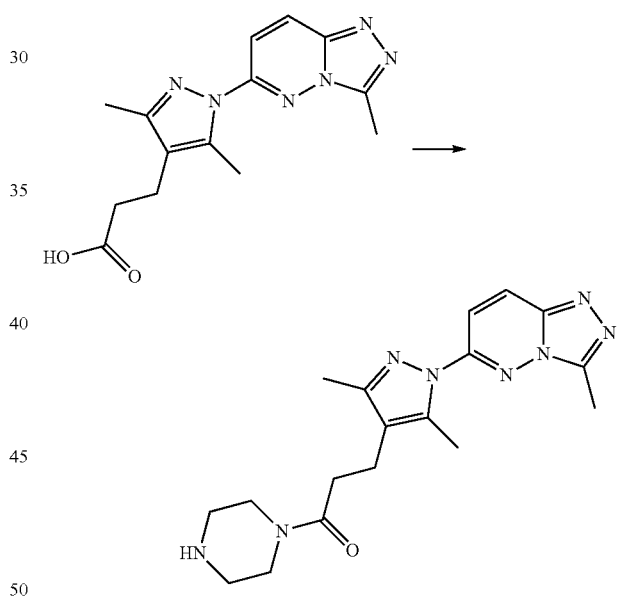

A solution of 3-(3,5-dimethyl-1-(3-methyl-[1,2,4]triazolo[4,3-b]pyridazin-6-yl)-1H-pyrazol-4-yl)propanoic acid (8.0 g, 0.027 mol) in dry DCM (220 mL) and dry DMF (220 mL) was cooled to 0° C. EDC hydrochloride (8.7 g, 0.046 mol), Oxyma (6.8 g, 0.048 mol) and NaHCO₃ (9.1 g, 0.110 mol) were added subsequently and the reaction mixture was stirred for 10 min. 1-Boc-piperazine (6.1 g, 0.033 mol) was added and the mixture was allowed to warm to room temperature. After stirring for 17 h saturated aqueous NH₄Cl solution was added and the mixture was extracted with EtOAc (3×). The combined organic layers were washed with saturated aqueous NaHCO₃ and NaCl solution. After drying over Na₂SO₄ and filtration the residue obtained was purified by flash chromatography eluting with a gradient of DCM/MeOH 100:00→95:05. The combination of the appropriate fractions yielded a colorless solid that was dissolved in DCM (20 mL) and trifluoroacetic acid (20 mL) was added. After stirring for 2 h at room temperature the reaction mixture was neutralized with 1 N NaOH solution and extracted with DCM (3×). The combined organic layers were dried over $Na_2SO_4$ and filtered. The title compound was obtained as a light yellow solid (5.9 g, 60% over two steps). LC-MS (ESI+) m/z: [M+H]$^+$ Calcd. for $C_{18}H_{24}N_8O$ 368.21 found 369.32, $t_R$=0.78 min (method a).

The compounds described in the table below were obtained in a similar fashion as described in the example procedure mentioned above. All used amines except for 3-benzyl-3-methylpyrrolidine are commercially available.

| Example | Structure | $t_R$/ method | Mass (calc./ found) | NMR data |
|---|---|---|---|---|
| 95 | 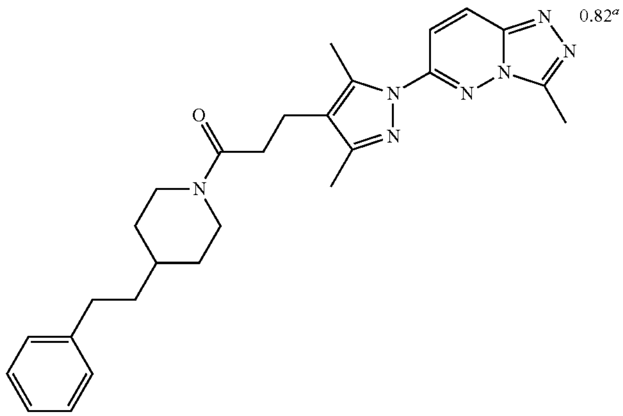 | 0.82$^a$ | 471.27/ 472.13 | CD$_3$OD: 8.16 (d, J = 10.0 Hz, 1 H), 8.01 (d, J = 10.0 Hz, 1 H), 7.19-7.05 (m, 3 H), 7.00-6.93 (m, 2 H), 4.54 (d, J = 13.2 Hz, 1 H), 3.84 (d, J = 13.6 Hz, 1 H), 2.97 (dd, J = 13.1, 2.5 Hz, 1 H), 2.92-2.67 (m, 3 H), 2.73 (s, 3 H), 2.65 (s, 3 H), 2.58-2.45 (m, 2 H), 2.48 (t, J = 8.2 Hz, 2 H), 2.30 (s, 3 H), 1.75 (d, J = 12.5 Hz, 1 H), 1.68 (d, J = 13.0 Hz, 1H), 1.55-1.44 (m, 1 H), 1.42-1.34 (m, 2 H), 1.06-0.93 (m, 1 H), 0.71-0.58 (m, 1 H) |
| 102 | *HCl | 0.86$^a$ | 458.25/ 459.21 | Mixture of Conformers (ca. 0.6:0.4), D$_2$O: 8.22 (t, J = 10.3 Hz, 1 H), 7.93-7.85 (m, 1 H), 7.27-7.06 (m, 5 H), 4.38 (d, J = 14.2 Hz, 0.6 H), 4.15 (d, J = 11.6 Hz, 0.4 H), 3.88 (d, J = 15.1 Hz, 0.4 H), ), 3.79 (d, J = 14.2 Hz, 0.6 H), 3.63-3.54 (m, 0.4 H), 3.47-3.35 (m, 1 H), 3.32-3.11 (m, 2.6 H), 2.99-2.84 (m, 1.6 H), 2.84-2.79 (m, 1 H), 2.76-2.61 (m, 3.4 H), 2.70 (s, 1.8 H), 2.68 (s, 1.2 H), 2.54-2.48 (m, 1 H), 2.46 (s, 1.2 H), 2.38 (s, 1.8 H), 2.18 (s, 1.2 H), 2.07 (s, 1.8 H) |
| 103 | 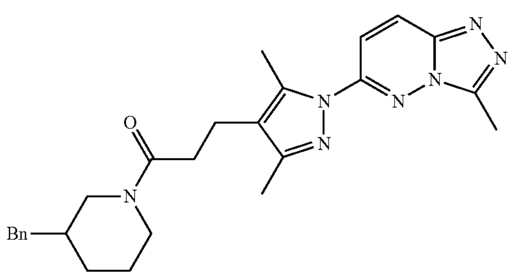 [SMILES: Cc1nn(-c2ccc3nnc(C)n3n2)c(C)c1CCC(=O)N1CCCC(Cc2ccccc2)C1] | 1.15$^a$ | 457.26/ 458.31 | Mixture of Conformers (ca. 0.6:0.4), CD3OD: 8.20 (t, J = 10.3 Hz, 1 H), 8.01 (d, J = 10.0 Hz, 1 H), 7.19-7.02 (m, 5 H), 4.38 (d, J = 12.6 Hz, 0.6 H), 4.21 (d, J = 9.1 Hz, 0.4 H), 3.70 (d, J = 13.4 Hz, 0.6 H), 3.64 (d, J = 15.2 Hz, 0.4 H), 3.14-3.06 (m, 0.4 H), 2.83-2.72 (m, 2.6 H), 2.71 (s, 3 H), 2.64 (s, 1.2 H), 2.62-2.57 (m, 1 H), 2.56 (s, 1.8 H), 2.54-2.48 (m, 1 H), 2.44 (d, J = 7.4 Hz, 1 H), 2.42-2.35 (m, 1 H), 2.28 (s, 1.2 H), 2.19 (s, 1.6 H), 1.79-1.54 (m, 3 H), 1.49-1.40 (m, 0.6 H), 1.36-1.27 (m, 0.8 H), 1.25-1.11 (m, 1.8 H) |
| 104 | 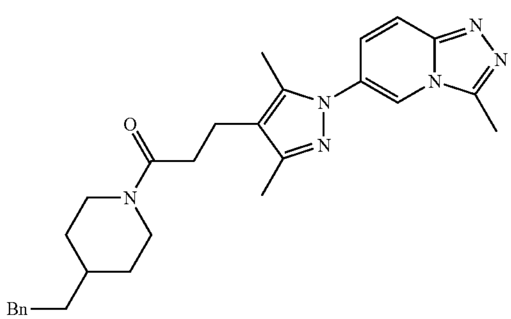 [SMILES: Cc1nn(-c2ccc3nnc(C)n3c2)c(C)c1CCC(=O)N1CCC(CCc2ccccc2)CC1] | 1.11$^a$ | 470.28/ 471.31 | CD3OD: 8.50-8.45 (m, 1 H), 7.77 (dd, J = 9.7, 0.8 Hz, 1 H), 7.55 (dd, J = 9.7, 1.8 Hz, 1 H), 7.25-7.17 (m, 2 H), 7.15-7.09 (m, 3 H), 4.53 (d, J = 13.1 Hz, 1 H), 3.88 (d, J = 13.6 Hz, 1 H), 3.00 (td, J = 13.0, 2.4 Hz, 1 H), 2.87-2.75 (m, 2 H), 2.74 (s, 3 H), 2.68-2.50 (m, 5 H), 2.32 (s, 3 H), 2.27 (s, 3 H), 1.79 (d, J = 13.1 Hz, 2 H), 1.59-1.47 (m, 3 H), 1.07-0.96 (m, 1 H), 0.92-0.82 (m, 1 H) |

| Example | Structure | $t_R$/ method | Mass (calc./ found) | NMR data |
|---|---|---|---|---|
| 105 | 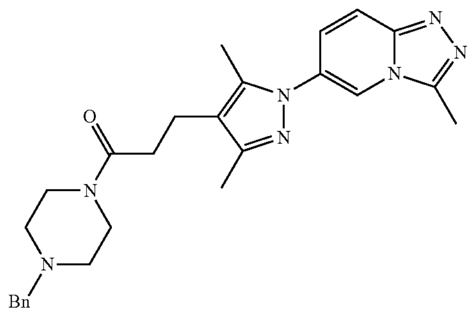 [SMILES: Cc1nn(-c2ccc3nnc(C)n3c2)c(C)c1CCC(=O)N1CCN(Cc2ccccc2)CC1] | 0.77[a] | 457.26/ 458.31 | CD3OD: 8.51-8.46 (m, 1 H), 7.85-7.78 (m, 1 H), 7.56 (dd, J = 9.7, 1.8 Hz, 1 H), 7.31-7.22 (m, 5 H), 3.60 (t, J = 5.0 Hz, 2 H), 3.50 (s, 2 H), 3.47 (t, J = 5.0 Hz, 2 H), 2.78 (t, J = 7.3 Hz, 2 H), 2.77 (s, 3 H), 2.59 (t, J = 7.3 Hz, 2 H), 2.41 (t, J = 5.1 Hz, 1 H), 2.32 (t, J = 5.2 Hz, 2 H), 2.31 (s, 3 H), 2.26 (s, 3 H) |
| 106 | 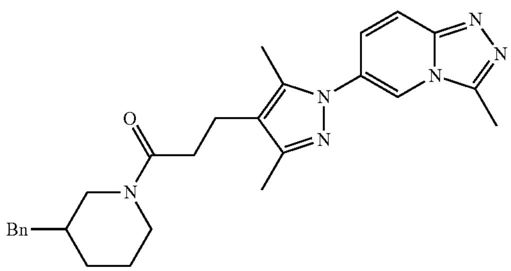 [SMILES: Cc1nn(-c2ccc3nnc(C)n3c2)c(C)c1CCC(=O)N1CCCC(Cc2ccccc2)C1] | 1.06[a] | 456.26/ 457.35 | Mixture of Conformers (ca. 0.5:0.5), CD$_3$OD: 8.42 (d, J = 6.1 Hz, 1 H), 7.78 (t, J = 9.0 Hz, 1 H), 7.53-7.45 (m, 1 H), 7.26-7.10 (m, 5 H), 4.37 (t, J = 15.9 Hz, 1 H), 3.78 (d, J = 13.6 Hz, 0.5 H), 3.69 (d, J = 11.9 Hz, 0.5 H), 3.11-3.01 (m, 0.5 H), 2.83-2.43 (m, 7.5 H), 2.63 (s, 3 H), 2.30 (s, 1.5 H), 2.26 (s, 1.5 H), 2.21 (s, 1.5 H), 2.16 (s, 1.5 H), 1.85-1.67 (m, 2 H), 1.65-1.54 (m, 1 H), 1.32-1.17 (m, 2 H) |
| 107 | 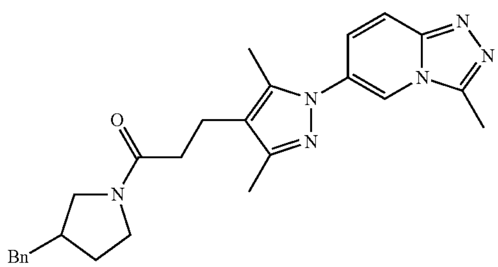 [SMILES: Cc1nn(-c2ccc3nnc(C)n3c2)c(C)c1CCC(=O)N1CCC(Cc2ccccc2)C1] | 1.00[a] | 442.25/ 443.35 | Mixture of Conformers (ca. 0.5:0.5), CD$_3$OD: 8.51-8.44 (m, 1 H), 7.79 (d, J = 9.6 Hz, 1 H), 7.57-7.49 (m, 1 H), 7.28-7.22 (m, 2 H), 7.20-7.14 (m, 3 H), 3.65-3.34 (m, 3 H), 3.12-3.03 (m, 1 H), 2.81-2.74 (m, 3 H), 2.69-2.62 (m, 2 H), 2.55-2.41 (m, 4 H), 2.31 (s, 1.5 H), 2.28 (s, 1.5 H), 2.27 (s, 1.5 H), 2.23 (s, 1.5 H), 2.05-1.92 (m, 1 H), 1.73-1.54 (m, 1 H), 1.38-1.12 (m, 1 H) |
| 119 | 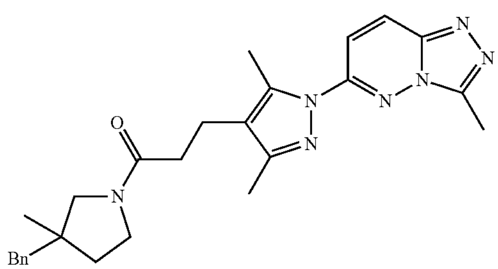 [SMILES: Cc1nn(-c2ccc3nnc(C)n3n2)c(C)c1CCC(=O)N1CCC(C)(Cc2ccccc2)C1] | 1.10[a] | 457.26/ 458.35 | CD$_3$OD: 8.15 (d, J = 10.0 Hz, 0.5 H), 8.12 (d, J = 10.0 Hz, 0.5 H), 7.98 (d, J = 3.7 Hz, 0.5 H), 7.96 (d, J = 3.7 Hz, 0.5 H), 7.17-7.06 (m, 2 H), 7.03-6.97 (m, 2 H), 3.56-3.47 (m, 0.5 H), 3.47-3.31 (m, 2 H), 3.21 (d, J = 10.1 Hz, 0.5 H), 3.07 (d, J = 11.7 Hz, 0.5 H), 2.92 (d, J = 10.0 Hz, 0.5 H), 2.87-2.77 (m, 2 H), 2.75 (s, 1.5 H), 2.72 (s, 1.5 H), 2.66 (s, 1.5 H), 2.62 (s, 1.5 H), 2.59-2.42 (m, 4 H), 2.31 (s, 1.5 H), 2.27 (s, 1.5 H), 1.88-1.73 (m, 1 H), 1.64-1.52 (m, 1 H), 0.90 (s, 1.5 H), 0.80 (s, 1.5 H) |
| 167 | 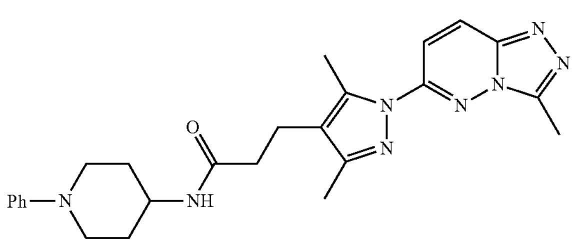 [SMILES: Cc1nn(-c2ccc3nnc(C)n3n2)c(C)c1CCC(=O)NC1CCN(c2ccccc2)CC1] | 0.84[a] | 458.25/ 459.30 | CD$_3$OD: 8.21 (d, J = 10.0 Hz, 1 H), 8.03 (d, J = 10.0 Hz, 1 H), 7.18-7.11 (m, 2 H), 6.90 (d, J = 8.8 Hz, 2 H), 6.76 (t, J = 6.8 Hz, 1 H), 3.82-3.72 (m, 1 H), 3.50-3.41 (m, 2 H), 2.84-2.76 (m, 4 H), 2.74 (s, 3H), 2.67 (s, 3 H), 2.39 (t, J = 7.3 Hz, 2 H), 2.29 (s, 3 H), 1.87 (dd, J = 12.8, 3.8 Hz, 2 H), 1.62-1.49 (m, 2 H) |

| Example | Structure | $t_R$/ method | Mass (calc./ found) | NMR data |
|---|---|---|---|---|
| 168 | 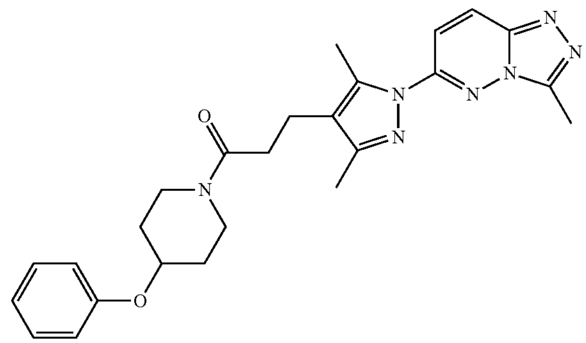 [SMILES: Cc1nn(-c2ccc3nnc(C)n3n2)c(C)c1CCC(=O)N1CCC(Oc2ccccc2)CC1] | 1.11<sup>a</sup> | 459.24/ 460.22 | CD$_3$OD: 8.24 (d, J = 10.0 Hz, 1H), 8.03 (d, 10.0 Hz, 1 H), 7.20-7.14 (m, 2 H), 6.86 (t, J = 7.3 Hz, 1 H), 6.77 (t, J = 8.7 Hz, 1 H), 4.56-4.48 (m, 2 H), 4.00-3.91 (m, 1 H), 3.74-3.63 (m, 1 H), 3.46-3.33 (m, 2 H), 2.90-2.68 (m, 3 H), 2.71 (s, 3 H), 2.66 (s, 3 H), 2.62-2.52 (m, 1 H), 2.30 (s, 3 H), 1.98-1.89 (m, 1 H), 1.88-1.80 (m, 1 H), 1.68-1.55 (m, 1 H), 1.42-1.31 (m, 1H) |

2.21) Preparation of Methyl 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-fluorobenzoate To a solution of 3-(3,5-dimethyl-1-(3-methyl-[1,2,4]triazolo[4,3-b]pyridazin-6-yl)-1H-pyrazol-4-yl)-1-(piperazin-1-yl)propan-1-one (50 mg, 0.14 mmol) in dry 1,2-dichloroethane (2 mL) methyl 2-fluoro-4-formylbenzoate (31 mg, 0.17 mmol) and NaBH(OAc)$_3$ (42 mg, 0.19 mmol) were added subsequently. The reaction mixture was stirred overnight at room temperature. Saturated aqueous NaHCO$_3$ solution was added and the aqueous layer extracted with EtOAc (1×). The organic layer was dried over Na$_2$SO$_4$ and filtered over silica eluting with DCM/MeOH (9:1). Evaporating the solvent yielded the title compound as colorless solid (61 mg, 84%). If necessary the products were purified by flash chromatography eluting with a gradient of DCM/MeOH 100:00→90:10. In case of precipitating products petroleum ether was added, the solid was filtered and applied to flash chromatography. In case of phenoles and free sulfonamides an alternative workup procedure was applied: Petroleum ether was added to the reaction mixture and the resulting precipitate was filtered. The remaining solid was suspended in 1 M HCl and stirred for 2 h at room temperature. Afterwards the mixture was neutralized with NaHCO$_3$ and purified by reverse phase flash chromatography eluting with a gradient of H$_2$O+0.05% TFA/MeCN+0.05% TFA 95:05→60:40.

2.22) Preparation of 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-fluorobenzoic acid hydrochloride To methyl 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-fluorobenzoate (61 mg, 0.11 mmol) in THF (1.5 mL) and water (0.5 mL) was added LiOH·H$_2$O (14 mg, 0.33 mmol). The reaction mixture was stirred at room temperature for 5 h. The mixture was neutralized with 1 M HCl and applied to reverse phase flash chromatography eluting with a gradient of H$_2$O+0.05% TFA/MeCN+0.05% TFA 95:05→60:40. Salt exchange yielded the title compound as a colorless solid (41 mg, 67%).

The compounds described in the table below were obtained in a similar fashion as described in the example procedures mentioned above. All used aldehydes are commercially available.

| Example | Structure | $t_R$/method | Mass (calc./found) | NMR data |
|---|---|---|---|---|
| 144 | 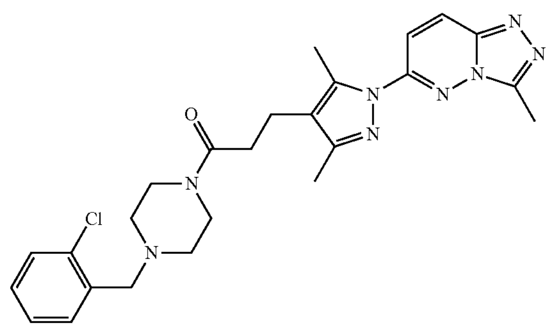 | 0.88[a] | 492.22/ 493.24 | CD$_3$OD: 8.25 (d, J = 10.0 Hz, 1 H), 8.05 (d, J = 10.1 Hz, 1 H), 7.41 (dd, J = 7.3, 2.0 Hz, 1 H), 7.30-7.16 (m, 3 H), 3.60 (t, J = 5.0 Hz, 2 H), 3.50 (s, 2 H), 3.43 (t, J = 5.0 Hz, 2 H), 2.81 (t, J = 7.1 Hz, 2 H), 2.73 (s, 3 H), 2.65 (s, 3 H), 2.60 (t, J = 7.1 Hz, 2 H), 2.43 (t, J = 5.1 Hz, 2 H), 2.28 (s, 3 H), 2.18 (t, J = 5.0 Hz, 2H) |
| 143 | 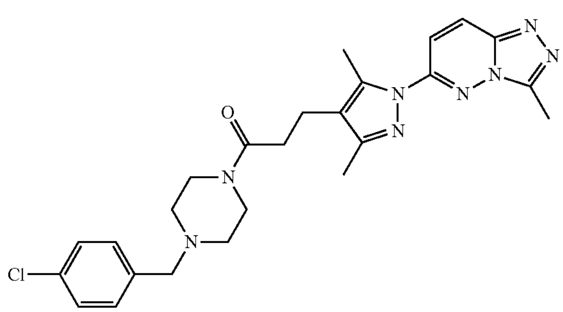 [SMILES: Cc1nn(-c2ccc3nnc(C)n3n2)c(C)c1CCC(=O)N1CCN(Cc2ccc(Cl)cc2)CC1] | 0.90[a] | 492.22/ 493.24 | CD$_3$OD: 8.25 (d, J = 10.0 Hz, 1 H), 8.05 (d, J = 10.0 Hz, 1 H), 7.24 (d, J = 8.3 Hz, 2 H), 7.20 (d, J = 8.5 Hz, 2 H), 3.59 (t, J = 5.0 Hz, 2 H), 3.44 (t, J = 5.0 Hz, 2 H), 3.40 (s, 2 H), 2.79 (t, J = 7.2 Hz, 2 H), 2.74 (s, 3 H), 2.64 (s, 3 H), 2.59 (t, J = 7.2 Hz, 2 H), 2.37 (t, J = 5.1 Hz, 2 H), 2.27 (s, 3 H), 2.20 (t, J = 4.9 Hz, 2H) |
| 142 | 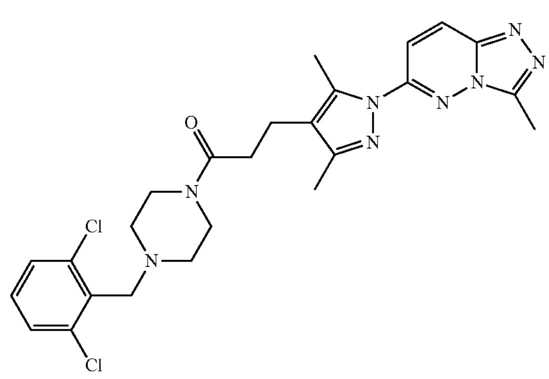 [SMILES: Cc1nn(-c2ccc3nnc(C)n3n2)c(C)c1CCC(=O)N1CCN(Cc2c(Cl)cccc2Cl)CC1] | 0.87[a] | 526.18/ 527.20 | CD$_3$OD: 8.25 (d, J = 10.0 Hz, 1 H), 8.07 (d, J = 10.0 Hz, 1 H), 7.34-7.28 (m, 2 H), 7.21 (dd, J = 8.8, 7.2 Hz, 1 H), 3.64 (s, 2 H), 3.55 (t, J = 5.0 Hz, 2 H), 3.36 (t, J = 5.0 Hz, 2 H), 2.81 (t, J= 7.1 Hz, 2 H), 2.76 (s, 3 H), 2.66 (s, 3 H), 2.59 (t, J = 7.1 Hz, 2 H), 2.48 (t, J = 5.1 Hz, 2 H), 2.29 (s, 3 H), 2.26 (t, J = 5.0 Hz, 2H) |
| 108 | 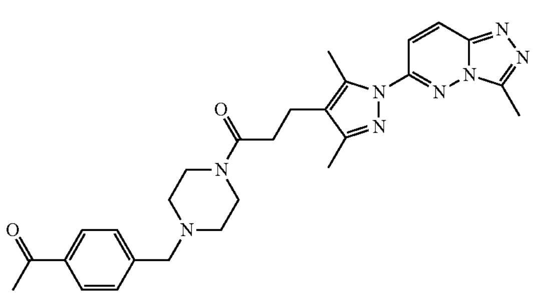 [SMILES: CC(=O)c1ccc(CN2CCN(C(=O)CCc3c(C)nn(-c4ccc5nnc(C)n5n4)c3C)CC2)cc1] | 0.82[a] | 500.26/ 501.32 | CD$_3$OD: 8.26 (d, J = 10.0 Hz, 1 H), 8.05 (d, J = 10.0 Hz, 1 H), 7.87 (d, J = 8.3 Hz, 2 H), 7.36 (d, J = 8.2 Hz, 2 H), 3.60 (t, J = 5.0 Hz, 2 H), 3.49 (s, 2 H), 3.46 (t, J = 5.0 Hz, 2 H), 2.80 (t, J = 7.2 Hz, 2 H), 2.73 (s, 3 H), 2.65 (s, 3 H), 2.63-2.57 (m, 2 H), 2.57 (s, 3 H), 2.39 (t, J = 5.1 Hz, 2 H), 2.28 (s, 3 H), 2.26 (t, J = 5.0 Hz, 2 H) |

| Example | Structure | $t_R$/method | Mass (calc./found) | NMR data |
|---|---|---|---|---|
| 141 | 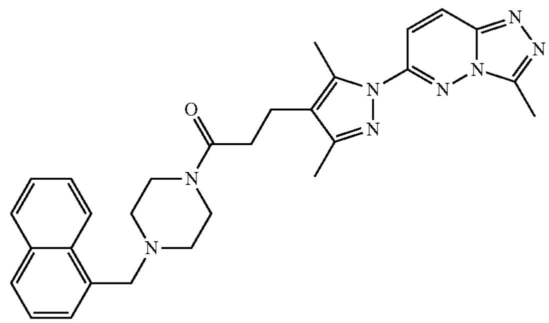 [SMILES: Cc1nn(-c2ccc3nnc(C)n3n2)c(C)c1CCC(=O)N1CCN(Cc2cccc3ccccc23)CC1] | 0.91[a] | 508.27/ 509.36 | CD$_3$OD: 8.24 (d, J = 10.0 Hz, 1 H), 8.20-8.15 (m, 1 H), 8.04 (d, J = 10.1 Hz, 1 H), 7.83-7.78 (m, 1 H), 7.73 (d, J = 8.0 Hz, 1 H), 7.45-7.38 (m, 2 H), 7.29-7.21 (m, 2 H), 3.79 (s, 2 H), 3.57 (t, J = 4.9 Hz, 2 H), 3.38 (t, J = 5.0 Hz, 2 H), 2.80 (t, J = 7.2 Hz, 2 H), 2.69 (s, 3 H), 2.62 (s, 3 H), 2.59 (t, J = 7.2 Hz, 2 H), 2.45 (t, J = 5.1 Hz, 2 H), 2.28 (s, 3 H), 2.20 (t, J = 4.9 Hz, 2 H) |
| 140 | 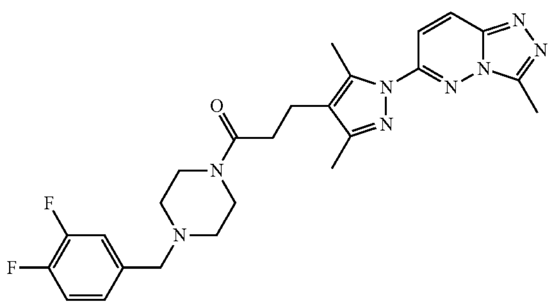 [SMILES: Cc1nn(-c2ccc3nnc(C)n3n2)c(C)c1CCC(=O)N1CCN(Cc2ccc(F)c(F)c2)CC1] | 0.88[a] | 494.24/ 495.24 | CD$_3$OD: 8.26 (d, J = 10.0 Hz, 1 H), 8.06 (d, J = 10.0 Hz, 1 H), 7.24-7.09 (m, 2 H), 7.05-6.98 (m, 1 H), 3.60 (t, J = 5.0 Hz, 2 H), 3.46 (t, J = 5.0 Hz, 2 H), 3.41 (s, 2 H), 2.80 (t, J = 7.3 Hz, 2 H), 2.76 (s, 3 H), 2.66 (s, 3 H), 2.60 (t, J = 7.3 Hz, 2 H), 2.38 (t, J = 5.1 Hz, 2 H), 2.28 (s, 3 H), 2.24 (t, J = 5.0 Hz, 2 H) |
| 109 | 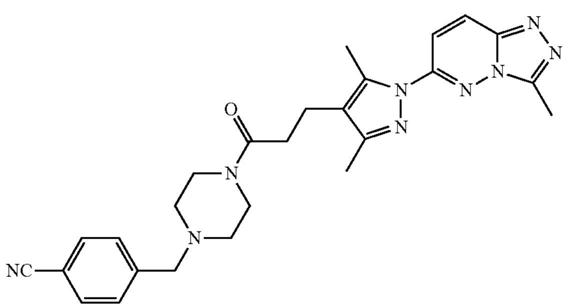 [SMILES: Cc1nn(-c2ccc3nnc(C)n3n2)c(C)c1CCC(=O)N1CCN(Cc2ccc(C#N)cc2)CC1] | 0.83[a] | 483.25/ 484.28 | CD$_3$OD: 8.26 (d, J = 10.1 Hz, 1 H), 8.05 (d, J = 10.0 Hz, 1 H), 7.63 (d, J = 8.3 Hz, 2 H), 7.45 (d, J = 8.3 Hz, 2 H), 3.60 (t, J = 5.0 Hz, 2 H), 3.51 (s, 2 H), 3.46 (t, J = 5.0 Hz, 2 H), 2.79 (t, J = 7.3 Hz, 2 H), 2.75 (s, 3 H), 2.65 (s, 3 H), 2.60 (t, J = 7.3 Hz, 2 H), 2.39 (t, J = 5.1 Hz, 2 H), 2.26 (s, 3 H), 2.25 (t, J = 5.0 Hz, 2 H) |
| 139 | 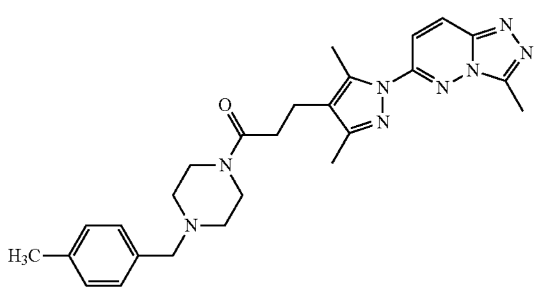 [SMILES: Cc1ccc(CN2CCN(C(=O)CCc3c(C)nn(-c4ccc5nnc(C)n5n4)c3C)CC2)cc1] | 0.88[a] | 482.27/ 473.35 | CD$_3$OD: 8.27 (d, J = 10.0 Hz, 1 H), 8.06 (d, J = 10.0 Hz, 1 H), 7.07-6.99 (m, 4 H), 3.58 (t, J = 5.0 Hz, 2 H), 3.42 (t, J = 5.0 Hz, 2 H), 3.35 (s, 2 H), 2.80 (t, J = 7.2 Hz, 2 H), 2.72 (s, 3 H), 2.65 (s, 3 H), 2.59 (t, J = 7.3 Hz, 2 H), 2.36 (t, J = 5.1 Hz, 2 H), 2.28 (s, 6 H), 2.14 (t, J = 5.4 Hz, 2 H) |
| 110 | 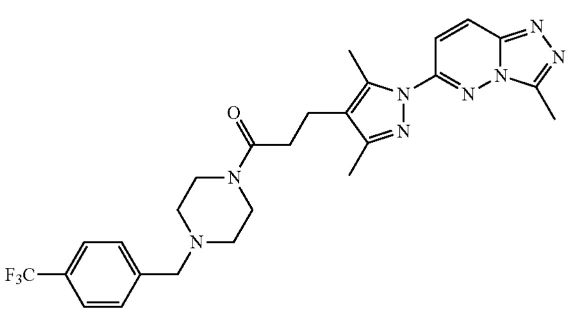 [SMILES: Cc1nn(-c2ccc3nnc(C)n3n2)c(C)c1CCC(=O)N1CCN(Cc2ccc(C(F)(F)F)cc2)CC1] | 0.92[a] | 526.24/ 527.32 | CD$_3$OD: 8.26 (d, J = 10.0 Hz, 1 H), 8.06 (d, J = 10.0 Hz, 1 H), 7.56 (d, J = 8.1 Hz, 2 H), 7.44 (d, J = 8.0 Hz, 2 H), 3.60 (t, J = 5.0 Hz, 2 H), 3.51 (s, 2 H), 3.46 (t, J = 5.0 Hz, 2 H), 2.80 (t, J = 7.3 Hz, 2 H), 2.74 (s, 3 H), 2.65 (s, 3 H), 2.60 (t, J = 7.3 Hz, 2 H), 2.40 (t, J = 5.1 Hz, 2 H), 2.28 (s, 3 H), 2.24 (t, J = 4.9 Hz, 2 H) |

-continued

| Example | Structure | $t_R$/method | Mass (calc./found) | NMR data |
|---|---|---|---|---|
| 111 | 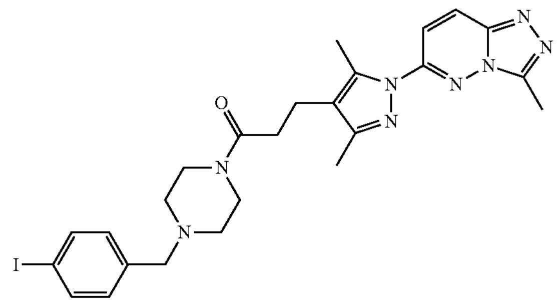 [SMILES: Cc1nn(-c2ccc3nnc(C)n3n2)c(C)c1CCC(=O)N1CCN(Cc2ccc(I)cc2)CC1] | 0.91$^a$ | 584.15/ 585.17 | CD$_3$OD: 8.26 (d, J = 10.0 Hz, 1 H), 8.06 (d, J = 10.0 Hz, 1 H), 7.59 (d, J = 8.3 Hz, 2 H), 7.00 (d, J = 8.2 Hz, 2 H), 3.59 (t, J = 5.0 Hz, 2 H), 3.44 (t, J = 5.0 Hz, 2 H), 3.37 (s, 2 H), 2.80 (t, J = 7.2 Hz, 2 H), 2.74 (s, 3 H), 2.65 (s, 3 H), 2.59 (t, J = 7.2 Hz, 2 H), 2.37 (t, J = 5.1 Hz, 2 H), 2.28 (s, 3 H), 2.19 (t, J = 4.9 Hz, 2 H) |
| 113 | 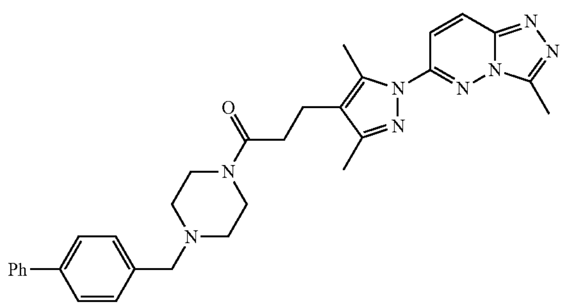 | 0.98$^a$ | 534.29/ 535.36 | CD$_3$OD: 8.26 (d, J = 10.0 Hz, 1H), 8.06 (d, J = 10.0 Hz, 1 H), 7.56 (d, J = 7.3 Hz, 2 H), 7.48 (d, J = 8.1 Hz, 2 H), 7.41 (t, J = 7.6 Hz, 2 H), 7.31 (d, J = 8.1 Hz, 1 H), 7.25 (d, J = 8.1 Hz, 2 H), 3.61 (t, J = 4.8 Hz, 2 H), 3.48-3.42 (m, 4 H), 2.80 (t, J = 7.2 Hz, 2 H), 2.71 (s, 3 H), 2.65 (s, 3 H), 2.60 (t, J = 7.2 Hz, 2 H), 2.41 (t, J = 5.0 Hz, 2 H), 2.28 (s, 3 H), 2.21 (t, J = 4.8 Hz, 2 H) |
| 116 | 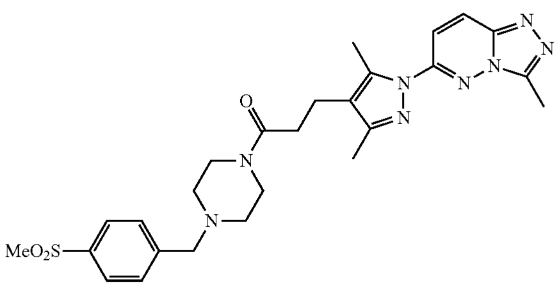 [SMILES: Cc1nn(-c2ccc3nnc(C)n3n2)c(C)c1CCC(=O)N1CCN(Cc2ccc(S(C)(=O)=O)cc2)CC1] | 0.81$^a$ | 536.23/ 537.24 | CD$_3$OD: 8.26 (d, J = 10.0 Hz, 1 H), 8.06 (d, J = 10.0 Hz, 1 H), 7.87 (d, J = 8.4 Hz, 2 H), 7.53 (d, J = 8.3 Hz, 2 H), 3.61 (t, J = 4.9 Hz, 2 H), 3.55 (s, 2 H), 3.47 (t, J = 5.0 Hz, 2 H), 3.10 (s, 3 H), 2.80 (t, J = 7.3 Hz, 2 H), 2.75 (s, 3 H), 2.66 (s, 3 H), 2.60 (t, J = 7.3 Hz, 2 H), 2.41 (t, J = 5.1 Hz, 2 H), 2.29-2.24 (m, 5 H) |
| 114 | 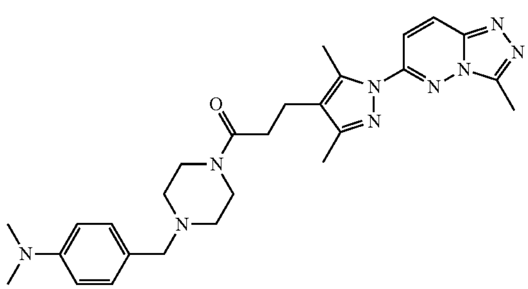 [SMILES: Cc1nn(-c2ccc3nnc(C)n3n2)c(C)c1CCC(=O)N1CCN(Cc2ccc(N(C)C)cc2)CC1] | 0.81$^a$ | 501.30/ 502.36 | CD$_3$OD: 8.26 (d, J = 10.0 Hz, 1H), 8.06 (d, J = 10.0 Hz, 1 H), 6.96 (d, J = 8.6 Hz, 2 H), 6.59 (d, J = 8.7 Hz, 2 H), 3.58 (t, J = 4.9 Hz, 2 H), 3.42 (t, J = 5.0 Hz, 2 H), 3.33-3.28 (m, 2 H), 2.87 (s, 6 H), 2.80 (t, J = 7.2 Hz, 2 H), 2.73 (s, 3 H), 2.64 (s, 3 H), 2.59 (t, J = 7.2 Hz, 2 H), 2.37 (t, J = 5.0 Hz, 2 H), 2.27 (s, 3H), 2.13 (t, J = 4.8 Hz, 2 H) |
| 138 | 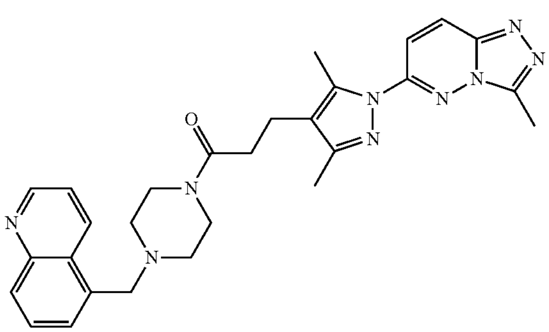 [SMILES: Cc1nn(-c2ccc3nnc(C)n3n2)c(C)c1CCC(=O)N1CCN(Cc2cccc3ncccc23)CC1] | 0.76$^a$ | 509.27/ 510.36 | CD$_3$OD: 8.81 (dd, J = 4.3, 1.6 Hz, 1 H), 8.78 (d, J = 8.6 Hz, 1 H), 8.27 (d, J = 10.0 Hz, 1 H), 7.93 (d, J = 8.5 Hz, 1 H), 7.62-7.56 (m, 1 H), 7.50 (dd, J = 8.6, 4.3 Hz, 1 H), 7.37 (d, J = 6.7 Hz, 2 H), 3.85 (s, 2 H), 3.57 (t, J = 4.8 Hz, 2 H), 3.39 (t, J = 5.0 Hz, 2 H), 2.80 (t, J = 7.2 Hz, 2 H), 2.72 (s, 3 H), 2.65 (s, 3 H), 2.59 (t, J = 7.2 Hz, 2 H), 2.45 (t, J = 5.1 Hz, 2 H), 2.28 (s, 3 H), 2.24 (t, J = 4.9 Hz, 2H) |

| Example | Structure | $t_R$/ method | Mass (calc./ found) | NMR data |
|---|---|---|---|---|
| 115 | 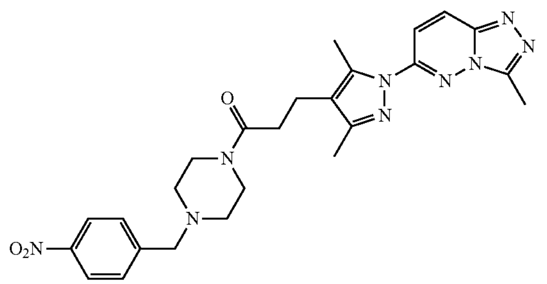 | 0.84[a] | 503.24/ 504.28 | CD₃OD: 8.26 (d, J = 10.0 Hz, 1 H), 8.15 (d, J = 8.7 Hz, 2 H), 8.06 (d, J = 10.0 Hz, 1 H), 7.51 (d, J = 8.7 Hz, 2 H), 3.61 (t, J = 5.0 Hz, 2 H), 3.56 (s, 2 H), 3.48 (t, J = 5.0 Hz, 2 H), 2.80 (t, J = 7.3 Hz, 2 H), 2.75 (s, 3 H), 2.66 (s, 3 H), 2.60 (t, J = 7.3 Hz, 2 H), 2.41 (t, J = 5.1 Hz, 2 H), 2.30-2.24 (m, 5 H) |
| 118 | 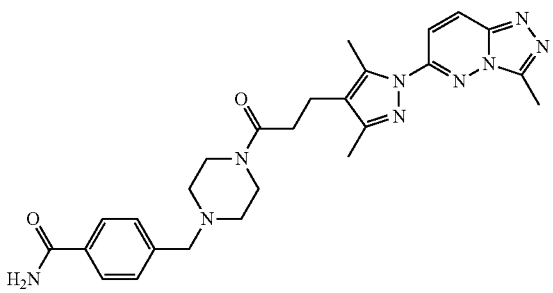 [SMILES: Cc1nn(-c2ccc3nnc(C)n3n2)c(C)c1CCC(=O)N1CCN(Cc2ccc(C(N)=O)cc2)CC1] | 0.75[a] | 501.26/ 502.32 | CD₃OD: 8.26 (d, J = 10.0 Hz, 1 H), 8.06 (d, J = 10.0 Hz, 1 H), 7.78 (d, J = 8.2 Hz, 2 H), 7.33 (d, J = 8.2 Hz, 2 H), 3.60 (t, J = 4.8 Hz, 2 H), 3.48 (s, 2 H), 3.46 (t, J = 4.9 Hz, 2 H), 2.80 (t, J = 7.2 Hz, 2 H), 2.74 (s, 3 H), 2.65 (s, 3 H), 2.60 (t, J = 7.3 Hz, 2 H), 2.39 (t, J = 4.8 Hz, 2 H), 2.28 (s, 3 H), 2.24 (t, J = 4.7 Hz, 2H) |
| 117 | 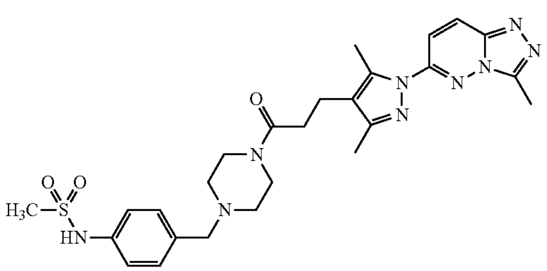 [SMILES: Cc1nn(-c2ccc3nnc(C)n3n2)c(C)c1CCC(=O)N1CCN(Cc2ccc(NS(C)(=O)=O)cc2)CC1] | 0.80[a] | 551.24/ 552.28 | CD₃OD: 8.27 (d, J = 10.0 Hz, 1 H), 8.08 (d, J = 10.0 Hz, 1 H), 7.19 (d, J = 8.6 Hz, 2 H), 7.15 (d, J = 8.6 Hz, 2 H), 3.59 (t, J = 4.8 Hz, 2 H), 3.44 (t, J = 4.9 Hz, 2 H), 3.39 (s, 2 H), 2.93 (s, 3 H), 2.81 (t, J = 7.2 Hz, 2 H), 2.76 (s, 3 H), 2.66 (s, 3 H), 2.60 (t, J = 7.2 Hz, 2 H), 2.38 (t, J = 4.9 Hz, 2 H), 2.28 (s, 3 H), 2.21 (t, J = 4.9 Hz, 2 H) |
| 137 | 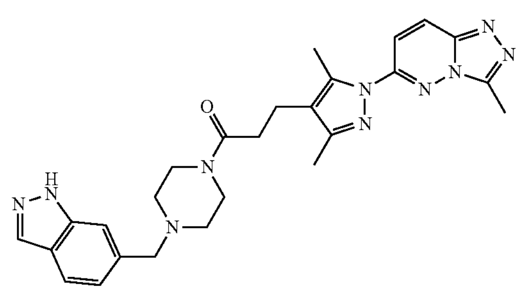 [SMILES: Cc1nn(-c2ccc3nnc(C)n3n2)c(C)c1CCC(=O)N1CCN(Cc2ccc3cn[nH]c3c2)CC1] | 0.79[a] | 498.26/ 499.32 | CD₃OD: 8.25 (d, J = 10.0 Hz, 1 H), 8.05 (d, J = 10.0 Hz, 1H), 7.97 (s, 1 H), 8.27 (d, J = 10.0 Hz, 1 H), 7.62 (d, J = 8.2 Hz, 1 H), 7.40 (s, 1 H), 7.03 (dd, J = 8.3, 1.1 Hz, 1 H), 3.60 (t, J = 4.9 Hz, 2 H), 3.56 (s, 2 H), 3.45 (t, J = 5.0 Hz, 2 H), 2.79 (t, J = 7.2 Hz, 2 H), 2.72 (s, 3 H), 2.64 (s, 3 H), 2.59 (t, J = 7.3 Hz, 2 H), 2.42 (t, J = 5.0 Hz, 2 H), 2.29-2.23 (m, 5 H) |
| 112 | 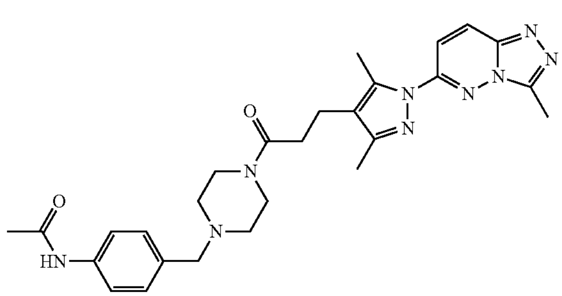 [SMILES: CC(=O)Nc1ccc(CN2CCN(C(=O)CCc3c(C)nn(-c4ccc5nnc(C)n5n4)c3C)CC2)cc1] | 0.79[a] | 515.28/ 516.28 | CD₃OD: 8.26 (d, J = 10.0 Hz, 1 H), 8.05 (d, J = 10.0 Hz, 1 H), 7.42 (d, 8.5 Hz, 2 H), 7.14 (d, J = 8.5 Hz, 2 H), 3.58 (t, J = 4.9 Hz, 2 H), 3.43 (t, J = 4.9 Hz, 2 H), 3.38 (s, 2 H), 2.79 (t, J = 7.2 Hz, 2 H), 2.74 (s, 3 H), 2.64 (s, 3 H), 2.59 (t, J = 7.3 Hz, 2 H), 2.37 (t, J = 5.0 Hz, 2 H), 2.27 (s, 3 H), 2.19 (t, J = 4.9 Hz, 2 H), 2.10 (s, 3 H) |

| Example | Structure | $t_R$/ method | Mass (calc./ found) | NMR data |
|---|---|---|---|---|
| 120 | 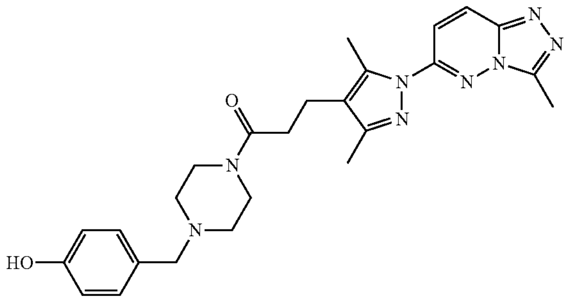 | 0.80$^a$ | 474.25/ 475.35 | d$_6$-DMSO: 9.34 (b, 1 H), 8.37 (d, J = 10.0 Hz, 1 H), 7.85 (d, J = 10.0 Hz, 1 H), 6.98 (d, J = 8.3 Hz, 2 H), 6.65 (d, J = 8.3 Hz, 2 H), 3.42 (b, 2 H), 3.38-3.31 (m, 2 H), 3.25 (s, 2 H), 2.67 (s, 3 H), 2.66-2.61 (m, 2 H), 2.58 (s, 3 H), 2.46 (t, J = 7.4 Hz, 2 H), 2.25-2.21 (m, 2 H), 2.22 (s, 3 H), 2.13 (b, 2 H) |
| 136 | 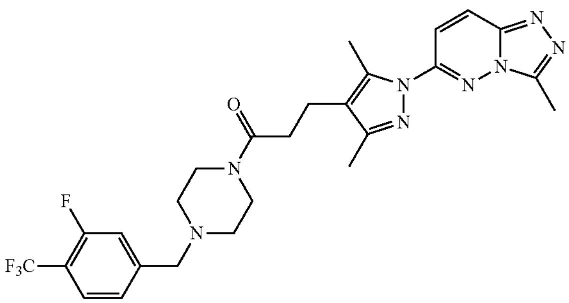 [SMILES: Cc1nn(-c2ccc3nnc(C)n3n2)c(C)c1CCC(=O)N1CCN(Cc2ccc(C(F)(F)F)c(F)c2)CC1] | 0.94$^a$ | 544.23/ 545.28 | CD$_3$OD: 8.26 (d, J = 10.0 Hz, 1 H), 8.06 (d, J = 10.1 Hz, 1 H), 7.58 (t, J = 7.7 Hz, 1 H), 7.29 (d, J = 11.7 Hz, 1 H), 7.23 (d, J = 8.0 Hz, 1 H), 3.62 (t, J = 5.0 Hz, 2 H), 3.52 (s, 2 H), 3.48 (t, J = 5.0 Hz, 2 H), 2.80 (t, J = 7.3 Hz, 2 H), 2.75 (s, 3 H), 2.66 (s, 3 H), 2.60 (t, J = 7.3 Hz, 2 H), 2.41 (t, J = 5.1 Hz, 2 H), 2.31-2.25 (m, 5 H) |
| 135 | 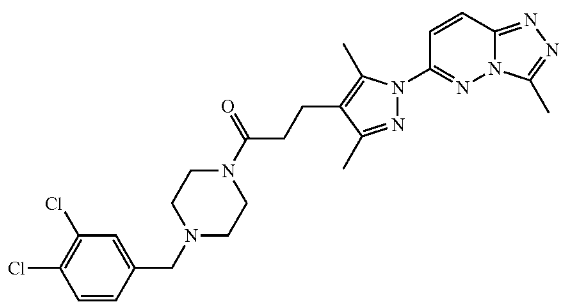 | 0.93$^a$ | 526.18/ 527.20 | CD$_3$OD: 8.26 (d, J = 10.0 Hz, 1 H), 8.06 (d, J = 10.0 Hz, 1 H), 7.45-7.38 (m, 2 H), 7.16 (dd, J = 8.2, 1.9 Hz, 1 H), 3.60 (t, J = 5.0 Hz, 2 H), 3.45 (t, J = 5.0 Hz, 2 H), 3.41 (s, 2 H), 2.80 (t, J = 7.3 Hz, 2 H), 2.75 (s, 3 H), 2.65 (s, 3 H), 2.60 (t, J = 7.3 Hz, 2 H), 2.39 (t, J = 5.1 Hz, 2 H), 2.28 (s, 3 H), 2.23 (t, J = 4.9 Hz, 2H) |
| 121 | 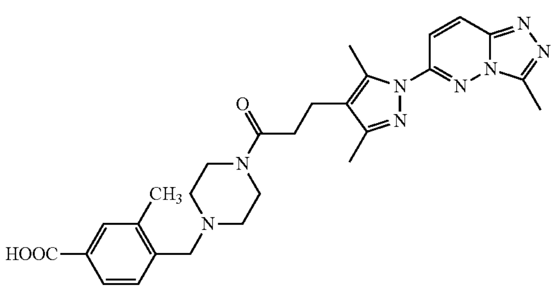 [SMILES: Cc1cc(C(=O)O)ccc1CN1CCN(C(=O)CCc2c(C)nn(-c3ccc4nnc(C)n4n3)c2C)CC1] | 0.82$^a$ | 516.26/ 517.32 | d$_5$-Pyridine: 8.34 (d, J = 10.0 Hz, 1 H), 8.31-8.26 (m, 2 H), 8.09 (d, J = 10.0 Hz, 1 H), 7.46 (d, J = 8.3 Hz, 1 H), 3.78 (b, 2 H), 3.45 (b, 2 H), 3.41 (s, 2 H), 2.98 (t, J = 7.5 Hz, 2 H), 2.70 (s, 3 H), 2.69 (s, 3 H), 2.72-2.66 (m, 2 H), 2.42 (s, 3 H), 2.40-2.30 (m, 7 H) |
| 122 | 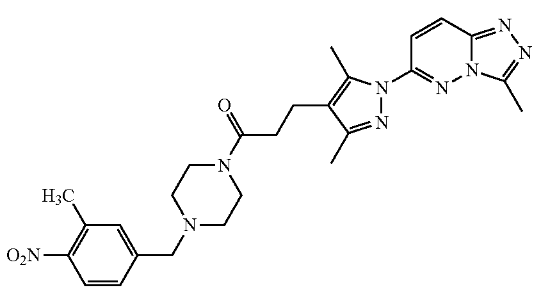 [SMILES: Cc1cc(CN2CCN(C(=O)CCc3c(C)nn(-c4ccc5nnc(C)n5n4)c3C)CC2)ccc1[N+](=O)[O-]] | 0.87$^a$ | 517.26/ 518.32 | CD$_3$OD: 8.26 (d, J = 10.0 Hz, 1 H), 8.06 (d, J = 10.0 Hz, 1 H), 7.87 (d, J = 8.3 Hz, 1 H), 7.34-7.27 (m, 2 H), 3.61 (t, J = 4.9 Hz, 2 H), 3.49 (s, 2 H), 3.49-3.45 (m, 2 H), 2.80 (t, J = 7.3 Hz, 2 H), 2.75 (s, 3 H), 2.66 (s, 3 H), 2.60 (t, J = 7.2 Hz, 2 H), 2.52 (s, 3 H), 2.40 (t, J = 5.0 Hz, 2 H), 2.28 (s, 3 H), 2.26 (t, J = 4.9 Hz, 2 H) |

| Example | Structure | $t_R$/method | Mass (calc./found) | NMR data |
|---|---|---|---|---|
| 123 | 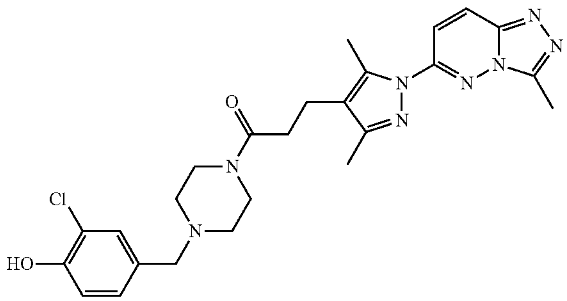 [SMILES: Cc1nn(-c2ccc3nnc(C)n3n2)c(C)c1CCC(=O)N1CCN(Cc2ccc(O)c(Cl)c2)CC1] | 0.84[a] | 508.21/ 509.28 | d$_6$-DMSO: 10.06 (s, 1 H), 8.36 (d, J = 9.9 Hz, 1 H), 7.85 (d, J = 10.0 Hz, 1 H), 7.17 (s, 1 H), 6.97 (d, J = 8.0 Hz, 1 H), 6.87 (d, J = 8.2 Hz, 1 H), 3.43 (b, 2 H), 3.38-3.34 (m, 2 H), 3.28 (b, 2 H), 2.70 (s, 3 H), 2.64 (t, J = 7.5 Hz, 2 H), 2.58 (s, 3 H), 2.48-2.43 (m, 2 H), 2.29-2.23 (m, 2 H), 2.22 (s, 3 H), 2.17 (b, 2 H) |
| 124 | 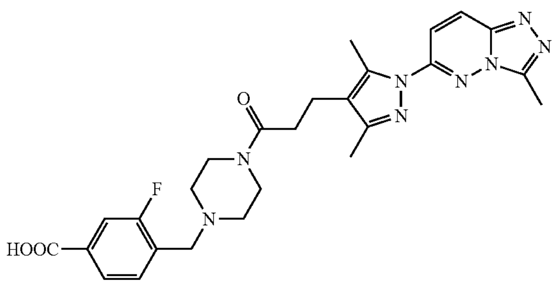 [SMILES: Cc1nn(-c2ccc3nnc(C)n3n2)c(C)c1CCC(=O)N1CCN(Cc2ccc(C(=O)O)cc2F)CC1] | 0.81[a] | 520.23/ 521.28 | d$_5$-Pyridine: 8.34 (d, J = 10.0 Hz, 1 H), 8.19 (dd, J = 7.8, 1.4 Hz, 1 H), 8.13-8.06 (m, 2 H), 7.63-7.58 (m, 1 H), 3.85-3.78 (m, 2 H), 3.59 (s, 2 H), 3.49 (t, J = 4.6 Hz, 2 H), 2.97 (t, J = 7.5 Hz, 2 H), 2.71-2.65 (m, 2 H), 2.69 (s, 6 H), 2.45-2.38 (m, 4 H), 2.41 (s, 3 H) |
| 134 | 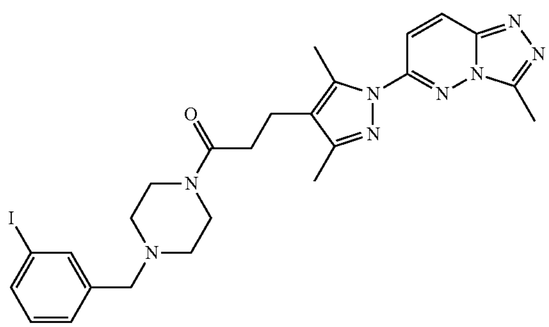 [SMILES: Cc1nn(-c2ccc3nnc(C)n3n2)c(C)c1CCC(=O)N1CCN(Cc2cccc(I)c2)CC1] | 0.90[a] | 584.15/ 585.21 | CD$_3$OD: 8.27 (d, J = 10.0 Hz, 1 H), 8.06 (d, J = 10.0 Hz, 1H), 7.64 (s, 1H), 7.57 (d, J = 7.9 Hz, 1 H), 7.20 (d, J = 7.7 Hz, 1 H), 7.01 (t, J = 7.7 Hz, 1 H), 3.60 (t, J = 4.9 Hz, 2 H), 3.44 (t, J = 5.0 Hz, 2 H), 3.39 (s, 2 H), 2.80 (t, J = 7.2 Hz, 2 H), 2.75 (s, 3 H), 2.65 (s, 3 H), 2.60 (t, J = 7.3 Hz, 2 H), 2.39 (t, J = 5.0 Hz, 2 H), 2.28 (s, 3 H), 2.21 (t, J = 4.8 Hz, 2 H) |
| 125 | 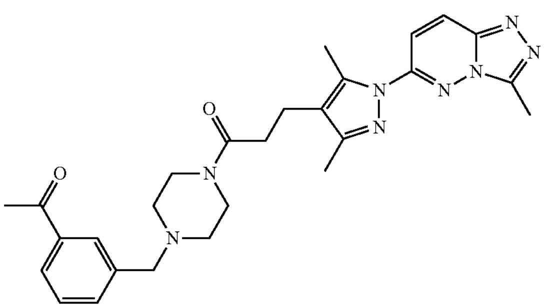 [SMILES: CC(=O)c1cccc(CN2CCN(C(=O)CCc3c(C)nn(-c4ccc5nnc(C)n5n4)c3C)CC2)c1] | 0.82[a] | 500.26/ 501.32 | CD$_3$OD: 8.26 (d, J = 10.1 Hz, 1 H), 8.05 (d, J = 10.1 Hz, 1 H), 7.89-7.84 (m, 2 H), 7.48 (d, J = 7.6 Hz, 1 H), 7.39 (t, J = 7.9 Hz, 1 H), 3.60 (t, J = 4.9 Hz, 2 H), 3.51 (s, 2 H), 3.45 (t, J = 5.0 Hz, 2 H), 2.80 (t, J = 7.2 Hz, 2 H), 2.74 (s, 3 H), 2.65 (s, 3 H), 2.63-2.57 (m, 2 H), 2.57 (s, 3 H), 2.41 (t, J = 5.0 Hz, 2 H), 2.28 (s, 3 H), 2.23 (t, J = 4.8 Hz, 2 H) |
| 126 | 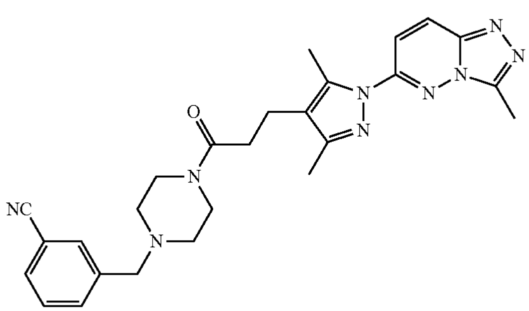 [SMILES: Cc1nn(-c2ccc3nnc(C)n3n2)c(C)c1CCC(=O)N1CCN(Cc2cccc(C#N)c2)CC1] | 0.82[a] | 483.25/ 484.32 | CD$_3$OD: 8.26 (d, J = 10.0 Hz, 1H), 8.06 (d, J = 10.0 Hz, 1H), 7.66 (s, 1 H), 7.61-7.54 (m, 2 H), 7.45 (t, J = 7.7 Hz, 1 H), 3.61 (t, J = 4.9 Hz, 2 H), 3.51 (s, 2 H), 3.47 (t, J = 5.0 Hz, 2 H), 2.79 (t, J = 7.3 Hz, 2 H), 2.75 (s, 3 H), 2.66 (s, 3 H), 2.60 (t, J = 7.3 Hz, 2 H), 2.41 (t, J = 5.0 Hz, 2 H), 2.28 (s, 3 H), 2.28-2.25 (m, 2 H) |

| Example | Structure | $t_R$/method | Mass (calc./found) | NMR data |
|---|---|---|---|---|
| 133 | 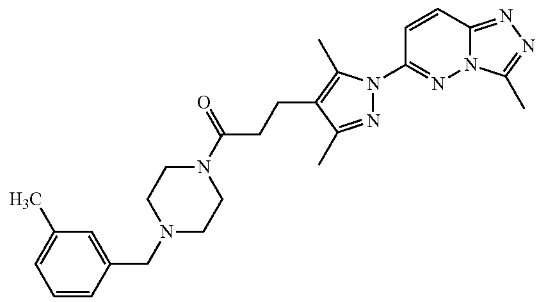 | 0.86$^a$ | 472.27/ 473.39 | CD$_3$OD: 8.26 (d, J = 10.0 Hz, 1 H), 8.06 (d, J = 10.0 Hz, 1 H), 7.13-7.06 (m, 1 H), 7.06-6.99 (m, 2 H), 6.96 (d, J = 7.4 Hz, 1 H), 3.59 (t, J = 4.6 Hz, 2 H), 3.44 (t, J = 5.0 Hz, 2 H), 3.40 (s, 2 H), 2.80 (t, J = 7.2 Hz, 2 H), 2.74 (s, 3 H), 2.64 (s, 3 H), 2.59 (t, J = 7.2 Hz, 2 H), 2.40 (t, J = 4.9 Hz, 2 H), 2.28 (s, 3 H), 2.27 (s, 3 H), 2.22 (t, J = 4.5 Hz, 2 H) |
| 127 | | 0.85$^a$ | 483.25/ 484.32 | CD$_3$OD: 8.24 (d, J = 10.0 Hz, 1 H), 8.05 (d, J = 10.0 Hz, 1 H), 7.65 (d, J = 7.8 Hz, 1 H), 7.58 (td, J = 7.6, 1.2 Hz, 1 H), 7.51 (d, J = 7.2 Hz, 1 H), 7.40 (td, J = 7.6, 1.1 Hz, 1 H), 3.64-3.55 (m, 4 H), 3.44 (t, J = 5.0 Hz, 2 H), 2.81 (t, J = 7.2 Hz, 2 H), 2.74 (s, 3 H), 2.65 (s, 3 H), 2.61 (t, J = 7.2 Hz, 2 H), 2.42 (t, J = 5.0 Hz, 2 H), 2.28 (s, 3 H), 2.24 (t, J = 4.9 Hz, 2 H) |
| 128 | | 0.90$^a$ | 534.29/ 535.36 | CD$_3$OD: 8.21 (d, J = 10.0 Hz, 1 H), 8.03 (d, J = 10.0 Hz, 1 H), 7.58-7.53 (m, 2 H), 7.51-7.48 (m, 1 H), 7.48-7.38 (m, 3 H), 7.35-7.26 (m, 2 H), 7.16 (d, J = 7.6 Hz, 1 H), 3.61 (t, J = 5.0 Hz, 2 H), 3.50 (s, 2 H), 3.44 (t, J = 5.0 Hz, 2 H), 2.80 (t, J = 7.2 Hz, 2 H), 2.72 (s, 3 H), 2.64 (s, 3 H), 2.59 (t, J = 7.2 Hz, 2 H), 2.43 (t, J = 5.1 Hz, 2 H), 2.28 (s, 3 H), 2.24 (t, J = 4.9 Hz, 2 H) |
| 129 | | 0.87$^a$ | 517.26/ 518.32 | CD$_3$OD: 8.27 (d, J = 10.1 Hz, 1 H), 8.07 (d, J = 10.0 Hz, 1 H), 7.96-7.93 (m, 2 H), 7.47 (s, 1 H), 3.62 (t, J = 5.0 Hz, 2 H), 3.52 (s, 2 H), 3.47 (t, J = 5.0 Hz, 2 H), 2.81 (t, J = 7.2 Hz, 2 H), 2.76 (s, 3 H), 2.66 (s, 3 H), 2.60 (t, J = 7.2 Hz, 2 H), 2.45-2.39 (m, 2 H), 2.42 (s, 3 H), 2.29 (s, 3 H), 2.26 (t, J = 5.0 Hz, 2 H) |
| 130 | 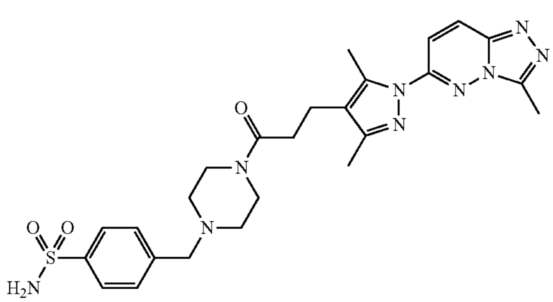 [SMILES: Cc1nn(-c2ccc3nnc(C)n3n2)c(C)c1CCC(=O)N1CCN(Cc2ccc(S(N)(=O)=O)cc2)CC1] | 0.85$^a$ | 537.23/ 538.26 | d$_6$-DMSO: 8.41 (d, J = 9.5 Hz, 1 H), 7.91 (d, J = 9.3 Hz, 1 H), 7.87 (d, J = 8.2 Hz, 2 H), 7.81 (d, J = 8.2 Hz, 2 H), 7.49 (b, 2 H), 4.45 (d, J = 14.3 Hz, 1 H), 4.38 (s, 2 H), 4.01 (d, J = 13.7 Hz, 1 H), 3.53 (t, J = 13.1 Hz, 1 H), 3.32-3.21 (m, 2 H), 3.11 (d, J = 12.3 Hz, 1 H), 3.06-2.86 (m, 2 H), 2.69 (s, 3 H), 2.66-2.61 (m, 2 H), 2.59 (s, 3 H), 2.57-2.53 (m, 2 H), 2.24 (s, 3 H) |
| 131 | 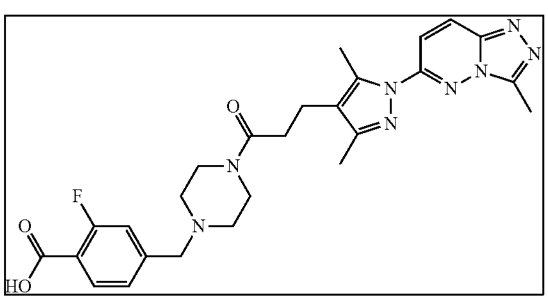 [SMILES: Cc1nn(-c2ccc3nnc(C)n3n2)c(C)c1CCC(=O)N1CCN(Cc2ccc(C(=O)O)c(F)c2)CC1] | 0.80$^a$ | 520.23/ 521.22 | d$_5$-Pyridine: 8.34 (d, J = 10.0 Hz, 1 H), 8.27 (t, J = 7.8 Hz, 1 H), 8.08 (d, J = 10.0 Hz, 1 H), 7.33 (d, J = 11.7 Hz, 1 H), 7.24 (d, J = 8.4 Hz, 1 H), 3.88-3.80 (m, 2 H), 3.56-3.50 (m, 2 H), 3.47 (s, 2 H), 2.97 (t, J = 7.5 Hz, 2 H), 2.73-2.66 (m, 2 H), 2.69 (s, 3 H), 2.68 (s, 3 H), 2.41 (s, 3 H), 2.40-2.34 (m, 4 H) |

-continued

| Example | Structure | $t_R$/method | Mass (calc./found) | NMR data |
|---|---|---|---|---|
| 132 | 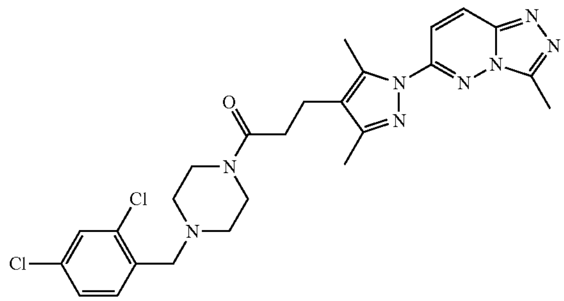 [SMILES: Cc1nn(-c2ccc3nnc(C)n3n2)c(C)c1CCC(=O)N1CCN(Cc2ccc(Cl)cc2Cl)CC1] | 0.90$^a$ | 526.18/ 527.18 | CD$_3$OD: 8.25 (d, J = 10.0 Hz, 1 H), 8.05 (d, J = 10.0 Hz, 1 H), 7.43 (d, J = 8.3 Hz, 1 H), 7.35 (d, J = 2.1 Hz, 1 H), 7.26 (dd, J = 8.3, 2.1 Hz, 1 H), 3.60 (t, J = 5.2 Hz, 2 H), 3.48 (s, 2 H), 3.44 (t, J = 4.9 Hz, 2 H), 2.81 (t, J = 7.1 Hz, 2 H), 2.74 (s, 3 H), 2.65 (s, 3 H), 2.61 (t, J = 7.2 Hz, 2 H), 2.43 (t, J = 4.9 Hz, 2 H), 2.28 (s, 3 H), 2.20 (t, J = 4.7 Hz, 2 H) |
| 146 | 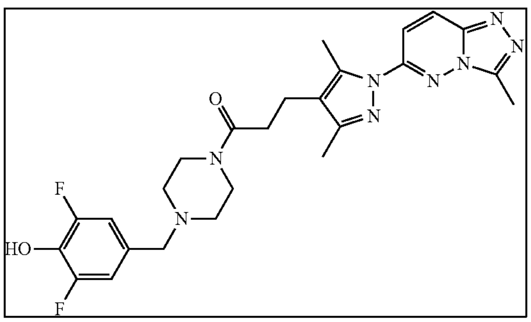 [SMILES: Cc1nn(-c2ccc3nnc(C)n3n2)c(C)c1CCC(=O)N1CCN(Cc2cc(F)c(O)c(F)c2)CC1] | 0.81$^a$ | 510.23/ 511.26 | d$_6$-DMSO: 11.56 (b, 1 H), 8.38 (d, J = 10.0 Hz, 1 H), 7.87 (d, J = 10.0 Hz, 1 H), 7.33 (d, J = 8.7 Hz, 2 H), 4.45 (d, J = 14.4 Hz, 1 H), 4.20 (s, 2 H), 4.00 (d, J = 14.0 Hz, 1 H), 3.48 (t, J = 12.7 Hz, 1 H), 3.27 (t, J = 14.3 Hz, 2 H), 3.07 (t, J = 12.3 Hz, 1 H), 2.98-2.77 (m, 2 H), 2.68 (s, 3 H), 2.66-2.57 (m, 2 H), 2.59 (s, 3 H), 2.57-2.50 (m, 2 H), 2.23 (s, 3 H) |
| 147 | 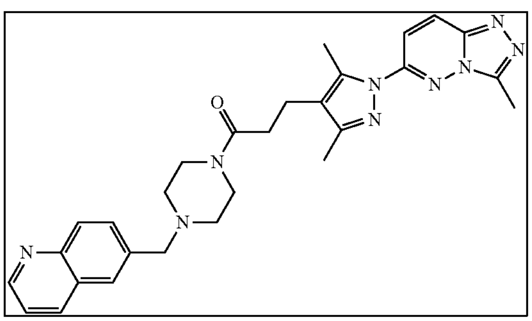 [SMILES: Cc1nn(-c2ccc3nnc(C)n3n2)c(C)c1CCC(=O)N1CCN(Cc2ccc3ncccc3c2)CC1] | 0.87$^a$ | 517.26/ 518.32 | CD$_3$OD: 8.82 (b, 1 H), 8.32-8.22 (m, 2 H), 8.06 (d, J = 9.9 Hz, 1 H), 7.97 (d, J = 9.1 Hz, 1H), 7.78-7.73 (m, 2 H), 7.52 (dd, J = 8.3, 4.2 Hz, 1 H), 3.69 (s, 2 H), 3.66-3.60 (m, 2 H), 3.49 (d, J = 4.7 Hz, 2 H), 2.80 (t, J = 7.2 Hz, 2 H), 2.72 (s, 3 H), 2.64 (s, 3 H), 2.60 (t, J = 7.3 Hz, 2 H), 2.52-2.46 (m, 2 H), 2.38-2.31 (m, 2 H), 2.28 (s, 3 H)H) |
| 148 | 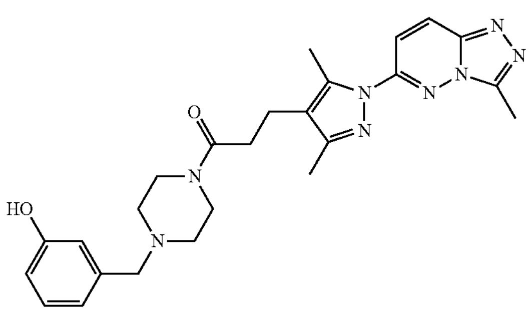 | 0.75$^a$ | 509.27/ 510.26 | d$_6$-DMSO: 11.35 (b, 1 H), 8.40 (d, J = 9.5 Hz, 1 H), 7.91 (d, J = 9.8 Hz, 1 H), 7.25-7.18 (m, 1 H), 7.03-6.93 (m, 2 H), 6.88-6.81 (m, 1 H), 4.45 (d, J = 13.4 Hz, 1 H), 4.19 (s, 2 H), 4.01 (d, J = 12.6 Hz, 1H), 3.55-3.41 (m, 1 H), 3.34-3.18 (m, 2 H), 3.14-3.02 (m, 1 H), 3.02-2.81 (m, 3 H), 2.70 (s, 3 H), 2.67-2.45 (m, 2 H), 2.59 (s, 3 H), 2.24 (s, 3 H) |

| Example | Structure | $t_R$/method | Mass (calc./found) | NMR data |
|---|---|---|---|---|
| 149 | 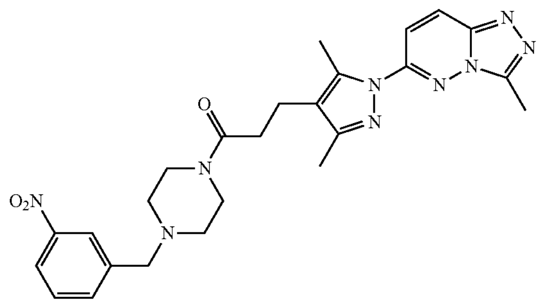 [SMILES: Cc1nn(-c2ccc3nnc(C)n3n2)c(C)c1CCC(=O)N1CCN(Cc2cccc([N+](=O)[O-])c2)CC1] | 0.85[a] | 503.24/ 504.32 | CD$_3$OD: 8.25 (d, J = 10.0 Hz, 1 H), 8.19-8.16 (m, 1 H), 8.14-8.09 (m, 1 H), 8.05 (d, J = 10.0, 1 H), 7.66 (d, J = 7.6 Hz, 1 H), 7.53 (d, J = 7.9 Hz, 1 H), 3.67-3.58 (m, 4 H), 3.49 (t, J = 4.7 Hz, 2 H), 2.80 (t, J = 7.2 Hz, 2 H), 2.75 (s, 3 H), 2.65 (s, 3 H), 2.60 (t, J = 7.3 Hz, 2 H), 2.50-2.43 (m, 2 H), 2.36-2.30 (m, 2 H), 2.28 (s, 3 H) |
| 150 | 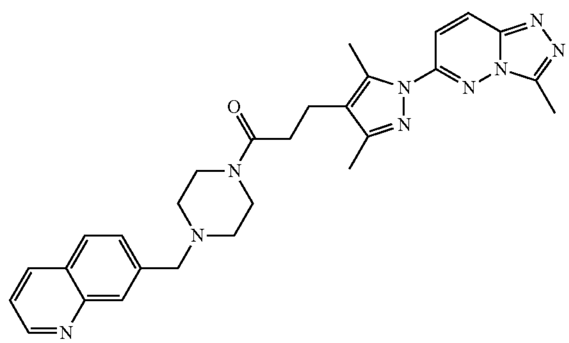 [SMILES: Cc1nn(-c2ccc3nnc(C)n3n2)c(C)c1CCC(=O)N1CCN(Cc2ccc3cccnc3c2)CC1] | 0.75[a] | 509.27/ 510.26 | CD$_3$OD: 8.81 (b, 1 H), 8.32 (d, J = 7.5 Hz, 1 H), 8.25 (d, J = 10.0 Hz, 1 H), 8.05 (d, J = 10.0 Hz, 1 H), 7.89 (s, 1 H), 7.86 (d, J = 8.4 Hz, 1 H), 7.56 (dd, J = 8.4, 1.2 Hz, 1 H), 7.50 (dd, J = 8.3, 4.3 Hz, 1 H), 3.69 (s, 2 H), 3.63 (t, J = 4.6 Hz, 2 H), 3.48 (t, J = 4.9 Hz, 2 H), 2.79 (t, J = 7.2 Hz, 2 H), 2.70 (s, 3 H), 2.64 (s, 3 H), 2.60 (t, J = 7.3 Hz, 2 H), 2.49 (t, J = 4.9 Hz, 2 H), 2.31 (t, J = 4.5 Hz, 2 H), 2.27 (s, 3 H), |
| 151 | 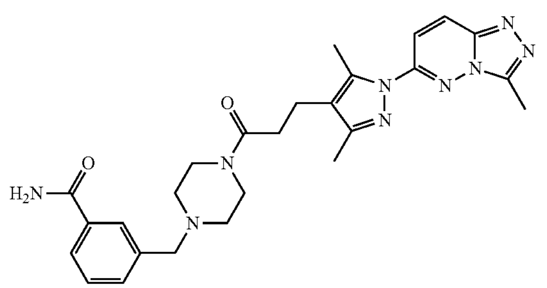 [SMILES: Cc1nn(-c2ccc3nnc(C)n3n2)c(C)c1CCC(=O)N1CCN(Cc2cccc(C(N)=O)c2)CC1] | 0.77[a] | 501.26/ 502.26 | CD$_3$OD: 8.26 (d, J = 10.0 Hz, 1 H), 8.06 (d, J = 10.0 Hz, 1 H), 7.82 (s, 1 H), 7.76 (d, J = 7.6 Hz, 1 H), 7.44 (d, J = 7.6 Hz, 1 H), 7.38 (t, J = 7.6 Hz, 1 H), 3.68-3.57 (m, 4 H), 3.52-3.46 (m, 2 H), 2.79 (t, J = 7.3 Hz, 2 H), 2.75 (s, 3 H), 2.65 (s, 3 H), 2.60 (t, J = 7.2 Hz, 2 H), 2.52 (b, 2 H), 2.37 (b, 2 H), 2.28 (s, 3 H) |
| 152 | 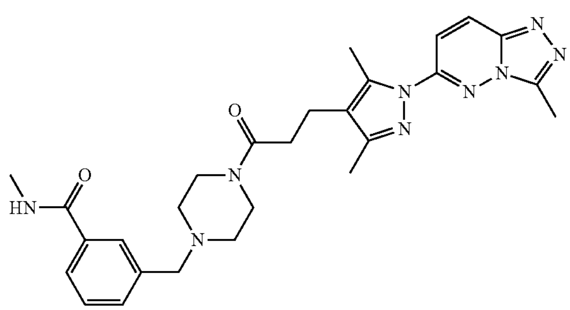 [SMILES: CNC(=O)c1cccc(CN2CCN(C(=O)CCc3c(C)nn(-c4ccc5nnc(C)n5n4)c3C)CC2)c1] | 0.78[a] | 515.28/ 516.26 | CD$_3$OD: 8.26 (d, J = 10.0 Hz, 1 H), 8.06 (d, J = 10.0 Hz, 1H), 7.72 (s, 1 H), 7.68-7.63 (m, 1 H), 7.41-7.31 (m, 2 H), 3.60 (t, J = 4.9 Hz, 2 H), 3.49 (s, 2 H), 3.45 (t, J = 4.9 Hz, 2 H), 2.90 (s, 3 H), 2.79 (t, J = 7.2 Hz, 2 H), 2.74 (s, 3 H), 2.65 (s, 3 H), 2.59 (t, J = 7.2 Hz, 2 H), 2.41 (t, J = 5.0 Hz, 2 H), 2.28 (s, 3 H), 2.25 (t, J = 4.9 Hz, 2 H) |
| 153 | 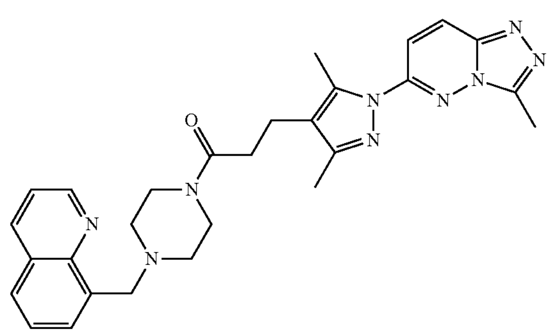 | 0.84[a] | 509.27/ 510.30 | CD$_3$OD: 8.75 (dd, J = 4.2, 1.7 Hz, 1 H), 8.28-8.20 (m, 2 H), 8.02 (d, J = 10.0 Hz, 1 H), 7.79 (d, J = 8.2 Hz, 1 H), 7.75 (d, J = 7.0 Hz, 1 H), 7.51 (d, J = 7.6 Hz, 1 H), 7.46 (dd, J = 8.3, 4.2 Hz, 1 H), 4.12 (s, 2 H), 3.62 (t, J = 4.6 Hz, 2 H), 3.45 (t, J = 4.9 Hz, 2 H), 2.80 (t, J = 7.1 Hz, 2 H), 2.69 (s, 3 H), 2.62 (s, 3 H), 2.62-2.57 (m, 2 H), 2.54 (t, J = 4.8 Hz, 2 H), 2.35-2.30 (m, 2 H), 2.28 (s, 3 H), |

| Example | Structure | $t_R$/method | Mass (calc./found) | NMR data |
|---|---|---|---|---|
| 154 | 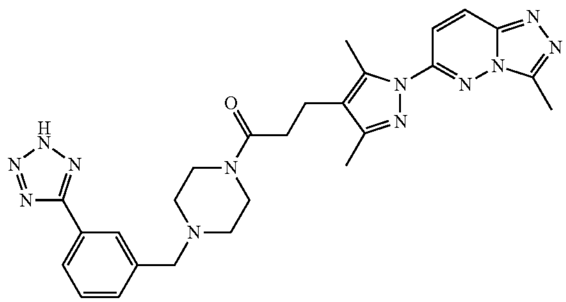 [SMILES: Cc1nn(-c2ccc3nnc(C)n3n2)c(C)c1CCC(=O)N1CCN(Cc2cccc(-c3nn[nH]n3)c2)CC1] | $0.79^a$ | 526.27/ 527.30 | d$_5$-Pyridine: 8.47 (s, 1 H), 8.39-8.32 (m, 2 H), 8.08 (d, J = 10.0 Hz, 1H), 7.57-7.49 (m, 2 H), 3.85-3.78 (m, 2 H), 3.57 (s, 2 H), 3.54-3.47 (m, 2 H), 2.97 (t, J = 7.5 Hz, 2 H), 2.71-2.65 (m, 2 H), 2.68 (s, 6 H), 2.47-2.42 (m, 4 H), 2.41 (s, 3 H) |
| 155 | 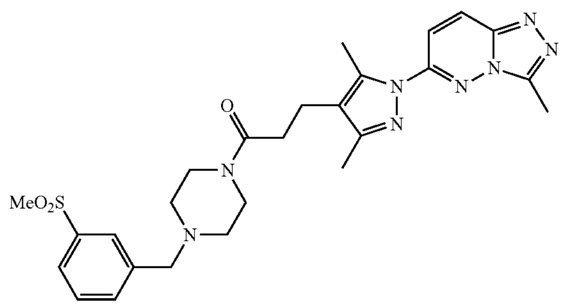 [SMILES: Cc1nn(-c2ccc3nnc(C)n3n2)c(C)c1CCC(=O)N1CCN(Cc2cccc(S(C)(=O)=O)c2)CC1] | $0.80^a$ | 536.23/ 537.22 | CD$_3$OD: 8.26 (d, J = 10.1 Hz, 1 H), 8.06 (d, J = 10.0 Hz, 1 H), 7.87 (s, 1 H), 7.85-7.81 (m, 1 H), 7.60 (d, J = 7.7 Hz, 1 H), 7.53 (t, J = 7.6 Hz, 1 H), 3.61 (t, J = 4.9 Hz, 2 H), 3.55 (s, 2 H), 3.46 (t, J = 5.0 Hz, 2 H), 3.09 (s, 3 H), 2.80 (t, J = 7.2 Hz, 2 H), 2.76 (s, 3 H), 2.66 (s, 3 H), 2.60 (t, J = 7.2 Hz, 2 H), 2.42 (t, J = 5.0 Hz, 2 H), 2.28 (s, 3 H), 2.26 (t, J = 5.0 Hz, 2 H) |
| 156 | 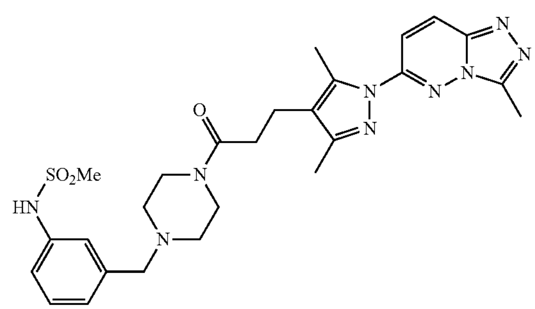 [SMILES: Cc1nn(-c2ccc3nnc(C)n3n2)c(C)c1CCC(=O)N1CCN(Cc2cccc(NS(C)(=O)=O)c2)CC1] | $0.81^a$ | 551.24/ 552.26 | d$_6$-DMSO: 8.37 (d, J = 10.0 Hz, 1 H), 7.85 (d, J = 10.0 Hz, 1 H), 7.02 (d, J = 7.7 Hz, 1 H), 6.90 (s, 1H), 6.86 (d, J = 8.0 Hz, 1 H), 6.60 (d, J = 7.5 Hz, 1 H), 3.48-3.41 (m, 2 H), 3.38-3.34 (m, 2 H), 3.29 (s, 2 H), 2.71 (s, 3 H), 2.67 (s, 3 H), 2.64 (t, J = 7.7 Hz, 2 H), 2.58 (s, 3 H), 2.50-2.44 (m, 2 H), 2.29-2.24 (m, 2 H), 2.22 (s, 3 H), 2.20-2.16 (m, 2 H) |
| 157 | 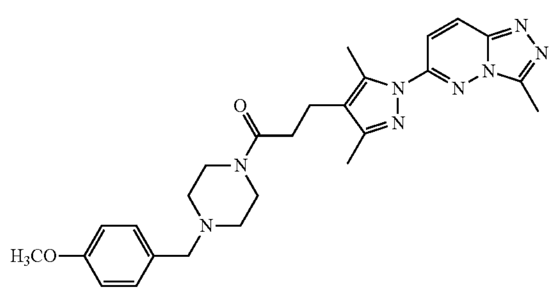 [SMILES: COc1ccc(CN2CCN(C(=O)CCc3c(C)nn(-c4ccc5nnc(C)n5n4)c3C)CC2)cc1] | $0.95^a$ | 488.26/ 489.32 | CD$_3$OD: 8.27 (d, J = 10.1 Hz, 1 H), 8.06 (d, J = 10.1 Hz, 1 H), 7.08 (d, J = 8.6 Hz, 2 H), 6.76 (d, J = 8.6 Hz, 2 H), 3.74 (s, 3 H), 3.58 (t, J = 5.0 Hz, 2 H), 3.42 (t, J = 5.0 Hz, 2 H), 3.35 (s, 2 H), 2.80 (t, J = 7.2 Hz, 2 H), 2.74 (s, 3 H), 2.65 (s, 3 H), 2.59 (t, J = 7.2 Hz, 2 H), 2.36 (t, J = 5.1 Hz, 2 H), 2.28 (s, 3 H), 2.15 (t, J = 5.0 Hz, 2 H) |
| 158 | 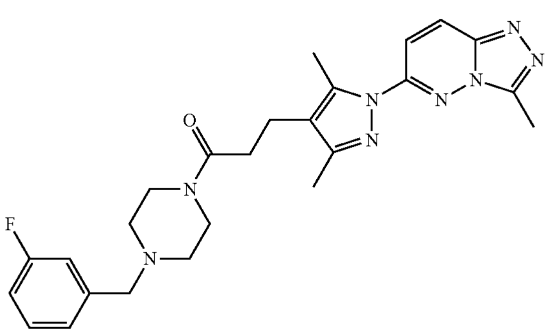 | $0.86^a$ | 476.24/ 477.30 | CD$_3$OD: 8.26 (d, J = 10.0 Hz, 1 H), 8.06 (d, J = 10.0 Hz, 1 H), 7.35-7.25 (m, 1 H), 7.08 (d, J = 7.4 Hz, 2 H), 7.04-7.00 (m, 1 H), 3.64 (b, 4 H), 3.52 (b, 2 H), 2.80 (t, J = 7.3 Hz, 2 H), 2.75 (s, 3 H), 2.65 (s, 3 H), 2.60 (b, 2 H), 2.61 (t, J = 7.3 Hz, 2 H), 2.44 (b, 2 H), 2.28 (s, 3 H) |

-continued

| Example | Structure | $t_R$/method | Mass (calc./found) | NMR data |
|---|---|---|---|---|
| 159 | 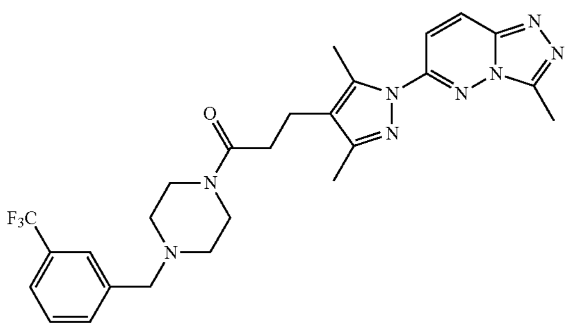 [SMILES: Cc1nn(-c2ccc3nnc(C)n3n2)c(C)c1CCC(=O)N1CCN(Cc2cccc(C(F)(F)F)c2)CC1] | 0.93$^a$ | 526.24/ 527.26 | CD$_3$OD: 8.26 (d, J = 10.0 Hz, 1 H), 8.06 (d, J = 10.0 Hz, 1 H), 7.60 (s, 1 H), 7.57-7.43 (m, 3 H), 3.62 (b, 2 H), 3.56 (s, 2 H), 3.50-3.45 (m, 2 H), 2.80 (t, J = 7.3 Hz, 2 H), 2.75 (s, 3 H), 2.66 (s, 3 H), 2.60 (t, J = 7.3 Hz, 2 H), 2.44 (b, 2 H), 2.30 (b, 2 H), 2.28 (s, 3 H) |
| 160 | | 0.88$^a$ | 472.27/ 473.30 | CD$_3$OD: 8.26 (d, J = 10.0 Hz, 1 H), 8.06 (d, J = 10.0 Hz, 1 H), 7.15-6.98 (m, 4 H), 3.59 (b, 2 H), 3.44 (b, 4 H), 2.80 (t, J = 7.2 Hz, 2 H), 2.74 (s, 3 H), 2.66 (s, 3 H), 2.60 (t, J = 7.2 Hz, 2 H), 2.45 (b, 2 H), 2.28 (s, 3 H), 2.27 (s, 3 H), 2.26 (b, 2 H) |
| 161 | 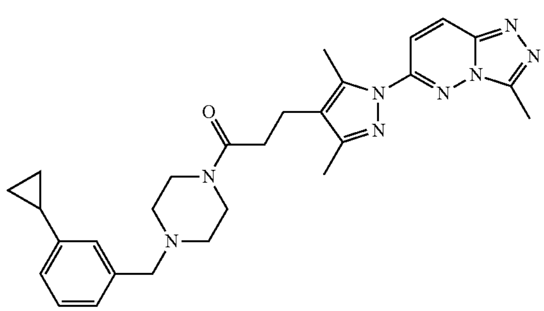 [SMILES: Cc1nn(-c2ccc3nnc(C)n3n2)c(C)c1CCC(=O)N1CCN(Cc2cccc(C3CC3)c2)CC1] | 0.94$^a$ | 498.29/ 499.30 | CD$_3$OD: 8.27 (d, J = 10.0 Hz, 1 H), 8.06 (d, J = 10.0 Hz, 1 H), 7.07 (t, J = 7.7 Hz, 2 H), 6.91 (t, J = 7.2 Hz, 2 H), 3.59 (t, J = 4.9 Hz, 2 H), 3.43 (t, J = 5.0 Hz, 2 H), 3.37 (s, 2 H), 2.80 (t, J = 7.2 Hz, 2 H), 2.74 (s, 3 H), 2.65 (s, 3 H), 2.59 (t, J = 7.2 Hz, 2 H), 2.38 (t, J = 5.0 Hz, 2 H), 2.28 (s, 3 H), 2.17 (t, J = 4.9 Hz, 2 H), 1.87-1.78 (m, 1 H), 0.96-0.88 (m, 2 H), 0.65-0.58 (m, 2 H) |
| 162 | 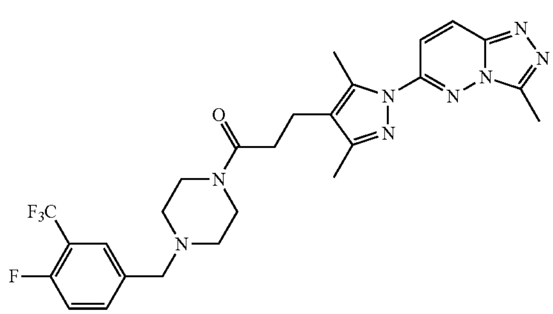 [SMILES: Cc1nn(-c2ccc3nnc(C)n3n2)c(C)c1CCC(=O)N1CCN(Cc2ccc(F)c(C(F)(F)F)c2)CC1] | 0.95$^a$ | 544.23/ 545.22 | CD$_3$OD: 8.25 (d, J = 10.0 Hz, 1 H), 8.06 (d, J = 10.0 Hz, 1 H), 7.61 (dd, J = 6.9, 1.9 Hz, 1 H), 7.58-7.51 (m, 1 H), 7.27-7.20 (m, 1 H), 3.60 (t, J = 4.9 Hz, 2 H), 3.49 (s, 2 H), 3.47 (t, J = 5.0 Hz, 2 H), 2.79 (t, J = 7.3 Hz, 2 H), 2.76 (s, 3 H), 2.66 (s, 3 H), 2.60 (t, J = 7.3 Hz, 2 H), 2.40 (t, J = 5.0 Hz, 2 H), 2.28 (s, 3 H), 2.30-2.25 (m, 2 H) |

-continued

| Example | Structure | $t_R$/method | Mass (calc./found) | NMR data |
|---|---|---|---|---|
| 163 | 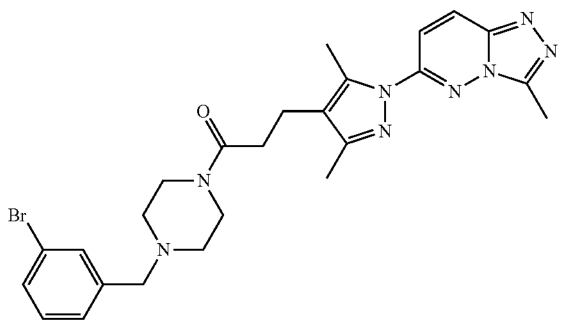 [SMILES: Cc1nn(-c2ccc3nnc(C)n3n2)c(C)c1CCC(=O)N1CCN(Cc2cccc(Br)c2)CC1] | 0.90[a] | 536.16/ 537.14 | CD$_3$OD: 8.26 (d, J = 10.0 Hz, 1 H), 8.06 (d, J = 10.0 Hz, 1 H), 7.43 (s, 1 H), 7.39-7.34 (m, 1 H), 7.20-7.12 (m, 2 H), 3.60 (t, J = 4.9 Hz, 2 H), 3.44 (t, J = 5.0 Hz, 2 H), 3.41 (s, 2 H), 2.80 (t, J = 7.2 Hz, 2 H), 2.75 (s, 3 H), 2.65 (s, 3 H), 2.59 (t, J = 7.2 Hz, 2 H), 2.38 (t, J = 5.0 Hz, 2 H), 2.28 (s, 3 H), 2.20 (t, J = 4.9 Hz, 2 H) |
| 164 | 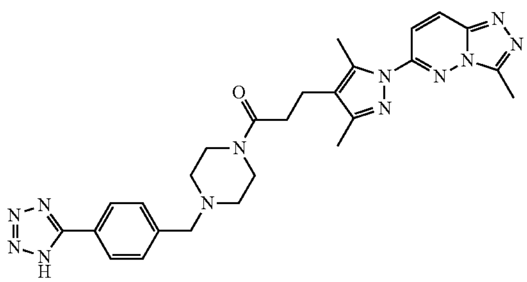 [SMILES: Cc1nn(-c2ccc3nnc(C)n3n2)c(C)c1CCC(=O)N1CCN(Cc2ccc(-c3nnn[nH]3)cc2)CC1] | 0.81[a] | 526.27/ 527.26 | Pyridine: 8.69 (d, J = 8.0 Hz, 2 H), 8.33 (d, J = 10.0 Hz, 1H), 8.07 (d, J = 10.0 Hz, 1 H), 7.43 (d, J = 7.7 Hz, 2 H), 3.80-3.74 (m, 2 H), 3.46-3.40 (m, 2 H), 3.40 (s, 2 H), 2.96 (t, J = 7.4 Hz, 2 H), 2.68 (s, 3 H), 2.67-2.63 (m, 2 H), 2.67 (s, 3 H), 2.41 (s, 3 H), 2.34 (t, J = 4.6 Hz, 2 H) 2.28 (t, J = 4.8 Hz, 2 H), |
| 165 | 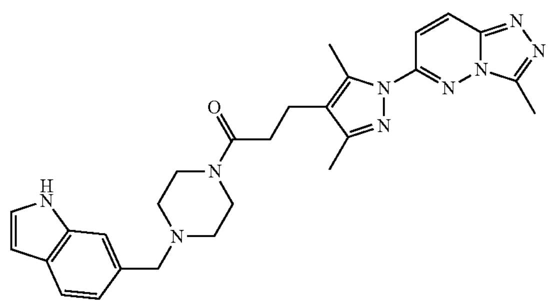 [SMILES: Cc1nn(-c2ccc3nnc(C)n3n2)c(C)c1CCC(=O)N1CCN(Cc2ccc3cc[nH]c3c2)CC1] | 0.88[a] | 497.27/ 498.26 | d$_6$-DMSO: 10.97 (b, 1 H), 8.37 (d, J = 10.0 Hz, 1 H), 7.85 (d, J = 10.0 Hz, 1 H), 7.42 (d, J = 7.8 Hz, 1 H), 7.27 (d, J = 14.3 Hz, 2 H), 6.86 (d, J = 7.9 Hz, 1 H), 6.36 (s, 1 H), 3.46 (b, 2 H), 3.36 (b, 2 H), 3.32 (s, 2 H), 2.67 (s, 3 H), 2.66-2.61 (m, 2 H), 2.58 (s, 3 H), 2.50-2.43 (m, 2 H), 2.30 (b, 2 H), 2.22 (s, 3 H), 2.22 (b, 2 H) |
| 166 | 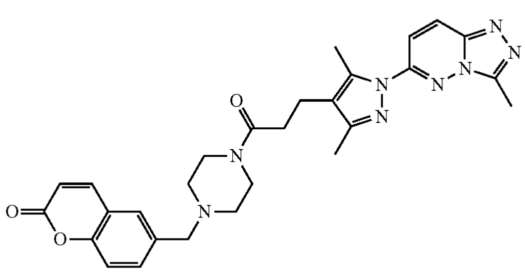 [SMILES: Cc1nn(-c2ccc3nnc(C)n3n2)c(C)c1CCC(=O)N1CCN(Cc2ccc3oc(=O)ccc3c2)CC1] | 0.83[a] | 526.24/ 527.26 | CD$_3$OD: 8.27 (d, J = 10.0 Hz, 1 H), 8.07 (d, J = 10.0 Hz, 1 H), 7.89 (d, J = 9.6 Hz, 1 H), 7.54-7.47 (m, 2 H), 7.27 (d, J = 8.2 Hz, 1 H), 6.42 (d, J = 9.6 Hz, 1 H), 3.60 (t, J = 4.9 Hz, 2 H), 3.50 (s, 2 H), 3.46 (t, J = 4.9 Hz, 2 H), 2.80 (t, J = 7.2 Hz, 2 H), 2.75 (s, 3 H), 2.66 (s, 3 H), 2.60 (t, J = 7.3 Hz, 2 H), 2.41 (t, J = 5.0 Hz, 2 H), 2.28 (s, 3 H), 2.32-2.24 (m, 2 H) |
| 96 | 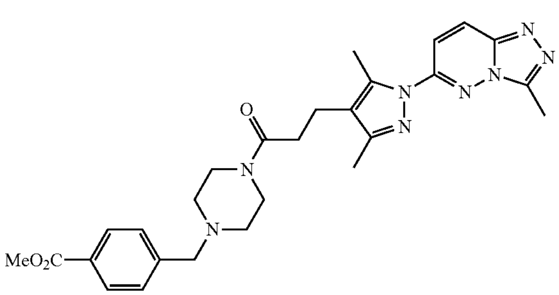 [SMILES: COC(=O)c1ccc(CN2CCN(C(=O)CCc3c(C)nn(-c4ccc5nnc(C)n5n4)c3C)CC2)cc1] | 3.34[b] | 516.26/ 517.3 | CDCl$_3$: 8.08 (d, J = 10.0 Hz, 1H), 8.02-7.94 (m, 3H), 7.38 (s, 2H), 3.91 (s, 3H), 3.75-3.33 (m, 6H), 2.78 (d, J = 7.9 Hz, 5H), 2.65 (s, 3H), 2.52-2.30 (m, 4H), 2.28 (s, 3H). |

-continued

| Example | Structure | $t_R$/method | Mass (calc./found) | NMR data |
|---|---|---|---|---|
| 97 | 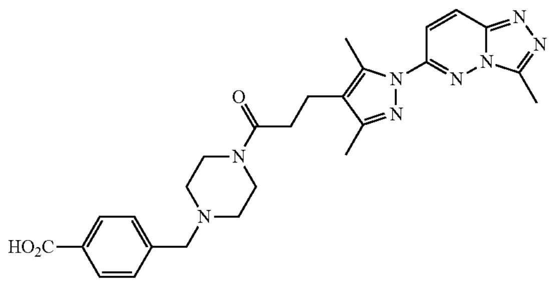 | 3.23[b] | 502.24/503.3 | CF$_3$COOD 8.66 (d, J = 7.2 Hz, 1H), 8.29 (s, 1H), 8.15 (d, J = 6.8 Hz, 2H), 7.53 (d, J = 7.8 Hz, 2H), 4.75 (d, J = 13.8 Hz, 1H), 4.43 (s, 2H), 4.25-4.01 (m, 1H), 3.91-3.52 (m, 3H), 3.21 (d, J = 42.5 Hz, 2H), 2.93 (d, J = 11.9 Hz, 5H), 2.71 (d, J = 41.3 Hz, 5H), 2.51 (s, 3H) |
| 98 | 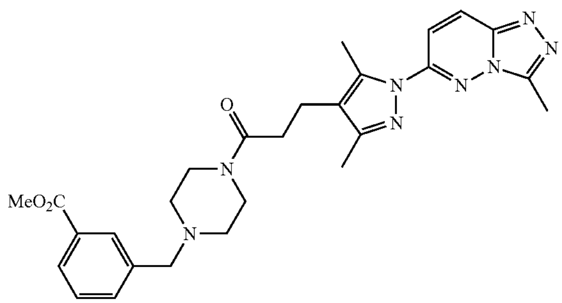 | 1.02[c] | 516.3/516.9 | CDCl$_3$: 8.09 (d, 1H, J = 9.9 Hz), 7.99 (d, 1H, J = 10.2 Hz), 7.92-7.97 (m, 2H), 7.48-7.52 (m, 1H), 7.39 (dd, 1H, J = 7.5, 7.5 Hz), 3.92 (s, 3H), 3.66 (t, 2H, J = 4.9 Hz), 3.53 (s, 3H), 3.41 (t, 2H, J = 4.9 Hz), 2.79-2.83 (m, 2H), 2.78 (s, 3H), 2.66 (s, 3H), 2.46-2.52 (m, 2H), 2.43 (t, 2H, J = 5.1 Hz), 2.35 (t, 2H, J = 4.8 Hz), 2.29 (s, 3H) |
| 99 | 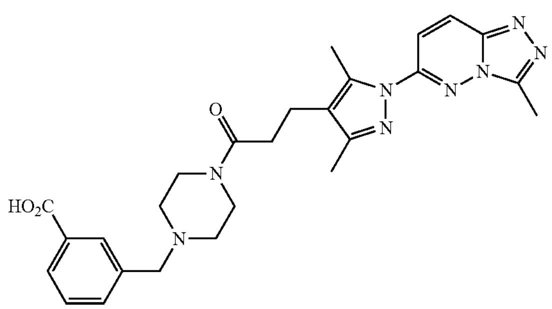 [SMILES: Cc1nn(-c2ccc3nnc(C)n3n2)c(C)c1CCC(=O)N1CCN(Cc2cccc(C(=O)O)c2)CC1] | 0.97[c] | 502.2/502.9 | CDCl$_3$: 8.12 (d, 1H, J = 10.2 Hz), 8.09-8.12 (m, 1H), 7.99 (d, 1H, J = 9.9 Hz), 7.95-7.99 (m, 1H), 7.42-7.46 (m, 1H), 7.35-7.40 (m, 1H), 3.73 (m, 2H), 3.58 (m, 2H), 3.49 (m, 2H), 2.77-2.82 (m, 2H), 2.77 (s, 3H), 2.64 (s, 3H), 2.42-2.54 (m, 6H), 2.28 (s, 3H) |

LCMS-measurements were performed on three different systems:

a) WATERS Acquity HUPL® CLASS System with a WATERS 515 HPLC pump and a WATERS 2767 sample manager in combination with a WATERS Acquity UPLC® BEH C18-Column (1.7 µm, 2.1×50 mm) and WATERS Aquity QDa mass spectrometer. Flow rate was 0.8 mL/min, the used gradient for a three minutes run was set as listed below:

| Time [min] | H$_2$O + 0.05% TFA | MeCN + 0.05% TFA |
|---|---|---|
| 0.00 | 95% | 5% |
| 1.00 | 5% | 95% |
| 2.25 | 5% | 95% |
| 2.27 | 95% | 5% | b) AGILENT 1100 equipped with a quaternary pump, a vacuum degasser, a VWD detector, a column oven, a Rheodyne-7725i manual sampler and an HPLC column (CNW Athena C18-WP, 3 µm, 2.1×50 mm). Flow rate was 0.4 mL/min, the used gradient for a six minutes run was set as listed below:

| Time [min] | 0.1% phosphoric acid in H$_2$O | MeCN |
|---|---|---|
| 0.0 | 95% | 5% |
| 4.0 | 5% | 95% |
| 5.9 | 5% | 95% |
| 6.0 | 95% | 5% | c) AGILENT 1200 series HPLC and pump system, a PHENOMENEX Luna 3 µm C18(2) 100 Å (10×2 mm, MercuryMS™) LC column coupled with an AGILENT Technologies 6130 Quadrupole LC/MS Flow rate was 0.8 mL/min, the used gradient for a three minutes run was set as listed below:

| Time [min] | H$_2$O + 0.05% TFA | MeCN + 0.05% TFA |
|---|---|---|
| 0.00 | 93% | 7% |
| 0.20 | 93% | 7% |
| 0.70 | 5% | 95% |
| 1.9 | 5% | 95% |
| 2.0 | 93% | 7% |

3) Biological and Pharmacological Tests

3.1) Recombinant Protein Purification

3.1.1) Purification of Strep-Tagged TRAF6 RZ1 Protein

The cDNA sequences of the RING-Zincfinger1 (RZ1) domain (residues 50-159) of human TRAF6 wildtype (TRAF6, UniProtKB deposition number Q9Y4K3 sequence wildtype: MEEIQGYDVEFDPPLESKYECPICLMAL-REAVQTPCGHRFCKACIIKSIRDAGHKCPVDNEIL LENQLFPDNFAKREILSLMVKCPNEGCLHK-MELRHLEDHQAHCEFALDHGLSAWSHPQFEK (SEQ ID NO:28) and an Ubc13 binding mutant (TRAF6 D57K, sequence D57K mutant: MEEIQGYKVEFDPPLESKY-ECPICLMALREAVQTPCGHRFCKACIIK-SIRDAGHKCPVDNEIL LENQLFPDN-FAKREILSLMVKCPNEGCLHKMELRHLEDHQAHCE-FALDHGLSAWSHPQFEK SEQ ID NO:29) were cloned into the pASK-IBA3+ vector (IBA Life Sciences). These proteins were expressed in BL21 codon plus RIPL cells (Agilent Technologies) in Luria/Miller medium supplemented with 100 µM $ZnCl_2$ and purified using the Strep-Tag®-Strep-Tactin® system developed by IBA Life Sciences using the ÄKTA purifier (GE Healthcare Life Sciences).

3.1.2) Purification of Untagged TRAF6 RZ1 Protein

The cDNA sequence of the wildtype human TRAF6 RZ1 domain (TRAF6, UniProtKB deposition number Q9Y4K3, sequence wildtype: GSMEEIQGYDVEFDPPLESKYECPI-CLMALREAVQTPCGHRFCKACIIK-SIRDAGHKCPVDN EILLENQLFPDN-FAKREILSLMVKCPNEGCLHKMELRHLEDHQAHCE-FAL (SEQ ID NO:30) was cloned into the pGex 4T1 vector (GE Healthcare Life Sciences). For the purification of untagged TRAF6 RZ1, the protein was expressed in BL21 codon plus RIPL cells in M9 mineral medium supplemented with 100 µM $ZnCl_2$. For $^{15}N$-labeled protein, the regular $NH_4$ was replaced by $^{15}NH_4$. Protein purification was performed using Glutathione Sepharose 4 fast flow beads (GE Healthcare Life Sciences), Thrombin cleavage (Sigma-Aldrich) and gel filtration chromatography (Superdex 75, GE Healthcare Life Sciences).

3.1.3) Purification of Flag-His-Tagged Ubc13 Protein (Ubc13-FH)

cDNA sequence for human Ubc13 (UniProtKB-P61088 (UBE2N_HUMAN) sequence:

SEQ ID NO: 31)
GSPEFAGLPRRIIKETQRLLAEPVPGIKAEPDESNARYFHVVIAGPQDSP

FEGGTFKLELFLPEEYPMAAPKVRFMTKIYHPNVDKLGRICLDILKDKWS

PALQIRTVLLSIQALLSAPNPDDPLANDVAEQWKTNEAQAIETARAWTRL

YAMNNIGADYKDDDDKGAHHHHHH,

1)

full length and the Flag-His-tag were cloned into the pGex 4T1 vector. The GST-tagged protein was expressed in BL21 codon plus RIPL cells in LB-medium and purified by Glutathione Sepharose 4 fast flow beads, Thrombin cleavage and gel filtration chromatography (Superdex 75, GE Healthcare Life Sciences).

3.1.4) Purification of GST Proteins (Including GST-OTUB1 (UniProtKB-Q96FW1

(OTUB1_HUMAN) sequence:
(SEQ ID NO: 32)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSAAEEPQQQKQEPLGSDSEGVNCLA

YDEAIMAQQDRIQQEIAVQNPLVSERLELSVLYKEYAEDDNIYQQKIKDL

HKKYSYIRKTRPDGNCFYRAFGFSHLEALLDDSKELQRFKAVSAKSKEDL

VSQGFTEFTIEDFHNTFMDLIEQVEKQTSVADLLASFNDQSTSDYLVVYL

RLLTSGYLQRESKFFEHFIEGGRTVKEFCQQEVEPMCKESDHIHIIALAQ

ALSVSIQVEYMDRGEGGTTNPHIFPEGSEPKVYLLYRPGHYDILYK
and

GST-Ubc13 (UniProtKB - P61088 (UBE2N_HUMAN))
sequence:
SEQ ID NO: 33)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSPEFAGLPRRIIKETQRLLAEPVPG

IKAEPDESNARYFHVVIAGPQDSPFEGGTFKLELFLPEEYPMAAPKVRFM

TKIYHPNVDKLGRICLDILKDKWSPALQIRTVLLSIQALLSAPNPDDPLA

NDVAEQWKTNEAQAIETARAWTRLYAMNNI
were produced as previously described in Weber,
E., Rothenaigner, I., Brandner, S., Hadian, K. &
Schorpp, K. A High-Throughput Screening Strategy
for Development of RNF8-Ubc13 Protein-Protein
Interaction Inhibitors. SLAS Discov 22, 316-323
(2017).

3.1.5) His-Tagged Uev1a (UniProtKB-Q13404 (UB2V1_HUMAN) Sequence:

SPGEVQASYLKSQSKLSDEGR-LEPRKFHCKGVKVPRN-FRLLEELEEGQKGVGDGTVSWGL EDDEDMTL-TRWTGMIIGPPRTIYENRIYSLKIECGPKYPEAPPFVR-FVTKINMNGVNSSNGVV DPRAISVLAKWQNSYS-IKVVLQELRRLMMSKENMK-LPQPPEGQCYSN*AAALEHHHHHH (SEQ ID NO:34) protein was purified according to GST-OTUB1 protocol with the following buffer: lysis buffer (20 mM $NaH_2PO_4$, 20 mM NaCl, 50 mM Imidazol), elution buffer (20 mM $NaH_2PO_4$, 20 mM NaCl, 500 mM Imidazol) and desalting buffer (20 mM $NaH_2PO_4$, 20 mM NaCl).

3.2) Identification and Characterization of TRAF6-Ubc13 PPI Inhibitors in Biochemical Assays

3.2.1) ALPHAScreen

In order to identify small molecules that specifically target the RZ1 domain of TRAF6 and thereby prevent its binding to Ubc13, the ALPHAScreen technology (PerkinElmer) was chosen to detect $TRAF6_{WT}$-StrepII-Ubc13FH interaction in High-Throughput-Screenings as well as Structure Activity Relationship (SAR) analysis.

For performance of an automated ALPHAScreen assay, all following components were pre-diluted in ALPHAScreen buffer (1×PBS, 0.5% BSA, 0.01% Tween-20). First, the TRAF6 protein (end concentration 100 nM, 30 µL volume) was added to 384-well-opti-plates involving the MultiFlo dispensing system (BioTek) followed by transfer of the compounds via the Sciclone G3 transfer station (PerkinElmer). After addition of Ubc13FH (end concentration 75 nM, 10 µL volume) with the MultiFlo system and incubation for one hour at room temperature, both beads (Strep-Tactin Alpha Donor beads and Nickel-Chelate acceptor beads; end concentrations 4 µg each, 10 µL volume each) were mixed and added using the MultiFlo system in subdued light. Read-out of the plates occurred after another hour of incubation at room temperature. Statistical parameters including the coefficient of variation, Z' factor and signal window were calculated to determine the quality of the HTS campaign. To evaluate the efficacy of the compounds, ALPHAScreen units of compound-treated samples were referred to DMSO control treated samples. Thereby, the TRAF6$D_{57K}$ mutant served as the control for minimum signal and was included on every plate of the screening. Compounds that inhibited TRAF6$_{WT}$StrepII-Ubc13FH by more than 25% were considered as actives. After elimination of ALPHAScreen frequent hitter compounds and His-tag frequent hitters (Schorpp, K., I. Rothenaigner, E. Salmina, et al., *Identification of Small-Molecule Frequent Hitters from AlphaScreen High-Throughput Screens*. J Biomol Screen, 2014. 19(5): p. 715-26), 178 compounds were defined as primary hits and were subsequently tested in five-point serial dilution assays (2.5-40 µM) in TRAF6$_{WT}$StrepII-Ubc13FH ALPHAScreen experiments. Only compounds with dose-dependent effects on TRAF6$_{WT}$StrepII-Ubc13FH (n=27) were taken for further research. For analog testing, all compounds were analyzed in ten-point titration (0.2-100 µM) in TRAF6$_{WT}$StrepII-Ubc13FH ALPHAScreen experiments. In parallel, the compounds were tested in the ALPHAScreen TruHits Kit (PerkinElmer) to rule out unspecific interference with the ALPHAScreen technology.

TABLE 2

$IC_{50}$ values for inhibition of TRAF6-UBC13 interaction.

| Compound of table 1 | $IC_{50}$ Alphascreen |
| --- | --- |
| 1 | ++++ |
| 2 | ++++ |
| 3 | ++++ |
| 4 | ++++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | ++ |
| 15 | ++ |
| 16 | ++ |
| 17 | ++ |
| 18 | ++ |
| 19 | ++ |
| 20 | ++ |
| 21 | ++ |
| 22 | + |
| 23 | + |
| 24 | + |
| 25 | + |
| 26 | + |
| 27 | + |
| 61 | ++++ |
| 96 | ++++ |
| 97 | ++++ |
| 98 | +++ |
| 99 | ++++ |
| 100 | + |
| 101 | ++ |
| 102 | ++ |
| 103 | + |
| 104 | + |
| 105 | + |
| 106 | + |
| 107 | + |
| 108 | +++ |
| 109 | ++ |
| 110 | ++ |
| 111 | ++ |
| 112 | +++ |
| 113 | +++ |
| 114 | +++ |
| 115 | ++++ |
| 116 | ++++ |
| 117 | +++ |
| 118 | +++ |
| 119 | ++++ |
| 120 | ++++ |
| 121 | ++++ |
| 122 | ++++ |
| 123 | ++++ |
| 125 | ++++ |
| 126 | ++++ |
| 127 | +++ |
| 128 | +++ |
| 129 | ++++ |
| 130 | ++++ |
| 131 | ++++ |
| 132 | +++ |
| 133 | +++ |
| 134 | ++++ |
| 135 | ++++ |
| 136 | +++ |
| 137 | +++ |
| 138 | +++ |
| 139 | ++ |
| 140 | ++ |
| 141 | ++ |
| 142 | +++ |
| 143 | ++ |
| 144 | +++ |
| 145 | +++ |
| 146 | ++++ |
| 147 | ++++ |
| 148 | +++ |
| 149 | +++ |
| 150 | +++ |
| 151 | +++ |
| 152 | ++ |
| 153 | ++++ |
| 154 | ++++ |
| 155 | ++++ |
| 156 | +++ |
| 157 | +++ |
| 158 | +++ |
| 159 | ++++ |
| 160 | ++++ |
| 161 | ++++ |
| 162 | +++ |
| 163 | ++++ |
| 164 | ++++ |
| 165 | +++ |
| 166 | +++ |
| 167 | + |
| 168 | +++ |
| 169 | +++ |
| 170 | ++++ |

TABLE 2-continued

IC$_{50}$ values for inhibition of TRAF6-UBC13 interaction.

| Compound of table 1 | IC$_{50}$ Alphascreen |
|---|---|
| 171 | ++++ |
| 172 | ++++ |
| 173 | ++++ |
| 174 | ++++ |
| 175 | ++++ |
| 176 | ++++ |
| 177 | ++++ |
| 178 | ++++ |
| 179 | ++++ |
| 180 | +++ |
| 181 | ++ |
| 182 | +++ |
| 183 | ++++ |
| 184 | +++ |
| 185 | ++++ |
| 186 | +++ |
| 187 | +++ |
| 188 | ++ |
| 189 | ++ |
| 190 | ++++ |
| 191 | +++ |

+≥30% Inhibition @ 100 µM
++IC 50 ≤ 30 µM
+++IC 50 ≤ 10 µM
++++IC 50 ≤ 3 µM

Further Alphascreen results are listed in FIG. 20.

3.2.2) Two-Dimensional-Nuclear-Magnetic-Resonance (2D-NMR)

To determine whether the inhibitory compounds directly bind to TRAF6 rather than to Ubc13, 2D-NMR experiments were conducted. Untagged $^{15}$N-labeled TRAF6 RZ1 protein (c=120 µM) and compound (c=20 mM) were incubated at a ratio of 1:5 in a 3 mm NMR tube for 10 minutes before spectra acquisition. To observe chemical shift perturbations upon compound addition, two-dimensional SOFAST-HMQC spectra were acquired. All measurements were performed using the Bruker Avance 600 MHz spectrometer.

3.2.3) In Vitro Ubiquitination Assay 3.2.3.1) Western-Blot-Based Assays

The ability of TRAF6 to form K63-linked poly-ubiquitin chains in conjunction with Ubc13 was analyzed after compound treatment. Therefore, untagged TRAF6$_{WT}$ and TRAF6$_{D57K}$, respectively were recombinantly purified. 0.125 µM of TRAF6 protein was pre-incubated with DMSO or compound in a total volume of 100 µL in K63 assay buffer (25 nM Tris —HCl pH 7.6; 250 nM MgCL$_2$; 500 nM creatine phosphate; 0.3 U/mL inorganic pyrophosphatase; 0.3 U/mL creatine phosphokinase) for 30 minutes at room temperature. Small aliquots for input samples were taken. A master mix containing 0.01 µM E1-activating enzyme (UBE1) (Boston Biochem), 0.2 µM E2-conjugating enzyme complex (Ubc13/Uev1a) (Boston Biochem), 1 mM ZnCl$_2$, 2 mM ATP und 4 µM mono-ubiquitin (Boston Biochem) was added to the TRAF6 protein and the reaction mixture was incubated for 120 minutes at 37° C. The reaction was stopped by adding 4×SDS loading buffer and boiling at 95° C. for 5 minutes. The input samples were analyzed using the Pierce Silver Stain Kit (Thermo Fisher Scientific). Ubiquitination was detected in Western Blot analysis using an ubiquitin antibody.

For analysis of cIAP1, MDM2, TRIM63, RNF4, ITCH and E6AP mediated poly-ubiquitination, the respective ubiquitin ligase kit from Boston Biochem (K-102, K-260, K-200B, K-220, K-240 and K-270) was used. Here, reaction buffer, E1, E2 and E3 enzyme (and p53 substrate in case of MDM2) were mixed and pre-incubated with compound or DMSO for 5 minutes at room temperature before adding Mg$^{2+}$-ATP and mono-ubiquitin for reaction start. Ubiquitination was visualized by Western Blot analyses.

3.2.3.2) Ubiquitin Profiler (Eurofins Pharma Discovery Services UK)

C25-140 was sent to Eurofins Pharma Discovery Services UK to perform a Single Point Ubiquitin Profiler testing of C25-140 effect at a concentration of 30 µM on 24 different Ubiquitin reaction cascades employing distinct combinations of E2, E3 and substrate. Each reaction was measured in duplicates. Cascade activity is expressed as a percentage of the mean cascade activity in the positive control samples. The positive control value is considered to be 100%, and all test samples are referred to this value.

3.3) Validation of TRAF6-Ubc13 PPI Inhibitors in Cell-Based Assays 3.3.1) Electrophoretic-Mobility-Shift-Assay (EMSA) to Measure NF-κB Activation For compound treatment, MEF cells were seeded in 6 well plates at 1.2×10$^5$ cells/well the day before treatment. Jurkat T-cells were seeded directly before treatment at 2×10$^5$ cells/sample. Six hours after compound or DMSO treatment cells were stimulated as indicated. Thereby, MEF cells were left untreated or stimulated with recombinant mouse IL-1β (1 ng/mL) or TNFα (10 ng/mL) for 20 minutes. Jurkat T-cells were stimulated with Phorbol-12-myristat-13-acetet (PMA) (400 ng/mL) and Ionomycin (600 ng/mL) for 30 minutes. Eventually, cells were lysed in high-salt lysis buffer (20 mM HEPES pH 7.9; 350 mM NaCl; 1 mM MgCl2; 0.5 mM EDTA; 0.1 mM EGTA; 20% Glycerol; 1% NP-40; 10 mM NaF; 8 mM β-Glycerophosphate; 1 mM DTT; 300 µM Sodium-vanadate; complete protease inhibitor) and analyzed in EMSA assays using H2K (NF-κB) or Oct-1 (loading control) probes. The following EMSA oligonucleotides were applied:

| H2K (NF-κB) | 5'GAT CCA GGG CTG GGG ATT CCC CAT CTC CAC AGG 3' (SEQ ID NO: 1) 5'GAT CCC TGT GGA GAT GGG GAA TCC CCA GCC CTG 3' (SEQ ID NO: 2) |
|---|---|
| Oct-1 | 5'GAT CTG TCG AAT GCA AAT CAC TAG AA 3' (SEQ ID NO: 3) 5'GAT CTT CTA GTG ATT TGC ATT CGA CA 3' (SEQ ID NO: 4) |

3.2. IKK Kinase Assay

For MEF cells, 5.5×10$^5$ cells were seeded, then treated with compound for 6 hours and eventually stimulated with IL-1β or TNFα for 8 minutes. 1×10$^6$ Jurkat T-cells were treated with compound for 6 hours and finally stimulated with PMA (400 ng/ml) and Ionomycin (600 ng/ml) for 8 minutes. After cell lysis in Co-IP lysis buffer (150 mM NaCl; 25 mM Hepes (pH 7.5); 0.2% NP-40; 1 mM Glycerol; 10 mM NaF; 8 mM β-Glycerophosphat; 1 mM DTT; 300 µM Sodium-vanadate; complete protease inhibitor), input samples were taken and the supernatant was then incubated with 6 µL IKKγ antibody FL-419 (Santa Cruz Biotechnology). Upon incubation with Protein-G-Sepharose beads (GE Healthcare), beads were washed in Co-IP wash buffer (150 mM NaCl; 25 mM Hepes (pH 7.5); 0.2% NP-40; 1 mM Glycerol) and transferred into kinase reaction buffer (20 µM HEPES pH7.9; 10 mM MgCl$_2$; 20 µM ATP; 20 mM β-Glycerophosphat; 200 µM Sodium-Vanadate; 1 mM DTT) supplemented with 1.5 mg GST-IκBα (1-53) and 0.5 µL $^{32}$P-γ-ATP. After 30 minutes incubation at 37° C., reaction was stopped and analyzed by autoradiography as well as Western Blot after separation on SDS-PAGE.

3.3.3) Analysis of mRNA Expression

For MEF cells, 1.2×10$^5$ cells per sample were seeded, treated with compound for 6 hours and stimulated with either IL-1β or TNFα for 60 minutes. Jurkat T-cells and primary mouse CD4$^+$ T-cells were seeded at 2×10$^5$ cells per sample, also treated with compound for 6 hours and stimulated with PMA/Ionomycin for 3 hours. RNA was isolated according to the manufacturer's protocol of the Qiagen RNeasy Kit (MEF cells) or the STRATEC INVITRAP® SPIN UNIVERSAL RNA MINI KIT (Jurkat T-cells). The isolation of mRNA from epidermal white adipose tissue from DIO mice was performed using TRIzol® Reagent according to manufacturer's instruction. To clear the isolated RNA from genomic DNA, samples (up to 5 μg RNA) were treated with RQ1 RNase-Free DNaseI (Promega) as described in the technical manual. For the reverse transcription of RNA into cDNA, the DNaseI digested RNA samples were processed using the SuperScript III First Strand cDNA Synthesis System (Invitrogen/ThermoFisher Scientific) following the manufacturer's protocol. Thereby, random hexamers provided with the kit were used for reverse transcription. cDNA samples were stored at −20° C. For quantification of cDNA in the samples, the LightCylcer480 (Roche) and the KAPA SYBR FAST qPCR Kit were used. For relative quantification, the ΔΔCp method first described by Pfaffl (Pfaffl, M. W., *A new mathematical model for relative quantification in real-time RT-PCR*. Nucleic Acids Res, 2001. 29(9): p. e45) was applied. The following primer were used for qRT-PCR:

| | |
|---|---|
| Mouse A20 for | 5'GCT CAA CTG GTG TCG TGA AG 3' (SEQ ID NO: 5) |
| Mouse A20 rev | 5'ATG AGG CAG TTT CCA TCA CC 3' (SEQ ID NO: 6) |
| Mouse β-Actin for | 5'CCT CTA TGC CAA CAC AGT GC 3' (SEQ ID NO: 7) |
| Mouse β-Actin rev | 5'GTA CTC CTG CTT GCT GAT CC 3' (SEQ ID NO: 8) |
| Mouse ICAM-1 for | 5'CGC TCA GAA GAA CCA CCT TC 3' (SEQ ID NO: 9) |
| Mouse ICAM-1 rev | 5'GGA GAC GCA GAG GAC CTT AAC 3' (SEQ ID NO: 10) |
| Mouse IL-1β for | 5'TCA GCA CCT CAC AAG CAG AG 3' (SEQ ID NO: 11) |
| Mouse IL-1β rev | 5'GCC CAT ACT TTA GGA AGA CAC G 3 (SEQ ID NO: 12) |
| Mouse IL-2 for | 5'GAG TGC CAA TTC GAT GAT GAG 3' (SEQ ID NO: 13) |
| Mouse IL-2 rev | 5'AGG GCT TGT TGA GAT GAT GC 3' (SEQ ID NO: 14) |
| Mouse VCAM for | 5'CCC CTC ATT CCT TAC CAC CC 3' (SEQ ID NO: 15) |
| Mouse VCAM rev | 5'AGT TGG GGA TTC GGT TGT TCT 3' (SEQ ID NO: 16) |
| Human IL-2 for | 5'CAC AGC TAC AAC TGG AGC ATT TAC 3'(SEQ ID NO: 17) |
| Human IL-2 rev | 5'TGC TGA TTA AGT CCC TGG GTC 3' (SEQ ID NO: 18) |
| Human TNFα for | 5'CCC AGG GAC CTC TCT CTA ATC 3' (SEQ ID NO: 19) |
| Human TNFα rev | 5'GCT ACA GGC TTG TCA CTC GG 3' (SEQ ID NO: 20) |
| Human RNA Polymerase II for | 5'GCA CCA CGT CCA ATG ACA 3' (SEQ ID NO: 21) |
| Human RNA Polymerase II rev | 5'GTG CGG CTG CTT CCA TAA 3' (SEQ ID NO: 22) |

3.3.4) ALPHASurefire

In order to detect protein levels of p-IκBα (Ser32/36) as well as total IκBa, 1×10$^4$ MEF cells were seeded in 96-well plates, treated with compound for 6 hours and stimulated with 1 ng/ml IL-1β for 7 minutes. The p-IκBα and total IκBα protein levels were analyzed using the ALPHASurefire kits (PerkinElmer) following the manufacturer's instruction. The general 2-plate protocol was conducted.

3.3.5) Immunoprecipitation of TRAF6 for Detection of Endogenous Ubiquitination 2.5×10$^6$ MEF cells were seeded, treated with compound for 6 hours and stimulated with IL-1β (3.5 ng/mL) for 10 minutes. Cells were lysed in Co-IP lysis buffer containing 1% SDS to eliminate all cellular interactions. After cell lysis and removal of input samples, the samples were diluted to 0.1% SDS and incubated with 5 μL TRAF6 antibody EP591Y (Abcam) and immunoprecipitated with Protein-G-Sepharose beads. After washing of the beads in Co-IP wash buffer, TRAF6 protein was eluted and levels of TRAF6 ubiquitination were detected by Western Blot analysis.

3.3.6) Enzyme-Linked ImmunoSorbent Assay (ELISA)

For measurement of cytokine secretion, 2×10$^5$ Jurkat T-cells or primary CD4$^+$ T-cells or human PBMCs per sample were seeded, treated with compound for 6 hours and stimulated as indicated. 20 hours after stimulation, supernatants were harvested and analyzed with the IL-2, IL-1β and TNFα Ready-Set-Go! ELISA (2$^{nd}$ Generation) kits provided by Affymatrix eBioscience.

3.3.7) Co-Immunoprecipitation Studies in HEK 293T Cells

To study the interaction of TRAF6 and Ubc13 in cells, 1×10$^6$ 293T cells were seeded and after 18 hours cells were transfected with 1 μg pEF-HA empty or pEF-HA-TRAF6 RZ1 plasmid using the X-tremeGENE HP DNA transfection reagent (Roche). 6 hours upon transfection, cells were treated with compound or DMSO. After 42 hours further incubation, cells were harvested in Co-IP lysis buffer and HA-TRAF6 was immunoprecipitated with anti-HA affinity matrix (Roche). Binding of Ubc13 to TRAF6 was examined in Western Blot analysis.

3.4) Viability, Cell Cycle, ADME and PK Studies 3.4.1) Viability Assay

For cell viability experiments using the CellTiter-Glo® 2.0 system (Promega), MEF cells (1.2×10$^3$ cells/well), HepG2 cells (4×10$^3$ cells/well) and Jurkat T-cells (5×10$^3$ cells/well) were seeded in 384 well plates. After 18 hours, cells were treated with compounds using the Sciclone G3 automation system. After 6 or 24 hours incubation, the luciferase measurement was performed according to the manufacturer's manual.

3.4.2) Cell Cycle Assessment

For cell cycle staining, cells were seeded at 2×10$^5$ cells per sample and treated with compound or DMSO. After the indicated incubation time (24 or 72 hours), cells were fixed in 100% Ethanol and subsequently stained with the Propidium Iodide staining solution (0.1% Triton X-100; 20 µg/ml Propidium Iodide; 200 µg/ml RNAse A in PBS) for 40 min in the dark. The Propidium Iodide fluorescence was collected using the Attune Flow Cytometer (Thermo Fisher Scientific). Analysis was performed using the Single Cell analysis software FlowJo.

3.4.3) Cell Growth Determination of the Osteosarcoma Cell Line U2OS

For analysis of the cell growth of the osteosarcoma cell line U2OS, $5×10^3$ cells were seeded in 96 well plates. 18 hours later, cells were treated with C25-140 (compound 3) or DMSO for 6 hours. Using a $^{137}$caesium source (HWM-D2000), selected samples were irradiated with a dose of either 2 Gy or 4 Gy. Cell growth was measured every 24 hours for a period of 7 days by counting Hoechst33342 positive cells in an Operetta High-Content Imaging System (PerkinElmer) and the Harmony/Columbus analysis software (PerkinElmer).

3.4.4) Determination of Cell Viability in DLBCL

To determine the effects of $C_{25}$-140 on MYD88-dependent ABC-DLBCL, we chose the HBL1 (ABC-DLBCL-MYD88 L265P), U2932 (ABC DLBCL-MYD88 wt) and BJAB (GCB DLBCL) cell lines. $1×10^6$ cells of each cell line was seeded in 5 ml and treated with 30 µM compound $C_{25}$-140 (compound 3) or DMSO. The entire experiment was carried out for 9 days. Every day 500 µl were taken and viable cell number was acquired using the ViCEII cell counter (Beckmann Coulter). At days 4 and 8 of the experiment the volume was again adjusted to 5 ml and samples were supplemented with 30 µM compound C25-140 or DMSO. This process was necessary to ensure linear proliferation of DMSO treated cells. All curves of C25-140 treated samples were referred to the corresponding DMSO treated controls.

3.4.5) ADME and Pharmacokinetic Studies

All ADME (plasma stability, plasma protein binding, microsomal stability, Log D, Caco-2 assay, CYP450 inhibition and hERG predictor assay) as well as pharmacokinetic studies ($T_{max}$, $C_{max}$, $AUC_{0-240min}$, Mean Residence Time, Elimination half life, Elimination rate constant, Volume of Distribution and Clearance) of C25-140 (compound 3) were conducted by Bienta Enamine Biology Services of Bienta/Enamine Ltd.

3.4.6) SafetyScreen87

The SafetyScreen87, a total of 87 assays, was carried out at Eurofins Cerep Panlabs. 87 primary molecular targets including 13 enzyme assays (kinases and non-kinase enzymes) and 74 binding assays (nuclear receptors, GPCRs, transporters and ion channels) were performed at a compound concentration of 10 µM C25-140. Each of the 87 assay reactions was performed at the optimised condition that was historically available at Eurofins Cerep Panlabs. In parallel to C25-140, a reference compound for each of the 87 reactions was concurrently tested to guarantee optimal setting of the assays. In this study the reference compounds performed in the same range as historic Ki values.

3.4.7) Omniscreen

The effect of C25-140 on cell viability of 80 cancer cell lines using the CellTiter-Glo luminescent cell viability assay was conducted at CrownBioscience Inc. at the testing facility in Beijing. Here, 80 selected cell lines were cultured in media supplemented with 10-15% FBS, in the temperature of 37° C., 5% $CO_2$ and 95% humidity. Culture medium was purchased from GIBCO or Sigma, USA. The cells were treated with C25-140 in 9 dose levels starting at 80 µM with 3.16-fold serial dilutions. Cisplatin served as a reference control and started with a top working concentration of 100 µM. Test samples were incubated for 72 hours and cell viability was measured by the CellTiter-Glo assay.

3.5) Mouse Studies 3.5.1) Isolation of Primary Mouse CD4 Positive T-Cells

Isolation of CD4$^+$ T-cells from the peripheral lymph nodes of Balb/C mice was conducted by negative magnetic-activation cell sorting (MACS) selection using the CD4$^+$ T-cell isolation kit II (Miltenyi). The primary CD4$^+$ T-cells were cultured in RPMI medium supplemented with 10% heat-inactivated FCS, 1% Penicillin/Streptomycin, 1% NEAA (Life Technologies), 1% HEPES, 1% L-glutamine, 1% sodium pyruvate (Life Technologies) and 0.1% β-mercaptoethanol. Per sample, $2×10^5$ cells were seeded and treated with compound for 6 hours. Cells were stimulated with anti-CD3 (0.5 mg/ml) and anti-CD28 (1 mg/ml) on plates that were pre-coated with rabbit anti-hamster IgG or anti-CD3/CD28-coated beads (3:1).

Samples for qRT-PCR were harvested after 4 hours whereas supernatants for analysis of cytokine secretion were harvested 20 hours after stimulation.

3.5.2) Diet-Induced-Obesity (DIO) Mouse Study

Mice were fed a high-fat-diet until they reached a body weight of at least 40 g and developed diabetes-induced-obesity. These mice were separated in control group and a group for C25-140 (compound 3) injection. Mice were treated every day with 14 µmol/kg (=7.4 mg/kg) C25-140 intraperitoneally for a period of 20 days. Thereby, C25-140 was dissolved in 2.9% DMSO, 1.5% Tween-80 and 1×PBS. Every day before injection, the body weight and food intake were measured. On day 20, mice were sacrificed two hours after compound injection and epidermal white adipose tissue from both body sites was removed, frozen in liquid nitrogen and stored at −80° C.

3.5.3) Psoriasis Mouse Study

To evaluate the anti-inflammatory activity of the compound C25-140 (compound 3), an Imiquimod (IMQ)-induced psoriasis mouse model was conducted by Washington Biotechnology, Inc. (Baltimore, USA). Per group, 8 male Balb/C mice were shaved in the back (1.5 cm×2 cm) and IMQ and C25-140 were applied topically to the shaved back and the right ear daily for 6 days. Thereby, C25-140 was dissolved in acetone and applied at a total dosage of 500 µg per day (2×250 µg). Mice were monitored and daily scores (erythema, scaling and thickness of back skin) were independently collected on a scale from 0 to 4: 0=none; 1=slight; 2=moderate; 3=marked and 4=very marked. Ear thickness was measured by electronic calipers as an indicator of edema. IL-17 cytokine secretion of the right ear tissue was measured by ELISA.

3.5.6) Collagen-Induced Arthritis Model

In order to test the potential of C25-140 to ameliorate RA symptoms, a Collagen-Induced Arthritis (CIA) Model in DBA1/J mice was performed by Washington Biotechnology, Inc. (Baltimore, USA). Each group of ten mice was subjected to a single subcutaneous injection of collagen/complete Freund's Adjuvant emulsion (0.05 ml/mouse; 100 µg collagen/CFA). After 20 days (day 21), mice were booster injected with collagen (0.05 ml/mouse; 100 µg/mouse collagen in Incomplete Freund's Adjuvant). On day 28, mice were scored for their Arthritic Index (AI) and 14 days intraperitoneally dosed twice daily with 6 mg/kg, 10 mg/kg and 14 mg/kg C25-140, respectively. Mice were scored of macroscopic signs of arthritis daily. Thereby, the following scoring index was applied to each individual paw: 0=no visible effects of arthritis; 1=edema and/or erythema of 1 digit; 2=edema and/or erythema of 2 digits; 3=edema and/or erythema of more than 2 digits; 4=severe arthritis of entire paw and digits. Single paw scores were added and recorded. On day 42, animals were euthanized, limbs were collected and histopathology was performed using Toluidine blue staining with scoring of several parameters.

3.6) Human Donor Experiments

For isolation of peripheral blood mononuclear cells (PBMCs) from 50 mL human blood of three different donors, blood was mixed with 800 units of Heparin (Sigma-Aldrich) and centrifuged at 300×g for 10 minutes without brake. After removal of the plasma fraction, buffy coat was diluted in 2 volumes PBS and added on top of 15 ml Lymphoprep (STEMCELL technologies). After centrifugation at 160×g for 20 minutes at room temperature without brake, platelets were removed and the cell suspension was centrifuged again at 350×g for 20 minutes without brake. Mononuclear cells from the intermediate layer were transferred to a new falcon and washed 3 times in PBS supplemented with 0.1% BSA and 2 mM EDTA. In the end, cells were resuspended in RPMI medium containing 10% FCS, 1% Penicillin/Streptomycin and 50 μM β-mercaptoethanol. Per sample, $2 \times 10^5$ cells were seeded and treated with compound for 6 hours. The cells were stimulated with either 1 μg/ml Lipopolysaccharide (LPS) or CD3/CD28 (1 μg hCD3 ($IgG_{2A}$), 4 μg hCD28 ($IgG_1$), 2 μg ant-$IgG_{2A}$ and 2 μg ant-$IgG_{2A}$) or 20 ng/IL-1β. Supernatants for analysis of cytokine secretion were harvested 20 hours after stimulation.

3.7) Statistical Analysis

Figure 1A:
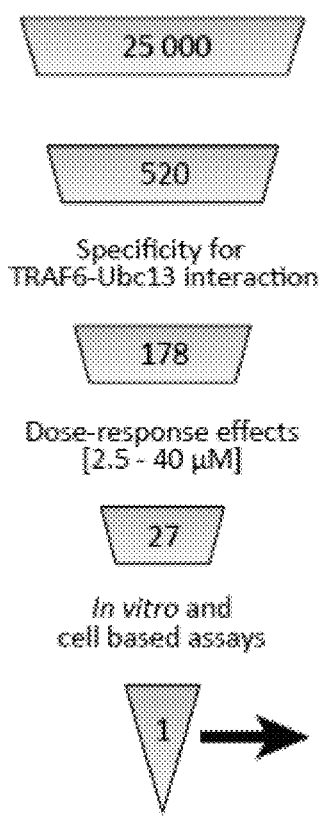
FIG. 1: Compound identification and C25 SAR study. (A) The identification process for TRAF6-Ubc13 inhibitors. 25.000 small molecules of three in-house libraries were screened using the ALPHAScreen technology. 520 molecules inhibited the TRAF6-Ubc13 binding by more than 25%. After elimination of ALPHA frequent hitter and His-tag frequent hitter, 178 compounds were re-tested in 5-point titration ALPHAScreen assays. The remaining 27 small molecules were re-ordered and tested in ALPHAScreen assays (10-point titration) as well as in EMSA experiments. C25 did show best results in in-vitro and cell-based assays. (B) C25-140 appears to be similar efficient in ALPHAScreen, but (C) more active in cell-based ALPHA-Surefire experiments. C25 is equal to compound 1, C25-140 is equal to compound 3, C25-167 is equal to compound 61 and C25-189 is equal to compound 2 of the description.
Figure 1B:
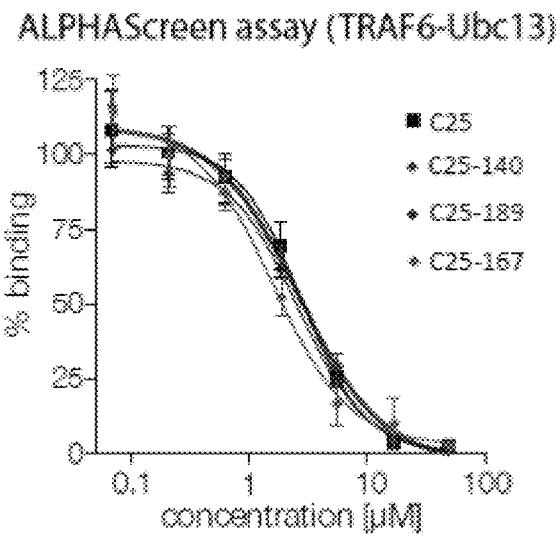
Figure 1C:
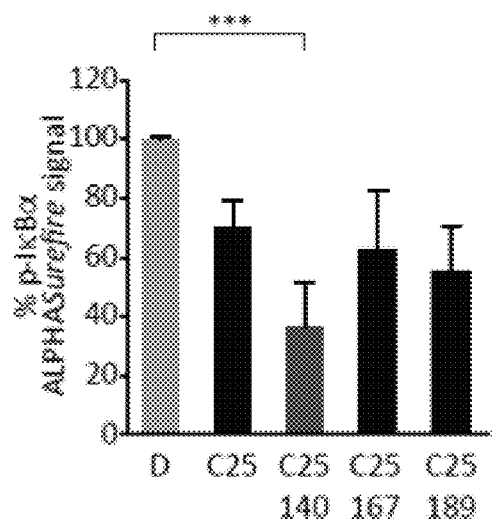
Figure 2A:
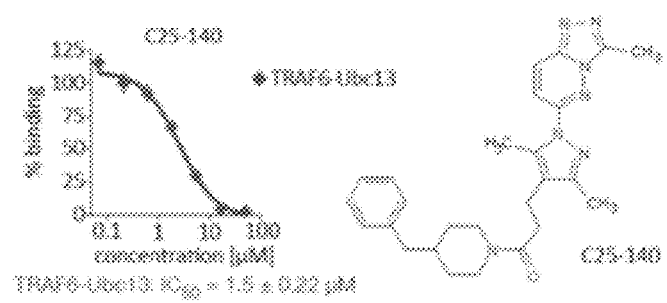
FIG. 2: Biochemical and cell-based characterization of C25-140. (A) The chemical structure of C25-140 is depicted. (B) C25-140 dose-dependently decreases the interaction of endogenous Ubc13 to ectopically expressed HA-tagged TRAF6 in HEK 293T cells. (C) C25-140 directly binds to TRAF6 RZ1 protein in NMR experiments as revealed by shifting or disappearing of distinct peaks. (D) The TRAF6 inhibitor C25-140 dose-dependently impairs the ability of TRAF6 and Ubc13 to form free poly-ubiquitin chains in an in vitro ubiquitination assay. (E) Interaction of Ubc13 with Uev1a was not affected by C25-140. C25-140 is equal to compound 3 of the description.
Figure 2B:
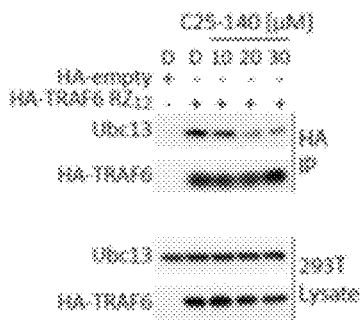
Figure 2C:
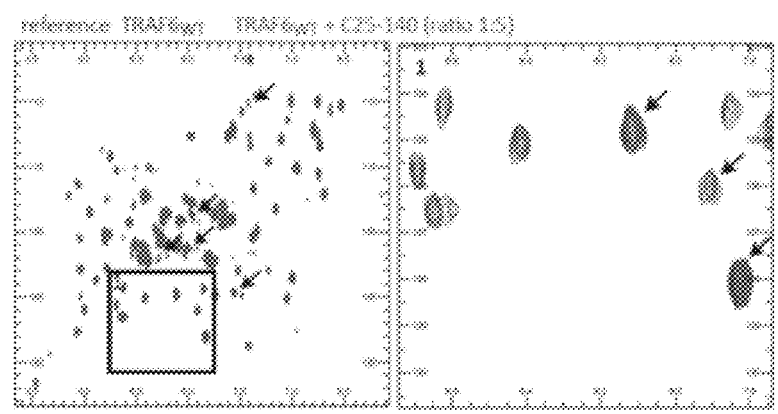
Figure 2D:
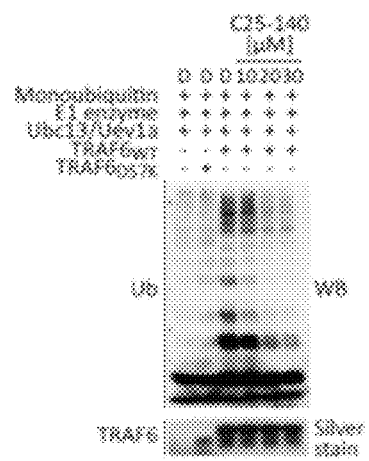
Figure 2E:
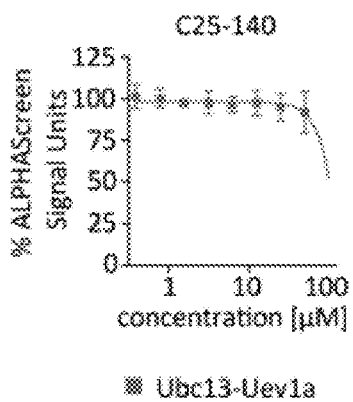

Experiments are depicted as mean±standard deviation of the mean. For statistical analysis, the "unpaired t-test" was applied and statistical significance was determined by a p-value<0.05. In the DIO-mouse-study, the statistical significance of bodyweight loss was calculated with the two-way-Anova test. To determine whether C25-140 (compound 3) treatment significantly influenced outcomes of psoriasis symptoms, the two-way-Anova test was applied. Finally, the two-way-Anova test was applied to DLBCL experiments looking at survival curves. Prism 6.0 software (GraphPad) was used to determine statistical parameters 4) Discussion In a High-Throughput-Screening (HTS) campaign to identify small molecules inhibiting TRAF6-Ubc13 interaction, C25 (which is equal to compound 1 of the description) was discovered as promising hit in a step-wise process employing in vitro and cell-based analyses (FIG. 1A). Structure Activity Relationship (SAR) studies around C25 revealed three compounds with similar in vitro efficacy (FIGS. 1B and 2A), but C25-140 (which is equal to compound 3 of the description) comprised improved inhibitory activity in cell-based NF-κB activation assays (FIG. 1C). In addition, C25-140 reduced interaction between endogenous Ubc13 and ectopically expressed TRAF6 in cells in a dose-dependent manner (FIG. 2B). Further characterization of C25-140 in in vitro experiments showed that this compound directly binds to the TRAF6 protein as proven in NMR studies (FIG. 2C) and C25-140 is able to dose-dependently diminished TRAF6 E3 ligase activity to form poly-ubiquitin chains (FIG. 2D). Importantly, C25-140 did not affect binding of Ubc13 to Uev1a (FIG. 2E). Hence, C25-140 has the capacity to bind TRAF6, subsequently disrupt its binding to Ubc13 and eventually reduce the TRAF6 activity.

Before expanding on in-depth cellular investigations of C25-140 the inventors first analyzed whether this compound affects cell viability and cell cycle phases. Here, C25-140 did not considerably impact cell viability in three different cell lines (Jurkat, MEF and HepG2) except at the highest concentration of 100 μM (FIG. 3A). Furthermore, no effects on cell cycle phases could be observed upon C25-140 treatment of Jurkat and U2OS cells (FIG. 3B-C). In total, we can demonstrate that C25-140 did not affect cell viability and cell cycle progression at concentrations up to 30 μM that were used for subsequent cell-based experiments.

Figure 4A:
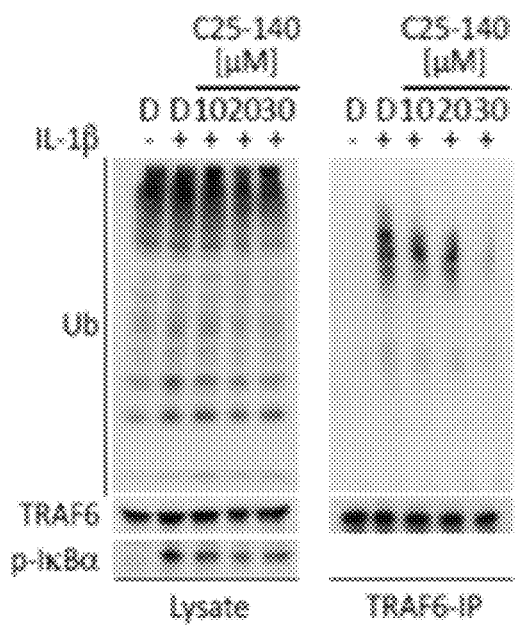
FIG. 4: C25-140 counteracts IL-1β and TNFα signaling in MEF cells. (A) Upon C25-140 treatment, IL-1β-induced auto-ubiquitination of TRAF6 is reduced. (B) In an IKK activity assay, C25-140 treatment causes a decreased phosphorylation of IκBα after IL-1β stimulation. (C) mRNA expression of IL-1β-induced target genes (e.g. ICAM-1 and A20) is impaired by C25-140 treatment. (D) C25-140 also affects TNFα-induced phosphorylation of IκBα in an IKK activity assay and (E) mRNA expression levels of the target genes ICAM-1 and A20. IKK KA means IKK kinase activity. C25-140 is equal to compound 3 of the description.
Figure 4B:
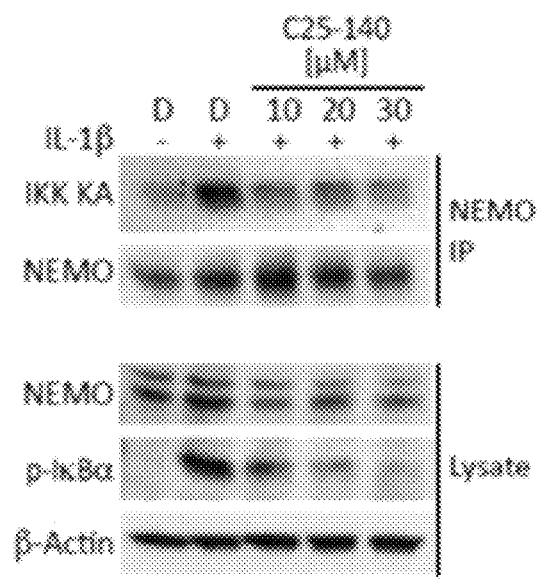
Figure 4C:
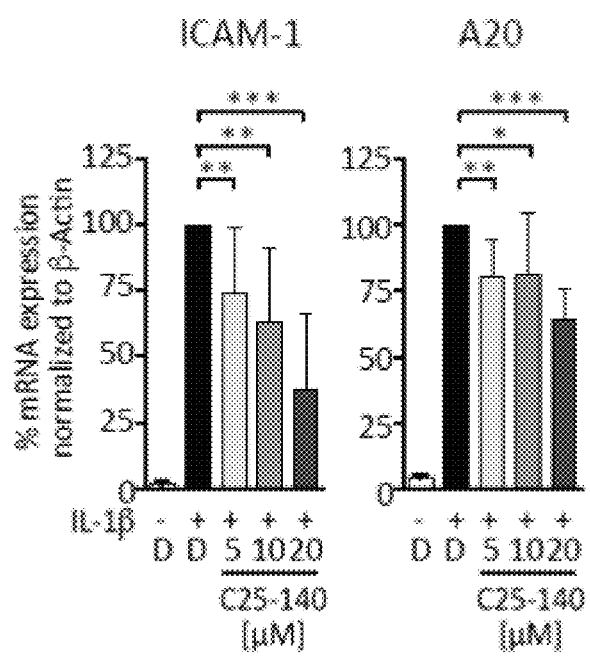
Figure 4D:
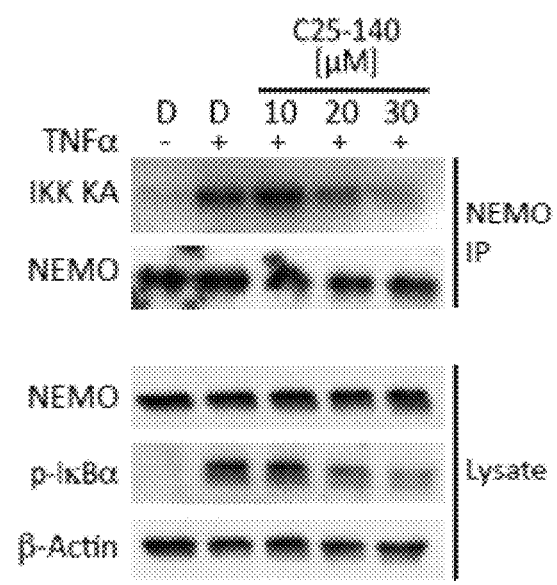
Figure 4E:
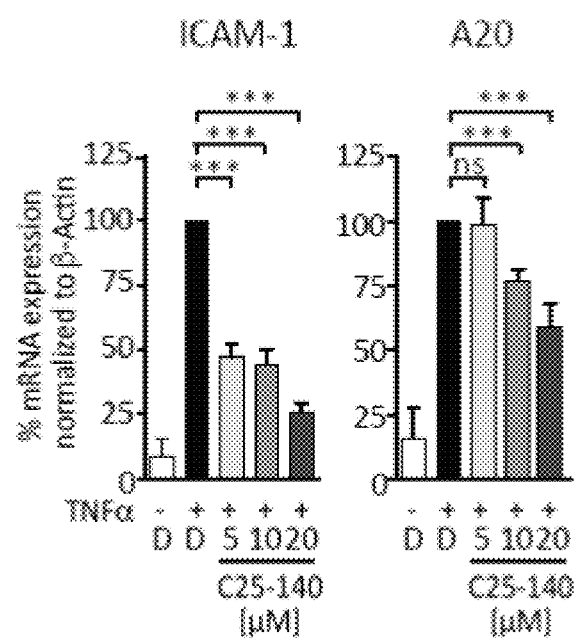
Figure 5A:
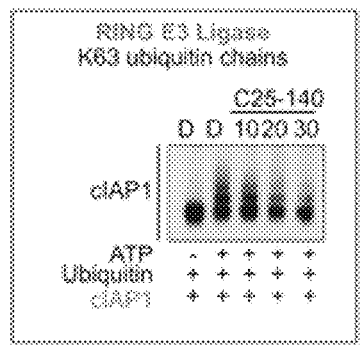
FIG. 5: (A) Using in vitro ubiquitination assays, we can demonstrate that auto-ubiquitination of cIAP1 (RING E3 ligase; K63 chain formation) is dose-dependently diminished upon C25-140 treatment. In contrast, (B) p53 ubiquitination by MDM2 and S5A ubiquitination by MURF/TRIM63 (both RING E3 ligases; K48 chain formation), (C) RNF4 auto-ubiquitination (SUMO targeted ubiquitin ligase) as well as (D) ITCH auto-ubiquitination and S5A ubiquitination by E6AP (both HECT E3 ligases; K48 chain formation) are not affected by C25-140. (E) A Ubiquitin Profiler panel was performed. Various E3 ligases in combination with different E2s and substrates were incubated with 30 μM of compound C25-140. None of the reactions is considerably inhibited by compound C25-140. C25-140 is equal to compound 3 of the description.
Figure 5B:
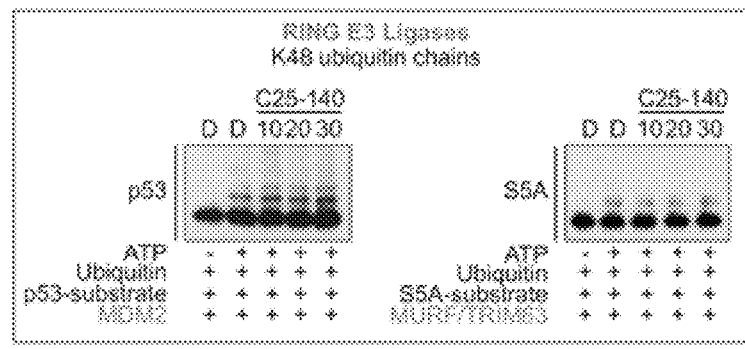
Figure 5C:
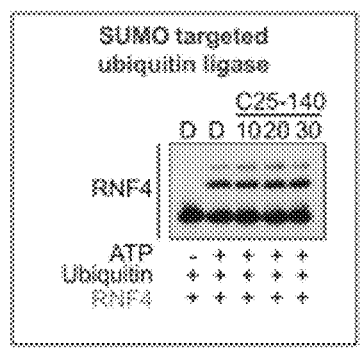
Figure 5D:
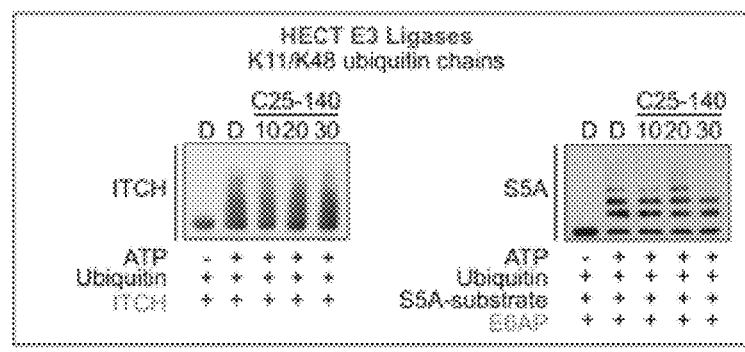
Figure 5E:
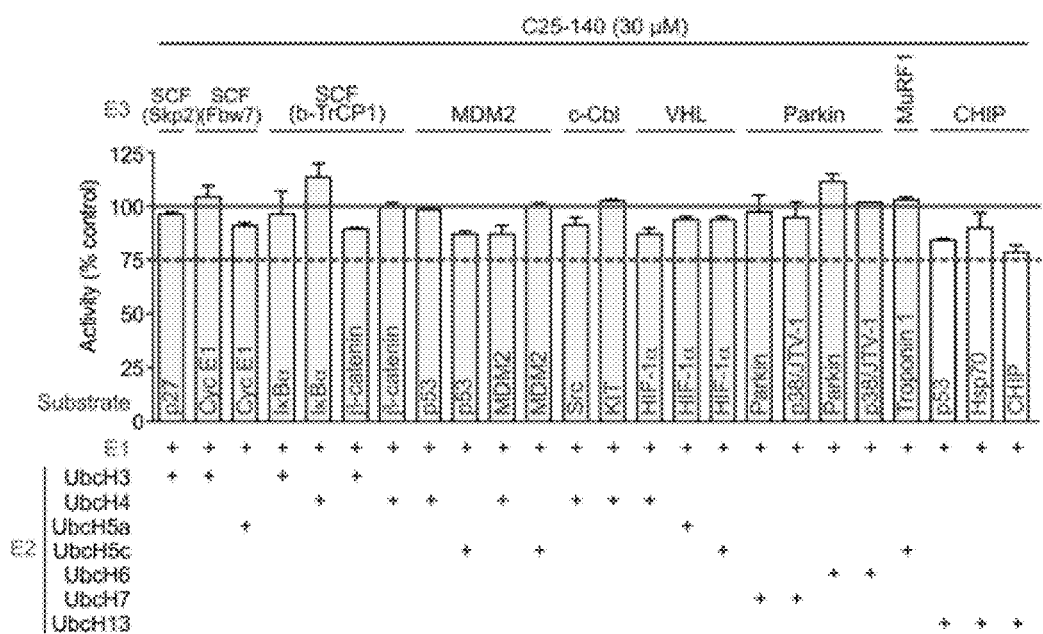

As the first cell model we chose the MEF cells that can be stimulated with IL-1β and TNFα. Stimulation of these cells with IL-1β induces TRAF6 auto-ubiquitination that is required for signal progression towards IκBα phosphorylation by the IKK complex, activation of NF-κB and expression of NF-κB-dependent target genes. C25-140 treatment of MEF cells led to reduced TRAF6 auto-ubiquitination (FIG. 4A) reflecting the in vitro ubiquitination results with recombinant proteins (FIG. 2D). The reduced TRAF6 auto-ubiquitination was followed by decreased IKK kinase activity (FIG. 4B), which translated into diminished target gene expression (FIG. 4C). These data depict that the inhibition of TRAF6 activity early during IL-1 receptor signaling is translated throughout different steps of signaling and the inhibition of TRAF6 activity can be visualized at all these distinct steps. Surprisingly, TNFα induced phosphorylation of IκBα (FIG. 4D) and NF-κB induced target gene expression (FIG. 4E) was also affected by C25-140 treatment. This was not expected as to the current knowledge the TNFα receptor signaling does barely involve TRAF6 for signal progression. To shed light on this finding we tested the effect of C25-140 on the activity of several other E3 ligases to understand whether there is any cross-reactivity. These studies revealed that the E3 ligase activity of cIAP1, an E3 ligase generating K63-linked poly-ubiquitin chains similar to TRAF6, was indeed affected by C25-140 (FIG. 5A). In contrast, several other E3 ligases (MDM2, TRIM63, ITCH, E6AP and RNF4) building different types of poly-ubiquitin chains (mainly K11 and K48) were not influenced by C25-140 (FIG. 5B-D). Furthermore, in an Ubiquitin Profiler study, further 24 ubiquitination reactions involving various E3-E2 complex and substrate combinations were tested. None of these reactions was inhibited by C25-140 (FIG. 5E). These data explain the inhibitory effects of C25-140 on TNFα signaling as the E3 ligase cIAP1 is a central regulator of TNFα signaling that is inhibited by C25-140. Very importantly, these data also illustrate that C25-140 is not a broadband E3 ligase inhibitor and thus retains good selectivity, although minor off-target effects on TNFα signaling are visible.

The inventors also tested C25-140 on T-cell receptor (TCR) signaling in a human T-cell line (Jurkat T-cells) of the adaptive immune response. Here, we can show that it also affects TCR signaling that relies on TRAF6 (Oeckinghaus, A., E. Wegener, V. Welteke, et al., Malt1 ubiquitination triggers NF-kappaB signaling upon T-cell activation. EMBO J, 2007. 26(22): p. 4634-45). In Jurkat T-cell, TCR stimulation led to TRAF6 auto-ubiquitination that was dose-dependently diminished by C25-140 (FIG. 6A). Decreased TRAF6 auto-ubiquitination resulted in reduced downstream events including IKK kinase activity, NF-κB activation as well as expression and secretion of the respective cytokines (FIG. 6B-E). These data underline that our compound also affects the TCR mediated adaptive immune response in human derived cell lines.

Figure 7A:
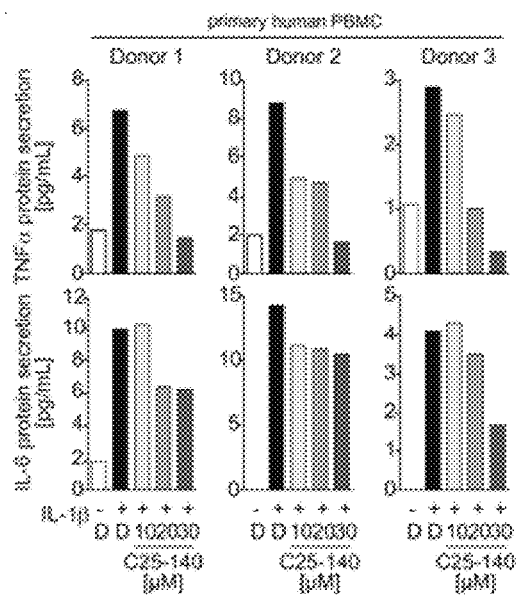
FIG. 7: C25-140 affects immune receptor signaling in primary human PBMCs. (A) Secretion of inflammatory cytokines (e.g. IL-6 and TNFα) of human peripheral blood mononuclear cells (PBMCs) that were stimulated with IL-1β could be attenuated by C25-140. (B) Human PBMCs that were stimulated with LPS secreted reduced levels of IL-1β and TNFα cytokines. (C) Human PBMCs stimulated with CD3/CD28 to induce TCR signaling show decreased levels of IL-2 and TNFα secretion upon C25-140 treatment. C25-140 is equal to compound 3 of the description.
Figure 7B:
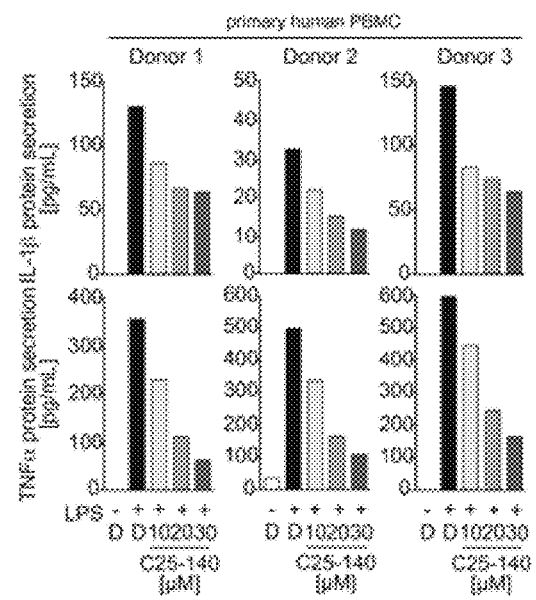
Figure 7C:
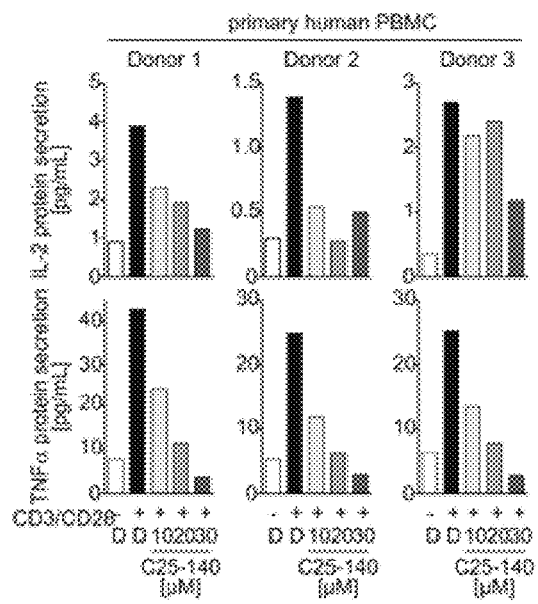
Figure 8:
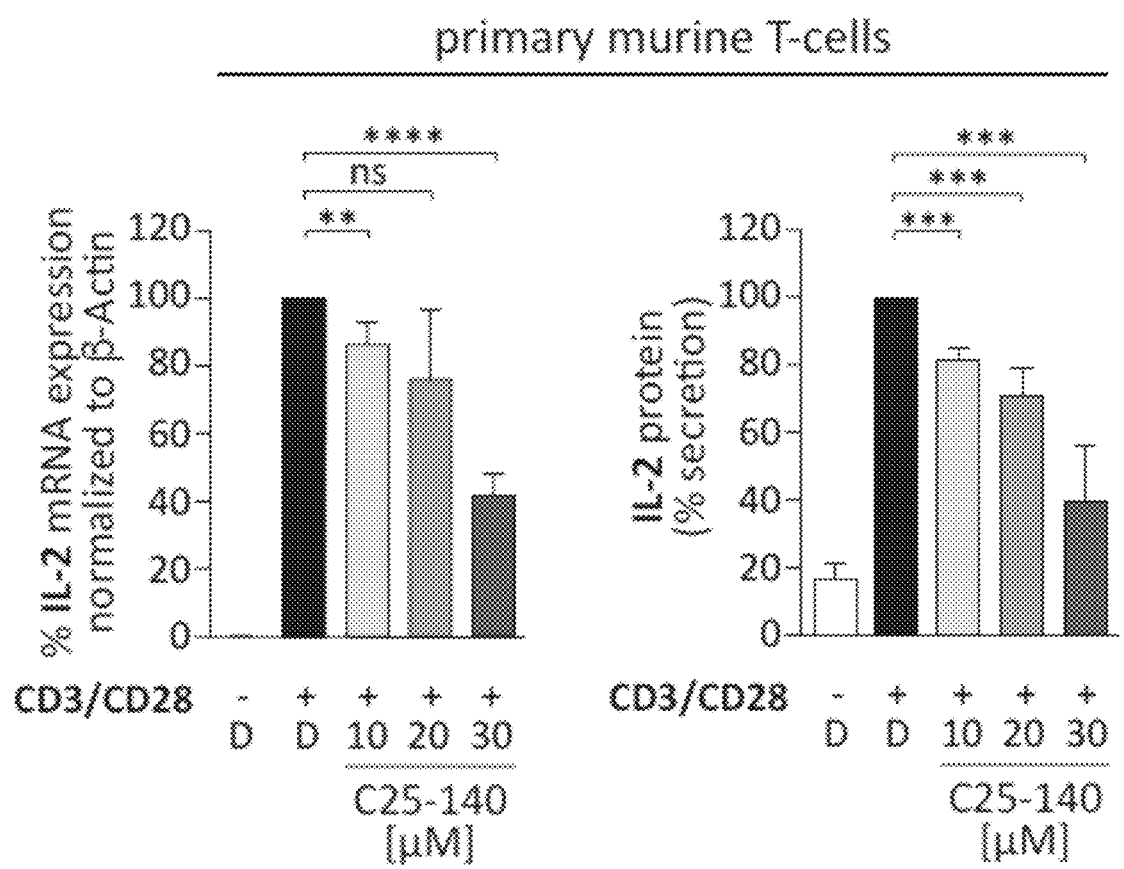
FIG. 8: C25-140 interferes with TCR signaling in primary murine T-cells. Isolated primary naïve CD4$^+$ T-cells show impaired IL-2 mRNA expression and IL-2 protein secretion in the presence of C25-140 when stimulated with CD3/CD28. C25-140 is equal to compound 3 of the description.

After the inventors had shown that C25-140 is successfully competing TRAF6-dependent receptor signaling in mouse and human cell lines they proceeded to work with more biologically relevant cells. To this end, the inventors isolated human peripheral blood mononuclear cells (PBMCs) from three different individuals and stimulated these cells with LPS to activate innate immune responses. In line with our previous data, C25-140 reduced secretion of NF-κB-driven inflammatory cytokines such as TNFα and IL-6 after IL-1β stimulation (FIG. 7A) or IL-1 and TNFα upon LPS stimulation (FIG. 7B) indicating that C25-140 does not only influence TRAF6 activity in immortalized cells, but more importantly it reduces innate immune processes in primary human blood cells. Similar inhibitory effects by C25-140 could be observed in human PBMCs by stimulating the adaptive immune response by CD3/CD28 (FIG. 7C). Finally, the inventors also isolated primary murine CD4$^+$ T-cells for precursor experiments to in vivo mouse studies. Again C25-140 counteracted CD3/CD28 mediated NF-κB activation and IL-2 production (FIG. 8).

Taken together, data from in vitro studies as well as cell-based studies involving immortalized cell lines as well as primary human and murine cells exhibit that C25-140 exerts inhibitory effects on various immune and inflammatory signaling pathways, which might be beneficial for treating a highly inflamed immune system.

In order to move into in vivo mouse studies, the inventors analyzed whether compound C25-140 has suitable properties for in vivo application. To this end, the inventors first ran an ADME study looking at the following parameter: (i) plasma stability, (ii) plasma protein binding, (iii) microsomal stability, (iv) log D, (v) Caco-2 permeability, (vi) CYP450 inhibition and (vii) hERG inhibition. Compound C25-140 comprised a fairly good set of properties in all these assays (FIG. 9A). Altogether, the compound is stable in plasma and microsomes, shows good penetration of the Caco-2 layer indicating good oral bioavailability, has decent good plasma protein binding capacity and very importantly does not very much inhibit hERG. Only in terms of CP450, it has some inhibitory potential on selected CYPs.

The inventors also tested the pharmacokinetics (PK) of C25-140 after intravenous (IV), peroral (PO) and intraperitoneal (IP) injection of each 10 mg/kg compound. All the analyzed data are summarized in FIG. 9B and the concentration/time-course graph for IP administration is shown in FIG. 9C. In case of IP administration, C25-140 exhibited higher calculated in vivo half-life in circulation (184 min) in comparison to IV (80 min) and PO (127 min) delivery. In total, a rapid initial distribution phase is observed. The compound has good calculated oral bioavailability of approx. 45%. During the PK studies no obvious adverse effects of the compound on animals were observed.

Subsequently, the inventors tested safety of C25-140 by applying the Cerep SafetyScreen87 panel, a set of critical receptors, proteins and enzymes that should not be affected to ensure good in vivo tolerance. Intriguingly, no significant binding of C25-140 to any of these targets was detectable (FIG. 10), clearly suggesting that C25-140 displays a high degree of safety for preclinical/clinical application.

Figure 11A:
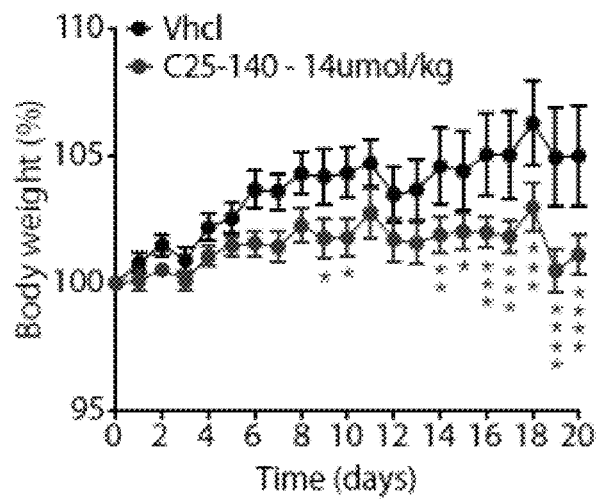
FIG. 11: C25-140 treatment of Diet-Induced-Obesity (DIO) mice affects body weight gain and inflammation of epidermal white adipose tissue. (A) C25-140 treated mice show milder body weight gain when compared to control mice, (B) whereas food intake remains unaffected in both groups. (C) mRNA levels of the pro-inflammatory cytokine IL-1β and the NF-κB dependent target gene VCAM are decreased in C25-140 treated mice. C25-140 is equal to compound 3 of the description. Vhcl means vehicle.
Figure 11B:
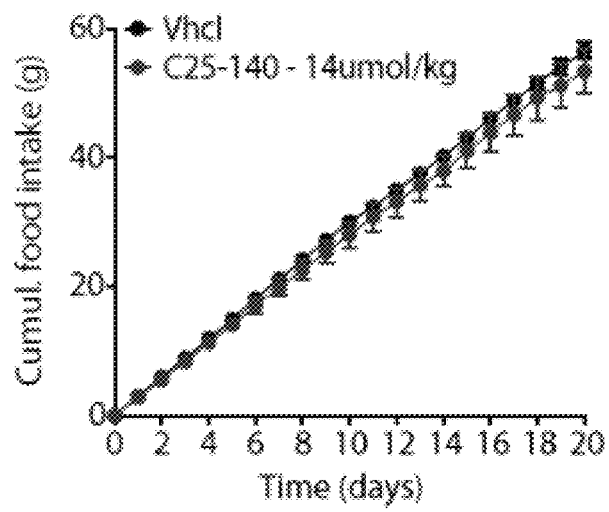
Figure 11C:
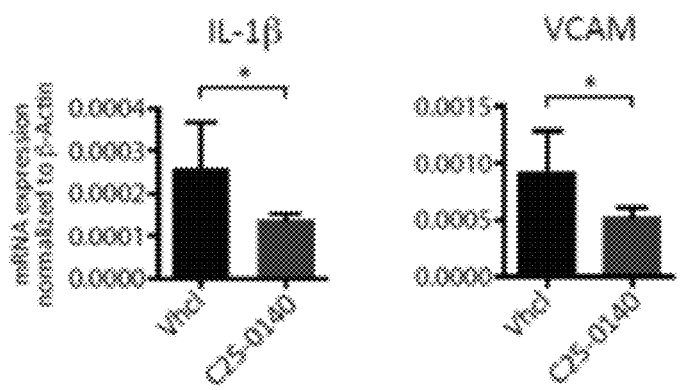

In a first mouse study the inventors wanted to explore the potential of the TRAF6 activity inhibitor C25-140 to counteract inflammation and body weight gain that is caused by high-fat-diet (HFD) induced obesity. In cooperation with the Institute for Diabetes and Obesity at Helmholtz Zentrum München GmbH-Deutsches Forschungszentrum für Gesundheit und Umwelt (HMGU), 16 mice that had been on HFD for at least 12 months were chosen. These mice had an average body weight of 55 g with obvious characteristics of obesity and type 2 diabetes (T2D). These mice were divided into two groups and once daily they were intraperitoneally treated with either vehicle or C25-140 at a dose of 7.4 mg/kg for a period of 20 days. Every day before injection, mice body weight and their food intake were monitored. Control treated mice continuously gained body weight over the 20 test days under HFD, while C25-140 treated mice hardly increased body weight (FIG. 11A). Importantly, food intake did not differ between the two groups (FIG. 11B) indicating that the treatment had no overall adverse effect on the mice. The inventors also looked into isolated adipocytes for IL-1 expression as a marker for inflammation as well as VCAM as a NF-κB target gene. Both genes were significantly reduced upon treatment providing molecular proof that the TRAF6 inhibitor had indeed worked correctly. In total, this study provides important information that the TRAF6 inhibitor C25-140 can reduce inflammation in vivo and thereby well contributes to reducing body weight gain under high-fat-diet conditions.

The second in vivo mouse model aimed at investigating C25-140 in a psoriasis mouse study as an autoimmune disease model, which was carried out by the CRO Washington Biotechnology. In this model, psoriasis is induced by imiquimod (IMQ) through activation of TLR7 signaling (Gilliet, M., C. Conrad, M. Geiges, et al., *Psoriasis triggered by toll-like receptor 7 agonist imiquimod in the presence of dermal plasmacytoid dendritic cell precursors*. Arch Dermatol, 2004. 140(12): p. 1490-5). More specifically, IMQ was applied once daily to the shaved back and the right ear of mice. On the same regions C25-140 was topically applied twice daily. Parameters capturing the disease outcome were scored every day and samples for IL-17 cytokine measurement were collected at day 6 (FIG. 12A). Compound 25-140 was able to significantly reduce the "cumulative score" (FIG. 12B) and the "thickness score" (FIG. 12C). These scores reflected individual scores such as "Scaling" (FIG. 12D), "erythema (FIG. 12E) and "ear thickness" (FIG. 12F). All these parameters reflected an improvement of the disease symptoms. Finally, analysis of the right ear tissue on IL-17 revealed that this cytokine was significantly reduced in its secretion/expression (FIG. 12G). Hence, this study did demonstrate that the C25-140 as an inhibitor of TRAF6 activity is able to ameliorate symptoms of an in vivo disease model of autoimmune psoriasis.

Figure 13A:
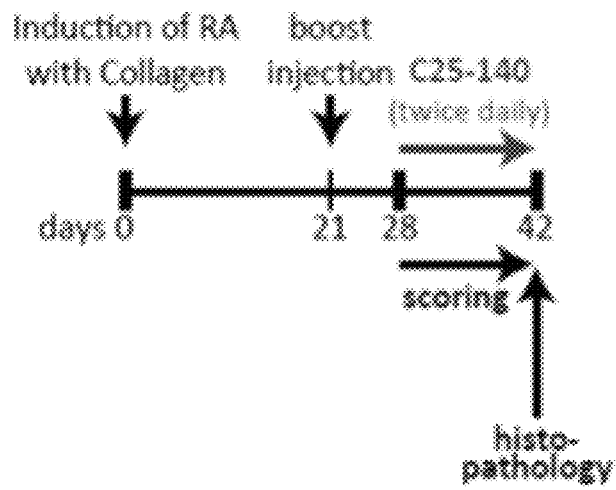
Figure 13B:
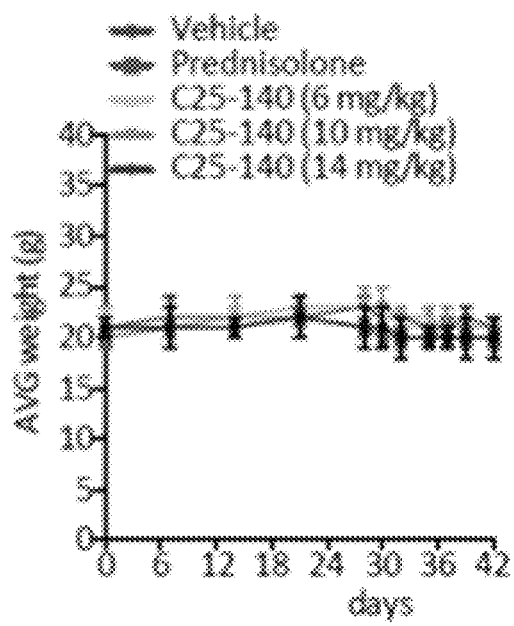
Figure 13C:
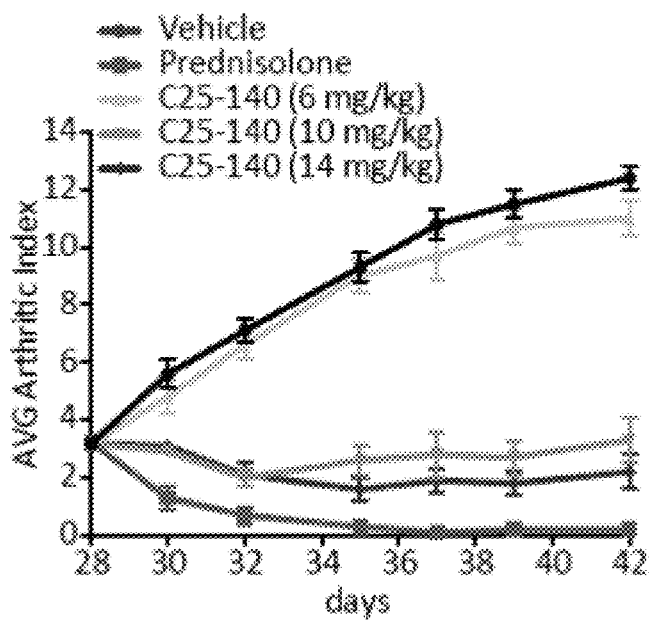
Figure 13D:
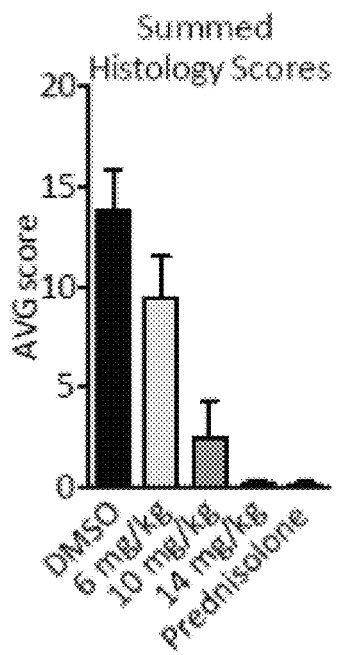
Figure 13E:
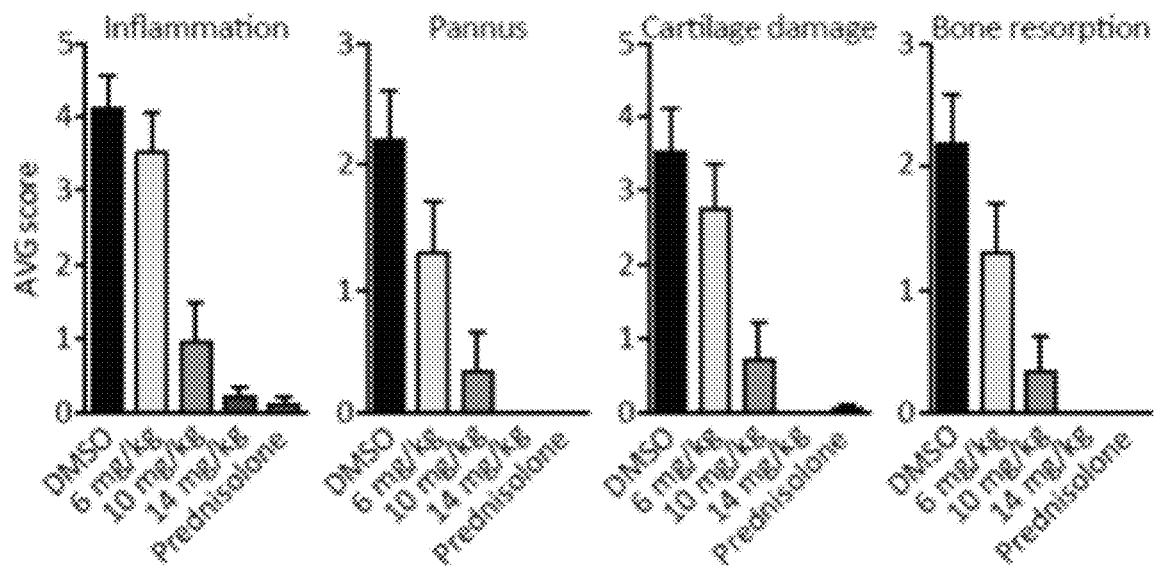
Figure 13F:
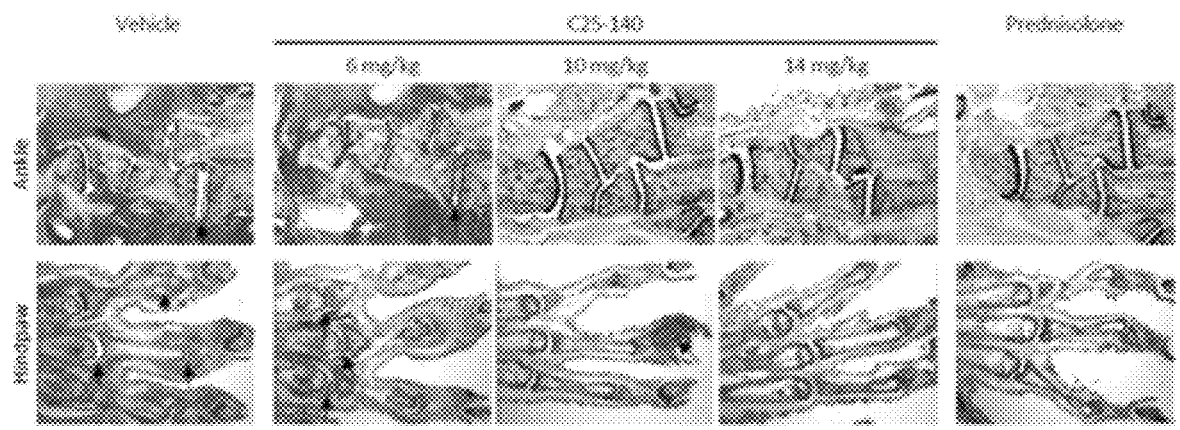

In a third in vivo mouse study, the inventors tested whether the compound C25-140 is effective in a preclinical mouse model for autoimmune Rheumatoid Arthritis (RA). Here, the inventors tested C25-140 in a Collagen-induced Arthritis (CIA) mouse model being the most commonly used RA efficacy model (Brand, D. D., K. A. Latham, and E. F. Rosloniec, *Collagen-induced arthritis*. Nat Protoc, 2007. 2(5): p. 1269-75). The study was again carried out by the CRO Washington Biotechnology. Here, Rheumatoid Arthritis (RA) was induced by injection of collagen at day 0. 21 days later mice received a collagen booster injection inducing the development of arthritic symptoms. At day 28, C25-140 was administered twice daily at three different doses (6 mg/kg, 10 mg/kg and 14 mg/kg) for a period of 14 days. Prednisolone served as a positive control. Mice were scored for the arthritic index (AI) daily and euthanized on day 42. Limbs were collected for histopathology analysis (FIG. 13A). Throughout the entire study the body weight was monitored and did not show any signs of reduction (FIG. 13B). Excitingly, our compound almost completely ameliorated the arthritic index to baseline levels in this efficacy model at the doses of 10 mg/kg and 14 mg/kg (FIG. 13C). More importantly, these results were backed-up by histology of the limbs. Quantification of various parameters (summed scores, inflammation, pannus, cartilage damage and bone resorption) of disease appearance (FIG. 13D-E) and tissue sections of the limbs (FIG. 13F) verified that C25-140 dose-dependently improves RA symptoms. This entire dataset demonstrates that C25-140 successfully counteracted clinical symptoms of RA and reversed the disease state. The inventors herewith present a successful proof of concept study for compound C25-140 in a preclinical RA efficacy model.

The inventors further investigated the potential of C25-140 to selectively kill a subset of aggressive ABC DLBCL. Survival of ABC DLBCL relies on a variety of different mutation leading to constitutive active NF-κB signaling. Major mutations are within the B-cell receptor (BCR) and MYD88 signaling (Nagel, D., M. Vincendeau, A. C. Eitelhuber, et al., *Mechanisms and consequences of constitutive NF-kappaB activation in B-cell lymphoid malignancies*. Oncogene, 2014. 33(50): p. 5655-65 and Ngo, V. N., R. M. Young, R. Schmitz, et al., *Oncogenically active MYD88 mutations in human lymphoma*. Nature, 2011. 470(7332): p. 115-9). To date, most available therapeutics concentrates on the BCR pathway. As TRAF6 is a major player of the MYD88 signaling, we sought to understand whether our TRAF6 inhibitor would selectively kill ABC DLBCL with a constitutive active MYD88 mutation. We used MYD88-dependent ABC DLBCL (HBL-1 with MYD88 L265P mutation), MYD88 wildtype ABC DLBCL (U2932) and a GCB DLBCL (BJAB) cell line. All cell lines were treated with C25-140 at day 0, 4 and 8. The study was carried out for 9 days and cell viability (cell count) was measured daily. C25-140 significantly reduced viability of MYD88-dependent HBL1, while MYD88-independent U2932 cells were only slightly affected (FIG. 14). Non-related GCB DLBCL cell line BJAB did not show any difference in viability upon C25-140 treatment (FIG. 14). These data show that the TRAF6 C25-140 is a selective inhibitor of MYD88-dependent ABC DLBCL and may serve as an important inhibitor for combinatorial treatments with current BCR acting therapeutics.

In a second cancer context the inventors explored whether our TRAF6 inhibitor C25-140 is effective against osteosarcoma derived cells and may be used for osteosarcoma therapy. The inventors either treated U2OS cells with irradiation (2Gy or 4Gy) or with C25-140 alone or with a combination of C25-140 and 2Gy irradiation. While C25-140 alone and 2Gy irradiation had the same inhibitory impact on cell proliferation of U2OS cells, the combination of both boosted the effect to the region of 4Gy irradiation (FIG. 15). These data indicate that C25-140 can augment effects of radiation therapy in a way that less exposure to irradiation in combination with C25-140 will still guarantee effective therapy.

To have a more comprehensive view on the effects of C25-140 on cancer cells, the inventors initiated a cancer study employing 78 cancer cell lines for different organ origins. These cancer cell lines were tested against nine concentrations of C25-140. The results indicate that the major effect is on cancer cells of blood origin (FIG. 16). However, also cancer cell lines of other tissues were affected including bladder, colorectum, liver, lung, pancreas, pharynx and prostate (FIG. 16). Importantly, the two control cell lines HS-5 and MCF 10A were not affected at all suggested that there are no signs of general toxicity (FIG. 16).

In the course of identifying compounds with no commercial availability and unique structures, compounds were synthesized and tested in ALPHAScreen assay for their ability to disrupt TRAF6-Ubc13 binding. In parallel, these compounds were tested on the TruHits kit to be able to exclude compounds that interfere with the ALPHAScreen technology. All novel compounds inhibited TRAF6-Ubc13 interaction with diverse IC50s ranging from 2.3 μM-19.6 μM (FIG. 17). None of the compounds interfered with the TruHits assay. These data verify the existence of novel TRAF6-Ubc13 binding inhibitors with novel structures that are not commercially available. Importantly, all compounds exhibited similar or better toxicity behavior when compared to C25-140. Up to 50 μM, all compounds had almost no toxic effect on three different cell lines (FIG. 18). Only at 100 μM compound concentration some toxicity was detectable for distinct compounds. Finally, all these new compounds were tested in cell-based co-Immunoprecipitation assays for their ability to interfere with TRAF6-Ubc13 binding. Besides C25-140, further new compounds HZM06-1 (which is equal to compound 28), HZM06-2 (which is equal to compound 29), HZM06-3 (which is equal to compound 30), HZM06-4 (which is equal to compound 31), HZM06-6 (which is equal to compound 32), HZM06-7 (which is equal to compound 33), HZM06-8 (which is equal to compound 34), HZM06-9 (which is equal to compound 35) and HZM06-10 (which is equal to compound 36) were also active in cells, wherein C25-140, HZM06-4, HZM06-7, HZM06-8 and HZM06-9 were the most active analogs (FIG. 19). Altogether, data from FIG. 14-16 depict a set of novel, commercially unavailable compounds with in vitro and cellular activity and little toxicity.

Further novel compounds were synthesized and tested in the ALPHAScreen assay. These compounds showed inhibitory effects to different extends, which is indicated in the table (FIG. 20).

5. A Further Assay for the Testing of TRAF6-Ubc13 PPI Inhibitors

5.1) Purification of Protein Components of the Assay 5.1.1 Purification of TRAF6-His Protein The cDNA sequence of wildtype human TRAF6 RZ1 (amino acids 1-159) domain (TRAF6, UniProtKB deposition number Q9Y4K3) containing RZ1 (residues 50-159) and of a 6×His-tag followed by a stop codon were cloned into pASK-IBA3+ vector (IBA, GmH Gottingen, Germany) fusing the TRAF6 RZ1 protein to a C-terminal 6×His-tag. For the purification, the protein was expressed in BL21 codon plus competent RIPL cells (Agilent Technologies) in Luria/Miller medium. For protein production, 200 μg anhydrotetracycline, 500 μM Isopropyl-b-D-thiogalactopyranosid and 100 μM $ZnCl_2$ were added at $OD_{600}$=0.6-0.7. After 16 hours incubation at 16° C., cells were centrifuged and the pellet was resuspended in 10 ml TRAF6 wash-buffer (100 mM Tris pH 8.0, 150 mM NaCl and 30 mM imidazole) including 1 complete mini protease inhibitor tablet (Roche Diagnostics). After sonification (8×30 seconds) and centrifugation (2×30 minutes at 53,000×g), the protein suspension was applied to a HisTrap HP 1 ml column (GE Healthcare) using the ÄKTA purifier. The protein was eluted using a buffer consisting of 100 mM Tris pH 8.0, 150 mM NaCl and 300 mM imidazole. Finally, the protein was desalted in TRAF6 storage buffer (20 mM Tris pH 8.0, 20 mM NaCl, 1 mM DTT and 100 μM ZnCl$_2$).

```
Sequence of TRAF6-His-protein:
                                     (SEQ ID NO: 23)
MEEIQGYDVEFDPPLESKYECPICLMALREAVQTPCGHRFCKACIIKSIR

DAGHKCPVDNEILLENQLFPDNFAKREILSLMVKCPNEGCLHKMELRHLE

DHQAHCEFALGAHHHHHH

Sequence of C70A mutant according to FIG. 22:
                                     (SEQ ID NO: 24)
MEEIQGYDVEFDPPLESKYEAPICLMALREAVQTPCGHRFCKACIIKSIR

DAGHKCPVDNEILLENQLFPDNFAKREILSLMVKCPNEGCLHKMELRHLE

DHQAHCEFALGAHHHHHH.
```

5.1.2 Purification of Untagged Ubc13 Protein

The cDNA sequence of wildtype human Ubc13 (UniProtKB-P61088 (UBE2N_HUMAN) sequence: GLPRRIIKETQRLLAEPVPGIKAEPDESNARYFHVVI-AGPQDSPFEGGTFKLELFLPEEYPMA APKVRFMTKIYHPNVDKLGRICLDILKDKWSPAL-QIRTVLLSIQALLSAPNPDDPLANDVAEQ WKTNEA-QAIETARAWTRLYAMNNI (SEQ ID NO:25)) was cloned into the pET-HSU vector (provided by Dr. Arie Geerlof, HelmholtzZentrum München) fusing the Ubc13 sequence to a N-terminal His —Sumo-tag. The purification was done according to TRAF6 RZ1 purification protocol, but instead using Ubc13 wash-buffer (1×PBS, 400 mM NaCl, 1 mM DTT and 1 complete mini protease inhibitor tablet) and 1×PBS as storage buffer.

5.1.3 Purification of Untagged Uev1a Protein

The cDNA sequence of wildtype Uev1a (UniProtKB-Q13404 (UB2V1_HUMAN) sequence: MASMTGGQQMGRGSPGEVQASYLKSQSKLSDEGR-LEPRKFHCKGVKVPRNFRLLEELEE GQKGVGDGTVSWGLEDDEDMTLTRWTGMIIGP-PRTIYENRIYSLKIECGPKYPEAPPFVRFV TKINMNGVNSSNGVVDPRAISVLAKWQNSYS-IKVVLQELRRLMMSKENMKLPQPPEGQCY SN (SEQ ID NO:26)) was cloned into the pET-28a vector fusing it to a N-terminal His-tag. The purification was done according to TRAF6 RZ1 purification, but instead using Uev1a wash-buffer (35 mM Tris —HCl pH 8.0, 150 mM NaCl, 5% Glycerol and 1 complete mini protease inhibitor tablet). The His-tag was cut off from the Uev1a protein by incubating the protein with 50 units Thrombin (Sigma-Aldrich) for 3 hours followed by buffer exchange to 20 mM Tris —HCl pH 8.0, 100 mM NaCl and 5% glycerol.

5.1.4 Purification of GST-Tagged Ubiquitin

The cDNA sequence of wildtype human Ubiquitin (UniProtKB-P0CG47 (UBB_HUMAN)sequence: MSPILGYWKIKGLVQPTRLLLEYLEEKYEEHLYER-DEGDKWRNKKFELGLEFPNLPYYIDGD VKLTQS-MAIIRYIADKHNMLGGCPKERAEISMLE-GAVLDIRYGVSRIAYSKDFETLKVDFLSKL PEMLKMFEDRLCHKTYLNGDHVTHPDFM-LYDALDVVLYMDPMCLDAFPKLVCFKKRIEAIP QID-KYLKSSKY-IAWPLQGWQATFGGGDHPPKSDLVPRGSPEFMQIFV-KTLTGKTITLEVEPS DTIENVKAKIQDKEG-IPPDQQRLIFAGKQLEDGRTLSDY-NIQKESTLHLVLRLRGG (SEQ ID NO:27)) was cloned into the pGex4T1-vector fusing it to a N-terminal GST-tag. The induction of protein production was done with 1 mM IPTG. After 16 hours incubation at 18° C. and centrifugation, the pellet was resuspended in Ubiquitin wash-buffer (100 mM Tris —HCl pH 8.0, 150 mM NaCl and 1 complete mini protease inhibitor tablet), sonified and cleared from cell debris. For purification of GST-Ubiquitin, the supernatant was applied to a GST-trap HP 1 ml column (GE Healthcare) using the ÄKTA purifier, then washed with wash buffer and eluted with elution buffer (100 mM Tris —HCl pH 8.0, 150 mM NaCl and 55 mM Glutathione). Buffer exchange occurred in 20 mM Tris —HCl pH 8.0, and 100 mM NaCl.

5.2) AlphaScreen Ubiquitination Assay

First, TRAF6-His protein was diluted to 166 nM (final concentration in 60 μl total volume) in 30 μl 1×E3 ligase buffer (Boston Biochem, B-71) and incubated with 0.8% DMSO for 5 min. A master mix of 1×E3 ligase buffer, 3.33 nM E1 (Boston Biochem, E-305), 660 nM Ubc13, 155 nM Uev1a and 333 nM GST-Ubiquitin in a volume of 10 μl was prepared and added to the TRAF6 solution. The reaction mix was incubated in a 384-Optiplate (PerkinElmer) for 6 hours at 37° C. 10 μl Glutathione-Donor beads (6.666 μg/ml beads in 1×E3 ligase buffer) and 10 μl Nickel-Chelate-Acceptor beads (6.666 μg/ml beads in 1×E3 ligase buffer) (both beads from PerkinElmer) were added to the reaction mix for another hour at 37° C. The readout was performed at an excitation of 680 nm and emission of 520-620 nm in an Envision plate reader (PerkinElmer).

It will be clear that the invention may be practiced otherwise than as particularly described in the foregoing description and examples. Numerous modifications and variations of the present invention are possible in light of the above teachings and, therefore, are within the scope of the appended claims.

The invention claimed is:

1. A compound having a structure according to formula (XX)

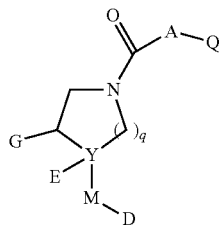

wherein in formula (XX),
Q is selected from group A) consisting of

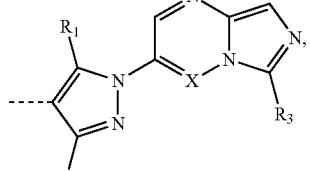

(XXa)

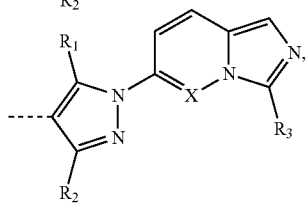

(XXb)

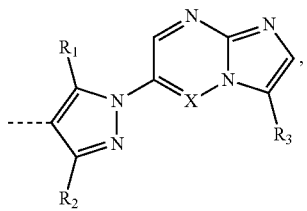 (XXc)

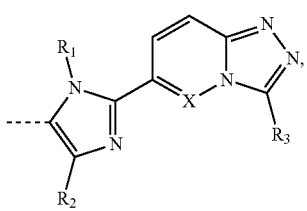 (XXd)

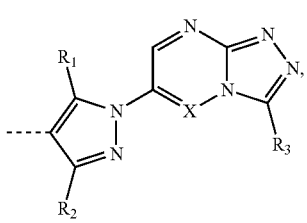 (XXe)

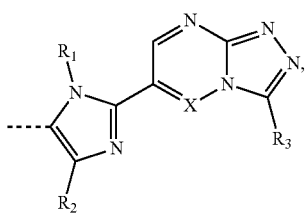 (XXf)

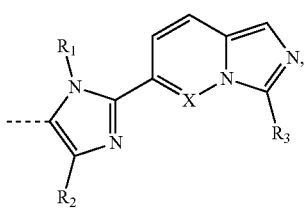 (XXg)

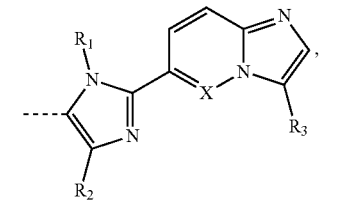 (XXh)

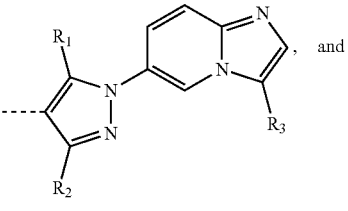 (XXi)

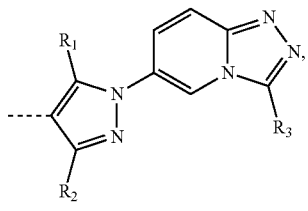 (XXj)

X is selected from the group consisting of CH, and N;
$R_1$ and $R_2$ are independently selected from the group consisting of hydrogen, —($C_1$-$C_6$)haloalkyl-($C_3$-$C_8$)cycloalkyl and =($C_1$-$C_6$)alkyl, —$R_3$ is selected from the group consisting of hydrogen, —($C_1$-$C_6$)alkyl, —($C_1$-$C_6$)haloalkyl, ($C_3$-$C_8$)cycloalkyl, —($C_6$-$C_{10}$)aryl, —($C_6$-$C_{10}$)aryl ($C_1$-$C_6$)alkyl, —($C_3$-$C_{10}$)heteroaryl, —($C_3$-$C_{10}$)heteroaryl ($C_1$-$C_6$)alkyl, —CONH($C_6$-$C_{10}$)Aryl, —$CONH_2$, and —CON(($C_1$-$C_6$)alkyl)($C_6$-$C_{10}$)Aryl;

or Q is selected from group B) consisting of

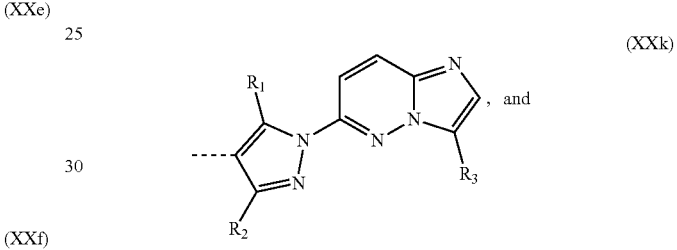 (XXk)

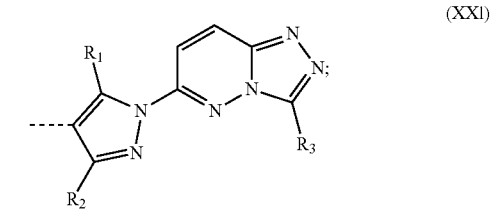 (XXl)

$R_1$ and $R_2$ are independently selected from the group consisting of hydrogen, —($C_1$-$C_6$)haloalkyl, —($C_3$-$C_8$)cycloalkyl, and =($C_1$-$C_6$)alkyl,
$R_3$ is selected from the group consisting of hydrogen, —($C_1$-$C_6$)alkyl, —($C_1$-$C_6$)haloalkyl, ($C_3$-$C_8$)cycloalkyl, —($C_6$-$C_{10}$)aryl, —($C_6$-$C_{10}$)aryl ($C_1$-$C_6$)alkyl, —($C_3$-$C_{10}$)heteroaryl-($C_3$-$C_{10}$)heteroaryl($C_1$-$C_6$)alkyl, —CONH($C_6$-$C_{10}$)Aryl, —$CONH_2$, and —CON(($C_1$-$C_6$)alkyl) ($C_6$-$C_{10}$)Aryl;

if Q is selected from group A), -then:
A is selected from the group consisting of —$(CH_2)_3$—, —$(CH_2)_2$—, —$CH_2$—, and cyclopropyl;
G is selected from the group consisting of hydrogen, —($C_3$-$C_{10}$)heteroaryl, ($C_6$-$C_{10}$)aryl ($C_1$-$C_6$)alkyl and ($C_6$-$C_{10}$)aryl; which are optionally substituted by one or more identical or different substituents, selected from the group consisting of halogen, —($C_1$-$C_4$)alkyl, —($C_1$-$C_4$)haloalkyl, —CO($C_1$-$C_4$)alkyl, —CN, —NC, —($C_6$-$C_{10}$)aryl, —($C_3$-$C_{10}$)heteroaryl, —NH($C_1$-$C_4$)alkyl), —N(($C_1$-$C_4$)alkyl)$_2$, —NO, —$SO_2$($C_1$-$C_4$)alkyl, —$NHSO_2$ ($C_1$-$C_4$)alkyl, —$CONH_2$, —$CF_3$, —COOH, —$NO_2$, —NHCO($C_1$-$C_4$)alkyl, —$CO_2$ ($C_1$-$C_4$)alkyl, —CONH($C_1$-$C_4$)alkyl, —$CONH_2$, —$OR_6$, —$SO_2NH_2$, —$CH_2COOH$, —$CH_2OR_6$, and —$SO_2Ph$:

D is selected from the group consisting of hydrogen, —(C$_3$-C$_{10}$)heteroaryl, —(C$_6$-C$_{10}$)aryl, —(C$_6$-C$_{10}$)aryl (C$_1$-C$_6$)alkyl, —(C$_3$-C$_{10}$)heteroaryl (C$_1$-C$_6$)alkyl, —(C$_1$-C$_6$)alkyl,

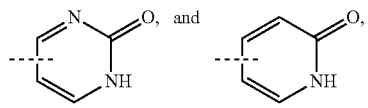

which are optionally substituted by one or more identical or different substituents selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —N((C$_1$-C$_4$)alkyl)$_2$, —NO, —SO$_2$ (C$_1$-C$_4$)alkyl, —NHSO(C$_1$-C$_4$)alkyl, —NHSO$_2$ (C$_1$-C$_4$)alkyl, —CONH$_2$, —CF$_3$, —COOH, —NO$_2$, —NHCO(C$_1$-C$_4$)alkyl, —CO$_2$ (C$_1$-C$_4$)alkyl, —CONH (C$_1$-C$_4$)alkyl, —CONH$_2$, —OR$_6$, —SO$_2$NH$_2$, —CH$_2$COOH, —CH$_2$OR$^6$; —COCH$_2$SO$_2$Ph, —NHCONHR$_6$, —CONHOR$_6$, —CONHCN, NHCOOR$_6$,

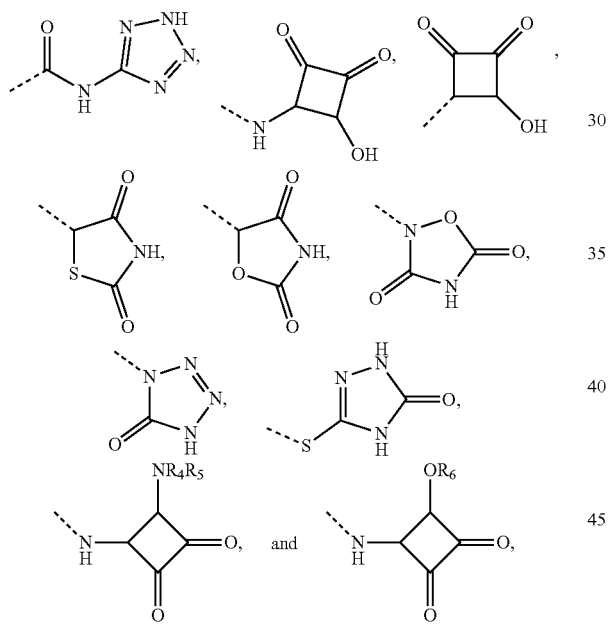

R$_6$ is selected from the group consisting of hydrogen, —(C$_1$-C$_4$)alkyl, and —(C$_1$-C$_4$)haloalkyl;
E is selected from the group consisting of hydrogen, —(C$_1$-C$_6$)alkyl and not present;
Y is selected from the group consisting of C, and N;
M is selected from the group consisting of —CR$_4$R$_5$—, —NH—, —O— and not present;
R$_4$ and R$_5$ are independently selected from the group consisting of hydrogen, —(C$_1$-C$_4$)alkyl
q is 1 or 2;
if Q is selected from group B) then
A is selected from the group consisting of —(CH$_2$)$_2$— and cyclopropyl;
G is selected from the group consisting of hydrogen, —(C$_1$-C$_6$)alkyl-, —(C$_3$-C$_{10}$)heteroaryl, —(C$_6$-C$_{10}$)aryl (C$_1$-C$_6$)alkyl and —(C$_6$-C$_{10}$)aryl; which are optionally substituted by one or more identical or different substituents selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$)aryl, —(C$_3$-C$_{10}$)heteroaryl, —NH(C$_1$-C$_4$)alkyl-, —N((C$_1$-C$_4$)alkyl)$_2$, —NO, —SO$_2$ (C$_1$-C$_4$)alkyl, —NHSO$_2$ (C$_1$-C$_4$)alkyl, —CONH$_2$, —CF$_3$, —COOH, —NO$_2$, —NHCO(C$_1$-C$_4$)alkyl, —CO$_2$ (C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; and —SO$_2$Ph;

D is selected from the group consisting of hydrogen, phenyl, napthyl, —(C$_3$-C$_{10}$)heteroaryl; benzyl, —(C$_3$-C$_{10}$)heteroaryl (C$_1$-C$_6$)alkyl, —(C$_1$-C$_6$)alkyl,

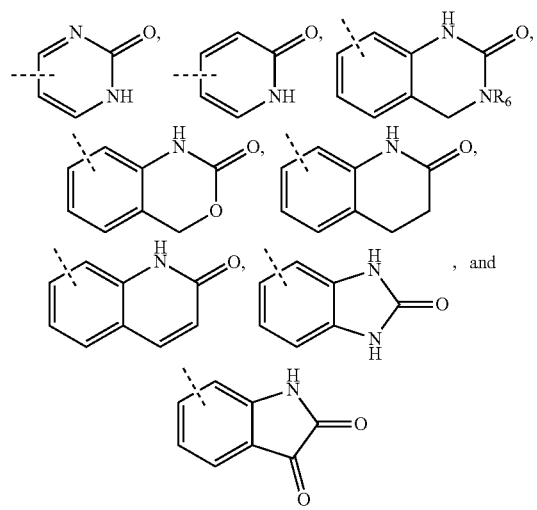

which are optionally substituted by one or more identical or different substituents selected from the group consisting of halogen, —(C$_1$-C$_4$)alkyl, —(C$_1$-C$_4$)haloalkyl, —CO(C$_1$-C$_4$)alkyl, —CN, —NC, —(C$_6$-C$_{10}$) aryl, —(C$_3$-C$_{10}$)heteroaryl, —NH(C$_1$-C$_4$)alkyl, —N((C$_1$-C$_4$)alkyl)$_2$, —NO, —SO$_2$(C$_1$-C$_4$)alkyl, —NHSO(C$_1$-C$_4$)alkyl, —NHSO$_2$(C$_1$-C$_4$)alkyl, —CONH$_2$, —CF$_3$, —COOH, —NO$_2$, —NHCO(C$_1$-C$_4$)alkyl, —CO$_2$ (C$_1$-C$_4$)alkyl, —CONH(C$_1$-C$_4$)alkyl, —CONH$_2$, —OR$_6$, —SO$_2$NH$_2$, —CH$_2$COOH, —CH$_2$OR$_6$; —COCH$_2$SO$_2$Ph, NHCONHR$_6$, —CONHOR$_6$, —SO$_2$Ph, —CONHCN, NHCOOR$_6$,

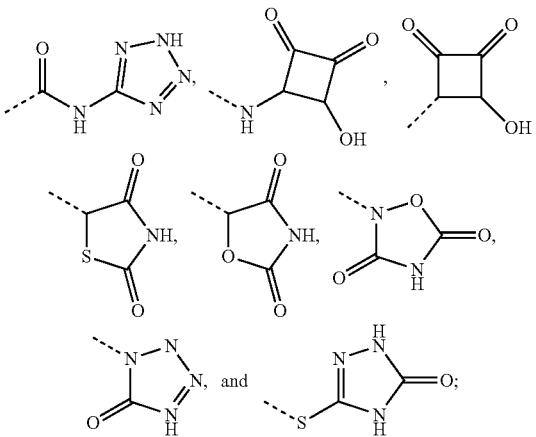

wherein D for formula (XXI) is not selected from the group consisting of pyrimidinyl, propyl, methyl, ethyl, phenyl, phenyl substituted with one —OCH$_3$ group, phenyl substituted with fluoro, phenyl substituted with two methyl groups;

R$_6$ is selected from the group consisting of hydrogen, —(C$_1$-C$_4$)alkyl, and —(C$_1$-C$_4$)haloalky E is selected from the group consisting of hydrogen, —(C$_1$-C$_6$)alkyl and not present;

Y is selected from the group consisting of C, and N;

M is selected from the group consisting of —CR$_4$R$_5$—, —NH—, —O— and not present;

R$_4$ and R$_5$ are independently selected from the group consisting of hydrogen, —(C$_1$-C$_4$)alkyl;

q is 1 or 2;

wherein D is not unsubstituted phenyl if R$_1$ and R$_2$ are both methyl, R$_3$ is methyl or unsubstituted phenyl, Q is formula (XXk), G is hydrogen, q is 2, E is H, M is —CH$_2$—, A is —CH$_2$CH$_2$— and Y is C;

wherein D is not unsubstituted phenyl if R$_1$ and R$_2$ are both methyl, or ethyl R$_3$ is methyl, ethyl, isopropyl, cyclopropyl, or unsubstituted benzyl, Q is formula (XXI), G is hydrogen, q is 2, E is H, M is —CH$_2$—, A is —CH$_2$CH$_2$— and Y is C;

wherein D is not unsubstituted phenyl if R$_1$ and R$_2$ are both methyl, or ethyl R$_3$ is methyl, ethyl, isopropyl, cyclopropyl, or unsubstituted benzyl, Q is formula (XXI), G is hydrogen, q is 2, E is not present, M is —C(CH$_3$)$_2$—, A is —CH$_2$CH$_2$— and Y is N;

wherein D is not unsubstituted 2-pyridyl, phenyl only substituted in meta position with —OMe, phenyl only substituted in para position with F if G is hydrogen, q is 2, E is H or not present if Y is N, M is —CH$_2$—, or not present, A is —CH$_2$CH$_2$— and Y is C or N, R$_1$ and R$_2$ are both methyl, R$_3$ is methyl and Q is formula (XXI);

wherein D is not unsubstituted 2-naphtyl, phenyl substituted only in meta position with Cl, 2-furyl or phenyl substituted only in meta and para position with —OMe if R$_1$ and R$_2$ are both methyl, R$_3$ is methyl, Q is formula (XXI), G is hydrogen, q is 2, E is not present, M is —CH$_2$—, A is —CH$_2$CH$_2$— and Y is N;

wherein D is not unsubstituted Bn if Q is formula (XXk), M is —CH$_2$, A is —CH$_2$CH$_2$—, E is H, Y is C, G is hydrogen, and q is 2, R$_1$ and R$_2$ are both methyl and R$_3$ is methyl;

wherein D is not hydrogen if M is —CH$_2$—, A is —CH$_2$CH$_2$—, q is 1, Y is C, E is methyl, R$_1$ and R$_2$ are both methyl or both ethyl, R$_3$ is methyl or isopropyl and Q is formula (XXI);

wherein D is not hydrogen while M is not present, if E is hydrogen, G is hydrogen, A is —CH$_2$CH$_2$—, q is 1 and Y is C, R$_1$ and R$_2$ are both methyl, R$_3$ is —CF$_3$, ethyl or isopropyl, and Q is formula (XXI);

wherein D is not unsubstituted phenyl if E is hydrogen, M is —CH$_2$—, A is —CH$_2$CH$_2$—, q is 1, Y is C, R$_1$ and R$_2$ are both methyl or ethyl, R$_3$ is methyl, ethyl or isopropyl, and Q is formula (XXI) and G is hydrogen;

wherein G is not benzyl if E is hydrogen, M is not present and D is -hydrogen, A is —CH$_2$CH$_2$—, q is 1, Y is C, R$_1$ and R$_2$ are both methyl or ethyl, R$_3$ is methyl, ethyl or isopropyl, and Q is formula (XXI);

wherein D is not unsubstituted phenyl if E is hydrogen, M is —CH$_2$—, A is —CH$_2$CH$_2$—, q is 1, Y is C, R$_1$ and R$_2$ are both methyl, R$_3$ is methyl, Q is formula (XXk) and G is hydrogen;

wherein G is not unsubstituted benzyl if E is hydrogen, M is not present and D is hydrogen, A is —CH$_2$CH$_2$—, q is 1, Y is C, R$_1$ and R$_2$ are both methyl or both ethyl, R$_3$ is methyl, and Q is formula (XXk);

wherein D is not unsubstituted phenyl if E is hydrogen, M is not present, q is 2, Y is C, A is —CH$_2$CH$_2$—, G is hydrogen, R$_1$ and R$_2$ are both methyl, R$_3$ is methyl and Q is formula (XXI);

or a pharmaceutically acceptable salt, solvate or hydrate thereof.

2. The compound according to claim 1, wherein

Q is selected from group A) or B), if Q is selected from group A), X is N; and D is not phenyl substituted in a meta position with —CONH$_2$;

if Q is selected from group B),

M is selected from the group hydrogen, —CH$_2$—, —NH—, and —O—.

3. The compound according to claim 1, wherein

Q is selected from group A) or B), if Q is selected from group A), X is N if Q is selected from group B), G is not present;

D is selected from the group consisting of —(C$_3$-C$_{10}$) heteroaryl, unsubstituted benzyl, unsubstituted phenyl, phenyl comprising at least one substituent in ortho position, phenyl comprising at least one substituent in meta position, wherein the meta substituent is selected from Cl, Br or I, —CONH$_2$—CO$_2$ (C$_1$-C$_4$)alkyl, —(C$_1$-C$_4$)alkyl, —NO$_2$, —COOH, —(C$_6$-C$_{10}$)aryl, preferably Ph, —CN, —CO(C$_1$-C$_4$)alkyl, —RO$^6$, —(C$_3$-C$_{10}$)heteroaryl, —NHSO$_2$ (C$_1$-C$_4$)alkyl, F if the para position is not substituted with F, —CF$_3$, and —SO$_2$ (C$_1$-C$_4$) alkyl;

phenyl comprising at least two different substituents in ortho and para position;

phenyl comprising at least one substituent in para position, wherein the para substituent is selected from the group consisting of, —OR$^6$, —CH$_2$OR$^6$— CH$_2$COOH—COOH, —NO$_2$, —(C$_6$-C$_{10}$)aryl, preferably Ph, —NHCO(C$_1$-C$_4$)alkyl, —CO(C$_1$-C$_4$)alkyl, —CO$_2$ (C$_1$-C$_4$)alkyl, —N((C$_1$-C$_4$)alkyl) 2, —SO$_2$ (C$_1$-C$_4$)alkyl, —NHSO$_2$ (C$_1$-C$_4$)alkyl, —CONH$_2$, —SO$_2$NH$_2$, —(C$_3$-C$_{10}$)heteroaryl, and not present;

R$_6$ is selected from the group consisting of hydrogen, —(C$_1$-C$_4$)alkyl, and —(C$_1$-C$_4$)haloalkyl, M is selected from the group consisting of hydrogen, —CH$_2$—, —NH—, —O—.

4. The compound according to claim 1, wherein Q is selected from group A) or B), if Q is selected from group A), X is N, if Q is selected from group B), G is not present;

D is selected from the group consisting of —(C$_3$-C$_{10}$) heteroaryl, wherein the —(C$_3$-C$_{10}$)heteroaryl group is not an unsubstituted quinoline-5-yl group, an unsubstituted quinoline-7-yl group, an unsubstituted indol group, an 2-oxo-2H-chromen-6-yl group, an unsubstituted 1H-indazole-6-yl, unsubstituted phenyl;

phenyl substituted in ortho position with —(C$_1$-C$_4$)alkyl, phenyl comprising at least one substituent in meta position, wherein the meta substituent is selected from Cl, Br or I, —(C$_1$-C$_4$)alkyl, —NO$_2$, —COOH, —CN, —CO(C$_1$-C$_4$)alkyl, —RO$^6$, —(C$_3$-C$_{10}$)heteroaryl, —CF$_3$, and —SO$_2$ (C$_1$-C$_4$)alkyl, phenyl comprising at least two different substituents in ortho and para position, phenyl comprising at least one substituent in para position, wherein the para substituent is selected from the group consisting of —OH, —CH$_2$OR$^6$, —CH$_2$COOH, —O(C$_1$-C$_4$)alkyl, —COOH, —CO$_2$ (C$_1$-C$_4$)alkyl, —SO$_2$NH$_2$, —(C$_3$-C$_{10}$)heteroaryl, and not present, R$_6$ is selected from the group consisting of hydrogen, —(C$_1$-C$_4$)alkyl, and —(C$_1$-C$_4$)haloalkyl M is selected from the group consisting of hydrogen, —CH$_2$—, and —NH—.

5. A compound selected from the group consisting of
3-(3,5-dimethyl-1-(3-methyl-[1,2,4]triazolo[4,3-b]pyridazin-6-yl)-1H-pyrazol-4-yl)-1-(4-phenethylpiperidin-1-yl)propan-1-one,
- 1-(3-benzylpiperidin-1-yl)-3-(3,5-dimethyl-1-(3-methyl-[1,2,4]triazolo[4,3-b]pyridazin-6-yl)-1H-pyrazol-4-yl)propan-1-one,
- 3-(3,5-dimethyl-1-(3-methyl-[1,2,4]triazolo[4,3-a]pyridin-6-yl)-1H-pyrazol-4-yl)-1-(4-phenethylpiperidin-1-yl)propan-1-one,
- 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzoic acid,
- 1-(3-benzylpiperidin-1-yl)-3-(3,5-dimethyl-1-(3-methyl-[1,2,4]triazolo[4,3-a]pyridin-6-yl)-1H-pyrazol-4-yl)propan-1-one,
- 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-methylbenzamide,
- 1-(3-benzylpyrrolidin-1-yl)-3-(3,5-dimethyl-1-(3-methyl-[1,2,4]triazolo[4,3-a]pyridin-6-yl)-1H-pyrazol-4-yl)propan-1-one,
- 1-(3-benzylpiperazin-1-yl)-3-(3,5-dimethyl-1-(3-methyl-[1,2,4]triazolo[4,3-b]pyridazin-6-yl)-1H-pyrazol-4-yl)propan-1-one hydrochloride,
- methyl 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzoate,
- 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzamide,
- 1-(4-benzylpiperazin-1-yl)-3-(3,5-dimethyl-1-(3-methyl-[1,2,4]triazolo[4,3-a]pyridin-6-yl)-1H-pyrazol-4-yl)propan-1-one,
- 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzoic acid,
- methyl 3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzoate,
- 1-(4-(2-chlorobenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 1-(4-(4-chlorobenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 1-(4-(2,6-dichlorobenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 1-(4-(4-acetylbenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 3-(3,5-dimethyl-1-(3-methyl-[1,2,4]triazolo[4,3-b]pyridazin-6-yl)-1H-pyrazol-4-yl)-1-(4-(naphthalen-1-ylmethyl) piperazin-1-yl)propan-1-one,
- 1-(4-(3,4-difluorobenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile,
- 3-(3,5-dimethyl-1-(3-methyl-[1,2,4]triazolo[4,3-b]pyridazin-6-yl)-1H-pyrazol-4-yl)-1-(4-(4-methylbenzyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(quinolin-5-ylmethyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(4-(trifluoromethyl) benzyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(4-iodobenzyl) piperazin-1-yl)propan-1-one,
- N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl) acetamide,
- 1-(4-([1,1'-biphenyl]-4-ylmethyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 3-(3,5-dimethyl-1-(3-methyl-[1,2,4]triazolo[4,3-b]pyridazin-6-yl)-1H-pyrazol-4-yl)-1-(4-(4-(dimethylamino)benzyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(4-nitrobenzyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(4-(methylsulfonyl)benzyl) piperazin-1-yl)propan-1-one,
- N-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl) methanesulfonamide,
- 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) benzamide,
- 1-(4-((1H-indazol-6-yl)methyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 1-(3-benzyl-3-methylpyrrolidin-1-yl)-3-(3,5-dimethyl-1-(3-methyl-[1,2,4]triazolo[4,3-b]pyridazin-6-yl)-1H-pyrazol-4-yl)propan-1-one,
- 3-(3,5-dimethyl-1-(3-methyl-[1,2,4]triazolo[4,3-b]pyridazin-6-yl)-1H-pyrazol-4-yl)-1-(4-(4-hydroxybenzyl) piperazin-1-yl)propan-1-one,
- 3-(3,5-dimethyl-1-(3-methyl-[1,2,4]triazolo[4,3-b]pyridazin-6-yl)-1H-pyrazol-4-yl)-1-(4-(3-fluoro-4-(trifluoromethyl) benzyl) piperazin-1-yl)propan-1-one,
- 1-(4-(3,4-dichlorobenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-methylbenzoic acid,
- 3-(3,5-dimethyl-1-(3-methyl-[1,2,4]triazolo[4,3-b]pyridazin-6-yl)-1H-pyrazol-4-yl)-1-(4-(3-methyl-4-nitrobenzyl) piperazin-1-yl)propan-1-one,
- 1-(4-(3-chloro-4-hydroxybenzyl) piperazin-1-yl)-3-(3,5-dimethyl-1-(3-methyl-[1,2,4]triazolo[4,3-b]pyridazin-6-yl)-1H-pyrazol-4-yl)propan-1-one,
- 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzoic acid, 3-(3,5-dimethyl-1-(3-methyl-[1,2,4]triazolo[4,3-b]
pyridazin-6-yl)-1H-pyrazol-4-yl)-1-(4-(3-iodobenzyl)
piperazin-1-yl)propan-1-one,
1-(4-(3-acetylbenzyl) piperazin-1-yl)-3-(3,5-dimethyl-1-
(3-methyl-[1,2,4]triazolo[4,3-b]pyridazin-6-yl)-1H-
pyrazol-4-yl)propan-1-one,
3-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl)benzonitrile,
3-(3,5-dimethyl-1-(3-methyl-[1,2,4]triazolo[4,3-b]
pyridazin-6-yl)-1H-pyrazol-4-yl)-1-(4-(3-methylbenzyl) piperazin-1-yl)propan-1-one,
2-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl)benzonitrile,
1-(4-([1,1'-biphenyl]-3-ylmethyl) piperazin-1-yl)-3-(3,5-
dimethyl-1-(3-methyl-[1,2,4]triazolo[4,3-b]pyridazin-
6-yl)-1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(3-methyl-5-nitrobenzyl) piperazin-1-yl)propan-1-one,
4-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl) benzenesulfonamide,
4-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl)-2-fluorobenzoic acid,
1-(4-(2,4-dichlorobenzyl) piperazin-1-yl)-3-(3,5-dimethyl-1-(3-methyl-[1,2,4]triazolo[4,3-b]pyridazin-6-
yl)-1H-pyrazol-4-yl)propan-1-one,
1-(4-(3,5-difluoro-4-hydroxybenzyl) piperazin-1-yl)-3-
(3,5-dimethyl-1-(3-methyl-[1,2,4]triazolo[4,3-b]
pyridazin-6-yl)-1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(3-hydroxybenzyl) piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(quinolin-6-ylmethyl) piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(3-nitrobenzyl)
piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(quinolin-7-ylmethyl) piperazin-1-yl)propan-1-one,
3-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl) benzamide,
3-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl)-N-methylbenzamid,
3-(3,5-dimethyl-1-(3-methyl-[1,2,4]triazolo[4,3-b]
pyridazin-6-yl)-1H-pyrazol-4-yl)-1-(4-(quinolin-8-ylmethyl) piperazin-1-yl)propan-1-one,
1-(4-(3-(2H-tetrazol-5-yl)benzyl) piperazin-1-yl)-3-(3,5-
dimethyl-1-(3-methyl-[1,2,4]triazolo[4,3-b]pyridazin-
6-yl)-1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(3-(methylsulfonyl)benzyl) piperazin-1-yl)propan-1-one,
N-(3-((4-(3-(3,5-dimethyl-1-(3-methyl-[1,2,4]triazolo[4,
3-b]pyridazin-6-yl)-1H-pyrazol-4-yl)propanoyl)piperazin-1-yl)methyl) phenyl) methanesulfonamide,
3-(3,5-dimethyl-1-(3-methyl-[1,2,4]triazolo[4,3-b]
pyridazin-6-yl)-1H-pyrazol-4-yl)-1-(4-(3-fluorobenzyl) piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(3-(trifluoromethyl) benzyl) piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(4-fluoro-3-(trifluoromethyl) benzyl) piperazin-1-yl)propan-1-one,
1-(4-(2,5-dichlorobenzyl) piperazin-1-yl)-3-(3,5-dimethyl-1-(3-methyl-[1,2,4]triazolo[4,3-b]pyridazin-6-
yl)-1H-pyrazol-4-yl)propan-1-one,
1-(4-(4-bromobenzyl) piperazin-1-yl)-3-(3,5-dimethyl-1-
(3-methyl-[1,2,4]triazolo[4,3-b]pyridazin-6-yl)-1H-
pyrazol-4-yl)propan-1-one,
1-(4-(3-bromobenzyl) piperazin-1-yl)-3-(3,5-dimethyl-1-
(3-methyl-[1,2,4]triazolo[4,3-b]pyridazin-6-yl)-1H-
pyrazol-4-yl)propan-1-one,
1-(4-(2,4-difluoro-3-hydroxybenzyl) piperazin-1-yl)-3-
(3,5-dimethyl-1-(3-methyl-[1,2,4]triazolo[4,3-b]
pyridazin-6-yl)-1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(2-methylbenzyl) piperazin-1-yl)propan-1-one,
3-(3,5-dimethyl-1-(3-methyl-[1,2,4]triazolo[4,3-b]
pyridazin-6-yl)-1H-pyrazol-4-yl)-1-(4-(2-methyl-4-nitrobenzyl) piperazin-1-yl)propan-1-one,
1-(4-(4-cyclopropylbenzyl) piperazin-1-yl)-3-(3,5-dimethyl-1-(3-methyl-[1,2,4]triazolo[4,3-b]pyridazin-6-
yl)-1H-pyrazol-4-yl)propan-1-one,
1-(4-(3-cyclopropylbenzyl) piperazin-1-yl)-3-(3,5-dimethyl-1-(3-methyl-[1,2,4]triazolo[4,3-b]pyridazin-6-
yl)-1H-pyrazol-4-yl)propan-1-one,
1-(4-(4-(2H-tetrazol-5-yl)benzyl) piperazin-1-yl)-3-(3,5-
dimethyl-1-(3-methyl-[1,2,4]triazolo[4,3-b]pyridazin-
6-yl)-1H-pyrazol-4-yl)propan-1-one,
3-(3,5-dimethyl-1-(3-methyl-[1,2,4]triazolo[4,3-b]
pyridazin-6-yl)-1H-pyrazol-4-yl)-1-(4-(isoquinolin-8-ylmethyl) piperazin-1-yl)propan-1-one,
1-(4-((1H-indol-6-yl)methyl) piperazin-1-yl)-3-(3,5-dimethyl-1-(3-methyl-[1,2,4]triazolo[4,3-b]pyridazin-6-
yl)-1H-pyrazol-4-yl)propan-1-one,
6-((4-(3-(3,5-dimethyl-1-(3-methyl-[1,2,4]triazolo[4,3-b]
pyridazin-6-yl)-1H-pyrazol-4-yl)propanoyl)piperazin-
1-yl)methyl)-2H-chromen-2-one,
3-(3,5-dimethyl-1-(3-methyl-[1,2,4]triazolo[4,3-b]
pyridazin-6-yl)-1H-pyrazol-4-yl)-1-(4-(4-(phenylsulfonyl)benzyl) piperazin-1-yl)propan-1-one,
1-(4-benzyl-4-methylpiperidin-1-yl)-3-(3,5-dimethyl-1-
(3-methyl-[1,2,4]triazolo[4,3-b]pyridazin-6-yl)-1H-
pyrazol-4-yl)propan-1-one,
1-(4-benzyl-4-ethylpiperidin-1-yl)-3-(3,5-dimethyl-1-(3-
methyl-[1,2,4]triazolo[4,3-b]pyridazin-6-yl)-1H-pyrazol-4-yl)propan-1-one,
1-(4-benzyl-4-propylpiperidin-1-yl)-3-(3,5-dimethyl-1-
(3-methyl-[1,2,4]triazolo[4,3-b]pyridazin-6-yl)-1H-
pyrazol-4-yl)propan-1-one,
1-(3-benzyl-3-ethylpyrrolidin-1-yl)-3-(3,5-dimethyl-1-
(3-methyl-[1,2,4]triazolo[4,3-b]pyridazin-6-yl)-1H-
pyrazol-4-yl)propan-1-one,
1-(3-benzyl-3-propylpyrrolidin-1-yl)-3-(3,5-dimethyl-1-
(3-methyl-[1,2,4]triazolo[4,3-b]pyridazin-6-yl)-1H-
pyrazol-4-yl)propan-1-one,
3-(3,5-dimethyl-1-(3-methyl-[1,2,4]triazolo[4,3-b]
pyridazin-6-yl)-1H-pyrazol-4-yl)-N-(1-phenylpiperidin-4-yl) propanamide,
3-(3,5-dimethyl-1-(3-methyl-[1,2,4]triazolo[4,3-b]
pyridazin-6-yl)-1H-pyrazol-4-yl)-1-(4-(phenylamino)
piperidin-1-yl)propan-1-one, 3-(3,5-dimethyl-1-(3-methyl-[1,2,4]triazolo[4,3-b]pyridazin-6-yl)-1H-pyrazol-4-yl)-1-(4-phenoxypiperidin-1-yl)propan-1-one, 1-(4-benzylpiperidin-1-yl)-3-(3,5-dimethyl-1-(7-methylimidazo[1,5-b]pyridazin-2-yl)-1H-pyrazol-4-yl)propan-1-one, 2-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl) acetic acid, 3-(3,5-dimethyl-1-(3-methyl-[1,2,4]triazolo[4,3-b]pyridazin-6-yl)-1H-pyrazol-4-yl)-1-(4-(4-(hydroxymethyl)benzyl) piperazin-1-yl)propan-1-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) pyridin-2 (1H)-one, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) pyridin-2 (1H)-one, 5-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-1,3-dihydro-2H-benzo[d]imidazol-2-one, 3-(3,5-dimethyl-1-(3-methyl-[1,2,4]triazolo[4,3-b]pyridazin-6-yl)-1H-pyrazol-4-yl)-1-(3-(1-phenylpropyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(4-hydroxyphenyl) propyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(1-(3-hydroxyphenyl) propyl)pyrrolidin-1-yl)propan-1-one, 1-(3-(4-(1H-tetrazol-5-yl)benzyl)pyrrolidin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(3-(2-methyl-4-(1H-tetrazol-5-yl)benzyl)pyrrolidin-1-yl)propan-1-one, 3-(3,5-dimethyl-1-(3-methyl-[1,2,4]triazolo[4,3-b]pyridazin-6-yl)-1H-pyrazol-4-yl)-1-(3-(2-(3-hydroxyphenyl)propan-2-yl)pyrrolidin-1-yl)propan-1-one, 1-(4-(3-(1H-tetrazol-5-yl)benzyl) piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-(trifluoromethyl) benzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-5-(1H-tetrazol-5-yl)benzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluorobenzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-4-(1H-tetrazol-5-yl)benzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl) piperazin-1-yl)propan-1-one, 1-(4-(2-chloro-4-(1H-tetrazol-5-yl)benzyl) piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl) piperazin-1-yl)propan-1-one, 1-(4-(2-cyclopropylbenzyl) piperazin-1-yl)-3-(3,5-dimethyl-1-(3-methyl-[1,2,4]triazolo[4,3-b]pyridazin-6-yl)-1H-pyrazol-4-yl)propan-1-one, 3-(3,5-dimethyl-1-(3-methyl-[1,2,4]triazolo[4,3-b]pyridazin-6-yl)-1H-pyrazol-4-yl)-1-(4-(2-ethylbenzyl) piperazin-1-yl)propan-1-one, N-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl) sulfonyl) acetamide, 4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-N-(methylsulfonyl)benzamide, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3,4-dihydroisoquinolin-1 (2H)-one, 6-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) isoquinolin-1 (2H)-one, 3-(3,5-dimethyl-1-(3-methyl-[1,2,4]triazolo[4,3-b]pyridazin-6-yl)-1H-pyrazol-4-yl)-1-(4-(4-(3-hydroxy-5-methylisoxazol-4-yl)benzyl) piperazin-1-yl)propan-1-one, 3-(3,5-dimethyl-1-(3-methyl-[1,2,4]triazolo[4,3-b]pyridazin-6-yl)-1H-pyrazol-4-yl)-1-(4-(4-(4-hydroxy-1,2,5-oxadiazol-3-yl)benzyl) piperazin-1-yl)propan-1-one, 3-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl)-4-hydroxycyclobutane-1,2-dione, 3-((4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl) phenyl)amino)-4-hydroxycyclobutane-1,2-dione, 5-(4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)phenyl)thiazolidine-2,4-dione, 3-(3,5-Dimethyl-1-(3-methyl-[1,2,4]triazolo[4,3-b]pyridazin-6-yl)-1H-pyrazol-4-yl)-1-(4-(2-fluoro-4-(1H-tetrazol-5-yl)benzyl) piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(2-fluoro-4-(1H-tetrazol-5-yl)benzyl) piperazin-1-yl)propan-1-one, 1-(4-(2-Chloro-5-(1H-tetrazol-5-yl)benzyl) piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-5-(1H-tetrazol-5-yl)benzyl) piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-4-(1H-tetrazol-5-yl)benzyl) piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-4-(1H-tetrazol-5-yl)benzyl) piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 1-(4-(2-Chloro-3-(1H-tetrazol-5-yl)benzyl) piperazin-1-yl)-3-(3,5-dimethyl-1-(3-methyl-[1,2,4]triazolo[4,3-b]pyridazin-6-yl)-1H-pyrazol-4-yl)propan-1-one, 1-(4-(2-Chloro-3-(1H-tetrazol-5-yl)benzyl) piperazin-1-yl)-3-(3,5-dimethyl-1-(3-(trifluoromethyl)-[1,2,4]triazolo[4,3-b]pyridazin-6-yl)-1H-pyrazol-4-yl)propan-1-one, 3-(3,5-Dimethyl-1-(3-methyl-[1,2,4]triazolo[4,3-b]pyridazin-6-yl)-1H-pyrazol-4-yl)-1-(4-(3-fluoro-5-(1H-tetrazol-5-yl)benzyl) piperazin-1-yl)propan-1-one, 3-(3,5-Dimethyl-1-(3-(trifluoromethyl)-[1,2,4]triazolo[4,3-b]pyridazin-6-yl)-1H-pyrazol-4-yl)-1-(4-(3-fluoro-5-(1H-tetrazol-5-yl)benzyl) piperazin-1-yl)propan-1-one,
3-(3,5-Dimethyl-1-(3-methyl-[1,2,4]triazolo[4,3-b]pyridazin-6-yl)-1H-pyrazol-4-yl)-1-(4-(2-methyl-3-(1H-tetrazol-5-yl)benzyl) piperazin-1-yl)propan-1-one,
3-(3,5-Dimethyl-1-(3-(trifluoromethyl)-[1,2,4]triazolo[4,3-b]pyridazin-6-yl)-1H-pyrazol-4-yl)-1-(4-(2-methyl-3-(1H-tetrazol-5-yl)benzyl) piperazin-1-yl)propan-1-one,
3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-5-fluorobenzonitrile,
4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-3-fluorobenzonitrile,
4-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile,
2-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile,
3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)-2-methylbenzonitrile,
3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-2-methylbenzonitrile,
2-chloro-3-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile,
3-chloro-4-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile,
3-chloro-4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)benzonitrile,
4-((4-(3-(3,5-dimethyl-1-(3-(trifluoromethyl)-[1,2,4]triazolo[4,3-b]pyridazin-6-yl)-1H-pyrazol-4-yl)propanoyl)piperazin-1-yl)methyl)-3-fluorobenzonitrile,
4-chloro-3-((4-(3-(3,5-dimethyl-1-(3-methyl-[1,2,4]triazolo[4,3-b]pyridazin-6-yl)-1H-pyrazol-4-yl)propanoyl)piperazin-1-yl)methyl)benzonitrile,
or a pharmaceutically acceptable salt, solvate or hydrate thereof.

6. A pharmaceutical composition comprising the compound according to claim 1.

7. A method of treatment of a condition or disorder associated with overexpression of TRAF6 comprising administering the compound according to claim 1, to an individual in need thereof.

8. A method for the treatment of cancer, an immune disease, Parkinson's disease, Cardiac Hypertrophy or Type-2 diabetes comprising administering the compound according to claim 1, to an individual in need thereof.

9. The method of claim 8, wherein the cancer is selected from the group consisting of lymphoma such as diffuse large B-cell lymphoma (DLBCL) and MALT lymphoma, multiple myeloma (MM), lung cancer, lung adenocarcinoma, colon cancer, prostate cancer, breast cancer, osteosarcoma, pancreatic cancer and esophageal squamous cell carcinoma (ESCC).

10. The method of claim 8, wherein the immune disease is an autoimmune disease, selected from the group consisting of psoriasis, rheumatoid arthritis, celiac disease, inflammatory bowel disease such as Crohn's disease and ulcerative colitis, multiple sclerosis, systemic lupus erythematosus, and diabetes mellitus type 1.

11. A compound or a pharmaceutically acceptable salt, solvate or hydrate thereof according to claim 1 wherein:

when Q is selected from group A)

$R_1$ and $R_2$ are independently selected from the group consisting of $(C_1-C_6)$alkyl, $R_3$ is selected from the group consisting of $—(C_1-C_6)$alkyl;

A is $—(CH_2)_2—$;

wherein D as $—(C_3-C_{10})$heteroaryl is selected from the group consisting of

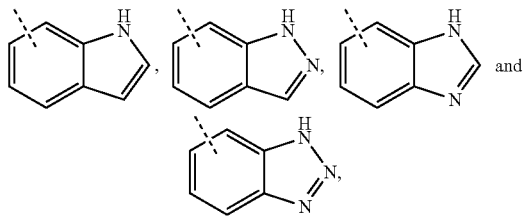

and D as $—(C_6-C_{10})$aryl, is selected from the group consisting of phenyl,

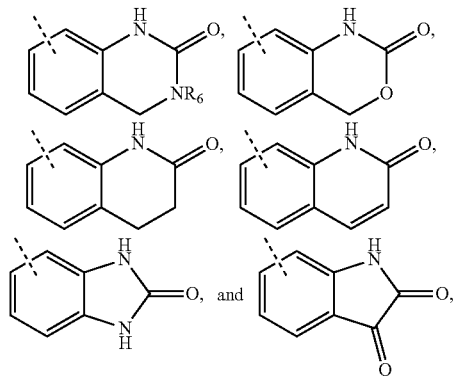

optionally substituted by one or more identical or different substituents selected from the group consisting of halogen, $—(C_1-C_4)$alkyl, $—(C_1-C_4)$haloalkyl, $—CO(C_1-C_4)$alkyl, $—CN$, $—NC$, $—(C_6-C_{10})$aryl, $—(C_3-C_{10})$heteroaryl, $—N((C_1-C_4)$alkyl)$_2$, $—NO$, $—SO_2 (C_1-C_4)$alkyl, $—NHSO(C_1-C_4)$alkyl, $—NHSO_2 (C_1-C_4)$alkyl, $—CONH_2$, $—CF_3$, $—COOH$, $—NO_2$, $—NHCO(C_1-C_4)$alkyl, $—CO_2 (C_1-C_4)$alkyl, $—CONH (C_1-C_4)$alkyl, $—CONH_2$, $—OR^6$, $—SO_2NH_2$, $—CH_2COOH$, $—CH_2OR^6$; $—COCH_2SO_2Ph$, $—NHCONHR_6$, $—CONHOR_6$, $—CONHCN$, $NHCOOR_6$,

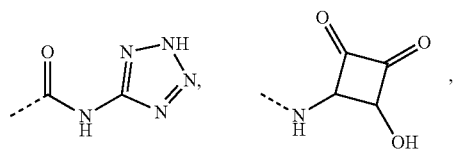

309

-continued

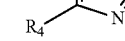

when Q is selected from group B)

R₁ and R₂ are independently selected from the group consisting of (C₁-C₆)alkyl,

R₃ is selected from the group consisting of —(C₁-C₆)alkyl,

A is —(CH₂)₂— or cyclopropyl;

wherein D as —(C₃-C₁₀)heteroaryl is selected from the group consisting of

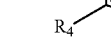

optionally substituted by one or more identical or different substituents selected from the group consisting of halogen, (C₁-C₄)alkyl, —(C₁-C₄)haloalkyl, —CO(C₁-C₄)alkyl, —CN, —NC, —(C₆-C₁₀)aryl, —(C₃-C₁₀)heteroaryl, —NH(C₁-C₄)alkyl, —N((C₁-C₄)alkyl)₂, —NO, —SO₂ (C₁-C₄)alkyl, —NHSO(C₁-C₄)alkyl, —NHSO₂ (C₁-C₄)alkyl, —CONH₂, —CF₃, —COOH, —NO₂, —NHCO(C₁-C₄)alkyl, —CO₂ (C₁-C₄)alkyl, —CONH(C₁-C₄)alkyl, —CONH₂, —OR⁶, —SO₂NH₂, —CH₂COOH, —CH₂OR⁶; —COCH₂SO₂Ph, —NHCONHR₆, —CONHOR₆, —SO₂Ph, —CONHCN, NHCOOR₆,

310

-continued

12. A compound or a pharmaceutically acceptable salt, solvate or hydrate thereof according to claim 1 wherein at least one —(C₃-C₁₀)heteroaryl substituent is selected from the group consisting of:

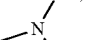

13. A method of treatment of a condition or disorder associated with overexpression of TRAF6 comprising administering the pharmaceutical composition according to claim 6, to an individual in need thereof.

14. A method for the treatment of cancer, an immune disease, Parkinson's disease, Cardiac Hypertrophy or Type-2 diabetes comprising administering the pharmaceutical composition of claim 6 to an individual in need thereof.

15. The method of claim 14, wherein the cancer is selected from the group consisting of lymphoma such as diffuse large B-cell lymphoma (DLBCL) and MALT lymphoma, multiple myeloma (MM), lung cancer, lung adenocarcinoma, colon cancer, prostate cancer, breast cancer, osteosarcoma, pancreatic cancer and esophageal squamous cell carcinoma (ESCC).

16. The method of claim 14, wherein the immune disease is an autoimmune disease selected from the group consisting of psoriasis, rheumatoid arthritis, celiac disease, inflammatory bowel disease such as Crohn's disease and ulcerative colitis multiple sclerosis, systemic lupus erythematosus, and diabetes mellitus type 1.

* * * * *